United States Patent
Vankayalapati et al.

(10) Patent No.: US 8,791,112 B2
(45) Date of Patent: Jul. 29, 2014

(54) **SUBSTITUTED 5-(PYRAZIN-2-YL)-1H-PYRAZOLO [3, 4-*B*] PYRIDINE AND PYRAZOLO [3, 4-*B*] PYRIDINE DERIVATIVES AS PROTEIN KINASE INHIBITORS**

(75) Inventors: Hariprasad Vankayalapati, Draper, UT (US); Rajendra P Appalaneni, Stamford, CT (US); Y. Vekata Krishna Reddy, Hyderabad (IN)

(73) Assignee: Arrien Pharmaceuticals LLC, Somerset, NJ (US)

( * ) Notice: Subject to any disclaimer, the term of this patent is extended or adjusted under 35 U.S.C. 154(b) by 0 days.

(21) Appl. No.: 13/435,327

(22) Filed: Mar. 30, 2012

(65) Prior Publication Data

US 2013/0102586 A1    Apr. 25, 2013

Related U.S. Application Data

(60) Provisional application No. 61/469,274, filed on Mar. 30, 2011.

(51) Int. Cl.
*A61K 31/535*    (2006.01)
*A61K 31/497*    (2006.01)
*C07D 401/04*    (2006.01)
*C07D 471/04*    (2006.01)

(52) U.S. Cl.
CPC .................................. *C07D 471/04* (2013.01)
USPC .............. 514/234.2; 514/210.21; 514/252.11; 514/255.05; 514/256

(58) Field of Classification Search
CPC .................................................... C07D 471/04
USPC .............. 514/210.21, 234.2, 252.11, 255.05, 514/256, 410, 412, 414; 544/120, 328, 357, 544/405
See application file for complete search history.

(56) References Cited

U.S. PATENT DOCUMENTS

| | | | | |
|---|---|---|---|---|
| 6,531,491 | B1 * | 3/2003 | Kania et al. ................. | 514/338 |
| 6,683,189 | B1 | 1/2004 | Deryan et al. | |
| 2004/0171634 | A1 * | 9/2004 | Kania et al. ................. | 514/303 |
| 2004/0224952 | A1 | 11/2004 | Cowart | |
| 2004/0224953 | A1 | 11/2004 | Cowart | |
| 2006/0024361 | A1 | 2/2006 | Odidi | |
| 2007/0203143 | A1 * | 8/2007 | Sheppard et al. ............ | 514/243 |
| 2009/0203687 | A1 | 8/2009 | Arnold et al. | |
| 2010/0035251 | A1 | 2/2010 | He et al. | |
| 2010/0261665 | A1 | 10/2010 | Laing et al. | |
| 2010/0317646 | A1 | 12/2010 | Melver et al. | |

FOREIGN PATENT DOCUMENTS

| | | |
|---|---|---|
| GB | 2298199 A | 8/1996 |
| KR | 2011062351 A | 6/2011 |
| RU | 2370496 C2 | 10/2009 |
| WO | 2005100353 A1 | 10/2005 |
| WO | 2006015123 A1 | 2/2006 |
| WO | 2006015124 A2 | 2/2006 |
| WO | 2006099075 A2 | 9/2006 |
| WO | 2007135398 A1 | 11/2007 |
| WO | 2007137030 A2 | 11/2007 |
| WO | 2008033858 A2 | 3/2008 |
| WO | 2008063888 A2 | 5/2008 |
| WO | 2008064255 A2 | 5/2008 |
| WO | 2008110508 A1 | 9/2008 |
| WO | 2008124849 A2 | 10/2008 |
| WO | 2008124850 A1 | 10/2008 |
| WO | 2008138448 A2 | 11/2008 |
| WO | 2009016460 A2 | 2/2009 |
| WO | 2009032652 A1 | 3/2009 |
| WO | 2009089352 A1 | 7/2009 |
| WO | 2010106333 A1 | 3/2010 |
| WO | 2010059771 A1 | 5/2010 |
| WO | 2011079133 A2 | 6/2011 |
| WO | 2011141756 A1 | 11/2011 |
| WO | 2011143646 A1 | 11/2011 |

OTHER PUBLICATIONS

Chioua et al., "Synthesis and biological evaluation of 3,6-diamino-1H-pyrazolo[3,4-b]pyridine derivatives as protein kinase inhibitors", Aug. 15, 2009, Bioorganic & Medicinal Chemistry Letters, vol. 19, Issue 16, pp. 4566-4569.*

I. F. Mata, W. J. Wedemeyer, M. J. Farrer, J. P. Taylor, and K.A. Gallo, LRRK2 in Parkinson's disease: protein domains and functional insights, Trends in Neurosciences, 29 (5) 286-293, (2006).

M. R. Cookson, The role of Leucine-Rich Repeat Kinase 2 (LRRK2) in Parkinson's disease, *Nature Reviews Neuroscience*, 11 (12) 791-797, (2010).

E. K. Tan and A. H. Schapira, LRRK2 as a therapeutic target in Parkinson's disease,*European Journal of Neurology*, 18 (4) 545-546, (2011).

E. Andres-Mateos, R. Mejias, M. Sasaki et al., Unexpected lack of hypersensitivity in LRRK2 knock-out mice to MPTP (1-methyl-4-phenyl-1,2,3,6-tetrahydropyridine), *Journal of Neuroscience*, 29 (50) 15846-15850, (2009).

(Continued)

*Primary Examiner* — My-Chau T Tran
(74) *Attorney, Agent, or Firm* — Timothy X. Gibson, Esq.; Gibson & Dernier LLP

(57) ABSTRACT

Substituted 5-(pyrazin-2-yl)-1H-pyrazolo[3,4-b]pyridine, 5-(pyrazin-2-yl)-1H-pyrrolo[2,3-b]pyridine and pyrazolo[3,4-b]pyridine derivatives according to formula I, II and VII, and methods for making same, which are inhibitors of constitutively activated Tyrosine Kinase-Like (TKL), CMGC protein kinases family members and can be useful in the treatment of Parkinson's disease, Alzheimer's disease, Down's Syndrome, Huntington's disease, other neurodegenerative and central nervous system disorders, cancer, metabolic disorders and inflammatory diseases. Also disclosed are pharmaceutical compositions including the compounds and methods of inhibiting wild type and/or mutated protein kinase activities of these families and the treatment of disorders associated therewith using compounds and pharmaceutical compositions including the compounds.

18 Claims, 6 Drawing Sheets

(56) References Cited

OTHER PUBLICATIONS

Kaul, S., Kanthasamy, A., Kitazawa, M., Anantharam, V., and Kanthasamy, A. G. Caspase-3 dependent proteolytic activation of protein kinase C delta mediates and regulates 1-methyl-4-phenylpyridinium (MPP+)-induced apoptotic cell death in dopaminergic cells: relevance to oxidative stress in dopaminergic degeneration. *Eur J Neurosci* 18:1387-1401, (2003).

Yang, Y., Kaul, S., Zhang, D., Anantharam, V., and Kanthasamy, A. G. Suppression of caspase-3-dependent proteolytic activation of protein kinase C delta by small interfering RNAA prevents MPP+-induced dopaminergic degeneration. *Mol Cell Neurosci*, 25:406-421, (2004).

Zhang, D., Anantharam, V., Kanthasamy, A., and Kanthasamy, A. G. Neuroprotective effect of protein kinase C delta inhibitor rottlerin in cell culture and animal models of Parkinson's disease. *J Pharmacol Exp Ther*, 322:913-922, (2007).

Ghosh, A., Roy, A., Liu, X., Kordower, J. H., Mufson, E. J., Hartley, D. M., Ghosh, S., Mosley, R. L., Gendelman, H. E., and Pahan, K. Selective inhibition of NF-kappaB activation prevents dopaminergic neuronal loss in a mouse model of Parkinson's disease. *Proc Natl Acad Sci. U S A*, 104 (47) 18754-18759, (2007).

B. D. Lee, J.-H. Shin, J. Vankampen et al , Inhibitors of Leucine-Rich Repeat Kinase-2 protect against models of Parkinson's disease, *Nature Medicine*, 16 (9) 998-1000, (2010).

W. W. Smith, Z. Pei, H. Jiang, V. L. Dawson, T. M. Dawson, and C. A. Ross, Kinase activity of mutant LRRK2 mediates neuronal toxicity, *Nature Neuroscience*, 9, (10) 1231-1233, (2006).

T. M. Dawson, H. S. Ko, and V. L. Dawson, Genetic animal models of Parkinson's disease, *Neuron*, 66, (5) 646-661, (2010).

T. M. Dawson and V. L. Dawson, Molecular Pathways of Neurodegeneration in Parkinson's Disease, *Science*, 302, 819-822, (2003).

L. Tianxia, Y. DeJun, S. Sarah, L. Zhaohui, and W.S Wanli, Models for LRRK2-Linked Parkinsonism, *Parkinsons Dis*, (2011) 1-16.

Z. K. Sweeney and J. W. Lewcock, ACS Chemical Neuroscience Spotlight on CEP-1347, *ACS Chem. Neurosci*, 2, 3-4 (2011).

L. K. Chico, L. J. Van Eldik and D. M. Watterson, Targeting protein kinases in central nervous system disorders, Nature Reviews Drug Discovery 8, 892-909, (2009).

D. C. Berwick, K. Harvey, LRRK2 signalling pathways: the key to unlocking, neurodegeneration?, Trends in Cell Biology, vol. 21, No. 5, p. 257-265, (2011).

N. Ramsden, J. Perrin, Z. Ren, B.D Lee, N. Zinn, V. L. Dawson, D. Tam, M. Bova, M. Lang, G. Drewes, M. Bantscheff, F. Bard, T. M. Dawson, and C. Hopf, Chemoproteomics-Based Design of Potent LRRK2-Selective Lead Compounds That Attenuate Parkinson's Disease-Related Toxicity in Human Neurons, *ACS Chem. Biol.*, 6 1021-1028, (2011).

T. Kramer, F. Lo Monte, S. Göring, G. M. O. Amombo, and B. Schmidt, Small Molecule Kinase Inhibitors for LRRK2 and Their Application to Parkinson's Disease Models, *ACS Chem. Neurosci.*, 3, 151-160, (2012).

B. Thomas and M. F. Beal, Molecular insights into Parkinson's disease, F1000 Medicine Reports, 3:7, 1-8, (2011).

R. Martin and S.L. Buchwald, Palladium-Catalyzed Suzuki—Miyaura Cross-Coupling Reactions Employing Dialkylbiaryl Phosphine Ligands, *Acc. Chem. Res.*, 41 (11) 1461-1473, (2008).

International Search Report and Written Opinion for corresponding application PCT/US2012/31471, dated Jul. 3, 2012.

\* cited by examiner

CLUSTAL W Multiple Sequence Alignment

```
LRRK2  1861  ------------LADLPRNIMLNNDELEFEQAPEFLLGDGSFGSVYRAAYEGEEVAVKIF  1908
MLK1    136  ---------------------LLEIDFAELTLEEIIGIGGFGKVYRAFWIGDEVAVKAA   173
Tak1     27  ----------------------SLHMIDYKEIEVEEVVGRGAFGVVCKAKWRAKDVAIKQI  65
BRAF    448  --------------------DDWEIPDGQITVGQRIGSGSFGTVYKGKWHGDVAVKMLN   486
Tie2    808  -------------KNNPDPTIYPVLDWNDIKFQDVIGEGNFGQVLKARIKKDGLRMDAA   853
TGFb    175  TTLKDLIYDMTTSGSGSGLPLLVQRTIARTIVLQESIGKGRFGEVWRGKWRGEEVAVKIF  234

LRRK2  1909  NKHTSLR--------LLRQELVVLCHL-HHPSLIISLLAAGIRP--------RMLVMELASKGS  1954
MLK1    174  RHDPDEDIS--QTIENVRQEAKLFAML-KHPNIIALRGVCLKEP----NLCLVMEFARGGR   277
Tak1     66  ESESER------KAFIVELRQLSRV-NHPNIVKLYGACLN------PVCLVMEYAEGGS    111
BRAF    487  VTAPTP------QQLQAFKNEVGVLRKT-RHVNILLFMGYSTKP------QLAIVTQWCEGSS  536
Tie2    854  IKRMKEYASKDDHRDFAGELEVLCKLGHHPNIINLLGACEHRG-----YLYLAIEYAPHGN  909
TGFb    235  SSREERS--------WFREAEIYQTVMLRHENILGFIAADNKDNGTWTQLWLVSDYHEHGS  287

LRRK2  1955  LDRLLQQDKASLTRTLQHR-------------IALHVADGLRYLHSAM---------II   1991
MLK1    278  LNRVLSGKRIPPDILVN-------------WAVQIARGMNYLHDEAI------VPII    265
Tak1    112  LYNVLHGAEPLPYYTAAHAM----------SWCLQCSQGVAYLHSMQP------KALI   153
BRAF    537  LYHHLHAS--ETKFEMKKLI-----------DIARQTARGMDYLHAKS---------II   573
Tie2    910  LLDFLRKSRVLETDPAFAIANSTASTLSSQQLLHFAADVARGMDYLSQKQ---------FI   961
TGFb    288  LFDYLNRYTVTVEGMIK-------------LALSTASGLAHLHMEIVGTQGKPAIA  330

LRRK2  1992  YRDLKPHNVLLFTLYPN----AAIIAKIADYIAQYCCRMGIKTS--------EGTPGFRAPE  2042
MLK1    266  HRDLKSSNILILQKVENGDLSNKILKITDFLAREWHRTTKMS--------AAGAYAWMAPE   319
Tak1    154  HRDLKPPNLLLVAGG--------TVLKIQDFTACDIQ-THMTN--------NKGSAAWMAPE   199
BRAF    574  HRDLKSNNIFLHEDN--------TVKIGDFLATVKSRWSGSHQFEQ--LSGSILWMAPE   623
Tie2    962  HRDLAARNILVGENY--------VAKIADFLSRGQEVYVKKTMG-----RLPVRWMAIE   1008
TGFb    331  HRDLKSKNILVKKNG--------TCCIADLLAVRHDSATDTIDIAPNHRVGTKRYMAPE   382

LRRK2  2043  VARGNV------IYNQQADVYSFGLLLYDILTTGGRIVEGLKFPNEFDELEIQGKLPDPVK  2097
MLK1    320  VIRASM------FSKGSDVWSYGVLLWELLTGE-VPFRGIDGLAVAYGVAMN-KLALPIP   371
Tak1    200  VFEGSN------YSEKCDVFSWGIILWEVITRR-KPFDEIGGPAFRIMWAVHNGTRPPLI   252
BRAF    624  VIRMQDSN----PYSFQSDVYAFGIVLYELMTGQ-LPYSNINNRDQIIEMVGRGSLSPDLS  679
Tie2   1009  SLNYSV------YTTNSDVWSYGVLLWEIVSLGGTPYCGMTCAELYEKLPQGYRLEKPLN  1062
TGFb    383  VLDDSINMKHFESFKRADIYAMGLVFWEIARRCSIGGIHEDYQLPYYDLVPSDPSVEEMR  442

LRRK2  2098  EYGCAPWPMVEKLIKQCLKENPQERPTSAQVFDILNSAELVCLTRRILLPKNVIVECMVA  2157
MLK1    372  ST----CPEPFAKLMEDCWNPDPHSRPSFTNILDQLTT----------- 405
Tak1    253  KN----LPKPIESLMTRCWSKDPSQRPSMEEIVKIMTHLMRYFPGADEPLQYPCQHSLPPG  473
BRAF    680  KVRSNCPKRMKRLMAECLKKKRDERPSFPRILAEIEELARELS-------- 722
Tie2   1063  CD------DEVYDLMRQCWREKPYERPSFAQILVSLNRMLEERKTYVNTTLYEKFTYAGID  1117
TGFb    443  KV---VCEQKLRPNIPNRWQSCEALRVMAKIMRECWYANGAARLTALRIKKTLSQLSQQEG  500
```

*FIG. 4*

SUBSTITUTED 5-(PYRAZIN-2-YL)-1H-PYRAZOLO [3, 4-*B*] PYRIDINE AND PYRAZOLO [3, 4-*B*] PYRIDINE DERIVATIVES AS PROTEIN KINASE INHIBITORS

CROSS-REFERENCE TO RELATED APPLICATIONS

The present application claims the benefit of U.S. Provisional Patent Application No. 61/469,274, filed Mar. 30, 2011, the entire disclosure of which is incorporated herein by reference.

INCORPORATION BY REFERENCE

The sequence listing submitted in the copies of the compact discs COPY 1 and COPY 2 filed in connection with this application and the files contained on each disc, each entitled "Sequence Listing", each 372KB, each created Jun. 8, 2012, are incorporated herein by reference.

FIELD OF THE INVENTION

The present invention relates to compounds useful as protein kinase inhibitors, specifically LRRK2 (Leucine-Rich Repeat Kinase-2) inhibitors, pharmaceutically acceptable compositions including such compounds and methods of using said compounds in the treatment of various diseases and or disorders.

BACKGROUND OF THE INVENTION

Parkinson's disease (PD) and Alzheimer's disease (AD) are the most common neurodegenerative disorders in the adult population. Parkinson's disease is characterized by slow movement, resting tremor, rigidity, bradykinesia and postural instability. The disease is characterized pathologically by the progressive loss of dopaminergic neurons in the substantia nigra pars compacta and the presence of intracytoplasmic aggregates called Lewy bodies in surviving neurons of the brainstem. The incidence of PD increases with age; it has been estimated 0.3% of those age 50 are afflicted, the number increasing to 4.3% by age of 85. No significant treatment is available for PD.

Alzheimer's disease is a fatal neurodegenerative disorder which results in progressive memory loss and behavioral abnormalities for which there is currently no cure. AD is characterized by the progressive formation of insoluble amyloid plaques and fibrillary tangles. These plaques primarily of consists of an aggregated $\alpha\beta$ (Amyloid-$\beta$) peptide that is formed by the proteolytic processing of amyloid precursor protein (APP) by $\beta$-site cleaving enzyme (BACE1). Current approaches targeting these proteins to treat AD do not arrest the underlying disease process and largely treat only the symptoms. Therapeutics to either slow or reverse the neuronal loss and the underlying cognitive decline are urgently needed.

The human gene LRRK2 (Leucine-Rich Repeat Kinase-2) (SEQ ID NO 62) encodes an enzyme also known as LRRK2 or dardarin. LRRK2 is a 144 Kb with 51 exons encoding 2527 amino acids. The LRRK2 protein domain consists of Ras belonging to the Ras/GTPase family, COR, LRR, a Leucine-Rich Repeat, consisting of MAPKKK kinase catalytic domain a (22-28 amino acid motif) directly involved in Ser/Thr phosphorylation, a WD40 domain and ankyrin repeats. LRRK2 is expressed in all tissues at low levels and in neurons of the brain regions including the cortex, striatum, hippocampus, and cerebellum and in dopaminergic neurons of the substantia nigra. Although the expression levels of LRRK2 in the dopaminergic neurons of the SNpc are very low, its expression level has been detected in Lewy neurites and in Lewy bodies of sporadic PD.

LRRK2 (SEQ ID NO 62) is reported to be the most prevalent cause for autosomal dominant PD. Overlapping neurodegenerative pathologies have been described in PD patients with Alzheimer's disease with LRRK2 mutations. A common G2019S mutation (SEQ ID NO 28) accounts for a significant proportion of sporadic PD in some populations and the location of the LRRK2 gene on chromosome 12q12 that causes late onset AD. More than 20 mutations have been reported in the gene encoding LRRK2 (SEQ ID NO 62) which have been linked recently with autosomal-dominant Parkinsonism that is clinically indistinguishable from typical, idiopathic, late-onset PD. Some of these mutations, R1441C, R1441G, Y1699C and G2019S, are amino acids conserved. Recent study demonstrates that LRRK2 R1628P (SEQ ID 29) variant is associated with a two-fold risk of AD.

SUMMARY OF THE INVENTION

Recent studies showed pathogenic mutations of LRRK2 (SEQ ID NO 62) increased LRRK2 kinase activity with autophosphorylation, suggesting a gain-of-function mechanism. Recent findings suggest that S2031 and T2032 are critical residues required for LRRK2 autophosphorylation, and T2035 is important for its catalytic activity. Dimeric LRRK2 undergoes intramolecular autophosphorylation for its kinase activity. PD patients having LRRK2 mutations are subject to neuronal degeneration in the brain, due to induced cell toxicity in multiple cell lines and rodent primary neurons with reduction of cell viability ranging from 10-40%. Expression of G2019S decreases neuronal cell viability 2 to 5 fold. Mice hybridization studies reveal that expression of LRRK2 (SEQ ID NO 62) overexpressed in the brain is higher within regions of the basal ganglia and directly associated with motor dysfunction in PD. It has been postulated that LRRK2 may be involved in some overlapping neurodegenerative pathways in AD.

The protein LRRK2 (SEQ ID NO 62) is a therapeutic target for the treatment of PD pathogenesis and the compounds of the invention of Formula I, II and VII associated matter are capable of inhibiting one or more protein kinases, more particularly LRRK2 (SEQ ID NO 62) and more particularly mutated LRRK2. Targeting of LRRK2 may be employed to treat PD and AD pathologies. The disclosed compounds are potent and selective LRRK2 inhibitors with efficacy in cellular/animal models with good in vivo pharmacokinetics (PK).

In one embodiment the invention includes the compounds of Formula I, II and VII and pharmaceutically acceptable salts thereof as described below.

In one embodiment the present invention includes compounds and compositions of matter including compounds active on protein kinases broadly, including but not limited to ABL1T315I (SEQ ID NO 1), ALK2 (SEQ ID NO 2), ARK5 (SEQ ID NO 64), Aurora A (SEQ ID NO 3), Aurora B (SEQ ID NO 4), Aurora C (SEQ ID NO 5), BRAF (SEQ ID NO 6), BRAF V599E (SEQ ID NO 7), CHK1 (SEQ ID NO 8), CHK2 (SEQ ID NO 9), C-KIT (SEQ ID NO 10), CLK1 (SEQ ID NO 11), CLK2 (SEQ ID NO 12), CLK3 (SEQ ID NO 13), CLK4 (SEQ ID NO 14), CSF1R (SEQ ID NO 15), DYRK1A (SEQ ID NO 16), DYRK1B (SEQ ID NO 17), DYRK2 (SEQ ID NO 18), DYRK3 (SEQ ID NO 19), DYRK4 (SEQ ID NO 20), FLT3 (SEQ ID NO 21), GSK3$\beta$ (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), LRRK2 (SEQ ID NO 62), LRRK2 G2019S (SEQ ID NO 28), LRRK2 T1602S R1628P T2352M (SEQ ID NO 29), MAP4K4 (SEQ ID NO 30), MELK (SEQ ID NO 31), MLK (SEQ ID NO 32), PDGFR (SEQ ID NO 41), PKA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) or TRKC (SEQ ID NO 58) kinases and mutations thereof. In another embodiment compounds disclosed herein target two common LRRK2 polymorphisms and Alzheimer's disease progression. The LRRK2 T1602S and T2352M are reported to be greatly associated with the conversion from mild cognitive impairment to AD. The polymorphism of LRRK2 is a suggestive biomarker and LRRK2 modulating agents can be used for the treatment of AD selected patients.

In another embodiment compounds disclosed herein target LRRK2 R1628P variant (SEQ ID NO 29). Dual PD and AD pathologies can co-exist where the LRRK2 R1628P (SEQ ID NO 29) variant is found.

Dual specificity tyrosine (Y) phosphorylation regulated kinase 1A (DYRK1A) (SEQ ID NO 16), a serine/threonine kinase known to play a vital role in neurodevelopment, is activated by autophosphorylation at the Tyr-321 residue. Transgenic mice in which DYRK1A (SEQ ID NO 16) is overexpressed showed hippocampal-dependent learning and memory deficits. Recent reports suggest that DYRK1A (SEQ ID NO 16) may also be involved in the pathological mechanisms of APP and Tau, and may accelerate the formation of amyloid plaques and NFTs which are insoluble deposits of β-amyloid and hyperphosphorylated Tau, respectively, causing the early onset of AD pathogenesis in Down's syndrome (DS). In one embodiment, the compounds of Formula I, II and VII are capable of inhibiting DYRK1A (SEQ ID NO 16), DYRK1B (SEQ ID NO 17) and DYRK2 (SEQ ID NO 18), DYRK3 (SEQ ID NO 19), DYRK4 (SEQ ID NO 20) kinases, benefiting individuals with DS in treating mental retardation and AD.

In another embodiment methods employing the disclosed compounds of Formula I, II and VII are disclosed for regulating protein kinases wherein said protein kinase includes but is not limited to ABL1 T315I (SEQ ID NO 1), ALK2 (SEQ ID NO 2), ARK5 (SEQ ID NO 64), Aurora A (SEQ ID NO 3), Aurora B (SEQ ID NO 4), Aurora C (SEQ ID NO 5), BRAF (SEQ ID NO 6), BRAF V599E (SEQ ID NO 7), CHK1 (SEQ ID NO 8), CHK2 (SEQ ID NO 9), C-KIT (SEQ ID NO 10), CLK1 (SEQ ID NO 11), CLK2 (SEQ ID NO 12), CLK3 (SEQ ID NO 13), CLK4 (SEQ ID NO 14), CSF1R (SEQ ID NO 15), DYRK1A (SEQ ID NO 16), DYRK1B (SEQ ID NO 17), DYRK2 (SEQ ID NO 18), DYRK3 (SEQ ID NO 19), DYRK4 (SEQ ID NO 20), FLT3 (SEQ ID NO 21), GSK3β (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), LRRK2 (SEQ ID NO 62), LRRK2 G2019S (SEQ ID NO 28), LRRK2 T1602S R1628P T2352M (SEQ ID NO 29), MAP4K4 (SEQ ID NO 30), MELK (SEQ ID NO 31), MLK (SEQ ID NO 32), PDGFR (SEQ ID NO 41), PICA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) or TRKC (SEQ ID NO 58) kinases. This set of kinases includes the mutations of these kinases and the use thereof in treating diseases and associated conditions with the regulation of the activity of these kinases.

In another embodiment methods employing the disclosed compounds of Formula I, II and VII are disclosed for regulating protein kinases wherein said protein kinase includes but is not limited to ABL1 T315I, ALK2, ARK5, Aurora A, B, C, BRAF, BRAF V599E, CHK1, CHK2, C-KIT CLK1-4, CSF1R, DYRK1A, DYRK1B, DYRK2-4, FLT3, GSK3β, JAK1-3, KDR, LCK, LRRK2, LRRK2 G2019, MAP4K4, MELK, MLK, PDGFR, PKA, PKCα, PKCτ, PIM1, RET, ROCK1, ROCK2, RSK1, RSK2, RET, p70S6K, SGK1, SNF1LK, SIK2, SYK, TNIK, TRKA, TRKB and TRKC kinases. This set of kinases includes the mutations of these kinases and the use thereof in treating diseases and associated conditions with the regulation of the activity of these kinases.

In another embodiment methods are disclosed for the treatment of pain of neuropathic origin, pain of inflammatory origin, cardiovascular disease, rheumatoid arthritis, osteoarthritis, type 2 diabetes, metabolic syndrome and obesity.

In a further embodiment the invention relates to the novel therapeutic uses of the disclosed compounds involved in the inhibition of protein kinases and the compounds used for treating the diseases associated with the protein kinase activities. They are useful as a drug for the treatment and/or prophylaxis of diseases such as cardiac disease, autoimmune disease, inflammatory disease, central nervous system disease, infectious disease, sepsis, septic shock and the like in mammals (e.g., cat, cattle, dog, horse, goat, monkey, human and the like), for example, ichorrhemia, endotoxin shock, exotoxin shock, heart failure, shock, hypotension, rheumatoid arthritis, arthrosteitis, gastritis, ulcerative colitis, peptic ulcer, stress gastric ulcer, Crohn's disease, autoimmune disease, tissue injury and rejection after organ transplantation, ischemic reperfusion disorder, acute coronary microvascular occlusion, shock vascular occlusion (disseminated intravascular coagulation syndrome (DIC) and the like), ischemic brain disorder, arteriosclerosis, pernicious anemia, Fanconi's anemia, sickle cell anemia, pancreatitis, nephrotic syndrome, nephritis, renal failure, insulin-dependent diabetes mellitus, non-insulin dependent diabetes mellitus, hepatic porphyria, alcoholism, Parkinson's disease, chronic leukemia, acute leukemia, tumor, myeloma, relief of side effects of anticancer agent, infant and adult respiratory distress syndrome, pulmonary emphysema, dementia, Alzheimer's disease, multiple sclerosis, vitamin E deficiency, aging, sunburn, myodystrophy, myocarditis, cardiac myopathy, myocardial infarction, sequela of myocardial infarction, osteoporosis, pneumonia, hepatitis, psoriasis, pain, cataract, influenza infection, malaria, human immunodeficiency virus (HIV) infection, radiation injury, burn, improved efficiency of in vitro fertilization, hyperkalaemia, ankylosing spondylitis, osteopenia, bone Behcet's disease, osteomalacia, bone fracture, acute bacterial meningitis, *Helicobacter pylori* infection, invasive staphylococcal infection, tuberculosis, systemic mycotic infection, herpes simplex virus infection, varicella-zoster virus infection, human papilloma virus infection, acute virus encephalitis, encephalitis, asthma, atopic dermatitis, allergic rhinitis, reflux esophagitis, fever, hypercholesterolemia, hyperglyceridemia, hyperlipidemia, diabetic complications, diabetic nephropathy, diabetic neuropathy, diabetic retinopathy, gout, gastric atony, hemorrhoid, systemic lupus erythematodes, spinal trauma, agrypnia, schizophrenia, epilepsy, cirrhosis, hepatic failure, unstable angina pectoris, valvular disease of heart, thrombocytopenia derived from dialysis, acute ischemic stroke, acute brain thrombosis, cancer metastasis, bladder cancer, breast cancer, cervical cancer, colon cancer, stomach cancer, ovarian cancer, prostate cancer, small cell lung cancer, non-small cell lung cancer, malignant melanoma, Hodgkin's disease, non-Hodgkin's lymphoma and the like.

BRIEF DESCRIPTION OF THE DRAWINGS

FIG. 4 depicts a structure-based sequence alignment in Clustal W of the catalytic protein kinase domains of LRRK2 Mixed Lineage Kinase 1 (MLK1) (SEQ ID NO 33), Transforming growth factor-beta (TGF-β)-activated Kinase 1 (TAK1) (SEQ ID NO 59), BRAF, Tie2 (SEQ ID NO 60) and Type I TGF-β receptor (TβR-I) (SEQ ID NO 61). Amino acid residue annotation were identical residues (*), highly conserved residues (:), and similar residues (.). The active site residues highlighted in yellow and the gatekeeper residues in turquoise and the DFG/DYG residues shown in gray and blue color a G2019S mutant site.

BRIEF DESCRIPTION OF THE SEQUENCES

Figure 1A:
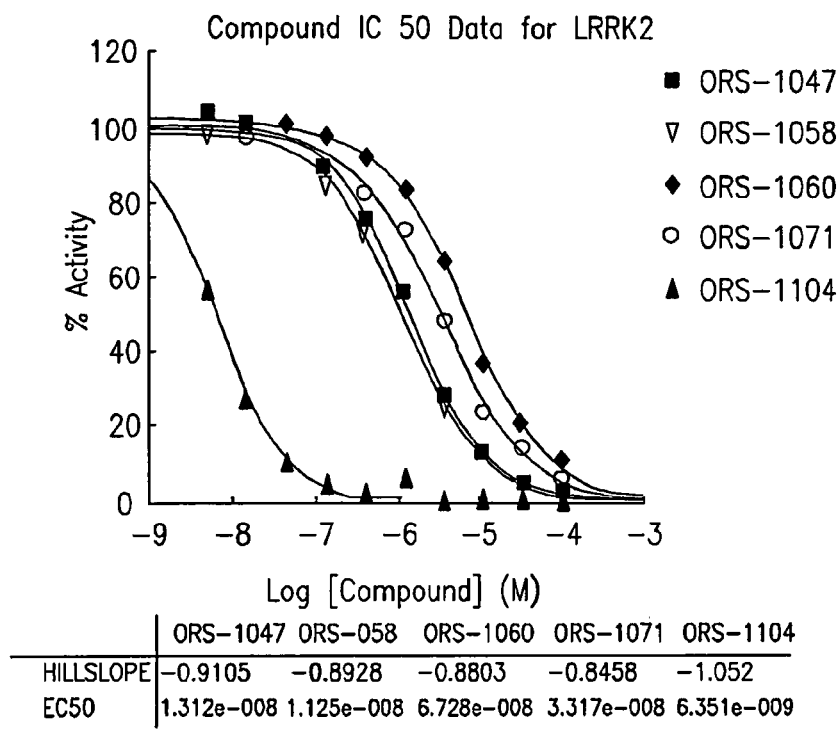
FIG. 1A-1D are graphical depictions of results of testing of selected compounds in accordance with the present disclosure in 10-dose $IC_{50}$ mode with 3 fold serial dilution starting at 100 µM. The control compound Staurosporine was tested in 10 dose IC50 with 3 fold serial dilution starting at 20 µM.
Figure 1B:
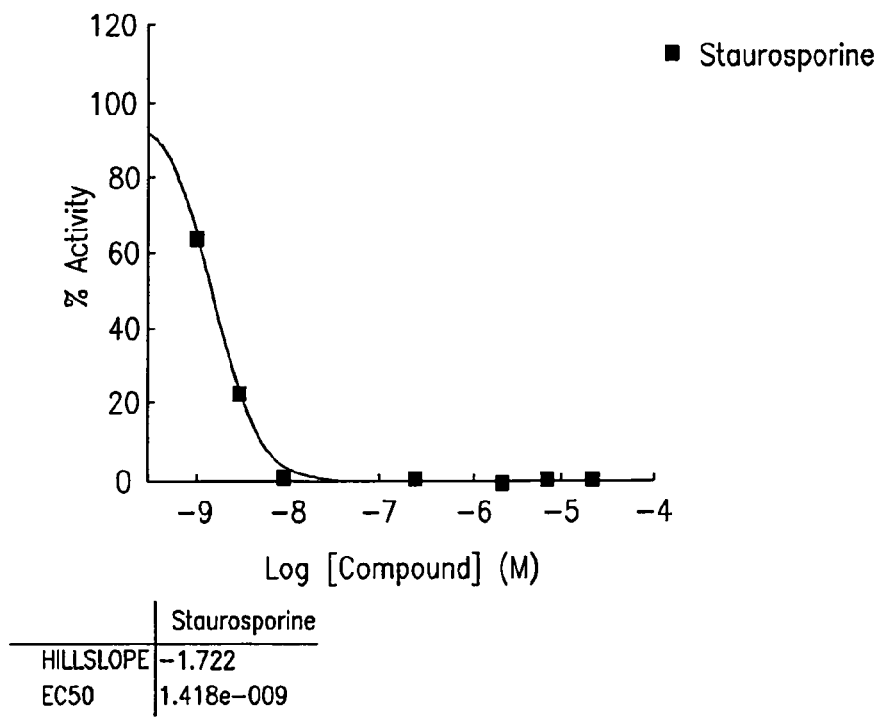
Figure 1C:
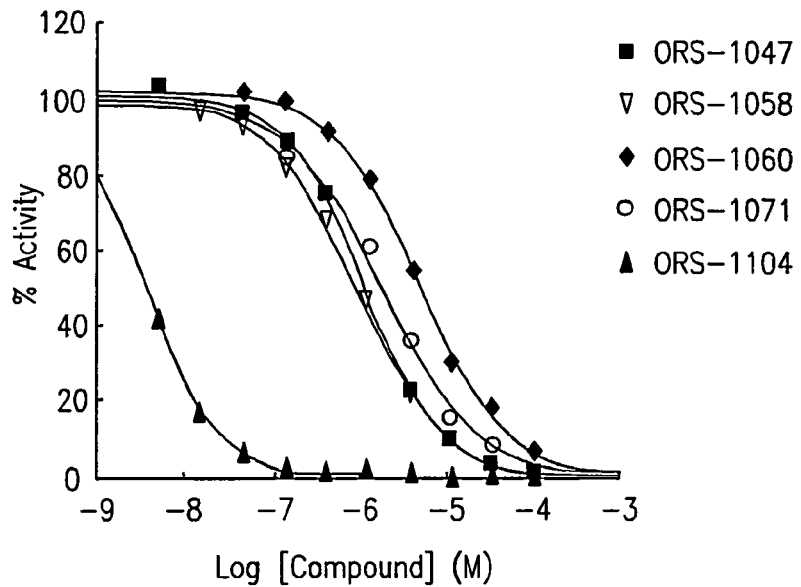
Figure 1D:
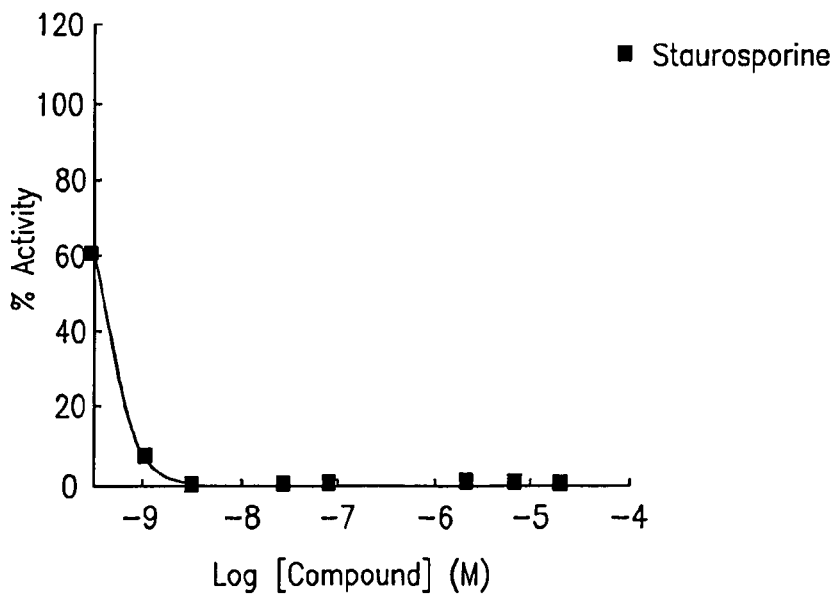

SEQ ID No. 1 is the *homo sapiens* (human) ABL T315I protein kinase sequence;
SEQ ID No. 2 is the *homo sapiens* ALK2 protein kinase sequence;
SEQ ID No. 3 is the human Aurora A protein kinase sequence;
SEQ ID No. 4 is the human Aurora B protein kinase sequence;
SEQ ID No. 5 is the human Aurora C protein kinase sequence;
SEQ ID No. 6 is the human BRAF protein kinase sequence;
SEQ ID No. 7 is the human BRAF V599E protein kinase sequence;
SEQ ID No. 8 is the human CHK1 protein kinase sequence;
SEQ ID No. 9 is the human CHK2 protein kinase sequence;
SEQ ID No. 10 is the human C-KIT protein kinase sequence;
SEQ ID No. 11 is the human CLK1 protein kinase sequence;
SEQ ID No. 12 is the human CLK2 protein kinase sequence;
SEQ ID No. 13 is the human CLK3 protein kinase sequence;
SEQ ID No. 14 is the human CLK4 protein kinase sequence;
SEQ ID No. 15 is the human CSF1R protein kinase sequence;
SEQ ID No. 16 is the human DYRK1A protein kinase sequence;
SEQ ID No. 17 is the human DYRK1B protein kinase sequence;
SEQ ID No. 18 is the human DYRK2 protein kinase sequence;
SEQ ID No. 19 is the human DYRK3 protein kinase sequence
SEQ ID No. 20 is the human DYRK4 protein kinase sequence;
SEQ ID No. 21 is the human FLT3 protein kinase sequence;
SEQ ID No. 22 is the human GSK3P protein kinase sequence;
SEQ ID No. 23 is the human JAK1 protein kinase sequence;
SEQ ID No. 24 is the human JAK2 protein kinase sequence;
SEQ ID No. 25 is the human JAK3 protein kinase sequence;
SEQ ID No. 26 is the human KDR protein kinase sequence;
SEQ ID No. 27 is the human LCK protein kinase sequence;
SEQ ID No. 28 is the human LRRK2 G2019S protein kinase sequence;
SEQ ID No. 29 is the human LRRK2 T1602S R 1628P T2352M protein kinase sequence;
SEQ ID No. 30 is the human MAP4K4 protein kinase sequence;
SEQ ID No. 31 is the human MELK protein kinase sequence;
SEQ ID No. 32 is the human MLK protein kinase sequence;
SEQ ID No. 33 is the human MLK1 protein kinase sequence;
SEQ ID No. 34 is the human MAP3K9 protein kinase sequence;
SEQ ID No. 35 is the human MAP4K5 protein kinase sequence;
SEQ ID No. 36 is the human MINK1 protein kinase sequence;
SEQ ID No. 37 is the human MARK1 protein kinase sequence;
SEQ ID No. 38 is the human MARK2 protein kinase sequence;
SEQ ID No. 39 is the human MARK3 protein kinase sequence;
SEQ ID No. 40 is the human MARK4 protein kinase sequence;
SEQ ID No. 41 is the human PDGFR protein kinase sequence;
SEQ ID No. 42 is the human PKCα protein kinase sequence;
SEQ ID No. 43 is the human PKCτ protein kinase sequence;
SEQ ID No. 44 is the human PIM1 protein kinase sequence;
SEQ ID No. 45 is the human RET protein kinase sequence;
SEQ ID No. 46 is the human ROCK1 protein kinase sequence;
SEQ ID No. 47 is the human ROCK2 protein kinase sequence;

SEQ ID No. 48 is the human RSK1 protein kinase sequence;

SEQ ID No. 49 is the human RSK2 protein kinase sequence;

SEQ ID No. 50 is the human p70S6K protein kinase sequence;

SEQ ID No. 51 is the human SGK1 protein kinase sequence;

SEQ ID No. 52 is the human SNF1LK protein kinase sequence;

SEQ ID No. 53 is the human SIK2 protein kinase sequence;

SEQ ID No. 54 is the human SYK protein kinase sequence;

SEQ ID No. 55 is the human TNIK protein kinase sequence;

SEQ ID No. 56 is the human TRKA protein kinase sequence;

SEQ ID No. 57 is the human TRKB protein kinase sequence;

SEQ ID No. 58 is the human TRKC protein kinase sequence;

SEQ ID No. 59 is the human TAK1 protein kinase sequence;

SEQ ID No. 60 is the human Tie2 protein kinase sequence;

SEQ ID No. 61 is the human TGFβ1 ALK5 protein kinase sequence;

SEQ ID No. 62 is the human LRRK2 protein kinase sequence;

SEQ ID No. 63 is the human PKA protein kinase sequence; and

SEQ ID No. 64 is the human ARK5 protein kinase sequence.

DETAILED DESCRIPTION OF THE INVENTION

The following is a detailed description of the subject matter provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

In one aspect the invention provides compounds having the chemical structure of Formula I and II:

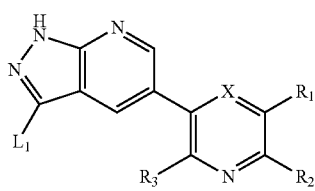

I

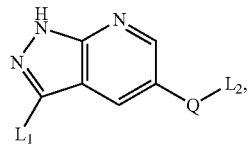

II and pharmaceutically acceptable salts, isomers and tautomers thereof, wherein:

in Formula I,

X is independently —N or —CH;

$L_1$ is independently a direct bond, substituted or unsubstituted 6-membered aryl, heteroaryl, substituted or unsubstituted 5-membered aryl or heteroaryl, substituted or unsubstituted cycloalkyl, substituted or unsubstituted heterocycloalkyl, —C(O)$_n$, S(O)n, —O, —NH, substituted or unsubstituted C1-C5 alkylene, substituted or unsubstituted 2 to 5 membered heteroalkylene groups; where "n" is from 0 to 2, hydrogen, —CH$_3$, halo, —OCH$_3$, —CF$_3$, OCF$_3$, —CN, —NH$_2$, —CH$_2$OCF$_2$, —COOH, —OR$_4$, —SR$_4$, —NHR$_4$, —C(O)R$_4$, —C(S)R$_4$, —C(O)NR$_4$, and —S(O)$_2$R$_4$, —S(O)$_2$NHR$_4$, —NHCOR$_4$, —CONHR$_4$, CONR$_4$, —CH═CHR$_4$, —NCH$_3$R$_4$, $R_4$ is optionally substituted at each occurrence and is selected from alkyl, heteroaryl, cycloalkyl, heterocycloalkyl, —C$_{1-6}$ alkyl, —C$_{1-4}$ haloaliphatic, —C$_{2-6}$ alkenyl, mono/dialkylamino, aryl C$_{4-7}$ heterocycloakyl, —C$_{5-6}$ aryl and, wherein the functional groups are each optionally substituted with one or more of fluoro, —NH$_2$, hydroxyl, fluoro substituted lower alkyl, alkoxy, alkylthio, mono/dialkylamino and cycloalkylamino functional groups or additional substituents selected from —NR$_5$R$_6$ and —CR$_5$R$_6$ respectively, and wherein;

$R_4$ together with the carbon to which it is attached may form a 3-7 member monocyclic cycloalkyl, 5-6 membered monocyclic heterocycloalkyl, heterocycloalkyl, heteroaryl; wherein the monocyclic cycloalkyl or heterocycloalkyl are each independently optionally substituted with one or more of fluoro, —NH$_2$, hydroxyl, fluoro substituted lower alkyl, alkoxy, alkylthio, mono/dialkylamino and cycloalkylamino;

$R_5$ and $R_6$ are each independently —H, cycloalkyl, alkyl, heterocycloalkyl, aryl, heteroaryl, —C$_{1-6}$ alkyl, —C$_{3-7}$ cycloalkyl, —C$_{3-6}$ heterocyclocycloalkyl, each optionally substituted with one or more of fluoro, —NH$_2$, hydroxyl, fluoro substituted C$_{1-6}$ alkyl, cyclopropyl, cyclobutyl, cyclopentyl, cyclohexyl, alkoxy, alkylthio, mono/dialkylamino and cycloalkylamino;

wherein L1 is optionally substituted with —R$_7$ or Y$_9$;

wherein R$_7$ is independently a bond, substituted or unsubstituted —C═S, C═O, —C$_{1-6}$ alkyl, each optionally further substituted by C$_{1-6}$ alkyl, (for example, (—CH$_{2)n}$, wherein n is an integer from 0-3), —O, —S, —SO, SO$_2$, —NH or —CH═CH groups; and R$_7$ may be cycloalkyl, heterocycloalkyl, aryl, or heteroaryl, C$_{1-6}$ alkyl, cyclopropyl, cyclobutyl, cyclopentyl and cyclohexyl, wherein C$_{1-6}$ alkyl, cyclopropyl, cyclobutyl, cyclopentyl and cyclohexyl are each optionally substituted with one or more of fluoro, —OH, —NH$_2$, OCH$_3$, CH$_2$OCH$_3$, methylthio, ethylthio, butylthio, isobutylthio, mono/dialkylamino, and alkyl carbon bound to the N of —C(O)NHR$_8$, —C(S)NHR$_8$ or —S(O)$_2$NHR$_8$; wherein the alkyl chain(s) of OCH$_3$, CH$_2$OCH$_3$, methylthio, ethylthio, butylthio, isobutylthio, and mono/dialkylamino are each optionally independently substituted with one or more of fluoro, —OH, —NH$_2$, wherein any substitution of the alkyl chain carbon bound to O of alkoxy, S of thioalkyl or N of mono/dialkylamino is fluoro;

R8 combines with the nitrogen to which it is attached to form a 5-7 member heterocycloalkyl optionally substituted with one or more of fluoro, —OH, —NH2, $C_{1-6}$ alkyl, cyclopropyl, cyclobutyl, cyclopentyl, cyclohexyl, fluoro substituted $C_{1-6}$ alkyl, cyclopropyl, cyclobutyl, cyclopentyl and cyclohexyl, $OCH_3$, $CH_2OCH_3$, fluoro substituted $OCH_3$, $CH_2OCH_3$, methylthio, ethylthio, butylthio, isobutylthio, and fluoro-substituted methylthio, ethylthio, butylthio, isobutylthio;

$Y_9$ is —$C_{1-6}$ alkyl, $C_{3-7}$ cycloalkyl, —$C_{1-6}$-alkyl-$C_{3-7}$-cycloalkyl, —$C_{1-6}$ alkyl heteroaryl, —$C_{4-7}$ heterocycloalkyl, aryl or heteroaryl, each optionally independently substituted with one or more substituents selected from $R_4$; and $R_1$, $R_2$ and $R_3$ are each independently —H, halo, —CN, —$NH_2$, —$C_{1-6}$ aliphatic, —$OC_{1-6}$ aliphatic, —$C_{3-6}$ cycloaliphatic, —$OC_{3-6}$ cycloaliphatic, —$NH_2$, —NH-$COC_{1-6}$ alkyl, —$NHCO_{1-6}$ cycloalkyl, —$NHCO_{1-6}$ heterocycloalkyl, —$CONHC_{1-6}$ alkyl, —$CONH_{1-6}$ cycloalkyl, —$CONH_{1-6}$ heterocycloalkyl, —$NHC_{1-6}$ aliphatic, —$NHC_{3-6}$ cycloaliphatic, —$NHS(O)_2C_{1-6}$ aliphatic, —$NHS(O)_2C_{3-6}$ cycloaliphatic, —$NHS(O)_2$ phenyl, —$NHS(O)_2$ benzyl, —$NHS(O)_2$ heteroaryl, —$S(O)_2C_{1-6}$ aliphatic, —$S(O)_2C_{3-6}$ cycloaliphatic, —$S(O)_2$ phenyl, —$S(O)_2$ benzyl, —$S(O)_2$ heteroaryl, —$S(O)_2NHC_{1-6}$ aliphatic, —$S(O)_2NHC_{3-6}$ cycloaliphatic, —$S(O)_2NHphenyl$, —$S(O)_2NHbenzyl$, or —$S(O)_2NHheteroaryl$, wherein each of said heteroaryl of $R_1$, $R_2$ and $R_3$ is independently a 5- or 6-member ring having 1, 2, or 3 atoms selected from N, O, or S, and wherein said aliphatic, cycloaliphatic, phenyl, benzyl, or heteroaryl of $R_1$, $R_2$ and $R_3$ is each optionally substituted with 1, 2, or 3 $ZR_{10}$ groups;

wherein $ZR_{10}$ is halo, oxo, —$C_{1-2}$ alkyl, substituted $C_{1-2}$ alkyl with 1-3 —F or —Cl atoms, —$C_{3-6}$ cycloalkyl, —OH, —$OC_{1-2}$ alkyl, —$OC_{1-2}$ alkyl substituted with 1-3 —F or Cl atoms, —$C(O)C_{1-2}$ alkyl, or —$SC_{1-2}$ alkyl.

In one embodiment, the invention relates to a compound having a structure represented by a Formula I where $L_1$ is more specifically;

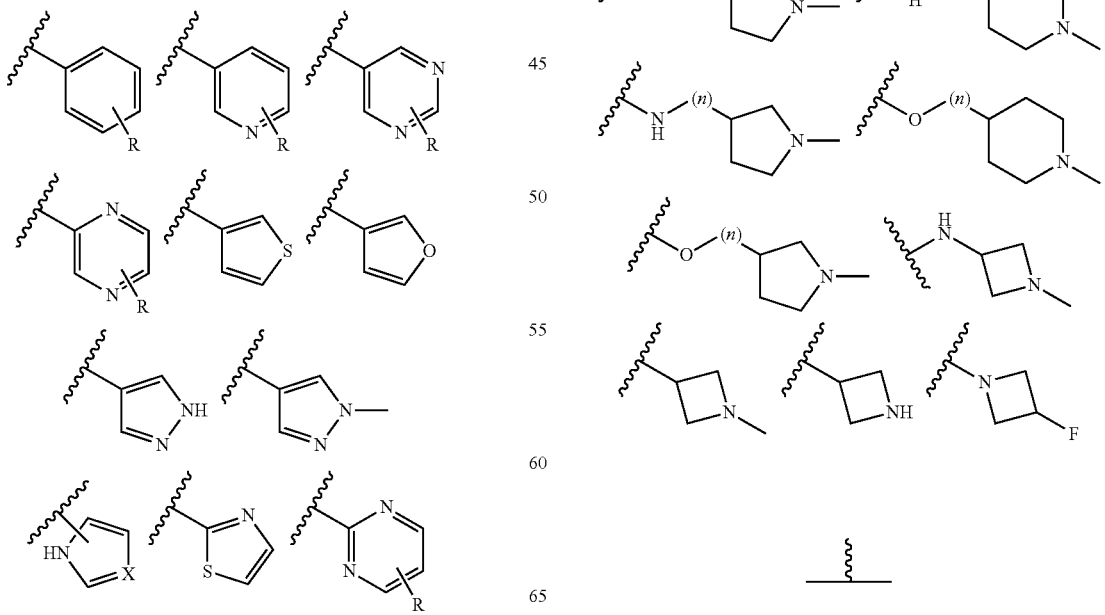

indicates the attachment to $L_1$ of Formula I;

wherein R is —H, halo, —CH$_3$, —CH$_2$CH$_3$, —OCH$_3$, —CF$_3$, OCF$_3$, —CN, —NH$_2$, —CH$_2$OCF$_2$, —COOH, OH, —CH$_2$OH, —SO$_2$CH$_3$, SO$_2$N(CH$_3$)$_2$, —COCH$_3$; and wherein "n" is an integer from 0 to 2.
In one embodiment R$_1$, R$_2$ and R$_3$ are each independently:
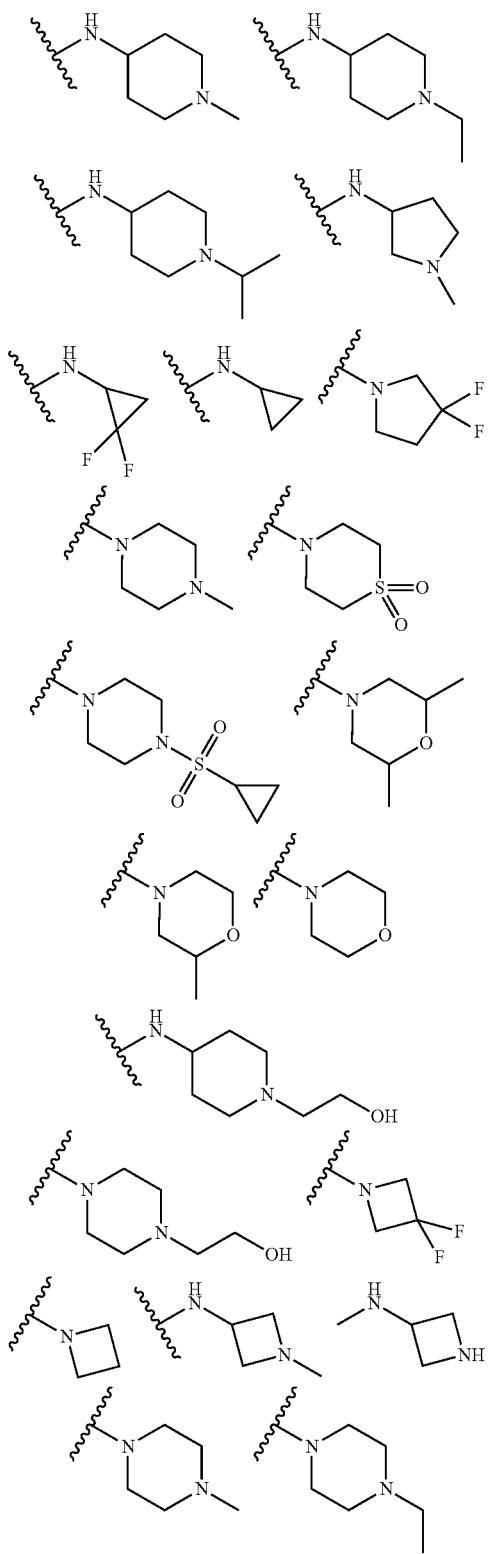
-continued
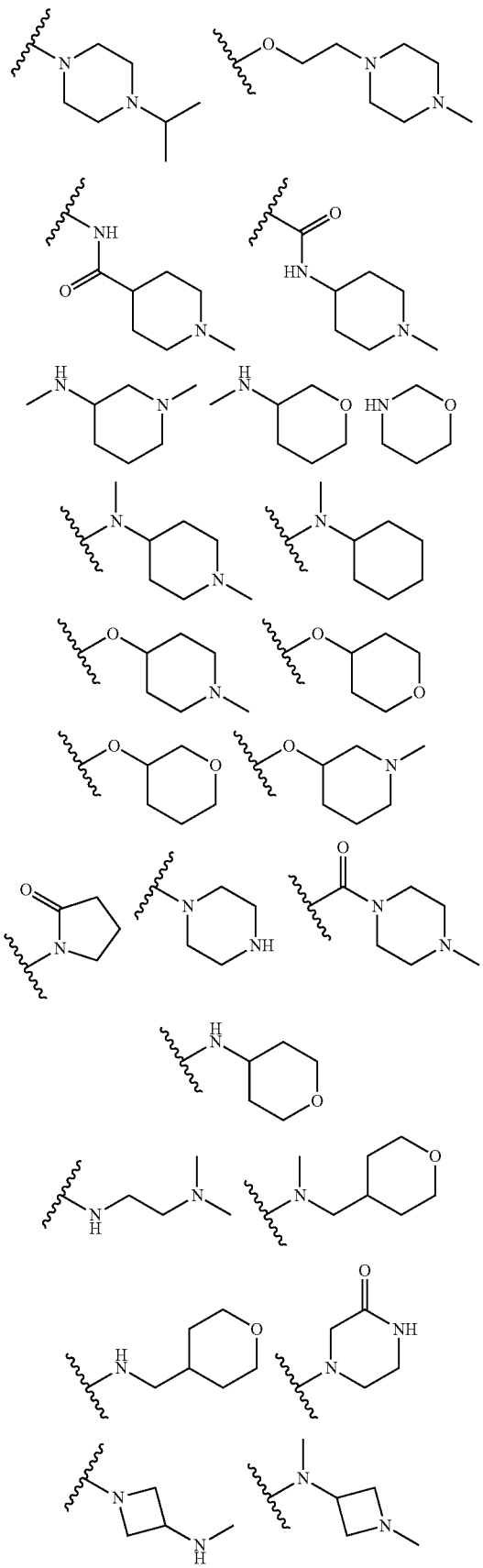

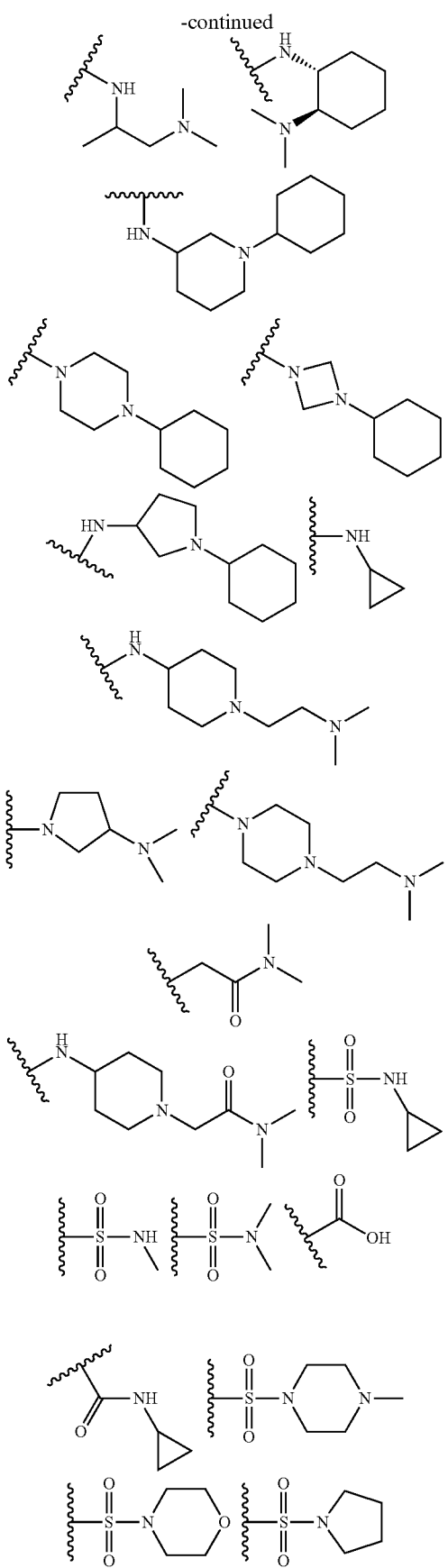

wherein

indicates the attachment to $R_1$, $R_2$ and $R_3$ of Formula I;

In another embodiment $R_1$, $R_2$ and $R_3$ at each occurrence is independently —H, optionally substituted lower alkyl, optionally substituted cycloalkyl, optionally substituted heterocycloalkyl, optionally substituted aryl, optionally substituted heteroaryl.

Lower alkyl as used herein means and includes $C_{1-6}$ alkyl including cyclopropyl, cyclobutyl, cyclopentyl and cyclohexyl.

In a further embodiment $R_1$, $R_2$ and $R_3$ are —NHCOC$_{1-6}$ alkyl, —NHCO$_{1-6}$ cycloalkyl, —NHCO$_{1-6}$ heterocycloalkyl, —CONHC$_{1-6}$ alkyl, —CONH$_{1-6}$ cycloalkyl, or —CONH$_{1-6}$ heterocycloalkyl.

In one embodiment $R_1$, $R_2$ and $R_3$ are each independently directly substituted by —H, —F, —Cl, —OCF$_3$, CF$_3$, —CH$_3$, —OCHF$_2$ or —OCH$_3$, wherein at least one of $R_1$ $R_2$ and $R_3$ is not hydrogen.

In a further embodiment $R_1$, $R_2$ and $R_3$ are each independently formula III and IV

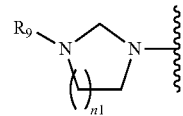

III

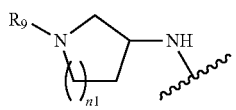

IV wherein

indicates the attachment to Formula I of one of $R_1$, $R_2$ and $R_3$ positions and
$R_9$ is —H, —CH$_3$, —CH(CH$_3$)$_2$, —CH$_2$CH$_3$, —CH$_2$CH$_2$—OH, or —C$_{3-6}$-alkyl.

In another embodiment, the invention relates to compound of formula VIII wherein

indicates attachment to $R_1$, $R_2$ and $R_3$ of Formula I respectively

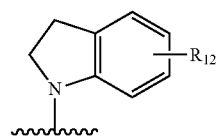

VIII wherein $R_{12}$ is —H, halo, —$CH_3$, —$CH_2CH_3$, —$OCH_3$, —$CF_3$, $OCF_3$, —CN, —$NH_2$, —$CH_2OCF_2$, —COOH, OH, —$CH_2OH$, —$SO_2CH_3$, $SO_2N(CH_3)_2$, or —$COCH_3$.

In another aspect, in Formula II,

Q is —NH, —O, —S, —$NCH_3$, —NHCO, —CONH, a direct bond, substituted or unsubstituted 6-membered aryl, heteroaryl, substituted or unsubstituted 5-membered aryl or heteroaryl, substituted or unsubstituted cycloalkyl, substituted or unsubstituted heterocycloalkyl, —$C(O)_n$, $S(O)n$, —O, —NH, substituted or unsubstituted C1-C5 alkylene, substituted or unsubstituted 2 to 5 membered heteroalkylene groups, where "n" is an integer from 0 to 2, or one of

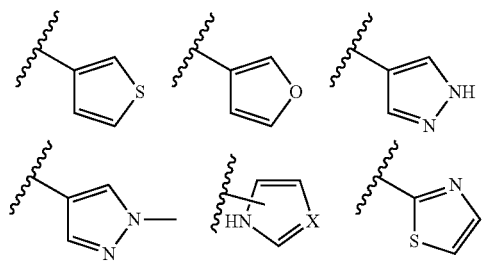

wherein

indicates the attachment to Q of Formula II;
$L_1$ is as described above for Formula I;
$L_2$ is a Formula V

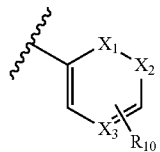

wherein $X_1$ is —N, —CH;
$X_2$ is —N, —CH and
$X_3$ is —N, —CH respectively

indicates the attachment to $L_2$ of Formula II;
$R_{10}$ is —H, halo, —CN, —$NH_2$, —$C_{1-6}$ aliphatic, —$OC_{1-6}$ aliphatic, —$C_{3-6}$ cycloaliphatic, —$OC_{3-6}$ cycloaliphatic, —$NH_2$, —$NHCOC_{1-6}$ alkyl, —$NHCO_{1-6}$ cycloalkyl, —$NHCO_{1-6}$ heterocycloalkyl, —$CONHC_{1-6}$ alkyl, —$CONH_{1-6}$ cycloalkyl, —$CONH_{1-6}$ heterocycloalkyl, —$NHC_{1-6}$ aliphatic, —$NHC_{3-6}$ cycloaliphatic, —$NHS(O)_2 C_{1-6}$ aliphatic, —$NHS(O)_2C_{3-6}$ cycloaliphatic, —$NHS(O)_2$ phenyl, —$NHS(O)_2$ benzyl, —$NHS(O)_2$ heteroaryl, —$S(O)_2 C_{1-6}$ aliphatic, —$S(O)_2C_{3-6}$ cycloaliphatic, —$S(O)_2$ phenyl, —$S(O)_2$ benzyl, —$S(O)_2$ heteroaryl, —$S(O)_2NHC_{1-6}$ aliphatic, —$S(O)_2NHC_{3-6}$ cycloaliphatic, —$S(O)_2NH$ phenyl, —$S(O)_2NH$ benzyl, or —$S(O)_2NH$ heteroaryl, wherein said heteroaryl of $R_{10}$ is a 5- or 6 member ring having 1, 2, or 3 atoms selected from N, O, or S, and wherein said aliphatic, cycloaliphatic, phenyl, benzyl, or heteroaryl of $R_{10}$ are each independently optionally substituted with 1, 2, or 3 $ZR_{10}$ groups;

wherein $ZR_{10}$ is halo, oxo, —$C_{1-2}$ alkyl, substituted $C_{1-2}$ alkyl with 1-3 —F, —Cl atoms, —$C_{3-6}$ cycloalkyl, —OH, —$OC_{1-2}$ alkyl, —$OC_{1-2}$ alkyl substituted with 1-3 —F, —Cl atoms, —$C(O)C_{1-2}$ alkyl, or —$SC_{1-2}$ alkyl.

In one embodiment $ZR_{10}$ is directly substituted by —H, —F, —Cl, —$OCF_3$, $CF_3$, —$CH_3$, —$OCHF_2$ or —$OCH_3$, wherein at least one of $R_{10}$ is not hydrogen;

In yet another embodiment, the invention comprises a compound of Formula II where $R_{10}$ is

wherein

indicates the attachment to $R_{10}$ of Formula V;
$X_3$ and $X_4$ are each independently either —N or —CH;
$Q_1$ is a bond, —$CH_2$, or —$CH_2$ and (n1) is 0, 1 or 2; and
$R_{11}$ is optionally substituted aryl, —$C_{5-6}$ aryl, —$C_{5-6}$ heteroaryl optionally substituted with one or more substituent —H, —$CH_3$, halo, —$OCH_3$, —$CF_3$, $OCF_3$, —CN, —$NH_2$, —$CH_2OCF_2$, —COOH, OH.

In another embodiment, $R_{10}$ is formula III or IV.

In another aspect, the invention relates to a compound of formula VII

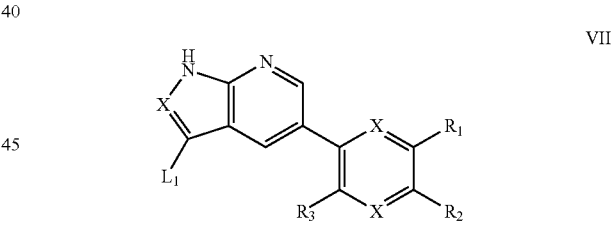

wherein X is independently —N or —CH, and $R_1$, $R_2$, $R_3$ and $L_1$ are as described in all embodiments above for Formula I.

The presently disclosed subject matter invention relates to the substituted 5-(pyrazin-2-yl)-1H-pyrazolo[3,4-b]pyridine, 5-(pyrazin-2-yl)-1H-pyrrolo[2,3-b]pyridine and pyrazolo[3,4-b]pyridine derivatives as protein kinase inhibitors. The invention is directed in one embodiment to pharmaceutical compositions containing the Formula I, II and VII compounds and methods of using the compounds, pharmaceutically acceptable salts thereof and/or compositions thereof to treat various types of diseases or conditions such as Parkinson's disease, Alzheimer's disease, Down's syndrome, Huntington's disease, other neurodegenerative diseases and or CNS diseases, cancer, metabolic and inflammatory disease.

In another embodiment methods are disclosed for the treatment of pain of neuropathic origin, pain of inflammatory origin, cardiovascular disease, rheumatoid arthritis, osteoarthritis, type 2 diabetes, metabolic syndrome and obesity.

The invention is also directed to methods of making the disclosed compounds and pharmaceuticals salts thereof.

In another embodiment methods employing the disclosed compounds of Formulae I, II and VII are disclosed for regulating protein kinases wherein said protein kinase i includes but is not limited to ABL1T315I (SEQ ID NO 1), ALK2 (SEQ ID NO 2), ARK5 (SEQ ID NO 64), Aurora A (SEQ ID NO 3), Aurora B (SEQ ID NO 4), Aurora C (SEQ ID NO 5), BRAF (SEQ ID NO 6), BRAF V599E (SEQ ID NO 7), CHK1 (SEQ ID NO 8), CHK2 (SEQ ID NO 9), C-KIT (SEQ ID NO 10), CLK1 (SEQ ID NO 11), CLK2 (SEQ ID NO 12), CLK3 (SEQ ID NO 13), CLK4 (SEQ ID NO 14), CSF1R (SEQ ID NO 15), DYRK1A (SEQ ID NO 16), DYRK1B (SEQ ID NO 17), DYRK2 (SEQ ID NO 18), DYRK3 (SEQ ID NO 19), DYRK4 (SEQ ID NO 20), FLT3 (SEQ ID NO 21), GSK3β (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), LRRK2 (SEQ ID NO 62), LRRK2 G2019S (SEQ ID NO 28), LRRK2 T1602S R1628P T2352M (SEQ ID NO 29), MAP4K4 (SEQ ID NO 30), MELK (SEQ ID NO 31), MLK (SEQ ID NO 32), PDGFR (SEQ ID NO 41), PKA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), RET, p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) or TRKC (SEQ ID NO 58) kinases. This set of kinases includes the mutations of these kinases and the use thereof in treating diseases and associated conditions with the regulation of the activity of these kinases.

In a further embodiment the invention relates to the novel therapeutic use of the disclosed compounds involved in the inhibition of protein kinases and the compounds used for treating the diseases associated with the protein kinase activities. They are useful as a drug for the treatment and/or prophylaxis of diseases such as cardiac disease, autoimmune disease, inflammatory disease, central nervous system disease, infectious disease, sepsis, septic shock and the like in mammals (e.g., cat, cattle, dog, horse, goat, monkey, human and the like), for example, ichorrhemia, endotoxin shock, exotoxin shock, heart failure, shock, hypotension, rheumatoid arthritis, arthrosteitis, gastritis, ulcerative colitis, peptic ulcer, stress gastric ulcer, Crohn's disease, autoimmune disease, tissue injury and rejection after organ transplantation, ischemic reperfusion disorder, acute coronary microvascular occlusion, shock vascular occlusion (disseminated intravascular coagulation syndrome (DIC) and the like), ischemic brain disorder, arteriosclerosis, pernicious anemia, Fanconi's anemia, sickle cell anemia, pancreatitis, nephrotic syndrome, nephritis, renal failure, insulin-dependent diabetes mellitus, non-insulin dependent diabetes mellitus, hepatic porphyria, alcoholism, Parkinson's disease, chronic leukemia, acute leukemia, tumor, myeloma, relief of side effects of anticancer agent, infant and adult respiratory distress syndrome, pulmonary emphysema, dementia, Alzheimer's disease, multiple sclerosis, vitamin E deficiency, aging, sunburn, myodystrophy, myocarditis, cardiac myopathy, myocardial infarction, sequela of myocardial infarction, osteoporosis, pneumonia, hepatitis, psoriasis, pain, cataract, influenza infection, malaria, human immunodeficiency virus (HIV) infection, radiation injury, burn, improved efficiency of in vitro fertilization, hypercalcemia, ankylosing spondylitis, osteopenia, bone Behcet's disease, osteomalacia, bone fracture, acute bacterial meningitis, *Helicobacter pylori* infection, invasive staphylococcal infection, tuberculosis, systemic mycotic infection, herpes simplex virus infection, varicella-zoster virus infection, human papilloma virus infection, acute virus encephalitis, encephalitis, asthma, atopic dermatitis, allergic rhinitis, reflux esophagitis, fever, hypercholesterolemia, hyperglyceridemia, hyperlipidemia, diabetic complications, diabetic nephropathy, diabetic neuropathy, diabetic retinopathy, gout, gastric atony, hemorrhoid, systemic lupus erythematodes, spinal trauma, agrypnia, schizophrenia, epilepsy, cirrhosis, hepatic failure, unstable angina pectoris, valvular disease of heart, thrombocytopenia derived from dialysis, acute ischemic stroke, acute brain thrombosis, cancer metastasis, bladder cancer, breast cancer, cervical cancer, colon cancer, stomach cancer, ovarian cancer, prostate cancer, small cell lung cancer, non-small cell lung cancer, malignant melanoma, Hodgkin's disease, non-Hodgkin's lymphoma and the like.

Methods of Preparation of Compounds

Examples

In certain embodiments, the Examples depicted below are compounds prepared according to general procedures given in the following sections. Although the synthetic methods and Schemes depict the syntheses of certain compounds of the present invention, the methods and other methods known to one of ordinary skill in the art can be applied to all the compounds of the genus, the genus sub-class and species of each of these compounds as described herein.

All aspects of this invention can be understood from the following Schemes. The following are exemplary and are not intended to limit the scope of the invention.

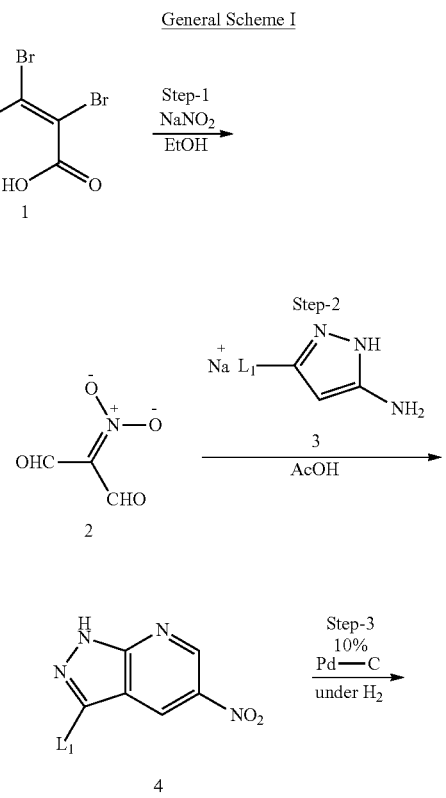

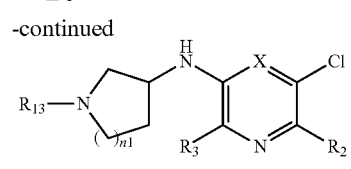

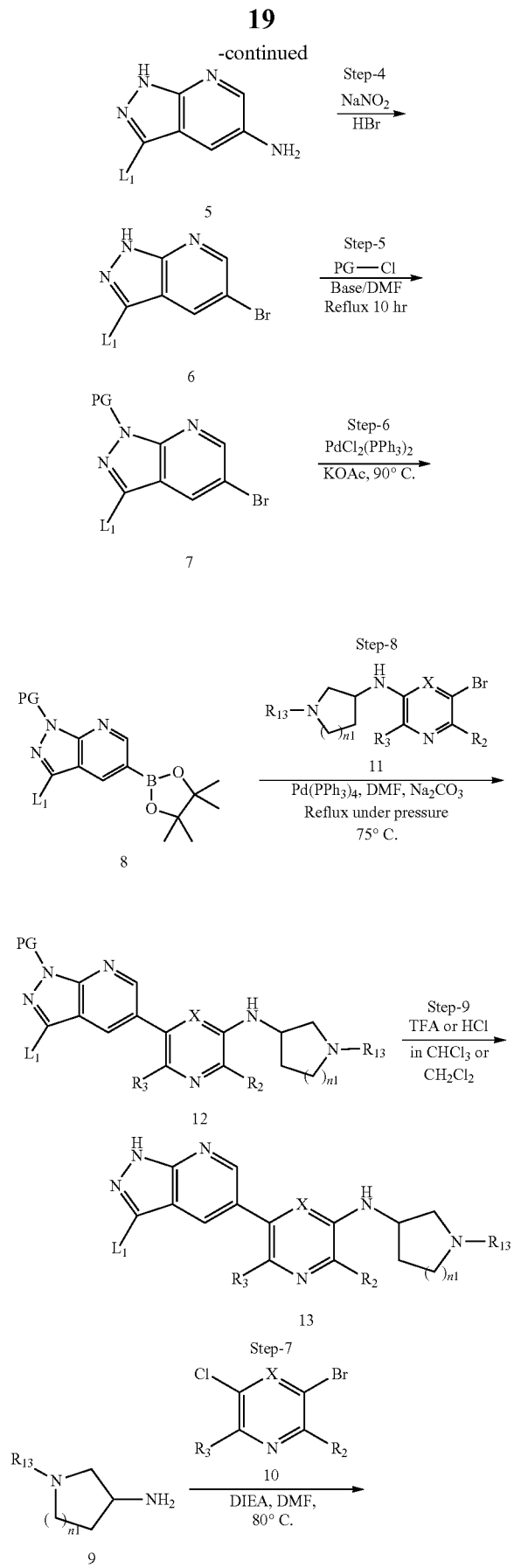

The synthesis of 5-(pyrazin-2-yl)-1H-pyrazolo[3,4-b]pyridine and pyrazolo[3,4-b]pyridine derivatives claimed in formula I and II will be apparent to the skilled artisan based on the methods of synthesis provided in the general Schemes 1 and 2. Some of these synthetic methods described here in the Examples section below may be employed and or expanded to obtain the compounds of Formula I and II.

$L_2$, $R_2$, $R_3$, $R_{13}$ and $()_{n1}$ are defined above. "PG" represents a protecting group, or protecting groups (PGs), and refers to a group used to protect a certain functional moiety to prevent it from participation in chemical reactions until the PG is removed. As is well known to the skilled artisan, these protective groups can be removed by acid, base, and hydrogenolysis conditions in the presence or absence of organic solvents. Such PGs employed in the above synthesis schemes include, but are not limited to p-methoxybenzyl (PMB), 2,4-dimethoxybenzyl, benzyl (Bn), 4-toluenesulfonyl chloride (tosyl chloride or TsCl), 2-(trimethylsilyl)ethoxymethyl chloride (SEM-Cl), trityl chloride (triphenylmethyl chloride), dimethoxytrityl, tetrahydropyranyl (THP), di-tert-butyl dicarbonate (tert-Boc), fluorenylmethyloxycarbonyl chloride (FMOC-Cl), tert-butyldimethylsilyl chloride (TBDMS-Cl), and carboxybenzyl (Cbz) groups.

Experimental Details and Examples

Melting points were determined in a MP-96 digital Polmon apparatus. $^1$H NMR and $^{13}$C NMR spectra were recorded at room temperature in $CDCl_3$ or DMSO-d6 at Jeol 400-MHz NMR spectrophotometer using solvent peaks for CDCl3: 7.27 and DMSO-d6 2.50 (D) as internal references. The assignment of chemical shifts is based on standard NMR experiments (1H, 13C). Mass spectra were recorded on a Shimadzu LCMS LC-210EV spectrometer with an API-ES ionization source. Jasco-FTIR-4100 was used to record the IR spectra. TLC analyses were performed on silica F254 and detection by UV light at 254 nm, or by spraying with phosphomolybdic-$H_2SO_4$ dyeing reagent, $KMnO_4$ or iodine. Column chromatography were performed on silica Gel 60 (230 mesh). Purifications and separations were performed on a standard silica flash chromatography system. The purity of the samples has been determined by HPLC for the % area peak corresponding to the retention of compound and elemental analysis for C, H, N and O was carried out using Perkin-Elmer 2400 elemental analyser and chloride analysis performed using calorimetric titration at the Intertek USA Inc., QTI.

ABBREVIATIONS

| | |
|---|---|
| $CH_2Cl_2$ or DCM | Dichloromethane |
| CHCl3 | Chloroform |
| DMF | N,N-Dimethylformamide |
| DME | 1,2-Dimethoxyethane |
| DMSO | Dimethylsulfoxide |
| THF | Tetrahydrofuran |
| MeOH | Methanol |

| | |
|---|---|
| EtOH | Ethanol |
| EtOAc | Ethylacetate |
| AcCN/MeCN | Acetonitrile |
| DIPEA | Diisopropylethylamine |
| IP | Isopropanol |
| $Na_2CO_3$ | Sodium Carbonate |
| $K_2CO_3$ | Potassium Carbonate |
| $Cs_2CO_3$ | Cesium Carbonate |
| TFA | Trifluoroacetic acid |
| RM | Reaction Mixture |
| RT | Room Temperature |
| SM | Starting Material |
| TLC | Thin Layer Chromatography |
| HPLC | High-Performance Liquid Chromatography |
| NMR | Nuclear Magnetic Resonance Spectrometer |
| MS | Mass Spectrometer |
| LCMS | Liquid Chromatography Mass Spectrometer |
| UV | Ultra Violet Spectrometer |
| PG | Protecting Group |
| DMSO-$d_6$ | Dimethylsulfoxide deuterated solvent |
| $CDCl_3$ | Chloroform deuterated solvent |
| $Pd(PPh_3)_4$ | Tetrakis(triphenylphosphine)palladium(0) |
| $Pd_2(dba)_3$ | Tris(dibenzylideneacetone)dipalladium(0) |
| Xantphos | 4,5-Bis(diphenylphosphino)-9,9-dimethylxanthene |
| ±BINAP | rac-2,2'-bis(diphenylphosphino)-1,1'-binaphthyl |
| $Pd(dppf)Cl_2 \cdot CH_2Cl_2$ | [1,1'-Bis(diphenylphosphino)ferrocene]dichloro-palladium(II) DCM |
| EDC HCl | N-Ethyl-N'-(3-dimethylaminopropyl)carbodiimide HCl |
| HOBT | 1-Hydroxybenzotriazole hydrate |

Example 1

Preparation of Sodium Nitromalonaldehyde

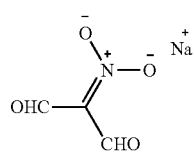

2

A stirred solution of mucobromic acid (51 g) in water (50 ml) was heated to 55° C., and then to it a hot solution of sodium nitrite in ethanol (50 ml) was added in about 45 minutes. The RM was then stirred at 50° C. for another 15 minutes. Then the RM was cooled to 0-5° C. and the reaction mixture was filtered. The wet cake was taken into 100 ml of EtOH and 25 ml of water heated to reflux for 15 minutes. The compound was filtered in hot condition. The unwanted yellow residue solid was discarded. The filtrate was cooled to 0° C.; solid was precipitated, the solid was filtered and dried under vacuum to afford the product as yellow solid, 8 g (Yield—26%) and was confirmed as the desired product 2, by IR and MR.

Example 2

3-Methyl-5-nitro-1H-pyrazole-[3,4-b]pyridine

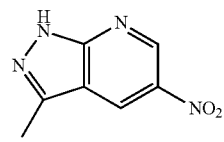

4

To a stirred solution of 3-Methyl-1H-pyrazole-5-amine (14 g, 144.15 mmol) in acetic acid (193.05 ml) and water (20 ml), sodium nitro-malonaldehyde (25 g, 158.56 mmol) was added at room temperature. The reaction mixture was heated to 100° C. for 12 h. TLC was checked. Then the reaction mass was cooled to RT and poured into water (200 ml). The precipitate was filtered and washed with water (200 ml) followed by diethyl ether (300 ml). It was dried to afford compound 4 as pale yellow solid; 14 g (Yield—55%). The product was confirmed by $^1$HNMR and MS spectrum analysis. $^1$H NMR (400 MHz, DMSO-$d_6$) δ: 14.1 (bs, 1H), 9.3 (s, 1H), 9.2 (s, 1H), 2.55 (s, 3H); (MS=178, [M+1]).

Example 3

3-Methyl-1H-pyrazolo[3,4-b]pyridin-5-amine

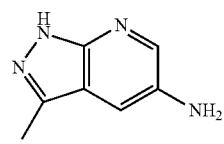

5

To a stirred solution 3-Methyl-5-nitro-1H-pyrazole[3,4-b] pyridine (14 g, 78.65 mmol) in ethanol, Pd/C (4 g) was added and the reaction mixture was stirred at RT for 5 h. Reaction mixture was filtered through a Celite bed. All volatiles were removed under reduced pressure to get the desired product as brown solid, 9 g (Yield—80%). The product 5 was confirmed by $^1$HNMR and MS spectrum analysis. $^1$H NMR (400 MHz, DMSO-$d_6$) δ: 12.62 (bs, 1H), 8 (s, 1H), 7.89 (s, 1H), 5.93 (s, 1H), 2.38 (s, 1H); MS=148, (M+1).

Example 4

5-Bromo-3-methyl-1H-pyrazolo-[3,4-b]pyridine

6

A stirred solution 3-Methyl-1H-pyrazole[3,4-b]pyridin-5-amine (200 mg, 1.35 mmol) in 48% hydrobromic acid (1.46 ml, 27.02 mmol) and water (1.5 ml) was cooled to −5° C. A solution of sodium nitrite (100 mg, 1.47 mmol) in water (0.5 ml) was added to this reaction mixture at 0° C. Then this reaction mixture was added to a suspension of copper (I) bromide (300 mg, 2.02 mmol) in 48% hydrobromic acid (0.4 ml) maintained at 0° C. Reaction mixture was stirred for 4 h at RT. Reaction mixture was extracted with ethyl acetate. The extract was washed with water (3×20 ml) and sodium carbonate solution (2×15 ml). The combined organic layer was dried over anhydrous sodium sulphate, filtered and concentrated. Purification was done by flash column over 230-400 mesh silica gel eluting with 25% ethyl acetate/petroleum ether to get the desired product 6, 100 mg (Yield—35%) as white solid. The product was confirmed by $^1$HNMR and MS spectrum analysis. $^1$H NMR (400 MHz, CDCl$_3$) δ: 10.92 (bs, 1H), 8.59 (s, 1H), 8.21 (s, 1H), 2.59 (s, 1H); MS: 212 (M+1).

Example 5

5-Bromo-1-(4-methoxybenzyl)-3-methyl-1H-pyrazolo[3,4-b]pyridine

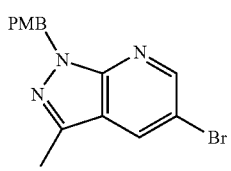

7

To a stirred solution of 5-Bromo-3-methyl-1H-pyrazolo[3,4-b]pyridine (1.3 g, 6.13 mmol) in DMF, sodium hydride (0.49 g, 12.24 mmol) was added portion wise at −5° C., then the reaction mixture was stirred at RT for 1 h. It was again cooled to 0° C., and 4-methoxybenzyl chloride slowly added and stirred overnight at RT. Reaction mixture was concentrated and diluted with water and extracted with ethyl acetate (3×50 ml). The combined extract was washed with water, dried over anhydrous sodium sulphate, filtered and concentrated. The product was purified by flash column chromatography over 230-400 mesh silica gel eluting with 20% ethyl acetate/petroleum ether to afford the desired product 7, 1 g (Yield: 55%) as white solid. The product was confirmed by $^1$HNMR and MS spectrum analysis. $^1$H NMR (400 MHz, CDCl$_3$) δ: 8.58 (s, 1H), 8.15 (s, 1H), 7.3 (d, 2H), 6.81 (d, 2H), 5.57 (s, 2H), 3.78 (s, 3H), 2.53 (s, 3H); MS: 333, (M+1), LCMS~87%.

Example 6

1-(4-methoxybenzyl)-3-methyl-5-(4,4,5,5-tetramethyl-1,3,2-dioxabolan-2-yl)-1H-pyrazolo[3,4-b]pyridine

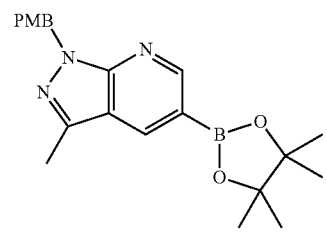

8

To a stirred solution of 5-Bromo-1-(4-methoxybenzyl)-3-methyl-1H-pyrazolo[3,4-b]pyridine (1 g, 3.003 mmol) in DMF, potassium acetate (883 mg, 19.009 mmol), followed by bis-(pinacolato-diborane) (1.5 g, 6.006 mmol) was added. The reaction mixture was degassed with argon for 30 min. Then bis-(triphenylphosphine)-palladium (II) chloride (210 mg, 0.30 mmol), was added and again degassed with argon for 30 minutes. Then RM was heated to 90° C., stirred overnight. Reaction mixture was concentrated under reduced pressure and the obtained residue was diluted with water and extracted with ethyl acetate (3×50 ml). The combined extract was washed with water, dried over anhydrous sodium sulphate, filtered and concentrated. Purification was done by flash column using 230-400 mesh silica gel and 20% ethyl acetate/petroleum ether to afford the desired product 8, 850 mg (Yield: 80%) as white solid. The product was confirmed by $^1$HNMR and LCMS spectrum analysis. $^1$H NMR (400 MHz, CDCl$_3$) δ: 1.38 (s, 9H), 2.55 (s, 3H), 3.77 (s, 3H), 5.59 (s, 2H), 6.8 (d, 2H), 7.29 (d, 2H); MS: 379 (M+1), LCMS~94%.

Example 7

6-bromo-N-(1-methylpiperidine-4-yl)pyrazine-2-amine

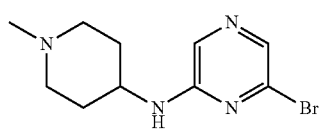

11

To a stirred solution of 2-bromo-6-chloro pyridine (500 mg, 2.58 mmol) in DMF, DIPEA was added followed by 4-amino-N-methylpiperidine and was heated at 80° C. overnight. Reaction mixture was concentrated and the residue was diluted with water and extracted with ethyl acetate (50 ml), the extract was washed with water. The organic layer was dried over anhydrous sodium sulphate, filtered and concentrated. Purification was done by flash column using 230-400 mesh silica gel eluting with 10% MeOH/DCM system to afford the desired product 11, 95 mg (Yield: 14%) as pale yellow solid. LCMS showed it as a mixture of Br/Cl isomers and so ¹HNMR was not clean, but characteristic peaks were present.

Example 8

6-(1-(4-methoxybenzyl)-3methyl-1H-pyrazolo[3,4-b]pyridine-5yl)-N-(1-methyl piperidine-4yl)pyrazin-2-amine

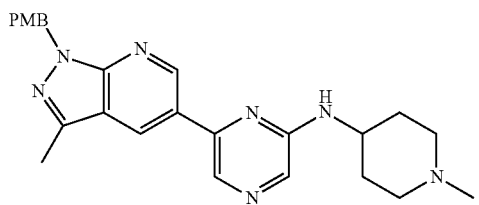

To a stirred solution of 1-(4-methoxybenzyl)-3-methyl-5-(4,4,5,5-tetramethyl-1,3,2-dioxabolan-2-yl)-1H-pyrazolo[3,4-b]pyridine (320 mg, 0.841 mmol) in EtOH (0.5 ml), water (0.5 ml) and DME, 6-bromo-N-(1-methylpiperidine-4-yl)pyrazine-2-amine (190 mg, 0.725 mmol) and sodium carbonate (163 mg, 1.54 mmol) were added. Then the reaction mixture was degassed with argon for 30 min. Tetrakis(triphenylphosphine)palladium (81 mg, 0.841 mmol) was added to this reaction mixture, which was degassed with argon for another 10 min. Then it was heated at 90° C. overnight. Reaction mixture was concentrated and diluted with water and extracted with ethyl acetate. The extract was dried over anhydrous sodium sulphate, filtered and concentrated. Purification was done by flash column using 230-400 mesh silica gel eluting with 10% MeOH/DCM system to afford the desired product 12, 35 mg (Yield: 10%) as dark brown solid. The product was confirmed by ¹HNMR (not clean but characteristic peaks were present) and LCMS (92%) spectrum analysis.

Example 9

6-(3methyl-1H-pyrazolo[3,4-b]pyridine-5yl)-N-(1-methylpiperidine-4yl) pyrazin-2-amine

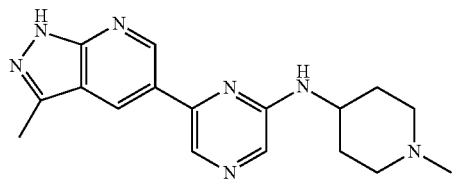

A stirred solution of 1-(4-methoxybenzyl)-3methyl-5-(4,4,5,5-tetramethyl-1,3,2-dioxabolan-2-yl)-1H-pyrazolo[3,4-b]pyridine (35 mg) in DCM (1 ml) was cooled to 0° C. Then TFA (4 ml) was added to it and the mixture was stirred overnight at 60° C. TLC was checked. Reaction mixture was concentrated and basified with saturated sodium bicarbonate solution, and again concentrated. The crude mass was purified by flash column chromatography over basic alumina using 1-3% MeOH/DCM system to afford the desired product 13 as pale yellow solid, 14 mg (Yield: 56%). The product was confirmed by ¹HNMR and MS spectrum analysis. ¹H NMR (400 MHz, CDCl₃) δ: 11.85 (bs, 1H), 9.2 (s, 1H), 8.59 (s, 1H), 8.38 (s, 1H), 7.86 (s, 1H), 7.26 (s, 1H), 4.77 (d, 1H), 3.85 (bs, 1H), 2.91 (d, 2H), 2.67 (s, 3H), 2.36 (s, 3H), 2.32 (t, 2H), 2.15 (d, 2H), 1.66 (m, 2H); MS: 324.10 (M+1), LCMS~98.99%.

Example 10

6-chloro-N-(1-methylpiperidin-4-yl)pyrazin-2-amine

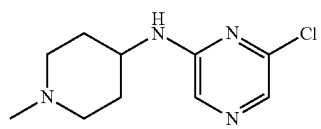

To a stirred solution of 2-bromo-6-chloro pyridine (500 mg, 2.58 mmol) in DMF, DIPEA was added followed by 4-amino-N-methylpiperidine and was heated at 80° C. overnight. Reaction mixture was concentrated and the residue was diluted with water and extracted with ethyl acetate (50 ml), the extract was washed with water. The organic layer was dried over anhydrous sodium sulphate, filtered and concentrated. Purification was done by flash column using 230-400 mesh silica gel eluting with 10% MeOH/DCM system to afford the desired product 11, 95 mg (Yield: 14%) as pale yellow solid. LCMS confirms the mixture of Br/Cl isomers, majorly compound 11. ¹H NMR (400 MHz, DMSO-d₆) δ: 8.41 (s, 1H), 7.95 (s, 1H), 3.70 (s, 4H), 2.89 (s, 2H), 2.73 (bs, 2H), 2.01 (s, 1H), 1.98 (bs, 3H); MS: 226.8 (M+1).

Reaction Scheme 2

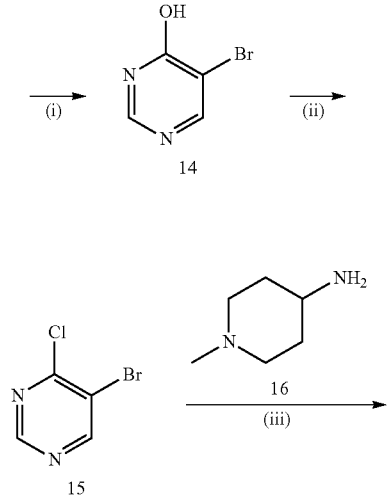

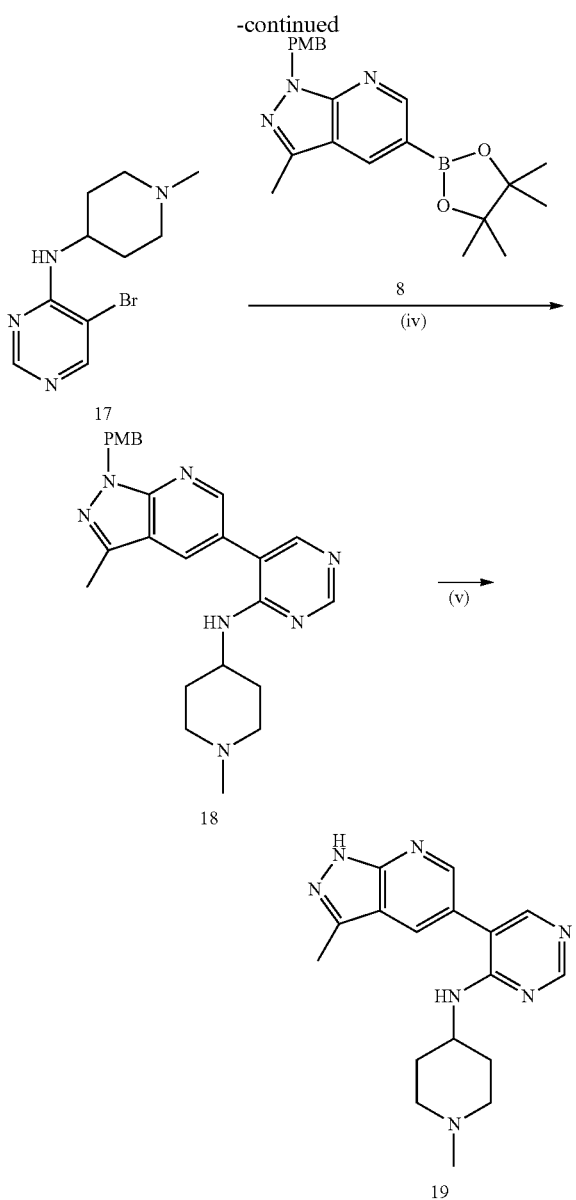

Reagents:
(i) Br₂, AcOH (ii) POCl₃ (iii) DIPEA, 100° C. (iv) Pd(PPh₃)₄, EtOH, Na₂CO₃, 70° C. (v) TEA, DCM 80° C.

Example 11

5-bromopyrimidin-4-ol

To a stirred solution pyridine-4-ol (500 mg, 5.208 mmol) in acetic acid maintained at 4-6° C., bromine was slowly added. The cooling mixture was removed and stirred at RT for 3 h. TLC was checked. Reaction mixture was concentrated and the residue was washed with ether to get the desired product 14, as brown solid, 650 mg (Yield—72%). The product was confirmed by ¹HNMR and MS spectrum analysis. ¹H NMR (400 MHz, CDCl₃) δ: 9.45-9.7 (bs, 3H), 8.29 (s, 1H), 8.23 (s, 1H); MS-174 (M+1).

Example 12

5-bromo-4-chloropyrimidine

A stirred solution of 5-bromopyrimidin-4-ol (650 mg, 3.73 mmol) in POCl₃ (in excess) was heated at 100° C. overnight. The reaction mixture was cooled and concentrated under reduced pressure. Crude product was dissolved in ethyl acetate and this mixture was slowly poured into saturated sodium bicarbonate solution. The ethyl acetate layer was separated and washed with brine solution, and dried over anhydrous sodium sulphate and concentrated to get the desired product as yellow solid, 300 mg (Yield—43%). The product was confirmed by ¹HNMR and MS spectrum analysis. ¹H NMR (400 MHz, CDCl₃) δ: 8.86 (s, 1H), 8.82 (s, 1H); MS-192 (M+1).

Example 13

5-bromo-N-(1-methylpiperidin-4-yl)pyridine-4-amine

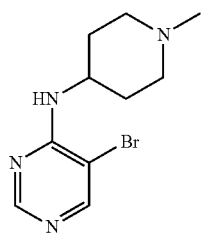

To a stirred solution of 5-bromo-4-chloropyrimidine (300 mg, 1.562 mmol) in DMF, DIPEA (400 mg, 3.124 mmol) was added followed by 1-methylpiperidine-4-amine (0.193 ml, 1.562 mmol) and the reaction mixture was heated at 80° C. overnight. TLC showed absence SM, and then reaction mixture was concentrated. The crude product was purified by flash column chromatography over 230-400 mesh silica gel and using a mixture of 30% EtOAc/petroleum ether to afford the desired product 17, 180 mg (Yield: 40%) as yellow solid. The product was confirmed by ¹HNMR and MS spectrum analysis. ¹H NMR (400 MHz, CDCl₃) δ: 8.4 (s, 1H), 8.35 (s, 1H), 6.81 (d, 1H), 4.95 (m, 1H), 2.78 (d, 2H), 2.17 (s, 3H), 1.95 (t, 2H), 1.6-1.8 (m, 4H); MS-270 (M+1).

Example 14

5-(1-(4-methoxybenzyl)-3methyl-1H-pyrazolo[3,4-b]pyridine-5yl)-N-(1-methyl-piperidine-4yl) pyrazin-4-amine

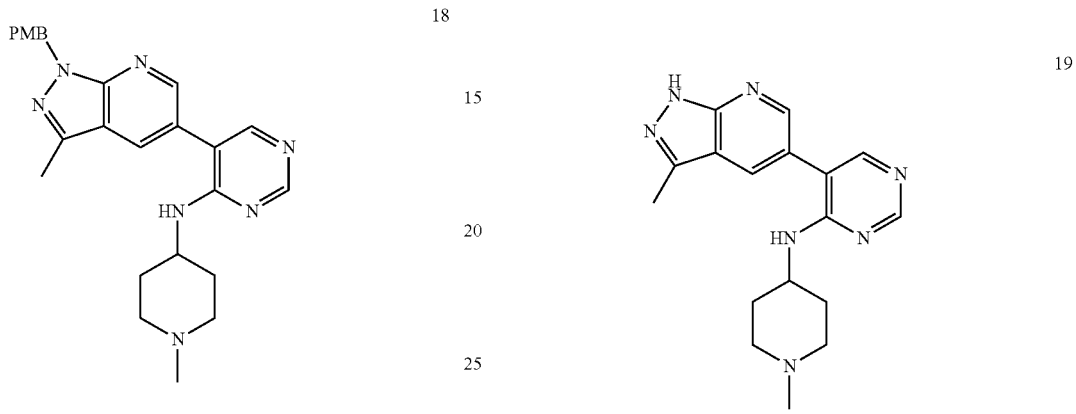

18

To a stirred solution of 1-(4-methoxybenzyl)-3-methyl-5-(4,4,5,5-tetramethyl-1,3,2-dioxabolan-2-yl)-1H-pyrazolo[3,4-b]pyridine (106 mg, 0.138 mmol) in toluene (2 ml), 5-bromo-N-(1-methylpiperid-4-yl)pyridine-4-amine (50 mg, 0.095 mmol), 2M sodium carbonate (0.2 ml), and EtOH (0.5 ml) were added. The reaction mixture was degassed with argon for 30 minutes. Tetrakis(triphenylphosphine)palladium (81 mg, 0.841 mmol) was added, degassed for another 30 minutes. Then RM was heated at 90° C. overnight. TLC was checked. Reaction mixture was concentrated and the residue was diluted with water and extracted with ethyl acetate (50 ml). The extract was washed with water and concentrated. The crude product was purified by flash column chromatography over 230-400 mesh silica gel using 10% MeOH/DCM system to afford the desired product 18, 30 mg (Yield: 25%) as white solid. The product was confirmed by ¹HNMR and LCMS spectrum analysis. ¹H NMR (400 MHz, CDCl₃) δ: 8.63 (s, 1H), 8.45 (s, 1H), 8.18 (s, 1H), 7.95 (s, 1H), 7.38 (d, 2H), 6.81 (d, 2H), 5.6 (s, 2H), 4.65 (bs, 1H), 4.17 (bs, 1H), 3.79 (s, 3H), 3.43 (s, 3H), 2.95 (bs, 1H), 2.59 (s, 3H), 22.22-2.45 (m, 5H), 2.13 (m, 2H); MS:443, (M+1), LCMS~95%.

Example 15

5-(3methyl-1H-pyrazolo[3,4-b]pyridine-5yl)-N-(1-methylpiperidine-4yl) pyrimidin-4-amine

19

To a stirred solution of 5-(1-(4-methoxybenzyl)-3methyl-1H-pyrazolo[3,4-b]pyridine-5yl)-N-(1-methylpiperidine-4yl)pyrazin-4-amine (150 mg) in DCM (2 ml) at 0° C., TFA (10 ml) was added and then heated at 60° C. overnight. TLC was checked. Reaction mixture was concentrated and basified with saturated sodium bicarbonate solution and again concentrated. The crude mass was purified by flash column chromatography over basic alumina using 1-3% MeOH/DCM as eluent to afford the desired product 19: 34 mg (Yield: 31.19%) as pale yellow solid. The product was confirmed by ¹HNMR and MS spectrum analysis. ¹H NMR (400 MHz, CDCl₃) δ: 10.64 (bs, 1H), 8.63 (s, 1H), 8.50 (s, 1H), 8.06 (s, 1H0, 8.03 (s, 1H), 4.67 (d, 1H), 4.075 (m, 1H), 2.89 (m, 2H), 2.61 (s, 3H), 2.29 (s, 3H), 2.24 (m, 2H), 2.04 (d, 2H); Ms: 324.31 (M+1), LCMS~99.39%; HPLC~97.49%.

Reaction Scheme 3

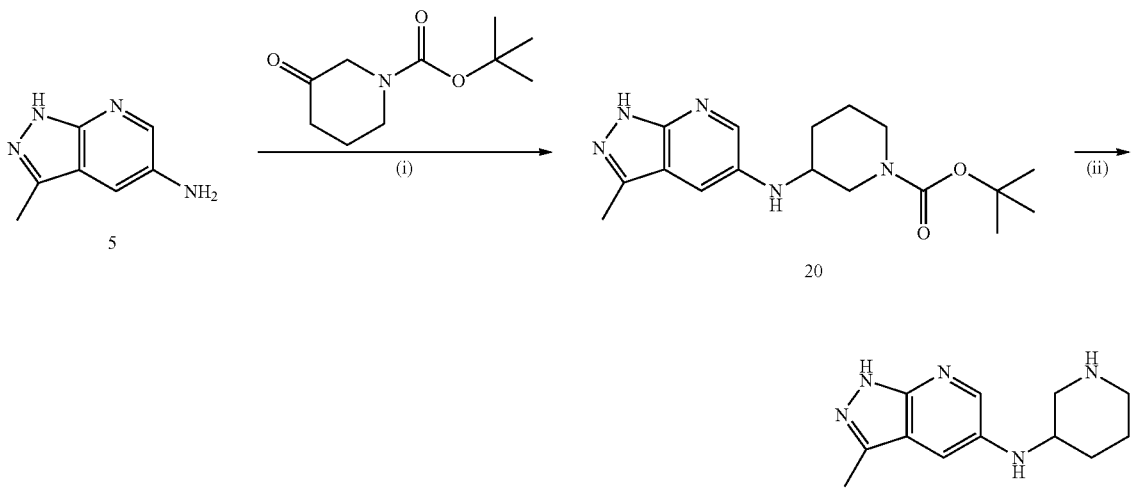

-continued
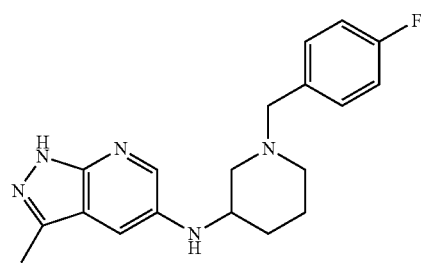
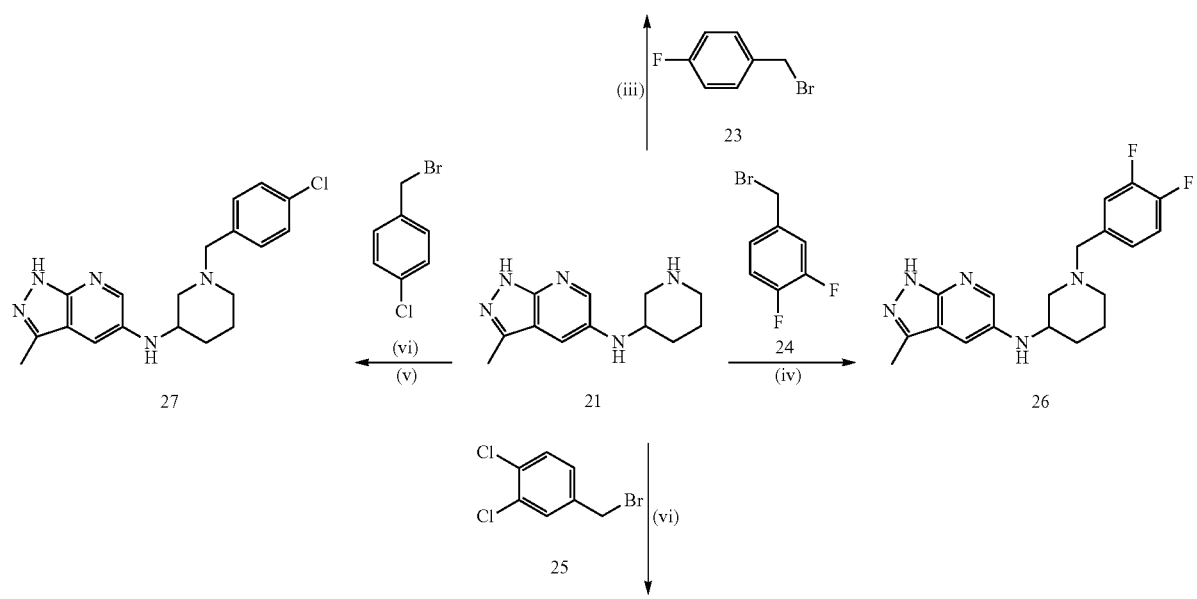

Reagents:
(i) EtOH, AcOH (4 drops), NaBH₃CN, rt, (ii, iii, iv) TFA, CH₂Cl₂

Example 16

Tetra-butyl 3-(3-methyl-1H-pyrazolo[3,4-b]pyridine-5-ylamino)piperidine-1-carboxylate

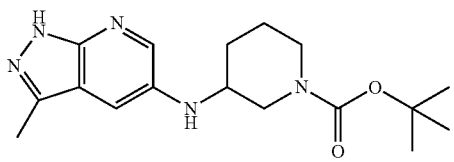

20

To a stirred solution of 3-Methyl-1H-pyrazole[3,4-b]pyridin-5-amine (500 mg, 3.3 mmol) in EtOH (50 ml), tert-butyl 3-oxopiperidine-1-carboxylate (74 mg, 1.1 mmol) was added and reaction mass was cooled to 0° C. Acetic acid (0.018 ml, 0.33 mmol) was added after which reaction mixture was stirred for 20 minutes. Sodium cyanoborohydride (42 mg, 0.66 mmol) was added and stirred for 12 h at RT. TLC showed absence of SM. The reaction mixture was quenched with brine solution and extracted with ethyl acetate. The extract was washed with water and concentrated. Organic layer was dried over anhydrous sodium sulphate, dried and concentrated. Product was purified by flash column chromatography over 230-400 mesh silica gel using 2-5% MeOH/DCM as eluent to afford the desired product 20, 500 mg (Yield: 45%) as white solid. The product was confirmed by ¹HNMR and MS spectrum analysis. ¹H NMR (400 MHz, CDCl₃) δ: 8.13 (s, 1H), 7.19 (s, 1H), 3.95 (m, 1H), 3.25 (m, 1H), 3.43 (m, 1H), 3-3.25 (m, 2H), 2.52 (s, 3H), 2.15 (m. 1H), 1.78 (m, 1H), 1.6 (m, 2H), 1.49 (s, 9H); Ms-331 (M-56), LCMS~97%.

Example 17

3-methyl-N-(piperidine-3yl)-1H-pyrazolo[3,4-b]pyridine-5-amine

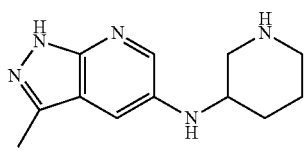

21

To a stirred solution of tert-butyl 3-(3-methyl-1H-pyrazolo[3,4-b]pyridine-5-ylamino)piperidine-1-carboxylate (100 mg, 0.3 mmol) in DCM (5 ml) at 0° C., was added TFA (0.3 ml), and then reaction mixture was stirred for 2 h at RT. TLC showed absence of SM. The reaction mixture was concentrated and basified with saturated sodium bicarbonate solution, and extracted with ethyl acetate (3×25 mL). The combined organic layer was dried over anhydrous sodium sulphate, filtered and concentrated. The product was purified by flash column chromatography over basic alumina using 1-5% MeOH/DCM as eluent to afford the desired product 21, 60 mg (Yield: 86%) as white solid. The product was confirmed by ¹HNMR and MS spectrum analysis. ¹H NMR (400 MHz, CDCl₃) δ: 12.7 (d, 1H), 8.12 (s, 1H), 7.54 (s, 1H), 5.4 (m, 1H), 4.09 (m, 1H), 3.15 (m, 2H), 2.9 (dd, 1H), 2.6 (m, 1H), 2.45 (s, 3H), 1.95 (m, 1H), 1.72 (m, 1H), 1.05 (m, 1H), 1.4 (m, 1H), 1.35 (m, 1H); Ms: 231 (M+1), LCMS~two peaks of same mass~50%+38%.

Example 18

N-(1-(4-fluorobenzyl)piperidine-3-yl)-3-methyl-1H-pyrazolo[3,4-b]pyridine-5-amine

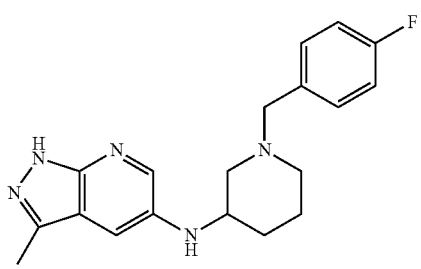

22

To a suspension of 3-methyl-N-(piperidine-3-yl)-1H-pyrazolo[3,4-b]pyridine-5-amine (60 mg, 0.259 mmol) in DCM (5 ml), TEA (0.04 ml, 0.31 mmol) was added and the reaction mixture was stirred for 20 min. Then to it 1-(bromomethyl)-4-fluorobenzene (58 mg, 0.311 mmol) was added and then the reaction mixture was stirred for 2 h at RT. TLC showed absence of SM. Reaction mixture was concentrated and the residue was purified by flash column chromatography over 230-400 mesh silica gel using 5-10% MeOH/DCM as eluent to afford the desired product 22, 70 mg (Yield: 28%) as pale yellow solid. The product was confirmed by ¹HNMR and MS spectrum analysis. ¹H NMR (400 MHz, CDCl₃) δ: 9.95 (bs, 1H), 8.05 (s, 1H), 2.27 (t, 2H), 6.99 (t, 2H), 4.11 (bs, 1H), 3.58-3.49 (m, 4H), 2.71 (m, 1H), 3.49 (s, 3H), 3.43 (m, 2H), 1.73 (m, 2H), 1.56 (bs, 2H); Ms: 339 (M+1), LCMS~99.5%; HPLC~98.27%.

Example 19

N-(1-(3,4-difluorobenzylpiperidin-3-yl)-3-methyl-1H-pyrazolo[3,4-b]pyridid-5-amine

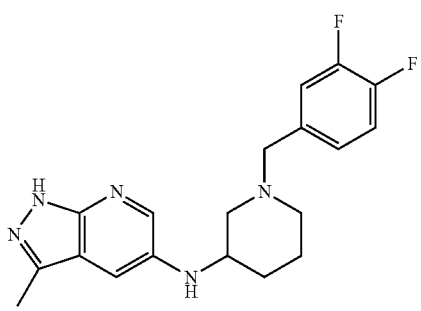

26

To a suspension of 3-methyl-N-(piperidine-3yl)-1H-pyrazolo[3,4-b]pyridine-5-amine (60 mg, 0.259 mmol) in DCM (5 ml) at rt, TEA (0.04 ml, 0.311 mmol) was added and the reaction mixture was stirred for 20 min. Then to this RM 1-(bromomethyl)-4-fluorobenzene (58 mg, 0.311 mmol) was added and was stirred for another 2 h at RT. TLC showed absence of SM. The reaction mixture was concentrated and was purified by flash column chromatography using 230-400 silica gel and 5-10% MeOH/DCM system to afford the desired product 26, 70 mg (Yield: 28%) as pale yellow solid. The product was confirmed by $^1$HNMR and MS spectrum analysis. $^1$H NMR (400 MHz, CDCl$_3$) δ: 9.83 (bs, 1H), 8.06 (d, 1H), 7.2-6.99 (m, 4H), 4.016 (m, 1H), 3.61 (m, 1H), 3.49-3.46 (m, 4H), 2.72 (m, 1H), 2.5-2.38 (m, 6H), 1.75 (m, 2H), 1.56 (m, 1H); Ms-357 (M+1), LCMS~98.83%; HPLC~98.5%.

Example 20

N-(1-(4-Chlorobenzyl)piperidin-3-yl)-3-methyl-1H-pyrazolo[3,4-b]pyridid-5-amine

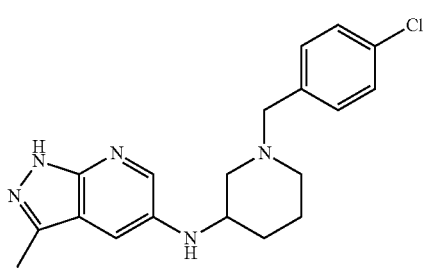

To a suspension of 3-methyl-1N-(piperidine-3yl)-1H-pyrazolo[3,4-b]pyridine-5-amine (70 mg, 0.262 mmol) in DCM (5 ml) at RT, TEA (0.052 ml, 0.386 mmol) was added and the reaction mixture was stirred for 20 min. Then to this RM 4-Chlorobenzylbromide (80 mg, 0.39 mmol) was added and was stirred for another 2 h at RT. TLC showed absence of SM. The reaction mixture was concentrated and was purified by flash column chromatography using 230-400 silica gel and 5-10% MeOH/DCM system to afford the desired product 27, 30 mg (Yield: 29%) as pale yellow solid. The product was confirmed by $^1$HNMR and MS spectrum analysis. $^1$H NMR (400 MHz, CDCl$_3$) δ: 10.25-10.1 (bs, 1H), 8.068 (s, 1H), 7.304-7.26 (m, 4H), 7.03 (s, 1H), 3.9-4.05 (bs, 1H), 3.58-3.49 (d, 3H), 2.7 (m, 1H), 2.5-2.3 (m, 6H), 1.7-1.6 (m, 4H); Ms: 357 (M+1), LCMS~98.8%, HPLC~98.48%.

Example 21

N-(1-(3,4-Chlorobenzyl)piperidin-3-yl)-3-methyl-1H-pyrazolo[3,4-b]pyridid-5-amine

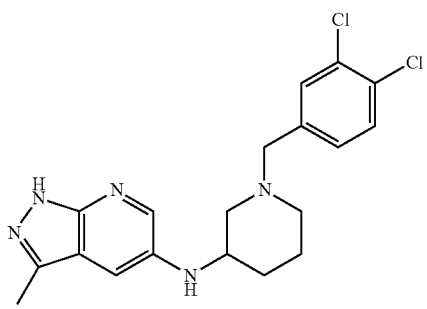

To a suspension of 3-methyl-1N-(piperidine-3yl)-1H-pyrazolo[3,4-b]pyridine-5-amine (75 mg, 0.324 mmol) in DCM (15 ml) at rt, TEA (0.056 ml, 0.422 mmol) was added and the reaction mixture was stirred for 20 min. Then to this RM 3,4-Dichlorobenzylbromide (101 mg, 0.422 mmol) was added and was stirred for another 2 h at RT. TLC showed absence of SM. The reaction mixture was concentrated and was purified by flash column chromatography over 230-400 silica gel using 5-10% MeOH/DCM as eluent to afford the desired product 28, 36 mg (Yield: 28%) as pale yellow solid. The product was confirmed by $^1$HNMR and MS spectrum analysis. $^1$H NMR (400 MHz, CDCl$_3$) δ: 10.1 (bs, 1H), 8.08 (d, 1H), 7.44 (bs, 1H), 7.38 (d, 1H), 7.17 (d, 1H), 7.04 (d, 1H), 4-3.9 (bs, 1H), 3.75 (d, 5H), 3.59 (m, 1H), 3.46 (s, 2H), 2.71 (m, 1H), 2.5 (s, 3H), 2.3 (m, 3H), 1.77 (m, 2H); Ms: 389, (M+1), LCMS~97%; HPLC~97%.

Reaction Scheme 4

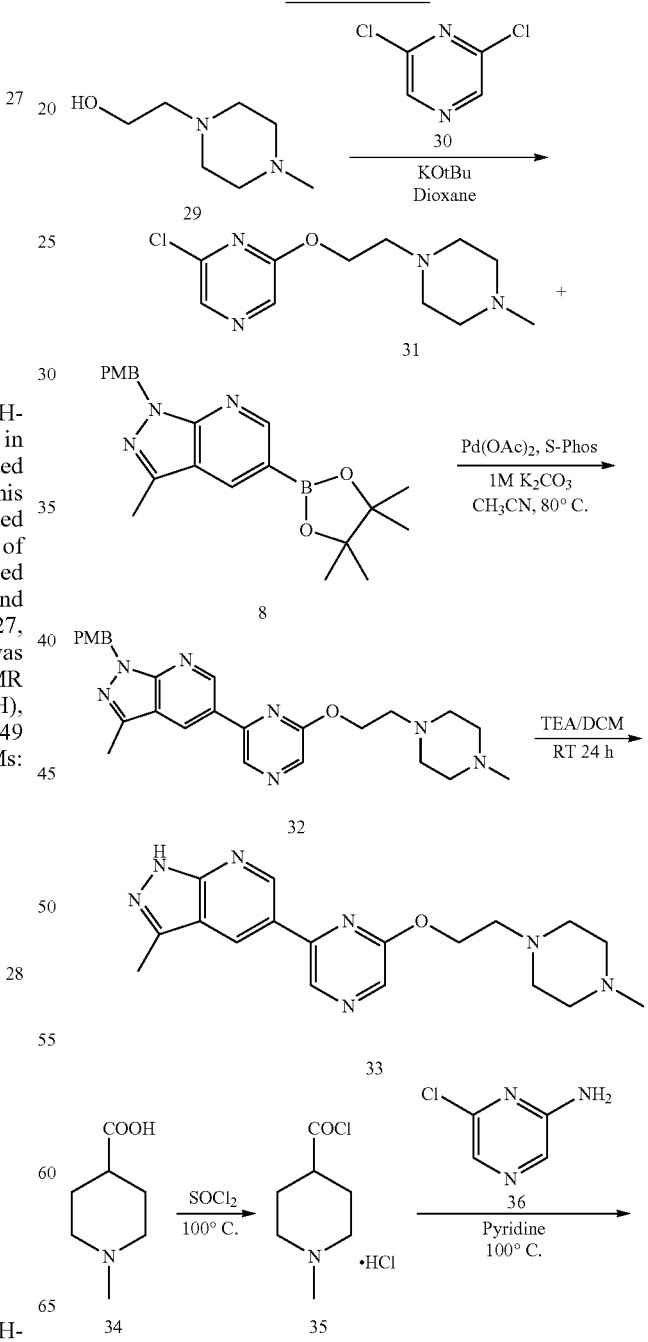

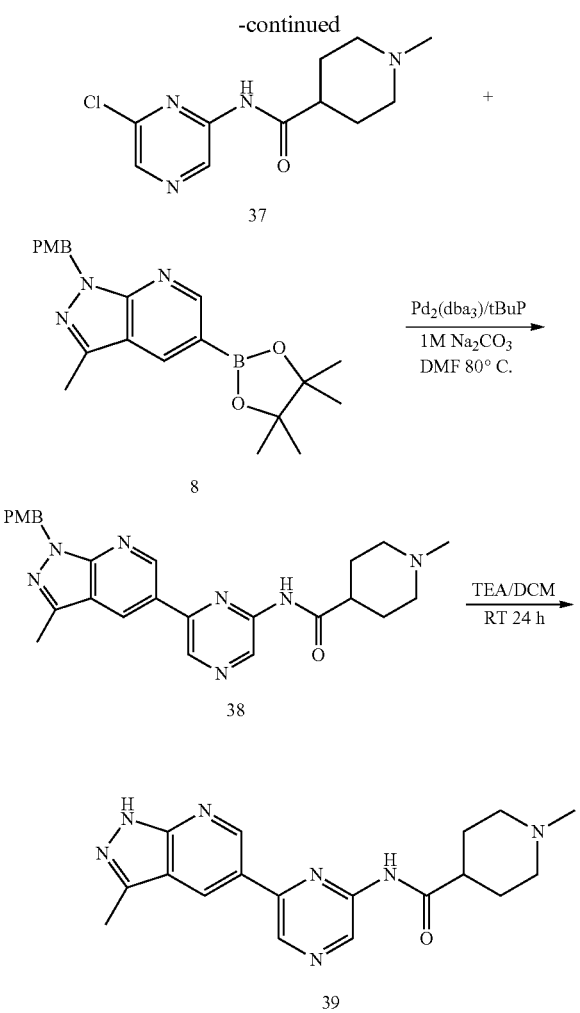

Example 22

2-Chloro-6-(2-(4-methylpiperazin-1-yl)methoxy)pyridine

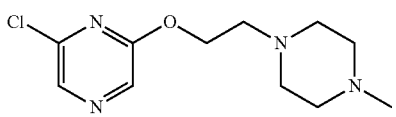

To a suspension of 2-(4-methylpiperazine-1-yl)ethanol (50 mg, 0.347 mmol) in dioxane (3 ml) at 0° C., KO'Bu (50 mg, 0.347 mmol) was added and the reaction mixture was stirred for 10 min. Ice bath was removed and the reaction mixture was allowed to attain room temperature. The mixture was again cooled to 0° C. and 2,6-Dichloropyrazine (200 mg, 1.04 mmol) was added. Reaction mixture was allowed to stir at RT for 24 h after which it was concentrated and was purified by flash column chromatography over 230-400 silica gel using 5-8% MeOH/DCM system to afford the desired product 31, 30 mg (Yield: 35%) as brown gummy liquid. The product was confirmed by ¹HNMR (not clean but characteristic peaks were present); MS: 256, (M+1), LCMS~90%.

Example 23

5-(6-(2-(3-methylimidazolidin-1-yl)ethoxy)pyarazin-2-yl)-1-(4-methoxy benzyl)-3-methyl-1H-pyrazolo[3,4-b]pyridine

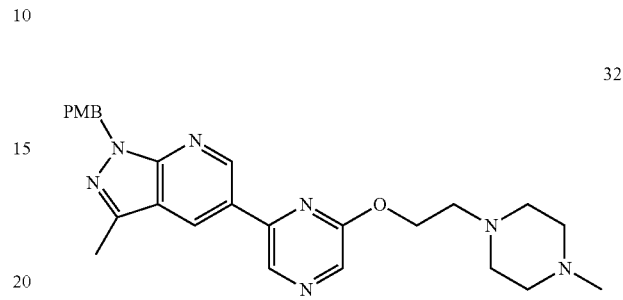

To a solution of 2-Chloro-6-(2-(4-methylpiperazin-1-yl)methoxy)pyridine (519 mg, 1.36 mmol) in acetonitrile, 1-(4-methoxybenzyl)-3methyl-5-(4,4,5,5-tetramethyl-1,3,2-dioxabolan-2-yl)-1H-pyrazolo[3,4-b]pyridine (350 mg, 1.36 mmol) and 1M solution $K_2CO_3$ (2.46 mL, 2.46 mmol) was added. The reaction mixture was degassed for 20 min with nitrogen. Palladium acetate (10 mg, 0.041 mmol) and S-Phos (45 mg, 0.1 mmol) were added and reaction mixture was again degassed for 10 minutes and heated to 80° C. and maintained overnight. The reaction mixture was concentrated and purified by flash column by loading on a glass column packed with 230-400 mesh silica gel and eluted with 2-8% methanol/DCM. The product 32 was obtained as brown solid, 230 mg (Yield—35%) and confirmed by ¹HNMR and LCMS. ¹H NMR was not clean but characteristics peaks were present. MS: 473 (M+1), LCMS showed it as 82% pure.

Example 24

5-(6-(2-(4-methylpiperazin-1-yl)ethoxy)pyrazin-2-yl)-3-methyl-1H-pyrazolo[3,4-b]pyridine

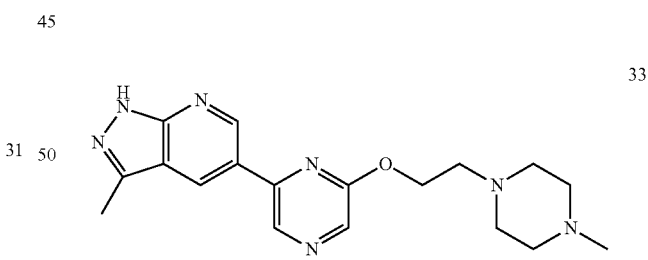

To a stirred solution of 5-(6-(2-(3-methylimidazolidin-1-yl)ethoxy)pyarazin-2-yl)-1-(4-methoxybenzyl)-3-methyl-1H-pyrazolo[3,4-b]pyridine (180 mg) in DCM (2 ml) TFA (8 ml) was added at 0° C. Ice-bath was removed and the mixture was heated to 50° C. and maintained for 16 h under stirring. Reaction mixture was cooled, concentrated and basified with saturated sodium bicarbonate solution, and again concentrated. The crude mixture was purified by flash column chromatography using basic alumina and 3% MeOH/DCM system to afford the desired product 33 as pale yellow solid, 60 mg (Yield: 47%) as pale yellow solid. The product was confirmed by ¹HNMR and LCMS. ¹H NMR (400 MHz, CDCl₃)

δ: 10.56 (bs, 1H), 9.2 (s, 1H), 8.65 (s, 1H), 8.60 (s, 1H), 8.22 (s, 1H), 4.63 (m, 2H), 2.919 (m, 2H), 2.67-2.54 (m, 11H), 2.33 (s, 3H); MS: 353, (M+1); LCMS~98%, HPLC~96%.

Example 25

N-(6-chloropyrazine-2-yl)-1-methylpiperidine-4-carboxamide

37

A solution of 1-methylpiperidine-4-carboxylic acid (500 mg, 3.1 mmol) in thionyl chloride (8 ml) was refluxed for 4 h. All volatiles are removed under nitrogen. To the crude acid chloride, pyridine (6 ml) was added followed by 2,6-Dichloropyrazine and the mixture was heated at 100° C. overnight. Reaction was completed as shown by TLC. Pyridine was removed under vacuum and the obtained crude product was purified by flash column over neutral alumina using 5% methanol/DCM as eluent. Compound 37 was obtained as dark brown solid, 130 mg (40%) and confirmed by $^1$HNMR and LCMS. $^1$H NMR (400 MHz, CDCl$_3$) δ: 11.06 (s, 1H), 9.30 (s, 1H), 8.46 (s, 1H), 2.77 (d, 2H), 2.58 (d, 2H), 2.15 (s, 3H), 1.86 (m, 4H), 1.8-1.74 (m. 2H); MS-254, (M+1), LCMS~98%.

Example 26

N-(6-(1-(4-methoxybenzyl)-3-methyl-1H-pyrazolo[3,4-b]pyridine-5-yl)pyrazin-2-oxamideyl)-1-methylpiperidine-4-carboxamide

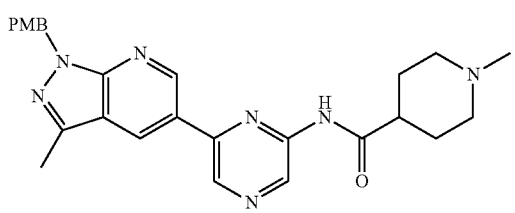

38

To a solution of N-(6-chloropyrazine-2-yl)-1-methylpiperidine-4-carboxamide (100 mg, 0.39 momol) in DMF, 1-(4-methoxybenzyl)-3-methyl-5-(4,4,5,5-tetramethyl-1,3,2-dioxabolan-2-yl)-1H-pyrazolo[3,4-b]pyridine (180 mg, 0.47 mmol) and 1M solution of Na$_2$CO$_3$ (0.4 mL) was added and the reaction mixture was degassed for 20 min with nitrogen. Pd$_2$dba$_3$ (36 mg, 0.039 mmol) and tri-t-butylphosphine (8 mg, 0.039 mmol) were added and degassed again for 10 minutes. The mixture was heated to 80° C. and maintained overnight. The reaction mixture was concentrated and purified by flash column using 230-400 mesh silica gel and 8% methanol/DCM system. The product 38 was obtained as brown solid, 60 mg (Yield—35%) and confirmed by $^1$HNMR and LCMS. $^1$H NMR (400 MHz, CDCl$_3$) δ: 9.50 (s, 1H), 9.14 (s, 1H), 8.84 (s, 1H), 8.53 (s, 1H), 7.96 (s, 1H), 7.35 (d, 2H), 6.83 (d, 2H), 5.61 (s, 2H), 3.76 (s, 3H), 3.0 (d, 2H), 2.62 (s, 3H), 2.38-2.3 (m, 3H), 2.02-1.95 (m, 7H); MS-471, (M+1), LCMS~96%.

Example 27

1-methyl-N-(6-(3-methyl-1H-pyrazolo[3,4-b]pyridine-5yl)pyrazin-2-yl)piperazine-4-carboxamide

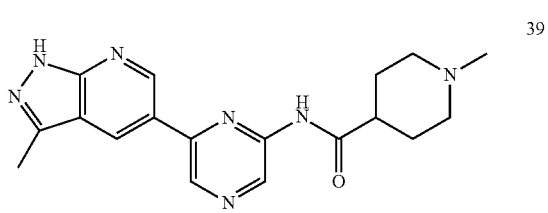 [SMILES: Cc1n[nH]c2ncc(-c3cncc(NC(=O)C4CCN(C)CC4)n3)cc12]

39

A stirred solution of N-(6-(1-(4-methoxybenzyl)-3-methyl-1H-pyrazolo[3,4-b]pyridine-5-yl)pyrazin-2-oxamideyl)-1-methylpiperidine-4-carboxamide (180 mg) in DCM (3 ml) was cooled to 0° C. Then TFA (10 ml) was added to it and heated to 60° C. and stirred overnight. TLC was checked. Reaction mixture was concentrated and basified with saturated sodium bicarbonate solution, and again concentrated. The crude product was purified by flash column chromatography using basic alumina eluting with 1-3% MeOH/DCM system to afford the desired product 39 as pale yellow solid, 60 mg (Yield: 30%). The product was confirmed by $^1$HNMR and LCMS. $^1$H NMR (400 MHz, DMSO) δ: 13.43 (s, 1H), 10.80 (s, 1H), 9.26 (d, 2H), 9.07 (s, 1H), 8.92 (s, 1H), 2.83 (d, 2H), 2.61-2.50 (m, 5H), 2.17 (s, 3H), 1.91-1.79 (m, 4H), 1.70-1.65 (m, 2H); MS: 351, (M+1), LCMS~99%; HPLC~98%.

Reaction Scheme 5

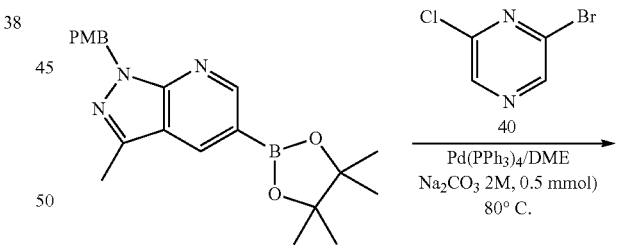

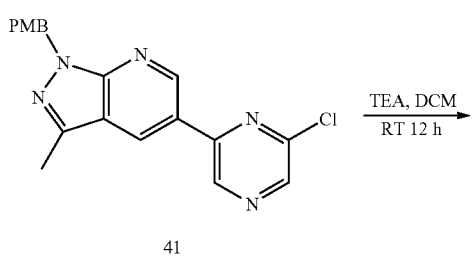

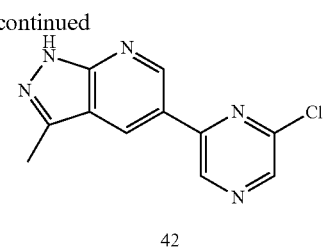

Example 28

5-(6-chloropyrazin-2-yl)-1-(4-methoxybenzyl)-3-methyl-1H-pyrazolo[3,4-b]pyridine

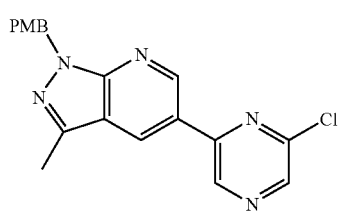

To a stirred solution of (1-(4-methoxybenzyl)-3-methyl-5-(4,4,5,5-tetramethyl-1,3,2-dioxaborolan-2-yl)-1H-pyrazolo[3,4-b]pyridine) 8 (105 mg, 0.276 mmol) and 2-bromo-6-chloropyrazine 40 (50 mg, 0.268 mmol, 1 equivalent) in DME (3 mL), ethanol (0.5 mL) and water (0.1 mL) was added sodium carbonate (2.0 M, 0.561 mmol, 2 equivalent) and degassed for min followed by charging Pd(PPh$_3$)$_4$ (9.5 mg, 0.0082 mmol, 0.03 equivalent). The resulting reaction mixture was purged with N$_2$ and degassing was submitted for heating at 80° C. overnight under pressure in a sealed tube. After completion of the reaction the reaction was diluted with ethyl acetate and water. The organic layer was separated and aqueous phase was extracted with ethyl acetate. The combined organic layer was washed with brine and dried over sodium sulphate and evaporated. The crude product was flash chromatographed with 100-200 mesh silica gel eluting the pure compound at 40% ethyl acetate in hexane as off white coloured solid of compound 41 in 25 mg. The product 41 was confirmed by LCMS. MS: 365.9, (M+1).

Example 29

5-(6-chloropyrazin-2-yl)-3-methyl-1H-pyrazolo[3,4-b]pyridine

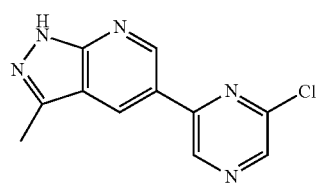

To a stirred solution of compound 41 (20 mg) in dichloromethane (10 mL) was added trifluoroacetic acid (5 mL) and heated at 50° C. overnight. After completion of the reaction the solvents were evaporated, diluted with cold water, pH was adjusted to 8-9 and the aqueous phase extracted with chloroform. The organic layer was washed with brine solution, dried over sodium sulphate and the solvents were evaporated to obtain the crude product. The crude material was passed through 100-200 mesh silica gel eluting to obtain the pure compound in 2% MeOH/CHCl$_3$ as pale yellow solid of compound 42 (5 mg). The product was confirmed by $^1$HNMR and LCMS. $^1$H NMR (400 MHz, CDCl$_3$) δ: 9.16 (s, 1H), 9.01 (s, 1H), 8.72 (d, J=2.19 Hz, 1H), 8.57 (s, 1H), 2.66 (bs, 3H); LCMS. MS: 245.9, (M+1).

Reaction Scheme 6

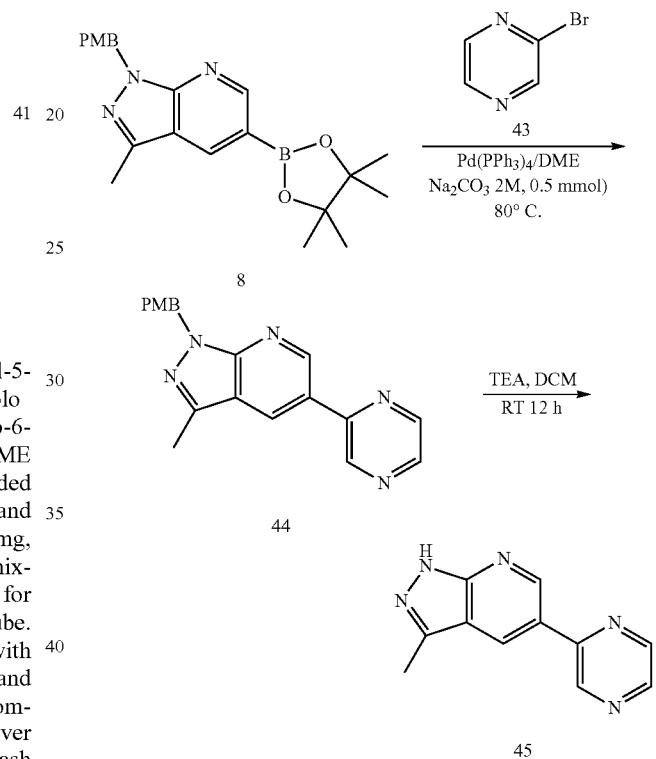

Example 30

1-(4-methoxybenzyl)-3-methyl-5-(pyrazin-2-yl)-1H-pyrazolo[3,4-b]pyridine

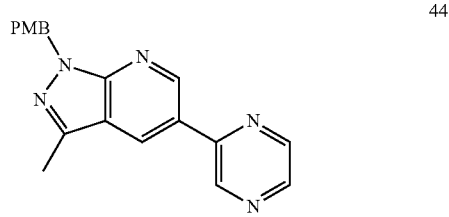

To a stirred solution of compound 8 (230 mg, 0.627 mmol) and 2-bromopyrazine 43 (100 mg, 0.63 mmol) in DME (3 mL), ethanol (1 mL) and water (0.2 mL) was added sodium carbonate (135 mg, 1.26 mmol) and was degassed for 10 min followed by the charging Pd(PPh₃)₄ (7.5 mg, 0.03 equivalent). The resulting reaction mixture was purged with N₂ and degassing was submitted for heating at 80° C. overnight under pressure in a sealed tube. After completion of the reaction the reaction was diluted with ethyl acetate and water. The organic layer was separated and aqueous phase was extracted with ethyl acetate. The combined organic layer was washed with brine and dried over sodium sulphate and evaporated. The crude product was flash chromatographed with 100-200 mesh silica gel eluting the pure compound at 20% ethyl acetate in hexane as off white colored solid of compound 44 in 30 mg. The product 44 was confirmed by ¹H NMR (400 MHz, CDCl₃) δ: 9.18 (s, 1H), 9.17 (s, 1H), 9.10 (d, J=1.58 Hz, 2H), 8.67 (s, 1H), 8.64 (s, 1H), 7.35 (d, 2H), 6.84 (d, 1H), 5.62 (d, 2H), 3.76 (s, 3H), 2.62 (s, 3H).

Example 31

3-methyl-5-(pyrazin-2-yl)-1H-pyrazolo[3,4-b]pyridine

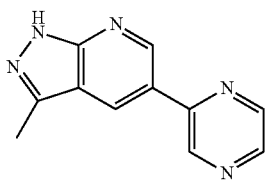

45

To a stirred solution of compound 44 (30 mg) in dichloromethane (10 mL) was added trifluoroacetic acid (5 mL) and heated at 50° C. overnight. After completion of the reaction the solvents were evaporated, diluted with cold water, pH was adjusted to 8 and the aqueous phase extracted with chloroform. The organic layer was washed with brine solution, dried over sodium sulphate and the solvents were evaporated to obtain the crude product. The crude material was passed through 100-200 mesh silica gel eluting to obtain the pure compound in 1% MeOH/CHCl₃ as pale yellow solid of compound 45 (20 mg). The product was confirmed by ¹HNMR and LCMS. ¹H NMR (400 MHz, DMSO-d₆) δ: 13.42 (s, 1H), 9.39 (s, 1H), 9.25 (d, J=2.07, 1H), 8.95 (d, J=2.07, 1H), 8.74 (m, 1H), 8.62 (d, J=2.43, 1H), 2.57 (s, 3H); LCMS. MS: 211.9, (M+1).

Reaction Scheme 7

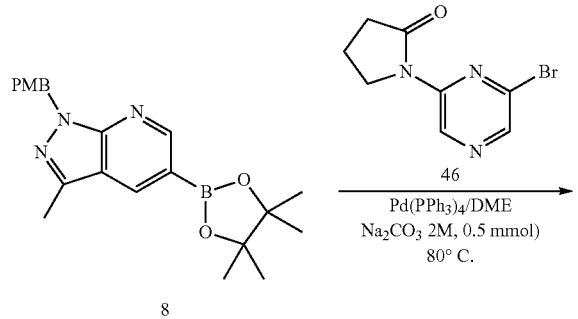

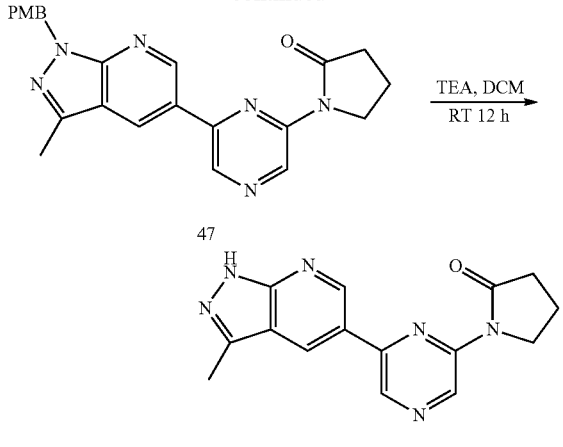

Example 32

1-(6-(1-(4-methoxybenzyl)-3-methyl-1H-pyrazolo[3,4-b]pyridin-5-yl)pyrazin-2-yl)pyrrolidin-2-one

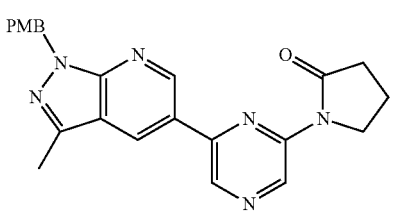

47

To a stirred solution of compound 8 (79 mg, 0.208 mmol) and compound 46 (50 mg, 0.208 mmol) in DME (3 mL), ethanol (1 mL) and water degassed and purged with nitrogen for 10 min was added sodium carbonate (45 mg, 0.420 mmol), again degassed for 10 min, then Pd(PPh₃)₄ (2.5 mg, 0.00207 mmol) was added and thoroughly degassed for another 10 min. The reaction mixture was heated at 80° C. overnight under sealed condition. After completion of the reaction the reaction mass was diluted with ethyl acetate and water and organic layer was separated and aqueous phase was again extracted with ethyl acetate. The combined organic layer was washed with brine and dried over sodium sulphate and the solvent completely distilled off to get the crude product. The crude was passed through 100-200 mesh silica gel eluting the pure compound at 40% ethyl acetate in hexane as off white coloured solid 47 (30 mg). MS m/z 415.0 (M+H)⁺.

Example 33

1-(6-(3-methyl-1H-pyrazolo[3,4-b]pyridin-5-yl)pyrazin-2-yl)pyrrolidin-2-one

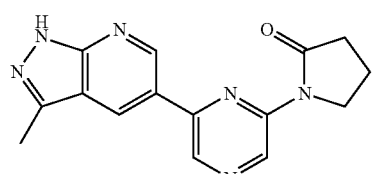

48

To a stirred solution of compound 47 (30 mg) in dichloromethane (10 mL) was added trifluoroacetic acid (5 mL) and the reaction mixture heated at 50° C. overnight. After completion of the reaction the solvents was distilled off and diluted with cold water and pH was adjusted to 8 and the aqueous phase extracted with chloroform twice. The organic layer was washed with brine solution and dried over sodium sulphate and the solvent completely distilled off to get the crude product. The crude was passed through 100-200 mesh silica gel eluting the pure compound at 1-3% methanol in chloroform as pale yellow solid 10 mg of compound 48. $^1$H NMR (400 MHz, DMSO-$d_6$) δ: 9.49 (s, 1H), 9.27 (d, J=2.07, 1H), 9.10 (s, 1H), 8.95 (d, J=2.07, 1H), 4.16 (m, J=6.95, 7.31, 2H), 2.58 (s, 2H), 2.65 (m, 2H), 2.17 (m, 3H); MS m/z 294.9 (M+H)$^+$.

Reaction Scheme 8

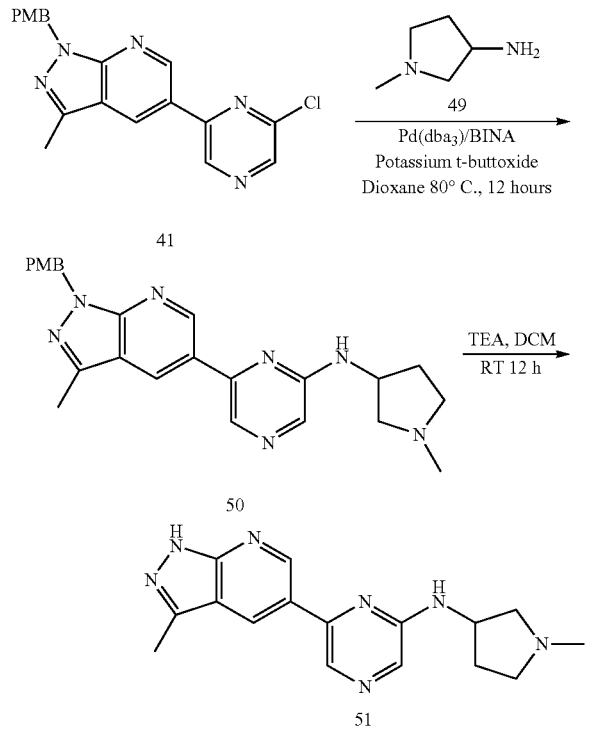

Example 34

6-(1-(4-methoxybenzyl)-3-methyl-1H-pyrazolo[3,4-b]pyridin-5-yl)-N-(1-methylpyrrolidin-3-yl)pyrazin-2-amine

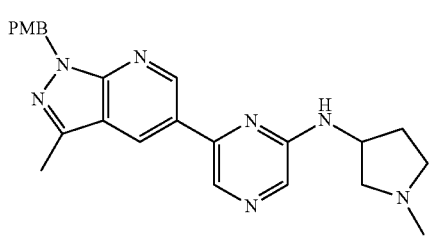

To a stirred solution of 41 (158 mg, 0.432 mmol, 1.0 eq) and 49 (75 mg, 0.432 mmol, 1.0 eq) in 1,4 dioxane (5 mL) was added potassium tert-butoxide (97 mg, 0864 mmol, 2.0 eq) degas, the solution purged with nitrogen for 15 min, then was added Pd$_2$(dba)$_3$ (11 mg, 0.013 mmol, 0.03 eq) and BINAP (0.04 eq) and again degassed for 20 min. The reaction mixture was heated at 80° C. under sealed tube conditions overnight. After completion of the reaction the reaction mixture was diluted with water and extracted with dichloromethane twice. The combined organic layer was dried over sodium sulphate and the solvent completely distilled off to get the crude. The crude was passed through 100-200 mesh silica gel eluting the pure compound 50 at 90% ethyl acetate in hexane as pale yellow coloured compound 50 (50 mg).

Example 35

6-(3-methyl-1H-pyrazolo[3,4-b]pyridin-5-yl)-N-(1-methylpyrrolidin-3-yl)pyrazin-2-amine

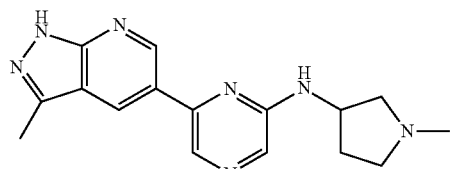

To a stirred solution of 50 (50 mg, 0.116 mmol, 1.0 eq) in dichloromethane (10 mL) was added trifluoroacetic acid (5 mL) and the reaction mixture heated at 50° C. overnight. After completion of the reaction the reaction mixture the solvent was completely distilled off and diluted with cold water and pH was adjusted to 8 and the aqueous phase extracted with chloroform twice. The organic layer was washed with brine solution and dried over sodium sulphate and the solvent completely distilled off to get the crude product. The crude was passed through aluminium oxide (neutral) the pure compound at 1-3% methanol in chloroform as white solid 51 (20 mg). MS m/z 310.0 (M+H)$^+$.

Reaction Scheme 9

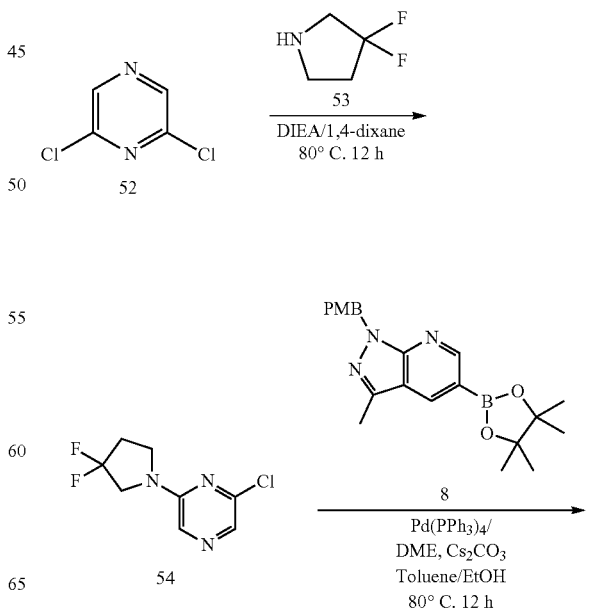

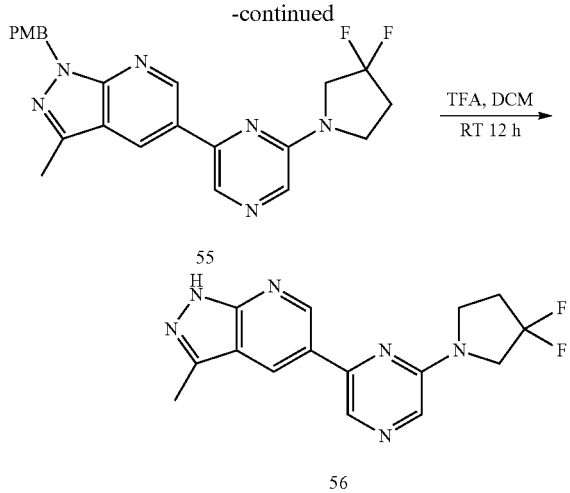

Example 36

2-chloro-6-(3,3-difluoropyrrolidin-1-yl)pyrazine

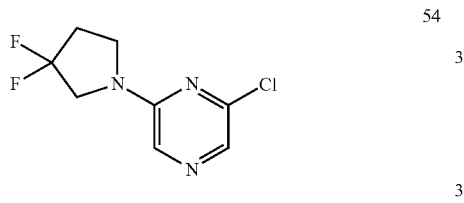

To a stirred solution of 52 (100 mg, 0.67 mmol, 1.0 eq) and 53 (80 mg, 0.73 mmol, 1.1 eq) in 1,4 dioxane (5 mL) was added DIPEA (216 mg, 1.34 eq, 2.0 eq) and the reaction mixture heated at 80° C. overnight. After completion of the reaction the reaction mixture was partitioned between ethyl acetate and water. The organic layer was separated and aqueous was again extracted with ethyl acetate. The combined organic layers were dried over sodium sulphate and the solvent completely distilled off to get the crude product. The crude was passed through 100-200 mesh silica gel eluting the pure compound at 10% ethyl acetate in hexane to obtain 80 mg of compound 54. MS m/z 219.8 (M+H)⁺.

Example 37

5-(6-(3,3-difluoropyrrolidin-1-yl)pyrazin-2-yl)-1-(4-methoxybenzyl)-3-methyl-1H-pyrazolo[3,4-b]pyridine

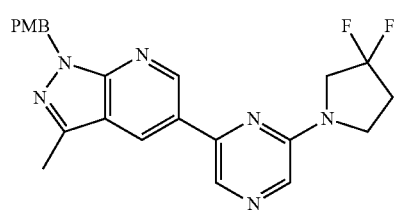

To a stirred solution of 54 (80 mg, 0.364 mmol, 1.1 eq) and 8 (152 mg, 4.0 mml, 1.0 eq) in toluene (8 mL) and ethanol (2 ml) was added cesium carbonate (296 mg, 0.91 mmol, 2.5 eq) and the solution degassed and purged with nitrogen for 15 min, then Pd(PPh$_3$)$_4$ (4.2 mg, 0.0036 mmol, 0.01 eq) added and again the solution purged with nitrogen for another 15 min. The reaction mass was heated at 100° C. in a sealed tube overnight. After completion of the reaction the reaction mixture was partitioned between ethyl acetate and water and the organic layer was separated and again extracted with ethyl acetate. The combined organic layer was dried over sodium sulphate and the solvent completely distilled off to get the crude. The crude was passed through 100-200 mesh silica gel eluting the pure compound at 30% ethyl acetate in hexane as off white coloured 54 compound as solid in 40 mg yield.

Example 38

5-(6-(3,3-difluoropyrrolidin-1-yl)pyrazin-2-yl)-3-methyl-1H-pyrazolo[3,4-b]pyridine

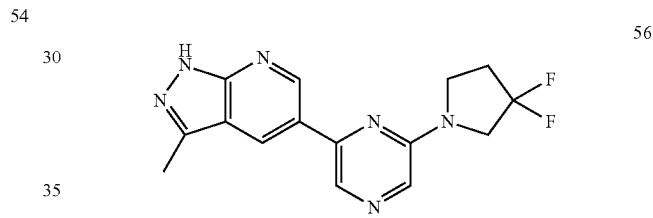

To a stirred solution of compound 55 (40 mg, 0.0916 mmol, 1.0 eq) in dichloromethane (5 mL) was added trifluoroacetic acid (5 ml) and the reaction mixture heated at 50° C. overnight. After completion of the reaction the solvents were removed and diluted with cold water and pH was adjusted to 8 and extracted into the aqueous phase with chloroform twice. The organic layer was washed with brine solution and dried over sodium sulphate and the solvent completely distilled off to get the crude product. The crude was passed through 100-200 mesh silica gel eluting the pure compound 56 in 90% ethyl acetate in hexane as pale yellow solid compound 56 (5 mg). MS m/z 217.0 (M+H)⁺.

Reaction Scheme 10

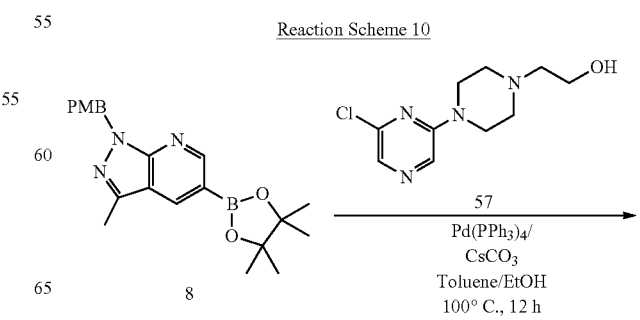

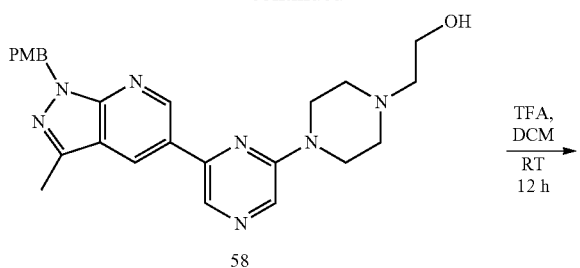

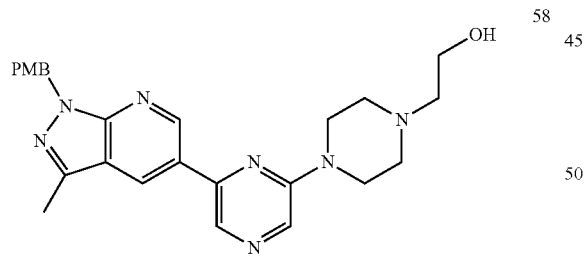

Example 39

2-(4-(6-(1-(4-methoxybenzyl)-3-methyl-1H-pyrazolo[3,4-b]pyridin-5-yl)pyrazin-2-yl)piperazin-1-yl)ethanol To a stirred solution of 8 (86 mg, 0.226 mmol, 1.1 eq) and 57 (50 mg, 0.206 mmol, 1.0 eq) in toluene (2 mL) and ethanol (0.1 ml) was added cesium carbonate (127 mg, 0.0389 mmol, 2.0 eq) with degassing and purging with nitrogen for 15 min, then was added Pd(PPh$_3$)$_4$ (2.3 mg, 0.00206 mmol, 0.01 eq). The reaction mixture was purged again with N$_2$ for another 15 min and was heated at 100° C. in a sealed tube overnight. After completion of the reaction the reaction was partitioned between ethyl acetate and water. The organic layer was separated and again extracted with ethyl acetate. The combined organic layer was dried over sodium sulphate and the solvent completely distilled off to get the crude. The crude was passed through 100-200 mesh silica gel eluting the pure compound at 30% ethyl acetate in hexane as off-white coloured solid 58 in 25 mg quantity.

Example 40

2-(4-(6-(3-methyl-1H-pyrazolo[3,4-b]pyridin-5-yl)pyrazin-2-yl)piperazin-1-yl) ethanol

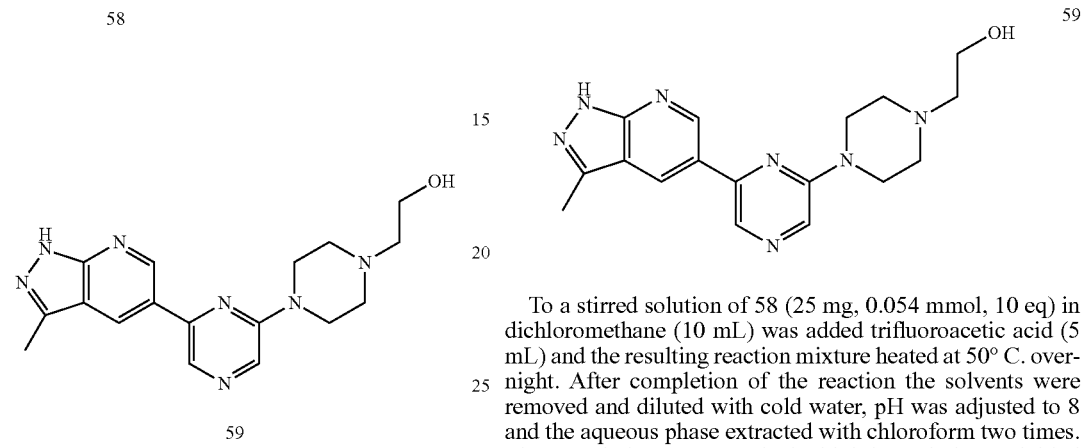

To a stirred solution of 58 (25 mg, 0.054 mmol, 10 eq) in dichloromethane (10 mL) was added trifluoroacetic acid (5 mL) and the resulting reaction mixture heated at 50° C. overnight. After completion of the reaction the solvents were removed and diluted with cold water, pH was adjusted to 8 and the aqueous phase extracted with chloroform two times. The organic layer was washed with brine solution and dried over sodium sulphate and the solvents were removed to get the crude product. The crude was passed through 100-200 mesh silica gel eluting the pure compound at 35-40% ethyl acetate in hexane as pale yellow solid compound 59 in 5 mg quantity. MS m/z 340.1 (M+H)$^+$.

Reaction Scheme 11

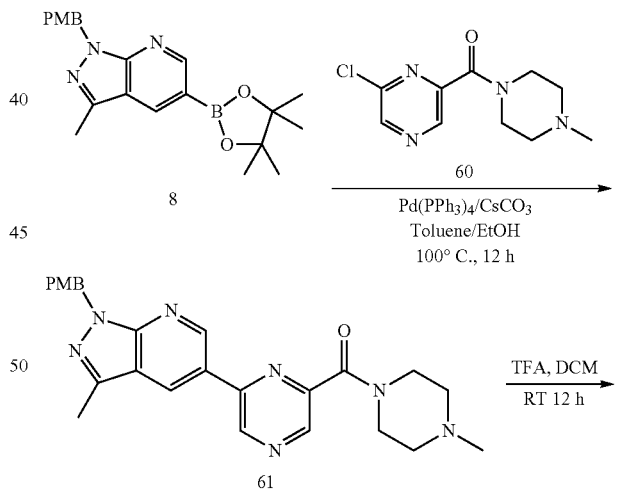

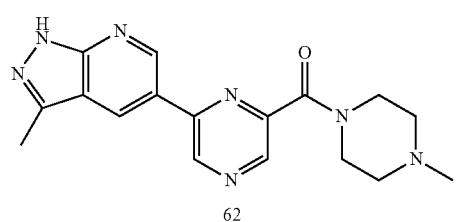

Example 41

(6-(1-(4-methoxybenzyl)-3-methyl-1H-pyrazolo[3,4-b]pyridin-5-yl)pyrazin-2-yl)(4-methylpiperazin-1-yl)methanone

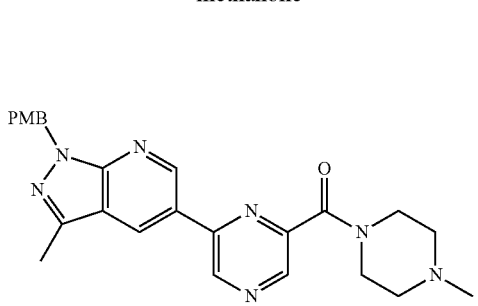

61

To a stirred solution of compound 8 and 60 in toluene and ethanol was added cesium carbonate, the solution degassed and purged with nitrogen for 15 min, then Pd(PPh3)4 added and again purged with nitrogen for another 15 min. The reaction mass was heated at 100° C. in a sealed tube overnight. After completion of the reaction, the reaction mixture was partitioned between ethyl acetate and water. The organic layer was separated and again extract with ethyl acetate. The combined organic layer was dried over sodium sulphate and the solvent completely distilled off to get the crude. The crude was passed through 100-200 mesh silica gel eluting the pure compound at 13% ethyl acetate in hexane as off-white colored solid 61 (100 mg).

Example 42

(6-(3-methyl-1H-pyrazolo[3,4-b]pyridin-5-yl)pyrazin-2-yl)(4-methylpiperazin-1-yl)methanone

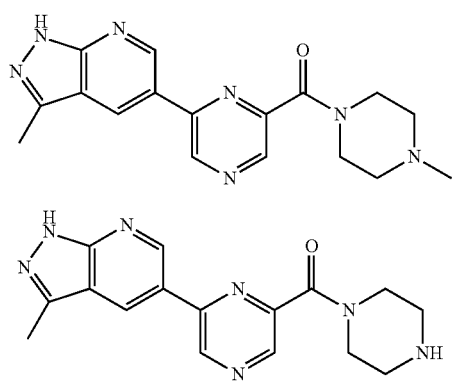

62

62

To a stirred solution of 61 in dichloromethane were added trifluoroacetic acid and the reaction mixture heated at 50° C. overnight. After completion of the reaction the solvents were distilled off, diluted with cold water, pH was adjusted to 8-9 and the aqueous phase extracted with chloroform twice. The organic layer was washed with brine solution and dried over sodium sulphate and solvents evaporated to get the crude product. The crude was passed through 100-200 mesh silica gel eluting the pure compound at 26% ethyl acetate in hexane as pale yellow solid of compound 62 in 25 mg. The spectral data shows that the compound is de-methylated compound 62. MS m/z 323.4 (M+H)+.

Reaction Scheme 12

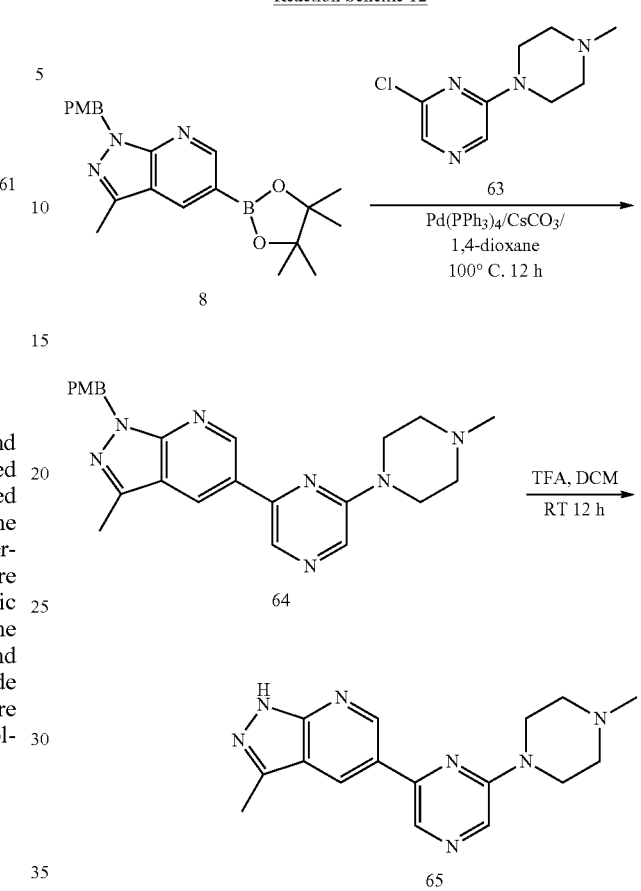

Example 43

1-(4-methoxybenzyl)-3-methyl-5-(6-(4-methylpiperazin-1-yl)pyrazin-2-yl)-1H-pyrazolo[3,4-b]pyridine

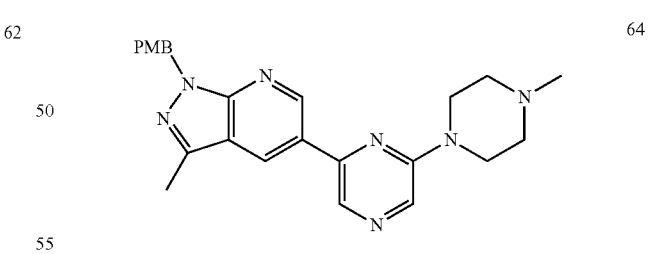

64

To a stirred solution of 8 and 63 in 1,4 dioxane and water was added Cs₂CO₃, the solution degassed, purged with nitrogen for 15 min, Pd(PPh₃)₄ was added and the reaction mass was again purged with nitrogen for another 15 min. The reaction mass was heated at 100° C. in a sealed tube overnight. After completion of the reaction the reaction mass was partitioned between ethyl acetate and water and the organic layer was separated and again extracted with ethyl acetate. The combined organic layer was dried over sodium sulphate and the solvent completely distilled off to get the crude. The crude was passed through 100-200 mesh silica gel eluting the pure compound at 70-80% ethyl acetate in hexane as off white coloured solid compound 64 (25 mg).

Example 44

3-methyl-5-(6-(4-methylpiperazin-1-yl)pyrazin-2-yl)-1H-pyrazolo[3,4-b]pyridine

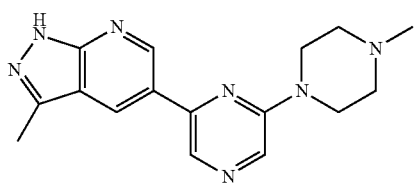

65

To a stirred solution of 64 in dichloromethane was added trifluoroacetic acid and the reaction mixture heated to 50° C. for 12 hours. After completion of the reaction the solvents were removed, diluted with cold water, pH was adjusted to 8 and the aqueous phase extracted with chloroform twice. The organic layer was washed with brine solution and dried over sodium sulphate and the solvent completely distilled off to get the crude product. The crude was passed through 100-200 mesh silica gel eluting the pure compound at 2% MeOH/CHCl$_3$ as pale yellow solid (10 mg) compound 65. MS m/z 310.4 (M+H)$^+$.

Reaction Scheme 13

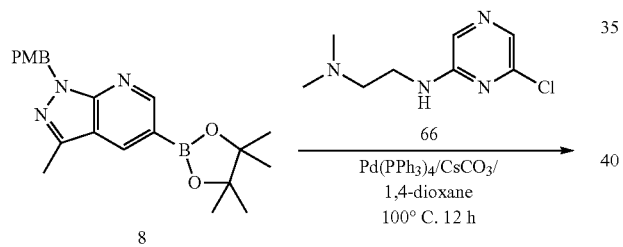

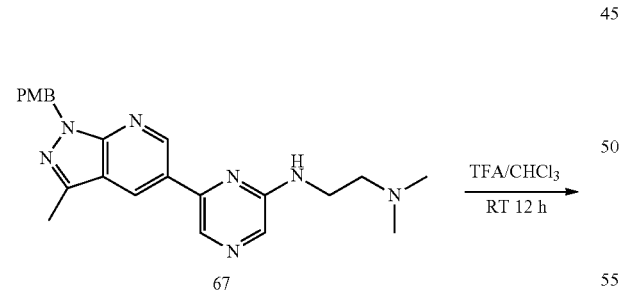

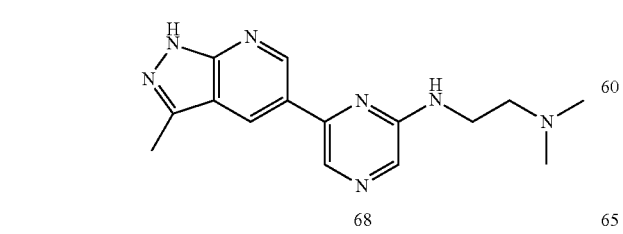

Example 45

N$^1$-(6-(1-(4-methoxybenzyl)-3-methyl-1H-pyrazolo[3,4-b]pyridin-5-yl)pyrazin-2-yl)-N$^2$,N$^2$-dimethyl-ethane-1,2-diamine

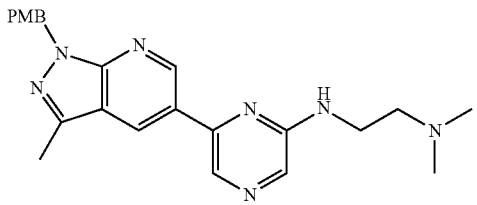

67

To a stirred solution of 8 and 66 in 1,4-dioxane and CH$_2$Cl$_2$ was added Cs$_2$CO$_3$, the solution degassed, purged under N$_2$ for 15 min, Pd(dppf)Cl$_2$ was added followed by purging again with N$_2$ for another 15 min. The reaction mass was heated at 100° C. in a sealed tube overnight. After completion of the reaction it was partitioned between ethyl acetate and water. The organic layer was separated and again extracted with ethyl acetate. The combined organic layers were dried over sodium sulphate and the solvent distilled off to get the crude. The crude was passed through 100-200 mesh silica gel eluting the pure compound at 1-2% of methanol in chloroform as off-white colored solid compound 67 (40 mg).

Example 46

N$^1$, N$^1$-dimethyl-N2-(6-(3-methyl-1H-pyrazolo[3,4-b]pyridin-5-yl)pyrazin-2-yl)ethane-1,2-diamine

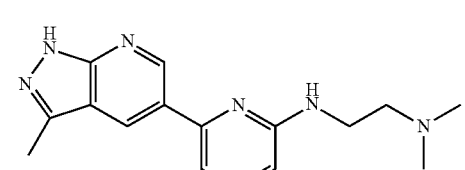

68

To a stirred solution of 67 in chloroform was added trifluoroacetic acid and the reaction mixture heated at 50° C. overnight. After completion of the reaction the solvents were removed and diluted with cold water and pH was adjusted to 8, the aqueous phase extracted with chloroform twice. The organic layer was washed with brine solution and dried over sodium sulphate and the solvent completely distilled off to get the crude product. The crude was passed through aluminium oxide (neutral) eluting the pure compound 68 at 2% MeOH/CHCl$_3$ as pale yellow solid (10 mg). MS m/z 298.0 (M+H)$^+$.

Reaction Scheme 14

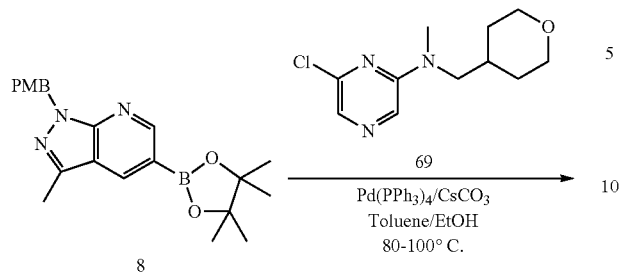

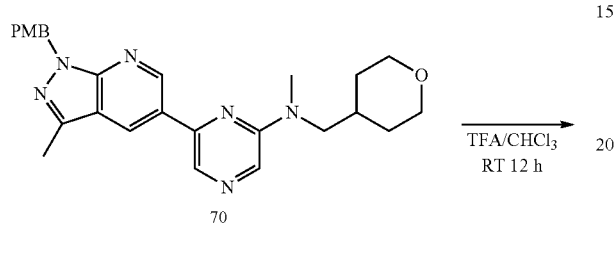

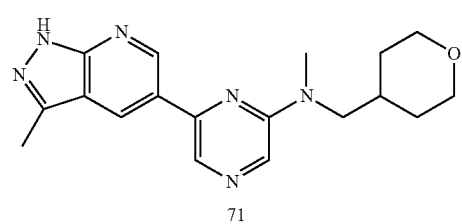

Example 47

6-(1-(4-methoxybenzyl)-3-methyl-1H-pyrazolo[3,4-b]pyridin-5-yl)-N-methyl-N-((tetrahydro-2H-pyran-4-yl)methyl)pyrazin-2-amine

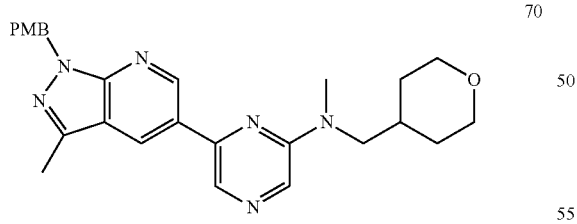

To a stirred solution of 8 and 69 in toluene and ethanol was added Cs$_2$CO$_3$, the solution degassed, purged with N$_2$ for 15 min then Pd (PPh$_3$)$_4$ added and the solution again purged with nitrogen for another 15 min. The reaction mass was heated at 100° C. in a sealed tube overnight. After completion of the reaction the reaction was partitioned between ethyl acetate and water. The organic layer was separated and again extracted with ethyl acetate. The combined organic layer was dried over sodium sulphate and the solvent completely distilled off to get the crude. The crude was passed through 100-200 mesh silica gel eluting the pure compound at 30% ethyl acetate in hexane as off-white colored solid 70 (30 mg).

Example 48

N-methyl-6-(3-methyl-1H-pyrazolo[3,4-b]pyridin-5-yl)-N-((tetrahydro-2H-pyran-4-yl)methyl)pyrazin-2-amine

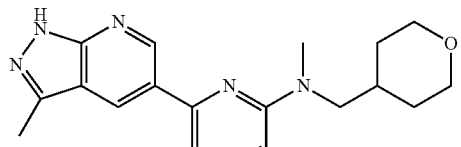

To a stirred solution of 70 in chloroform was added trifluoroacetic acid and the mixture heated at 50° C. overnight. After completion of the reaction the solvents were removed and diluted with cold water and pH was adjusted to 8, the aqueous phase extracted with chloroform twice. The organic layer was washed with brine solution and dried over sodium sulphate and the solvent completely distilled off to get the crude product. The crude was passed through aluminium oxide (neutral) eluting the pure compound 71 at with 40% EtOAc and hexane to yield pale yellow solid compound 71 (10 mg). MS m/z 339.13 (M+H)$^+$.

Reaction Scheme 15

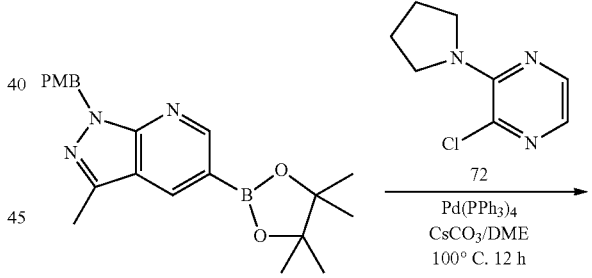

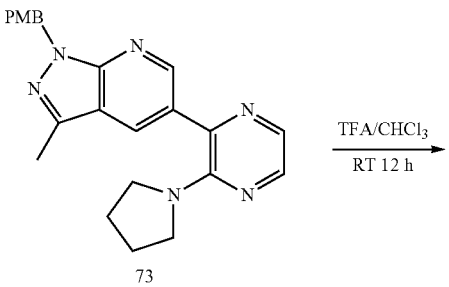

-continued

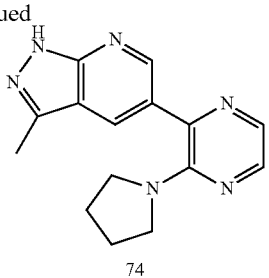

74

Example 49

1-(4-methoxybenzyl)-3-methyl-5-(3-(pyrrolidin-1-yl)pyrazin-2-yl)-1H-pyrazolo[3,4-b]pyridine

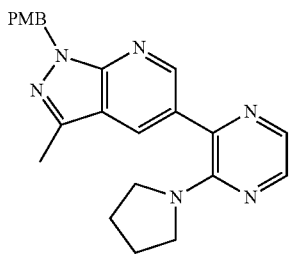

73

To a stirred solution of 8 and 72 in dimethoxyethane was added $Cs_2CO_3$. The reaction mixture was degassed, purged with $N_2$ for 15 min Pd $(PPh_3)_4$ was added, the mixture purged again for another 15 min. The resulting reaction mixture was heated at 100° C. in a sealed tube overnight. After completion of the reaction, the mixture was partitioned between ethyl acetate and water. The organic layer was separated and again extracted with ethyl acetate. The combined organic layers were dried over sodium sulphate and distilled off to get the crude. The crude was passed through 100-200 mesh silica gel eluting the pure compound at 30% ethyl acetate in hexane as off-white coloured solid 73 (30 mg).

Example 50

3-methyl-5-(3-(pyrrolidin-1-yl)pyrazin-2-yl)-1H-pyrazolo[3,4-b]pyridine

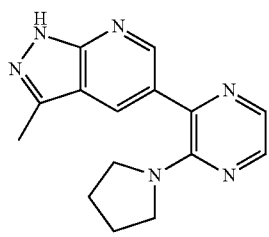

74

To a stirred solution of 73 in chloroform was added trifluoroacetic acid and heated at 50° C. overnight. The solvents were removed and diluted with cold water and pH was adjusted to 8, the aqueous phase extracted with chloroform twice. The organic layer was washed with brine solution and dried over sodium sulphate and the solvent distilled off to get the crude product. The crude was passed through aluminium oxide (neutral) eluting with 70% EtOAc and hexane to yield pale yellow solid compound 74 (15 mg). MS m/z 280.93 $(M+H)^+$.

Reaction Scheme 16

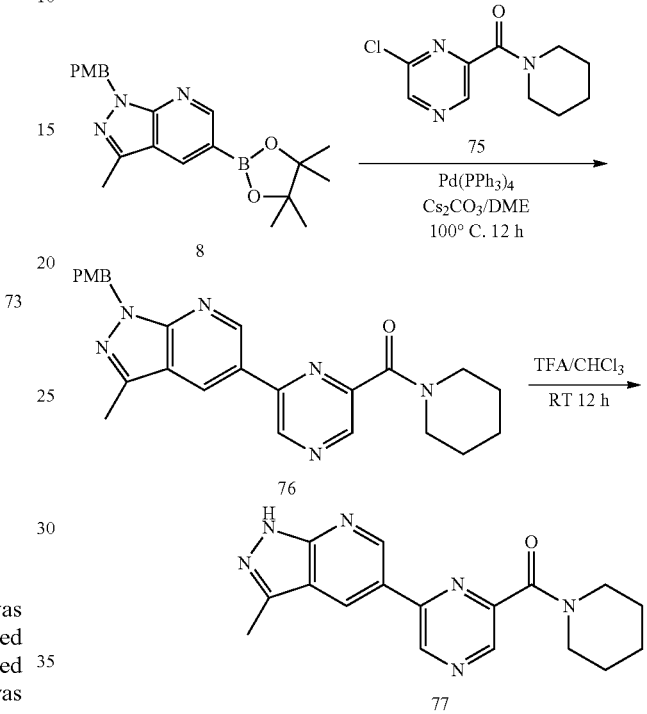

Example 51

(6-(1-(4-methoxybenzyl)-3-methyl-1H-pyrazolo[3,4-b]pyridin-5-yl)pyrazin-2-yl)(piperidin-1-yl)methanone

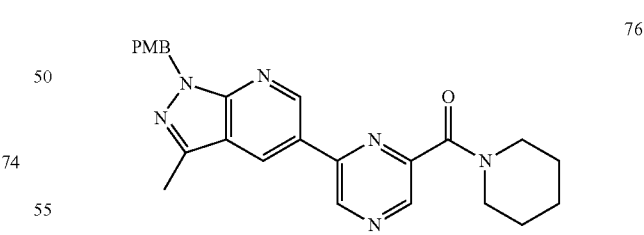

76

To a stirred solution of 8 and 75 in dimethoxyethane was added $Cs_2CO_3$. The reaction mixture was degassed, purged with $N_2$ for 15 min Pd $(PPh_3)_4$ was added, purged again for another 15 min. The resulting reaction mixture was heated at 100° C. in a sealed tube for 12 hours. After completion of the reaction, the mixture was partitioned between ethyl acetate and water. The organic layer was separated and again extracted with ethyl acetate. The combined organic layers were dried over sodium sulphate and distilled off to get the crude. The crude was passed through 100-200 mesh silica gel

Example 52

(6-(3-methyl-1H-pyrazolo[3,4-b]pyridin-5-yl)pyrazin-2-yl)(piperidin-1-yl)metha-none

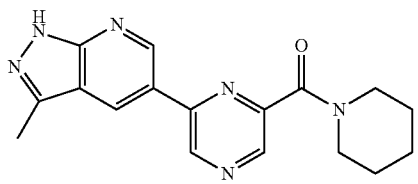

77

To a stirred solution of 76 in chloroform was added trifluoroacetic acid and the solution heated at 50° C. overnight. The solvents were removed and diluted with cold water and pH was adjusted to 8, the aqueous phase extracted with chloroform twice. The organic layer was washed with brine solution and dried over sodium sulphate and the solvent distilled off to get the crude product. The crude was passed through aluminium oxide (neutral) eluting with 60% EtOAc and hexane to yield pale yellow solid compound 77 (15 mg). MS m/z 323.00 (M+H)⁺.

Example 53

2-(4-((6-chloropyrazin-2-yl)amino)piperidin-1-yl)ethanol

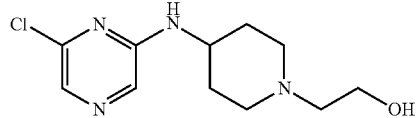

79

To a stirred solution of 52 and 2-(4-aminopiperidin-1-yl)ethanol in DMF was added DIPEA and the reaction mixture was heated at 100° C. overnight under sealed conditions. After completion of the reaction the reaction was partitioned between water and DCM, the aqueous phase was separated and extracted with DCM again. The combined organic layers were dried over sodium sulphate and the solvent completely distilled off to get the crude product. The crude was passed through 100-200 mesh silica gel eluting with 10% methanol in chloroform to yield 30 mg of compound 79.

Reaction Scheme 17

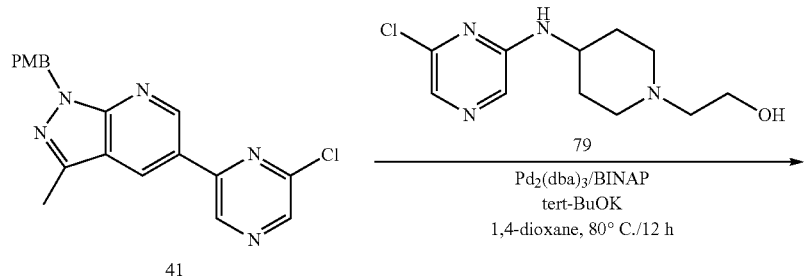

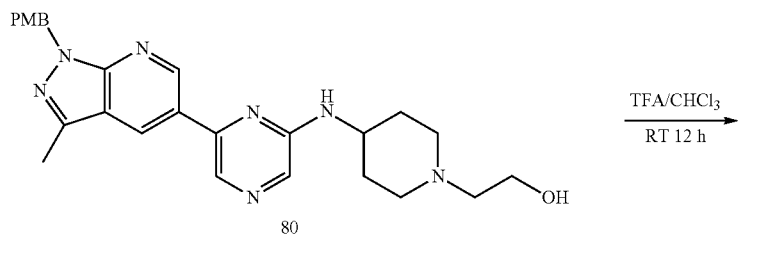

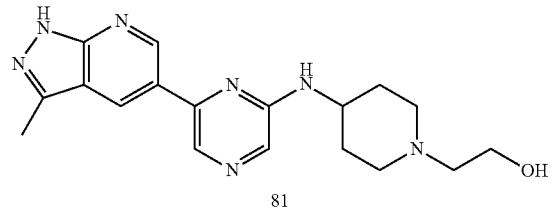

Example 54

2-(4-((6-(1-(4-methoxybenzyl)-3-methyl-1H-pyrazolo[3,4-b]pyridin-5-yl)pyrazin-2-yl)amino)piperidin-1-yl)ethanol

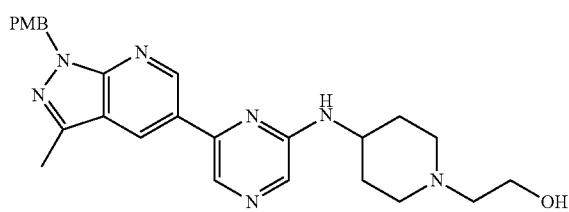

80

To a stirred solution of 41 and 79 in 1,4-dioxane was added rac-BINAP and tert-BuOK. The reaction mixture was degassed, purged with $N_2$ for 15 min Pd (dba)$_3$ was added, the mixture was purged again for another 15 min. The resulting reaction mixture was heated to 80° C. in sealed tube for 12 hours. After completion of the reaction, the solvents were removed and extracted with dichloromethane. The organic layers were dried over sodium sulphate and distilled off to get the crude product. The crude was passed through 100-200 mesh silica gel eluting with 1-2% MeOH and CHCl$_3$ as off-white coloured solid 80 (45 mg).

Example 55

2-(4-((6-(3-methyl-1H-pyrazolo[3,4-b]pyridin-5-yl)pyrazin-2-yl)amino)piperidin-1-yl)ethanol

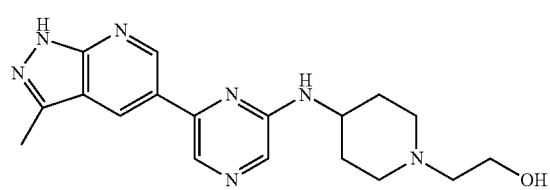

81

To a stirred solution of 80 in chloroform was added trifluoroacetic acid and the mixture heated at 50° C. overnight. The solvents were removed and diluted with cold water and pH was adjusted to 8, the aqueous phase extracted with CH$_2$Cl$_2$ twice. The organic layer was washed with brine solution and dried over sodium sulphate and the solvent distilled off to get the crude product. The crude was passed through silica gel eluting with 1-2% MeOH and CHCl$_3$ to yield pale yellow solid compound 81 (45 mg). MS m/z 352.9 (M+H)$^+$.

Reaction Scheme 18

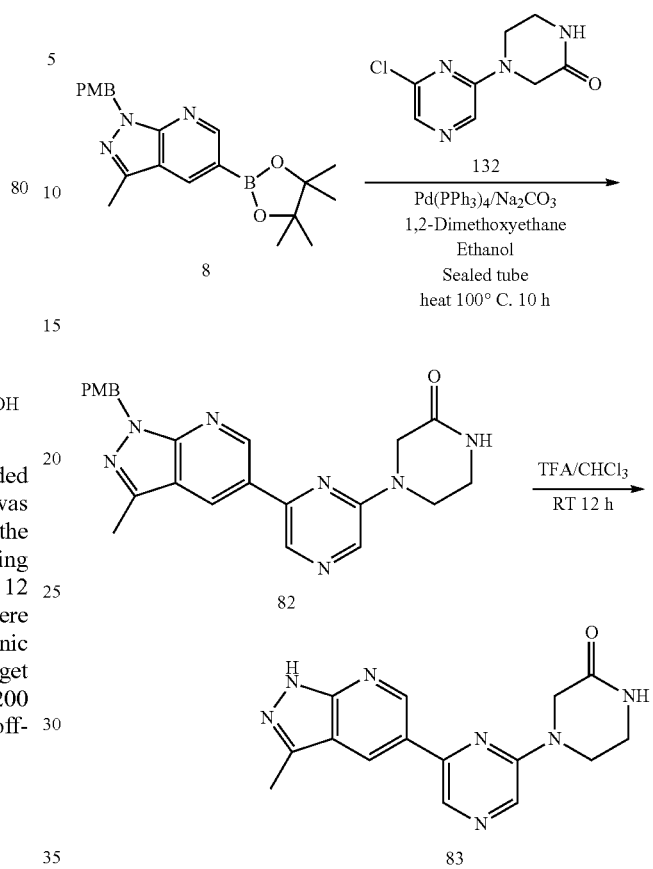

Example 56

4-(6-(1-(4-methoxybenzyl)-3-methyl-1H-pyrazolo[3,4-b]pyridin-5-yl)pyrazin-2-yl)piperazin-2-one

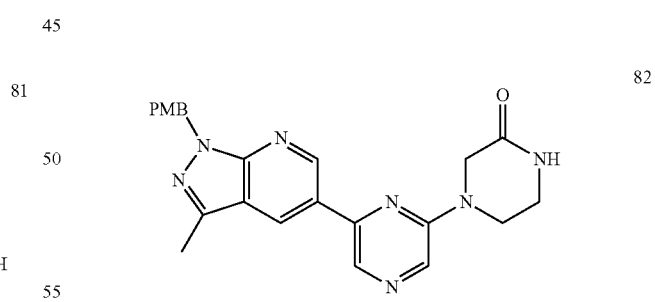

82

To a stirred solution of 8 and 132 in dimethoxyethane was added Na$_2$CO$_3$. The reaction mixture was degassed, purged with N$_2$ for 15 min Pd (PPh$_3$)$_4$ was added, the mixture purged again for another 15 min. The resulting reaction mixture was heated at 100° C. in a sealed tube for 10 hours. After completion of the reaction, the mixture was partitioned between ethyl acetate and water. The organic layer was separated and again extracted with ethyl acetate. The combined organic layers were dried over sodium sulphate and distilled off to get the crude. The crude was passed through 100-200 mesh silica gel eluting the pure compound at 30% ethyl acetate in hexane as off-white coloured solid 82 (15 mg).

Example 57

4-(6-(3-methyl-1H-pyrazolo[3,4-b]pyridin-5-yl)pyrazin-2-yl)piperazin-2-one

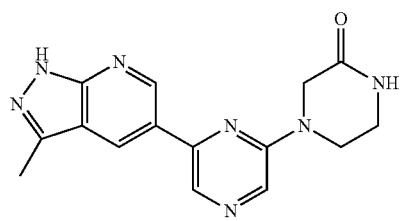

83

To a stirred solution of 82 in chloroform was added trifluoroacetic acid and the mixture heated at 50° C. overnight. The solvents were removed and diluted with cold water and pH was adjusted to 8, the aqueous phase extracted with $CH_2Cl_2$ twice. The organic layer was washed with brine solution and dried over sodium sulphate and the solvent distilled off to get the crude product. The crude was passed through aluminium oxide (neutral) eluting with 3% MeOH and $CHCl_3$ to yield pale yellow solid compound 83 (15 mg).

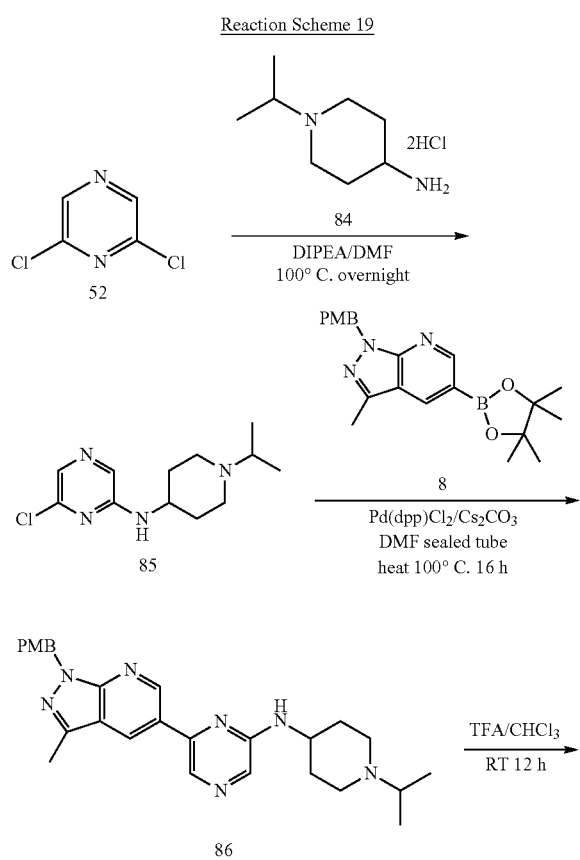

Reaction Scheme 19

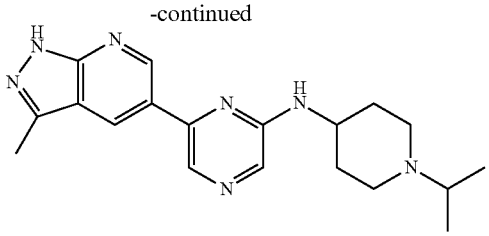

87

Example 58

6-chloro-N-(1-isopropylpiperidin-4-yl)pyrazin-2-amine

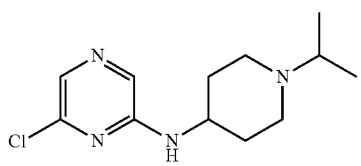

85

To a stirred solution of 52 and 84 in DMF was added DIPEA and the reaction mixture was heated at 100° C. overnight under sealed conditions. After completion of the reaction the reaction was partitioned between water and DCM, the aqueous phase was separated and extracted with DCM again. The combined organic layers were dried over sodium sulphate and the solvent completely distilled off to get the crude product. The crude was passed through 100-200 mesh silica gel eluting the pure compound at 8% methanol in chloroform to yield 80 mg of compound 85.

Example 59

N-(1-isopropylpiperidin-4-yl)-6-(1-(4-methoxybenzyl)-3-methyl-1H-pyrazolo[3,4-b]pyridin-5-yl)pyrazin-2-amine

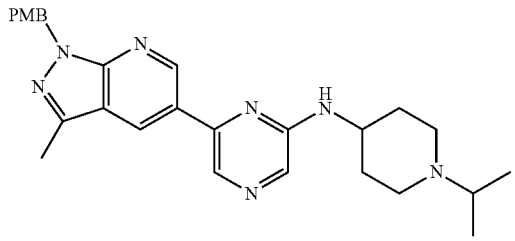

86

To a stirred solution of 8 and 86 in DMF was added $Cs_2CO_3$. The reaction mixture was degassed, purged with $N_2$ for 15 min and $Pd(dppf)Cl_2$ was added. The reaction mixture was heated at 100° C. in a sealed tube overnight. After completion of the reaction the reaction mixture was partitioned between ethyl acetate and water. The organic layer was separated and again extracted with ethyl acetate. The combined organic layer was dried over sodium sulphate and the solvent distilled off to get the crude. The crude was passed through 100-200 mesh silica gel eluting the pure compound at 6% MeOH/CHCl₃ (30 mg) to give compound 86.

Example 60

N-(1-isopropylpiperidin-4-yl)-6-(3-methyl-1H-pyrazolo[3,4-b]pyridin-5-yl)pyrazin-2-amine

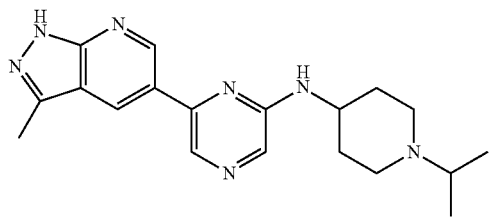

87

To a stirred solution of 86 in CHCl₃ was added trifluoroacetic acid. The mixture was heated at 50° C. overnight. After completion of the reaction the solvents were removed, diluted with cold water, pH was adjusted to 8 and the aqueous phase extracted with chloroform twice. The organic layer was washed with brine solution and dried over sodium sulphate and the solvent completely distilled off to get the crude product. The crude was passed through neutral alumina eluting the pure compound at 3% MeOH/CHCl₃ as pale yellow solid 87 (10 mg). MS m/z 352.1 (M+H)⁺.

Reaction Scheme 20

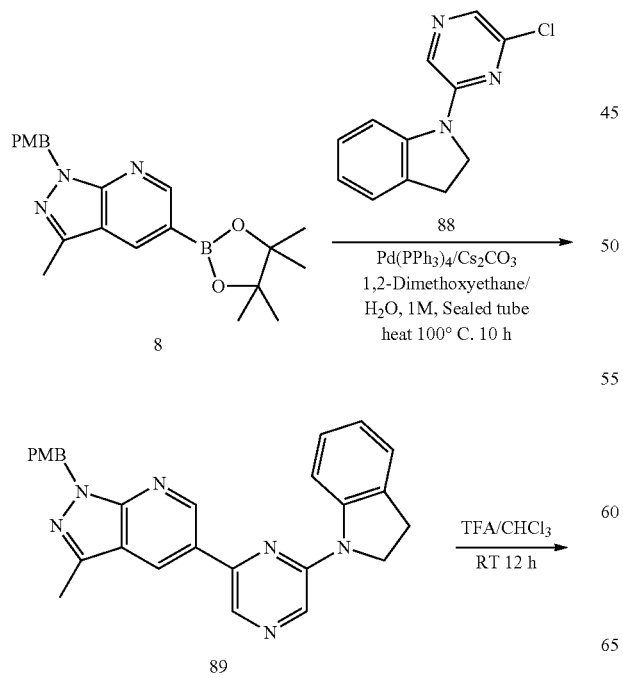

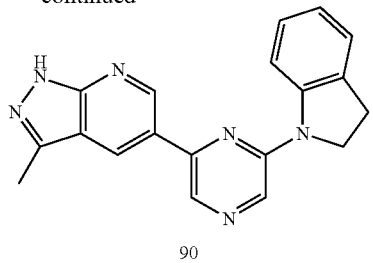

90

Example 61

5-(6-(indolin-1-yl)pyrazin-2-yl)-1-(4-methoxybenzyl)-3-methyl-1H-pyrazolo[3,4-b]pyridine

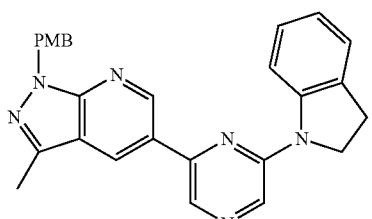

89

To a stirred solution of 8 and 88 in 1,2-dimethoxyethane was added water, Cs₂CO₃ followed by degassing, purging with N₂ for 15 min and addition of Pd(PPh₃)₄. The reaction mixture was heated at 100° C. in a sealed tube overnight. After completion of the reaction the reaction mass was partitioned between ethyl acetate and water and the organic layer was separated and again extracted with ethyl acetate. The combined organic layers were dried over sodium sulphate and the solvent completely distilled off to get the crude. The crude was passed through 100-200 mesh silica gel eluting the pure compound at 50% ethyl acetate in hexane as off-white coloured solid compound 89 (40 mg).

Example 62

5-(6-(indolin-1-yl)pyrazin-2-yl)-3-methyl-1H-pyrazolo[3,4-b]pyridine

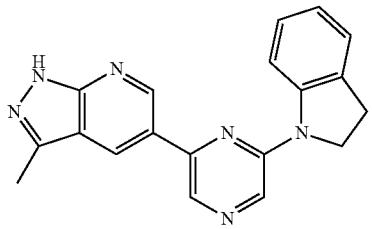

90

To a stirred solution of 89 in chloroform was added trifluoroacetic acid and the mixture heated at 50° C. overnight. The solvents were removed and diluted with cold water and pH was adjusted to 8, the aqueous phase extracted with CH₂Cl₂ twice. The organic layer was washed with brine solution and dried over sodium sulphate and the solvent distilled off to get the crude product. The crude was passed through aluminium oxide (neutral) eluting with 30% EtOAc and hexane to yield pale yellow solid compound 90 (15 mg). MS m/z 329.0 (M+H)+.

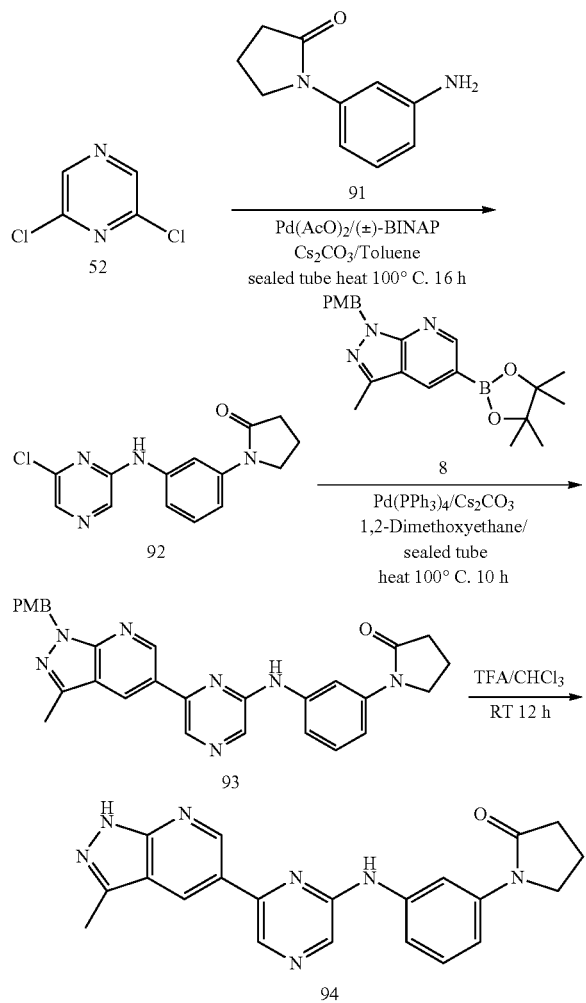

Example 63

1-(3-((6-chloropyrazin-2-yl)amino)phenyl)pyrrolidin-2-one

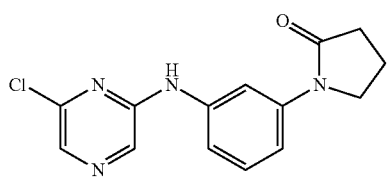

To a stirred solution of 52 and 91 in toluene was added Pd(OAc)₂, Cs₂CO₃ and the resulting reaction mixture was degassed, purged with N₂, racemic BINAP was added and the reaction mixture was heated at 100° C. overnight under sealed conditions. After completion of the reaction the solvents were removed and the product was passed through 100-200 mesh silica gel eluting the pure compound at 8% methanol in DCM to obtain the intermediate 92 (10 mg).

Example 64

1-(3-((6-(1-(4-methoxybenzyl-3-methyl-1H-pyrazolo[3,4-b]pyridin-5-yl)pyrazin-2-yl)amino)phenyl)pyrrolidin-2-one

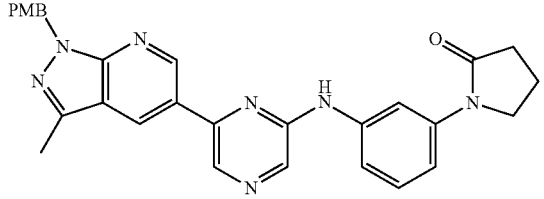

To a stirred solution of 8 and 92 in 1,2-dimethoxyethane was added Cs₂CO₃ followed by degassing, purging with N₂ for 15 min and addition of Pd(PPh₃)₄. The reaction mixture was heated at 100° C. in a sealed tube overnight. After completion of the reaction the reaction mass was partitioned between ethyl acetate and water and the organic layer was separated and again extracted with ethyl acetate. The combined organic layers were dried over sodium sulphate and the solvent completely distilled off to get the crude. The crude was passed through 100-200 mesh silica gel eluting the pure compound at 50% ethyl acetate in hexane as off-white coloured solid compound 93 (40 mg).

Example 65

1-(3-((6-(3-methyl-1H-pyrazolo[3,4-b]pyridin-5-yl)pyrazin-2-yl)amino)phenyl)pyrrolidin-2-one

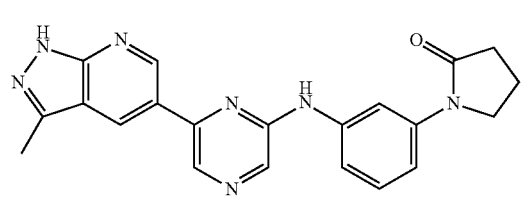

To a stirred solution of 93 in chloroform was added trifluoroacetic acid and the mixture heated at 50° C. overnight. The solvents were removed and diluted with cold water and pH was adjusted to 8, the aqueous phase extracted with CHCl₃ twice. The organic layer was washed with brine solution and dried over sodium sulphate and the solvent distilled off to get the crude product. The crude was passed through neutral alumina eluting the pure compound at 4% MeOH/CHCl₃ as pale yellow solid 94 (20 mg). MS m/z 386.1 (M+H)+.

Reaction Scheme 22

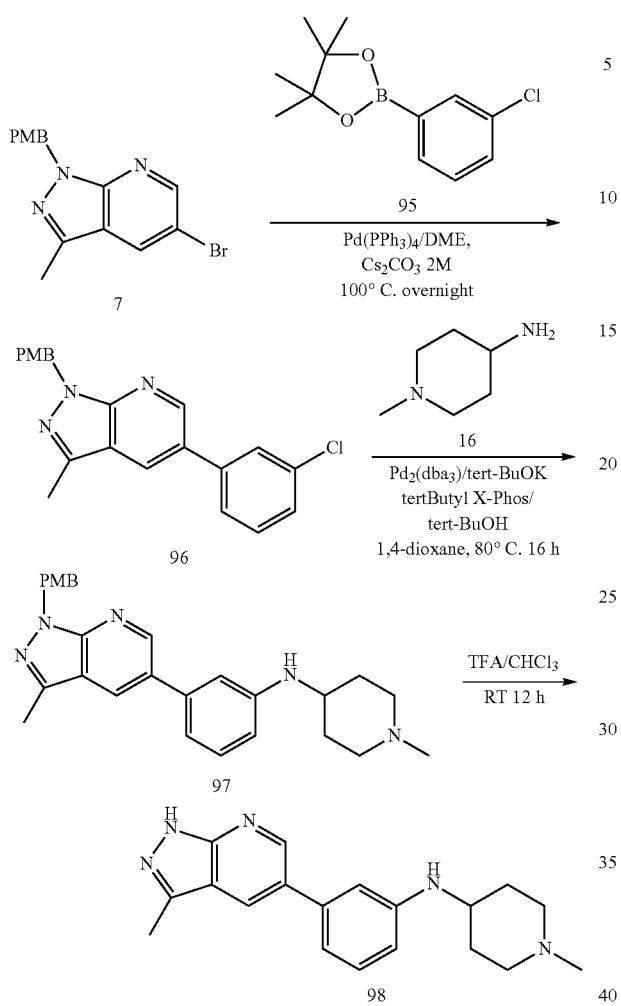

Example 66

5-(3-chlorophenyl)-1-(4-methoxybenzyl)-3-methyl-1H-pyrazolo[3,4-b]pyridine

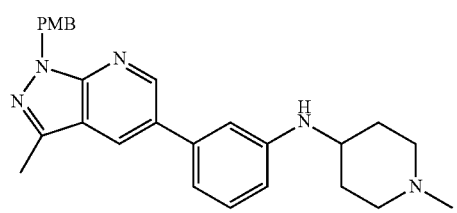

To a stirred solution of 5-bromo-1-(4-methoxybenzyl)-3-methyl-1H-pyrazolo[3,4-b]pyridine (7) (100 mg, 0.301 mmol, 1 eq) and 2-(3-chlorophenyl)-4,4,5,5-tetramethyl-1,3,2-dioxaborolane (95) (71 mg, 0.301 mmol, 1 eq) in 1,2-dimethoxyethane (10 mL) was added $Cs_2CO_3$ (244 mg, 0.752 mmol, 25 eq) 2M aqueous solution followed by degassing, purging with $N_2$ for 15 min and addition of $Pd(PPh_3)_4$ (13 mg, 0.012 mmol, 0.04 eq). The reaction mixture was heated at 100° C. in a sealed tube overnight. After completion of the reaction the mixture was partitioned between ethyl acetate and water and the organic layer was separated and again extracted with ethyl acetate. The combined organic layers were dried over sodium sulphate and the solvent completely distilled off to get the crude. The crude was passed through 100-200 mesh silica gel eluting the pure compound at 50% ethyl acetate in hexane as off-white coloured solid compound 96 (60 mg).

Example 67

N-(3-(1-(4-methoxybenzyl)-3-methyl-1H-pyrazolo[3,4-b]pyridin-5-yl)phenyl)-1-methylpiperidin-4-amine

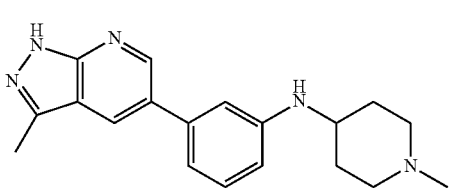

To a stirred solution of 5-(3-chlorophenyl)-1-(4-methoxybenzyl)-3-methyl-1H-pyrazolo[3,4-b]pyridine (96) (50 mg, 0.137 mmol) in tert-BuOH (4 mL), 1,4 dioxane (6 mL) was added 1-methylpiperidin-4-amine (16) (14 mg, 0.23 mmol, 0.9 eq) and tert-BuOK (38 mg, 0.344 mmol, 2.5 eq). The resulting reaction mixture was degassed, purged with $N_2$ for 10 min and $Pd_2(dba)_3$ (5 mg, 0.00549 mmol, 0.04 eq) and tertButyl X-phos (0.08 eq) was added, the mixture was degassed and purged with nitrogen for 15 min. The reaction mixture was stirred overnight at 80° C. under sealed condition for 16 h. After completion of the reaction the reaction mass was diluted with water and extracted with ethyl acetate. The organic layer was dried over sodium sulphate and solvent completely distilled off to get the crude. The crude was passed through 100-200 mesh silica gel. Eluting the pure compound at 5% MeOH/CHCl$_3$ gave 25 mg of N-(3-(1-(4-methoxybenzyl)-3-methyl-1H-pyrazolo[3,4-b]pyridin-5-yl)phenyl)-1-methylpiperidin-4-amine 97.

Example 68

1-methyl-N-(3-(3-methyl-1H-pyrazolo[3,4-b]pyridin-5-yl)phenyl)piperidin-4-amine

To a stirred solution of N-(3-(1-(4-methoxybenzyl)-3-methyl-1H-pyrazolo[3,4-b]pyridin-5-yl)phenyl)-1-methylpiperidin-4-amine (97) (25 mg, 0.056 mmol) in chloroform (10 mL) was added trifluoroacetic acid (5 mL) and the mixture was heated at 50° C. overnight. The solvents were removed and diluted with cold water and pH was adjusted to 8, the aqueous phase extracted with CHCl₃ twice. The organic layer was washed with brine solution and dried over sodium sulphate and the solvent distilled off to get the crude product. The crude was passed through neutral alumina eluting the pure compound at 2% MeOH/CHCl₃ as pale yellow solid 1-methyl-N-(3-(3-methyl-1H-pyrazolo[3,4-b]pyridin-5-yl)phenyl)piperidin-4-amine 98 (8 mg).

Reaction Scheme 23

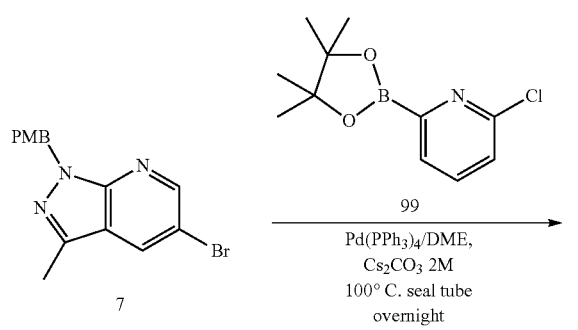

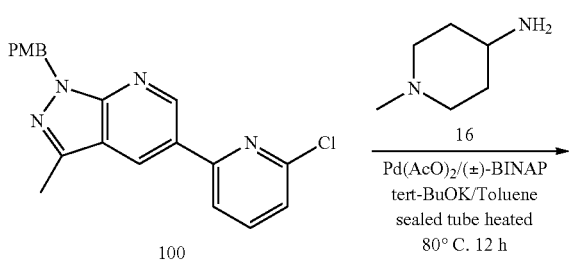

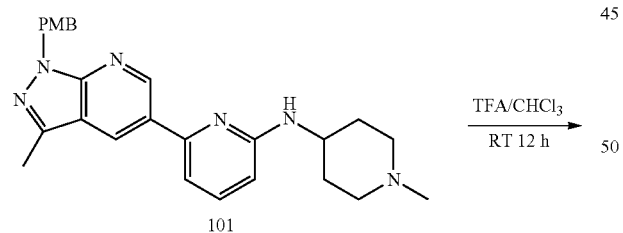

Example 69

5-(6-chloropyridin-2-yl)-1-(4-methoxybenzyl)-3-methyl-1H-pyrazolo[3,4-b]pyridine

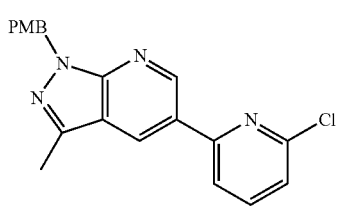

To a stirred solution of 5-bromo-1-(4-methoxybenzyl)-3-methyl-1H-pyrazolo[3,4-b]pyridine (7) (139 mg, 0.418 mmol) in 1,2-dimethoxyethane (10 mL) was added 2-chloro-6-(4,4,5,5-tetramethyl-1,3,2-dioxaborolan-2-yl)pyridine (99) (100 mg, 0.418 mmol) and Cs₂CO₃ (32 mg, 0.104 mmol). The resulting reaction mixture was degassed, purged with N₂ for 15 min, Pd(PPh₃)₄ (19 mg, 0.0167 mmol) was added and the mixture purged again under nitrogen for another 15 min. The reaction mass was heated at 100° C. in a sealed tube for 12 h. After completion of the reaction the reaction mass was partitioned between ethyl acetate and water and the organic layer was separated and extracted with ethyl acetate. The combined organic layer was dried over Na₂SO₄ and the solvent completely distilled off to get the crude product. The crude material was passed through 100-200 mesh silica gel eluting the pure compound at 50% ethyl acetate in hexane to yield off white colored solid compound 5-(6-chloropyridin-2-yl)-1-(4-methoxybenzyl)-3-methyl-1H-pyrazolo[3,4-b]pyridine 100 (60 mg).

Example 70

6-(1-(4-methoxybenzyl)-3-methyl-1H-pyrazolo[3,4-b]pyridin-5-yl)-N-(1-methyl-piperidin-4-yl)pyridin-2-amine

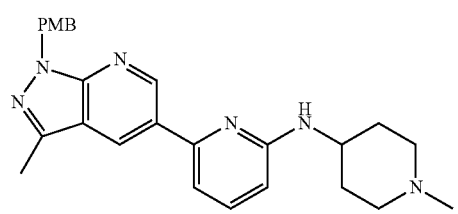

To a stirred solution of 5-(3-chlorophenyl)-1-(4-methoxybenzyl)-3-methyl-1H-pyrazolo[3,4-b]pyridine (96) (60 mg, 0.164 mmol, 1 eq) and 1-methylpiperidin-4-amine (16) (81 mg, 0.164 mmol, 1.0 eq) in 1,4 dioxane (10 mL) was added tert-BuOK (46 mg, 0.411 mmol, 2.5 eq), the mixture was then degassed and purged with nitrogen for 10 min. Pd₂(dba)₃ (5 mg, 0.00549 mmol, 0.04 eq) and racemic BINAP (0.03 eq) was added and the reaction mixture again degassed and purged again with nitrogen for 15 min. The reaction mass was stirred overnight at 80° C. under sealed condition. After completion of the reaction the reaction mass was diluted with water and extracted with ethyl acetate. The organic layer was dried over sodium sulphate and the solvents were removed to get the crude material which was passed through 100-200 mesh silica gel eluting the pure 6-(1-(4-methoxybenzyl)-3-methyl-1H-pyrazolo[3,4-b]pyridin-5-yl)-N-(1-methylpiperidin-4-yl)pyridin-2-amine 101 at 2% MeOH/CHCl₃ to yield 30 mg.

Example 71

6-(3-methyl-1H-pyrazolo[3,4-b]pyridin-5-yl)-N-(1-methylpiperidin-4-yl)pyridin-2-amine

102

To a stirred solution of 6-(1-(4-methoxybenzyl)-3-methyl-1H-pyrazolo[3,4-b]pyridin-5-yl)-N-(1-methylpiperidin-4-yl)pyridin-2-amine (101) (25 mg, 0.0678 mmol) in chloroform (10 mL) was added trifluoroacetic acid (5 mL) and the mixture heated at 50° C. overnight. The solvents were removed and diluted with cold water and pH was adjusted to 8, the aqueous phase extracted with CHCl₃ twice. The organic layer was washed with brine solution and dried over sodium sulphate and the solvent distilled off to get the crude product. The crude was passed through neutral alumina eluting the pure compound at 2% MeOH/CHCl₃ as pale yellow solid 6-(3-methyl-1H-pyrazolo[3,4-b]pyridin-5-yl)-N-(1-methylpiperidin-4-yl)pyridin-2-amine 102 obtained in 8 mg yield.

Reaction Scheme 24

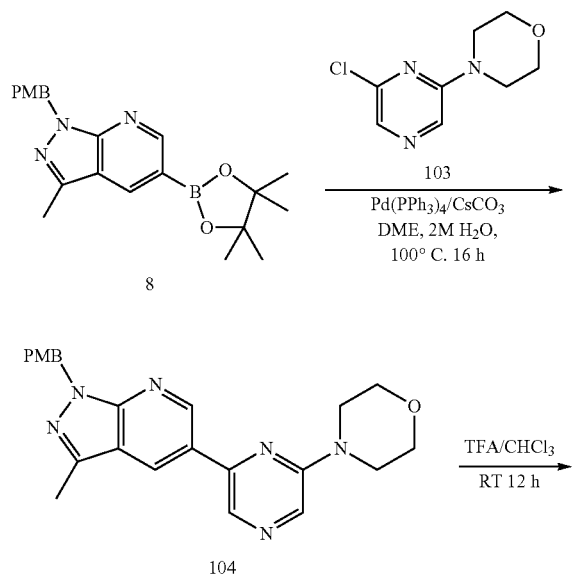

-continued

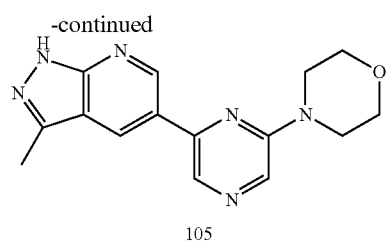

105

Example 72

4-(6-(1-(4-methoxybenzyl)-3-methyl-1H-pyrazolo[3,4-b]pyridin-5-yl)pyrazin-2-yl)morpholine

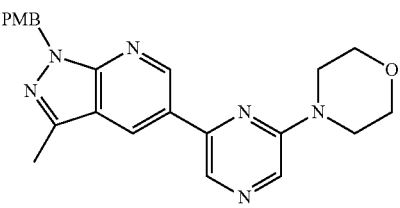

104

To a stirred solution of 1-(4-methoxybenzyl)-3-methyl-5-(4,4,5,5-tetramethyl-1,3,2-dioxaborolan-2-yl)-1H-pyrazolo[3,4-b]pyridine (8) (190 mg, 0.50 mmol, 1 eq) and 4-(6-chloropyrazin-2-yl)morpholine (103) (100 mg, 0.50 mmol, 1 eq) in 1,2-diemthoxyethane (5 mL) was added CsCO₃ (400 mg, 2.5 eq) in 2M H₂O and the resulting reaction mixture was degassed and purged with nitrogen for 10 min. Pd(PPh)₃ (0.023 mg, 0.04 mmol) was charged and the reaction mixture degassed and purged again with nitrogen for another 15 min. The reaction mass was stirred overnight at 100° C. under sealed condition 12 hrs. After completion of the reaction the reaction mass was diluted with water and extracted with ethyl acetate. The organic layer was dried over sodium sulphate and the solvents were removed to get the crude material which was passed through 100-200 mesh silica gel eluting the pure 4-(6-(1-(4-methoxybenzyl)-3-methyl-1H-pyrazolo[3,4-b]pyridin-5-yl)pyrazin-2-yl)morpholine 104 at 50% EtOAc in hexane, providing off-white solid in yield of 60 mg.

Example 73

4-(6-(3-methyl-1H-pyrazolo[3,4-b]pyridin-5-yl)pyrazin-2-yl)morpholine

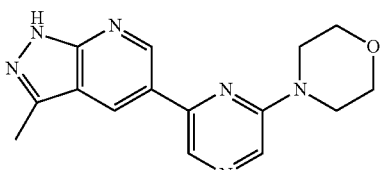

105

To a stirred solution of 4-(6-(1-(4-methoxybenzyl)-3-methyl-1H-pyrazolo[3,4-b]pyridin-5-yl)pyrazin-2-yl)morpholine (104) (60 mg, 0.144 mmol) in chloroform (10 mL) was added trifluoroacetic acid (5 mL) and the reaction mixture was heated at 50° C. overnight. The solvents were removed and diluted with cold water and pH was adjusted to 8, the aqueous phase extracted with CHCl₃ twice. The organic layer was washed with brine solution and dried over sodium sulphate and the solvent distilled off to get the crude product. The crude was passed through 100-200 mesh silica gel eluting the compound at 50% ethyl acetate in hexane as pale yellow solid 4-(6-(3-methyl-1H-pyrazolo[3,4-b]pyridin-5-yl)pyrazin-2-yl)morpholine 105 in 30 mg quantity. MS m/z 296.9 (M+H)⁺.

Reaction Scheme 25

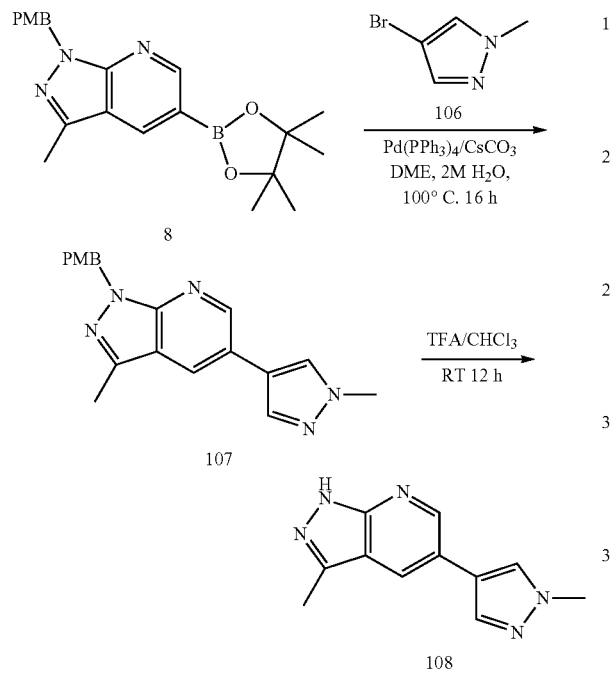

Example 74

1-(4-methoxybenzyl)-3-methyl-5-(1-methyl-1H-pyrazol-4-yl)-1H-pyrazolo[3,4-b]pyridine

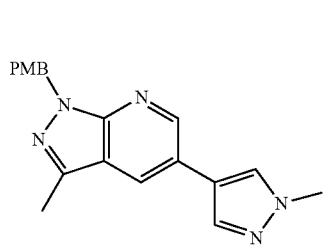

107

To a solution of 1-(4-methoxybenzyl)-3-methyl-5-(4,4,5,5-tetramethyl-1,3,2-dioxaborolan-2-yl)-1H-pyrazolo[3,4-b]pyridine (8) (100 mg, 0.302 mmol, 1 eq) and 4-bromo-1-methyl-1H-pyrazole (106) (62 mg, 0.302 mmol, 1 eq) in 1,2-dimethoxyethane (8 mL) was added Cs₂CO₃ (325.18 mg, 0.604 mmol, 2 eq), the reaction mixture was degassed and purged under N₂ for 15 min and Pd(PPh3)₄ (10 mg, 0.009, 0.03 eq) was added and the reaction mixture again purged under N₂ for another 15 min. The reaction mixture was heated at 100° C. in a sealed tube overnight. After completion, the reaction mixture was partitioned between ethyl acetate/water; the organic layer was separated and extracted again into ethyl acetate. The combined organic layer was dried over sodium sulphate and the solvents were removed to get the crude product. The crude material was flashed through 100-200 mesh silica gel eluting the pure compound in 25% EtOAc/Hexane as off-white coloured solid 1-(4-methoxybenzyl)-3-methyl-5-(1-methyl-1H-pyrazol-4-yl)-1H-pyrazolo[3,4-b]pyridine 107 (60 mg).

Example 75

3-methyl-5-(1-methyl-1H-pyrazol-4-yl)-1H-pyrazolo[3,4-b]pyridine

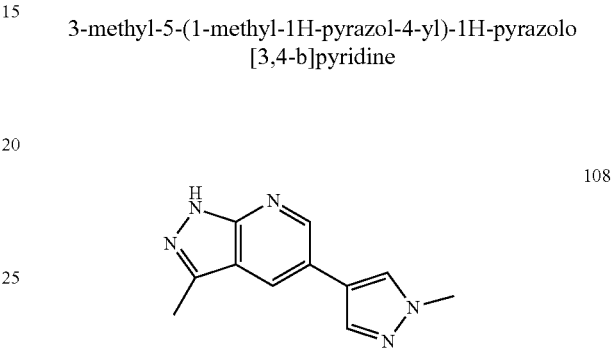

To a solution of 1-(4-methoxybenzyl)-3-methyl-5-(1-methyl-1H-pyrazol-4-yl)-1H-pyrazolo[3,4-b]pyridine (107) (60 mg, 0.179 mmol) dissolved in chloroform (10 mL) was added trifluoroacetic acid (5 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 80% ethyl acetate in hexane as pale yellow solid 3-methyl-5-(1-methyl-1H-pyrazol-4-yl)-1H-pyrazolo[3,4-b]pyridine Reaction Scheme 26

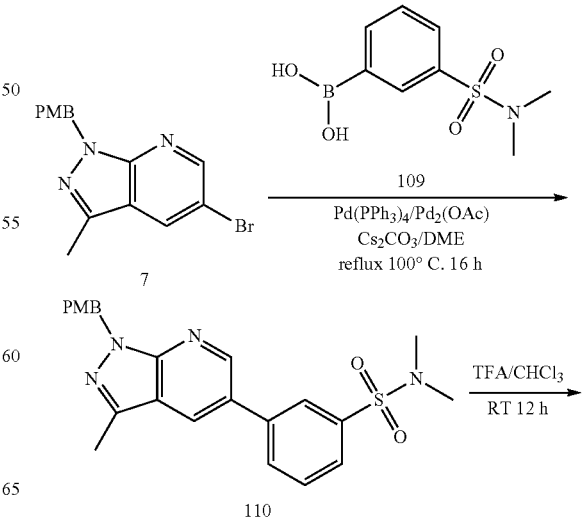

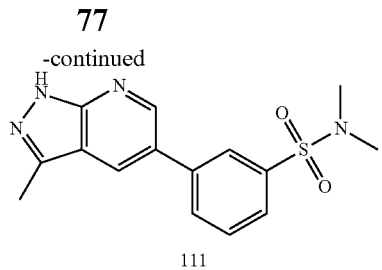

111

Example 76

3-(1-(4-methoxybenzyl)-3-methyl-1H-pyrazolo[3,4-b]pyridin-5-yl)-N,N-dimethyl benzenesulfonamide

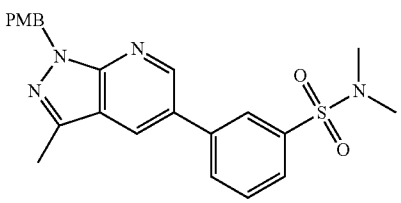

110

To a stirred solution of 5-bromo-1-(4-methoxybenzyl)-3-methyl-1H-pyrazolo[3,4-b]pyridine (7) (100 mg, 0.302 mmol, 1 eq) and (3-(N,N-dimethylsulfamoyl)phenyl)boronic acid (109) (54 mg, 0.302 mmol, 1 eq) in 1,2-dimethoxyethane (6 mL) was added $Cs_2CO_3$ (189 mg, 0.604 mmol, 2 eq), the reaction mixture was degassed and purged under $N_2$ for 15 min and Pd(PPh3)$_4$ (10 mg, 0.008, 0.03 eq) was added and again purged under $N_2$ for another 15 min. The reaction mixture was heated to 100° C. in sealed tube for 16 hrs. After completion, the reaction mixture was partitioned between ethyl acetate/water; the organic layer was separated and extracted again into ethyl acetate. The combined organic layer was dried over sodium sulphate and the solvents were removed to get the crude product. The crude material was flashed through 100-200 mesh silica gel eluting the pure compound in 40% EtOAc/Hexane as off-white colored solid 3-(1-(4-methoxybenzyl)-3-methyl-1H-pyrazolo[3,4-b]pyridin-5-yl)-N,N-dimethyl benzenesulfonamide 110 (50 mg).

Example 77

N,N-dimethyl-3-(3-methyl-1H-pyrazolo[3,4-b]pyridin-5-yl)benzenesulfonamide

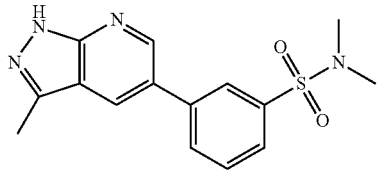

111

To a solution of 3-(1-(4-methoxybenzyl)-3-methyl-1H-pyrazolo[3,4-b]pyridin-5-yl)-N,N-dimethylbenzene-sulfonamide (110) (50 mg, 0.114 mmol) dissolved in chloroform (10 mL) was added trifluoroacetic acid (5 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 70% ethyl acetate in hexane as pale yellow solid N,N-dimethyl-3-(3-methyl-1H-pyrazolo[3,4-b]pyridin-5-yl)benzenesulfonamide 111 (30 mg). MS m/z 316.9 (M+H)$^+$.

Reaction Scheme 27

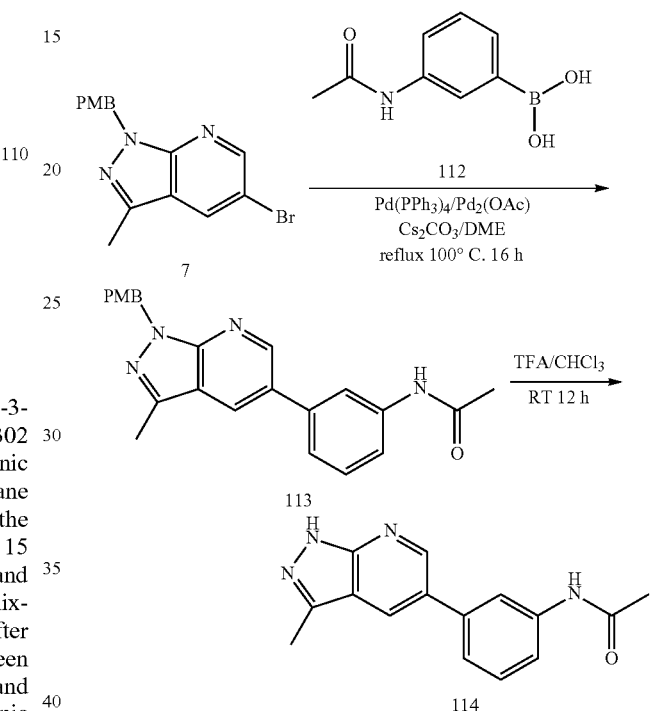

Example 78

N-(3-(1-(4-methoxybenzyl)-3-methyl-1H-pyrazolo[3,4-b]pyridin-5-yl)phenyl)acetamide

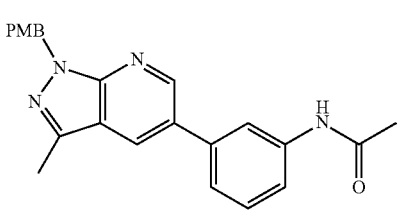

113

To a stirred solution of 5-bromo-1-(4-methoxybenzyl)-3-methyl-1H-pyrazolo[3,4-b]pyridine (7) (160 mg, 0.505 mmol, 1 eq) and (3-acetamidophenyl)boronic acid (112) (100 mg, 0.505 mmol, 1 eq) in 1,2-dimethoxyethane (6 mL) was added $Cs_2CO_3$ (246 mg, 0.750 mmol, 1.5 eq) and Pd$_2$(OAc), the reaction mixture was degassed and purged under $N_2$ for 15 min and Pd(PPh3)$_4$ (10 mg, 0.008, 0.03 eq) was added and the mixture was again purged under $N_2$ for another 15 min. The reaction mixture was heated to 100° C. in a sealed tube for 16 hrs. After completion, the reaction mixture was partitioned between ethyl acetate/water; the organic layer was separated and extracted again into ethyl acetate. The combined organic layer was dried over sodium sulphate and the solvents were removed to get the crude product. The crude material was flashed through 100-200 mesh silica gel eluting the pure compound in 40% EtOAc/Hexane as off-white coloured solid N-(3-(1-(4-methoxybenzyl)-3-methyl-1H-pyrazolo[3,4-b]pyridin-5-yl)phenyl)acetamide 113 (50 mg).

Example 79

N-(3-(3-methyl-1H-pyrazolo[3,4-b]pyridin-5-yl)phenyl)acetamide

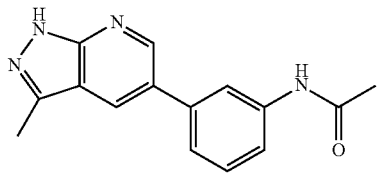

114

To a solution of N-(3-(1-(4-methoxybenzyl)-3-methyl-1H-pyrazolo[3,4-b]pyridin-5-yl)phenyl)acetamide (113) (50 mg, 0.129 mmol) dissolved in chloroform (10 mL) was added trifluoroacetic acid (5 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 40% ethyl acetate in hexane as pale yellow solid N-(3-(3-methyl-1H-pyrazolo[3,4-b]pyridin-5-yl)phenyl)acetamide 114 (30 mg). MS m/z 266.9 (M+H)+.

Reaction Scheme 28

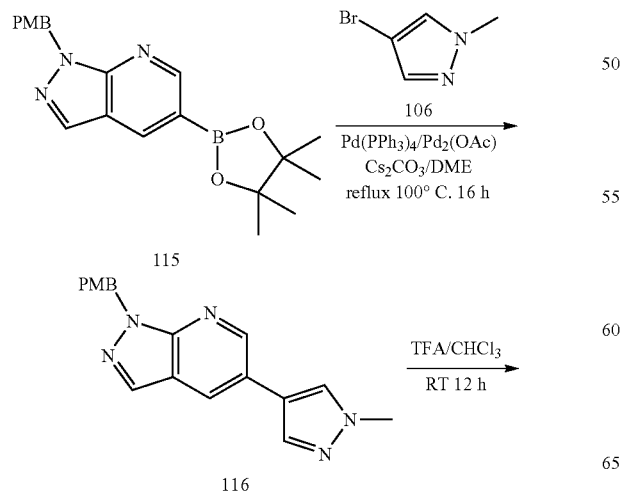

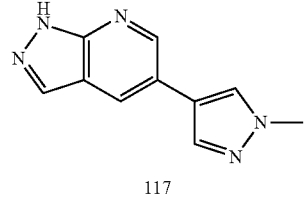

117

Example 80

1-(4-methoxybenzyl)-5-(1-methyl-1H-pyrazol-4-yl)-1H-pyrazolo[3,4-b]pyridine

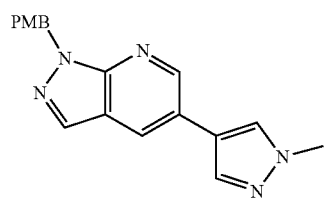

116

To a stirred solution of 1-(4-methoxybenzyl)-5-(4,4,5,5-tetramethyl-1,3,2-dioxaborolan-2-yl)-1H-pyrazolo[3,4-b]pyridine (115) (100 mg, 0.302 mmol, 1 eq) and 4-bromo-1-methyl-1H-pyrazole (106) (54 mg, 0.302 mmol, 1 eq) in 1,2-dimethoxyethane (6 mL) was added Cs$_2$CO$_3$ (189 mg, 0.604 mmol, 2 eq) and Pd$_2$(OAc) (0.03 eq), the reaction mixture was degassed and purged under N$_2$ for 15 min and Pd(PPh3)$_4$ (17 mg, 0.0151, 0.03 eq) was added and the reaction mixture again purged under N$_2$ for another 15 min. The reaction mixture was heated to 100° C. in a sealed tube for 16 hrs. After completion, the reaction mixture was partitioned between ethyl acetate/water; the organic layer was separated and extracted again into ethyl acetate. The combined organic layer was dried over sodium sulphate and the solvents were removed to get the crude product. The crude material was flashed through 100-200 mesh silica gel eluting the pure compound in 25% EtOAc/Hexane as off-white coloured solid 1-(4-methoxybenzyl)-5-(1-methyl-1H-pyrazol-4-yl)-1H-pyrazolo[3,4-b]pyridine 116 (40 mg).

Example 81

5-(1-methyl-1H-pyrazol-4-yl)-1H-pyrazolo[3,4-b]pyridine

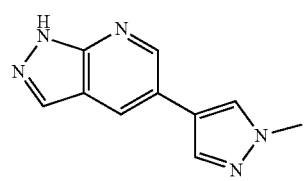

117

To a solution of 1-(4-methoxybenzyl)-5-(1-methyl-1H-pyrazol-4-yl)-1H-pyrazolo[3,4-b]pyridine (116) (40 mg, 0.125 mmol) dissolved in chloroform (10 mL) was added trifluoroacetic acid (5 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 40% ethyl acetate in hexane as pale yellow solid of 5-(1-methyl-1H-pyrazol-4-yl)-1H-pyrazolo[3,4-b]pyridine 117 obtained in 10 mg quantity. MS m/z 199.9 (M+H)+.

Reaction Scheme 29

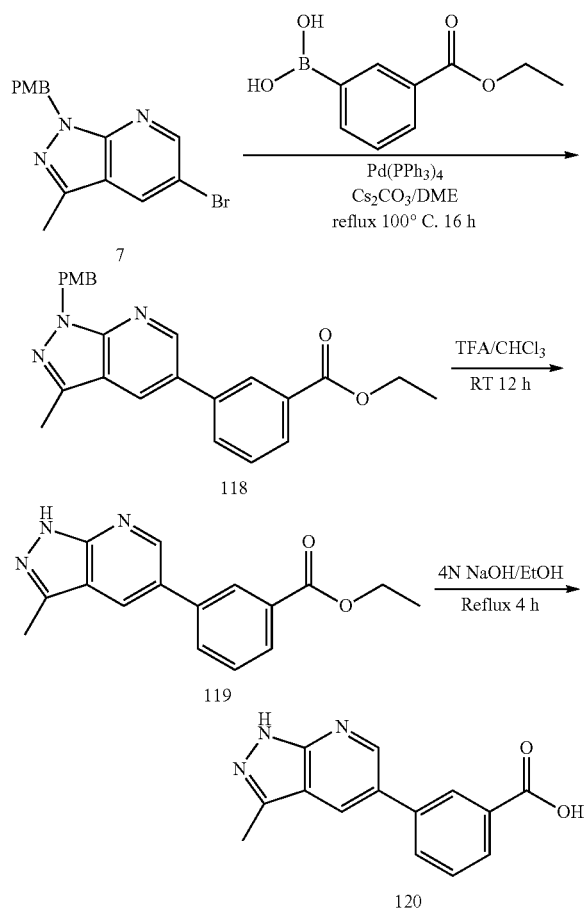

Example 82 ethyl 3-(1-(4-methoxybenzyl)-3-methyl-1H-pyrazolo[3,4-b]pyridin-5-yl)benzoate

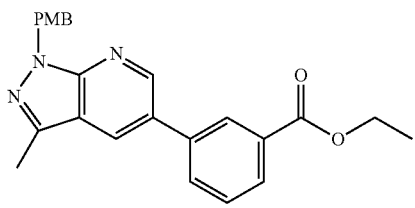

To a stirred solution of 5-bromo-1-(4-methoxybenzyl)-3-methyl-1H-pyrazolo[3,4-b]pyridine (7) (171 mg, 0.515 mmol, 1 eq) and (3-(ethoxycarbonyl)phenyl)boronic acid (100 mg, 0.515 mmol, 1 eq) in 1,2-dimethoxyethane (6 mL) was added Cs$_2$CO$_3$ (335 mg, 1.03 mmol, 2.0 eq). The reaction mixture was degassed and purged under N$_2$ for 15 min and Pd(PPh3)$_4$ (0.0238 mg, 0.0206, 0.04 eq) was added and the reaction mixture again purged under N$_2$ for another 15 min. The reaction mixture was heated at 100° C. in a sealed tube for 16 hrs. After completion, the reaction was partitioned between ethyl acetate/water; the organic layer was separated and extracted again into ethyl acetate. The combined organic layer was dried over sodium sulphate and the solvents were removed to get the crude product. The crude material was flashed through 100-200 mesh silica gel eluting the pure compound in 25% EtOAc/Hexane as off-white coloured solid ethyl 3-(1-(4-methoxybenzyl)-3-methyl-1H-pyrazolo[3,4-b]pyridin-5-yl)benzoate 118 (70 mg).

Example 83 ethyl 3-(3-methyl-1H-pyrazolo[3,4-b]pyridin-5-yl)benzoate

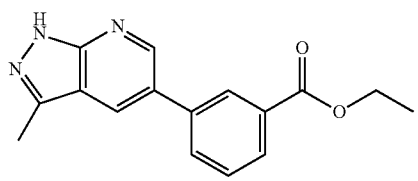

To a solution of 3-(1-(4-methoxybenzyl)-3-methyl-1H-pyrazolo[3,4-b]pyridin-5-yl)benzoate (118) (70 mg, 0.74 mmol) dissolved in chloroform (5 mL) was added trifluoroacetic acid (8 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 40% ethyl acetate in hexane as pale yellow solid of ethyl 3-(3-methyl-1H-pyrazolo[3,4-b]pyridin-5-yl)benzoate 119 obtained in 10 mg quantity. MS m/z 281.9 (M+H)+.

Example 84

3-(3-methyl-1H-pyrazolo[3,4-b]pyridin-5-yl)benzoic acid

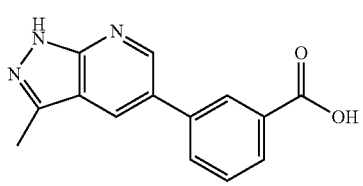

To a stirred solution of ethyl 3-(3-methyl-1H-pyrazolo[3,4-b]pyridin-5-yl)benzoate (119) (10 mg, 0.142, 1 eq) in ethanol (5 mL) was added 4N sodium hydroxide solution (4 mL) and the reaction mixture was stirred at room temperature for 4 hrs. After completion of the reaction the solvents were distilled off and diluted with water and the pH adjusted to 4 and extracted into chloroform. The organic layer was dried over sodium sulphate and the solvents were removed to get the compound 3-(3-methyl-1H-pyrazolo[3,4-b]pyridin-5-yl)benzoic acid 120 and this was further titrated with hexane and diethyl ether to get 15 mg of 120.

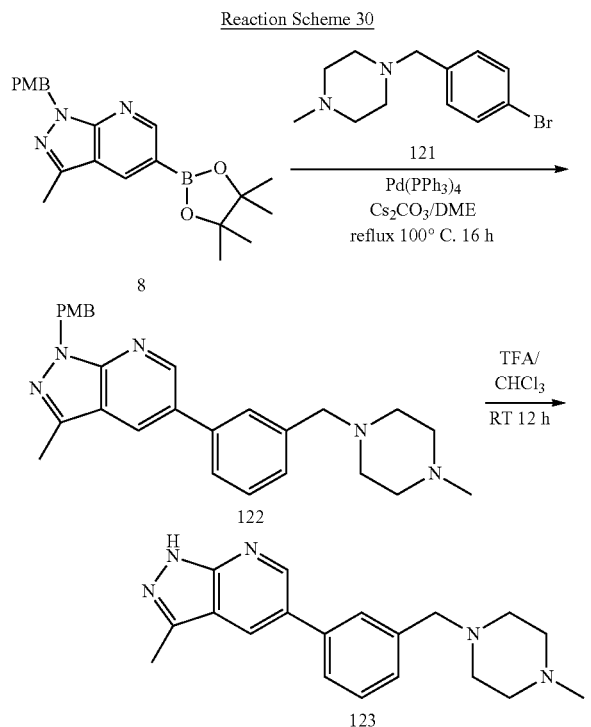

Example 85

1-(4-methoxybenzyl)-3-methyl-5-(3-((4-methylpiperazin-1-yl)methyl)phenyl)-1H-pyrazolo[3,4-b]pyridine

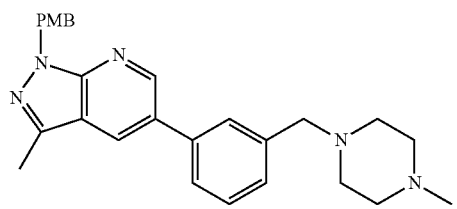

To a solution of 1-(4-methoxybenzyl)-3-methyl-5-(4,4,5,5-tetramethyl-1,3,2-dioxaborolan-2-yl)-1H-pyrazolo[3,4-b]pyridine (8) (100 mg, 0.263 mmol, 1 eq) and 1-(4-bromobenzyl)-4-methylpiperazine (121) (77 mg, 0.29 mmol, 1 eq) in 1,2-dimethoxyethane (10 mL) was added $Cs_2CO_3$ (257 mg, 0.791 mmol, 3 eq), the reaction mixture was degassed and purged under $N_2$ for min and $Pd(PPh_3)_4$ (12 mg, 0.00105, 0.04 eq) was added and again the reaction mixture was purged under $N_2$ for another 15 min. The reaction mixture was heated at 100° C. in a sealed tube overnight. After completion, the reaction mixture was partitioned between $CHCl_3/H_2O$; the organic layer was separated and extracted again into $CHCl_3$. The combined organic layer was dried over sodium sulphate and the solvents were removed to get the crude product. The crude material was flashed through 100-200 mesh silica gel eluting the pure compound in 6% $MeOH/CHCl_3$ as off-white coloured solid 1-(4-methoxybenzyl)-3-methyl-5-(3-((4-methylpiperazin-1-yl)methyl)phenyl)-1H-pyrazolo[3,4-b]pyridine 122 (50 mg). MS m/z 442.1 $(M+H)^+$.

Example 86

3-methyl-5-(3-((4-methylpiperazin-1-yl)methyl)phenyl)-1H-pyrazolo[3,4-b]pyridine To a solution of 1-(4-methoxybenzyl)-3-methyl-5-(3-((4-methylpiperazin-1-yl)methyl)phenyl)-1H-pyrazolo[3,4-b]pyridine (122) (30 mg, 0.136 mmol) dissolved in chloroform (25 mL) was added trifluoroacetic acid (6 mL) and the reaction mixture was heated at 50° C. for 12 h. After completion of the reaction the solvents were removed and diluted with cold water, pH was adjusted to 8 and the aqueous phase extracted with chloroform two times. The organic layer was washed with brine solution and dried over sodium sulphate and the solvents were removed. The crude was passed through 100-200 mesh silica gel eluting the compound at 7% $MeOH/CHCl_3$ as pale yellow solid of 3-methyl-5-(3-((4-methylpiperazin-1-yl)methyl)phenyl)-1H-pyrazolo[3,4-b]pyridine 123 obtained in 10 mg quantity. MS m/z 322.1 $(M+H)^+$.

General Procedures for the Schemes 31-46

The key building block 5-(4,4,5,5-tetramethyl-1,3,2-dioxaborolan-2-yl)-1H-pyrrolo[2,3-b]pyridine 124 (1 eq), 2-substituted heteroaryl halogen containing scaffolds (1.0 eq) in either DMF, DME, toluene, acetonitrile, tert-BuOH, THF and or 1,4-dioxane was taken in a sealed tube. The resulting reaction mixture was degassed, purged with argon or $N_2$ gas a few times and was charged with $NaCO_3$, $Cs_2CO_3$, $K_2CO_3$, potassium acetate or $NaHCO_3$ (between 1.5 to 2 equivalents) followed by the addition of palladium catalysts (0.01 to 0.05 eq). After the addition of catalysts the contents of the reaction were purged and degassed again and the reaction mixture was heated at between 80 to 100° C. for 8 to 16 hrs. After completion of the reaction monitored from TL, the contents were cooled to room temperature and diluted with $CH_2Cl_2$, $CHCl_3$ or EtOAc. The organic layers were passed through a Celite pad then the solvent was completely distilled off to get the crude product. The crude was subjected to flash column chromatography purification to get the title compounds.

Example 87

5-(6-(4-methylpiperazin-1-yl)pyrazin-2-yl)-1H-pyrrolo[2,3-b]pyridine

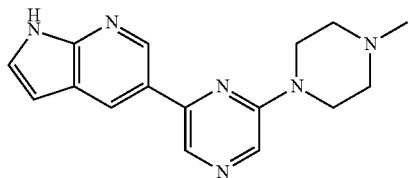
125

The starting material 5-(4,4,5,5-tetramethyl-1,3,2-dioxaborolan-2-yl)-1H-pyrrolo[2,3-b]pyridine (124) (50 mg, 0.2 mmol, 1 eq) and 2-chloro-6-(4-methylpiperazin-1-yl)pyrazine (63) (44 mg, 0.2 mmol, 1 eq) in DMF (5 mL) was degassed and purged under argon atmosphere for 10 min. To this reaction mixture was charged $Cs_2CO_3$ (133 mg, 0.4 mmol, 2 eq) followed by addition of $Pd(PPh_3)_4$ (0.01 mg, 0.04 mmol) and degassing and purging under argon for an additional 10 min. The reaction mixture was heated at 100° C. for 12 h in a sealed tube. After completion of the reaction, the reaction mixture was diluted with $CHCl_3$ and filtered through Celite. The solvents were distilled off and the crude material was submitted for flash column purification in neutral alumina using 2% $MeOH/CHCl_3$ to obtain pale yellow solid compound 5-(6-(4-methylpiperazin-1-yl)pyrazin-2-yl)-1H-pyrrolo[2,3-b]pyridine 125 in 20 mg quantity. The compound 125 was confirmed by $^1$HNMR and LCMS. $^1$H NMR (400 MHz, $CDCl_3$) δ: 8.96 (d, J=1.5 Hz 1H), 8.55 (d, J=1.70 Hz, 1H), 8.30 (s, 1H), 8.08 (s, 1H), 7.35 (m, J=3.04, 1H), 6.60 (m, J=1.95 1H), 3.75 (m, J=5.00, 4H), 2.58 (m, J=5.12, 4H), 2.38 (s, 3H); MS m/z 294.9 $(M+H)^+$.

Example 88

2-(4-(6-(1H-pyrrolo[2,3-b]pyridin-5-yl)pyrazin-2-yl)piperazin-1-yl)ethanol

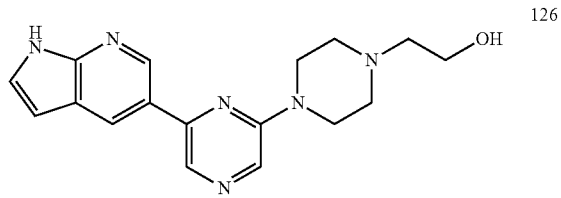 [SMILES: OCCN1CCN(c2cncc(-c3cnc4[nH]ccc4c3)n2)CC1]
126

The starting material 5-(4,4,5,5-tetramethyl-1,3,2-dioxaborolan-2-yl)-1H-pyrrolo[2,3-b]pyridine (124) (50 mg, 0.2 mmol, 1 eq) and 2-(4-(6-chloropyrazin-2-yl)piperazin-1-yl)ethanol (57) (49.5 mg, 0.2 mmol, 1 eq) in DME (5 mL) was degassed and purged under argon atmosphere for 10 min. To this reaction mixture was charged $Cs_2CO_3$ (133 mg, 0.4 mmol, 2 eq) followed by addition of $Pd(PPh_3)_4$ (1.0 mg, 0.04 mmol) and degassing and purging under argon for additional min. The reaction mixture was heated at 100° C. for 12 h in a sealed tube. After completion of the reaction, the reaction mixture was diluted with $CHCl_3$ and filtered through Celite. The solvents were distilled off and the crude material was submitted for flash column purification in neutral alumina using 3% $MeOH/CHCl_3$ to obtain pale yellow solid compound 2-(4-(6-(1H-pyrrolo[2,3-b]pyridin-5-yl)pyrazin-2-yl)piperazin-1-yl)ethanol 126 in 15 mg quantity. The compound 126 was confirmed by $^1$HNMR and LCMS. $^1$H NMR (400 MHz, $CDCl_3$) δ: 8.96 (s, 1H), 8.90 (s, 1H), 8.54 (s, 1H), 8.40 (s, 1H), 8.09 (s, 1H), 7.36 (m, J=289.99, 1H), 6.61 (m, J=301.8, 1H), 3.75 (m, J=5.0, 6H), 2.69 (m, J=4.84, 6H); MS m/z 324.9 $(M+H)^+$.

Reaction Scheme 31

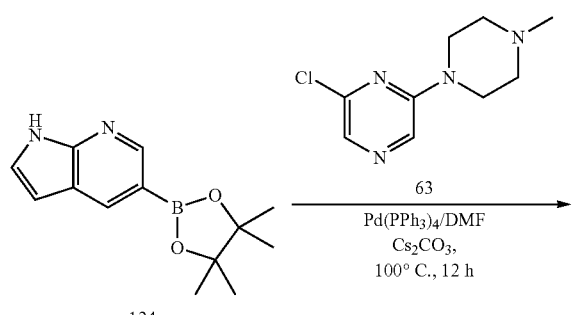

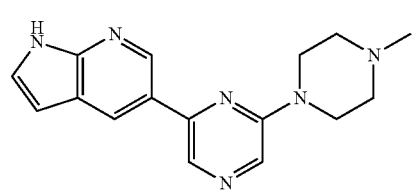

Reaction Scheme 32

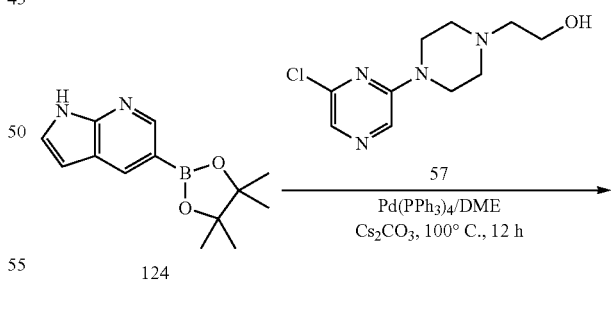

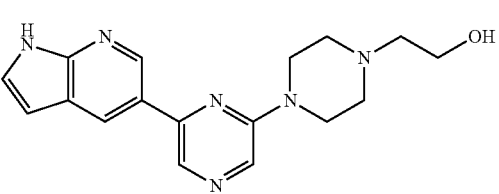

Example 89

N1-(6-(1H-pyrrolo[2,3-b]pyridin-5-yl)pyrazin-2-yl)-N2,N2-dimethylethane-1,2-diamine

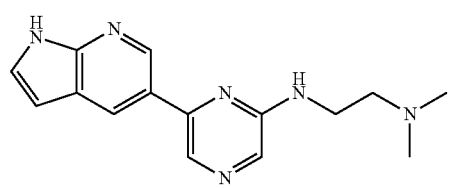

127

The starting material 5-(4,4,5,5-tetramethyl-1,3,2-dioxaborolan-2-yl)-1H-pyrrolo[2,3-b]pyridine (124) (70 mg, 0.286 mmol, 1 eq) and N1-(6-chloropyrazin-2-yl)-N2,N2-dimethylethane-1,2-diamine (66) (457 mg, 0.286 mmol, 1 eq) in 1,4-dioxane (5 mL) was degassed and purged under argon atmosphere for 10 min. To this reaction mixture was charged $Cs_2CO_3$ (150 mg, 0.614 mmol, 1.5 eq) followed by addition of Pd(dpp)Cl$_2$ (6.2 mg, 0.0086 mmol, 0.03 eq) and degassing and purging under argon for additional 10 min. The reaction mixture was heated at 100° C. for 12 h in a sealed tube. After completion of the reaction, the reaction mixture was diluted with $CHCl_3$ and filtered through oCelite. The solvents were distilled off and the crude material was submitted for flash column purification in neutral alumina using 1% MeOH/$CHCl_3$ to obtain pale yellow solid compound N1-(6-(1H-pyrrolo[2,3-b]pyridin-5-yl)pyrazin-2-yl)-N1,N1-dimethylethane-1,2-diamine 127 in 10 mg quantity. The compound 127 was confirmed by $^1$HNMR and LCMS. $^1$H NMR (400 MHz, CDCl$_3$) δ: 11.78 (s, 1H), 8.90 (d, J=1.82, 1H), 8.57 (s, 1H), 8.30 (s, 1H), 7.89 (s, 1H), 7.51 (m, J=151.58, 1H), 7.01 (m, J=201.21, 1H), 6.53 (m, J=191.45, 1H), 3.48 (m, J=5.85, 2H), 2.22 (s, 6-H); MS m/z 283 (M+H)$^+$.

Example 90

5-(3-(pyrrolidin-1-yl)pyrazin-2-yl)-1H-pyrrolo[2,3-b]pyridine

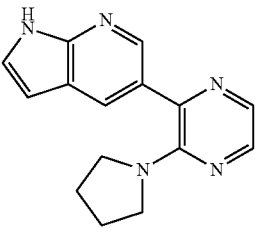

128

The starting material 5-(4,4,5,5-tetramethyl-1,3,2-dioxaborolan-2-yl)-1H-pyrrolo[2,3-b]pyridine (124) (50 mg, 0.2048 mmol, 1 eq) and 2-chloro-3-(pyrrolidin-1-yl)pyrazine (72) (33 mg, 0.184 mmol, 1 eq) in DME (8 mL) was degassed and purged under argon atmosphere for 10 min. To this reaction mixture was charged $Cs_2CO_3$ (133 mg, 0.409 mmol, 2 eq) followed by addition of Pd(dpp)Cl$_2$ (6 mg, 0.00819 mmol, 0.04 eq) and degassing and purging under argon for additional min. The reaction mixture was heated at 100° C. for 12 h in a sealed tube. After completion of the reaction, the reaction mixture was diluted with $CHCl_3$ and filtered through Celite. The solvents were distilled off and the crude material was submitted for flash column purification in neutral alumina using 1% MeOH/$CHCl_3$ to obtain pale yellow solid compound 5-(3-(pyrrolidin-1-yl)pyrazin-2-yl)-1H-pyrrolo[2,3-b]pyridine 128 in 10 mg quantity. The compound 128 was confirmed by $^1$HNMR and LCMS. $^1$H NMR (400 MHz, CDCl$_3$) δ: 9.50 (s, 1H), 8.58 (d, J=1.95, 1H), 8.15 (d, J=1.58, 1H), 8.04 (m, J=2.56, 2H), 7.38 (m, J=3.45, 1H), 6.56 (m, J=1.58, 1H), 3.18 (m, J=6.70, 1H), 1.81 (m, J=2.92, 4H; MS m/z 265.9 (M+H)$^+$.

Reaction Scheme 33

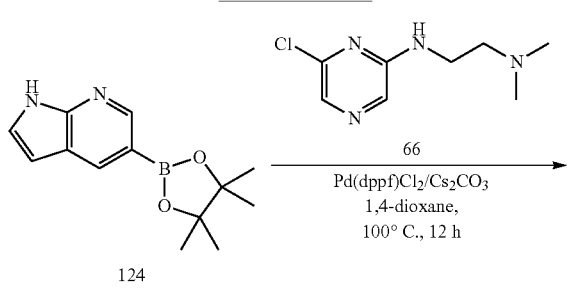

Reactionn Scheme 34

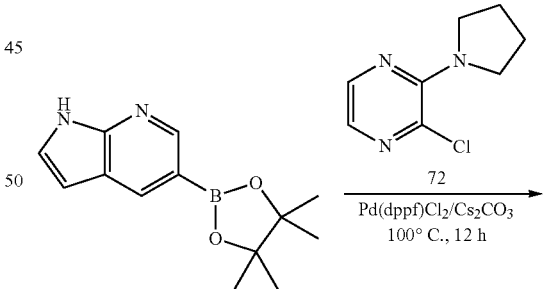

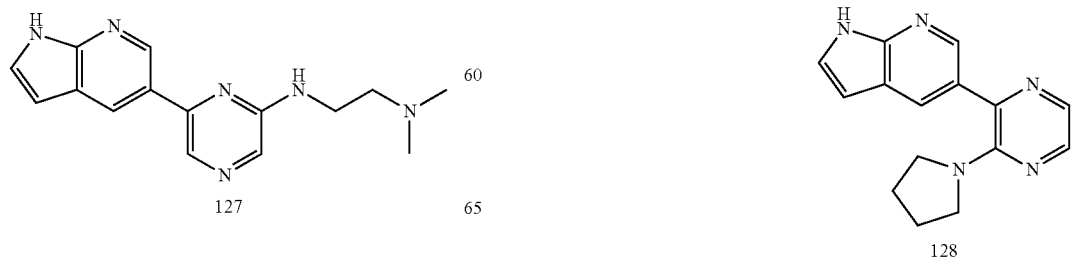

Example 91

N-(1-methylazetidin-3-yl)-6-(1H-pyrrolo[2,3-b]pyridin-5-yl)pyrazin-2-amine

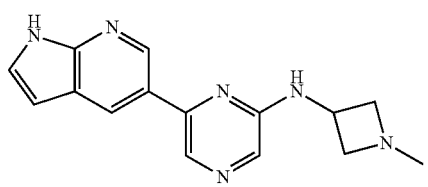

130

To the starting material 5-(4,4,5,5-tetramethyl-1,3,2-dioxaborolan-2-yl)-1H-pyrrolo[2,3-b]pyridine (124) (50 mg, 0.205 mmol, 1 eq) and 2-chloro-6-((1-methylazetidin-3-yl)oxy)pyrazine (129) (40.9 mg, 0.410 mmol, 1 eq) in 1,4-dioxane was added Pd(dpp)Cl$_2$ (1.184 mg, 0.1024 mmol, 0.005 eq) and Cs$_2$CO$_3$ (2 eq) followed by degassing and purging under argon for additional 10 min. The reaction mixture was heated at 100° C. for 12 h in a sealed tube. After completion of the reaction, the reaction mixture was diluted with CHCl$_3$ and filtered through Celite. The solvents were distilled off and the crude material was submitted for flash column purification in neutral alumina using 1% MeOH/CHCl$_3$ to obtain pale yellow solid compound N-(1-methylazetidin-3-yl)-6-(1H-pyrrolo[2,3-b]pyridin-5-yl)pyrazin-2-amine 130 in 16 mg quantity.

Reaction Scheme 35

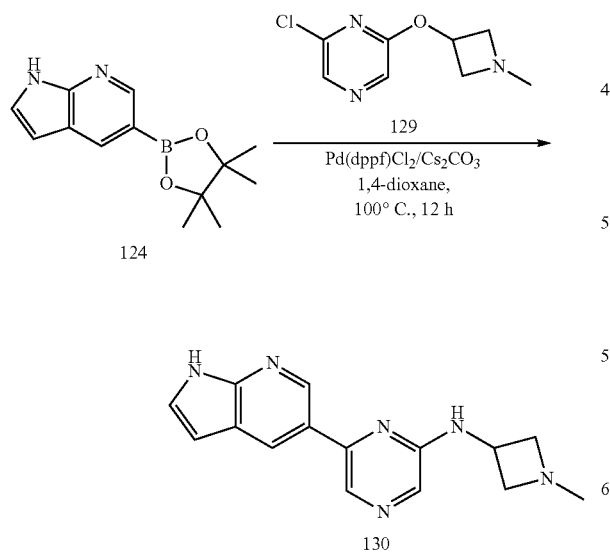

2-chloro-6-((1-methylazetidin-3-yl)oxy)pyrazine (129) was prepared by reacting 1-methylazetidin-3-ol (50 mg, 0.336 mmol, 1 eq) and 2,6-dichloropyrazine (32) (29.2 mg, 0.336 mmol, 1 eq) in DMF (5 mL) and sodium hydride (16.11 mg, 0.671 mmol, 2 eq) under refluxing temperature for 8 hrs.

Example 92

1-(6-(1H-pyrrolo[2,3-b]pyridin-5-yl)pyrazin-2-yl)pyrrolidin-2-one

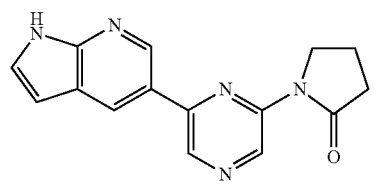

131

To the starting material 5-(4,4,5,5-tetramethyl-1,3,2-dioxaborolan-2-yl)-1H-pyrrolo[2,3-b]pyridine (124) (50 mg, 0.205 mmol, 1 eq) and 1-(6-bromopyrazin-2-yl)pyrrolidin-2-one (46) (49 mg, 0.205 mmol, 1 eq) in DME (5 mL), was added Pd(PPh$_3$)$_4$ (7.1 mg, 0.00614 mmol, 0.02 eq) Cs$_2$CO$_3$ (133 mg, 0.410 mmol, 2 eq) and degassing and purging under argon for additional 10 min was performed. The reaction mixture was heated at 100° C. for 12 h in a sealed tube. After completion of the reaction, the reaction mixture was diluted with CHCl$_3$ and filtered through Celite. The solvents were distilled off and the crude material was submitted for flash column purification in neutral alumina using 1% MeOH/CHCl$_3$ to obtain pale yellow solid compound 1-(6-(1H-pyrrolo[2,3-b]pyridin-5-yl)pyrazin-2-yl)pyrrolidin-2-one 131 in 9 mg quantity. The compound 131 was confirmed by $^1$HNMR and LCMS. $^1$H NMR (400 MHz, CDCl$_3$) δ: 11.90 (s, 1H), 9.46 (s, 1H), 9.02 (d, J=10.48, 2H), 8.71 (s, 1H), 7.56 (s, 1H), 6.58 (s, 1H)], 4.13 (m, $_f$=7.0, 2H), 2.65 (m, J=8.04, 2H), 2.14 (m, J=192.19, 2H); MS m/z 279.9 (M+H)$^+$.

Reaction Scheme 36

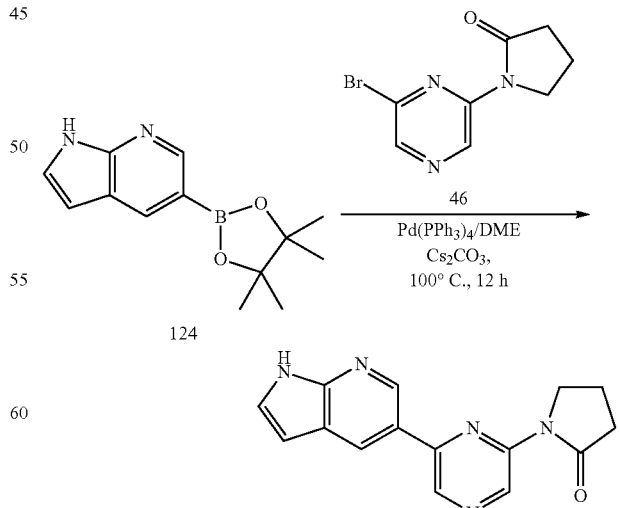

Example 93

4-(6-(1H-pyrrolo[2,3-b]pyridin-5-yl)pyrazin-2-yl)piperazin-2-one

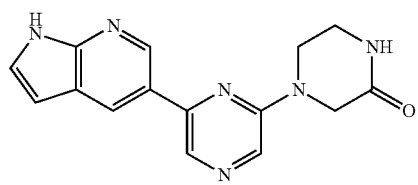

133

The starting material 5-(4,4,5,5-tetramethyl-1,3,2-dioxaborolan-2-yl)-1H-pyrrolo[2,3-b]pyridine (124) (50 mg, 0.205 mmol, 1 eq) and 4-(6-chloropyrazin-2-yl)piperazin-2-one (132) (33 mg, 0.184 mmol, 0.9 eq) in DME (8 mL) was degassed and purged under argon atmosphere for 10 min. To this reaction mixture was charged $Cs_2CO_3$ (133 mg, 0.409 mmol, 2 eq) followed by addition of $Pd(dpp)Cl_2$ (6 mg, 0.00819 mmol, 0.04 eq) and degassing and purging under argon for additional 10 min. The reaction mixture was heated at 100° C. for 12 h in a sealed tube. After completion of the reaction, the reaction mixture was diluted with $CHCl_3$ and filtered through Celite. The solvents were distilled off and the crude material was submitted for flash column purification in neutral alumina using 1% $MeOH/CHCl_3$ to obtain pale yellow solid compound 4-(6-(1H-pyrrolo[2,3-b]pyridin-5-yl)pyrazin-2-yl)piperazin-2-one 133 in 9 mg quantity. The compound 133 was confirmed by $^1HNMR$ and LCMS. $^1H$ NMR (400 MHz, $CDCl_3$) δ: 11.84 (s, 1H), 8.95 (d, J=2.07, 1H), 8.64 (d, J=1.95, 1H), 8.57 (s, 1H), 8.23 (s, 1H), 8.18 (s, 1H, 7.53 (m, J=2.92, 1H), 6.56 (m, J=1.70, 1H), 4.18 (s, 2H), 3.89 (m, J=5.36 2H); MS m/z 294.9 $(M+H)^+$.

Example 94

5-(6-(indolin-1-yl)pyrazin-2-yl)-1H-pyrrolo[2,3-b]pyridine

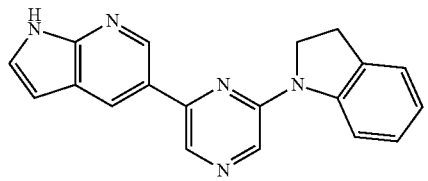

134

The starting material 5-(4,4,5,5-tetramethyl-1,3,2-dioxaborolan-2-yl)-1H-pyrrolo[2,3-b]pyridine (124) (50 mg, 0.205 mmol, 1 eq) and 1-(6-chloropyrazin-2-yl)indoline (88) 423 mg, 0.185 mmol, 0.9 eq) in DME (7 mL) was degassed and purged under argon atmosphere for 10 min. To this reaction mixture was charged $Cs_2CO_3$ (133 mg, 0.410 mmol, 2 eq) followed by addition of $Pd(dpp)Cl_2$ (6 mg, 0.00819 mmol, 0.04 eq) and degassing and purging under argon for additional minutes was performed. The reaction mixture was heated at 90° C. for 12 h in a sealed tube. After completion of the reaction, the reaction mixture was diluted with $CHCl_3$ and filtered through Celite. The solvents were distilled off and the crude material was submitted for flash column purification in neutral alumina using 1% $MeOH/CHCl_3$ to obtain pale yellow solid compound 5-(6-(indolin-1-yl)pyrazin-2-yl)-1H-pyrrolo[2,3-b]pyridine 134 in 12 mg quantity. The compound 134 was confirmed by $^1HNMR$ and LCMS. $^1H$ NMR (400 MHz, $CDCl_3$) δ: 9.06 (s, 2H), 8.59 (s, 1H), 8.60 (s, 1H), 8.55 (s, 1H), 8.44 (m, 1H), 8.16 (s, 1H), 7.41 (m, 1H), 6.99 (m, 1H), 4.21 (m, J=8.53, 2H), 3.33 (m, J=341.82, 2H); MS m/z 313.9 $(M+H)^+$.

Reaction Scheme 37

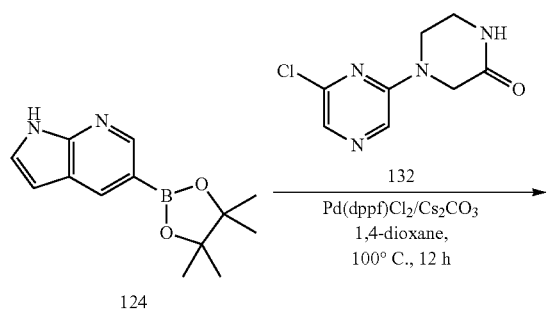

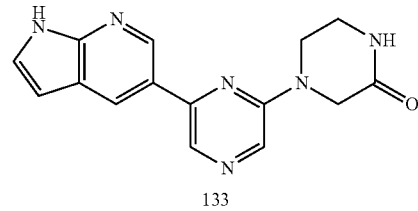

133

Reaction Scheme 38

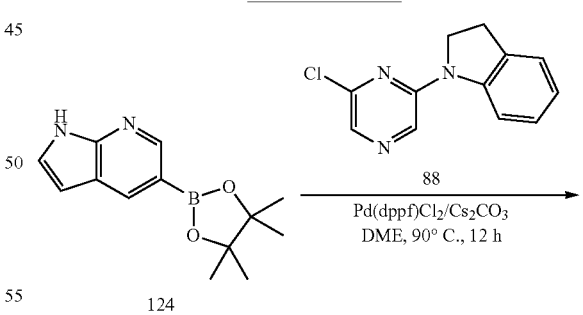

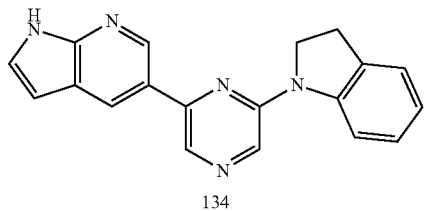

134

Example 95

5-(6-(3,3-difluoropyrrolidin-1-yl)pyrazin-2-yl)-1H-pyrrolo[2,3-b]pyridine

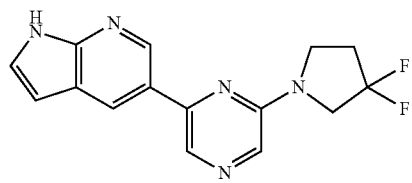

135

A stirred solution of 5-(4,4,5,5-tetramethyl-1,3,2-dioxaborolan-2-yl)-1H-pyrrolo[2,3-b]pyridine (124) (50 mg, 1 eq) and 2-chloro-6-(3,3-difluoropyrrolidin-1-yl)pyrazine (54) (1 eq) in 1,4-dioxane (5 mL) was degassed and purged under argon atmosphere for 10 min. To this reaction mixture was charged $Cs_2CO_3$ (2 eq) followed by addition of Pd(dpp)Cl$_2$ (0.04 eq) and degassing and purging under argon for additional 10 min. The reaction mixture was heated at 100° C. for 12 h in a sealed tube. After completion of the reaction, the reaction mixture was diluted with CHCl$_3$ and filtered through Celite. The solvents were distilled off and the crude material was submitted for flash column purification in neutral alumina using 1% MeOH/CHCl$_3$ to obtain pale yellow solid compound 5-(6-(3,3-difluoropyrrolidin-1-yl)pyrazin-2-yl)-1H-pyrrolo[2,3-b]pyridine 135 in 6 mg quantity.

Example 96

1-(6-(1H-pyrrolo[2,3-b]pyridin-5-yl)pyrazin-2-yl)piperidin-4-ol

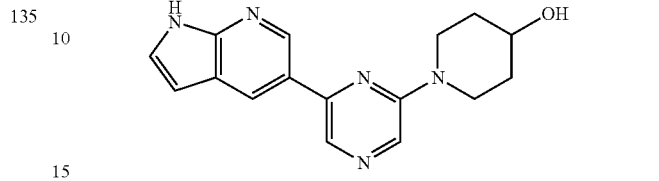

137

A stirred solution of 5-(4,4,5,5-tetramethyl-1,3,2-dioxaborolan-2-yl)-1H-pyrrolo[2,3-b]pyridine (124) (50 mg, 0.205 mmol, 1 eq) and 1-(6-chloropyrazin-2-yl)piperidin-4-ol (136) (44 mg, 0.205 mmol, 1 eq) in 1,2-dimethoxyethane (5 mL) was degassed and purged under argon atmosphere for 10 min. To this reaction mixture was charged $Cs_2CO_3$ (133 mg, 0.410 mmol, 2 eq) followed by addition of Pd(dpp)Cl$_2$ (0.006 mg, 0.00819 mmol, 0.04 eq) and degassing and purging under argon for additional 10 min. The reaction mixture was heated at 90° C. for 12 h in a sealed tube. After completion of the reaction, the reaction mixture was diluted with CHCl$_3$ and filtered through Celite. The solvents were distilled off and the crude material was submitted for flash column purification in neutral alumina using 1% MeOH/CHCl$_3$ to obtain pale yellow solid compound (6-(1H-pyrrolo[2,3-b]pyridin-5-yl)pyrazin-2-yl)(piperidin-1-yl)methanone 137 in 12 mg quantity. The compound 137 was confirmed by $^1$HNMR and LCMS. $^1$H NMR (400 MHz, CDCl$_3$) δ: 11.81 (s, 1H), 8.91 (d, J=2.07, 1H), 8.60 (d, J=2.07, 1H), 8.45 (s, 1H), 8.26 (s, 1H), 7.52 (m, J=2.56, 1H), 6.55 (m, J=1.82, 1H), 4.74 (m, J=4.26 1H), 4.14 (m, J=13.65, 2H), 3.75 (m, J=4.14, 1H), 3.34 (m, J=163.12, 1H), 3.26 (m, J=11.21, 2H), 1.84 (m, J=9.14, 2H), 1.42 (m, J=9.51, 2H); MS m/z 295.9 (M+H)$^+$.

Reaction Scheme 39

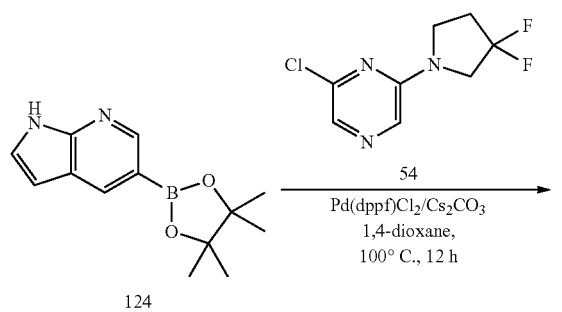

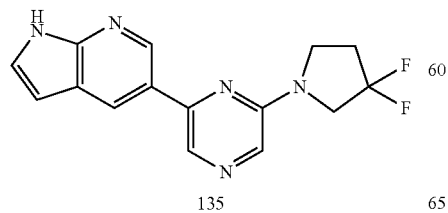

135

Reaction Scheme 40

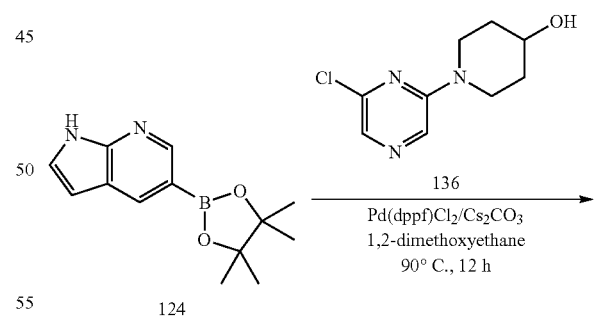

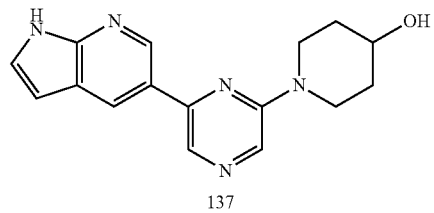

137

Example 97

(6-(1H-pyrrolo[2,3-b]pyridin-5-yl)pyrazin-2-yl)(piperidin-1-yl)methanone

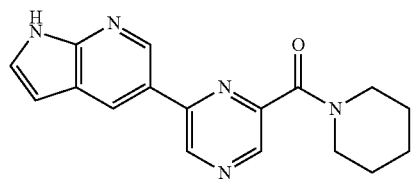

138

A stirred solution of 5-(4,4,5,5-tetramethyl-1,3,2-dioxaborolan-2-yl)-1H-pyrrolo[2,3-b]pyridine (124) (50 mg, 0.205 mmol, 1 eq) and (6-chloropyrazin-2-yl)(piperidin-1-yl)methanone (75) (41 mg, 0.184 mmol, 0.9 eq) in DME (8 mL) was degassed and purged under argon atmosphere for min. To this reaction mixture was charged $Cs_2CO_3$ (133 mg, 0.410 mmol, 2 eq) followed by addition of Pd(dpp)Cl$_2$ (6 mg, 0.00819 mmol, 0.04 eq) and degassing and purging under argon for additional 10 min. The reaction mixture was heated at 90° C. for 12 h in a sealed tube. After completion of the reaction, the reaction mixture was diluted with CHCl$_3$ and filtered through Celite. The solvents were distilled off and the crude material was submitted for flash column purification in neutral alumina using 1% MeOH/CHCl$_3$ to obtain pale yellow solid compound (6-(1H-pyrrolo[2,3-b]pyridin-5-yl)pyrazin-2-yl)(piperidin-1-yl)methanone 138 in 10 mg quantity. The compound 138 was confirmed by $^1$HNMR and LCMS. $^1$H NMR (400 MHz, CDCl$_3$) δ: 9.61 (s, 1H), 9.12 (s, 1H), 9.02 (s, 1H), 8.80 (m, J=87.55 1H), 8.60 (d, J=1.82, 1H), 7.42 (m, J=3.17, 1H), 6.64 (m, J=1.58, 1H), 3.87 (s, 2H), 3.59 (m, J=88.29, 1H), 1.75 (s, 4H), 1.69 (m, J=24.99, 2H); MS m/z 307.9 (M+H)$^+$.

Example 98

(6-(1H-pyrrolo[2,3-b]pyridin-5-yl)pyrazin-2-yl)(4-methylpiperazin-1-yl)methanone

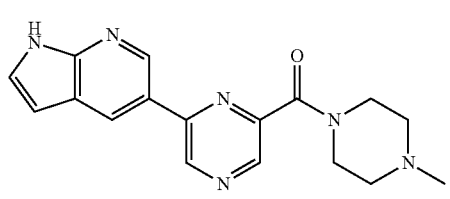

139

A stirred solution of 5-(4,4,5,5-tetramethyl-1,3,2-dioxaborolan-2-yl)-1H-pyrrolo[2,3-b]pyridine (124) (70 mg, 0.287 mmol, 1 eq) and (6-chloropyrazin-2-yl)(4-methylpiperazin-1-yl)methanone (60) (69 mg, 0.287 mmol, 1.0 eq) in DME (5 mL) was degassed and purged under argon atmosphere for 10 min. To this reaction mixture was charged $Cs_2CO_3$ (140 mg, 0.430 mmol, 1.5 eq) followed by addition of Pd(dpp)Cl$_2$ (13.2 mg, 0.0114 mmol, 0.04 eq) and degassing and purging under argon for additional 10 min. The reaction mixture was heated at 90° C. for 12 h in a sealed tube. After completion of the reaction, the reaction mixture was diluted with CHCl$_3$ and filtered through Celite. The solvents were distilled off and the crude material was submitted for flash column purification in neutral alumina using 1-2% MeOH/CHCl$_3$ to obtain pale yellow solid compound (6-(1H-pyrrolo[2,3-b]pyridin-5-yl)pyrazin-2-yl)(4-methylpiperazin-1-yl)methanone 139 in 20 mg quantity. The compound 139 was confirmed by $^1$HNMR and LCMS. $^1$H NMR (400 MHz, CDCl$_3$) δ: 11.98 (s, 1H), 9.45 (s, 1H), 9.04 (d, J=1.95, 1H), 8.76 (m, J=12.43, 2H), 7.63 (m, J=2.68, 1H), 6.64 (m, J=1.58, 1H), 3.76 (s, 2H), 3.59 (m, J=69.03, 2H), 2.42 (m, 4H), 2.28 (s, 3H); MS m/z 321.4 (M+H)$^+$.

Reaction Scheme 41

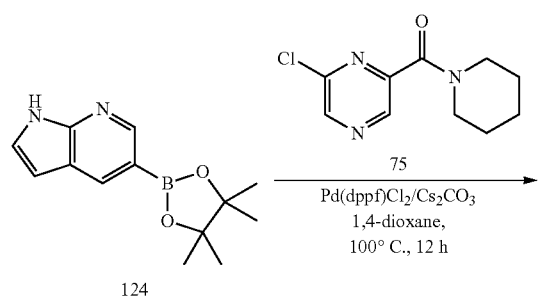

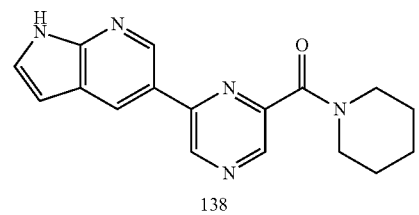

Reaction Scheme 42

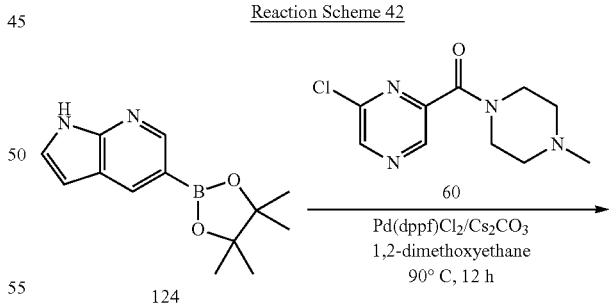

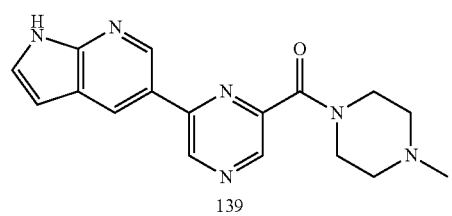

Example 99

N-(1-methylpiperidin-4-yl)-6-(1H-pyrrolo[2,3-b]pyridin-5-yl)pyrazin-2-amine

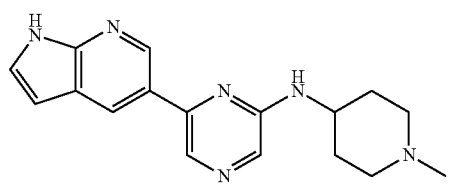

A stirred solution of 5-(4,4,5,5-tetramethyl-1,3,2-dioxaborolan-2-yl)-1H-pyrrolo[2,3-b]pyridine (124) (100 mg, 0.410 mmol) and 6-bromo-N-(1-methylpiperidin-4-yl)pyrazin-2-amine (11) (83 mg, 0.410 mmol) in DMSO (5 mL) was degassed and purged with nitrogen for 10 min. To this reaction mixture was added $Cs_2CO_3$ (226 mg, 2.0 eq) and the reaction mixture was purged again for another 10 min followed by the addition of $Pd(PPh_3)_4$ (0.03 eq). The resulting reaction mixture was heated at 80° C., overnight under sealed tube condition. After completion of the reaction the reaction mass was diluted with chloroform and filtered through Celite and the solvents were removed to obtain the crude product. The crude was passed through neutral alumina eluting with 2-3% $MeOH/CHCl_3$ providing beige coloured solid (12 mg) compound N-(1-methylpiperidin-4-yl)-6-(1H-pyrrolo[2,3-b]pyridin-5-yl)pyrazin-2-amine 140. $^1H$ NMR (400 MHz, $CDCl_3$) δ: 8.94 (d, J=2.07, 1H), 8.80 (s, 1H), 8.50 (s, 1H), 8.32 (s, 1H), 7.81 (s, 1H), 7.35 (d, J=3.2 HZ, 1H), 6.59 (m, 1H), 2.89 (m, 2H), 2.24 (s, 3H), 2.17 (m, 4H), 1.25 m, 1H); MS m/z 309.1 $(M+H)^+$.

Reaction Scheme 43

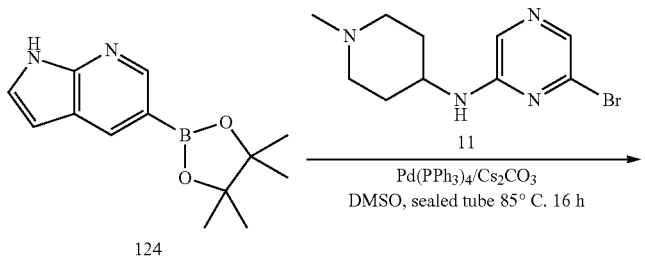

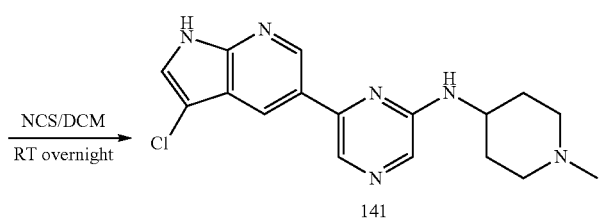

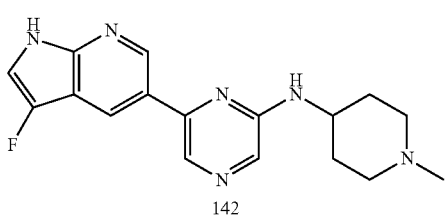

Example 100

6-(3-chloro-1H-pyrrolo[2,3-b]pyridin-5-yl)-N-(1-methylpiperidin-4-yl)pyrazin-2-amine

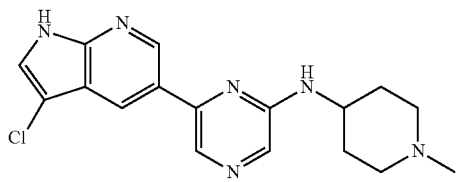

141

Compound N-(1-methylpiperidin-4-yl)-6-(1H-pyrrolo[2,3-b]pyridin-5-yl)pyrazin-2-amine (140).

Example 101

6-(3-fluoro-1H-pyrrolo[2,3-b]pyridin-5-yl)-N-(1-methylpiperidin-4-yl)pyrazin-2-amine

142

Example 102

N-methyl-6-(1H-pyrrolo[2,3-b]pyridin-5-yl)-N-((tetrahydro-2H-pyran-4-yl)methyl)pyrazin-2-amine

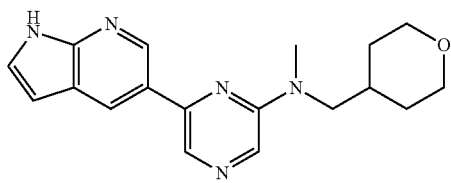

143

A stirred solution of 5-(4,4,5,5-tetramethyl-1,3,2-dioxaborolan-2-yl)-1H-pyrrolo[2,3-b]pyridine (124) (100 mg, 0.409 mmol) and 6-chloro-N-methyl-N-((tetrahydro-2H-pyran-4-yl)methyl)pyrazin-2-amine (69) (90 mg, 0.409 mmol) in toluene (8 mL) and ethanol (2 ml) was degassed and purged under nitrogen for 10 min followed by the addition of $Cs_2CO_3$ (260 mg, 0.819 mmol, 2.0 eq) and $Pd(PPh3)_4$ (14 mg, 0.022 mmol, 0.03 eq) and the reaction mixture was degassed and purged again for 15 min. The resulting reaction contents were heated at 80° C. overnight under sealed condition. After completion of the reaction the mixture was diluted with chloroform and filtered through Celite and the organic layer was distilled off to get the crude product. The crude was passed through neutral alumina eluting with 1-2% $MeOH/CHCl_3$ to give off white colored solid N-methyl-6-(1H-pyrrolo[2,3-b]pyridin-5-yl)-N-((tetrahydro-2H-pyran-4-yl)methyl)pyrazin-2-amine 143 in 9 mg quantity. $^1H$ NMR (400 MHz, $CDCl_3$) δ: 9.05 (s, 1H), 8.97 (d, J=1.95, 1H), 8.53 (d, J=1.95, 1H), 8.34 (s, 1H), 7.94 (s, 1H), 7.36 (s, 1H), 6.60 (d, J=3.29, 1H), 4.01 (s, 2H), 3.56 (d, 2H), 3.21 (s, 3H), 3.01 (m, 4H), 2.24 (m, 2H), 2.22 (s, 1H); MS m/z 324.1 $(M+H)^+$.

Reaction Scheme 44

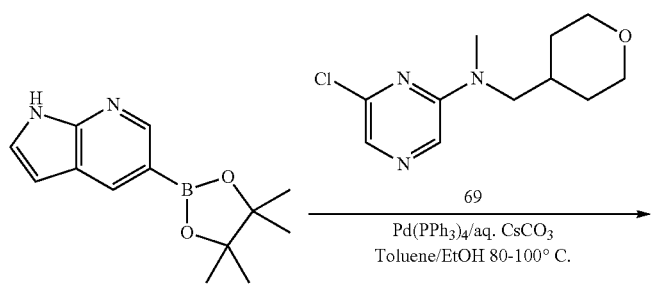

101

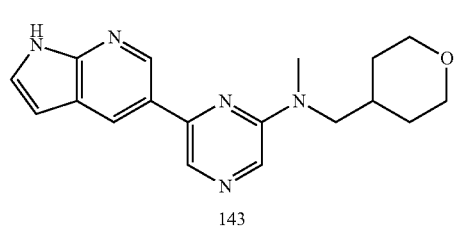
143

NCS/DCM
RT overnight

102

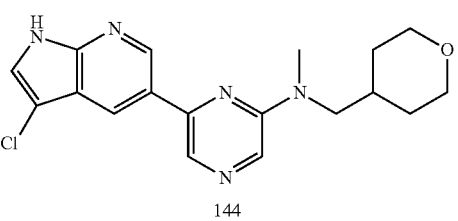
144

Selectfluor
NaHCO₃/H₂O
MeCN, 4 h

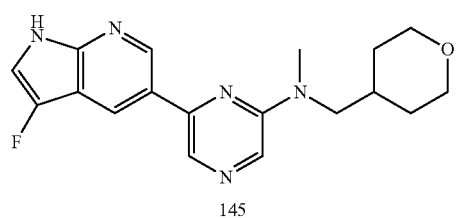
145

Example 103

6-(3-chloro-1H-pyrrolo[2,3-b]pyridin-5-yl)-N-methyl-N-((tetrahydro-2H-pyran-4-yl)methyl)pyrazin-2-amine

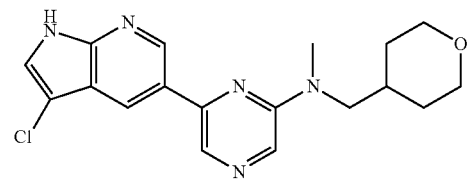
144

To a solution of compound N-methyl-6-(1H-pyrrolo[2,3-b]pyridin-5-yl)-N-((tetrahydro-2H-pyran-4-yl)methyl)pyrazine-2-amine (143) (20 mg, 1.0 eq) in dichloromethane (5 mL) was added n-chlorosuccinamide (2.0 eq) and the resulting reaction mixture was stirred at room temperature overnight. After completion of the reaction the solvents were removed and extracted into CH₂Cl₂. The organic layer was separated and the aqueous phase was extracted with CH₂Cl₂ to retain the crude material. The combined organic layer was washed with brine solution and dried over sodium sulphate and the solvents were removed by rotary evaporator. The crude material was purified by flash column with 100-200 mesh silica gel employing 40% EtOAc/hexane eluents to obtain the pure off-white coloured solid of 6-(3-chloro-1H-pyrrolo[2,3-b]pyridin-5-yl)-N-methyl-N-((tetrahydro-2H-pyran-4-yl)methyl)pyrazin-2-amine compound 144.

Example 104

6-(3-fluoro-1H-pyrrolo[2,3-b]pyridin-5-yl)-N-methyl-N-((tetrahydro-2H-pyran-4-yl)methyl)pyrazin-2-amine

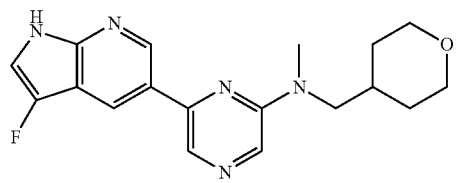
145

Fluorination of 6-(1H-pyrrolo[2,3-b]pyridin-5-yl)-N-((tetrahydro-2H-pyran-4yl) methyl)pyrazin-2-amine (143), carried out using the reported procedures published in Organic Letters, 2011, 13(18), 4498-4501, incorporated herein by reference in its entirety, provided the title compound 6-(3-fluoro-1H-pyrrolo[2,3-b]pyridin-5-yl)-N-methyl-N-((tetrahydro-2H-pyran-4-yl)methyl)pyrazin-2-amine 145.

Example 105

5-(4,4,5,5-tetramethyl-1,3,2-dioxaborolan-2-yl)-1H-pyrrolo[2,3-b]pyridine

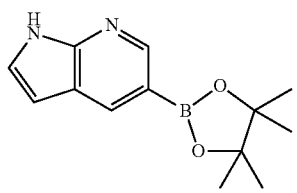
147

To a stirred solution of 5-bromo-1H-pyrrolo[2,3-b]pyridine (146) (1 g, 1 eq) in DMF, potassium acetate (6 eq), followed by bis-(pinacolato-diborane) (2 eq), was added. The reaction mixture was degassed with argon for 30 min. Then bis-(triphenylphosphine)-palladium (II) chloride (0.1 eq) was added and the reaction mixture was again degassed with argon for 30 minutes. Then the reaction mixture was heated to 90° C., stirred for 6 hr. Reaction mixture was concentrated under reduced pressure and the obtained residue was diluted with water and extracted with ethyl acetate (3×50 ml). The combined extract was washed with water, dried over anhydrous sodium sulphate, filtered and concentrated. Purification was done by flash column using 230-400 mesh silica gel and 20% ethyl acetate/petroleum ether to afford the desired product 5-(4,4,5,5-tetramethyl-1,3,2-dioxaborolan-2-yl)-1H-pyrrolo[2,3-b]pyridine 147 in 70% yields as white solid.

Reaction Scheme 45

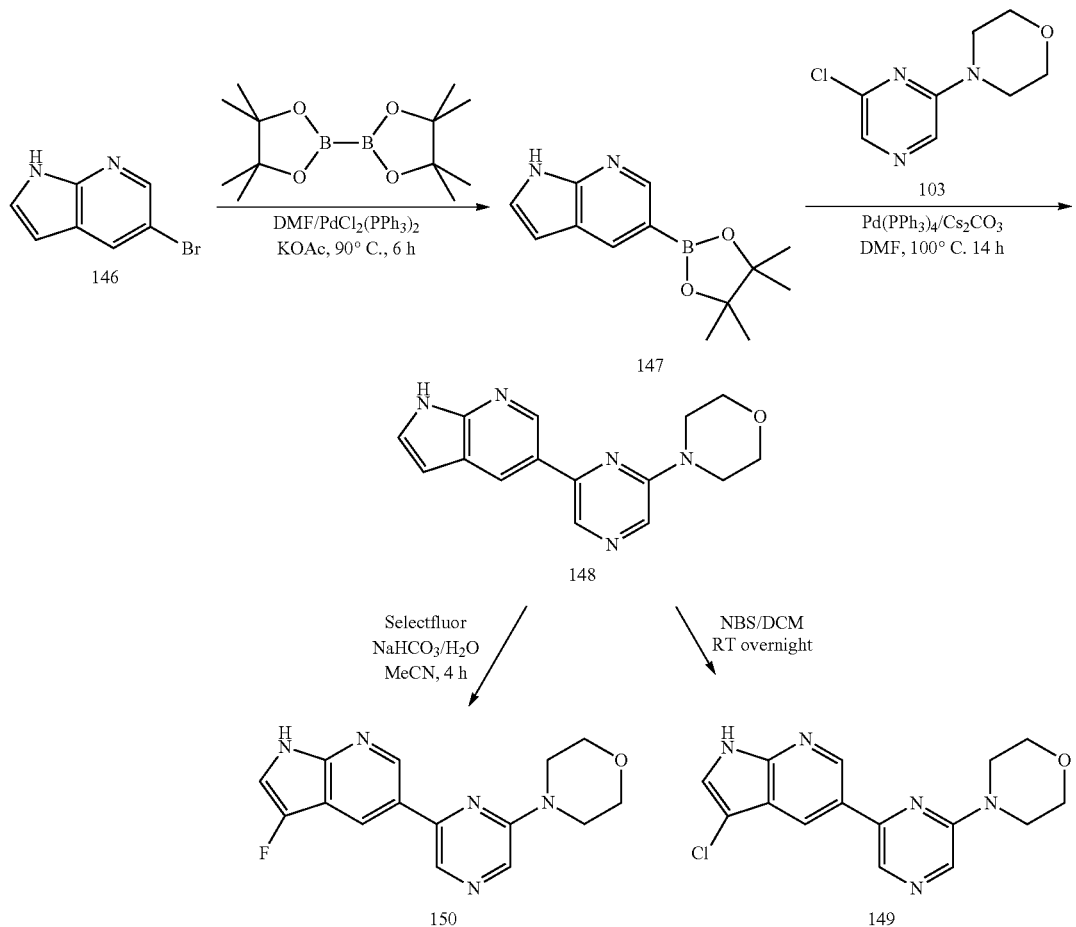

Example 106

4-(6-(1H-pyrrolo[2,3-b]pyridin-5-yl)pyrazin-2-yl)morpholine

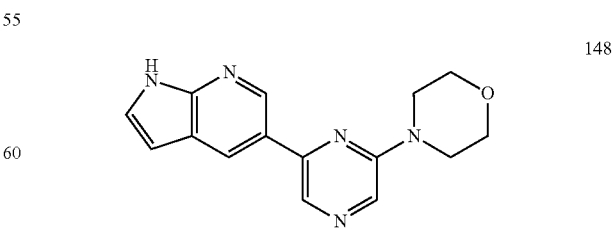

A stirred solution of 5-(4,4,5,5-tetramethyl-1,3,2-dioxaborolan-2-yl)-1H-pyrrolo[2,3-b]pyridine (147) (100 mg, 0.4 mmol) and 4-(6-chloropyrazin-2-yl)morpholine (103)

(80 mg, 0.4 mmol) in DMF (5 mL) was degassed and purged with nitrogen for 10 min. To this reaction mixture was added Cs$_2$CO$_3$ (333 mg, 1.0 mmol, 2.5 eq) and the reaction mixture was purged again for another min followed by the addition of Pd(PPh$_3$)$_4$ (0.018 mg, 0.016 mmol, 0.04 eq). The resulting reaction mixture was heated to 100° C., overnight under sealed tube condition. After completion of the reaction the mass was diluted with chloroform and filtered through Celite and the solvents were removed to obtain the crude product. The crude was passed through neutral alumina eluting with 2-3% MeOH/CHCl$_3$ provided a white coloured solid 25 mg of 4-(6-(1H-pyrrolo[2,3-b]pyridin-5-yl)pyrazin-2-yl)morpholine 148. $^1$H NMR (400 MHz, CDCl$_3$) δ: 8.96 (s, 1H), 8.95 (s, 1H), 8.84 (s, 1H), 8.54 (d, J=1.95, 1H), 8.43 (s, 1H), 8.07 (s, H), 7.36 (m, 1H), 3.71 (t, 4H), 3.69 (bt, 4H); MS m/z 281.90 (M+H)$^+$.

Example 107

4-(6-(3-chloro-1H-pyrrolo[2,3-b]pyridin-5-yl)pyrazin-2-yl)morpholine

149

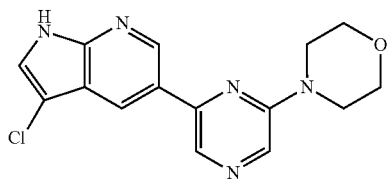

To a solution of compound 4-(6-(1H-pyrrolo[2,3-b]pyridin-5-yl)pyrazin-2-yl)morpholine (148) (40 mg, 0.142 mmol, 1.0 eq) in dichloromethane (6 mL) was added n-chlorosuccinamide (38 mg, 0.283 mmol, 2.0 eq) and the resulting reaction mixture was stirred at room temperature overnight. After completion of the reaction the solvents were removed and extracted into CH$_2$Cl$_2$. The organic layer was separated and the aqueous phase was extracted with CH$_2$Cl$_2$ to retain the crude material. The combined organic layer was washed with brine solution and dried over sodium sulphate and the solvents were removed by rotary evaporator. The crude material was purified by flash column with 100-200 mesh silica gel employing 70% EtOAc/hexane eluents to obtain the pure off-white colored solid of 4-(6-(3-chloro-1H-pyrrolo[2,3-b]pyridin-5-yl)pyrazin-2-yl)morpholine 149 (10 mg). $^1$H NMR (400 MHz, CDCl$_3$) δ: 9.0 (s, 1H), 8.83 (s, 1H), 8.52 (s, 1H), 8.45 (s, 1H), 8.10 (s, 1H), 7.34 (d, J=2.31 Hz, 1H), 3.89 (m, 4H), 3.70 (m, 4H); MS m/z 315.9 (M+H)$^+$.

Example 108

4-(6-(3-fluoro-1H-pyrrolo[2,3-b]pyridin-5-yl)pyrazin-2-yl)morpholine

150

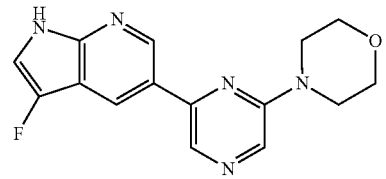

Fluorination of 4-(6-(1H-pyrrolo[2,3-b]pyridin-5-yl)pyrazin-2-yl)morpholine (148) carried out using the reported procedures published in Organic Letters, 2011, 13(18), 4498-4501, incorporated herein by reference in its entirety, provided the title compound 4-(6-(3-fluoro-1H-pyrrolo[2,3-b]pyridin-5-yl)pyrazin-2-yl)morpholine 150 in 6 mg quantity.

Example 109

1-(4-methoxybenzyl)-5-(3-((4-methylpiperazin-1-yl)methyl)phenyl)-1H-pyrrolo[2,3-b]pyridine

151

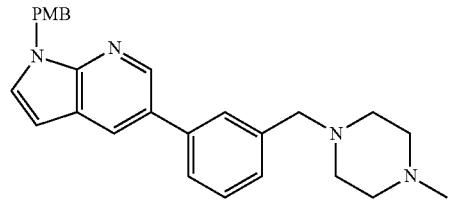

A stirred solution of 1-(4-methoxybenzyl)-5-(4,4,5,5-tetramethyl-1,3,2-dioxaborolan-2-yl)-1H-pyrrolo[2,3-b]pyridine (147PG) (50 mg, 0.137 mmol) and 1-(4-bromobenzyl)-4-methylpiperazine (121) (37 mg, 0.137 mmol, 1.1 eq) in DME (10 mL) was degassed and purged with N$_2$ for 10 min and Cs$_2$CO$_3$ (2.0 eq) was added and the reaction mixture purged and degassed again. To this reaction mixture was added Pd(PPh3)$_4$ (0.04 eq) and the resulting reaction was heated at 90° C. for 12 hrs in sealed tube condition. After completion of the reaction the contents were was cooled and diluted with CH$_2$Cl$_2$ and filtered through Celite bed. The CH$_2$Cl$_2$ layer was completely distilled off to get the crude product. The crude was passed through 100-200 mesh silica gel, eluting the pure compound 1-(4-methoxybenzyl)-5-(3-((4-methylpiperazin-1-yl)methyl)phenyl)-1H-pyrrolo[2,3-b]pyridine 151 obtained with 5% MeOH in CH$_2$Cl$_2$ as an off-white coloured solid in 30 mg quantity.

Reaction Scheme 46

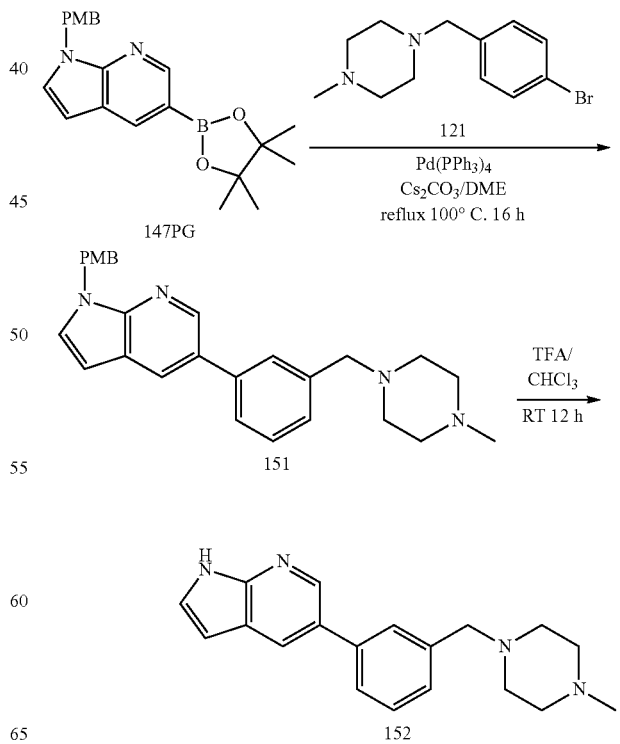

Example 110

5-(3-((4-methylpiperazin-1-yl)methyl)phenyl)-1H-pyrrolo[2,3-b]pyridine

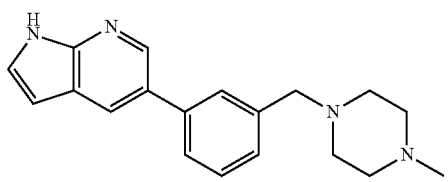

152

To a stirred solution of 1-(4-methoxybenzyl)-5-(3-((4-methylpiperazin-1-yl)methyl)phenyl)-1H-pyrrolo[2,3-b]pyridine (151) (30 mg) in CHCl$_3$ (8 mL) was added trifluoroacetic acid (5 mL) and heated at 50° C. for 12. After completion of the reaction the solvents were removed, diluted with cold water, pH was adjusted to 8 and the aqueous phase extracted with CHCl$_3$ twice. The organic layer was washed with brine solution and dried over sodium sulphate and the solvent completely distilled off to get the crude product. The crude was passed through 100-200 mesh silica gel, eluting the pure compound in 2% MeOH/CHCl$_3$ gave pale yellow solid compound 5-(3-((4-methylpiperazin-1-yl)methyl)phenyl)-1H-pyrrolo[2,3-b]pyridine 152.

Example 111

N-(3-(1-(4-methoxybenzyl)-3-methyl-1H-pyrazolo[3,4-b]pyridin-5-yl)phenyl)acrylamide

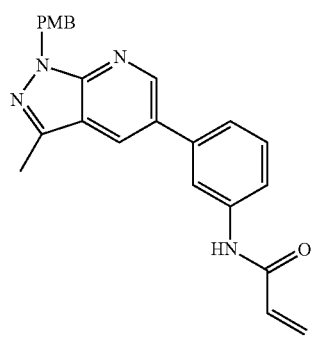

154

The starting material 5-bromo-1-(4-methoxybenzyl)-3-methyl-1H-pyrazolo[3,4-b]pyridine (7) (134 mg, 0.402 mmol, 1 eq) and (3-acrylamidophenyl)boronic acid (153) (100 mg, 0.366 mmol, 1 eq) in DME (10 mL) was degassed and purged under argon atmosphere for 10 min. To this reaction mixture was charged Cs$_2$CO$_3$ (233 mg, 0.732 mmol, 2 eq) followed by addition of Pd(PPh$_3$)$_4$ (0.016 mg, 0.03 mmol) and degassing and purging under argon for additional 10 min. The reaction mixture was heated at 100° C. for 16 h in a sealed tube. After completion of the reaction, the solvents were removed and reaction mixtures were extracted into EtOAc, dried over Na$_2$SO$_4$ and the solvents distilled off. The crude material was submitted for flash column purification using 40% EtOAc in hexane to obtain off-white solid compound N-(3-(1-(4-methoxybenzyl)-3-methyl-1H-pyrazolo[3,4-b]pyridin-5-yl)phenyl)acrylamide 154. MS m/z 397.2 (M+H)$^+$.

Reaction Scheme 47

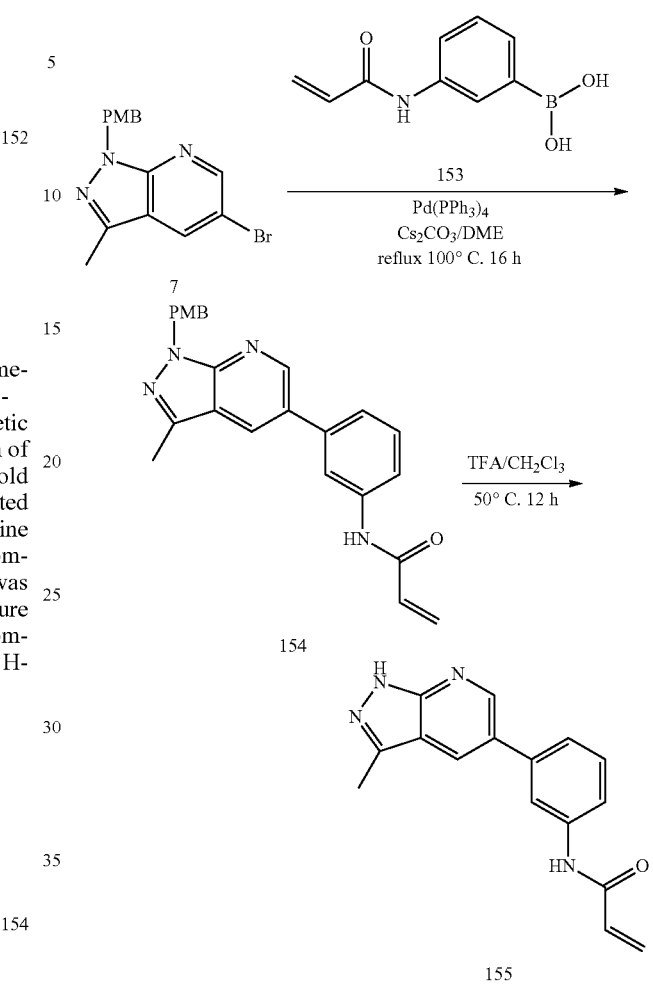

Example 112

N-(3-(3-methyl-1H-pyrazolo[3,4-b]pyridin-5-yl)phenyl)acrylamide

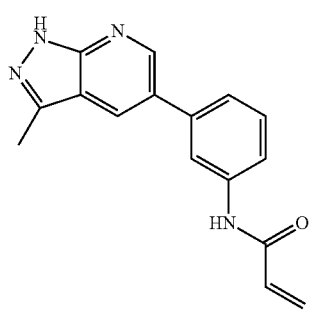

155

To a stirred solution of N-(3-(1-(4-methoxybenzyl)-3-methyl-1H-pyrazolo[3,4-b]pyridin-5-yl)phenyl)acrylamide (154) (70 mg) in CHCl$_3$ (20 mL) was added trifluoroacetic acid (5 mL) and the reaction mixture heated at 50° C. for 12. After completion of the reaction the solvents were removed, diluted with cold water, pH was adjusted to 8 and the aqueous phase extracted with chloroform twice. The organic layer was washed with brine solution and dried over sodium sulphate and the solvent completely distilled off to get the crude product. The crude was passed through 100-200 mesh silica gel, eluting the pure compound in 60% EtOAc/hexane gave pale yellow solid compound N-(3-(3-methyl-1H-pyrazolo[3,4-b]pyridin-5-yl)phenyl)acrylamide 155. ¹H NMR (400 MHz, CDCl₃) δ: 10.29 (s, H), 8.75 (d, J=2.07, 1H), 8.40 (d, J=1.95, 1H), 8.03 (s, 1H), 7.69 (s, 1H), 7.43 (m, 1H), 6.50 (m, 1H), 6.46 (m, 1H), 6.26 (m, 1H), 2.55 (bs, 3H); MS m/z 277.9 (M+H)⁺.

Example 113

2-(3-(1-(4-methoxybenzyl)-3-methyl-1H-pyrazolo[3,4-b]pyridin-5-yl)phenyl)acetonitrile

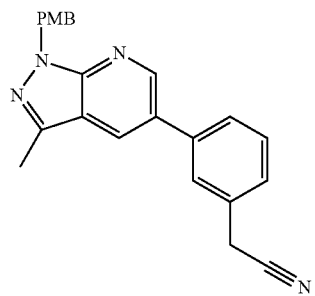

157

The starting material 5-bromo-1-(4-methoxybenzyl)-3-methyl-1H-pyrazolo[3,4-b]pyridine (7) (136 mg, 0.41 mmol, 1 eq) and 2-(3-(4,4,5,5-tetramethyl-1,3,2-dioxaborolan-2-yl)phenyl)acetonitrile (156) (100 mg, 0.41 mmol, 1 eq) in DME (10 mL) was degassed and purged under argon atmosphere for 10 min. To this reaction mixture was charged Cs₂CO₃ (260 mg, 0.82 mmol, 2 eq) followed by addition of Pd(PPh₃)₄ (15 mg, 0.03 mmol), degassing and purging under argon for additional 10 min. The reaction mixture was heated at 80° C. for 12 h in a sealed tube. After completion of the reaction, the solvents were removed and reaction mixtures were extracted into EtOAc, dried over Na2SO4 and the solvents distilled off. The crude material was submitted for flash column purification using 20% EtOAc in hexane to obtain off-white solid compound 2-(3-(1-(4-methoxybenzyl)-3-methyl-1H-pyrazolo[3,4-b]pyridin-5-yl)phenyl)acetonitrile 157.

Reaction Scheme 48

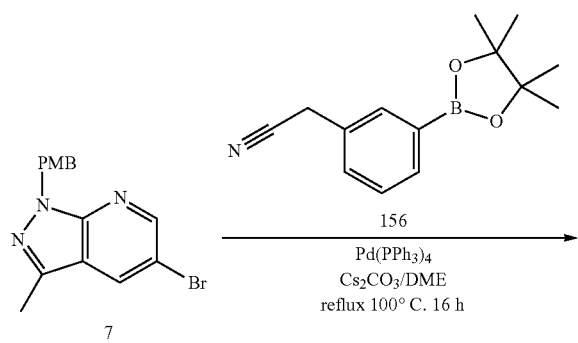

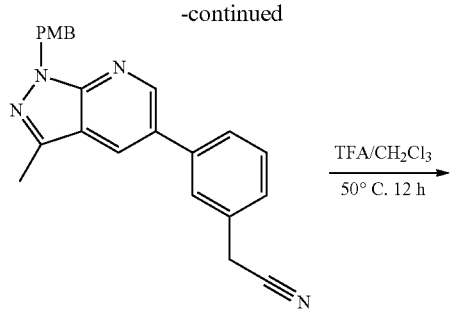

Example 114

2-(3-(3-methyl-1H-pyrazolo[3,4-b]pyridin-5-yl)phenyl)acetonitrile

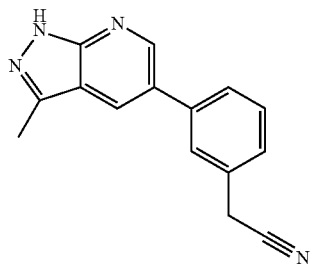

158

To a stirred solution of 2-(3-(1-(4-methoxybenzyl)-3-methyl-1H-pyrazolo[3,4-b]pyridin-5-yl)phenyl)acetonitrile (157) (60 mg) in CHCl₃ (20 mL) was added trifluoroacetic acid (5 mL) and the reaction mixture was heated at 50° C. for 12. After completion of the reaction the solvents were removed, diluted with cold water, pH was adjusted to 8 and the aqueous phase extracted with chloroform twice. The organic layer was washed with brine solution and dried over sodium sulphate and the solvent completely distilled off to get the crude product. The crude was passed through 100-200 mesh silica gel, eluting the pure compound in 50% EtOAc/hexane gave pale yellow solid compound 158 in 20 mg quantity.

Example 115

1-(4-methoxybenzyl)-3-methyl-5-(4-(4-methylpiperazin-1-yl)phenyl)-1H-pyrazolo[3,4-b]pyridine

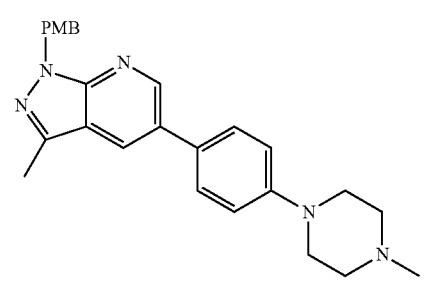

160

The starting material 5-bromo-1-(4-methoxybenzyl)-3-methyl-1H-pyrazolo[3,4-b]pyridine (7) (145 mg, 0.44 mmol, 1 eq) and 1-methyl-4-(4-(4,4,5,5-tetramethyl-1,3,2-dioxaborolan-2-yl)phenyl)piperazine (159) (135 mg, 0.44 mmol, 1 eq) in DME (10 mL) was degassed and purged under argon atmosphere for 10 min. To this reaction mixture was charged Cs$_2$CO$_3$ (280 mg, 0.88 mmol, 2 eq) followed by addition of Pd(PPh$_3$)$_4$ (15 mg, 0.01 mmol), degassing and purging under argon for additional 10 min. The reaction mixture was heated at 80° C. for 12 h in a sealed tube. After completion of the reaction, the solvents were removed and reaction mixtures were extracted into EtOAc, dried over Na2SO4 and the solvents distilled off. The crude material was submitted for flash column purification using 5% MeOH/CHCl$_3$ to obtain off-white solid compound 1-(4-methoxybenzyl)-3-methyl-5-(4-(4-methylpiperazin-1-yl)phenyl)-1H-pyrazolo[3,4-b]pyridine 160 in 65 mg quantity.

Reaction Scheme 49

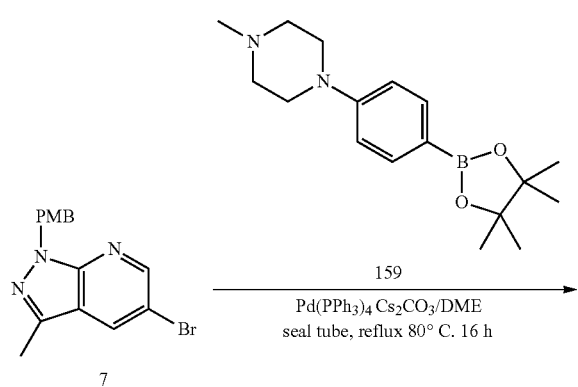

Example 116

3-methyl-5-(4-(4-methylpiperazin-1-yl)phenyl)-1H-pyrazolo[3,4-b]pyridine

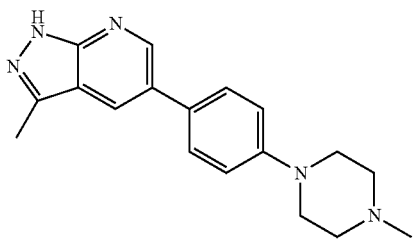

161

To a stirred solution of 1-(4-methoxybenzyl)-3-methyl-5-(4-(4-methylpiperazin-1-yl)phenyl)-1H-pyrazolo[3,4-b]pyridine (160) in CHCl$_3$ (20 mL) was added trifluoroacetic acid (5 mL) and heated at 50° C. for 12 hours. After completion of the reaction the solvents were removed, diluted with cold water, pH was adjusted to 8 and the aqueous phase extracted with chloroform twice. The organic layer was washed with brine solution and dried over sodium sulphate and the solvent completely distilled off to get the crude product. The crude was passed through 100-200 mesh silica gel, eluting the pure compound in 10% MeOH/CHCl$_3$ as pale yellow solid compound 161 (8 mg).

Example 117

2-(4-(3-((1-(4-methoxybenzyl)-3-methyl-1H-pyrazolo[3,4-b]pyridin-5-yl)amino)benzyl)piperazin-1-yl)ethanol

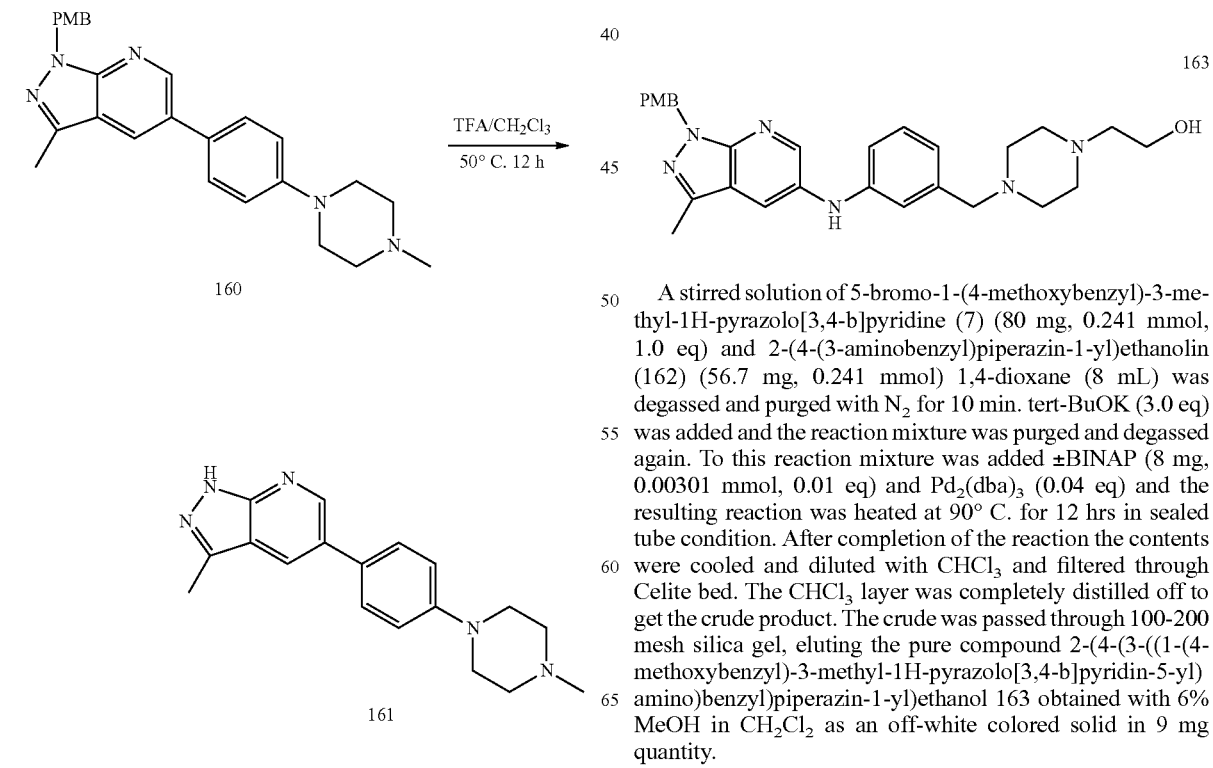

A stirred solution of 5-bromo-1-(4-methoxybenzyl)-3-methyl-1H-pyrazolo[3,4-b]pyridine (7) (80 mg, 0.241 mmol, 1.0 eq) and 2-(4-(3-aminobenzyl)piperazin-1-yl)ethanolin (162) (56.7 mg, 0.241 mmol) 1,4-dioxane (8 mL) was degassed and purged with N$_2$ for 10 min. tert-BuOK (3.0 eq) was added and the reaction mixture was purged and degassed again. To this reaction mixture was added ±BINAP (8 mg, 0.00301 mmol, 0.01 eq) and Pd$_2$(dba)$_3$ (0.04 eq) and the resulting reaction was heated at 90° C. for 12 hrs in sealed tube condition. After completion of the reaction the contents were cooled and diluted with CHCl$_3$ and filtered through Celite bed. The CHCl$_3$ layer was completely distilled off to get the crude product. The crude was passed through 100-200 mesh silica gel, eluting the pure compound 2-(4-(3-((1-(4-methoxybenzyl)-3-methyl-1H-pyrazolo[3,4-b]pyridin-5-yl)amino)benzyl)piperazin-1-yl)ethanol 163 obtained with 6% MeOH in CH$_2$Cl$_2$ as an off-white colored solid in 9 mg quantity.

Reaction Scheme 50

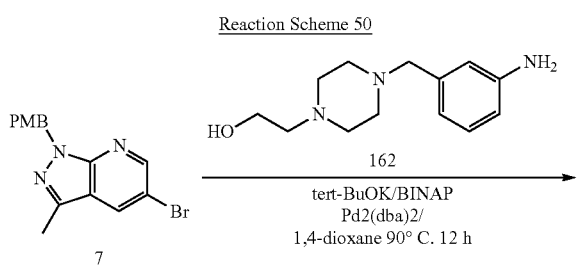

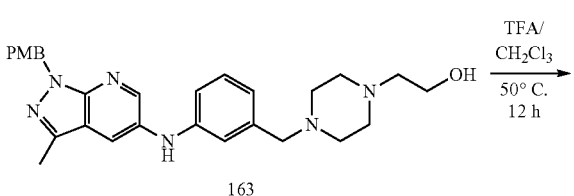

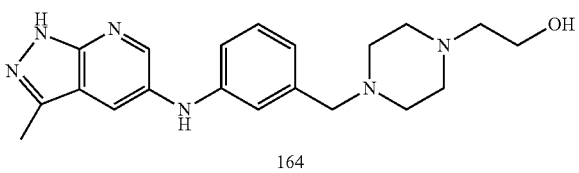

Example 118

2-(4-(3-((3-methyl-1H-pyrazolo[3,4-b]pyridin-5-yl)amino)benzyl)piperazin-1-yl)ethanol

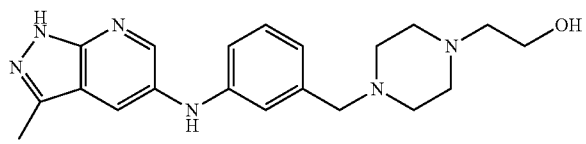

To a stirred solution of 2-(4-(3-((1-(4-methoxybenzyl)-3-methyl-1H-pyrazolo[3,4-b]pyridin-5-yl)amino)benzyl)piperazin-1-yl)ethanol (163) (50 mg, 0.103 mmol) in CHCl₃ (10 mL) was added trifluoroacetic acid (6 mL) and the reaction mass heated at 60° C. overnight. After completion of the reaction the solvents were completely distilled off and diluted with water and the pH was adjusted to 9 and extracted with chloroform twice. The combined organic layer was washed with brine solution and dried over sodium sulphate and the solvents were removed and the crude material was passed through 100-200 mesh silica gel, eluting with 10% MeOH/CH₂Cl₂ obtained pure 2-(4-(3-((3-methyl-1H-pyrazolo[3,4-b]pyridin-5-yl)amino)benzyl)piperazin-1-yl)ethanol 164 as a pale yellow colored solid (6 mg). MS m/z 353.54 (M+H)⁺.

Example 119

1-(4-methoxybenzyl)-3-methyl-N-(4-((4-methylpiperazin-1-yl)methyl)phenyl)-1H-pyrazolo[3,4-b]pyridin-5-amine

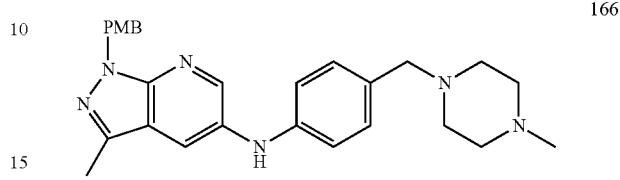

A stirred solution of 5-bromo-1-(4-methoxybenzyl)-3-methyl-1H-pyrazolo[3,4-b]pyridine (7) (50 mg, 0.150 mmol) and 4-((4-methylpiperazin-1-yl)methyl)aniline (165) (30 mg, 0.165 mmol, 1.1 eq) in 1,4-dioxane (10 mL) was degassed and purged with N₂ for 10 min. tert-BuOK (50 mg, 0.451 mmol, 3.0 eq) was added and the reaction mixture was purged and degassed again. To this reaction mixture was added ±BINAP (1.8 mg, 0.00301 mmol, 0.01 eq) and Pd₂(dba)₃ (5 mg, 0.0012 mmol, 0.04 eq) and the resulting reaction was heated at 90° C. for 12 hrs in sealed tube condition. After completion of the reaction the contents were cooled and diluted with CHCl₃ and filtered through Celite bed. The CHCl₃ layer was completely distilled off to get the crude product. The crude was passed through 100-200 mesh silica gel, eluting the pure compound 1-(4-methoxybenzyl)-3-methyl-N-(4-((4-methylpiperazin-1-yl)methyl)phenyl)-1H-pyrazolo[3,4-b]pyridin-5-amine 166 obtained with 6% MeOH in CH₂Cl₂ as an off-white coloured solid in 30 mg quantity.

Reaction Scheme 51

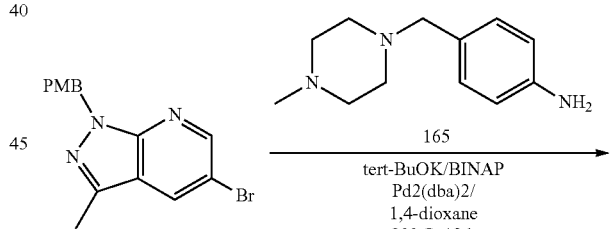

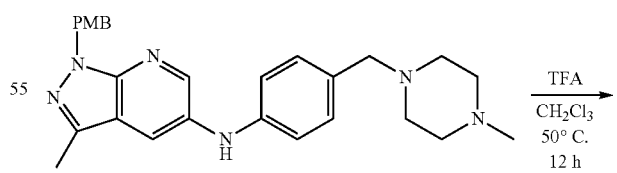

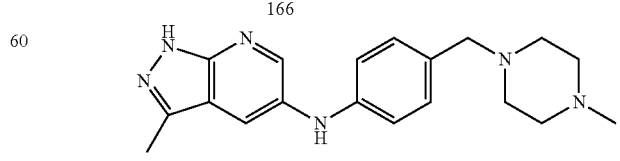

Example 120

3-methyl-N-(4-((4-methylpiperazin-1-yl)methyl) phenyl)-1H-pyrazolo[3,4-b]pyridin-5-amine

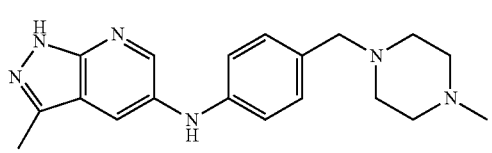

167

To a stirred solution of 1-(4-methoxybenzyl)-3-methyl-N-(4-((4-methylpiperazin-1-yl)methyl)phenyl)-1H-pyrazolo[3,4-b]pyridin-5-amine (166) (40 mg, 0.657 mmol) in CHCl$_3$ (10 mL) was added trifluoroacetic acid (6 mL) and the reaction mass heated at 60° C. overnight. After completion of the reaction the solvents were completely distilled off and diluted with water and the pH was adjusted to 9 and extracted with chloroform twice. The combined organic layer was washed with brine solution and dried over sodium sulphate and the solvents were removed and the crude material was passed through 100-200 mesh silica gel, eluting with 8% MeOH/CH$_2$Cl$_2$ obtained pure 3-methyl-N-(4-((4-methylpiperazin-1-yl)methyl)phenyl)-1H-pyrazolo[3,4-b]pyridin-5-amine 167 as a pale yellow colored solid (10 mg). $^1$H NMR (400 MHz, CDCl$_3$) δ: 8.38 (s, 1H), 7.76 (s, 1H), 7.52 (s, 1H), 7.21 (d, 1H), 7.19 (d, J=8.41, 1H), 7.19 (s, 1H), 6.89 (d, J=7.92, 1H), 3.46 (s, 2H), 2.54 (m, 8H), 2.31 (s, 3H), 2.05 (s, 3H); MS m/z 336.9 (M+H)$^+$.

Example 121

N-(3-fluoro-4-(4-methylpiperazin-1-yl)phenyl)-1-(4-methoxybenzyl)-3-methyl-1H-pyrazolo[3,4-b]pyridin-5-amine

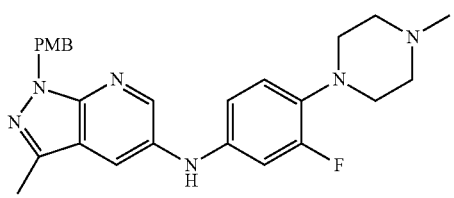

169

A stirred solution of 5-bromo-1-(4-methoxybenzyl)-3-methyl-1H-pyrazolo[3,4-b]pyridine (7) (100 mg, 0.301 mmol) and 3-fluoro-4-(4-methylpiperazin-1-yl)aniline (168) (77 mg, 0.33 mmol, 1.1 eq) in 1,4-dioxane (10 mL) was degassed and purged with N$_2$ for 10 min. tert-BuOK (101 mg, 0.903 mmol, 3.0 eq) was added and the reaction mixture purged and degassed again. To this reaction mixture was added ±BINAP (8 mg, 0.00301 mmol, 0.01 eq) and Pd$_2$(dba)$_3$ (11 mg, 0.0012 mmol, 0.04 eq) and the resulting reaction was heated at 90° C. for 12 hrs in sealed tube condition. After completion of the reaction the contents were cooled and diluted with CHCl$_3$ and filtered through Celite bed. The CHCl$_3$ layer was completely distilled off to get the crude product. The crude was passed through 100-200 mesh silica gel, eluting the pure compound N-(3-fluoro-4-(4-methylpiperazin-1-yl)phenyl)-1-(4-methoxybenzyl)-3-methyl-1H-pyrazolo[3,4-b]pyridin-5-amine 169 obtained with 6% MeOH in CH$_2$Cl$_2$ as an off-white colored solid in 40 mg quantity.

Reaction Scheme 52

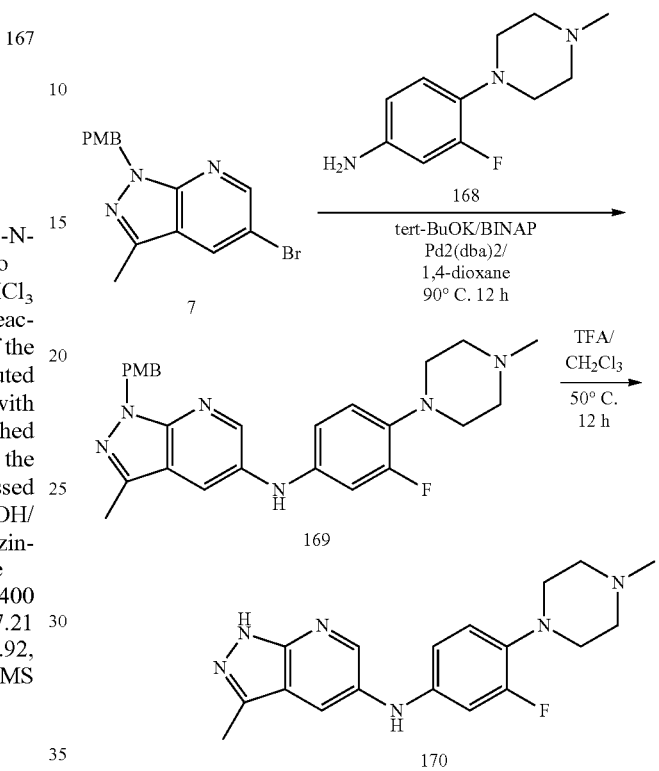

Example 122

N-(3-fluoro-4-(4-methylpiperazin-1-yl)phenyl)-3-methyl-1H-pyrazolo[3,4-b]pyridin-5-amine

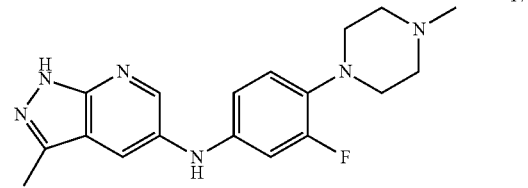

170

To a stirred solution of N-(3-fluoro-4-(4-methylpiperazin-1-yl)phenyl)-1-(4-methoxybenzyl)-3-methyl-1H-pyrazolo[3,4-b]pyridin-5-amine (169) (30 mg, 0.063 mmol) in CHCl$_3$ (15 mL) was added trifluoroacetic acid (6 mL) and the reaction mass heated to 60° C. overnight. After completion of the reaction the solvents were completely distilled off and diluted with water and the pH was adjusted to 9 and extracted with chloroform twice. The combined organic layer was washed with brine solution and dried over sodium sulphate and the solvents were removed and the crude material was passed through 100-200 mesh silica gel, eluting with 8% MeOH/CH$_2$Cl$_2$ obtained pure N-(3-fluoro-4-(4-methylpiperazin-1-yl)phenyl)-3-methyl-1H-pyrazolo[3,4-b]pyridin-5-amine 170 as a pale yellow colored solid (10 mg). $^1$H NMR (400 MHz, CDCl$_3$) δ: 8.36 (s, 1H), 7.71 (s, J=2.31, 1H), 6.90 (m, 1H), 6.71 (m, 2H), 5.56 (s, 1H), 3.07 (bs, 4H), 2.62 (bs, 4H), 2.54 (bs, 3H), 2.36 (s, 3H); MS m/z 341.0 (M+H)$^+$.

Example 123

N-(6-chloropyrazin-2-yl)-3-methyl-1H-pyrazolo[3,4-b]pyridin-5-amine

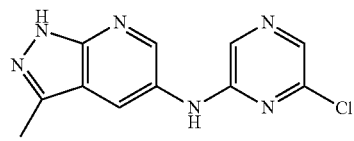

171

To a stirred solution of 5-bromo-3-methyl-1H-pyrazolo[3,4-b]pyridin (6) and 2,6-dichloropyrazine (52) in tert-butanol which was degassed and purged with nitrogen was added tert-BuOK, Pd$_2$(dba)$_3$ and s-phos and the reaction materials were again degassed, purged with nitrogen for 15 min. The reaction mass was heated at 90° C. for 14 hrs under sealed condition. After completion of the reaction the RM was diluted with water and extracted with dichloromethane twice. The combined organic layer was dried over sodium sulphate and the solvent completely distilled off to get the crude product. The crude was passed through 100-200 mesh silica gel eluting the pure compound at 30% EtOAc in hexane as brown colour solid 171 (50 mg). $^1$H NMR (400 MHz, CDCl$_3$) δ: 9.52 (s, 1H), 8.55 (s, 1H), 8.41 (d, J=2.56, 1H), 7.00 (s, 1H), 3.77 (s, 3H).

Reaction Scheme 53

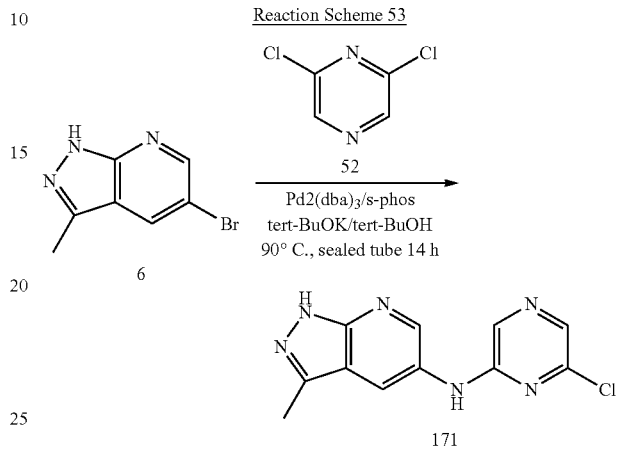

TABLE 1

| | List of Compounds | | |
|---|---|---|---|
| Exp. ID | Structure | Chemical Name | Mol. Wt. |
| 13 | | 6-(3-methyl-1H-pyrazolo[3,4-b]pyridine-5-yl)-N-(1-methylpiperidine-4-yl)prazin-2-amine | 323.40 |
| 13HCL | | 6-(3-methyl-1H-pyrazolo[3,4-b]pyridin-5-yl)-N-(1-methylpiperidin-4-yl)pyrazin-2-amine hydrochloride | 359.51 |
| 19 | | 5-(3-methyl-1H-pyrazolo[3,4-b]pyridin-5-yl)-N-(1-methylpiperidin-4-yl)pyrimidin-4-amine | 323.40 |

TABLE 1-continued

List of Compounds

| Exp. ID | Structure | Chemical Name | Mol. Wt. |
|---|---|---|---|
| 22 | 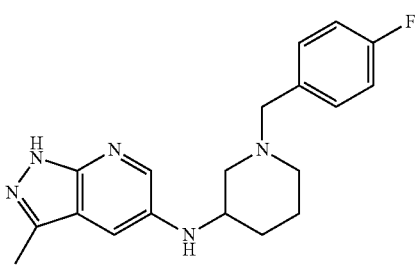 [SMILES: Cc1n[nH]c2ncc(NC3CCCN(Cc4ccc(F)cc4)C3)cc12] | N-(1-(4-fluorobenzyl)piperidin-3-yl)-3-methyl-1H-pyrazolo[3,4-b]pyridin-5-amine | 339.41 |
| 26 | 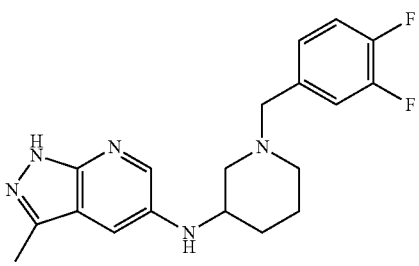 [SMILES: Cc1n[nH]c2ncc(NC3CCCN(Cc4ccc(F)c(F)c4)C3)cc12] | N-(1-(3,4-difluorobenzylpiperidin-3-yl)-3-methyl-1H-pyrazolo[3,4-b]pyridid-5-amine | 357.40 |
| 27 | 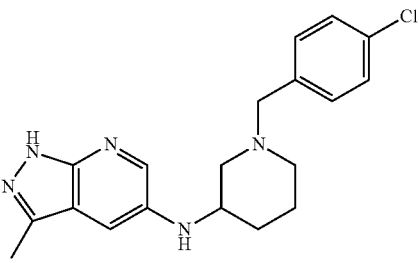 [SMILES: Cc1n[nH]c2ncc(NC3CCCN(Cc4ccc(Cl)cc4)C3)cc12] | N-(1-(4-chlorobenzyl)piperidin-3-yl)-3-methyl-1H-pyrazolo[3,4-b]pyridin-5-amine | 355.86 |
| 28 | 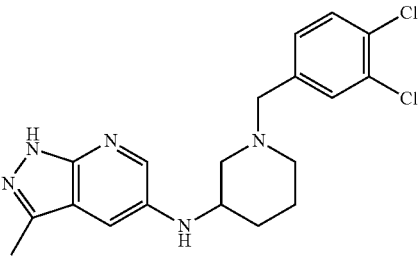 [SMILES: Cc1n[nH]c2ncc(NC3CCCN(Cc4ccc(Cl)c(Cl)c4)C3)cc12] | N-(1-(3,4-difluorobenzyl)piperidin-3-yl)-3-methyl-1H-pyrazolo[3,4-b]pyridin-5-amine | 390.31 |
| 33 | 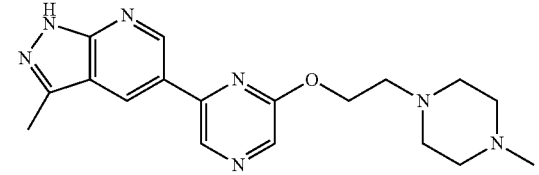 [SMILES: Cc1n[nH]c2ncc(-c3cncc(OCCN4CCN(C)CC4)n3)cc12] | 3-methyl-5-(6-(2-(4-methylpiperazin-1-yl)ethoxy)pyrazin-2-yl)-1H-pyrazolo[3,4-b]pyridine | 353.20 |
| 39 | 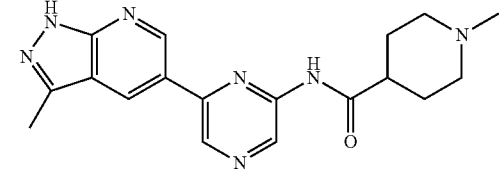 [SMILES: Cc1n[nH]c2ncc(-c3cncc(NC(=O)C4CCN(C)CC4)n3)cc12] | 1-methyl-N-(6-(3-methyl-1H-pyrazolo[3,4-b]pyridin-5-yl)pyrazin-2-yl)piperidine-4-carboxamide | 351.41 |

TABLE 1-continued

List of Compounds

| Exp. ID | Structure | Chemical Name | Mol. Wt. |
|---|---|---|---|
| 42 | 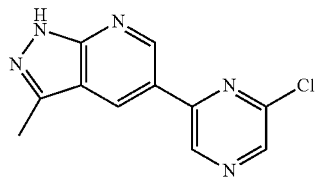 [SMILES: Cc1n[nH]c2ncc(-c3cncc(Cl)n3)cc12] | 5-(6-chloropyrazin-2-yl)-3-methyl-1H-pyrazolo[3,4-b]pyridine | 245.67 |
| 45 | 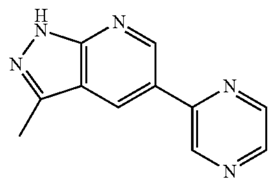 [SMILES: Cc1n[nH]c2ncc(-c3cnccn3)cc12] | 3-methyl-5-(pyrazin-2-yl)-1H-pyrazolo[3,4-b]pyridine | 211.22 |
| 48 | 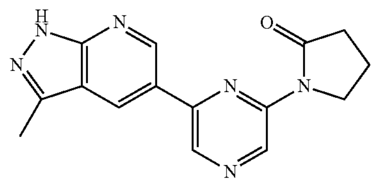 [SMILES: Cc1n[nH]c2ncc(-c3cncc(N4CCCC4=O)n3)cc12] | 1-(6-(3-methyl-1H-pyrazolo[3,4-b]pyridin-5-yl)pyrazin-2-yl)pyrrolidin-2-one | 294.31 |
| 51 | 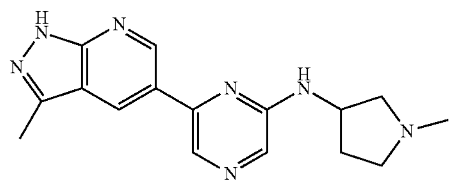 [SMILES: Cc1n[nH]c2ncc(-c3cncc(NC4CCN(C)C4)n3)cc12] | 6-(3-methyl-1H-pyrazolo[3,4-b]pyridin-5-yl)-N-(1-methylpyrrolidin-3-yl)pyrazin-2-amine | 309.37 |
| 56 | 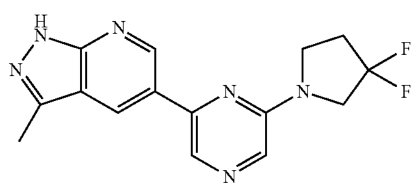 [SMILES: Cc1n[nH]c2ncc(-c3cncc(N4CCC(F)(F)C4)n3)cc12] | 5-(6-(3,3-difluoropyrrolidin-1-yl)pyrazin-2-yl)-3-methyl-1H-pyrazolo[3,4-b]pyridine | 316.31 |
| 59 | 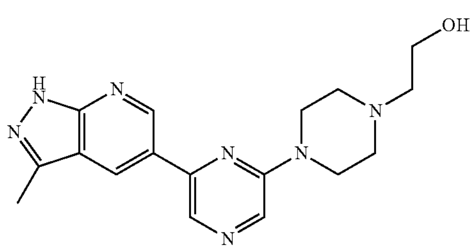 [SMILES: Cc1n[nH]c2ncc(-c3cncc(N4CCN(CCO)CC4)n3)cc12] | 2-(4-(6-(3-methyl-1H-pyrazolo[3,4-b]pyridin-5-yl)pyrazin-2-yl)piperazin-1-yl)ethanol | 339.39 |
| 62 | 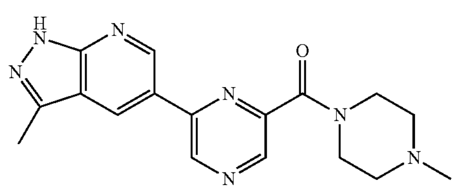 [SMILES: Cc1n[nH]c2ncc(-c3cncc(C(=O)N4CCN(C)CC4)n3)cc12] | (6-(3-methyl-1H-pyrazolo[3,4-b]pyridin-5-yl)pyrazin-2-yl)(4-methylpiperazin-1-yl)methanone | 337.38 |
| 65 | 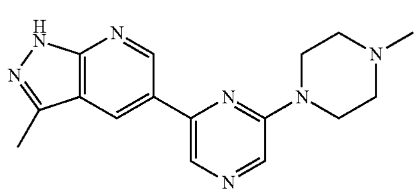 [SMILES: Cc1n[nH]c2ncc(-c3cncc(N4CCN(C)CC4)n3)cc12] | 3-methyl-5-(6-(4-methylpiperazin-1-yl)pyrazin-2-yl)-1H-pyrazolo[3,4-b]pyridine | 309.37 |

TABLE 1-continued

List of Compounds

| Exp. ID | Structure | Chemical Name | Mol. Wt. |
|---|---|---|---|
| 68 | 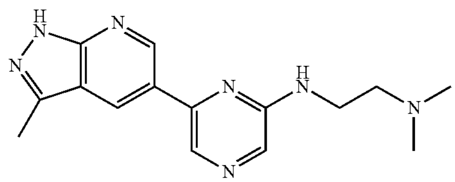 [SMILES: Cc1n[nH]c2ncc(-c3cncc(NCCN(C)C)n3)cc12] | N1,N1-dimethyl-N2-(6-(3-methyl-1H-pyrazolo[3,4-b]pyridin-5-yl)pyrazin-2-yl)ethane-1,2-diamine | 297.36 |
| 71 | 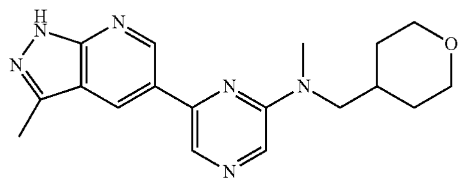 [SMILES: Cc1n[nH]c2ncc(-c3cncc(N(C)CC4CCOCC4)n3)cc12] | N-methyl-6-(3-methyl-1H-pyrazolo[3,4-b]pyridin-5-yl)-N-((tetrahydro-2H-pyran-4-yl)methyl)pyrazin-2-amine | 338.41 |
| 74 | 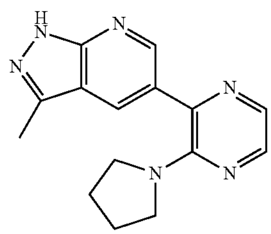 [SMILES: Cc1n[nH]c2ncc(-c3nccnc3N3CCCC3)cc12] | 3-methyl-5-(3-(pyrrolidin-1-yl)pyrazin-2-yl)-1H-pyrazolo[3,4-b]pyridine | 280.33 |
| 77 | 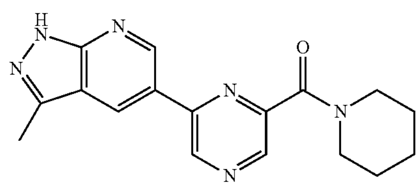 [SMILES: Cc1n[nH]c2ncc(-c3cncc(C(=O)N4CCCCC4)n3)cc12] | (6-(3-methyl-1H-pyrazolo[3,4-b]pyridin-5-yl)pyrazin-2-yl)(piperidin-1-yl)methanone | 322.36 |
| 81 | 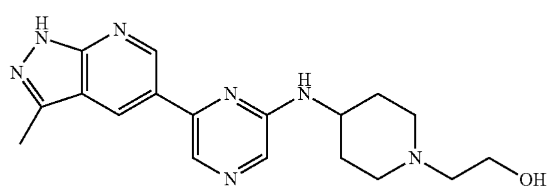 [SMILES: Cc1n[nH]c2ncc(-c3cncc(NC4CCN(CCO)CC4)n3)cc12] | 2-(4-((6-(3-methyl-1H-pyrazolo[3,4-b]pyridin-5-yl)pyrazin-2-yl)amino)piperidin-1-yl)ethanol | 353.42 |
| 83 | 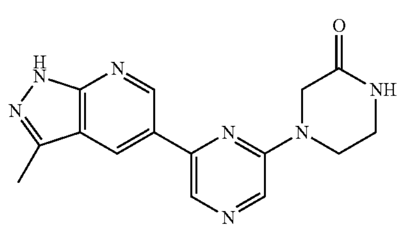 [SMILES: Cc1n[nH]c2ncc(-c3cncc(N4CCNC(=O)C4)n3)cc12] | 4-(6-(3-methyl-1H-pyrazolo[3,4-b]pyridin-5-yl)pyrazin-2-yl)piperazin-2-one | 309.33 |
| 87 | 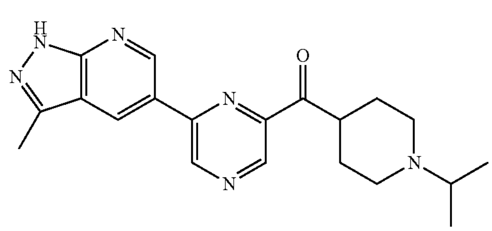 [SMILES: Cc1n[nH]c2ncc(-c3cncc(C(=O)C4CCN(C(C)C)CC4)n3)cc12] | N-(1-isopropylpiperidin-4-yl)-6-(3-methyl-1H-pyrazolo[3,4-b]pyridin-5-yl)pyrazin-2-amine | 351.45 |

TABLE 1-continued

List of Compounds

| Exp. ID | Structure | Chemical Name | Mol. Wt. |
|---|---|---|---|
| 90 | 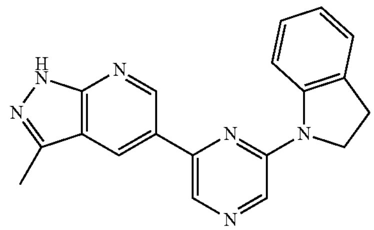 [SMILES: Cc1n[nH]c2ncc(-c3cncc(N4CCc5ccccc54)n3)cc12] | 5-(6-(indolin-1-yl)pyrazin-2-yl)-3-methyl-1H-pyrazol-[3,4-b]pyridine | 328.37 |
| 94 | 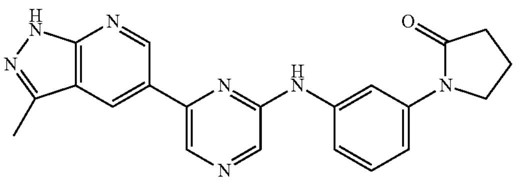 [SMILES: Cc1n[nH]c2ncc(-c3cncc(Nc4cccc(N5CCCC5=O)c4)n3)cc12] | 1-(3-((6-(3-methyl-1H-pyrazolo[3,4-b]pyridin-5-yl)pyrazin-2-yl)amino)phenyl)pyrrolidin-2-one | 385.42 |
| 98 | 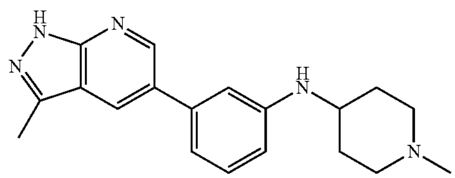 [SMILES: Cc1n[nH]c2ncc(-c3cccc(NC4CCN(C)CC4)c3)cc12] | 1-methyl-N-(3-(3-methyl-1H-pyrazolo[3,4-b]pyridin-5-yl)phenyl)piperidin-4-amine | 321.42 |
| 102 | 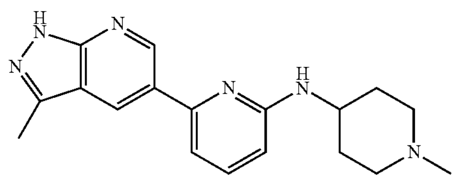 [SMILES: Cc1n[nH]c2ncc(-c3cccc(NC4CCN(C)CC4)n3)cc12] | 6-(3-methyl-1H-pyrazolo[3,4-b]pyridin-5-yl)-N-(1-methylpiperidin-4-yl)pyridin-2-amine | 322.41 |
| 105 | 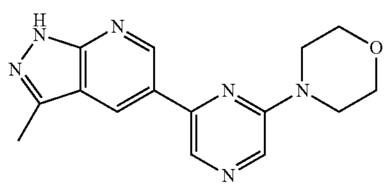 [SMILES: Cc1n[nH]c2ncc(-c3cncc(N4CCOCC4)n3)cc12] | 4-(6-(3-methyl-1H-pyrazolo[3,4-b]pyridin-5-yl)pyrazin-2-yl)morpholine | 296.33 |
| 108 | 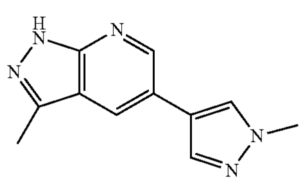 [SMILES: Cc1n[nH]c2ncc(-c3cnn(C)c3)cc12] | 3-methyl-5-(1-methyl-1H-pyrazol-4-yl)-1H-pyrazolo[3,4-b]pyridine | 213.24 |
| 111 | 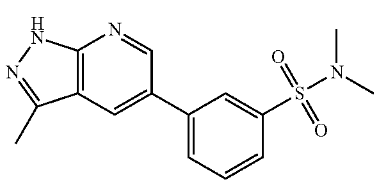 [SMILES: Cc1n[nH]c2ncc(-c3cccc(S(=O)(=O)N(C)C)c3)cc12] | N,N-dimethyl-3-(3-methyl-1H-pyrazolo[3,4-b]pyridin-5-yl)benzenesulfonamide | 316.38 |
| 114 | 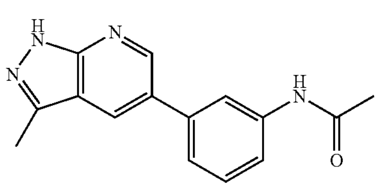 [SMILES: CC(=O)Nc1cccc(-c2cnc3[nH]nc(C)c3c2)c1] | N-(3-(3-methyl-1H-pyrazolo[3,4-b]pyridin-5-yl)phenyl)acetamide | 266.30 |

TABLE 1-continued

List of Compounds

| Exp. ID | Structure | Chemical Name | Mol. Wt. |
|---|---|---|---|
| 117 | 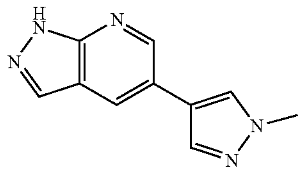 | 5-(1-methyl-1H-pyrazol-4-yl)-1H-pyrazolo[3,4-b]pyridine | 199.21 |
| 119 | 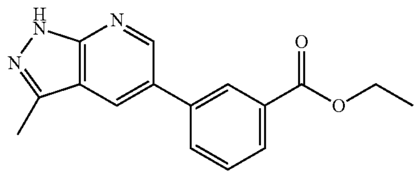 [SMILES: CCOC(=O)c1cccc(-c2cnc3[nH]nc(C)c3c2)c1] | ethyl 3-(3-methyl-1H-pyrazolo[3,4-b]pyridin-5-yl)benzoate | 281.31 |
| 123 | 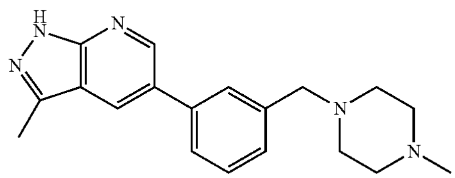 [SMILES: Cc1n[nH]c2ncc(-c3cccc(CN4CCN(C)CC4)c3)cc12] | 3-methyl-5-(3-((4-methylpiperazin-1-yl)methyl)phenyl)-1H-pyrazolo[3,4-b]pyridine | 321.42 |
| 125 | 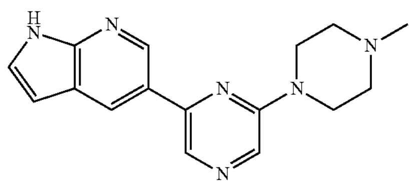 [SMILES: CN1CCN(c2cncc(-c3cnc4[nH]ccc4c3)n2)CC1] | 5-(6-(4-methylpiperazin-1-yl)pyrazin-2-yl)-1H-pyrrolo[2,3-b]pyridine | 429.35 |
| 126 | 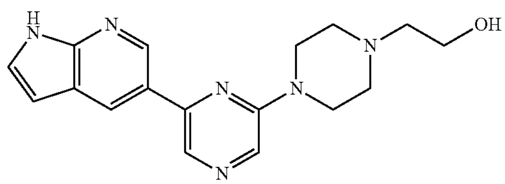 [SMILES: OCCN1CCN(c2cncc(-c3cnc4[nH]ccc4c3)n2)CC1] | 2-(4-(6-(1H-pyrrolo[2,3-b]pyridin-5-yl)pyrazin-2-yl)piperazin-1-yl)ethanol | 324.38 |
| 127 | 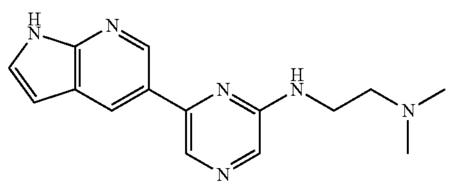 [SMILES: CN(C)CCNc1cncc(-c2cnc3[nH]ccc3c2)n1] | N1-(6-(1H-pyrrolo[2,3-b]pyridin-5-yl)pyrazin-2-yl)-N2,N2-dimethylethane-1,2-diamine | 282.34 |
| 128 | 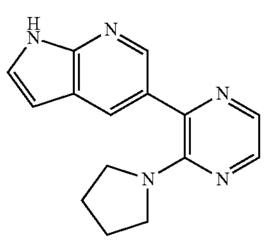 [SMILES: c1cnc(N2CCCC2)c(-c2cnc3[nH]ccc3c2)n1] | 5-(3-(pyrrolidin-1-yl)pyrazin-2-yl)-1H-pyrrolo[2,3-b]pyridine | 265.31 |
| 130 | 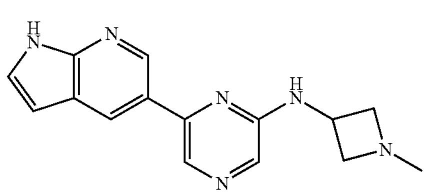 [SMILES: CN1CC(Nc2cncc(-c3cnc4[nH]ccc4c3)n2)C1] | N-(1-methylazetidin-3-yl)-6-(1H-pyrrolo[2,3-b]pyridin-5-yl)pyrazin-2-amine | 280.33 |

TABLE 1-continued

List of Compounds

| Exp. ID | Structure | Chemical Name | Mol. Wt. |
|---|---|---|---|
| 131 | 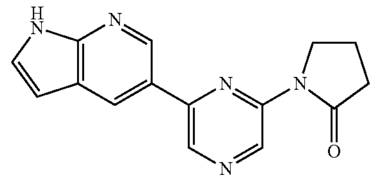 [SMILES: O=C1CCCN1c1cncc(-c2cnc3[nH]ccc3c2)n1] | 1-(6-(1H-pyrrolo[2,3-b]pyridin-5-yl)pyrazin-2-yl)pyrrolidin-2-one | 279.30 |
| 133 | 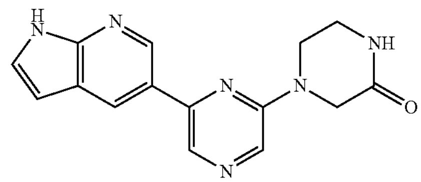 [SMILES: O=C1CN(c2cncc(-c3cnc4[nH]ccc4c3)n2)CCN1] | 4-(6-(1H-pyrrolo[2,3-b]pyridin-5-yl)pyrazin-2-yl)piperazin-2-one | 294.31 |
| 134 | 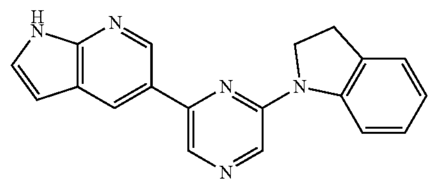 [SMILES: c1ccc2c(c1)CCN2c1cncc(-c2cnc3[nH]ccc3c2)n1] | 5-(6-(indolin-1-yl)pyrazin-2-yl)-1H-pyrrolo[2,3-b]pyridine | 313.36 |
| 135 | 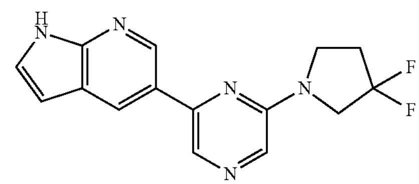 [SMILES: FC1(F)CCN(c2cncc(-c3cnc4[nH]ccc4c3)n2)C1] | 5-(6-(3,3-difluoropyrrolidin-1-yl)pyrazin-2-yl)-1H-pyrrolo[2,3-b]pyridine | 301.29 |
| 137 | 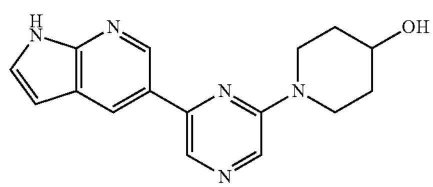 [SMILES: OC1CCN(c2cncc(-c3cnc4[nH]ccc4c3)n2)CC1] | 1-(6-(1H-pyrrolo[2,3-b]pyridin-5-yl)pyrazin-2-yl)piperidin-4-ol | 295.34 |
| 138 | 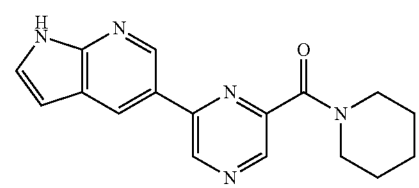 [SMILES: O=C(c1cncc(-c2cnc3[nH]ccc3c2)n1)N1CCCCC1] | (6-(1H-pyrrolo[2,3-b]pyridin-5-yl)pyrazin-2-yl)(piperidin-1-yl)methanone | 307.35 |
| 139 | 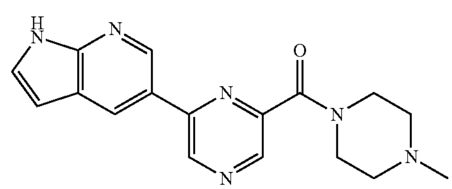 [SMILES: CN1CCN(C(=O)c2cncc(-c3cnc4[nH]ccc4c3)n2)CC1] | (6-(1H-pyrrolo[2,3-b]pyridin-5-yl)pyrazin-2-yl)(4-methylpiperazin-1-yl)methanone | 322.36 |
| 140 | 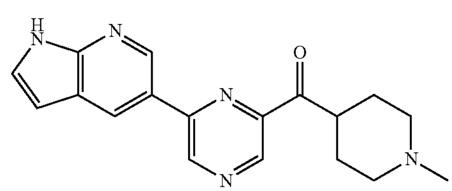 [SMILES: CN1CCC(C(=O)c2cncc(-c3cnc4[nH]ccc4c3)n2)CC1] | N-(1-methylpiperidin-4-yl)-6-(1H-pyrrolo[2,3-b]pyridin-5-yl)pyrazin-2-amine | 308.38 |

TABLE 1-continued

List of Compounds

| Exp. ID | Structure | Chemical Name | Mol. Wt. |
|---|---|---|---|
| 141 | 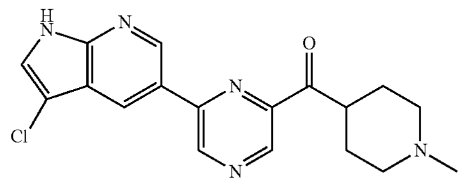 [SMILES: CN1CCC(C(=O)c2cncc(-c3cnc4[nH]cc(Cl)c4c3)n2)CC1] | 6-(3-chloro-1H-pyrrolo[2,3-b]pyridin-5-yl)-N-(1-methylpiperidin-4-yl)pyrazin-2-amine | 342.83 |
| 142 | 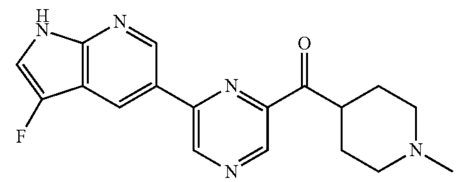 [SMILES: CN1CCC(C(=O)c2cncc(-c3cnc4[nH]cc(F)c4c3)n2)CC1] | 6-(3-fluoro-1H-pyrrolo[2,3-b]pyridin-5-yl)-N-(1-methylpiperidin-4-yl)pyrazin-2-amine | 326.37 |
| 143 | 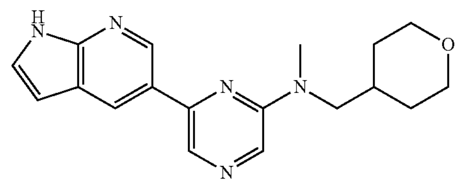 [SMILES: CN(CC1CCOCC1)c1cncc(-c2cnc3[nH]ccc3c2)n1] | N-methyl-6-(1H-pyrrolo[2,3-b]pyridin-5-yl)-N-((tetrahydro-2H-pyran-4-yl)methyl)pyrazin-2-amine | 323.39 |
| 144 | 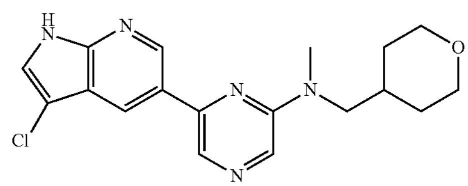 [SMILES: CN(CC1CCOCC1)c1cncc(-c2cnc3[nH]cc(Cl)c3c2)n1] | 6-(3-chloro-1H-pyrrolo[2,3-b]pyridin-5-yl)-N-methyl-N-((tetrahydro-2H-pyran-4-yl)methyl)pyrazin-2-amine | 357.84 |
| 145 | 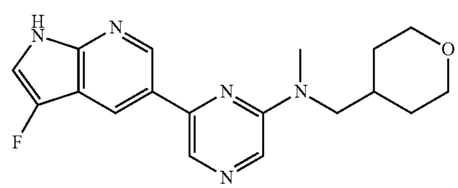 [SMILES: CN(CC1CCOCC1)c1cncc(-c2cnc3[nH]cc(F)c3c2)n1] | 6-(3-fluoro-1H-pyrrolo[2,3-b]pyridin-5-yl)-N-methyl-N-((tetrahydro-2H-pyran-4-yl)methyl)pyrazin-2-amine | 341.38 |
| 148 | 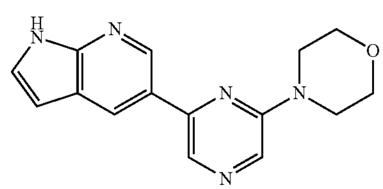 [SMILES: c1cc2cc(-c3cncc(N4CCOCC4)n3)cnc2[nH]1] | 4-(6-(1H-pyrrolo[2,3-b]pyridin-5-yl)pyrazin-2-yl)morpholine | 281.31 |
| 149 | 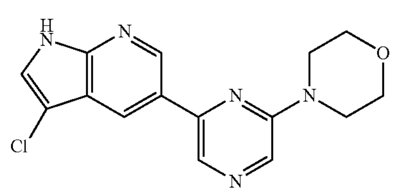 [SMILES: Clc1c[nH]c2ncc(-c3cncc(N4CCOCC4)n3)cc12] | 4-(6-(3-chloro-1H-pyrrolo[2,3-b]pyridin-5-yl)pyrazin-2-yl)morpholine | 315.76 |
| 150 | 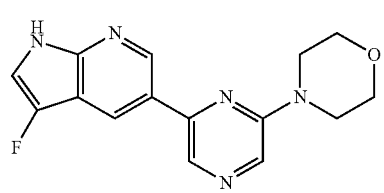 | 4-(6-(3-fluoro-1H-pyrrolo[2,3-b]pyridin-5-yl)pyrazin-2-yl)morpholine | 299.30 |

TABLE 1-continued

List of Compounds

| Exp. ID | Structure | Chemical Name | Mol. Wt. |
|---|---|---|---|
| 152 | 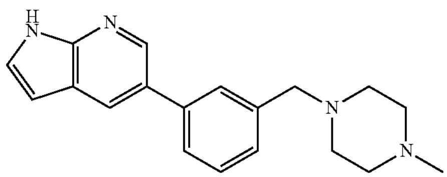 [SMILES: CN1CCN(Cc2cccc(-c3cnc4[nH]ccc4c3)c2)CC1] | 5-(3-((4-methylpiperazin-1-yl)methyl)phenyl)-1H-pyrrolo[2,3-b]pyridine | 306.40 |
| 155 | 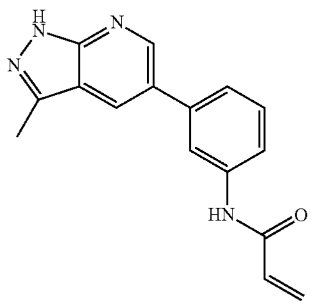 [SMILES: C=CC(=O)Nc1cccc(-c2cnc3[nH]nc(C)c3c2)c1] | N-(3-(3-methyl-1H-pyrazolo[3,4-b]pyridin-5-yl)phenyl)acrylamide | 278.31 |
| 158 | 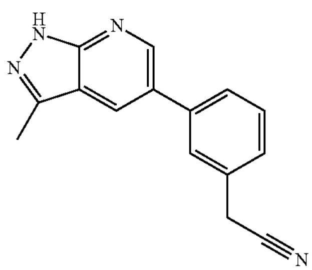 [SMILES: Cc1n[nH]c2ncc(-c3cccc(CC#N)c3)cc12] | 2-(3-(3-methyl-1H-pyrazolo[3,4-b]pyridin-5-yl)phenyl)acetonitrile | 248.28 |
| 161 | 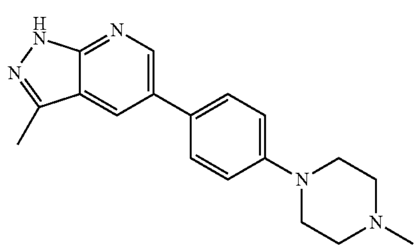 [SMILES: Cc1n[nH]c2ncc(-c3ccc(N4CCN(C)CC4)cc3)cc12] | 3-methyl-5-(4-(4-methylpiperazin-1-yl)phenyl)-1H-pyrazolo[3,4-b]pyridine | 307.39 |
| 164 | 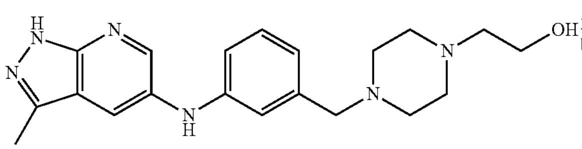 | 2-(4-(3-((3-methyl-1H-pyrazolo[3,4-b]pyridin-5-yl)amino)benzyl)piperazin-1-yl)ethanol | 366.46 |
| 167 | 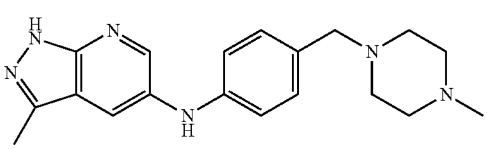 [SMILES: Cc1n[nH]c2ncc(Nc3ccc(CN4CCN(C)CC4)cc3)cc12] | 3-methyl-N-(4-((4-mehtylpiperazin-1-yl)methyl)phenyl)-1H-pyrazolo[3,4-b]pyridin-5-amine | 336.43 |
| 170 | 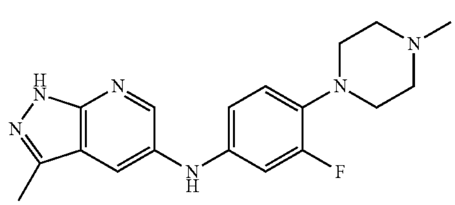 [SMILES: Cc1n[nH]c2ncc(Nc3ccc(N4CCN(C)CC4)c(F)c3)cc12] | N-(3-fluoro-4-(4-methylpiperazin-1-yl)methyl)phenyl)-1H-pyrazolo[3,4-b]pyridin-5-amine | 340.40 |

TABLE 1-continued

List of Compounds

| Exp. ID | Structure | Chemical Name | Mol. Wt. |
|---|---|---|---|
| 171 | 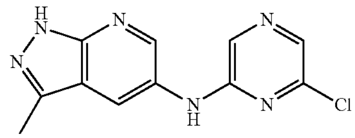 [SMILES: Cc1n[nH]c2ncc(Nc3cncc(Cl)n3)cc12] | N-(6-chloropyrazin-2-yl)-3-methyl-1H-pyrazolo[3,4-b]pyridin-5-amine | 260.68 |

General Procedures for the Preparation Compounds 173-182

The key compound 3-methyl-5-(4,4,5,5-tetramethyl-1,3,2-dioxaborolan-2-yl)-1H-pyrrolo[2,3-b]pyridine 172 protected with either triphenylmethyl chloride (trityl chloride), p-toluenesulfonyl chloride (p-TsCl) and/or tert-Butyloxycarbonyl (BOC) group (1 eq) was reacted with 2-substituted heteroaryl halogen containing scaffolds; 11, 46, 57, 63, 69, 72, 88, 103, 109 and 129 (0.9 to 1.0 eq) in either DMF, DME, Toluene, Acetonitrile, tert-BuOH, THF and or 1,4-dioxane were taken in a sealed tube. The resulting reaction mixture was degassed, purged with argon or $N_2$ gas a few times and was charged with $NaCO_3$, $Cs_2CO_3$, $K_2CO_3$, potassium acetate or $NaHCO_3$ (1.5 to 2 equivalents) followed by the addition of palladium catalysts (0.01 to 0.05 eq). After the addition of catalysts the contents of the reaction were purged and degassed again and heated at 80 to 100° C. for 8 to 16 hrs. After completion of the reaction monitored from TL, the contents were cooled to room temperature and diluted with $CH_2Cl_2$, $CHCl_3$ or EtOAc. The organic layers were passed through a Celite pad then the solvent was completely distilled off to get the crude product. The crude was subjected to flash to column chromatography purification to get the title compounds.

-continued

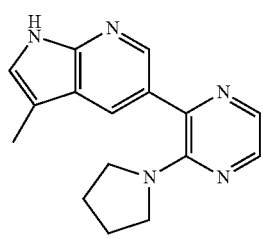

181

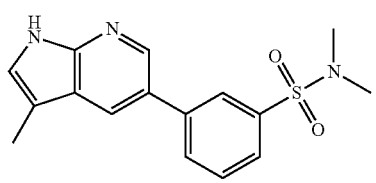

182

General Procedures for the Deprotection to give Compounds 173-182

Deprotection reactions were carried out (unless specified otherwise) in CH$_2$Cl$_3$, CHCl$_3$ or 1,4-dioxane (5-10 mL) and trifluoroacetic acid (5 mL) or concentrated HCl. The reaction mixture was stirred at RT or heated at 40° to 50° C. for 4 to 10 hrs. After completion of the reaction the solvents were completely distilled off and diluted with water and the pH was adjusted to 9 and extracted with chloroform twice. The combined organic layer was washed with brine solution and dried over sodium sulphate and the solvents were removed and the crude material was passed through 100-200 mesh silica gel, eluting with 1 to 10% MeOH/CH$_2$Cl$_2$ or CHCl$_3$ to obtain off-white to pale yellow coloured compounds 173-182.

Example 124

6-(3-methyl-1H-pyrrolo[2,3-b]pyridin-5-yl)-N-(1-methylpiperidin-4-yl)pyrazin-2-amine (173)

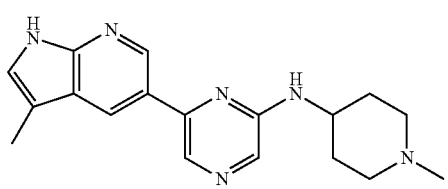

173

$^1$HNMR and LCMS. $^1$H NMR (400 MHz, CDCl$_3$) δ: 8.91 (d, J=1.82 Hz 1H), 8.55 (s, 1H), 8.42 (d, J=1.70 Hz 1H), 8.33 (s, J=34.04 Hz 1H), 7.81 (s, 1H), 7.10 (s, 1H), 4.57 (d, J=8.29 Hz 1H), 3.85 (s, 1H), 2.86 (s, 2H), 2.34 (m, J=13.65 Hz 6H), 2.18 (s, 4H), 1.68 (s, 2H), 1.25 (s, 2H); MS m/z 322.9 (M+H)$^+$.

Example 125

N-methyl-6-(3-methyl-1H-pyrrolo[2,3-b]pyridin-5-yl)-N-((tetrahydro-2H-pyran-4-yl)methyl)pyrazin-2-amine (174)

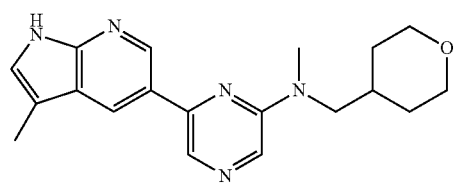

174

$^1$HNMR and LCMS. $^1$H NMR (400 MHz, CDCl$_3$) δ: 8.96 (d, J=1.82 Hz 1H), 8.45 (d, J=1.70 Hz 2H), 8.35 (d, J=40.85 Hz 1H), 7.94 (s, 1H), 7.10 (s, 1H), 3.99 (m, J=7.43 Hz 2H), 3.55 (m, J=7.19 Hz 2H), 3.38 (m, J=1.82 Hz 2H), 3.22 (s, 3H), 2.37 (s, 3H), 1.68 (m, J=13.29 2H), 1.46 (m, J=7.31 Hz 2H); MS m/z 337.9 (M+H)$^+$.

Example 126

4-(6-(3-methyl-1H-pyrrolo[2,3-b]pyridin-5-yl)pyrazin-2-yl)morpholine (175)

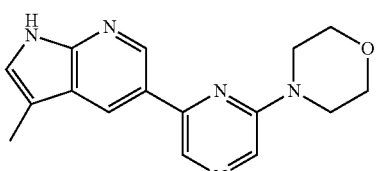

175

$^1$HNMR and LCMS. $^1$H NMR (400 MHz, CDCl$_3$) δ: 8.93 (d, J=1.95 Hz 1H), 8.57 (s, 1H), 8.44 (s, 1H), 8.07 (s, 1H), 7.11 (s, 1H), 3.88 (m, J=5.12 Hz 4H), 3.69 (m, J=5.12 Hz 4H), 2.38 (s, 3H); MS m/z 259.9 (M+H)$^+$.

TABLE 2

List of additional compounds

| 83 | [structure] | 3-(2-methoxyphenyl)-5-(thiophen-3-yl)-1H-pyrazolo[3,4-b]pyridine | MS m/z 307.37 (M + H)⁺. |
|---|---|---|---|
| 84 | [structure] | 5-(furan-3-yl)-3-(2-methoxyphenyl)-1H-pyrazolo[3,4-b]pyridine | MS m/z 291.30 (M + H)⁺. |

Pharmaceutical Salts

Hydrochloric acid salts of the foregoing compounds were prepared by solubilizing the compound in a minimum of ethanol and a solution of ethanolic HCl 20% was added drop wise and the mixture stirred for 1 hour followed by addition of diethyl ether. A precipitated off-white solid hydrochloride was separated by filtration, washer with diethyl ether and dried.

Additional Examples

Usage Method

The subject matter disclosed herein relates to the substituted 5-(pyrazin-2-yl)-1H-pyrazolo[3,4-b]pyridine and pyrazolo[3,4-b]pyridine derivatives as protein kinase inhibitors. Pharmaceutical compositions containing the Formula I, II and VII compounds and methods of using the compounds or compositions to treat various types of diseases or conditions such as Parkinson's disease, Alzheimer's disease, Down's syndrome, Huntington's disease, other neurodegenerative and or CNS, cancer, metabolic and inflammatory disease patients are disclosed. Additionally these compounds and compositions containing the compounds may be employed to treat pain of neuropathic origin, pain of inflammatory origin, cardiovascular disease, rheumatoid arthritis, osteoarthritis, type 2 diabetes, metabolic syndrome and obesity. Methods of making the compounds and pharmaceutical salts thereof are also described herein.

The in vivo neuroprotective efficacy of 5-(pyrazin-2-yl)-1H-pyrazolo[3,4-b]pyridine, 5-(pyrazin-2-yl)-1H-pyrrolo[2,3-b]pyridine and pyrazolo[3,4-b]pyridine in an established MPTP model of PD is described. The C57 black mouse has been used since it is the most sensitive strain for MPTP-induced dopaminergic neurotoxicity model. Sub-chronic MPTP dosing is performed with multiple doses spread out over a 5 day period. MPTP at a dose of 20-25 mg/kg (i.p.) once a day for 5 days results in over 80% depletion of striatal dopamine and significant neuronal damage seven days after MPTP treatment. Importantly, the sub-chronic model produces substantial apoptotic cell death, without overt toxicity, and significant necrotic cell death. PD and similar models were tested for post-treatment studies. The series of compounds was administered after significant depletion of striatal dopamine.

In Vitro Inhibition Assay

LRRK2 Kinase Assay

Procedure: Enzyme was incubated with substrate peptide in reaction buffer in the presence and absence of test compounds or Staurosporine. All additions were done on ice, followed by the addition of ATP mix. Wells were uniformly mixed using an Eppendorff plate shaker and incubated at 30° C. for 20 min, and stopped by the addition of 5 µl of 3% phosphoric acid. Volume was increased to 100 µl by adding 0.8% phosphoric acid which was then transferred to PC filter mats (Millipore), pre-equilibrated with 70% ethanol and water. Plates were washed thrice with 100 µl 0.8% phosphoric acid and dried for an hour at 60° C. 100 µl scintillation fluid was added into each well and reading taken in Perkin Elmer TOPCOUNT beta counter. The data analysis was performed by averaging the duplicate top count readings for each standard, negative, positive control (enzyme control) and samples and subtracting the average negative control from each reading which results in corrected values. A validation EC50 curve was generated by plotting CPM for each Staurosporine concentration on y-axis against the Log concentration of Staurosporine (nM) on the x-axis followed by a best fit curve through the points.

% Inhibition=((Enzyme Control−Compound Treated)/Enzyme Control)×100 Coefficient of Variance (% CV) between replicates: The % CV values between the replicates were mostly within the acceptable limits of a radiometric experiment. Z' factor evaluation: The value of Z' factor was found to be 0.8 for LRRK2 (SEQ ID NO 62) WT and 0.9 was derived for LRRK2 G2019S (SEQ ID NO 28).

All the compounds were tested in 10-dose $IC_{50}$ mode with 3 fold serial dilution starting at 100 µM. The control compound Staurosporine was tested in 10 dose IC50 with 3 fold serial dilution starting at 20 µM. The reactions were carried out at 10 µM ATP for LRRK2 (SEQ ID NO 62) and LRRK2 G2019S (SEQ ID NO 28) (FIG. 1).

General Protein Kinase Assay Methodology employed for Selected Kinases

In vitro profiling of the 317 member kinase panel was performed at Reaction Biology Corporation using the "HotSpot" assay platform. Briefly, specific kinase/substrate pairs along with required cofactors were prepared in reaction buffer; 20 mM Hepes (pH 7.5), 10 mM MgCl2, 1 mM EGTA, 0.02% Brij35, 0.02 mg/ml BSA, 0.1 mM $Na_3VO_4$, 2 mM DTT, 1% DMSO. Compounds were delivered into the reaction, followed ~20 min later by addition of a mixture of ATP (Sigma) and 33P ATP (PerkinElmer) to a final concentration of 10 µM. Reactions were carried out at 25° C. for 120 min, followed by spotting of the reactions onto P81 ion exchange filter paper (Whatman). Unbound phosphate was removed by extensive washing of filters in 0.75% phosphoric acid. After subtraction of background derived from control reactions containing inactive enzyme, kinase activity data were expressed as the percent remaining kinase activity in test samples compared to vehicle (dimethyl sulfoxide) reactions. IC50 values and curve fits were obtained using Prism (Graph-Pad Software). Kinome tree representations were prepared using Kinome Mapper (http://www.reactionbiology.com/apps/kinome/mapper/Launch Kinome.htm). Specifically for the LRRK2 enzyme the substrate LRRKtide (gene bank and protein access numbers NP_940980.2 Q5S007) and clone aa 970-2527 expressed in baculovirus in insect cells with N-terminal GST tag was employed in the study protocol. In the case of DYRK1A (SEQ ID NO 16) the substrate casein (gene bank and protein access numbers NP_001387 Q13627) full length clone expressed in insect with n-terminal tag was used.

Adapta Screening Assay Conditions

The ADP Transcreener uses direct immunodetection of ADP with three different fluorescent detection modes (FP, TR-FRET and FI) and provides the most sensitive HTS method for kinases/ATP-utilizing enzymes. The HTRF Transcreener ADP assay is based on the direct detection of ADP using anti-phospho LRRKtide antibody labelled with $Eu^{3+}$ cryptate. LRRK2 undergoes weak autophosphorylation whereas it exhibits high activity towards the peptidic substrate LRRKtide. This assay can be used for high throughput screening or profiling of any ATP/ADP dependent target such as LRRK2.

For the wild type LRRK the 2X LRRK2/ERM (LRRKtide) mixture was prepared in 50 mM Tris pH 8.5, 0.01% BRIJ-35, 10 mM MgCl2, 1 mM EGTA, 0.02% NaN3. The final 10 µL Kinase Reaction consisted of 3.5-20.8 ng LRRK2 and 200 µM ERM (LRRKtide) in 25 mM Tris/7.5 mM HEPES pH 8.2, 0.005% BRIJ-35, 5 mM MgCl2, 0.5 mM EGTA, 0.01% NaN3. After 1 hour Kinase Reaction incubation, 5 µL of Detection Mix was added.

In the case of LRRK2 G2019S the 2X LRRK2 G2019S/ERM (LRRKtide) mixture was prepared in 50 mM Tris pH 8.5, 0.01% BRIJ-35, 10 mM MgCl2, 1 mM EGTA, 0.02% NaN3. The final 10 µL Kinase Reaction consisted of 2-10 ng LRRK2 G2019S and 200 µM ERM (LRRKtide) in 25 mM Tris/7.5 mM HEPES pH8.2, 0.005% BRIJ-35, 5 mM MgCl2, 0.5 mM EGTA, 0.01% NaN3. After 1 hour Kinase Reaction incubation, 5 µL of Detection Mix was added.

In Vitro DYRK1A, DYRK1B, DYRK2 and DYRK3 Inhibition Assay

The 2xDYRK1A/Ser/Thr 18 mixture was prepared in 50 mM HEPES pH 7.5, 0.01% BRIJ-35, 10 mM MgCl2, 1 mM EGTA. The final 10 µL Kinase Reaction consisted of 1.68-12.5 ng DYRK1A (SEQ ID NO 16) and 2 µM Ser/Thr 18 in 50 mM HEPES pH 7.5, 0.01% BRIJ-35, 10 mM MgCl2, 1 mM EGTA. After 1 hour Kinase Reaction incubation, 5 µL of a 1:1024 dilution of Development Reagent A was added.

The 2xDYRK1B (SEQ ID NO 17)/Ser/Thr 18 mixture was prepared in 50 mM HEPES pH 6.5, 0.01% BRIJ-35, 10 mM MgCl2, 1 mM EGTA, 0.02% $NaN_3$. The final 10 µL Kinase Reaction consisted of 0.47-5.84 ng DYRK1B (SEQ ID NO 17) and 2 µM Ser/Thr 18 in 50 mM HEPES pH 7.0, 0.01% BRIJ-35, 10 mM MgCl2, 1 mM EGTA, 0.01% NaN3. After 1 hour Kinase Reaction incubation, 5 µL of a 1:1024 dilution of Development Reagent A was added.

The 2xDYRK2 (SEQ ID NO 18)/Ser/Thr 09 mixture was prepared in 50 mM HEPES pH 7.5, 0.01% BRIJ-35, 10 mM MgCl2, 1 mM EGTA. The final 10 µL Kinase Reaction consisted of 1.92-10.7 ng DYRK2 (SEQ ID NO 18) and 2 µM Ser/Thr 09 in 50 mM HEPES pH 7.5, 0.01% BRIJ-35, 10 mM MgCl2, 1 mM EGTA. After 1 hour Kinase Reaction incubation, 5 µL of a 1:256 dilution of Development Reagent A is added.

The 2xDYRK3 (SEQ ID NO 19)/Ser/Thr 09 mixture was prepared in 50 mM HEPES pH 7.5, 0.01% BRIJ-35, 10 mM MgCl2, 1 mM EGTA. The final 10 µL Kinase Reaction consisted of 1.92-10.7 ng DYRK3 (SEQ ID NO 19) and 2 µM Ser/Thr 09 in 50 mM HEPES pH 7.5, 0.01% BRIJ-35, 10 mM MgCl2, 1 mM EGTA. After 1 hour Kinase Reaction incubation, 5 µL of a 1:256 dilution of Development Reagent A is added.

TABLE 3

List of Compounds and Corresponding Protein Kinase Inhibition *

| Compound ID | LRRK2 $IC_{50}$ µM | LRRK2 G2019S $IC_{50}$ µM | DYRK1A |
|---|---|---|---|
| 13 | *** | *** | *** |
| 13 | *** | *** | *** |
| 19 | ** | ** | ND |
| 22 | ** | ** | ** |
| 26 | ** | ** | ND |
| 27 | ** | ** | ** |
| 28 | ** | ** | ** |
| 33 | ** | ** | ** |
| 39 | ** | ** | ** |
| 42 | * | * | ND |
| 45 | * | * | ND |
| 48 | ** | ** | * |
| 51 | ** | ** | * |
| 56 | ** | ** | * |
| 59 | *** | *** | ** |
| 62 | ** | ** | ** |
| 65 | *** | *** | * |
| 68 | *** | *** | * |
| 71 | *** | *** | *** |
| 74 | * | * | ND |
| 77 | ** | ** | * |
| 81 | *** | *** | *** |
| 83 | ** | ** | ** |
| 87 | ** | ** | ** |
| 90 | *** | *** | *** |
| 94 | *** | *** | ** |
| 98 | * | * | * |
| 102 | ** | ** | ** |
| 105 | *** | *** | *** |
| 108 | ** | ** | ** |
| 111 | * | * | ND |
| 114 | * | * | ND |
| 117 | * | * | ND |
| 119 | * | * | ND |
| 123 | * | * | ND |
| 125 | *** | *** | *** |
| 126 | *** | *** | *** |
| 127 | ** | ** | ** |
| 128 | ** | ** | ** |
| 130 | ** | ** | ND |
| 131 | ** | ** | ** |
| 133 | ** | ** | ND |
| 134 | *** | *** | *** |
| 135 | ** | ** | ** |
| 137 | *** | *** | *** |
| 138 | ** | ** | ND |
| 139 | * | * | ND |
| 140 | *** | *** | ND |

TABLE 3-continued

List of Compounds and Corresponding Protein Kinase Inhibition *

| Compound ID | LRRK2 IC$_{50}$ μM | LRRK2 G2019S IC$_{50}$ μM | DYRK1A |
|---|---|---|---|
| 141 | *** | *** | ND |
| 142 | *** | *** | *** |
| 143 | *** | *** | *** |
| 144 | *** | *** | *** |
| 145 | *** | *** | *** |
| 148 | *** | *** | *** |
| 149 | *** | *** | *** |
| 150 | *** | *** | *** |
| 152 | *** | *** | *** |
| 155 | * | * | ND |
| 158 | * | * | ND |
| 161 | * | * | ND |
| 164 | * | * | ND |
| 167 | * | * | ND |
| 170 | * | * | ND |
| 171 | * | * | ND |
| 183 | *** | *** | *** |
| 184 | *** | *** | *** |

* Kinase Inhibition Result for Selected Compounds
*** <0.5 μM,
** >0.5 μM,
* >1 μM
ND = Not Determined Protein Kinase Selectivity Profiler Selected LRRK2 (SEQ ID NO 62) and LRRK2 G2019S (SEQ ID NO 28) inhibiting compounds 13, 13HCl, 71, 105, 134 and 148 were tested against 299 protein kinases +17 additional preview kinases in single dose duplicate mode at a concentration of 0.5 μM, 1 μM and 1 μM). A control compound was tested in 10-dose IC$_{50}$ mode with 3-fold serial dilution starting at 20 μM. Reactions were carried out at 10 μM ATP. Data pages include raw data, % Enzyme activity (relative to DMSO controls), and curve fits. The compounds 105, 134 and 148 are selective in inhibiting some kinases including LRRK2 (SEQ ID NO 62), LRRK2 G2019S (SEQ ID NO 28), CHK1 (SEQ ID NO 8), DYRK1A (SEQ ID NO 16), FLT3 (SEQ ID NO 21), MLK1 (SEQ ID NO 33), TNIK (SEQ ID NO 55), TRKA (SEQ ID NO 56) with % enzyme inhibition of 5-15% relative to DMSO controls, whereas the compounds 13 and 71 had activity against kinases in broader scope, inhibiting ABL1 T315I (SEQ ID NO 1), ALK2 (SEQ ID NO 2), ARK5 (SEQ ID NO 64), Aurora A (SEQ ID NO 3), Aurora, B (SEQ ID NO 4), Aurora; C (SEQ ID NO 5), BRAF (SEQ ID NO 6), BRAF V599E, C-KIT (SEQ ID NO 10), CLK1 (SEQ ID NO 11), CLK2 (SEQ ID NO 12), CLK3 (SEQ ID NO 13), CLK4 (SEQ ID NO 14)-4, CSF1R (SEQ ID NO 15), DYRK1A (SEQ ID NO 16), DYRK1B (SEQ ID NO 17), DYRK 2 (SEQ ID NO 18), DYRK3 (SEQ ID NO 19), DYRK4 (SEQ ID NO 20), FLT3 (SEQ ID NO 21), GSK3β (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), MAP4K4 (SEQ ID NO 30), MELK (SEQ ID NO 31), MLK (SEQ ID NO 32), PDGFR (SEQ ID NO 41), PKA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) or TRKC (SEQ ID NO 58) kinases in the range of 5 to 15% relative to DMSO control.

Cell Culture Models of Parkinsons Disease

Rat Mesencephalic Cell Line (N27 Cells):

N27 dopaminergic neuronal cell line has been widely used as a useful model for testing neuroprotective agents ((Kaul et al., 2003; Yang et al., 2004; Zhang et al., 2007). N27 cells were grown in RPMI 1640 medium containing 10% fetal bovine serum, 2 mM L-glutamine, 50 units penicillin, and 50 μg/ml streptomycin (Kaul et al., 2003; Yang et al., 2004). The cell line was incubated at 37° C. in a humidified atmosphere containing 5% $CO_2$.

Primary Mesencephalic Neuronal Cultures:

Primary mesencephalic neuronal cultures were prepared from the ventral mesencephalon of gestational 16- to 18-day-old mouse embryos, as previously described (Zhang et al., 2007). Mesencephalic tissues were dissected from E16 to E18 mouse embryos maintained in ice cold Ca2+-free Hanks' balanced salt solution and then dissociated in Hanks' balanced salt solution containing trypsin-0.25% EDTA for 30 min at 37° C. The dissociated cells were then plated at equal density (0.5×106 cells) on 12 mm coverslips precoated with 0.1 mg/ml poly-D-lysine. Cultures were maintained in neurobasal medium fortified with B-27 supplements, 500 μM 1-glutamine, 100 IU/ml penicillin, and 100 μg/ml streptomycin (Invitrogen). The cells were maintained in a humidified CO2 incubator (5% CO2 and 37° C.). Half of the culture medium was replaced every 2 days. Primary mesencephalic cultures (7-10 days old) were co-treated with 10 μM MPP+ ±test compound (1, 3 and 10 μM) for 24 h. Following the treatments, the survival of dopaminergic neurons were assessed by TH-immunostaining.

Data Analysis:

Data were analyzed with Prism 4.0 software (GraphPad Software, San Diego, Calif.). Dunnett post-hoc multiple comparison testing was used, if appropriate, to delineate significance between treated groups and the untreated samples. Differences with *$p<0.05$ and ** $p<0.01$ were considered significant. Results are from at least two independent experiments performed in triplicate. The 5-(pyrazin-2-yl)-1H-pyrazolo[3,4-b]pyridine, 5-(pyrazin-2-yl)-1H-pyrrolo[2,3-b]pyridine and pyrazolo[3,4-b]pyridine exhibited IC50 between 0.7 to 3 M activity on these cell lines Summary of Cell Culture Findings:

Several compounds in the claimed series dose-dependently protected against MPP+-induced cytotoxic cell death in N27 dopaminergic neuronal cells, dose-dependently protected against MPP+-induced increase in caspase-3 activity in N27 cells. Increase in caspase-3 activity correlates directly with apoptotic cell death. These series compounds also protected TH neurons from MPP+-induced dopaminergic neurodegeneration. Thus these compounds exhibit promising neuroprotective effect in cell culture models of PD; further validation of in an animal model of PD is undertaken.

In Vivo Models of Parkinsons Disease

Neuroprotective effect of orally administered series in MPTP (1-methyl-4-phenyl-1,2,3,6-tetrahydropyridine)-mouse model of Parkinson's disease (PD):

32 C57 black mice (C57/bl6, 6-8 week old, 25-30 g) were purchased from Charles River Laboratories, Ohio. Animals were divided into 4 groups of 8 animals each, group A for saline-treatment, group B for MPTP-treatment, group C for compounds 13, 13 HCl, 71, 105, 134 and 148, (10 mg/kg)+MPTP and group D for compounds 13, 13 HCl, 71, 105, 134 and 148 (30 mg/kg)+MPTP. All animals were housed under standard conditions: constant temperature (22±1° C.), humidity (relative, 30%), and a 12-h light/dark cycle. Mice were allowed free access to food and water. Use of the animals and protocol procedures were approved and supervised by the Committee on Animal Care at Iowa State University (Ames, Iowa). The test compounds 13, 13 HCl, 71, 105, 134 and 148 were dissolved in sterile water for this study. Prior to treatment animals were pre-trained on rotarod for at least 3 minutes every day for three successive days. For the pre-treatment study, test compounds 13, 13 HCl, 71, 105, 134 and 148 were administered once by oral gavage to group C animals (10 mg/kg) and group D animals at 30 mg/kg, 24 h prior to MPTP-injection and continued daily for additional 11 days. MPTP was dissolved in PBS and injected intraperitoneally (i.p.) at doses of 25 mg/kg, once daily for 5 days to group B, C and D animals. Group A animals were injected with saline (i.p.) to be used as controls. Urine and feces were collected on Day 8, behavioural studies were performed on Day 9 (4-days post-MPTP). On day 12 (7 days post-MPTP), 4 animals/group were sacrificed, different brain regions including striatum and substantia nigra were dissected. Left striatum were used for neurochemical analysis. Other 4 animals/group were perfused and used for TH immunohistological studies. Reference: Ghosh et al., Free Radic Biol Med. 2010 Dec. 1; 49(11):1674-84. Zhang et al., J Pharmacol Exp. Ther., 2007 September; 322(3):913-22, both of which are incorporated by reference herein in their entireties.

Orally Administered Test Compounds 13, 13 HCl, 71, 105, 134 and 148 Improve Locomotor Activities in MPTP-Injected Mice:

MPTP-treatment reduced the time-spent on the rotarod by 44% compared to saline-treated animals, whereas test compounds at 10 mg/kg increased the time spent by MPTP-treated mice to 101% suggesting that test compounds at 10 mg/kg completely restored MPTP-induced motor deficits to that of saline-treated animals. Similarly, test compounds at 30 mg/kg increased the time spent by MPTP-treated mice to 89% suggesting that test compounds at 30 mg/kg almost completely restored MPTP-induced motor deficits to that of saline-treated animals. Together, these results suggest that test compounds significantly restored MPTP induced motor co-ordination impairments.

Orally Administered Test Compounds 13, 13 HCl, 71, 105, 134 and 148 Restore Striatal Dopamine Levels in MPTP Treated Mice:

MPTP treatment decreased the striatal dopamine levels by 59% compared to that of saline-treated animals, whereas test compounds at 10 mg/kg and 30 mg/kg increased the dopamine levels in the presence of MPTP to 71% and 106% respectively suggesting that test compounds dose-dependently restored MPTP-induced dopamine loss. Together, these results suggest that test compounds rescues MPTP-induced neurochemical depletion in animal models of PD.

Orally Administered Test Compounds 13, 13 HCl, 71, 105, 134 and 148 Protect Against MPTP-Induced TH Neuronal Loss in the Substantia Nigra and in the Striatum:

Seven days after MPTP treatment, brains from 4 groups were harvested and grouped into sets 1-4 as described in the method section. Nigral and striatal sections were then subject to tyrosine hydroxylase (TH) immunostaining. MPTP treatment led to degeneration of TH positive dopaminergic neurons and its terminals in the striatum (2×), substantia nigra at lower (2×) and higher magnification (10×) compared to saline-treated animals, clearly visualized severe and significant loss of neurons in substantia nigra pars compacta (SNpc), substantia nigra lateralis and substantia nigra reticularis regions of nigral tract in MPTP-treated animals compared to saline-treated animals. Importantly, test compound 13, 13 HCl, 71, 105, 134 and 148 at 10 mg/kg and 30 mg/kg offered dose-dependent protection against MPTP-induced TH cell loss and dopaminergic degeneration both in the substantia nigra and in the striatum.

Intravenous Administration of Test Compounds 13, 13 HCl, 71, 105, 134 and 148:

24 C57 black mice (C57/bl6, 6-8 week old, and 25-30 g) were purchased from Charles River Laboratories, Ohio. Animals were divided into 3 groups of 8 animals each, group A for saline-treatment, group B for MPTP-treatment and group C compounds 13, 13 HCl, 71, 105, 134 and 148, (5 mg/kg)+ MPTP. Compounds 13, 13 HCl, 71, 105, 134 and 148 were dissolved in PBS pH7.4 for this study. Prior to treatment animals were pre-trained on rotarod for at least 3 minutes every day for three successive days. Test compound (5 mg/kg) was administered intravenously to group C animals, 24 h prior to MPTP-injection and continued daily for additional 11 days. MPTP was dissolved in PBS and injected intraperitoneally (i.p.) at doses of 25 mg/kg, once daily for 5 days to group B and C animals. Group A animals were injected with saline (i.p.) to be used as controls. Urine and Faeces were collected on Day 8, behavioural studies were performed on Day 9 (4-days post-MPTP). On day 12 (7 days post-MPTP), 4 animals/group were sacrificed, different brains regions including striatum and substantia nigra were dissected. Left striatum were used for neurochemical analysis. Other 4 animals/group were perfused and used for TH immunohistological studies.

Intravenously Administered Test Compound Improves Locomotor Activities in MPTP-Injected Mice:

MPTP-treatment reduced the time spent on the rotarod by 53% compared to saline-treated animals, whereas test compounds at 10 mg/kg increased the time spent by MPTP-treated mice to 102% suggesting that test compounds at 5 mg/kg, i.v. completely restored MPTP-induced motor deficits to that of saline-treated animals. These results suggest that intravenous test compounds administration significantly restored MPTP induced motor co-ordination impairments.

Intravenously Administered Test Compounds Restore Striatal Dopamine Levels in MPTP Treated Mice:

MPTP-treatment decreased the striatal dopamine levels by 60% compared to that of saline-treated animals, whereas test compounds at 5 mg/kg restored dopamine levels in the presence of MPTP to 85%, nearly to that of saline treated animals. Together, these results suggest that test compounds rescues MPTP-induced neurochemical depletion in animal models of PD.

Intravenously Administered Compounds 13 HCl, 71, 105 and 134 Protect Against MPTP-Induced TH Neuronal Loss in the Substantia Nigra and in the Striatum:

MPTP treatment led to degeneration of TH positive dopaminergic neurons and its terminals in the striatum (2×), substantia nigra at lower (2×) and higher magnification (10×) compared to saline-treated animal clearly visualized severe and significant loss of neurons in substantia nigra pars compacta (SNpc), substantia nigra lateralis and substantia nigra reticularis regions of nigral tract in MPTP-treated animals. Importantly, test compounds at 5 mg/kg offered an almost a complete protection against MPTP-induced TH cell loss and dopaminergic degeneration both in the substantia nigra and in the striatum.

TABLE 4

BBB Pre-treatment results

| Group 4 Sample ID | Concentrations of test compounds in Mouse Brain Homogenate (ng/gm) |
|---|---|
| 1 | 0 ng/gm |
| 2 | 5 ng/gm |
| 3 | 10 ng/gm |
| 4 | 11 ng/gm |
| 5 | 2 ng/gm |

BQL = below quantitation limit of 1.00 ng/mL, whole brain/buffer homogenates

Summary of Oral and Intravenous Pre-Treatment

The results indicate that both orally and intravenously administered 5-(pyrazin-2-yl)-1H-pyrazolo[3,4-b]pyridine, 5-(pyrazin-2-yl)-1H-pyrrolo[2,3-b]pyridine and pyrazolo[3,4-b]pyridine derivatives improve behavioural functions, restore striatal dopamine levels and protect nigrostriatum in MPTP-treated mice. However, orally administered compounds were more effective than intravenously administered compounds in protecting against MPTP-induced motor deficits, dopamine depletion and TH neuronal loss. Together, these results strongly suggest that these compounds are effective neuroprotective agents in therapeutic intervention of PD. This data further supports the C57 black mice models are promising models for proof of concept studies targeting LRRK2 protein where its expression in mice shares ~86% homology with the human protein NM-25730.

Post-Treatment Study

Neuroprotective Effect of Test Compounds 13, 13 HCl, 71, 105, 134 and 148 in MPTP (1-methyl-4-phenyl-1,2,3,6-tetrahydropyridine)-Mouse Model of Parkinson's Disease (PD):

32 C57 black mice (C57/bl6, 6-8 week old, 25-30 g) were purchased from Charles River Laboratories, Ohio. Animals were divided into 4 groups of 8 animals each, group A for saline-treatment, group B for MPTP-treatment, group C for MPTP+13 HCl, 71, 105 and 134 (30 mg/kg, oral) and group D for MPTP+13 HCl, 71, 105 and 134 (5 mg/kg, i.v.). All animals were housed in Laboratory of Animal Resources vivarium at Iowa State University under standard conditions: constant temperature (22±1° C.), humidity (relative, 30%), and a 12-h light/dark cycle. Mice were allowed free access to food and water. Use of the animals and protocol procedures were approved and supervised by the Committee on Animal Care at Iowa State University (Ames, Iowa). Test compounds were dissolved in PBS for this study. Prior to treatment animals were pre-trained on rotarod for at least 3 minutes every day for three successive days.

Group A animals were injected with saline (i.p.) to be used as controls. MPTP was dissolved in PBS and injected intraperitoneally (i.p.) at doses of 25 mg/kg, once daily for 5 days to group B, C and D animals. On day 4, prior to $4^{th}$ MPTP injection, group C animals received test compounds (30 mg/kg, oral) daily for eight days. Similarly, on day 4, prior to $4^{th}$ MPTP injection, group D animals received test compounds (5 mg/kg, i.v) daily for eight days. On day 9 (Post-test compounds administration) or day 12 (7 days post-MPTP), 4 animals/group were sacrificed, different brain regions including striatum and substantia nigra were dissected. Left striatum were used for neurochemical analysis. Other 4 animals/group were perfused and used for TH immunohistological studies.

TABLE 5

BBB Post-treatment results for 13 HCl

| PK20.155 Pooled Regions Subject ID | Calc. Conc. (ng/g) of test compound 13 HCl in Mice Brains |
|---|---|
| 70703 | 2.74 |
| 70704 | 3.03 |
| 70705 | 2.72 |
| 70706 | 2.92 |
| 70711 | 1.36 |
| 70712 | 2.32 |
| 70713 | 3.09 |
| 70714 | 3.79 |
| Mean | 2.75 |
| % CV | 25.5 |
| 70688 (control) | BQL <1 ng/g |

Summary of Oral and Intravenous

Post-administration of test compounds 13 HCl, 105 and 148 by oral and i.v routes significantly protected against MPTP-induced motor-deficits and histological deficits and but not against neurochemical deficits.

Pharmacokinetics

Figure 2:
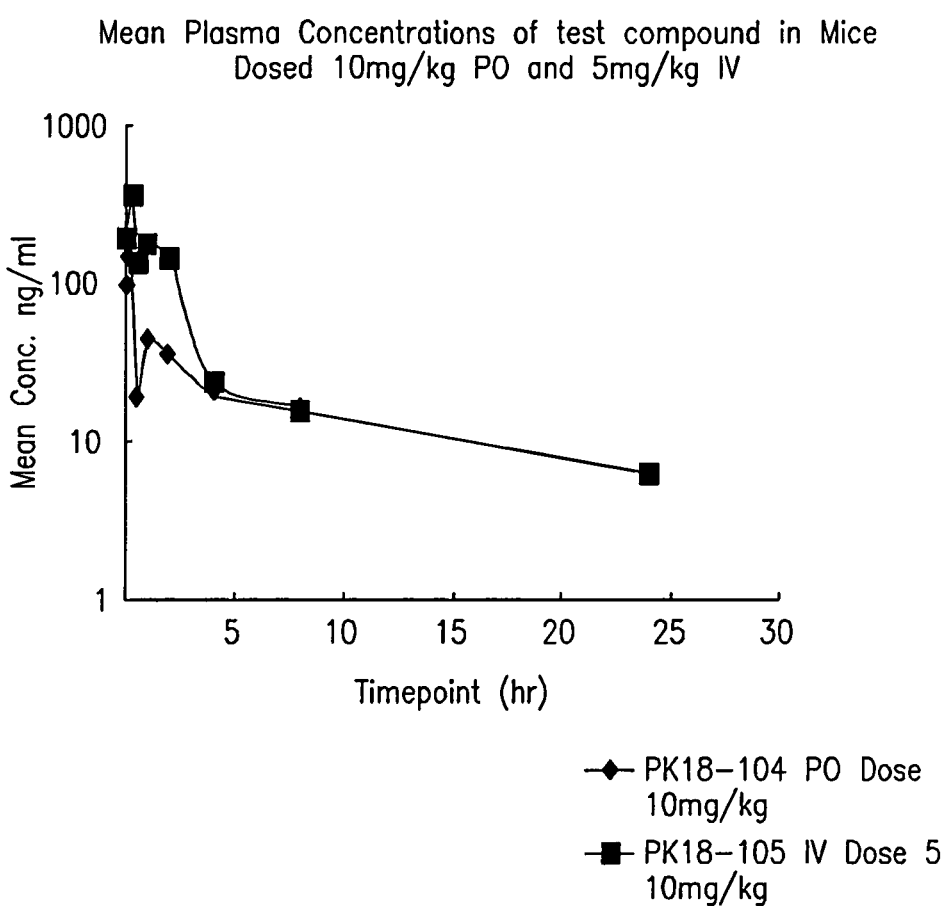
FIG. 2 is a graphical depiction of mean plasma concentrations of test compound in mice dosed 10 mg/kg PO and 5 mg/kg IV in accordance with one aspect of the invention.

Referring now to FIG. 2, mice PK: Mean Plasma Concentrations of test compounds 13 HCl, 71 and 105 in Mice Dosed 10 mg/kg PO and 5 mg/kg IV is shown. Table 6 reflects mice pharmacokinetics parameters.

TABLE 6

Mice Pharmacokinetics Parameters

| IV Dose (5 mg/kg) | | | | | | |
|---|---|---|---|---|---|---|
| $t_{1/2}$ (hr) | Vb (L/kg) | Vss (L/kg) | AUC0-¥ (h*ng/mL) | AUC0-last (h*ng/mL) | $C_0$ (ng/mL) | Cl (L/hr/kg) |
| 10.6 | 87.1 | 45.2 | 882 | 787 | 193 | 5.67 |

| Oral Dose (10 mg/kg) | | | | | |
|---|---|---|---|---|---|
| Cmax (ng/mL) | Tmax (hr) | $t_{1/2}$ (hr) | AUC0-¥ (h*n2/mL) | AUC0-last (h*ng/mL) | F (%) |
| 144 | 0.250 | 5.12 | 351 | 228 | 19.9 |

Rat PK:

To investigate the pharmacokinetic profiles of test compound following intravenous bolus administration and oral gavage in male Sprague Dawley rats.

TABLE 7

Rat Pharmacokinetics Parameters

| Route/Dose (mg/kg) | $T_{max}$ (h) | $C_0$ (ng/mL) | $C_{max}$ (ng/mL) | $AUC_{0-t}$ (h*ng/mL) | $AUC_{0-inf}$ (h*ng/mL) | $T_{1/2}$ (h) | CL (mL/min/kg) | $V_{ss}$ (L/kg) | F (%) |
|---|---|---|---|---|---|---|---|---|---|
| IV (5) | NA | 902.15 ± 355.65 | NA | 1020.46 ± 646.82 | 685.61 | 2.26 | 122.84 | 15.15 | — |

TABLE 7-continued

Rat Pharmacokinetics Parameters

| Route/Dose (mg/kg) | $T_{max}$ (h) | $C_0$ (ng/mL) | $C_{max}$ (ng/mL) | $AUC_{0-t}$ (h*ng/mL) | $AUC_{0-inf}$ (h*ng/mL) | $T_{1/2}$ (h) | CL (mL/min/kg) | $V_{ss}$ (L/kg) | F (%) |
|---|---|---|---|---|---|---|---|---|---|
| PO (30) | 6.67 ± 2.31 | NA | 132.66 ± 40.84 | 1043.74 ± 497.14 | NR | NA | NA | NA | 23.87 |

The plasma concentration-time data and plasma pharmacokinetic parameters of one of the compounds 13, 13 HCl, 71, 105, 134 and 148, following IV and PO administration in male Sprague Dawley rats are presented in Table 7. The individual and mean plasma concentration-time profiles following IV bolus administration of test compounds (5 mg/kg) to rats, the mean $AUC_{0-t}$ and $T_{1/2}$ were 1020.46 ng·h/mL and 2.26 h, respectively (Table 7) test compounds 13, 13 HCl, 71, 105, 134 and 148 showed clearance (CL) 122.84 mL/min/kg which is more than 100% of normal hepatic blood flow in rats. The mean apparent steady-state volume of distribution ($V_{ss}$) of compounds 13, 13 HCl, 71, 105, 134 and 148 was 15.15 L/kg, which is approximately 30-fold higher than the total body water normalized to body weight (i.e. 0.7 L/kg). Following oral administration of compounds 13, 13 HCl, 71, 105, 134 and 148 (30 mg/kg) solution, mean $C_{max}$ was found to be 132.66 ng/mL and mean $T_{max}$ was found to be 6.7 h. The mean $AUC_{0-t}$ was found to be 1043.71 ng·h mL and the absolute oral bioavailability was found to be 24%.

Toxicology—In vitro

Rat Hepatoma (H4IIE) Cell Line:

Cells were seeded into 96-well plates and cultured in medium containing 20% bovine serum. Following an equilibration period, cells were treated with compounds 13 and 13 HCl at concentrations of 0, 5, 10, and 50 μM for 24 hrs (overnight) at 37° C. in 5% $CO_2$. General cytotoxicity was evaluated by monitoring membrane integrity (MBR, cell supernatant), cell mass (PI) and mitochondrial function (cellular ATP levels). Rotenone was included as a positive control because it produces measurable effects in all three assays. DMSO at 0.5% in medium was included as a negative control. Three wells per exposure concentration were used in each assay. Results are summarized in Table 8 and are expressed as percent of control, with control values set at 100%. $TC_{50}$ values were calculated if the half-maximal response (50%) was achieved. Test compounds 13 and 13 HCl were rank-ordered from most to least toxic based on individual membrane integrity and ATP responses as well as resultant $TC_{50}$ values.

TABLE 8

Summary of the acute toxicity data

| Compound | Solubility | ATP % Control | | | Cell Mass % Control | | | Mem Tox % Control | | | ATP $TC_{50}$ | Cell Mass $TC_{50}$ | Mem Tox $TC_{50}$ |
|---|---|---|---|---|---|---|---|---|---|---|---|---|---|
| | | 5 μM | 10 μM | 50 μM | 5 μM | 10 μM | 50 μM | 5 μM | 10 μM | 50 μM | | | |
| 13 | 50 μM | 99% | 99% | 74% | 93% | 88% | 71% | 100% | 96% | 94% | >50 μM | >50 μM | >50 μM |
| 13 HCl | 50 μM | 93% | 91% | 78% | 89% | 81% | 62% | 93% | 91% | 90% | >50 μM | >50 μM | >50 μM |
| | | 0.001 μM | 0.1 μM | 1 μM | 0.001 μM | 0.1 μM | 1 μM | 0.001 μM | 0.1 μM | 1 μM | | | |
| Rotenone | 1 μM | 98% | 34% | 4% | 105% | 54% | 25% | 100% | 98% | 46% | 0.08 μM | 0.23 μM | 0.93 μM |

Results Summary:

Test compounds 13 and 13 HCl were rank-ordered from highest to lowest probability of producing toxicity based first on membrane toxicity, then on ATP, and finally on cell mass (PI). It is important to note that within a given grouping compounds may be classified as to their primary effect being either cytotoxic, cytostatic, or reducing mitochondrial function. In general, compound responses above 80% of vehicle control are considered to be low-to-no effect, moderates generally rank 80% to 50% of vehicle control, and those compounds that cross the 50% mark are considered to have higher probability of toxicity.

Test Compounds 13 HCl and 148 Inhibition of Monoamine Oxidases (MAO-A and MAO-B)

Experimental Procedure:

Test compounds (0.01-100 μM) final DMSO concentration 0.1%, were incubated with recombinant human MAO-A (2 μg/mL) or MAO-B (2 μg/mL) in the presence of the probe substrate kynuramine (50 μM) for 25 min at 37° C. The non-selective MAO modulator, tranylcypromine, was screened alongside the test agents with tranylcypromine as a positive control. The reactions were terminated by addition of methanol containing internal standard for analytical quantification. The quenched samples were incubated at 4° C. for 10 min and centrifuged at 4° C. for 10 min. The supernatant was removed and analyzed by LC-MS/MS for the probe metabolite 4-hydroxyquinoline. A decrease in the formation of the metabolite compared to vehicle control was used to calculate an IC50 value (the test concentration which produces 50% inhibition.

TABLE 9

MAO inhibition summary of IC$_{50}$ values

| | Control Inhibitors | |
|---|---|---|
| | MAO-A<br>IC$_{50}$ (µM) | MAO-B<br>IC$_{50}$ (µM) |
| Tranylcypromine | 0.12 | 0.11 |
| Compound 13 | >100 | >100 |
| Compound 148 | >100 | 8.8 |

Primary Biochemical Assay

Test compounds in Table 1 have been profiled in a standard in vitro compound selection program to detect potential adverse activity, additional unexpected activity, and relative selectivity and specificity to choose the "lead drug candidate" for further development. The screen covered 65 primary molecular targets, including adenosine, adrenergic, bradykinin, dopamine, glutamate, histamine, muscarinic, serotonin, opiate, and potassium channels including hERG. The test compounds in Table 1 at 10 µM did not inhibit the molecular targets greater than 50%.

Structural Homology Modeling—LRRK2 and G2019S

Figure 3:
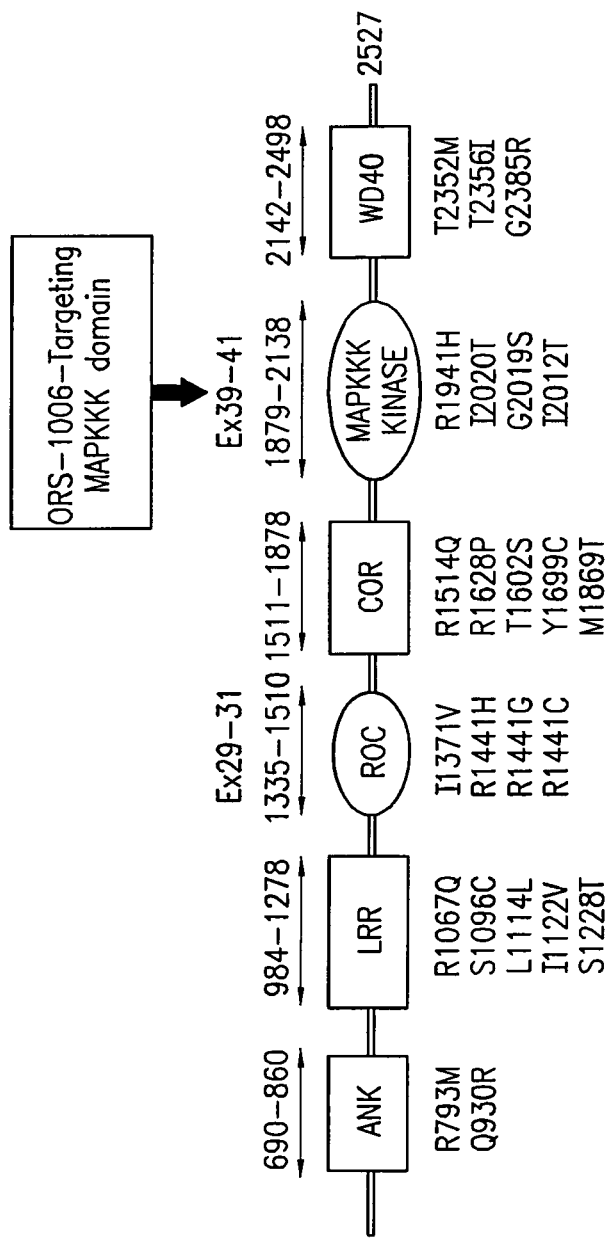
FIG. 3 is a listing including the Leucine-Rich Repeat Kinase (LRRK2) (SEQ ID NO 62) domain region sequence (1879-2140) from the full length protein sequence NP_940980.

The compounds of Formula I, II and VII and in Table 1 and 2 were designed using a structural homology model of LRRK2 and its mutant form of LRRK2 G2019S. The homology model of structural model of the kinase domain of LRRK2 was constructed using Leucine-Rich Repeat Kinase (LRRK2) domain region sequence (1879-2140) from the full length protein sequence NP_940980 (FIG. 3). Sequence search with in the RCSB provided the 5 homologues X-ray crystal structure templates with 30-32% sequence identity and ~50% sequence similarities was considered as starting point for multiple sequence alignment using Clustal W alignment (FIG. 4) and homology modeling. The Swiss-Model was applied in sequence alignment, model building, loop prediction and refinement. With the application of FFDD (Fragment-Field Drug Design) workflow design strategy, the final models of LRRK2 shown in FIG. 5 were utilized and served as template for designing claimed compounds.

Figures 5A, 5B, 5C:
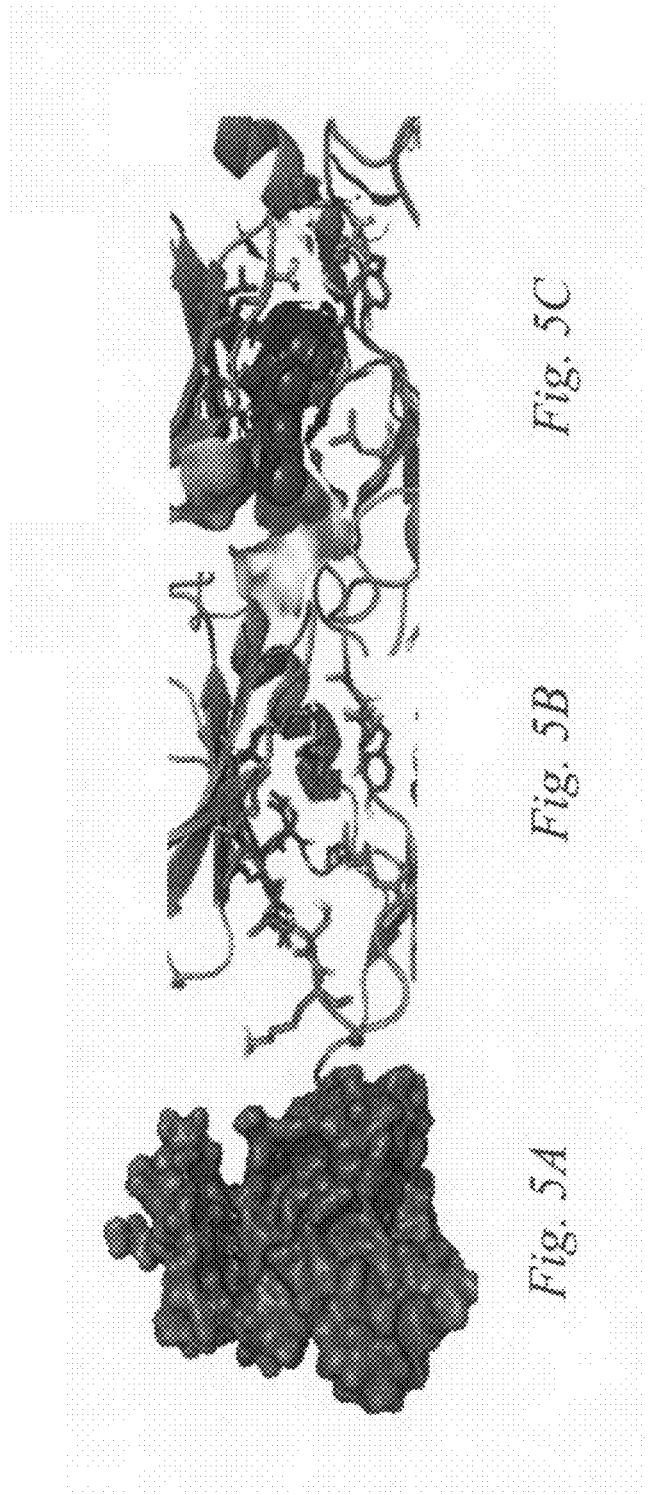
FIG. 5 is a graphical depiction of A) Homology model of LRRK2 (SEQ ID NO 62) in complex with one of the lead inhibitors 13; B) The critical active site residues shown in color-by-atom in stick representations; C) The LRRK2 active site depicted in surface in complex with one of the lead series compounds belongs to 5-(pyrazin-2-yl)-1H-pyrazolo[3,4-b] pyridine, 5-(pyrazin-2-yl)-1H-pyrrolo[2,3-b]pyridine structural class in accordance with at least one aspect of the invention.

Based on the 3-D profile scoring the structural template chosen from PDB database and were both MLK and BRAF crystal structures. Several models were built and refined to check the 3D profile and are shown in FIG. 5.

General Administration and Pharmaceutical Compositions

When used as pharmaceuticals, the compounds disclosed herein are typically administered in the form of a pharmaceutical composition. Such compositions can be prepared using procedures well known in the pharmaceutical art and include at least one compound disclosed herein. The compounds may also be administered alone or in combination with adjuvants that enhance stability of the compounds, facilitate administration of pharmaceutical compositions containing them in certain embodiments, provide increased dissolution or dispersion, increased inhibitory activity, provide adjunct therapy, and the like. The compounds may be used on their own or in conjunction with other active substances, optionally also in conjunction with other pharmacologically active substances. In general, the compounds may be administered in a therapeutically or pharmaceutically effective amount, but may be administered in lower amounts for diagnostic or other purposes.

When the compounds of the present invention are administered to a human, the compound itself or the compound after admixing with a suitable pharmacologically acceptable carrier, excipient, diluent and the like can be administered orally or parenterally as a safe pharmaceutical composition, such as an oral administration agent (e.g., powder, granule, tablet, capsule etc.), a parenteral administration agent (e.g., injection, an external preparation (e.g., nasal preparation, percutaneous preparation etc.)), a suppository (e.g., rectal suppository, vaginal suppository and the like) and the like.

Thus, administration can be, for example, orally, in the form of solid, semi-solid, lyophilized powder, or liquid dosage forms, such as, for example, tablets, pills, soft elastic and hard gelatin capsules, powders, solutions, suspensions, or the like, preferably in unit dosage forms suitable for simple administration of precise dosages. The pharmaceutical compositions will generally include a conventional pharmaceutical carrier and/or excipient and a compound as disclosed herein as the/an active agent, and, in addition, may include other agents such as but not limited to medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; and H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. It will be noted that in all of the pharmaceutical compositions enumerated herein, the compounds of the invention are formulated with an acceptable carrier or excipient. The carriers or excipients used must, of course, be acceptable in the sense of being compatible with the other ingredients of the composition and must not be deleterious to the recipient. The carrier or excipient can be a solid or a liquid, or both, and is preferably formulated with the compound of the invention as a unit-dose composition, for example, a tablet. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyvinylpyrrolidone, hydroxypropylcellulose, polyethylene glycol, waxes, and the like. Lubricants include sodium oleate, sodium stearate, magnesium stearate, sodium benzoate, sodium acetate, sodium chloride, and the like. Disintegrants include starch, methyl cellulose, agar, bentonite, xanthan gum, and the like. Examples of a coating agent include hydroxypropylmethylcellulose, ethylcellulose, hydroxymethylcellulose, hydroxypropylcellulose, polyoxyethylene glycol, Tween 80, pluronic F68, cellulose acetate phthalate, hydroxypropylmethyl cellulose phthalate, hydroxymethylcellulose acetate succinate, Eudragit (Rohm Pharm GmbH, Germany, a copolymer of methacrylic acid with acrylic acid), pigment (e.g., titanium oxide, bengara etc.) and the like.

As one of skill in the art would expect, the forms of the compounds of the invention utilized in a particular pharmaceutical formulation will be selected that possess suitable physical characteristics (e.g., water solubility) that is required for the formulation to be efficacious.

The content of the selected active compound of the present invention in the preparation varies depending on the dosage form. For example, the content thereof in the aforementioned oral administration agent is about 1 to about 99 wt %, preferably about 10 to 99 wt %, more preferably about 10 to about 95 wt %. In the aforementioned parenteral administration agent, for example, it is about 0.001 to about 99 wt %, preferably about 0.001 to about 95 wt %. The content of the components other than the active compound in the preparation is generally about 1 to 99.999 wt %, preferably about 10 to about 90 wt %. For injection, for example, an aqueous injection can be prepared using a compound of the present invention together with a solubilizer (e.g., beta.-cyclodextrins etc.), a dispersing agent (e.g., Tween 80 (Atlas Powder Co., USA), HCO60 (Nikko Chemicals Co., Ltd.), carboxymethylcellulose, sodium alginate etc.), a preservative (e.g., methylparaben, propylparaben, benzyl alcohol, chlorobutanol etc.), an isotonic agent (e.g., sodium chloride, glycerine, sorbitol, glucose etc.) and the like according to a conventional method. Alternatively, an oily injection can be formed by dissolving, suspending or emulsifying as appropriate the compound in a vegetable oil (e.g., olive oil, sesame oil, peanut oil, cottonseed oil, corn oil etc.), propylene glycol and solid like dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like.

Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

A solid external agent can be produced from the compound of the present invention as it is, or by adding an excipient (e.g., glycol, mannitol, starch, crystalline cellulose etc.), a thickener (e.g., natural gums, cellulose derivative, acrylic polymer etc.) and the like, mixing the same and preparing into a powdery composition. A semi-solid external agent can be produced by a conventional method and preferably used as an aqueous or oily gel, or an ointment. A liquid external preparation can be produced by preparing into an oily or aqueous suspension according to a method employed for production of injection or a similar method. In addition, a pH-adjusting agent (e.g., carbonic acid, phosphoric acid, citric acid, hydrochloric acid, sodium hydroxide etc.), a preservative (e.g., p-oxybenzoic acid esters, chlorobutanol, benzalkonium chloride etc.) and the like may be added as appropriate to a solid, semi-solid or liquid external agent. To be specific, for example, an ointment can be prepared, which contains a compound of the present invention in an amount of about 0.1 to about 100 mg per 1 g, using petrolatum, lanolin and the like as a base material. Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. The formulations may also contain compatible conventional carriers, such as cream or ointment bases and ethanol or oleyl alcohol for lotions. Such carriers may be present as from about 1% up to about 98% of the formulation, preferably they will form up to about 80% of the formulation.

Formulations including a compound of the present invention can be also prepared as an oily or aqueous solid, semi-solid or liquid suppository. The oily base used as appropriate for producing suppository may be, for example, hard fat, higher fatty acid glyceride (e.g., cacao butter, Witepsols (Dynamitnobel Ltd.) etc.), middle fatty acid (e.g., migriol acid (Dynamitnobel Co., Ltd.) etc.), vegetable oil (e.g., sesame oil, soybean oil, cottonseed oil etc.) and the like. As an aqueous base, for example, polyethylene glycols, propylene glycol and the like may be used, and as an aqueous gel base, for example, natural gums, cellulose derivative, vinyl polymer, acrylic polymer and the like may be used as appropriate.

While the dose of a compound of the present invention varies depending on the age, body weight, condition, dosage form, administration method, administration period and the like, for example, it is generally about 0.01 to about 1000 mg/kg, preferably about 0.01 to about 100 mg/kg, more preferably about 0.1 to about 100 mg/kg, particularly about 0.1 to about 50 mg/kg, specifically about 1.5 to about 30 mg/kg per day, as an amount of a compound of the present invention, for one patient (adult, body weight about 60 kg) with AD, PD or disease or condition as enumerated herein, which is orally or parenterally administered once to several times a day. The dose varies depending on various conditions as mentioned above, and in some cases an amount smaller than the aforementioned dose is sufficient and in other cases administration beyond the above range may be necessary.

Examples of Dosage Forms

| Treatment of Parkinson's disease symptoms | |
|---|---|
| Dosage Recommended: | 2 capsules 2 times daily |
| Active Compound 13 | 90 mg |
| Treatment of Alzheimer's disease symptoms | |
| Dosage Recommended: | 2 capsules 3 times daily |
| Active Compound 13 | 90 mg |

Examples of Formulations

| A. TABLETS | |
|---|---|
| Component | Amount per tablet (mg) |
| active substance | 400 |
| lactose | 40 |
| corn starch | 40 |
| polyvinylpyrrolidone | 15 |
| magnesium stearate | 5 |
| TOTAL | 500 |

The finely ground active substance, lactose, and some of the corn starch are mixed together. The mixture is screened, and then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
| --- | --- |
| active substance | 75 |
| lactose | 5 |
| corn starch | 5 |
| polyvinylpyrrolidone | 4 |
| magnesium stearate | 1 |
| microcrystalline cellulose | 5 |
| sodium-carboxymethyl starch | 5 |
| TOTAL | 100 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
| --- | --- |
| active substance | 65 |
| Lactose | 10 |
| corn starch | 11.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
| --- | --- |
| active substance | 90 |
| corn starch | 8.5 |
| magnesium stearate | 1.5 |
| TOTAL | 100 |

The substance and corn starch are mixed and moistened with water. The moist mass is screened and dried. The dry granules are screened and mixed with magnesium stearate. The finished mixture is packed into size 1 hard gelatin capsules.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

The following references, as well as all references cited in this specification, are incorporated by reference herein in their entirety:

1. I. F. Mata, W. J. Wedemeyer, M. J. Farrer, J. P. Taylor, and K. A. Gallo, LRRK2 in Parkinson's disease: protein domains and functional insights, *Trends in Neurosciences*, 29 (5) 286-293, 2006.
2. M. R. Cookson, The role of Leucine-Rich Repeat Kinase 2 (LRRK2) in Parkinson's disease, *Nature Reviews Neuroscience*, 11 (12) 791-797, 2010
3. E. K. Tan and A. H. Schapira, "LRRK2 as a therapeutic target in Parkinson's disease, *European Journal of Neurology*, 18 (4) 545-546, 2011.
4. E. Andres-Mateos, R. Mejias, M. Sasaki et al., Unexpected lack of hypersensitivity in LRRK2 knock-out mice to MPTP (1-methyl-4-phenyl-1,2,3,6-tetrahydropyridine), *Journal of Neuroscience*, 29 (5) 15846-15850, 2009.
5. Kaul, S., Kanthasamy, A., Kitazawa, M., Anantharam, V., and Kanthasamy, A. G. (2003) Caspase-3 dependent proteolytic activation of protein kinase C delta mediates and regulates 1-methyl-4-phenylpyridinium (MPP+)-induced apoptotic cell death in dopaminergic cells: relevance to oxidative stress in dopaminergic degeneration. *Eur J Neurosci* 18:1387-1401.
6. Yang, Y., Kaul, S., Zhang, D., Anantharam, V., and Kanthasamy, A. G. (2004) Suppression of caspase-3-dependent proteolytic activation of protein kinase C delta by small interfering RNA prevents MPP+-induced dopaminergic degeneration. *Mol Cell Neurosci*, 25:406-421.
7. Zhang, D., Anantharam, V., Kanthasamy, A., and Kanthasamy, A. G. (2007) Neuroprotective effect of protein kinase C delta inhibitor rottlerin in cell culture and animal models of Parkinson's disease. *J Pharmacol Exp Ther*, 322:913-922.
8. Ghosh, A., Roy, A., Liu, X., Kordower, J. H., Mufson, E. J., Hartley, D. M., Ghosh, S., Mosley, R. L., Gendelman, H. E., and Pahan, K. (2007) Selective inhibition of NF-kappaB activation prevents dopaminergic neuronal loss in a mouse model of Parkinson's disease. *Proc Natl Acad. Sci. USA*, 104:18754-18759.
9. B. D. Lee, J.-H. Shin, J. Vankampen et al., Inhibitors of Leucine-Rich Repeat Kinase-2 protect against models of Parkinson's disease, *Nature Medicine*, 16 (9) 998-1000, 2010.
10. W. W. Smith, Z. Pei, H. Jiang, V. L. Dawson, T. M. Dawson, and C. A. Ross, Kinase activity of mutant LRRK2 mediates neuronal toxicity, *Nature Neuroscience*, 9, (10) 1231-1233, 2006.
11. T. M. Dawson, H. S. Ko, and V. L. Dawson, Genetic animal models of Parkinson's disease, *Neuron*, 66, (5) 646-661, 2010.
12. T. M. Dawson and V. L. Dawson, Molecular Pathways of Neurodegeneration in Parkinson's Disease, *Science*, 302, (5646)-822, 2003.

13. L. Tianxia, Y. DeJun, S. Sarah, L. Zhaohui, and W. S Wanli, Models for LRRK2-Linked Parkinsonism, Parkinson's Disease, *Parkinsons Dis,* 7, 2011.
14. Z. K. Sweeney and J. W. Lewcock, ACS Chemical Neuroscience Spotlight on CEP-1347, *ACS Chem. Neurosci,* 2, 2-4 (2011).
15. L. K. Chico, L. J. Van Eldik and D. M. Watterson, Targeting protein kinases in central nervous system disorders, Nature Reviews Drug Discovery 8, 892-909, 2009.
16. D. C. Berwick, K. Harvey, LRRK2 signalling pathways: the key to unlocking, neurodegeneration?, Trends in Cell Biology, V21, (5) 257-265, 2011.
17. N. Ramsden, J. Perrin, Z. Ren, B. D Lee, N. Zinn, V. L. Dawson, D. Tam, M. Bova, M. Lang, G. Drewes, M. Bantscheff, F. Bard, T. M. Dawson, and C. Hopf, Chemoproteomics-Based Design of Potent LRRK2-Selective Lead Compounds That Attenuate Parkinson's Disease-Related Toxicity in Human Neurons, *ACS Chem. Biol.,* 6 (10) 1021-1028, 2011.
18. T. Kramer, F. Lo, M. S. Goring, G. M. O. Amombo, and B. Schmidt, Small Molecule Kinase Inhibitors for LRRK2 and Their application to Parkinson's Disease Models, *ACS Chem. Neurosci.,* 2012.
19. B. Thomas and M. F. Beal, Molecular insights into Parkinson's disease, F1000 Medicine Reports, 3:7, 2011.
20. R. Martin and S. L. Buchwald, Palladium-Catalyzed Suzuki-Miyaura Cross-Coupling Reactions Employing Dialkylbiaryl Phosphine Ligands, *Acc. Chem. Res.,* 41 (11) 1461-1473, 2008.

What is claimed is:

1. A compound of formula VII

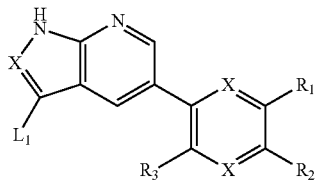

VII wherein X is independently —N or —CH, $L_1$ is independently a direct bond, substituted or unsubstituted 6-membered aryl, heteroaryl, substituted or unsubstituted 5-membered aryl or heteroaryl, substituted or unsubstituted cycloalkyl, substituted or unsubstituted heterocycloalkyl, —C(O)$_n$, S(O)$_n$, —O, —NH, substituted or unsubstituted C1-C5 alkylene, substituted or unsubstituted 2 to 5 membered heteroalkylene groups; where "n" is from 0 to 2, hydrogen, —CH$_3$, halo, —OCH$_3$, —CF$_3$, OCF$_3$, —CN, —NH$_2$, —CH$_2$OCF$_2$, —COOH, —OR$_4$ —SR$_4$, —NHR$_4$, —C(O)R$_4$—, —C(S)R$_4$, —C(O)NR$_4$, and —S(O)$_2$R$_4$, —S(O)$_2$NHR$_4$, —NHCOR$_4$, —CONHR$_4$, CONR$_4$, —CH=CHR$_4$, —NCH$_3$R$_4$, $R_4$ is optionally substituted at each occurrence and is selected from alkyl, heteroaryl, cycloalkyl, heterocycloalkyl, —C$_{1-6}$ alkyl, —C$_{1-4}$ haloaliphatic, —C$_{2-6}$ alkenyl, mono/dialkylamino, aryl C$_{4-7}$ heterocycloakyl, —C$_{5-6}$ aryl and, wherein the functional groups are each optionally substituted with one or more of fluoro, —NH$_2$, hydroxyl, fluoro substituted lower alkyl, alkoxy, alkylthio, mono/dialkylamino and cycloalkylamino functional groups or additional substituents selected from —NR$_5$R$_6$ and —CR$_5$R$_6$ respectively, and wherein $R_4$ together with the carbon to which it is attached may form a 3-7 member monocyclic cycloalkyl, 5-6 membered monocyclic heterocycloalkyl, heterocycloalkyl, heteroaryl; wherein the monocyclic cycloalkyl or heterocycloalkyl are each independently optionally substituted with one or more of fluoro, —NH$_2$, hydroxyl, fluoro substituted lower alkyl, alkoxy, alkylthio, mono/dialkylamino and cycloalkylamino;

$R_5$ and $R_6$ are each independently —H, cycloalkyl, alkyl, heterocycloalkyl, aryl, heteroaryl, —C$_{1-6}$ alkyl, —C$_{3-7}$ cycloalkyl, —C$_{3-6}$ heterocyclocycloalkyl, each optionally substituted with one or more of fluoro, —NH$_2$, hydroxyl, fluoro substituted C$_{1-6}$ alkyl, cyclopropyl, cyclobutyl, cyclopentyl, cyclohexyl, alkoxy, alkylthio, mono/dialkylamino and cycloalkylamino;

wherein $L_1$ is optionally substituted with —R$_7$ or $Y_9$;

wherein $R_7$ is independently a bond, substituted or unsubstituted —C=S, C=O, —C$_{1-6}$ alkyl, each optionally further substituted by C$_{1-6}$ alkyl, (for example, (—CH$_2$)$_n$, wherein n is an integer from 0-3), —O, —S, —SO, SO$_2$, —NH or —CH=CH groups; and $R_7$ may be cycloalkyl, heterocycloalkyl, aryl, or heteroaryl, C$_{1-6}$ alkyl, cyclopropyl, cyclobutyl, cyclopentyl and cyclohexyl, wherein C$_{1-6}$ alkyl, cyclopropyl, cyclobutyl, cyclopentyl and cyclohexyl are each optionally substituted with one or more of fluoro, —OH, —NH$_2$, OCH$_3$, CH$_2$OCH$_3$, methylthio, ethylthio, butylthio, isobutylthio, mono/dialkylamino, and alkyl carbon bound to the N of —C(O)NHR$_8$, —C(S)NHR$_8$ or —S(O)$_2$NHR$_8$; wherein the alkyl chain(s) of OCH$_3$, CH$_2$OCH$_3$, methylthio, ethylthio, butylthio, isobutylthio, and mono/dialkylamino are each optionally independently substituted with one or more of fluoro, —OH, —NH$_2$, wherein any substitution of the alkyl chain carbon bound to O of alkoxy, S of thioalkyl or N of mono/dialkylamino is fluoro;

$R_8$ combines with the nitrogen to which it is attached to form a 5-7 member heterocycloalkyl optionally substituted with one or more of fluoro, —OH, —NH2, C$_{1-6}$ alkyl, cyclopropyl, cyclobutyl, cyclopentyl, cyclohexyl, fluoro substituted C$_{1-6}$ alkyl, cyclopropyl, cyclobutyl, cyclopentyl and cyclohexyl, OCH$_3$, CH$_2$OCH$_3$, fluoro substituted OCH$_3$, CH$_2$OCH$_3$, methylthio, ethylthio, butylthio, isobutylthio, and fluoro-substituted methylthio, ethylthio, butylthio, isobutylthio;

Y$_9$ is —C$_{1-6}$ alkyl, C$_{3-7}$ cycloalkyl, —C$_{1-6}$-alkyl-C$_{3-7}$-cycloalkyl, —C$_{1-6}$ alkyl heteroaryl, —C$_{4-7}$ heterocycloalkyl, aryl or heteroaryl, each optionally independently substituted with one or more substituents selected from R$_4$;

R$_1$, R$_2$ and R$_3$ are each independently —H, halo, —CN, —NH$_2$, —C$_{1-6}$ aliphatic, —OC$_{1-6}$ aliphatic, —C$_{3-6}$ cycloaliphatic, —OC$_{3-6}$ cycloaliphatic, —NH$_2$, —NHCOC$_{1-6}$ alkyl, —NHCO$_{1-6}$ cycloalkyl, —NHCO$_{1-6}$ heterocycloalkyl, —CONHC$_{1-6}$ alkyl, —CONH$_{1-6}$ cycloalkyl, —CONH$_{1-6}$ heterocycloalkyl, —NHC$_{1-6}$ aliphatic, —NHC$_{3-6}$ cycloaliphatic, —NHS(O)$_2$C$_{1-6}$ aliphatic, —NHS(O)$_2$C$_{3-6}$ cycloaliphatic, —NHS(O)$_2$ phenyl, —NHS(O)$_2$ benzyl, —NHS(O)$_2$ heteroaryl, —S(O)$_2$C$_{1-6}$ aliphatic, —S(O)$_2$C$_{3-6}$ cycloaliphatic, —S(O)$_2$ phenyl, —S(O)$_2$ benzyl, —S(O)$_2$ heteroaryl, —S(O)$_2$NHC$_{1-6}$ aliphatic, —S(O)$_2$NHC$_{3-6}$ cycloaliphatic, —S(O)$_2$NHphenyl, —S(O)$_2$NHbenzyl, or —S(O)$_2$NHheteroaryl, wherein each of said heteroaryl of R$_1$, R$_2$ and R$_3$ is independently a 5- or 6-member ring having 1, 2, or 3 atoms selected from N, O, or S, and wherein said aliphatic, cycloaliphatic, phenyl, benzyl, or heteroaryl of R$_1$, R$_2$ and R$_3$ is each optionally substituted with 1, 2, or 3 ZR$_{10}$ groups;

wherein ZR$_{10}$ is halo, oxo, —C$_{1-2}$ alkyl, substituted C$_{1-2}$ alkyl with 1-3 —F or —Cl atoms, —C$_{3-6}$ cycloalkyl, —OH, —OC$_{1-2}$ alkyl, —OC$_{1-2}$ alkyl substituted with 1-3 —F or —Cl atoms, —C(O)C$_{1-2}$ alkyl, or —SC$_{1-2}$ alkyl, and the pharmaceutically acceptable salts, isomers and tautomers thereof.

2. A compound selected from the group consisting of

6-(3-methyl-1H-pyrazolo[3,4-b]pyridin-5-yl)-N-(1-methylpiperidine-4yl)pyrazin-2-amine

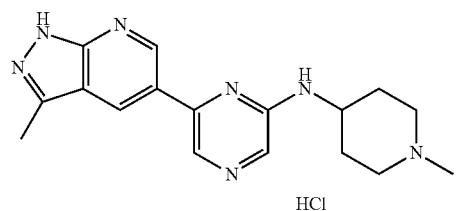 [SMILES: Cc1n[nH]c2ncc(-c3cncc(NC4CCN(C)CC4)n3)cc12 ; Cl]

6-(3-methyl-1H-pyrazolo[3,4-b]pyridin-5-yl)-N-(1-methylpiperidin-4-yl)pyrazin-2-amine hydrochloride

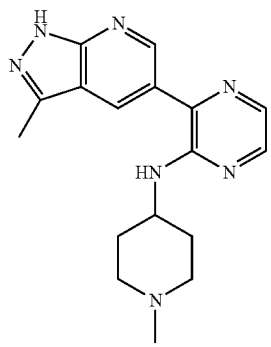 [SMILES: Cc1n[nH]c2ncc(-c3nccnc3NC3CCN(C)CC3)cc12]

5-(3-methyl-1H-pyrazolo[3,4-b]pyridin-5-yl)-N-(1-methylpiperidin-4-yl)pyrimidin-4-amine

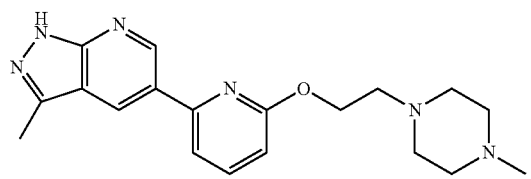 [SMILES: Cc1n[nH]c2ncc(-c3cccc(OCCN4CCN(C)CC4)n3)cc12]

3-methyl-5-(6-(2-(4-methylpiperazin-1-yl)ethoxy)pyrazin-2-yl)-1H-pyrazolo[3,4-b]pyridine

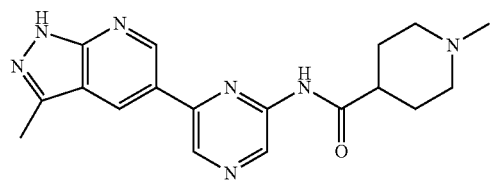 [SMILES: Cc1n[nH]c2ncc(-c3cncc(NC(=O)C4CCN(C)CC4)n3)cc12]

1-methyl-N-(6-(3-methyl-1H-pyrazolo[3,4-b]pyridin-5-yl)pyrazin-2-yl)piperidine-4-carboxamide

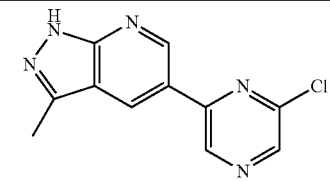
5-(6-chloropyrazin-2-yl)-3-methyl-1H-pyrazolo[3,4-b]pyridine

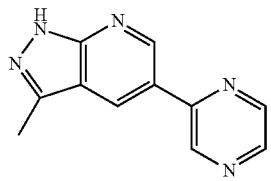
3-methyl-5-(pyrazin-2-yl)-1H-pyrazolo[3,4-b]pyridine

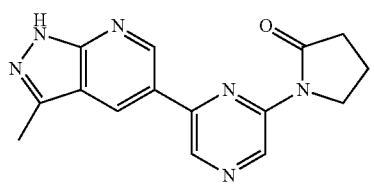
1-(6-(3-methyl-1H-pyrazolo[3,4-b]pyridin-5-yl)pyrazin-2-yl)pyrrolidin-2-one

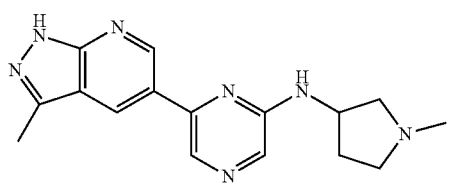 [SMILES: Cc1n[nH]c2ncc(-c3cncc(NC4CCN(C)C4)n3)cc12]
6-(3-methyl-1H-pyrazolo[3,4-b]pyridin-5-yl)-N-(1-methylpyrrolidin-3-yl)pyrazin-2-amine

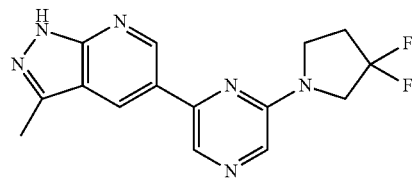
5-(6-(3,3-difluoropyrrolidin-1-yl)pyrazin-2-yl)-3-methyl-1H-pyrazolo[3,4-b]pyridine

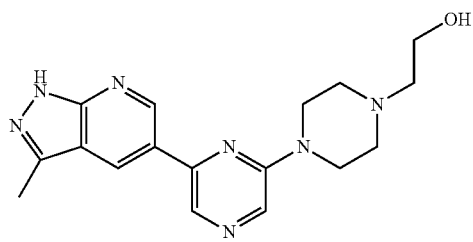 [SMILES: Cc1n[nH]c2ncc(-c3cncc(N4CCN(CCO)CC4)n3)cc12]
2-(4-(6-(3-methyl-1H-pyrazolo[3,4-b]pyridin-5-yl)pyrazin-2-yl)piperazin-1-yl)ethanol

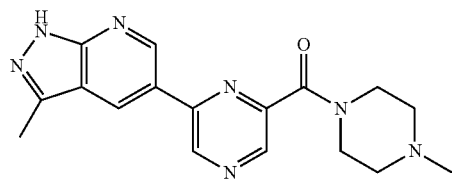 [SMILES: Cc1n[nH]c2ncc(-c3cncc(C(=O)N4CCN(C)CC4)n3)cc12]
(6-(3-methyl-1H-pyrazolo[3,4-b]pyridin-5-yl)pyrazin-2-yl)(4-methylpiperazin-1-yl)methanone

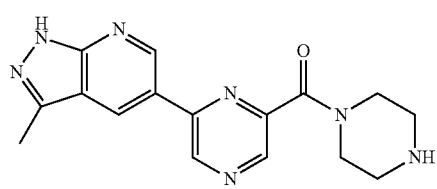 [SMILES: Cc1n[nH]c2ncc(-c3cncc(C(=O)N4CCNCC4)n3)cc12]
(6-(3-methyl-1H-pyrazolo[3,4-b]pyridin-5-yl)pyrazin-2-yl)(piperazin-1-yl)methanone

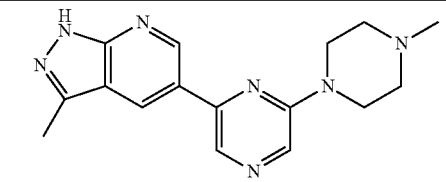
3-methyl-5-(6-(4-methylpiperazin-1-yl)pyrazin-2-yl)-1H-pyrazolo[3,4-b]pyridine

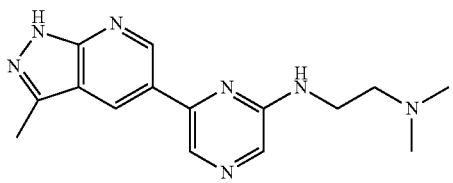 [SMILES: Cc1n[nH]c2ncc(-c3cncc(NCCN(C)C)n3)cc12]
N1,N1-dimethyl-N2-(6-(3-methyl-1H-pyrazolo[3,4-b]pyridin-5-yl)pyrazin-2-yl)ethane-1,2-diamine

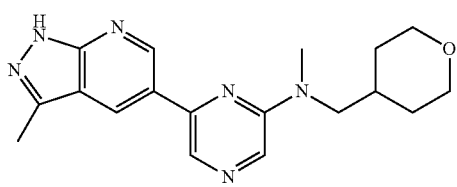 [SMILES: Cc1n[nH]c2ncc(-c3cncc(N(C)CC4CCOCC4)n3)cc12]
N-methyl-6-(3-methyl-1H-pyrazolo[3,4-b]pyridin-5-yl)-N-((tetrahydro-2H-pyran-4-yl)methyl)pyrazin-2-amine

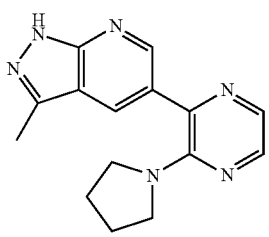
3-methyl-5-(3-(pyrrolidin-1-yl)pyrazin-2-yl)-1H-pyrazolo[3,4-b]pyridine

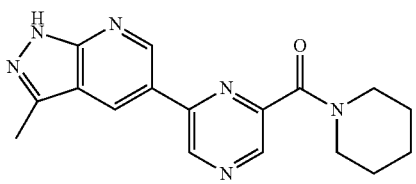 [SMILES: Cc1n[nH]c2ncc(-c3cncc(C(=O)N4CCCCC4)n3)cc12]
(6-(3-methyl-1H-pyrazolo[3,4-b]pyridin-5-yl)pyrazin-2-yl)(piperidin-1-yl)methanone

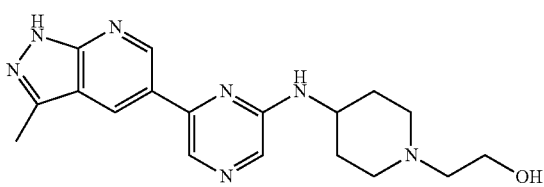
2-(4-((6-(3-methyl-1H-pyrazolo[3,4-b]pyridin-5-yl)pyrazin-2-yl)amino)piperidin-1-yl)ethanol

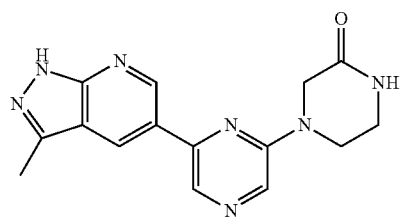 [SMILES: Cc1n[nH]c2ncc(-c3cncc(N4CCNC(=O)C4)n3)cc12]
4-(6-(3-methyl-1H-pyrazolo[3,4-b]pyridin-5-yl)pyrazin-2-yl)piperazin-2-one

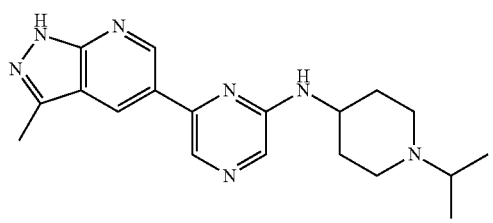 [SMILES: Cc1n[nH]c2ncc(-c3cncc(NC4CCN(C(C)C)CC4)n3)cc12]
N-(1-isopropylpiperidin-4-yl)-6-(3-methyl-1H-pyrazolo[3,4-b]pyridin-5-yl)pyrazin-2-amine

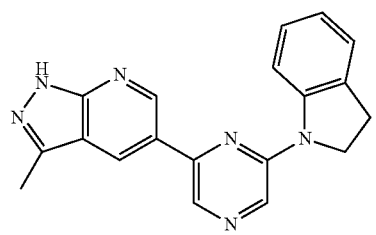 5-(6-(indolin-1-yl)pyrazin-2-yl)-3-methyl-1H-pyrazolo[3,4-b]pyridine

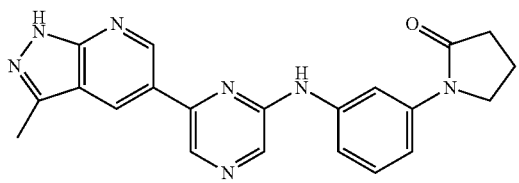 [SMILES: Cc1n[nH]c2ncc(-c3cncc(Nc4cccc(N5CCCC5=O)c4)n3)cc12] 1-(3-(((6-(3-methyl-1H-pyrazolo[3,4-b]pyridin-5-yl)pyrazin-2-yl)amino)phenyl)pyrrolidin-2-one

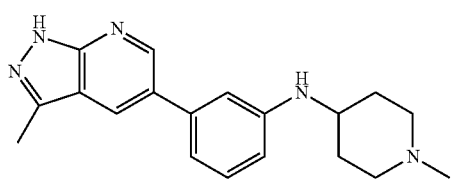 1-methyl-N-(3-(3-methyl-1H-pyrazolo[3,4-b]pyridin-5-yl)phenyl)piperidin-4-amine

 6-(3-methyl-1H-pyrazolo[3,4-b]pyridin-5-yl)-N-(1-methylpiperidin-4-yl)pyridin-2-amine

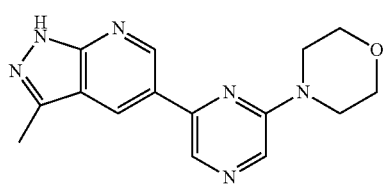 [SMILES: Cc1n[nH]c2ncc(-c3cncc(N4CCOCC4)n3)cc12] 4-(6-(3-methyl-1H-pyrazolo[3,4-b]pyridin-5-yl)pyrazin-2-yl)morpholine

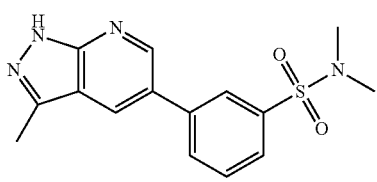 [SMILES: Cc1n[nH]c2ncc(-c3cccc(S(=O)(=O)N(C)C)c3)cc12] N,N-dimethyl-3-(3-methyl-1H-pyrazolo[3,4-b]pyridin-5-yl)benzenesulfonamide

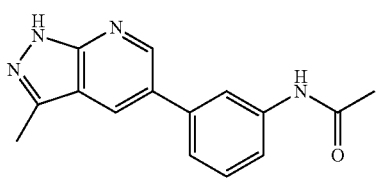 [SMILES: CC(=O)Nc1cccc(-c2cnc3[nH]nc(C)c3c2)c1] N-(3-(3-methyl-1H-pyrazolo[3,4-b]pyridin-5-yl)phenyl)acetamide

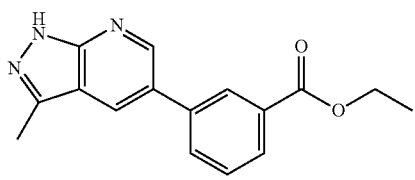 ethyl 3-(3-methyl-1H-pyrazolo[3,4-b]pyridin-5-yl)benzoate

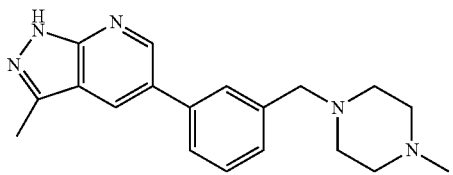 [SMILES: Cc1n[nH]c2ncc(-c3cccc(CN4CCN(C)CC4)c3)cc12] 3-methyl-5-(3-((4-methylpiperazin-1-yl)methyl)phenyl)-1H-pyrazolo[3,4-b]pyridine

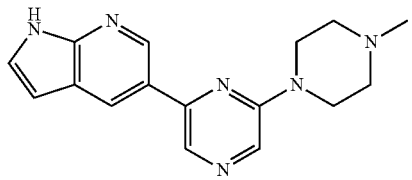 [SMILES: CN1CCN(c2cncc(-c3cnc4[nH]ccc4c3)n2)CC1] 5-(6-(4-methylpiperazin-1-yl)pyrazin-2-yl)-1H-pyrrolo[2,3-b]pyridine

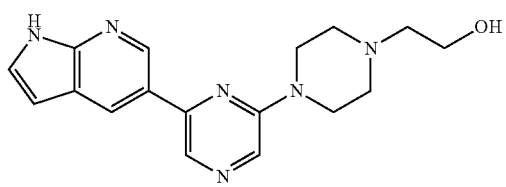 [SMILES: OCCN1CCN(c2cncc(-c3cnc4[nH]ccc4c3)n2)CC1] 2-(4-(6-(1H-pyrrolo[2,3-b]pyridin-5-yl)pyrazin-2-yl)piperazin-1-yl)ethanol

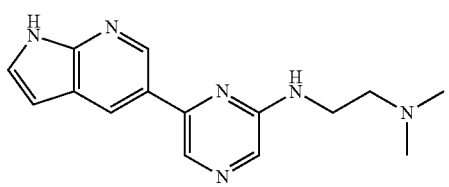 [SMILES: CN(C)CCNc1cncc(-c2cnc3[nH]ccc3c2)n1] N1-(6-(1H-pyrrolo[2,3-b]pyridin-5-yl)pyrazin-2-yl)-N2,N2-dimethylethane-1,2-diamine

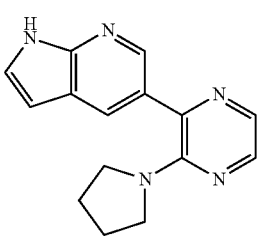 [SMILES: c1cnc(N2CCCC2)c(-c2cnc3[nH]ccc3c2)n1] 5-(3-(pyrrolidin-1-yl)pyrazin-2-yl)-1H-pyrrolo[2,3-b]pyridine

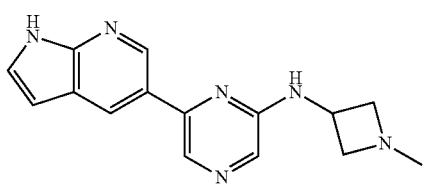 [SMILES: CN1CC(Nc2cncc(-c3cnc4[nH]ccc4c3)n2)C1] N-(1-methylazetidin-3-yl)-6-(1H-pyrrolo[2,3-b]pyridin-5-yl)pyrazin-2-amine

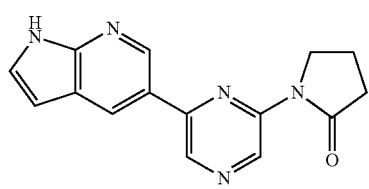 [SMILES: O=C1CCCN1c1cncc(-c2cnc3[nH]ccc3c2)n1] 1-(6-(1H-pyrrolo[2,3-b]pyridin-5-yl)pyrazin-2-yl)pyrrolidin-2-one

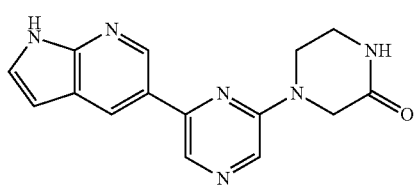 [SMILES: O=C1CN(c2cncc(-c3cnc4[nH]ccc4c3)n2)CCN1] 4-(6-(1H-pyrrolo[2,3-b]pyridin-5-yl)pyrazin-2-yl)piperazin-2-one

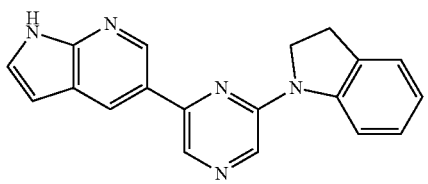 [SMILES: c1ccc2c(c1)CCN2c1cncc(-c2cnc3[nH]ccc3c2)n1] 5-(6-(indolin-1-yl)pyrazin-2-yl)-1H-pyrrolo[2,3-b]pyridine

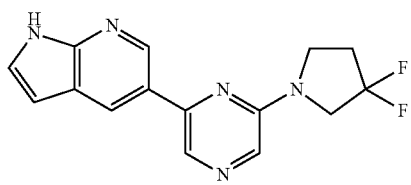 [SMILES: FC1(F)CCN(c2cncc(-c3cnc4[nH]ccc4c3)n2)C1] 5-(6-(3,3-difluoropyrrolidin-1-yl)pyrazin-2-yl)-1H-pyrrolo[2,3-b]pyridine

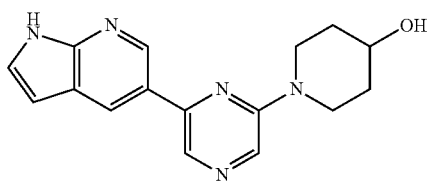 [SMILES: OC1CCN(c2cncc(-c3cnc4[nH]ccc4c3)n2)CC1] 1-(6-(1H-pyrrolo[2,3-b]pyridin-5-yl)pyrazin-2-yl)piperidin-4-ol

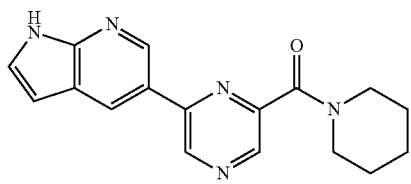 [SMILES: O=C(c1cncc(-c2cnc3[nH]ccc3c2)n1)N1CCCCC1] (6-(1H-pyrrolo[2,3-b]pyridin-5-yl)pyrazin-2-yl)(piperidin-1-yl)methanone

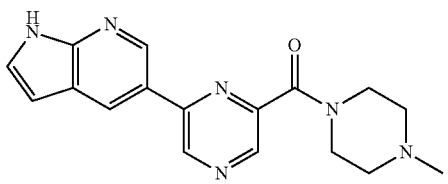 [SMILES: CN1CCN(C(=O)c2cncc(-c3cnc4[nH]ccc4c3)n2)CC1] (6-(1H-pyrrolo[2,3-b]pyridin-5-yl)pyrazin-2-yl)(4-methylpiperazin-1-yl)methanone

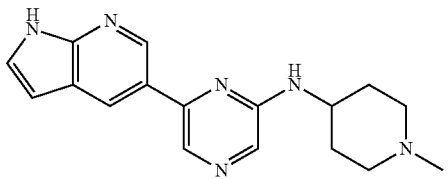 [SMILES: CN1CCC(Nc2cncc(-c3cnc4[nH]ccc4c3)n2)CC1] N-(1-methylpiperidin-4-yl)-6-(1H-pyrrolo[2,3-b]pyridin-5-yl)pyrazin-2-amine

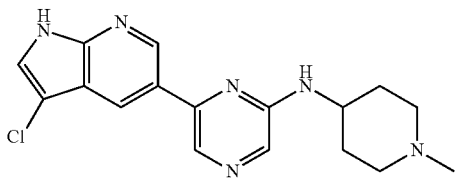 [SMILES: CN1CCC(Nc2cncc(-c3cnc4[nH]cc(Cl)c4c3)n2)CC1] 6-(3-chloro-1H-pyrrolo[2,3-b]pyridin-5-yl)-N-(1-methylpiperidin-4-yl)pyrazin-2-amine

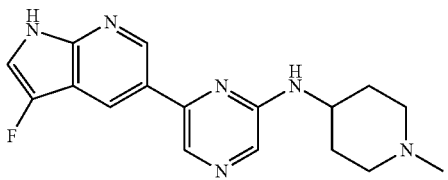 6-(3-fluoro-1H-pyrrolo[2,3-b]pyridin-5-yl)-N-(1-methylpiperidin-4-yl)pyrazin-2-amine

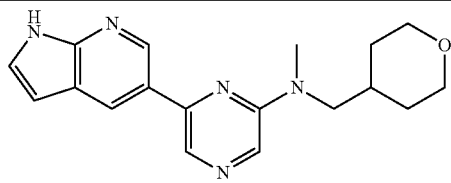 N-methyl-6-(1H-pyrrolo[2,3-b]pyridin-5-yl)-N-((tetrahydro-2H-pyran-4-yl)methyl)pyrazin-2-amine

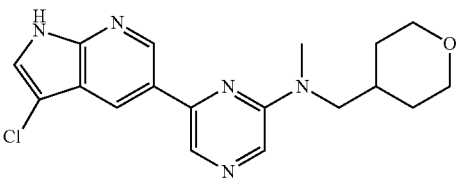 [SMILES: CN(CC1CCOCC1)c1cncc(-c2cnc3[nH]cc(Cl)c3c2)n1] 6-(3-chloro-1H-pyrrolo[2,3-b]pyridin-5-yl)-N-methyl-N-((tetrahydro-2H-pyran-4-yl)methyl)pyrazin-2-amine

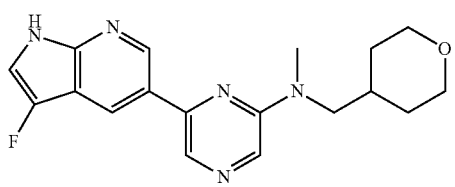 [SMILES: CN(CC1CCOCC1)c1cncc(-c2cnc3[nH]cc(F)c3c2)n1] 6-(3-fluoro-1H-pyrrolo[2,3-b]pyridin-5-yl)-N-methyl-N-((tetrahydro-2H-pyran-4-yl)methyl)pyrazin-2-amine

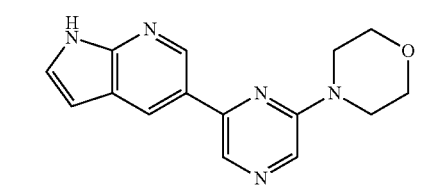 [SMILES: c1cc2cc(-c3cncc(N4CCOCC4)n3)cnc2[nH]1] 4-(6-(1H-pyrrolo[2,3-b]pyridin-5-yl)pyrazin-2-yl)morpholine

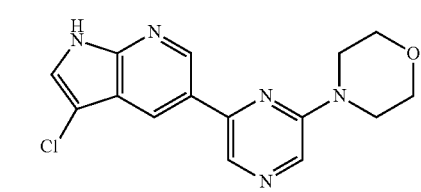 [SMILES: Clc1c[nH]c2ncc(-c3cncc(N4CCOCC4)n3)cc12] 4-(6-(3-chloro-1H-pyrrolo[2,3-b]pyridin-5-yl)pyrazin-2-yl)morpholine

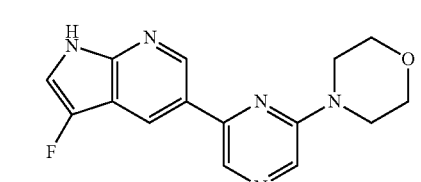 4-(6-(3-fluoro-1H-pyrrolo[2,3-b]pyridin-5-yl)pyrazin-2-yl)morpholine

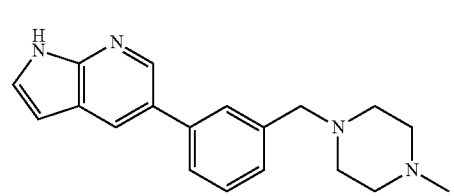 [SMILES: CN1CCN(Cc2cccc(-c3cnc4[nH]ccc4c3)c2)CC1] 5-(3-((4-methylpiperazin-1-yl)methyl)phenyl)-1H-pyrrolo[2,3-b]pyridine

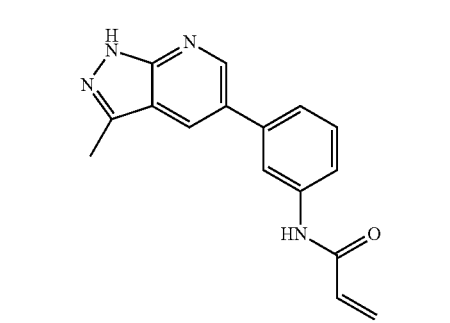 N-(3-(3-methyl-1H-pyrazolo[3,4-b]pyridin-5-yl)phenyl)acrylamide

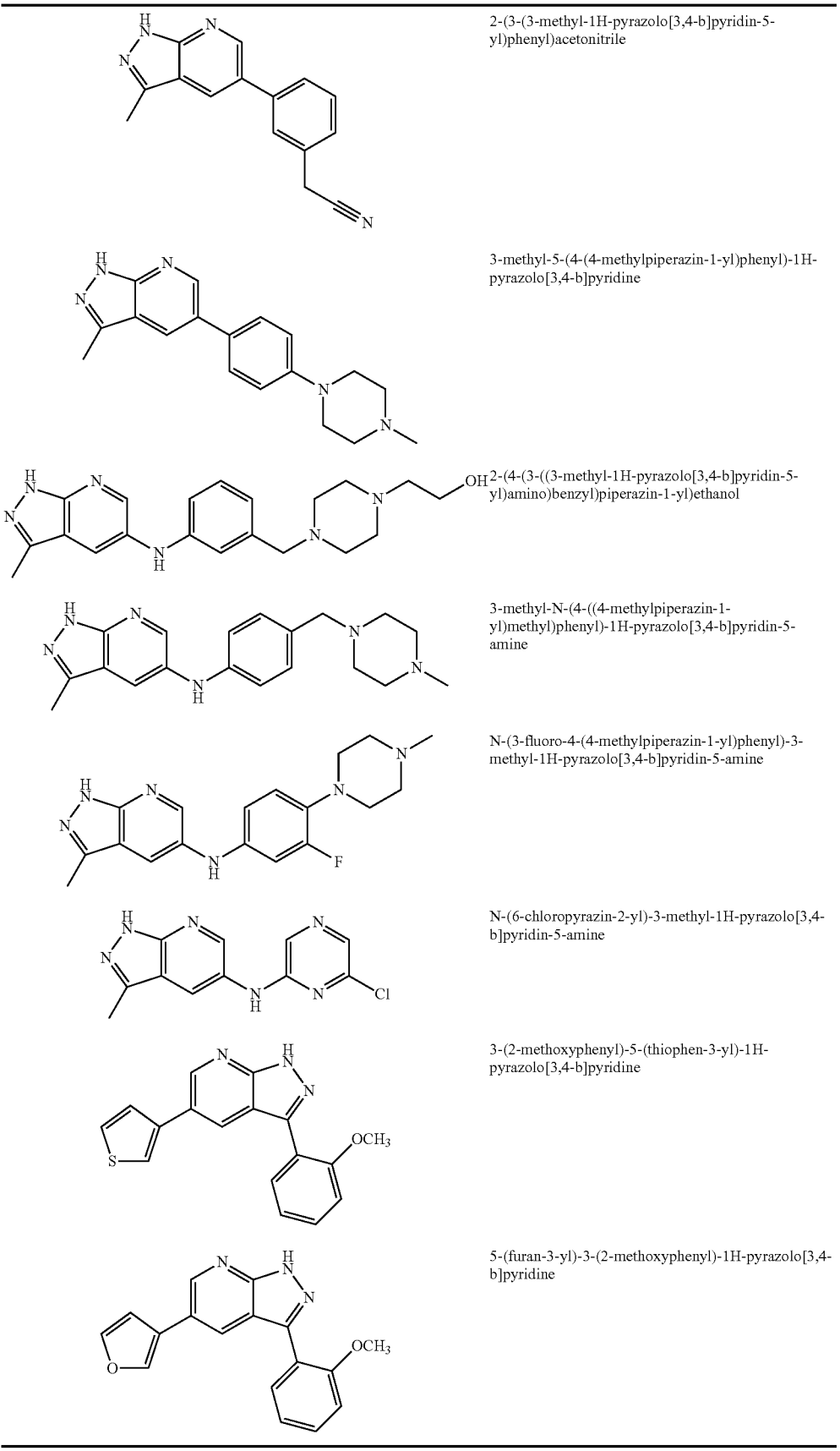

| | |
|---|---|
| | 2-(3-(3-methyl-1H-pyrazolo[3,4-b]pyridin-5-yl)phenyl)acetonitrile |
| | 3-methyl-5-(4-(4-methylpiperazin-1-yl)phenyl)-1H-pyrazolo[3,4-b]pyridine |
| | 2-(4-(3-((3-methyl-1H-pyrazolo[3,4-b]pyridin-5-yl)amino)benzyl)piperazin-1-yl)ethanol |
| | 3-methyl-N-(4-((4-methylpiperazin-1-yl)methyl)phenyl)-1H-pyrazolo[3,4-b]pyridin-5-amine |
| | N-(3-fluoro-4-(4-methylpiperazin-1-yl)phenyl)-3-methyl-1H-pyrazolo[3,4-b]pyridin-5-amine |
| | N-(6-chloropyrazin-2-yl)-3-methyl-1H-pyrazolo[3,4-b]pyridin-5-amine |
| | 3-(2-methoxyphenyl)-5-(thiophen-3-yl)-1H-pyrazolo[3,4-b]pyridine |
| | 5-(furan-3-yl)-3-(2-methoxyphenyl)-1H-pyrazolo[3,4-b]pyridine |

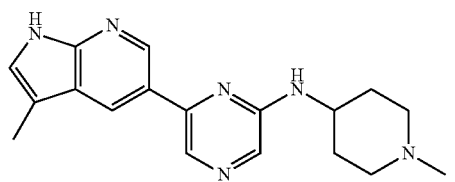

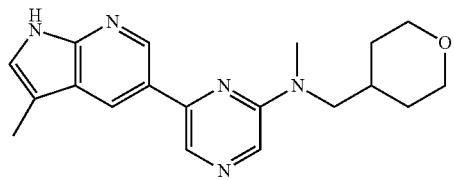

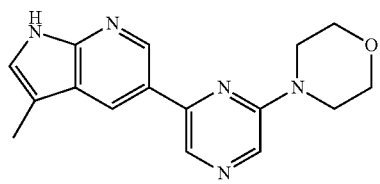

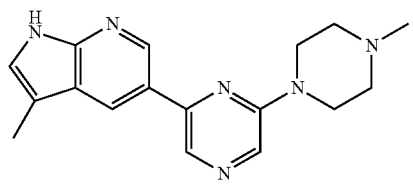

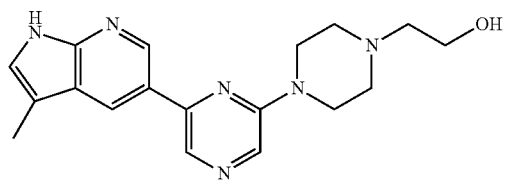

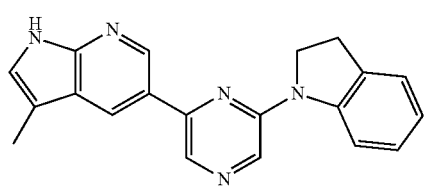

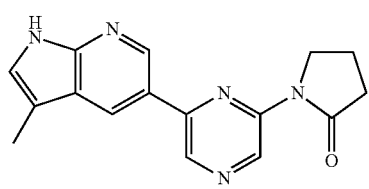

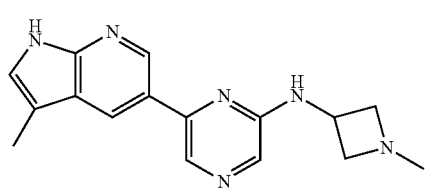

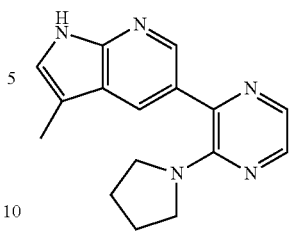

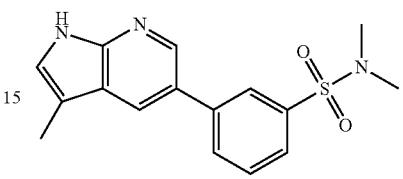

and the pharmaceutically acceptable salts, isomers and tautomers thereof.

3. A compound according to claim 1 which is a protein kinase inhibitor.

4. A compound according to claim 3 wherein the compound is an inhibitor of a protein kinase selected from the group consisting of ABL1 T315I (SEQ ID NO 1), ALK2 (SEQ ID NO 2), ARK5 (SEQ ID NO 64), Aurora A (SEQ ID NO 3), Aurora B (SEQ ID NO 4), Aurora C (SEQ ID NO 5), BRAF (SEQ ID NO 6), BRAF V599E (SEQ ID NO 7), CHK1 (SEQ ID NO 8), CHK2 (SEQ ID NO 9), C-KIT (SEQ ID NO 10), CLK1 (SEQ ID NO 11), CLK2 (SEQ ID NO 12), CLK3 (SEQ ID NO 13), CLK4 (SEQ ID NO 14), CSF1R (SEQ ID NO 15), DYRK1A (SEQ ID NO 16), DYRK1B (SEQ ID NO 17), DYRK2 (SEQ ID NO 18), DYRK3 (SEQ ID NO 19), DYRK4 (SEQ ID NO 20), FLT3 (SEQ ID NO 21), GSK3β (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), LRRK2 (SEQ ID NO 62), LRRK2 G2019S (SEQ ID NO 28), LRRK2 T1602S R1628P T2352M (SEQ ID NO 29), MAP4K4 (SEQ ID NO 30), MELK (SEQ ID NO 31), MLK (SEQ ID NO 32), PDGFR (SEQ ID NO 41), PKA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) and TRKC (SEQ ID NO 58) and mutations thereof.

5. A compound according to claim 3 wherein the compound is an inhibitor of at least one of LRRK2 T1602S R1628P and T2352M (SEQ ID NO 29) variants.

6. A composition comprising a compound according to claim 1 and at least one pharmaceutically acceptable carrier.

7. A method of treatment of a disease or condition mediated by ABL1T315I (SEQ ID NO 1), ALK2 (SEQ ID NO 2), ARK5 (SEQ ID NO 64), Aurora A (SEQ ID NO 3), Aurora B (SEQ ID NO 4), Aurora C (SEQ ID NO 5), BRAF (SEQ ID NO 6), BRAF V599E (SEQ ID NO 7), CHK1 (SEQ ID NO 8), CHK2 (SEQ ID NO 9), C-KIT (SEQ ID NO 10), CLK1 (SEQ ID NO 11), CLK2 (SEQ ID NO 12), CLK3 (SEQ ID NO 13), CLK4 (SEQ ID NO 14), CSF1R (SEQ ID NO 15), DYRK1A (SEQ ID NO 16), DYRK1B (SEQ ID NO 17), DYRK2 (SEQ ID NO 18), DYRK3 (SEQ ID NO 19), DYRK4 (SEQ ID NO 20), FLT3 (SEQ ID NO 21), GSK3β (SEQ ID NO 22), JAK1 (SEQ ID NO 23), JAK2 (SEQ ID NO 24), JAK3 (SEQ ID NO 25), KDR (SEQ ID NO 26), LCK (SEQ ID NO 27), LRRK2 (SEQ ID NO 62), LRRK2 G2019S (SEQ ID NO 28), LRRK2 T1602S R1628P T2352M (SEQ ID NO 29), MAP4K4 (SEQ ID NO 30), MELK (SEQ ID NO 31), MLK (SEQ ID NO 32), PDGFR (SEQ ID NO 41), PKA (SEQ ID NO 63), PKCα (SEQ ID NO 42), PKCτ (SEQ ID NO 43), PIM1 (SEQ ID NO 44), RET (SEQ ID NO 45), ROCK1 (SEQ ID NO 46), ROCK2 (SEQ ID NO 47), RSK1 (SEQ ID NO 48), RSK2 (SEQ ID NO 49), p70S6K (SEQ ID NO 50), SGK1 (SEQ ID NO 51), SNF1LK (SEQ ID NO 52), SIK2 (SEQ ID NO 53), SYK (SEQ ID NO 54), TNIK (SEQ ID NO 55), TRKA (SEQ ID NO 56), TRKB (SEQ ID NO 57) or TRKC (SEQ ID NO 58) and mutations thereof comprising administering to a mammal a compound according to claim 1.

8. A method of treatment according to claim 7 wherein the disease or condition is selected from the group consisting of Parkinson's disease, Alzheimer's disease, Down's syndrome, Huntington's disease, neurodegenerative disease, central nervous system disease, cancer, metabolic disorder, inflammatory disease, pain of neuropathic origin, pain of inflammatory origin, cardiovascular disease, rheumatoid arthritis, osteoarthritis, type 2 diabetes, metabolic syndrome and obesity.

9. A method of treatment according to claim 7 wherein the disease or condition is mediated by one of LRRK2 T1602ST2352M and R1628P (SEQ ID NO 29) variants.

10. A method of treatment of Alzheimer's disease, Parkinson's disease or Down's syndrome comprising administering to a mammal a compound according to claim 1.

11. A method of making a compound according to claim 1 comprising:

12. The invention of claim 1 wherein $L_1$ is selected from the group consisting of

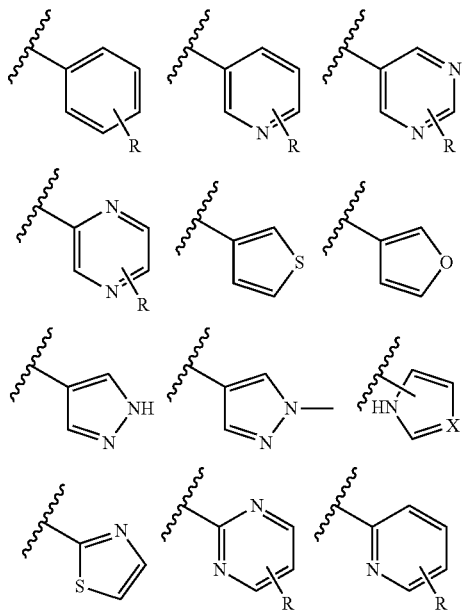

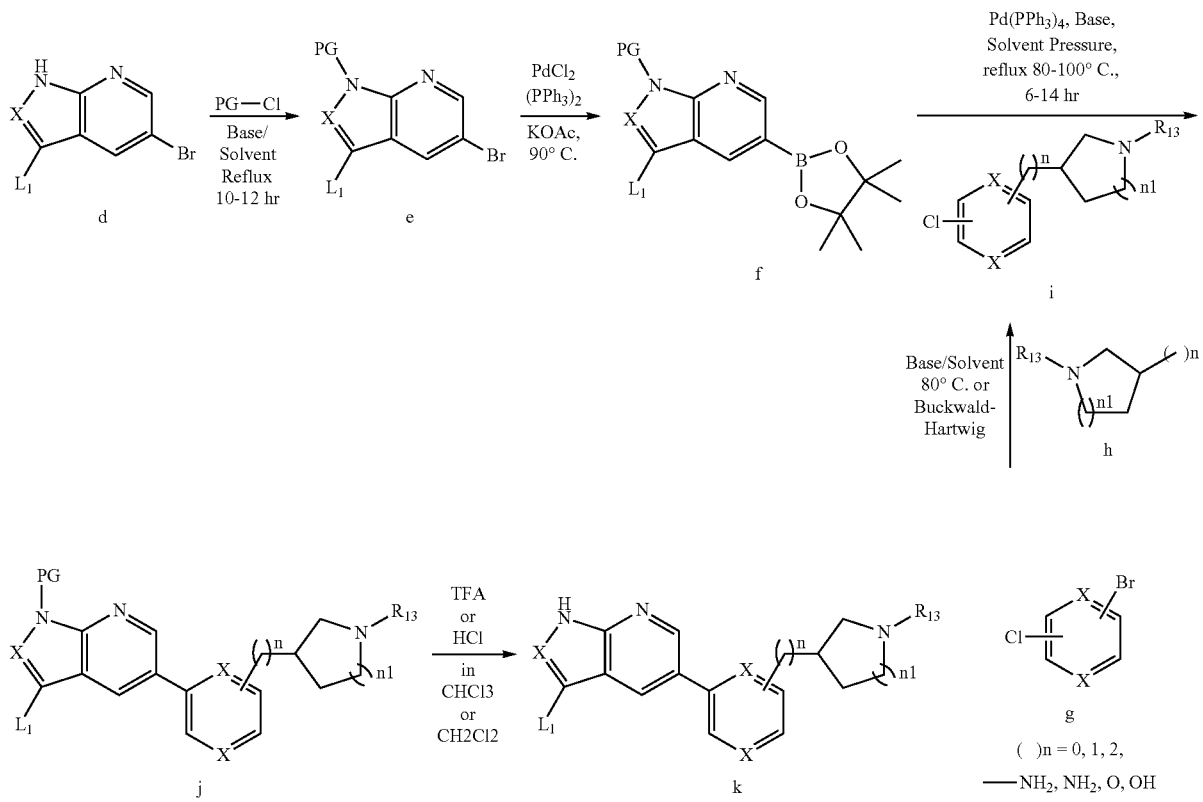

-continued
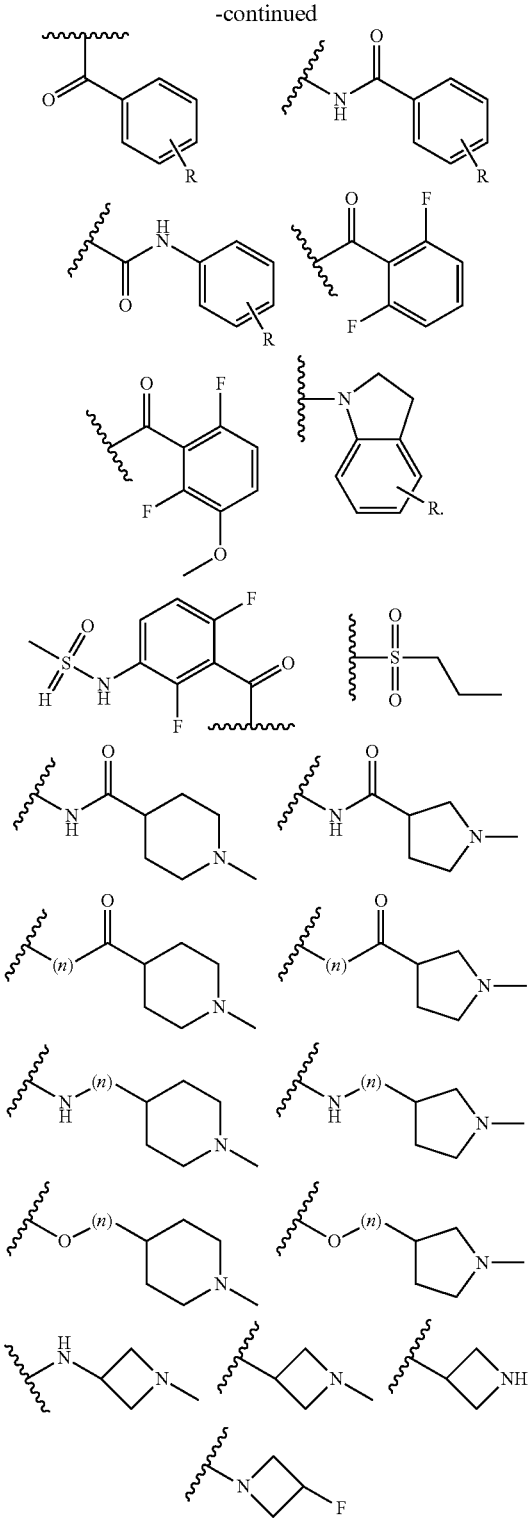
wherein
indicates the attachment to $L_1$ of Formula VII;
wherein R is —H, halo, —CH$_3$, —CH$_2$CH$_3$, —OCH$_3$, —CF$_3$, OCF$_3$, —CN, —NH$_2$, —CH$_2$OCF$_2$, —COOH, OH, —CH$_2$OH, —SO$_2$CH$_3$, SO$_2$N(CH$_3$)$_2$, —COCH$_3$; and
wherein "n" is an integer from 0 to 2.
13. The invention of claim 1 wherein $R_1$, $R_2$ and $R_3$ are each independently:
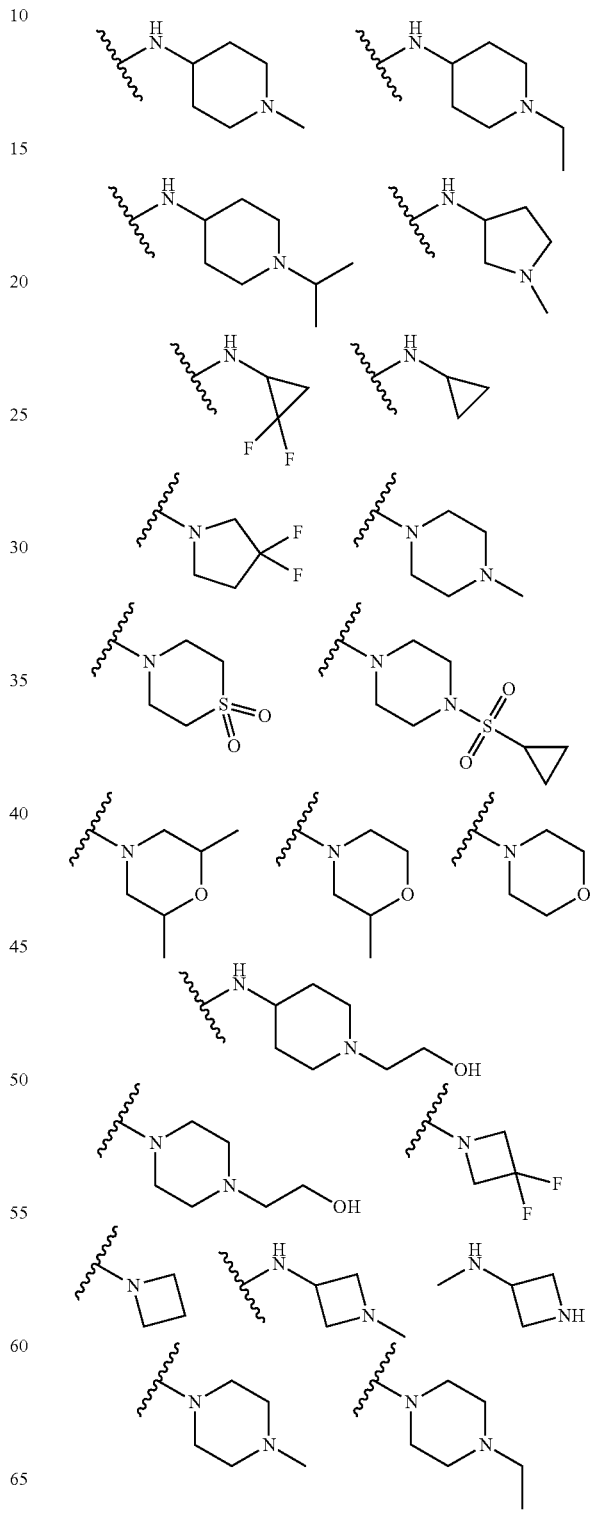

475
-continued
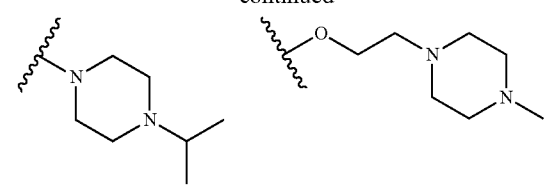
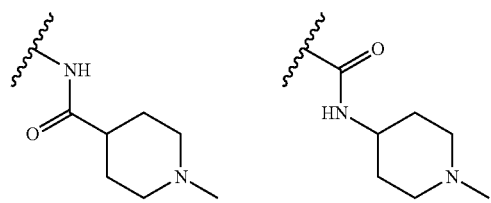
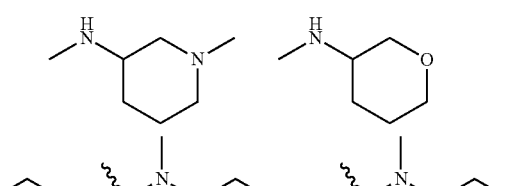
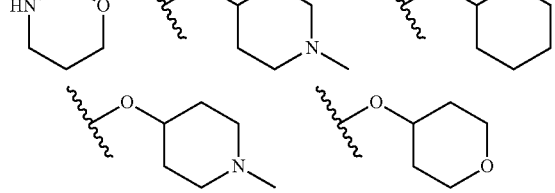
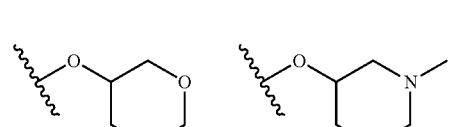
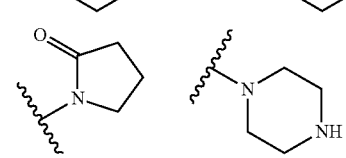
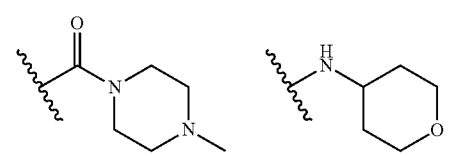
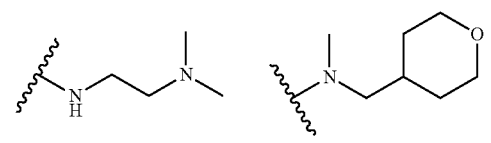
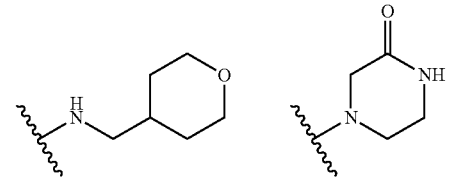
476
-continued
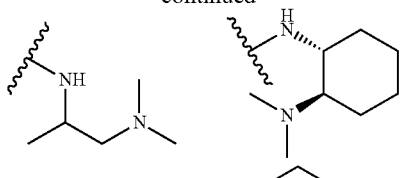
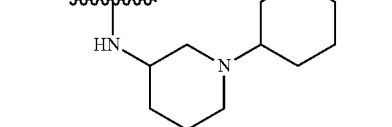
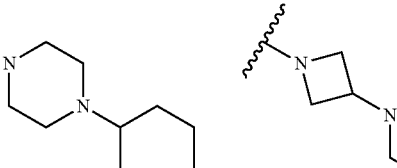
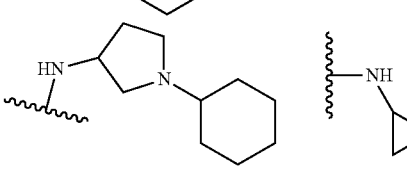
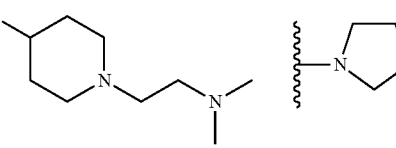
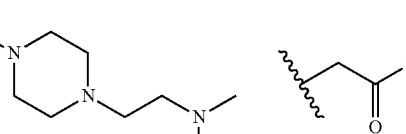
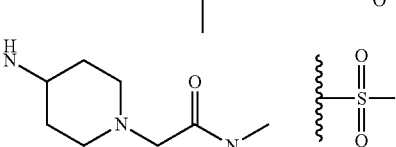
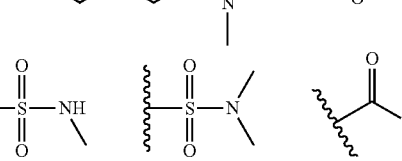
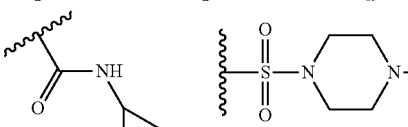
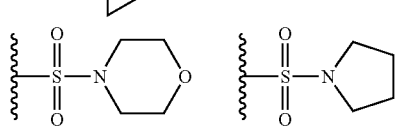
wherein
indicates the attachment to $R_1$, $R_2$ and $R_3$ of Formula VII.

14. The invention of claim 1 wherein $R_1$, $R_2$ and $R_3$ at each occurrence is independently —H, optionally substituted $C_{1-6}$ alkyl, optionally substituted cycloalkyl, optionally substituted heterocycloalkyl, optionally substituted aryl or optionally substituted heteroaryl.

15. The invention of claim 1 wherein $R_1$, $R_2$ and $R_3$ are each independently —NHCOC$_{1-6}$ alkyl, —NHCO$_{1-6}$ cycloalkyl, —NHCO$_{1-6}$ heterocycloalkyl, —CONHC$_{1-6}$ alkyl, —CONH$_{1-6}$ cycloalkyl, or —CONH$_{1-6}$ heterocycloalkyl.

16. The invention of claim 1 wherein $R_1$, $R_2$ and $R_3$ are each independently directly substituted by —H, —F, —Cl, —OCF$_3$, CF$_3$, —CH$_3$, —OCHF$_2$ or —OCH$_3$, wherein at least one of $R_1$, $R_2$ and $R_3$ is not hydrogen.

17. The invention of claim 1 wherein $R_1$, $R_2$ and $R_3$ are each independently formula III or IV

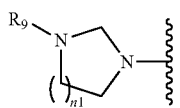

III

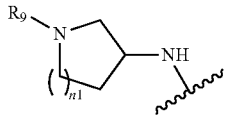

IV wherein

indicates the attachment to Formula VII of one of $R_1$, $R_2$ and $R_3$ positions and $R_9$ is —H, —CH$_3$, —CH(CH$_3$)$_2$, —CH$_2$CH$_3$, —CH$_2$CH$_2$—OH, or —C$_{3-6}$-alkyl.

18. The invention of claim 1 comprising a compound of Formula VIII wherein

indicates attachment to $R_1$, $R_2$ and $R_3$ of Formula VII respectively

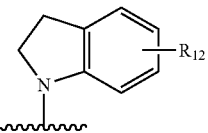

VIII wherein $R_{12}$ is —H, halo, —CH$_3$, —CH$_2$CH$_3$, —OCH$_3$, —CF$_3$, OCF$_3$, —CN, —NH$_2$, —CH$_2$OCF$_2$, —COOH, OH, —CH$_2$OH, —SO$_2$CH$_3$, SO$_2$N(CH$_3$)$_2$, or —COCH$_3$.

* * * * *

SEQUENCE LISTING

```
<160> NUMBER OF SEQ ID NOS: 64

<210> SEQ ID NO 1
<211> LENGTH: 1130
<212> TYPE: PRT
<213> ORGANISM: Homo sapiens (human)
<220> FEATURE:
<221> NAME/KEY: Abl1
<222> LOCATION: (1)..(1130)
<223> OTHER INFORMATION: ABl1 T315I
<220> FEATURE:
<221> NAME/KEY: Abl1
<222> LOCATION: (1)..(1130)
<223> OTHER INFORMATION: Abl1 T315I Tyrosine-protein kinase ABL1
      Isoform A
<300> PUBLICATION INFORMATION:
<308> DATABASE ACCESSION NUMBER: NP_005148
<309> DATABASE ENTRY DATE: 2012-05-06
<313> RELEVANT RESIDUES IN SEQ ID NO: (1)..(1130)

<400> SEQUENCE: 1

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His His Ser Thr Val Ala Asp Gly
```

```
              195                 200                 205
Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gln Tyr Gly Glu Val
                    245                 250                 255

Tyr Glu Gly Val Trp Lys Lys Tyr Ser Leu Thr Val Ala Val Lys Thr
                260                 265                 270

Leu Lys Glu Asp Thr Met Glu Val Glu Glu Phe Leu Lys Glu Ala Ala
                275                 280                 285

Val Met Lys Glu Ile Lys His Pro Asn Leu Val Gln Leu Leu Gly Val
290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
                340                 345                 350

Tyr Leu Glu Lys Lys Asn Phe Ile His Arg Asp Leu Ala Ala Arg Asn
                355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
                420                 425                 430

Ala Thr Tyr Gly Met Ser Pro Tyr Pro Gly Ile Asp Leu Ser Gln Val
                435                 440                 445

Tyr Glu Leu Leu Glu Lys Asp Tyr Arg Met Glu Arg Pro Glu Gly Cys
                450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
                500                 505                 510

Gln Gly Val Arg Gly Ala Val Ser Thr Leu Leu Gln Ala Pro Glu Leu
                515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
                580                 585                 590

Lys Asp Lys Lys Thr Asn Leu Phe Ser Ala Leu Ile Lys Lys Lys Lys
                595                 600                 605

Lys Thr Ala Pro Thr Pro Pro Lys Arg Ser Ser Ser Phe Arg Glu Met
610                 615                 620
```

```
Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
            645                 650                 655

Ala Lys Ser Pro Lys Pro Ser Asn Gly Ala Gly Val Pro Asn Gly Ala
                660                 665                 670

Leu Arg Glu Ser Gly Ser Gly Phe Arg Ser Pro His Leu Trp Lys
            675                 680                 685

Lys Ser Ser Thr Leu Thr Ser Ser Arg Leu Ala Thr Gly Glu Glu Glu
690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
                740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro
770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
                820                 825                 830

Lys Glu Glu Ala Gly Lys Gly Ser Ala Leu Gly Thr Pro Ala Ala Ala
                835                 840                 845

Glu Pro Val Thr Pro Thr Ser Lys Ala Gly Ser Gly Ala Pro Gly Gly
850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Ala Ala Ser Ala Gly Lys Ala Gly Gly
                900                 905                 910

Lys Pro Ser Gln Ser Pro Ser Gln Glu Ala Ala Gly Glu Ala Val Leu
                915                 920                 925

Gly Ala Lys Thr Lys Ala Thr Ser Leu Val Asp Ala Val Asn Ser Asp
930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ser Ala Leu
                980                 985                 990

Ala Gly Asp Gln Pro Ser Ser Thr Ala Phe Ile Pro Leu Ile Ser Thr
            995                 1000                1005

Arg Val Ser Leu Arg Lys Thr Arg Gln Pro Pro Glu Arg Ile Ala
        1010                1015                1020

Ser Gly Ala Ile Thr Lys Gly Val Val Leu Asp Ser Thr Glu Ala
        1025                1030                1035
```

```
Leu Cys Leu Ala Ile Ser Arg Asn Ser Glu Gln Met Ala Ser His
    1040                1045                1050

Ser Ala Val Leu Glu Ala Gly Lys Asn Leu Tyr Thr Phe Cys Val
    1055                1060                1065

Ser Tyr Val Asp Ser Ile Gln Gln Met Arg Asn Lys Phe Ala Phe
    1070                1075                1080

Arg Glu Ala Ile Asn Lys Leu Glu Asn Asn Leu Arg Glu Leu Gln
    1085                1090                1095

Ile Cys Pro Ala Thr Ala Gly Ser Gly Pro Ala Ala Thr Gln Asp
    1100                1105                1110

Phe Ser Lys Leu Leu Ser Ser Val Lys Glu Ile Ser Asp Ile Val
    1115                1120                1125

Gln Arg
    1130

<210> SEQ ID NO 2
<211> LENGTH: 509
<212> TYPE: PRT
<213> ORGANISM: Homo sapiens
<300> PUBLICATION INFORMATION:
<301> AUTHORS: Ambrosio,E.P., Drigo,S.A., Bergamo,N.A., Rosa,F.E.,
       Bertonha,F.B.,
<302> TITLE: Recurrent copy number gains of ACVR1 and corresponding
       transcript
<303> JOURNAL: Histopathology
<304> VOLUME: 59
<305> ISSUE: 1
<306> PAGES: 81-89
<307> DATE: 2011-05-01
<308> DATABASE ACCESSION NUMBER: NP_001104537
<309> DATABASE ENTRY DATE: 2012-04-22
<313> RELEVANT RESIDUES IN SEQ ID NO: (1)..(509)
<300> PUBLICATION INFORMATION:
<308> DATABASE ACCESSION NUMBER: NP_001104537
<309> DATABASE ENTRY DATE: 2012-04-22
<313> RELEVANT RESIDUES IN SEQ ID NO: (1)..(509)

<400> SEQUENCE: 2

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
                20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Ile Asn Asp Gly Phe His
        50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175
```

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 3
<211> LENGTH: 403
<212> TYPE: PRT
<213> ORGANISM: Human
<300> PUBLICATION INFORMATION:
<301> AUTHORS: Brodie,K.M. and Henderson,B.R.
<303> JOURNAL: J. Biol. Chem.
<304> VOLUME: 287
<305> ISSUE: 10
<306> PAGES: 7701-7716
<307> DATE: 2012-01-18
<308> DATABASE ACCESSION NUMBER: NP_940839
<309> DATABASE ENTRY DATE: 2012-05-06
<313> RELEVANT RESIDUES IN SEQ ID NO: (1)..(403)
<300> PUBLICATION INFORMATION:

```
<301> AUTHORS: Brodie,K.M. and Henderson,B.R.
<302> TITLE: Characterization of BRCA1 protein targeting, dynamics, and
      function
<303> JOURNAL: J. Biol. Chem.
<304> VOLUME: 287
<305> ISSUE: 10
<306> PAGES: 7701-7716
<307> DATE: 2012-01-18
<308> DATABASE ACCESSION NUMBER: NP_940839
<309> DATABASE ENTRY DATE: 2012-05-06
<313> RELEVANT RESIDUES IN SEQ ID NO: (1)..(403)
<300> PUBLICATION INFORMATION:
<308> DATABASE ACCESSION NUMBER: NP_940839
<309> DATABASE ENTRY DATE: 2012-05-06
<313> RELEVANT RESIDUES IN SEQ ID NO: (1)..(403)

<400> SEQUENCE: 3
```

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu

```
                     325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
            355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 4
<211> LENGTH: 344
<212> TYPE: PRT
<213> ORGANISM: Human
<300> PUBLICATION INFORMATION:
<301> AUTHORS: Yoon,M.J., Park,S.S., Kang,Y.J., Kim,I.Y., Lee,J.A.,
      Lee,J.S.,
<302> TITLE: Aurora B confers cancer cell resistance to TRAIL-induced
      apoptosis
<303> JOURNAL: Carcinogenesis
<304> VOLUME: 33
<305> ISSUE: 3
<306> PAGES: 492-500
<307> DATE: 2011-12-19
<308> DATABASE ACCESSION NUMBER: NP_004208
<309> DATABASE ENTRY DATE: 2012-05-13
<313> RELEVANT RESIDUES IN SEQ ID NO: (1)..(344)
<300> PUBLICATION INFORMATION:
<308> DATABASE ACCESSION NUMBER: NP_004208
<309> DATABASE ENTRY DATE: 2012-05-13
<313> RELEVANT RESIDUES IN SEQ ID NO: (1)..(344)

<400> SEQUENCE: 4

Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205
```

```
Gly Leu Lys Gly Glu Leu Lys Ile Ala Asp Phe Gly Trp Ser Val His
            210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Met Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340

<210> SEQ ID NO 5
<211> LENGTH: 309
<212> TYPE: PRT
<213> ORGANISM: Human
<300> PUBLICATION INFORMATION:
<301> AUTHORS: en Khelifa,M., Zouari,R., Harbuz,R., Halouani,L.,
      Arnoult,C.,
<302> TITLE: A new AURKC mutation causing macrozoospermia: implications
      for
<303> JOURNAL: Mol. Hum. Reprod
<304> VOLUME: 17
<305> ISSUE: 12
<306> PAGES: 762-768
<307> DATE: 2011-07-06
<308> DATABASE ACCESSION NUMBER: NP_001015878
<309> DATABASE ENTRY DATE: 2012-04-21
<313> RELEVANT RESIDUES IN SEQ ID NO: (1)..(309)
<300> PUBLICATION INFORMATION:
<308> DATABASE ACCESSION NUMBER: NP_001015878
<309> DATABASE ENTRY DATE: 2012-04-21
<313> RELEVANT RESIDUES IN SEQ ID NO: (1)..(309)

<400> SEQUENCE: 5

Met Ser Ser Pro Arg Ala Val Val Gln Leu Gly Lys Ala Gln Pro Ala
1               5                   10                  15

Gly Glu Glu Leu Ala Thr Ala Asn Gln Thr Ala Gln Gln Pro Ser Ser
            20                  25                  30

Pro Ala Met Arg Arg Leu Thr Val Asp Asp Phe Glu Ile Gly Arg Pro
        35                  40                  45

Leu Gly Lys Gly Lys Phe Gly Asn Val Tyr Leu Ala Arg Leu Lys Glu
    50                  55                  60

Ser His Phe Ile Val Ala Leu Lys Val Leu Phe Lys Ser Gln Ile Glu
65                  70                  75                  80

Lys Glu Gly Leu Glu His Gln Leu Arg Arg Glu Ile Glu Ile Gln Ala
                85                  90                  95

His Leu Gln His Pro Asn Ile Leu Arg Leu Tyr Asn Tyr Phe His Asp
            100                 105                 110

Ala Arg Arg Val Tyr Leu Ile Leu Glu Tyr Ala Pro Arg Gly Glu Leu
        115                 120                 125

Tyr Lys Glu Leu Gln Lys Ser Glu Lys Leu Asp Glu Gln Arg Thr Ala
    130                 135                 140
```

```
Thr Ile Ile Glu Glu Leu Ala Asp Ala Leu Thr Tyr Cys His Asp Lys
145                 150                 155                 160

Lys Val Ile His Arg Asp Ile Lys Pro Glu Asn Leu Leu Leu Gly Phe
                165                 170                 175

Arg Gly Glu Val Lys Ile Ala Asp Phe Gly Trp Ser Val His Thr Pro
            180                 185                 190

Ser Leu Arg Arg Lys Thr Met Cys Gly Thr Leu Asp Tyr Leu Pro Pro
        195                 200                 205

Glu Met Ile Glu Gly Arg Thr Tyr Asp Glu Lys Val Asp Leu Trp Cys
    210                 215                 220

Ile Gly Val Leu Cys Tyr Glu Leu Leu Val Gly Tyr Pro Pro Phe Glu
225                 230                 235                 240

Ser Ala Ser His Ser Glu Thr Tyr Arg Arg Ile Leu Lys Val Asp Val
                245                 250                 255

Arg Phe Pro Leu Ser Met Pro Leu Gly Ala Arg Asp Leu Ile Ser Arg
            260                 265                 270

Leu Leu Arg Tyr Gln Pro Leu Glu Arg Leu Pro Leu Ala Gln Ile Leu
        275                 280                 285

Lys His Pro Trp Val Gln Ala His Ser Arg Arg Val Leu Pro Pro Cys
    290                 295                 300

Ala Gln Met Ala Ser
305

<210> SEQ ID NO 6
<211> LENGTH: 766
<212> TYPE: PRT
<213> ORGANISM: Human
<300> PUBLICATION INFORMATION:
<301> AUTHORS: Gupta,S., Ajise,O., Dultz,L., Wang,B., Nonaka,D.,
      Ogilvie,J.,
<302> TITLE: Follicular variant of papillary thyroid cancer:
      encapsulated,
<303> JOURNAL: Arch. Otolaryngol. Head Neck Surg.
<304> VOLUME: 138
<305> ISSUE: 3
<306> PAGES: 227-233
<307> DATE: 2012-03-20
<308> DATABASE ACCESSION NUMBER: NP_004324
<309> DATABASE ENTRY DATE: 2012-05-13
<313> RELEVANT RESIDUES IN SEQ ID NO: (1)..(766)

<400> SEQUENCE: 6

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125
```

-continued

```
Ser Val Leu Pro Ser Ser Leu Ser Val Phe Gln Asn Pro Thr Asp Val
130                 135                 140
Ala Arg Ser Asn Pro Lys Ser Pro Gln Lys Pro Ile Val Arg Val Phe
145                 150                 155                 160
Leu Pro Asn Lys Gln Arg Thr Val Val Pro Ala Arg Cys Gly Val Thr
            165                 170                 175
Val Arg Asp Ser Leu Lys Lys Ala Leu Met Met Arg Gly Leu Ile Pro
            180                 185                 190
Glu Cys Cys Ala Val Tyr Arg Ile Gln Asp Gly Glu Lys Lys Pro Ile
            195                 200                 205
Gly Trp Asp Thr Asp Ile Ser Trp Leu Thr Gly Glu Glu Leu His Val
210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
            245                 250                 255
Gln Gly Phe Arg Cys Gln Thr Cys Gly Tyr Lys Phe His Gln Arg Cys
            260                 265                 270
Ser Thr Glu Val Pro Leu Met Cys Val Asn Tyr Asp Gln Leu Asp Leu
            275                 280                 285
Leu Phe Val Ser Lys Phe Phe Glu His His Pro Ile Pro Gln Glu Glu
            290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
            325                 330                 335
Ser Lys Ser Ile Pro Ile Pro Gln Pro Phe Arg Pro Ala Asp Glu Asp
            340                 345                 350
His Arg Asn Gln Phe Gly Gln Arg Asp Arg Ser Ser Ser Ala Pro Asn
            355                 360                 365
Val His Ile Asn Thr Ile Glu Pro Val Asn Ile Asp Asp Leu Ile Arg
            370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
            405                 410                 415
Gln Lys Ser Pro Gly Pro Gln Arg Glu Arg Lys Ser Ser Ser Ser Ser
            420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
            485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
Glu Thr Lys Phe Glu Met Ile Lys Leu Ile Asp Ile Ala Arg Gln Thr
```

```
                545                 550                 555                 560
Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
            755                 760                 765

<210> SEQ ID NO 7
<211> LENGTH: 766
<212> TYPE: PRT
<213> ORGANISM: HUMAN
<300> PUBLICATION INFORMATION:
<301> AUTHORS: Stephens,R.M., Sithanandam,G., Copeland,T.D.,
      Kaplan,D.R.,
<302> TITLE: 95-kilodalton B-Raf serine/threonine kinase: identification
      of the
<303> JOURNAL: Mol. Cell. Biol.
<304> VOLUME: 12
<305> ISSUE: 9
<306> PAGES: 3733-3742
<307> DATE: 1992-09-01
<308> DATABASE ACCESSION NUMBER: NP_004324
<309> DATABASE ENTRY DATE: 2012-05-13
<313> RELEVANT RESIDUES IN SEQ ID NO: (1)..(766)

<400> SEQUENCE: 7

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95
```

```
Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510
```

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Val Lys Ser Arg Trp Ser Gly Ser His
    595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
    675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
    755                 760                 765

<210> SEQ ID NO 8
<211> LENGTH: 476
<212> TYPE: PRT
<213> ORGANISM: Human
<300> PUBLICATION INFORMATION:
<301> AUTHORS: Pabla,N., Bhatt,K. and Dong,Z.
<302> TITLE: Checkpoint kinase 1 (Chk1)-short is a splice variant and endogenous
<303> JOURNAL: Proc. Natl. Acad. Sci. U.S.A.
<304> VOLUME: 190
<305> ISSUE: 1
<306> PAGES: 197-202
<307> DATE: 2011-12-19
<308> DATABASE ACCESSION NUMBER: NP_001107594.1
<309> DATABASE ENTRY DATE: 2012-05-13
<313> RELEVANT RESIDUES IN SEQ ID NO: (1)..(476)

<400> SEQUENCE: 8

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

```
Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                 85                  90                  95

Glu Pro Asp Ile Gly Met Pro Glu Pro Asp Ala Gln Arg Phe Phe His
                100                 105                 110

Gln Leu Met Ala Gly Val Val Tyr Leu His Gly Ile Gly Ile Thr His
                115                 120                 125

Arg Asp Ile Lys Pro Glu Asn Leu Leu Leu Asp Glu Arg Asp Asn Leu
                130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
                180                 185                 190

Ser Cys Gly Ile Val Leu Thr Ala Met Leu Ala Gly Glu Leu Pro Trp
                195                 200                 205

Asp Gln Pro Ser Asp Ser Cys Gln Glu Tyr Ser Asp Trp Lys Glu Lys
                210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
                260                 265                 270

Ala Lys Arg Pro Arg Val Thr Ser Gly Gly Val Ser Glu Ser Pro Ser
                275                 280                 285

Gly Phe Ser Lys His Ile Gln Ser Asn Leu Asp Phe Ser Pro Val Asn
                290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
                340                 345                 350

Met Leu Leu Asn Ser Gln Leu Leu Gly Thr Pro Gly Ser Ser Gln Asn
                355                 360                 365

Pro Trp Gln Arg Leu Val Lys Arg Met Thr Arg Phe Phe Thr Lys Leu
                370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
                420                 425                 430

Met Asp Asp Lys Ile Leu Val Asp Phe Arg Leu Ser Lys Gly Asp Gly
                435                 440                 445

Leu Glu Phe Lys Arg His Phe Leu Lys Ile Lys Gly Lys Leu Ile Asp
                450                 455                 460

Ile Val Ser Ser Gln Lys Ile Trp Leu Pro Ala Thr
465                 470                 475
```

<210> SEQ ID NO 9
<211> LENGTH: 543
<212> TYPE: PRT
<213> ORGANISM: HUMAN
<300> PUBLICATION INFORMATION:
<301> AUTHORS: Gogineni,V.R., Nalla,A.K., Gupta,R., Dinh,D.H., Klopfenstein,J.D.
<302> TITLE: Chk2-mediated G2/M cell cycle arrest maintains radiation resistance
<303> JOURNAL: Cancer Lett.
<304> VOLUME: 313
<305> ISSUE: 1
<306> PAGES: 64-75
<307> DATE: 2011-09-06
<308> DATABASE ACCESSION NUMBER: NP_009125
<309> DATABASE ENTRY DATE: 2012-05-20
<313> RELEVANT RESIDUES IN SEQ ID NO: (1)..(543)

<400> SEQUENCE: 9

Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Thr Ser Thr Met Pro Asn
        35                  40                  45

Ser Ser Gln Ser Ser His Ser Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Cys Val Asn Asp Asn
            100                 105                 110

Tyr Trp Phe Gly Arg Asp Lys Ser Cys Glu Tyr Cys Phe Asp Glu Pro
        115                 120                 125

Leu Leu Lys Arg Thr Asp Lys Tyr Arg Thr Tyr Ser Lys Lys His Phe
    130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190

Leu Ser Arg Asn Lys Val Phe Val Phe Phe Asp Leu Thr Val Asp Asp
        195                 200                 205

Gln Ser Val Tyr Pro Lys Ala Leu Arg Asp Glu Tyr Ile Met Ser Lys
    210                 215                 220

Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ser Lys Arg Lys Phe
                245                 250                 255

Ala Ile Gly Ser Ala Arg Glu Ala Asp Pro Ala Leu Asn Val Glu Thr
            260                 265                 270

Glu Ile Glu Ile Leu Lys Lys Leu Asn His Pro Cys Ile Ile Lys Ile
        275                 280                 285

Lys Asn Phe Phe Asp Ala Glu Asp Tyr Tyr Ile Val Leu Glu Leu Met
    290                 295                 300

Glu Gly Gly Glu Leu Phe Asp Lys Val Val Gly Asn Lys Arg Leu Lys

-continued

```
                305                 310                 315                 320

Glu Ala Thr Cys Lys Leu Tyr Phe Tyr Gln Met Leu Leu Ala Val Gln
                325                 330                 335

Tyr Leu His Glu Asn Gly Ile Ile His Arg Asp Leu Lys Pro Glu Asn
                340                 345                 350

Val Leu Leu Ser Ser Gln Glu Asp Cys Leu Ile Lys Ile Thr Asp
                355                 360                 365

Phe Gly His Ser Lys Ile Leu Gly Glu Thr Ser Leu Met Arg Thr Leu
                370                 375                 380

Cys Gly Thr Pro Thr Tyr Leu Ala Pro Glu Val Leu Ser Val Gly
385                 390                 395                 400

Thr Ala Gly Tyr Asn Arg Ala Val Asp Cys Trp Ser Leu Gly Val Ile
                405                 410                 415

Leu Phe Ile Cys Leu Ser Gly Tyr Pro Pro Phe Ser Glu His Arg Thr
                420                 425                 430

Gln Val Ser Leu Lys Asp Gln Ile Thr Ser Gly Lys Tyr Asn Phe Ile
                435                 440                 445

Pro Glu Val Trp Ala Glu Val Ser Glu Lys Ala Leu Asp Leu Val Lys
                450                 455                 460

Lys Leu Leu Val Val Asp Pro Lys Ala Arg Phe Thr Thr Glu Glu Ala
465                 470                 475                 480

Leu Arg His Pro Trp Leu Gln Asp Glu Asp Met Lys Arg Lys Phe Gln
                485                 490                 495

Asp Leu Leu Ser Glu Glu Asn Glu Ser Thr Ala Leu Pro Gln Val Leu
                500                 505                 510

Ala Gln Pro Ser Thr Ser Arg Lys Arg Pro Arg Glu Gly Glu Ala Glu
                515                 520                 525

Gly Ala Glu Thr Thr Lys Arg Pro Ala Val Cys Ala Ala Val Leu
                530                 535                 540

<210> SEQ ID NO 10
<211> LENGTH: 976
<212> TYPE: PRT
<213> ORGANISM: Human
<300> PUBLICATION INFORMATION:
<301> AUTHORS: Terada,T.
<302> TITLE: Protein expression and gene mutation status of KIT and
      PDGFRA in
<303> JOURNAL: Histol. Histopathol.
<304> VOLUME: 27
<305> ISSUE: 3
<306> PAGES: 297-302
<307> DATE: 2012-03-27
<308> DATABASE ACCESSION NUMBER: NP_000213
<309> DATABASE ENTRY DATE: 2012-05-20
<313> RELEVANT RESIDUES IN SEQ ID NO: (1)..(796)

<400> SEQUENCE: 10

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
                35                  40                  45

Arg Val Gly Asp Glu Ile Arg Leu Leu Cys Thr Asp Pro Gly Phe Val
                50                  55                  60

Lys Trp Thr Phe Glu Ile Leu Asp Glu Thr Asn Glu Asn Lys Gln Asn
65                  70                  75                  80
```

```
Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
            115                 120                 125

Asp Asn Asp Thr Leu Val Arg Cys Pro Leu Thr Asp Pro Glu Val Thr
            130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
            195                 200                 205

Lys Ala Val Pro Val Val Ser Val Ser Lys Ala Ser Tyr Leu Leu Arg
            210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
            290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
            370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
            450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
```

```
                500                 505                 510
Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925
```

```
Ser Glu Ser Thr Asn His Ile Tyr Ser Asn Leu Ala Asn Cys Ser Pro
        930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Val
                965                 970                 975

<210> SEQ ID NO 11
<211> LENGTH: 484
<212> TYPE: PRT
<213> ORGANISM: HUMAN
<300> PUBLICATION INFORMATION:
<301> AUTHORS: Colwill,K., Pawson,T., Andrews,B., Prasad,J.,
      Manley,J.L.,
<302> TITLE: The Clk/Sty protein kinase phosphorylates SR splicing
      factors and
<303> JOURNAL: EMBO J.
<304> VOLUME: 15
<305> ISSUE: 2
<306> PAGES: 265-275
<307> DATE: 1996-01-15
<308> DATABASE ACCESSION NUMBER: NP_004062
<309> DATABASE ENTRY DATE: 2012-04-29
<313> RELEVANT RESIDUES IN SEQ ID NO: (1)..(484)

<400> SEQUENCE: 11

Met Arg His Ser Lys Arg Thr Tyr Cys Pro Asp Trp Asp Asp Lys Asp
1               5                   10                  15

Trp Asp Tyr Gly Lys Trp Arg Ser Ser Ser His Lys Arg Arg Lys
                20                  25                  30

Arg Ser His Ser Ser Ala Gln Glu Asn Lys Arg Cys Lys Tyr Asn His
            35                  40                  45

Ser Lys Met Cys Asp Ser His Tyr Leu Glu Ser Arg Ser Ile Asn Glu
    50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
                100                 105                 110

Tyr Lys Ser Lys His Arg Ile His His Ser Thr Ser His Arg Arg Ser
            115                 120                 125

His Gly Lys Ser His Arg Arg Lys Arg Thr Arg Ser Val Glu Asp Asp
        130                 135                 140

Glu Glu Gly His Leu Ile Cys Gln Ser Gly Asp Val Leu Ser Ala Arg
145                 150                 155                 160

Tyr Glu Ile Val Asp Thr Leu Gly Glu Gly Ala Phe Gly Lys Val Val
                165                 170                 175

Glu Cys Ile Asp His Lys Ala Gly Gly Arg His Val Ala Val Lys Ile
                180                 185                 190

Val Lys Asn Val Asp Arg Tyr Cys Glu Ala Ala Arg Ser Glu Ile Gln
            195                 200                 205

Val Leu Glu His Leu Asn Thr Thr Asp Pro Asn Ser Thr Phe Arg Cys
    210                 215                 220

Val Gln Met Leu Glu Trp Phe Glu His His Gly His Ile Cys Ile Val
225                 230                 235                 240

Phe Glu Leu Leu Gly Leu Ser Thr Tyr Asp Phe Ile Lys Glu Asn Gly
                245                 250                 255
```

```
Phe Leu Pro Phe Arg Leu Asp His Ile Arg Lys Met Ala Tyr Gln Ile
                260                 265                 270

Cys Lys Ser Val Asn Phe Leu His Ser Asn Lys Leu Thr His Thr Asp
            275                 280                 285

Leu Lys Pro Glu Asn Ile Leu Phe Val Gln Ser Asp Tyr Thr Glu Ala
        290                 295                 300

Tyr Asn Pro Lys Ile Lys Arg Asp Glu Arg Thr Leu Ile Asn Pro Asp
305                 310                 315                 320

Ile Lys Val Val Asp Phe Gly Ser Ala Thr Tyr Asp Asp Glu His His
                325                 330                 335

Ser Thr Leu Val Ser Thr Arg His Tyr Arg Ala Pro Glu Val Ile Leu
            340                 345                 350

Ala Leu Gly Trp Ser Gln Pro Cys Asp Val Trp Ser Ile Gly Cys Ile
        355                 360                 365

Leu Ile Glu Tyr Tyr Leu Gly Phe Thr Val Phe Pro Thr His Asp Ser
370                 375                 380

Lys Glu His Leu Ala Met Met Glu Arg Ile Leu Gly Pro Leu Pro Lys
385                 390                 395                 400

His Met Ile Gln Lys Thr Arg Lys Arg Lys Tyr Phe His His Asp Arg
                405                 410                 415

Leu Asp Trp Asp Glu His Ser Ser Ala Gly Arg Tyr Val Ser Arg Arg
            420                 425                 430

Cys Lys Pro Leu Lys Glu Phe Met Leu Ser Gln Asp Val Glu His Glu
        435                 440                 445

Arg Leu Phe Asp Leu Ile Gln Lys Met Leu Glu Tyr Asp Pro Ala Lys
450                 455                 460

Arg Ile Thr Leu Arg Glu Ala Leu Lys His Pro Phe Phe Asp Leu Leu
465                 470                 475                 480

Lys Lys Ser Ile

<210> SEQ ID NO 12
<211> LENGTH: 498
<212> TYPE: PRT
<213> ORGANISM: HUMAN
<300> PUBLICATION INFORMATION:
<301> AUTHORS: Nam,S.Y., Seo,H.H., Park,H.S., An,S., Kim,J.Y.,
      Yang,K.H.,
<302> TITLE: Phosphorylation of CLK2 at serine 34 and threonine 127 by
      AKT
<303> JOURNAL: 31157-31163
<304> VOLUME: 285
<305> ISSUE: 41
<306> PAGES: 31157-31163
<307> DATE: 2010-08-01
<308> DATABASE ACCESSION NUMBER: NP_003984
<309> DATABASE ENTRY DATE: 2012-04-21
<313> RELEVANT RESIDUES IN SEQ ID NO: (1)..(498)

<400> SEQUENCE: 12

Met Pro His Pro Arg Arg Tyr His Ser Ser Glu Arg Gly Ser Arg Gly
1               5                   10                  15

Ser Tyr Arg Glu His Tyr Arg Ser Arg Lys His Lys Arg Arg Arg Ser
                20                  25                  30

Arg Ser Trp Ser Ser Ser Ser Asp Arg Thr Arg Arg Arg Arg Arg Glu
            35                  40                  45

Asp Ser Tyr His Val Arg Ser Arg Ser Tyr Asp Asp Arg Ser Ser
        50                  55                  60

Asp Arg Arg Val Tyr Asp Arg Arg Tyr Cys Gly Ser Tyr Arg Arg Asn
65                  70                  75                  80
```

```
Asp Tyr Ser Arg Asp Arg Gly Asp Ala Tyr Tyr Asp Thr Asp Tyr Arg
                85                  90                  95

His Ser Tyr Glu Tyr Gln Arg Glu Asn Ser Ser Tyr Arg Ser Gln Arg
            100                 105                 110

Ser Ser Arg Arg Lys His Arg Arg Arg Arg Arg Ser Arg Thr Phe
        115                 120                 125

Ser Arg Ser Ser Ser His Ser Ser Arg Arg Ala Lys Ser Val Glu Asp
        130                 135                 140

Asp Ala Glu Gly His Leu Ile Tyr His Val Gly Asp Trp Leu Gln Glu
145                 150                 155                 160

Arg Tyr Glu Ile Val Ser Thr Leu Gly Glu Gly Thr Phe Gly Arg Val
                165                 170                 175

Val Gln Cys Val Asp His Arg Arg Gly Gly Ala Arg Val Ala Leu Lys
            180                 185                 190

Ile Ile Lys Asn Val Glu Lys Tyr Lys Glu Ala Ala Arg Leu Glu Ile
            195                 200                 205

Asn Val Leu Glu Lys Ile Asn Glu Lys Asp Pro Asp Asn Lys Asn Leu
        210                 215                 220

Cys Val Gln Met Phe Asp Trp Phe Asp Tyr His Gly His Met Cys Ile
225                 230                 235                 240

Ser Phe Glu Leu Leu Gly Leu Ser Thr Phe Asp Phe Leu Lys Asp Asn
                245                 250                 255

Asn Tyr Leu Pro Tyr Pro Ile His Gln Val Arg His Met Ala Phe Gln
                260                 265                 270

Leu Cys Gln Ala Val Lys Phe Leu His Asp Asn Lys Leu Thr His Thr
            275                 280                 285

Asp Leu Lys Pro Glu Asn Ile Leu Phe Val Asn Ser Asp Tyr Glu Leu
        290                 295                 300

Thr Tyr Asn Leu Glu Lys Lys Arg Asp Glu Arg Ser Val Lys Ser Thr
305                 310                 315                 320

Ala Val Arg Val Val Asp Phe Gly Ser Ala Thr Phe Asp His Glu His
                325                 330                 335

His Ser Thr Ile Val Ser Thr Arg His Tyr Arg Ala Pro Glu Val Ile
            340                 345                 350

Leu Glu Leu Gly Trp Ser Gln Pro Cys Asp Val Trp Ser Ile Gly Cys
            355                 360                 365

Ile Ile Phe Glu Tyr Tyr Val Gly Phe Thr Leu Phe Gln Thr His Asp
370                 375                 380

Asn Arg Glu His Leu Ala Met Met Glu Arg Ile Leu Gly Pro Ile Pro
385                 390                 395                 400

Ser Arg Met Ile Arg Lys Thr Arg Lys Gln Lys Tyr Phe Tyr Arg Gly
                405                 410                 415

Arg Leu Asp Trp Asp Glu Asn Thr Ser Ala Gly Arg Tyr Val Arg Glu
            420                 425                 430

Asn Cys Lys Pro Leu Arg Arg Tyr Leu Thr Ser Glu Ala Glu Glu His
        435                 440                 445

His Gln Leu Phe Asp Leu Ile Glu Ser Met Leu Glu Tyr Glu Pro Ala
    450                 455                 460

Lys Arg Leu Thr Leu Gly Glu Ala Leu Gln His Pro Phe Phe Ala Arg
465                 470                 475                 480

Leu Arg Ala Glu Pro Pro Asn Lys Leu Trp Asp Ser Ser Arg Asp Ile
                485                 490                 495
```

Ser Arg

<210> SEQ ID NO 13
<211> LENGTH: 638
<212> TYPE: PRT
<213> ORGANISM: HUMAN
<300> PUBLICATION INFORMATION:
<301> AUTHORS: Duncan,P.I., Stojdl,D.F., Marius,R.M., Scheit,K.H. and
    Bell,J.C.
<302> TITLE: The Clk2 and Clk3 dual-specificity protein kinases regulate
    the
<303> JOURNAL: Exp. Cell Res.
<304> VOLUME: 241
<305> ISSUE: 2
<306> PAGES: 200-205
<307> DATE: 1998-06-15
<308> DATABASE ACCESSION NUMBER: NP_001123500
<309> DATABASE ENTRY DATE: 2012-03-31
<313> RELEVANT RESIDUES IN SEQ ID NO: (1)..(638)

<400> SEQUENCE: 13

```
Met Pro Val Leu Ser Ala Arg Arg Arg Glu Leu Ala Asp His Ala Gly
1               5                   10                  15

Ser Gly Arg Arg Ser Gly Pro Ser Pro Thr Ala Arg Ser Gly Pro His
                20                  25                  30

Leu Ser Ala Leu Arg Ala Gln Pro Ala Arg Ala Ala His Leu Ser Gly
            35                  40                  45

Arg Gly Thr Tyr Val Arg Asp Thr Ala Gly Gly Pro Gly Gln
50                  55                  60

Ala Arg Pro Leu Gly Pro Gly Thr Ser Leu Leu Gly Arg Gly Ala
65                  70                  75                  80

Arg Arg Ser Gly Glu Gly Trp Cys Pro Gly Ala Phe Glu Ser Gly Ala
                85                  90                  95

Arg Ala Ala Arg Pro Pro Ser Arg Val Glu Pro Arg Leu Ala Thr Ala
            100                 105                 110

Ala Ser Arg Glu Gly Ala Gly Leu Pro Arg Ala Glu Val Ala Ala Gly
        115                 120                 125

Ser Gly Arg Gly Ala Arg Ser Gly Glu Trp Gly Leu Ala Ala Ala Gly
130                 135                 140

Ala Trp Glu Thr Met His His Cys Lys Arg Tyr Arg Ser Pro Glu Pro
145                 150                 155                 160

Asp Pro Tyr Leu Ser Tyr Arg Trp Lys Arg Arg Ser Tyr Ser Arg
                165                 170                 175

Glu His Glu Gly Arg Leu Arg Tyr Pro Ser Arg Glu Pro Pro Pro
            180                 185                 190

Arg Arg Ser Arg Ser Arg Ser His Asp Arg Leu Pro Tyr Gln Arg Arg
        195                 200                 205

Tyr Arg Glu Arg Arg Asp Ser Asp Thr Tyr Arg Cys Glu Glu Arg Ser
    210                 215                 220

Pro Ser Phe Gly Glu Asp Tyr Tyr Gly Pro Ser Arg Ser Arg His Arg
225                 230                 235                 240

Arg Arg Ser Arg Glu Arg Gly Pro Tyr Arg Thr Arg Lys His Ala His
                245                 250                 255

His Cys His Lys Arg Arg Thr Arg Ser Cys Ser Ser Ala Ser Ser Arg
            260                 265                 270

Ser Gln Gln Ser Ser Lys Arg Ser Ser Arg Ser Val Glu Asp Asp Lys
        275                 280                 285

Glu Gly His Leu Val Cys Arg Ile Gly Asp Trp Leu Gln Glu Arg Tyr
290                 295                 300
```

Glu Ile Val Gly Asn Leu Gly Glu Gly Thr Phe Gly Lys Val Val Glu
305                 310                 315                 320

Cys Leu Asp His Ala Arg Gly Lys Ser Gln Val Ala Leu Lys Ile Ile
                325                 330                 335

Arg Asn Val Gly Lys Tyr Arg Glu Ala Ala Arg Leu Glu Ile Asn Val
                340                 345                 350

Leu Lys Lys Ile Lys Glu Lys Asp Lys Glu Asn Lys Phe Leu Cys Val
                355                 360                 365

Leu Met Ser Asp Trp Phe Asn Phe His Gly His Met Cys Ile Ala Phe
370                 375                 380

Glu Leu Leu Gly Lys Asn Thr Phe Glu Phe Leu Lys Glu Asn Asn Phe
385                 390                 395                 400

Gln Pro Tyr Pro Leu Pro His Val Arg His Met Ala Tyr Gln Leu Cys
                405                 410                 415

His Ala Leu Arg Phe Leu His Glu Asn Gln Leu Thr His Thr Asp Leu
                420                 425                 430

Lys Pro Glu Asn Ile Leu Phe Val Asn Ser Glu Phe Glu Thr Leu Tyr
                435                 440                 445

Asn Glu His Lys Ser Cys Glu Glu Lys Ser Val Lys Asn Thr Ser Ile
450                 455                 460

Arg Val Ala Asp Phe Gly Ser Ala Thr Phe Asp His Glu His His Thr
465                 470                 475                 480

Thr Ile Val Ala Thr Arg His Tyr Arg Pro Pro Glu Val Ile Leu Glu
                485                 490                 495

Leu Gly Trp Ala Gln Pro Cys Asp Val Trp Ser Ile Gly Cys Ile Leu
                500                 505                 510

Phe Glu Tyr Tyr Arg Gly Phe Thr Leu Phe Gln Thr His Glu Asn Arg
                515                 520                 525

Glu His Leu Val Met Met Glu Lys Ile Leu Gly Pro Ile Pro Ser His
530                 535                 540

Met Ile His Arg Thr Arg Lys Gln Lys Tyr Phe Tyr Lys Gly Gly Leu
545                 550                 555                 560

Val Trp Asp Glu Asn Ser Ser Asp Gly Arg Tyr Val Lys Glu Asn Cys
                565                 570                 575

Lys Pro Leu Lys Ser Tyr Met Leu Gln Asp Ser Leu Glu His Val Gln
                580                 585                 590

Leu Phe Asp Leu Met Arg Arg Met Leu Glu Phe Asp Pro Ala Gln Arg
                595                 600                 605

Ile Thr Leu Ala Glu Ala Leu Leu His Pro Phe Phe Ala Gly Leu Thr
                610                 615                 620

Pro Glu Glu Arg Ser Phe His Thr Ser Arg Asn Pro Ser Arg
625                 630                 635

<210> SEQ ID NO 14
<211> LENGTH: 481
<212> TYPE: PRT
<213> ORGANISM: HUMAN
<300> PUBLICATION INFORMATION:
<301> AUTHORS: Katsu,R., Onogi,H., Wada,K., Kawaguchi,Y. and Hagiwara,M.
<302> TITLE: Novel SR-rich-related protein clasp specifically interacts
       with
<303> JOURNAL: J. Biol. Chem.
<304> VOLUME: 277
<305> ISSUE: 46
<306> PAGES: 44220-44228
<307> DATE: 2002-08-06
<308> DATABASE ACCESSION NUMBER: NP_065717

<309> DATABASE ENTRY DATE: 2012-03-25
<313> RELEVANT RESIDUES IN SEQ ID NO: (1)..(481)

<400> SEQUENCE: 14

```
Met Arg His Ser Lys Arg Thr His Cys Pro Asp Trp Asp Ser Arg Glu
1               5                   10                  15

Ser Trp Gly His Glu Ser Tyr Arg Gly Ser His Lys Arg Lys Arg Arg
            20                  25                  30

Ser His Ser Ser Thr Gln Glu Asn Arg His Cys Lys Pro His His Gln
        35                  40                  45

Phe Lys Glu Ser Asp Cys His Tyr Leu Glu Ala Arg Ser Leu Asn Glu
    50                  55                  60

Arg Tyr Arg Asp Arg Arg Tyr Val Asp Glu Tyr Arg Asn Asp Tyr
65                  70                  75                  80

Cys Glu Gly Tyr Val Pro Arg His Tyr Arg Asp Ile Glu Ser Gly
                    85                  90                  95

Tyr Arg Ile His Cys Ser Lys Ser Ser Val Arg Ser Arg Ser Ser
                100                 105                 110

Pro Lys Arg Lys Arg Asn Arg His Cys Ser Ser His Gln Ser Arg Ser
        115                 120                 125

Lys Ser His Arg Arg Lys Arg Ser Arg Ser Ile Glu Asp Asp Glu Glu
130                 135                 140

Gly His Leu Ile Cys Gln Ser Gly Asp Val Leu Arg Ala Arg Tyr Glu
145                 150                 155                 160

Ile Val Asp Thr Leu Gly Glu Gly Ala Phe Gly Lys Val Val Glu Cys
                165                 170                 175

Ile Asp His Gly Met Asp Gly Met His Val Ala Val Lys Ile Val Lys
                180                 185                 190

Asn Val Gly Arg Tyr Arg Glu Ala Ala Arg Ser Glu Ile Gln Val Leu
            195                 200                 205

Glu His Leu Asn Ser Thr Asp Pro Asn Ser Val Phe Arg Cys Val Gln
    210                 215                 220

Met Leu Glu Trp Phe Asp His His Gly His Val Cys Ile Val Phe Glu
225                 230                 235                 240

Leu Leu Gly Leu Ser Thr Tyr Asp Phe Ile Lys Glu Asn Ser Phe Leu
                245                 250                 255

Pro Phe Gln Ile Asp His Ile Arg Gln Met Ala Tyr Gln Ile Cys Gln
            260                 265                 270

Ser Ile Asn Phe Leu His His Asn Lys Leu Thr His Thr Asp Leu Lys
        275                 280                 285

Pro Glu Asn Ile Leu Phe Val Lys Ser Asp Tyr Val Val Lys Tyr Asn
    290                 295                 300

Ser Lys Met Lys Arg Asp Glu Arg Thr Leu Lys Asn Thr Asp Ile Lys
305                 310                 315                 320

Val Val Asp Phe Gly Ser Ala Thr Tyr Asp Asp Glu His His Ser Thr
                325                 330                 335

Leu Val Ser Thr Arg His Tyr Arg Ala Pro Glu Val Ile Leu Ala Leu
                340                 345                 350

Gly Trp Ser Gln Pro Cys Asp Val Trp Ser Ile Gly Cys Ile Leu Ile
            355                 360                 365

Glu Tyr Tyr Leu Gly Phe Thr Val Phe Gln Thr His Asp Ser Lys Glu
    370                 375                 380

His Leu Ala Met Met Glu Arg Ile Leu Gly Pro Ile Pro Gln His Met
385                 390                 395                 400
```

```
Ile Gln Lys Thr Arg Lys Arg Lys Tyr Phe His His Asn Gln Leu Asp
            405                 410                 415

Trp Asp Glu His Ser Ser Ala Gly Arg Tyr Val Arg Arg Cys Lys
            420                 425                 430

Pro Leu Lys Glu Phe Met Leu Cys His Asp Glu His Glu Lys Leu
            435                 440                 445

Phe Asp Leu Val Arg Arg Met Leu Glu Tyr Asp Pro Thr Gln Arg Ile
    450                 455                 460

Thr Leu Asp Glu Ala Leu Gln His Pro Phe Phe Asp Leu Leu Lys Lys
465                 470                 475                 480

Lys

<210> SEQ ID NO 15
<211> LENGTH: 972
<212> TYPE: PRT
<213> ORGANISM: Human
<300> PUBLICATION INFORMATION:
<301> AUTHORS: Elegheert,J., Desfosses,A., Shkumatov,A.V., Wu,X.,
      Bracke,N.,
<302> TITLE: Extracellular complexes of the hematopoietic human and
      mouse CSF-1
<303> JOURNAL: Structure
<304> VOLUME: 19
<305> ISSUE: 12
<306> PAGES: 1762-1772
<307> DATE: 2011-12-07
<308> DATABASE ACCESSION NUMBER: NP_005202
<309> DATABASE ENTRY DATE: 2012-04-29
<313> RELEVANT RESIDUES IN SEQ ID NO: (1)..(972)

<400> SEQUENCE: 15

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
```

```
            210                 215                 220
Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
            515                 520                 525

Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640
```

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 16
<211> LENGTH: 763
<212> TYPE: PRT
<213> ORGANISM: HUMAN
<300> PUBLICATION INFORMATION:
<301> AUTHORS: Malinge,S., Bliss-Moreau,M., Kirsammer,G., Diebold,L.,
      Chlon,T.,
<302> TITLE: Increased dosage of the chromosome 21 ortholog Dyrk1a
      promotes
<303> JOURNAL: J. Clin. Invest.
<304> VOLUME: 122
<305> ISSUE: 3
<306> PAGES: 958-962
<307> DATE: 2012-03-01

-continued

```
<308> DATABASE ACCESSION NUMBER: NP_001387
<309> DATABASE ENTRY DATE: 2012-05-06
<313> RELEVANT RESIDUES IN SEQ ID NO: (1)..(763)

<400> SEQUENCE: 16
```

| | | | | | | | | | | | | | | | |
|---|---|---|---|---|---|---|---|---|---|---|---|---|---|---|---|
| Met | His | Thr | Gly | Gly | Glu | Thr | Ser | Ala | Cys | Lys | Pro | Ser | Ser | Val | Arg |
| 1 | | | | 5 | | | | | 10 | | | | | 15 | |
| Leu | Ala | Pro | Ser | Phe | Ser | Phe | His | Ala | Ala | Gly | Leu | Gln | Met | Ala | Gly |
| | | | 20 | | | | | 25 | | | | | 30 | | |
| Gln | Met | Pro | His | Ser | His | Gln | Tyr | Ser | Asp | Arg | Arg | Gln | Pro | Asn | Ile |
| | | | 35 | | | | | 40 | | | | | 45 | | |
| Ser | Asp | Gln | Gln | Val | Ser | Ala | Leu | Ser | Tyr | Ser | Asp | Gln | Ile | Gln | Gln |
| 50 | | | | | 55 | | | | | 60 | | | | | |
| Pro | Leu | Thr | Asn | Gln | Val | Met | Pro | Asp | Ile | Val | Met | Leu | Gln | Arg | Arg |
| 65 | | | | | 70 | | | | | 75 | | | | | 80 |
| Met | Pro | Gln | Thr | Phe | Arg | Asp | Pro | Ala | Thr | Ala | Pro | Leu | Arg | Lys | Leu |
| | | | | 85 | | | | | 90 | | | | | 95 | |
| Ser | Val | Asp | Leu | Ile | Lys | Thr | Tyr | Lys | His | Ile | Asn | Glu | Val | Tyr | Tyr |
| | | | 100 | | | | | 105 | | | | | 110 | | |
| Ala | Lys | Lys | Lys | Arg | Arg | His | Gln | Gln | Gly | Gln | Gly | Asp | Asp | Ser | Ser |
| | | 115 | | | | | 120 | | | | | 125 | | | |
| His | Lys | Lys | Glu | Arg | Lys | Val | Tyr | Asn | Asp | Gly | Tyr | Asp | Asp | Asp | Asn |
| | 130 | | | | | 135 | | | | | 140 | | | | |
| Tyr | Asp | Tyr | Ile | Val | Lys | Asn | Gly | Glu | Lys | Trp | Met | Asp | Arg | Tyr | Glu |
| 145 | | | | | 150 | | | | | 155 | | | | | 160 |
| Ile | Asp | Ser | Leu | Ile | Gly | Lys | Gly | Ser | Phe | Gly | Gln | Val | Val | Lys | Ala |
| | | | | 165 | | | | | 170 | | | | | 175 | |
| Tyr | Asp | Arg | Val | Glu | Gln | Glu | Trp | Val | Ala | Ile | Lys | Ile | Ile | Lys | Asn |
| | | | 180 | | | | | 185 | | | | | 190 | | |
| Lys | Lys | Ala | Phe | Leu | Asn | Gln | Ala | Gln | Ile | Glu | Val | Arg | Leu | Leu | Glu |
| | | 195 | | | | | 200 | | | | | 205 | | | |
| Leu | Met | Asn | Lys | His | Asp | Thr | Glu | Met | Lys | Tyr | Tyr | Ile | Val | His | Leu |
| | 210 | | | | | 215 | | | | | 220 | | | | |
| Lys | Arg | His | Phe | Met | Phe | Arg | Asn | His | Leu | Cys | Leu | Val | Phe | Glu | Met |
| 225 | | | | | 230 | | | | | 235 | | | | | 240 |
| Leu | Ser | Tyr | Asn | Leu | Tyr | Asp | Leu | Leu | Arg | Asn | Thr | Asn | Phe | Arg | Gly |
| | | | | 245 | | | | | 250 | | | | | 255 | |
| Val | Ser | Leu | Asn | Leu | Thr | Arg | Lys | Phe | Ala | Gln | Gln | Met | Cys | Thr | Ala |
| | | | 260 | | | | | 265 | | | | | 270 | | |
| Leu | Leu | Phe | Leu | Ala | Thr | Pro | Glu | Leu | Ser | Ile | Ile | His | Cys | Asp | Leu |
| | | 275 | | | | | 280 | | | | | 285 | | | |
| Lys | Pro | Glu | Asn | Ile | Leu | Leu | Cys | Asn | Pro | Lys | Arg | Ser | Ala | Ile | Lys |
| | 290 | | | | | 295 | | | | | 300 | | | | |
| Ile | Val | Asp | Phe | Gly | Ser | Ser | Cys | Gln | Leu | Gly | Gln | Arg | Ile | Tyr | Gln |
| 305 | | | | | 310 | | | | | 315 | | | | | 320 |
| Tyr | Ile | Gln | Ser | Arg | Phe | Tyr | Arg | Ser | Pro | Glu | Val | Leu | Leu | Gly | Met |
| | | | | 325 | | | | | 330 | | | | | 335 | |
| Pro | Tyr | Asp | Leu | Ala | Ile | Asp | Met | Trp | Ser | Leu | Gly | Cys | Ile | Leu | Val |
| | | | 340 | | | | | 345 | | | | | 350 | | |
| Glu | Met | His | Thr | Gly | Glu | Pro | Leu | Phe | Ser | Gly | Ala | Asn | Glu | Val | Asp |
| | | | 355 | | | | | 360 | | | | | 365 | | |
| Gln | Met | Asn | Lys | Ile | Val | Glu | Val | Leu | Gly | Ile | Pro | Pro | Ala | His | Ile |
| | 370 | | | | | 375 | | | | | 380 | | | | |
| Leu | Asp | Gln | Ala | Pro | Lys | Ala | Arg | Lys | Phe | Phe | Glu | Lys | Leu | Pro | Asp |

```
                385                 390                 395                 400
Gly Thr Trp Asn Leu Lys Lys Thr Lys Asp Gly Lys Arg Glu Tyr Lys
                    405                 410                 415
Pro Pro Gly Thr Arg Lys Leu His Asn Ile Leu Gly Val Glu Thr Gly
                420                 425                 430
Gly Pro Gly Gly Arg Arg Ala Gly Glu Ser Gly His Thr Val Ala Asp
            435                 440                 445
Tyr Leu Lys Phe Lys Asp Leu Ile Leu Arg Met Leu Asp Tyr Asp Pro
450                 455                 460
Lys Thr Arg Ile Gln Pro Tyr Tyr Ala Leu Gln His Ser Phe Phe Lys
465                 470                 475                 480
Lys Thr Ala Asp Glu Gly Thr Asn Thr Ser Asn Ser Val Ser Thr Ser
                485                 490                 495
Pro Ala Met Glu Gln Ser Gln Ser Ser Gly Thr Thr Ser Ser Thr Ser
                500                 505                 510
Ser Ser Ser Gly Gly Ser Ser Gly Thr Ser Asn Ser Gly Arg Ala Arg
            515                 520                 525
Ser Asp Pro Thr His Gln His Arg His Ser Gly Gly His Phe Thr Ala
530                 535                 540
Ala Val Gln Ala Met Asp Cys Glu Thr His Ser Pro Gln Val Arg Gln
545                 550                 555                 560
Gln Phe Pro Ala Pro Leu Gly Trp Ser Gly Thr Glu Ala Pro Thr Gln
                565                 570                 575
Val Thr Val Glu Thr His Pro Val Gln Glu Thr Thr Phe His Val Ala
                580                 585                 590
Pro Gln Gln Asn Ala Leu His His His Gly Asn Ser Ser His His
            595                 600                 605
His His His His His His His His Gly Gln Gln Ala Leu
            610                 615                 620
Gly Asn Arg Thr Arg Pro Arg Val Tyr Asn Ser Pro Thr Asn Ser Ser
625                 630                 635                 640
Ser Thr Gln Asp Ser Met Glu Val Gly His Ser His His Ser Met Thr
                645                 650                 655
Ser Leu Ser Ser Ser Thr Thr Ser Ser Ser Thr Ser Ser Ser Ser Thr
                660                 665                 670
Gly Asn Gln Gly Asn Gln Ala Tyr Gln Asn Arg Pro Val Ala Ala Asn
            675                 680                 685
Thr Leu Asp Phe Gly Gln Asn Gly Ala Met Asp Val Asn Leu Thr Val
        690                 695                 700
Tyr Ser Asn Pro Arg Gln Glu Thr Gly Ile Ala Gly His Pro Thr Tyr
705                 710                 715                 720
Gln Phe Ser Ala Asn Thr Gly Pro Ala His Tyr Met Thr Glu Gly His
                725                 730                 735
Leu Thr Met Arg Gln Gly Ala Asp Arg Glu Glu Ser Pro Met Thr Gly
                740                 745                 750
Val Cys Val Gln Gln Ser Pro Val Ala Ser Ser
            755                 760

<210> SEQ ID NO 17
<211> LENGTH: 629
<212> TYPE: PRT
<213> ORGANISM: HUMAN
<300> PUBLICATION INFORMATION:
<301> AUTHORS: Leder,S., Weber,Y., Altafaj,X., Estivill,X., Joost,H.G.
      and
```

<302> TITLE: Cloning and characterization of DYRK1B, a novel member of the DYRK
<303> JOURNAL: Biochem. Biophys. Res. Commun.
<304> VOLUME: 254
<305> ISSUE: 2
<306> PAGES: 474-479
<307> DATE: 1999-01-19
<308> DATABASE ACCESSION NUMBER: NP_004705
<309> DATABASE ENTRY DATE: 2012-04-21
<313> RELEVANT RESIDUES IN SEQ ID NO: (1)..(629)

<400> SEQUENCE: 17

```
Met Ala Val Pro Pro Gly His Gly Pro Phe Ser Gly Phe Pro Gly Pro
1               5                   10                  15

Gln Glu His Thr Gln Val Leu Pro Asp Val Arg Leu Leu Pro Arg Arg
            20                  25                  30

Leu Pro Leu Ala Phe Arg Asp Ala Thr Ser Ala Pro Leu Arg Lys Leu
        35                  40                  45

Ser Val Asp Leu Ile Lys Thr Tyr Lys His Ile Asn Glu Val Tyr Tyr
50                  55                  60

Ala Lys Lys Lys Arg Arg Ala Gln Gln Ala Pro Pro Gln Asp Ser Ser
65                  70                  75                  80

Asn Lys Lys Glu Lys Lys Val Leu Asn His Gly Tyr Asp Asp Asp Asn
                85                  90                  95

His Asp Tyr Ile Val Arg Ser Gly Glu Arg Trp Leu Glu Arg Tyr Glu
            100                 105                 110

Ile Asp Ser Leu Ile Gly Lys Gly Ser Phe Gly Gln Val Val Lys Ala
        115                 120                 125

Tyr Asp His Gln Thr Gln Glu Leu Val Ala Ile Lys Ile Ile Lys Asn
    130                 135                 140

Lys Lys Ala Phe Leu Asn Gln Ala Gln Ile Glu Leu Arg Leu Leu Glu
145                 150                 155                 160

Leu Met Asn Gln His Asp Thr Glu Met Lys Tyr Tyr Ile Val His Leu
                165                 170                 175

Lys Arg His Phe Met Phe Arg Asn His Leu Cys Leu Val Phe Glu Leu
            180                 185                 190

Leu Ser Tyr Asn Leu Tyr Asp Leu Leu Arg Asn Thr His Phe Arg Gly
        195                 200                 205

Val Ser Leu Asn Leu Thr Arg Lys Leu Ala Gln Gln Leu Cys Thr Ala
    210                 215                 220

Leu Leu Phe Leu Ala Thr Pro Glu Leu Ser Ile Ile His Cys Asp Leu
225                 230                 235                 240

Lys Pro Glu Asn Ile Leu Leu Cys Asn Pro Lys Arg Ser Ala Ile Lys
                245                 250                 255

Ile Val Asp Phe Gly Ser Ser Cys Gln Leu Gly Gln Arg Ile Tyr Gln
            260                 265                 270

Tyr Ile Gln Ser Arg Phe Tyr Arg Ser Pro Glu Val Leu Leu Gly Thr
        275                 280                 285

Pro Tyr Asp Leu Ala Ile Asp Met Trp Ser Leu Gly Cys Ile Leu Val
    290                 295                 300

Glu Met His Thr Gly Glu Pro Leu Phe Ser Gly Ser Asn Glu Val Asp
305                 310                 315                 320

Gln Met Asn Arg Ile Val Glu Val Leu Gly Ile Pro Pro Ala Ala Met
                325                 330                 335

Leu Asp Gln Ala Pro Lys Ala Arg Lys Tyr Phe Glu Arg Leu Pro Gly
            340                 345                 350
```

```
Gly Gly Trp Thr Leu Arg Arg Thr Lys Glu Leu Arg Lys Asp Tyr Gln
            355                 360                 365

Gly Pro Gly Thr Arg Arg Leu Gln Glu Val Leu Gly Val Gln Thr Gly
        370                 375                 380

Gly Pro Gly Gly Arg Arg Ala Gly Glu Pro Gly His Ser Pro Ala Asp
385                 390                 395                 400

Tyr Leu Arg Phe Gln Asp Leu Val Leu Arg Met Leu Glu Tyr Glu Pro
                405                 410                 415

Ala Ala Arg Ile Ser Pro Leu Gly Ala Leu Gln His Gly Phe Phe Arg
            420                 425                 430

Arg Thr Ala Asp Glu Ala Thr Asn Thr Gly Pro Ala Gly Ser Ser Ala
        435                 440                 445

Ser Thr Ser Pro Ala Pro Leu Asp Thr Cys Pro Ser Ser Ser Thr Ala
    450                 455                 460

Ser Ser Ile Ser Ser Ser Gly Gly Ser Ser Gly Ser Ser Ser Asp Asn
465                 470                 475                 480

Arg Thr Tyr Arg Tyr Ser Asn Arg Tyr Cys Gly Gly Pro Gly Pro Pro
                485                 490                 495

Ile Thr Asp Cys Glu Met Asn Ser Pro Gln Val Pro Pro Ser Gln Pro
            500                 505                 510

Leu Arg Pro Trp Ala Gly Gly Asp Val Pro His Lys Thr His Gln Ala
        515                 520                 525

Pro Ala Ser Ala Ser Ser Leu Pro Gly Thr Gly Ala Gln Leu Pro Pro
    530                 535                 540

Gln Pro Arg Tyr Leu Gly Arg Pro Pro Ser Pro Thr Ser Pro Pro Pro
545                 550                 555                 560

Pro Glu Leu Met Asp Val Ser Leu Val Gly Gly Pro Ala Asp Cys Ser
                565                 570                 575

Pro Pro His Pro Ala Pro Ala Pro Gln His Pro Ala Ala Ser Ala Leu
            580                 585                 590

Arg Thr Arg Met Thr Gly Gly Arg Pro Pro Leu Pro Pro Pro Asp Asp
        595                 600                 605

Pro Ala Thr Leu Gly Pro His Leu Gly Leu Arg Gly Val Pro Gln Ser
    610                 615                 620

Thr Ala Ala Ser Ser
625

<210> SEQ ID NO 18
<211> LENGTH: 528
<212> TYPE: PRT
<213> ORGANISM: Human
<300> PUBLICATION INFORMATION:
<301> AUTHORS: Becker,W., Weber,Y., Wetzel,K., Eirmbter,K., Tejedor,F.J.
      and
<302> TITLE: Sequence characteristics, subcellular localization, and
      substrate
<303> JOURNAL: J. Biol. Chem.
<304> VOLUME: 273
<305> ISSUE: 40
<306> PAGES: 25893-25902
<307> DATE: 1998-10-02
<308> DATABASE ACCESSION NUMBER: NP_003574
<309> DATABASE ENTRY DATE: 2012-05-06
<313> RELEVANT RESIDUES IN SEQ ID NO: (1)..(528)

<400> SEQUENCE: 18

Met Asn Asp His Leu His Val Gly Ser His Ala His Gly Gln Ile Gln
1               5                   10                  15

Val Gln Gln Leu Phe Glu Asp Asn Ser Asn Lys Arg Thr Val Leu Thr
```

```
                    20                  25                  30
Thr Gln Pro Asn Gly Leu Thr Thr Val Gly Lys Thr Gly Leu Pro Val
                 35                  40                  45
Val Pro Glu Arg Gln Leu Asp Ser Ile His Arg Arg Gln Gly Ser Ser
 50                  55                  60
Thr Ser Leu Lys Ser Met Glu Gly Met Gly Lys Val Lys Ala Thr Pro
 65                  70                  75                  80
Met Thr Pro Glu Gln Ala Met Lys Gln Tyr Met Gln Lys Leu Thr Ala
                 85                  90                  95
Phe Glu His His Glu Ile Phe Ser Tyr Pro Glu Ile Tyr Phe Leu Gly
                100                 105                 110
Leu Asn Ala Lys Lys Arg Gln Gly Met Thr Gly Gly Pro Asn Asn Gly
                115                 120                 125
Gly Tyr Asp Asp Asp Gln Gly Ser Tyr Val Gln Val Pro His Asp His
                130                 135                 140
Val Ala Tyr Arg Tyr Glu Val Leu Lys Val Ile Gly Lys Gly Ser Phe
145                 150                 155                 160
Gly Gln Val Val Lys Ala Tyr Asp His Lys Val His Gln His Val Ala
                165                 170                 175
Leu Lys Met Val Arg Asn Glu Lys Arg Phe His Arg Gln Ala Ala Glu
                180                 185                 190
Glu Ile Arg Ile Leu Glu His Leu Arg Lys Gln Asp Lys Asp Asn Thr
                195                 200                 205
Met Asn Val Ile His Met Leu Glu Asn Phe Thr Phe Arg Asn His Ile
                210                 215                 220
Cys Met Thr Phe Glu Leu Leu Ser Met Asn Leu Tyr Glu Leu Ile Lys
225                 230                 235                 240
Lys Asn Lys Phe Gln Gly Phe Ser Leu Pro Leu Val Arg Lys Phe Ala
                245                 250                 255
His Ser Ile Leu Gln Cys Leu Asp Ala Leu His Lys Asn Arg Ile Ile
                260                 265                 270
His Cys Asp Leu Lys Pro Glu Asn Ile Leu Leu Lys Gln Gln Gly Arg
                275                 280                 285
Ser Gly Ile Lys Val Ile Asp Phe Gly Ser Ser Cys Tyr Glu His Gln
                290                 295                 300
Arg Val Tyr Thr Tyr Ile Gln Ser Arg Phe Tyr Arg Ala Pro Glu Val
305                 310                 315                 320
Ile Leu Gly Ala Arg Tyr Gly Met Pro Ile Asp Met Trp Ser Leu Gly
                325                 330                 335
Cys Ile Leu Ala Glu Leu Leu Thr Gly Tyr Pro Leu Leu Pro Gly Glu
                340                 345                 350
Asp Glu Gly Asp Gln Leu Ala Cys Met Ile Glu Leu Leu Gly Met Pro
                355                 360                 365
Ser Gln Lys Leu Leu Asp Ala Ser Lys Arg Ala Lys Asn Phe Val Ser
                370                 375                 380
Ser Lys Gly Tyr Pro Arg Tyr Cys Thr Val Thr Thr Leu Ser Asp Gly
385                 390                 395                 400
Ser Val Val Leu Asn Gly Gly Arg Ser Arg Gly Lys Leu Arg Gly
                405                 410                 415
Pro Pro Glu Ser Arg Glu Trp Gly Asn Ala Leu Lys Gly Cys Asp Asp
                420                 425                 430
Pro Leu Phe Leu Asp Phe Leu Lys Gln Cys Leu Glu Trp Asp Pro Ala
                435                 440                 445
```

```
Val Arg Met Thr Pro Gly Gln Ala Leu Arg His Pro Trp Leu Arg Arg
    450                 455                 460

Arg Leu Pro Lys Pro Pro Thr Gly Glu Lys Thr Ser Val Lys Arg Ile
465                 470                 475                 480

Thr Glu Ser Thr Gly Ala Ile Thr Ser Ile Ser Lys Leu Pro Pro Pro
            485                 490                 495

Ser Ser Ser Ala Ser Lys Leu Arg Thr Asn Leu Ala Gln Met Thr Asp
            500                 505                 510

Ala Asn Gly Asn Ile Gln Gln Arg Thr Val Leu Pro Lys Leu Val Ser
            515                 520                 525
```

<210> SEQ ID NO 19
<211> LENGTH: 588
<212> TYPE: PRT
<213> ORGANISM: HUMAN
<300> PUBLICATION INFORMATION:
<301> AUTHORS: Becker,W., Weber,Y., Wetzel,K., Eirmbter,K., Tejedor,F.J. and
<302> TITLE: Sequence characteristics, subcellular localization, and substrate
<303> JOURNAL: J. Biol. Chem.
<304> VOLUME: 273
<305> ISSUE: 40
<306> PAGES: 25893-25902
<307> DATE: 1998-10-02
<308> DATABASE ACCESSION NUMBER: NP_003573
<309> DATABASE ENTRY DATE: 2012-03-24
<313> RELEVANT RESIDUES IN SEQ ID NO: (1)..(588)

<400> SEQUENCE: 19

```
Met Gly Gly Thr Ala Arg Gly Pro Gly Arg Lys Asp Ala Gly Pro Pro
1               5                   10                  15

Gly Ala Gly Leu Pro Pro Gln Gln Arg Arg Leu Gly Asp Gly Val Tyr
                20                  25                  30

Asp Thr Phe Met Met Ile Asp Glu Thr Lys Cys Pro Pro Cys Ser Asn
                35                  40                  45

Val Leu Cys Asn Pro Ser Glu Pro Pro Pro Arg Arg Leu Asn Met
    50                  55                  60

Thr Thr Glu Gln Phe Thr Gly Asp His Thr Gln His Phe Leu Asp Gly
65                  70                  75                  80

Gly Glu Met Lys Val Glu Gln Leu Phe Gln Glu Phe Gly Asn Arg Lys
                85                  90                  95

Ser Asn Thr Ile Gln Ser Asp Gly Ile Ser Asp Ser Glu Lys Cys Ser
                100                 105                 110

Pro Thr Val Ser Gln Gly Lys Ser Ser Asp Cys Leu Asn Thr Val Lys
            115                 120                 125

Ser Asn Ser Ser Lys Ala Pro Lys Val Val Pro Leu Thr Pro Glu
    130                 135                 140

Gln Ala Leu Lys Gln Tyr Lys His His Leu Thr Ala Tyr Glu Lys Leu
145                 150                 155                 160

Glu Ile Ile Asn Tyr Pro Glu Ile Tyr Phe Val Gly Pro Asn Ala Lys
                165                 170                 175

Lys Arg His Gly Val Ile Gly Gly Pro Asn Asn Gly Gly Tyr Asp Asp
            180                 185                 190

Ala Asp Gly Ala Tyr Ile His Val Pro Arg Asp His Leu Ala Tyr Arg
            195                 200                 205

Tyr Glu Val Leu Lys Ile Ile Gly Lys Gly Ser Phe Gly Gln Val Ala
            210                 215                 220
```

| | | | | | | | | | | | | | | |
|---|---|---|---|---|---|---|---|---|---|---|---|---|---|---|
| Arg | Val | Tyr | Asp | His | Lys | Leu | Arg | Gln | Tyr | Val | Ala | Leu | Lys | Met | Val |
| 225 | | | | | 230 | | | | | 235 | | | | | 240 |

| | | | | | | | | | | | | |
|---|---|---|---|---|---|---|---|---|---|---|---|---|
| Arg | Asn | Glu | Lys | Arg | Phe | His | Arg | Gln | Ala | Ala | Glu | Glu | Ile | Arg | Ile |
| | | | 245 | | | | | 250 | | | | | 255 | | |

| Leu | Glu | His | Leu | Lys | Lys | Gln | Asp | Lys | Thr | Gly | Ser | Met | Asn | Val | Ile |
|---|---|---|---|---|---|---|---|---|---|---|---|---|---|---|---|
| | | | 260 | | | | | 265 | | | | | 270 | | |

| His | Met | Leu | Glu | Ser | Phe | Thr | Phe | Arg | Asn | His | Val | Cys | Met | Ala | Phe |
|---|---|---|---|---|---|---|---|---|---|---|---|---|---|---|---|
| | | | 275 | | | | | 280 | | | | | 285 | | |

| Glu | Leu | Leu | Ser | Ile | Asp | Leu | Tyr | Glu | Leu | Ile | Lys | Lys | Asn | Lys | Phe |
|---|---|---|---|---|---|---|---|---|---|---|---|---|---|---|---|
| | 290 | | | | | 295 | | | | | 300 | | | | |

| Gln | Gly | Phe | Ser | Val | Gln | Leu | Val | Arg | Lys | Phe | Ala | Gln | Ser | Ile | Leu |
|---|---|---|---|---|---|---|---|---|---|---|---|---|---|---|---|
| 305 | | | | | 310 | | | | | 315 | | | | | 320 |

| Gln | Ser | Leu | Asp | Ala | Leu | His | Lys | Asn | Lys | Ile | Ile | His | Cys | Asp | Leu |
|---|---|---|---|---|---|---|---|---|---|---|---|---|---|---|---|
| | | | 325 | | | | | 330 | | | | | 335 | | |

| Lys | Pro | Glu | Asn | Ile | Leu | Leu | Lys | His | His | Gly | Arg | Ser | Ser | Thr | Lys |
|---|---|---|---|---|---|---|---|---|---|---|---|---|---|---|---|
| | | | 340 | | | | | 345 | | | | | 350 | | |

| Val | Ile | Asp | Phe | Gly | Ser | Ser | Cys | Phe | Glu | Tyr | Gln | Lys | Leu | Tyr | Thr |
|---|---|---|---|---|---|---|---|---|---|---|---|---|---|---|---|
| | | 355 | | | | | 360 | | | | | 365 | | | |

| Tyr | Ile | Gln | Ser | Arg | Phe | Tyr | Arg | Ala | Pro | Glu | Ile | Ile | Leu | Gly | Ser |
|---|---|---|---|---|---|---|---|---|---|---|---|---|---|---|---|
| 370 | | | | | 375 | | | | | 380 | | | | | |

| Arg | Tyr | Ser | Thr | Pro | Ile | Asp | Ile | Trp | Ser | Phe | Gly | Cys | Ile | Leu | Ala |
|---|---|---|---|---|---|---|---|---|---|---|---|---|---|---|---|
| 385 | | | | | 390 | | | | | 395 | | | | | 400 |

| Glu | Leu | Leu | Thr | Gly | Gln | Pro | Leu | Phe | Pro | Gly | Glu | Asp | Glu | Gly | Asp |
|---|---|---|---|---|---|---|---|---|---|---|---|---|---|---|---|
| | | | 405 | | | | | 410 | | | | | 415 | | |

| Gln | Leu | Ala | Cys | Met | Met | Glu | Leu | Leu | Gly | Met | Pro | Pro | Lys | Leu |
|---|---|---|---|---|---|---|---|---|---|---|---|---|---|---|
| | | | 420 | | | | | 425 | | | | | 430 | | |

| Leu | Glu | Gln | Ser | Lys | Arg | Ala | Lys | Tyr | Phe | Ile | Asn | Ser | Lys | Gly | Ile |
|---|---|---|---|---|---|---|---|---|---|---|---|---|---|---|---|
| | | | 435 | | | | | 440 | | | | | 445 | | |

| Pro | Arg | Tyr | Cys | Ser | Val | Thr | Thr | Gln | Ala | Asp | Gly | Arg | Val | Val | Leu |
|---|---|---|---|---|---|---|---|---|---|---|---|---|---|---|---|
| | 450 | | | | | 455 | | | | | 460 | | | | |

| Val | Gly | Gly | Arg | Ser | Arg | Arg | Gly | Lys | Lys | Arg | Gly | Pro | Pro | Gly | Ser |
|---|---|---|---|---|---|---|---|---|---|---|---|---|---|---|---|
| 465 | | | | | 470 | | | | | 475 | | | | | 480 |

| Lys | Asp | Trp | Gly | Thr | Ala | Leu | Lys | Gly | Cys | Asp | Asp | Tyr | Leu | Phe | Ile |
|---|---|---|---|---|---|---|---|---|---|---|---|---|---|---|---|
| | | | 485 | | | | | 490 | | | | | 495 | | |

| Glu | Phe | Leu | Lys | Arg | Cys | Leu | His | Trp | Asp | Pro | Ser | Ala | Arg | Leu | Thr |
|---|---|---|---|---|---|---|---|---|---|---|---|---|---|---|---|
| | | | 500 | | | | | 505 | | | | | 510 | | |

| Pro | Ala | Gln | Ala | Leu | Arg | His | Pro | Trp | Ile | Ser | Lys | Ser | Val | Pro | Arg |
|---|---|---|---|---|---|---|---|---|---|---|---|---|---|---|---|
| | | 515 | | | | | 520 | | | | | 525 | | | |

| Pro | Leu | Thr | Thr | Ile | Asp | Lys | Val | Ser | Gly | Lys | Arg | Val | Val | Asn | Pro |
|---|---|---|---|---|---|---|---|---|---|---|---|---|---|---|---|
| | 530 | | | | | 535 | | | | | 540 | | | | |

| Ala | Ser | Ala | Phe | Gln | Gly | Leu | Gly | Ser | Lys | Leu | Pro | Pro | Val | Val | Gly |
|---|---|---|---|---|---|---|---|---|---|---|---|---|---|---|---|
| 545 | | | | | 550 | | | | | 555 | | | | | 560 |

| Ile | Ala | Asn | Lys | Leu | Lys | Ala | Asn | Leu | Met | Ser | Glu | Thr | Asn | Gly | Ser |
|---|---|---|---|---|---|---|---|---|---|---|---|---|---|---|---|
| | | | 565 | | | | | 570 | | | | | 575 | | |

| Ile | Pro | Leu | Cys | Ser | Val | Leu | Pro | Lys | Leu | Ile | Ser |
|---|---|---|---|---|---|---|---|---|---|---|---|
| | | | 580 | | | | | 585 | | | |

<210> SEQ ID NO 20
<211> LENGTH: 520
<212> TYPE: PRT
<213> ORGANISM: HUMAN
<300> PUBLICATION INFORMATION:
<301> AUTHORS: Becker,W., Weber,Y., Wetzel,K., Eirmbter,K., Tejedor,F.J.
    and
<302> TITLE: Sequence characteristics, subcellular localization, and
    substrate

```
<303> JOURNAL: J. Biol. Chem.
<304> VOLUME: 273
<305> ISSUE: 40
<306> PAGES: 25893-25902
<307> DATE: 1998-10-02
<308> DATABASE ACCESSION NUMBER: NP_003836
<309> DATABASE ENTRY DATE: 2012-03-25
<313> RELEVANT RESIDUES IN SEQ ID NO: (1)..(520)

<400> SEQUENCE: 20
```

| | | | | | | | | | | | | | | | |
|---|---|---|---|---|---|---|---|---|---|---|---|---|---|---|---|
| Met | Pro | Ala | Ser | Glu | Leu | Lys | Ala | Ser | Glu | Ile | Pro | Phe | His | Pro | Ser |
| 1 | | | | 5 | | | | | 10 | | | | | 15 | |
| Ile | Lys | Thr | Gln | Asp | Pro | Lys | Ala | Glu | Glu | Lys | Ser | Pro | Lys | Lys | Gln |
| | | | 20 | | | | | 25 | | | | | 30 | | |
| Lys | Val | Thr | Leu | Thr | Ala | Ala | Glu | Ala | Leu | Lys | Leu | Phe | Lys | Asn | Gln |
| | | | 35 | | | | 40 | | | | | 45 | | | |
| Leu | Ser | Pro | Tyr | Glu | Gln | Ser | Glu | Ile | Leu | Gly | Tyr | Ala | Glu | Leu | Trp |
| 50 | | | | | 55 | | | | | 60 | | | | | |
| Phe | Leu | Gly | Leu | Glu | Ala | Lys | Lys | Leu | Asp | Thr | Ala | Pro | Glu | Lys | Phe |
| 65 | | | | | 70 | | | | | 75 | | | | | 80 |
| Ser | Lys | Thr | Ser | Phe | Asp | Asp | Glu | His | Gly | Phe | Tyr | Leu | Lys | Val | Leu |
| | | | | 85 | | | | | 90 | | | | | 95 | |
| His | Asp | His | Ile | Ala | Tyr | Arg | Tyr | Glu | Val | Leu | Glu | Thr | Ile | Gly | Lys |
| | | | 100 | | | | | 105 | | | | | 110 | | |
| Gly | Ser | Phe | Gly | Gln | Val | Ala | Lys | Cys | Leu | Asp | His | Lys | Asn | Asn | Glu |
| | | 115 | | | | | 120 | | | | | 125 | | | |
| Leu | Val | Ala | Leu | Lys | Ile | Ile | Arg | Asn | Lys | Lys | Arg | Phe | His | Gln | Gln |
| 130 | | | | | 135 | | | | | 140 | | | | | |
| Ala | Leu | Met | Glu | Leu | Lys | Ile | Leu | Glu | Ala | Leu | Arg | Lys | Lys | Asp | Lys |
| 145 | | | | | 150 | | | | | 155 | | | | | 160 |
| Asp | Asn | Thr | Tyr | Asn | Val | Val | His | Met | Lys | Asp | Phe | Phe | Tyr | Phe | Arg |
| | | | | 165 | | | | | 170 | | | | | 175 | |
| Asn | His | Phe | Cys | Ile | Thr | Phe | Glu | Leu | Leu | Gly | Ile | Asn | Leu | Tyr | Glu |
| | | | 180 | | | | | 185 | | | | | 190 | | |
| Leu | Met | Lys | Asn | Asn | Asn | Phe | Gln | Gly | Phe | Ser | Leu | Ser | Ile | Val | Arg |
| | | 195 | | | | | 200 | | | | | 205 | | | |
| Arg | Phe | Thr | Leu | Ser | Val | Leu | Lys | Cys | Leu | Gln | Met | Leu | Ser | Val | Glu |
| 210 | | | | | 215 | | | | | 220 | | | | | |
| Lys | Ile | Ile | His | Cys | Asp | Leu | Lys | Pro | Glu | Asn | Ile | Val | Leu | Tyr | Gln |
| 225 | | | | | 230 | | | | | 235 | | | | | 240 |
| Lys | Gly | Gln | Ala | Ser | Val | Lys | Val | Ile | Asp | Phe | Gly | Ser | Ser | Cys | Tyr |
| | | | | 245 | | | | | 250 | | | | | 255 | |
| Glu | His | Gln | Lys | Val | Tyr | Thr | Tyr | Ile | Gln | Ser | Arg | Phe | Tyr | Arg | Ser |
| | | | | 260 | | | | | 265 | | | | | 270 | |
| Pro | Glu | Val | Ile | Leu | Gly | His | Pro | Tyr | Asp | Val | Ala | Ile | Asp | Met | Trp |
| | | | 275 | | | | | 280 | | | | | 285 | | |
| Ser | Leu | Gly | Cys | Ile | Thr | Ala | Glu | Leu | Tyr | Thr | Gly | Tyr | Pro | Leu | Phe |
| | | 290 | | | | | 295 | | | | | 300 | | | |
| Pro | Gly | Glu | Asn | Glu | Val | Glu | Gln | Leu | Ala | Cys | Ile | Met | Glu | Val | Leu |
| 305 | | | | | 310 | | | | | 315 | | | | | 320 |
| Gly | Leu | Pro | Pro | Ala | Gly | Phe | Ile | Gln | Thr | Ala | Ser | Arg | Arg | Gln | Thr |
| | | | | 325 | | | | | 330 | | | | | 335 | |
| Phe | Phe | Asp | Ser | Lys | Gly | Phe | Pro | Lys | Asn | Ile | Thr | Asn | Asn | Arg | Gly |
| | | | 340 | | | | | 345 | | | | | 350 | | |
| Lys | Lys | Arg | Tyr | Pro | Asp | Ser | Lys | Asp | Leu | Thr | Met | Val | Leu | Lys | Thr |
| | | 355 | | | | | 360 | | | | | 365 | | | |

```
Tyr Asp Thr Ser Phe Leu Asp Phe Leu Arg Arg Cys Leu Val Trp Glu
        370                 375                 380

Pro Ser Leu Arg Met Thr Pro Asp Gln Ala Leu Lys His Ala Trp Ile
385                 390                 395                 400

His Gln Ser Arg Asn Leu Lys Pro Gln Pro Arg Pro Gln Thr Leu Arg
                405                 410                 415

Lys Ser Asn Ser Phe Phe Pro Ser Glu Thr Arg Lys Asp Lys Val Gln
                420                 425                 430

Gly Cys His His Ser Ser Arg Lys Ala Asp Glu Ile Thr Lys Glu Thr
                435                 440                 445

Thr Glu Lys Thr Lys Asp Ser Pro Thr Lys His Val Gln His Ser Gly
        450                 455                 460

Asp Gln Gln Asp Cys Leu Gln His Gly Ala Asp Thr Val Gln Leu Pro
465                 470                 475                 480

Gln Leu Val Asp Ala Pro Lys Lys Ser Glu Ala Ala Val Gly Ala Glu
                485                 490                 495

Val Ser Met Thr Ser Pro Gly Gln Ser Lys Asn Phe Ser Leu Lys Asn
                500                 505                 510

Thr Asn Val Leu Pro Pro Ile Val
                515                 520

<210> SEQ ID NO 21
<211> LENGTH: 993
<212> TYPE: PRT
<213> ORGANISM: HUMAN
<300> PUBLICATION INFORMATION:
<301> AUTHORS: Kiyoi,H., Ohno,R., Ueda,R., Saito,H. and Naoe,T.
<302> TITLE: Mechanism of constitutive activation of FLT3 with internal
       tandem
<303> JOURNAL: Oncogene
<304> VOLUME: 21
<305> ISSUE: 16
<306> PAGES: 2555-2563
<307> DATE: 2002-04-11
<308> DATABASE ACCESSION NUMBER: NP_004110
<309> DATABASE ENTRY DATE: 2012-05-06
<313> RELEVANT RESIDUES IN SEQ ID NO: (1)..(993)

<400> SEQUENCE: 21

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
        130                 135                 140

Ile Gln Ser Glu Ala Thr Asn Tyr Thr Ile Leu Phe Thr Val Ser Ile
```

```
            145                 150                 155                 160
Arg Asn Thr Leu Leu Tyr Thr Leu Arg Arg Pro Tyr Phe Arg Lys Met
                        165                 170                 175

Glu Asn Gln Asp Ala Leu Val Cys Ile Ser Glu Ser Val Pro Glu Pro
                    180                 185                 190

Ile Val Glu Trp Val Leu Cys Asp Ser Gln Gly Glu Ser Cys Lys Glu
                195                 200                 205

Glu Ser Pro Ala Val Val Lys Lys Glu Lys Val Leu His Glu Leu
            210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                    245                 250                 255

Leu Pro Gln Leu Phe Leu Lys Val Gly Glu Pro Leu Trp Ile Arg Cys
                260                 265                 270

Lys Ala Val His Val Asn His Gly Phe Gly Leu Thr Trp Glu Leu Glu
                275                 280                 285

Asn Lys Ala Leu Glu Glu Gly Asn Tyr Phe Glu Met Ser Thr Tyr Ser
                290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Lys His Pro
                    325                 330                 335

Ser Gln Ser Ala Leu Val Thr Ile Val Glu Lys Gly Phe Ile Asn Ala
                340                 345                 350

Thr Asn Ser Ser Glu Asp Tyr Glu Ile Asp Gln Tyr Glu Glu Phe Cys
                355                 360                 365

Phe Ser Val Arg Phe Lys Ala Tyr Pro Gln Ile Arg Cys Thr Trp Thr
                370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                    405                 410                 415

Ile Phe His Ala Glu Asn Asp Asp Ala Gln Phe Thr Lys Met Phe Thr
                420                 425                 430

Leu Asn Ile Arg Arg Lys Pro Gln Val Leu Ala Glu Ala Ser Ala Ser
                435                 440                 445

Gln Ala Ser Cys Phe Ser Asp Gly Tyr Pro Leu Pro Ser Trp Thr Trp
            450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                    485                 490                 495

Ser Ser Ser Thr Leu Asn Met Ser Glu Ala Ile Lys Gly Phe Leu Val
                500                 505                 510

Lys Cys Cys Ala Tyr Asn Ser Leu Gly Thr Ser Cys Glu Thr Ile Leu
            515                 520                 525

Leu Asn Ser Pro Gly Pro Phe Pro Phe Ile Gln Asp Asn Ile Ser Phe
                530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                    565                 570                 575
```

```
Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990
```

Ser

<210> SEQ ID NO 22
<211> LENGTH: 433
<212> TYPE: PRT
<213> ORGANISM: HUMAN
<300> PUBLICATION INFORMATION:
<301> AUTHORS: Hughes,K., Nikolakaki,E., Plyte,S.E., Totty,N.F. and
      Woodgett,J.R.
<302> TITLE: Modulation of the glycogen synthase kinase-3 family by
      tyrosine
<303> JOURNAL: EMBO J.
<304> VOLUME: 12
<305> ISSUE: 2
<306> PAGES: 803-808
<307> DATE: 1993-02-01
<308> DATABASE ACCESSION NUMBER: NP_002084
<309> DATABASE ENTRY DATE: 2012-05-13
<313> RELEVANT RESIDUES IN SEQ ID NO: (1)..(433)

<400> SEQUENCE: 22

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300
```

-continued

```
Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr
```

<210> SEQ ID NO 23
<211> LENGTH: 1154
<212> TYPE: PRT
<213> ORGANISM: HUMAN
<300> PUBLICATION INFORMATION:
<301> AUTHORS: Simoncic,P.D., Lee-Loy,A., Barber,D.L., Tremblay,M.L. and
<302> TITLE: The T cell protein tyrosine phosphatase is a negative
      regulator of
<303> JOURNAL: Curr. Biol.
<304> VOLUME: 12
<305> ISSUE: 6
<306> PAGES: 446-453
<307> DATE: 2002-03-19
<308> DATABASE ACCESSION NUMBER: NP_002218
<309> DATABASE ENTRY DATE: 2012-05-13
<313> RELEVANT RESIDUES IN SEQ ID NO: (1)..(1154)

<400> SEQUENCE: 23

```
Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175
```

-continued

```
Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
            340                 345                 350

Asp Glu Glu Lys Asn Lys Ile Arg Glu Glu Trp Asn Asn Phe Ser Tyr
        355                 360                 365

Phe Pro Glu Ile Thr His Ile Val Ile Lys Glu Ser Val Val Ser Ile
    370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Glu Gly Met Tyr Val
    450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
        515                 520                 525

Gln Ile Leu Arg Thr Asp Asn Ile Ser Phe Met Leu Lys Arg Cys Cys
    530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575

Arg Ile Leu Lys Lys Asp Leu Val Gln Gly Glu His Leu Gly Arg Gly
            580                 585                 590
```

```
Thr Arg Thr His Ile Tyr Ser Gly Thr Leu Met Asp Tyr Lys Asp Asp
            595                 600                 605

Glu Gly Thr Ser Glu Lys Lys Ile Lys Val Ile Leu Lys Val Leu
610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
                660                 665                 670

Gly Pro Leu Asp Leu Phe Met His Arg Lys Ser Asp Val Leu Thr Thr
            675                 680                 685

Pro Trp Lys Phe Lys Val Ala Lys Gln Leu Ala Ser Ala Leu Ser Tyr
690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
            740                 745                 750

Ile Glu Arg Ile Pro Trp Ile Ala Pro Glu Cys Val Glu Asp Ser Lys
            755                 760                 765

Asn Leu Ser Val Ala Ala Asp Lys Trp Ser Phe Gly Thr Thr Leu Trp
            770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
            835                 840                 845

Glu Glu Gln Asn Pro Asp Ile Val Ser Glu Lys Lys Pro Ala Thr Glu
850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
            915                 920                 925

Leu Arg Asn Leu Tyr His Glu Asn Ile Val Lys Tyr Lys Gly Ile Cys
            930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
                980                 985                 990

Tyr Leu Gly Ser Arg Gln Tyr Val His Arg Asp Leu Ala Ala Arg Asn
            995                 1000                1005

Val Leu Val Glu Ser Glu His Gln Val Lys Ile Gly Asp Phe Gly
```

-continued

```
                     1010                1015                1020
Leu Thr Lys Ala Ile Glu Thr Asp Lys Glu Tyr Tyr Thr Val Lys
            1025                1030                1035

Asp Asp Arg Asp Ser Pro Val Phe Trp Tyr Ala Pro Glu Cys Leu
        1040                1045                1050

Met Gln Ser Lys Phe Tyr Ile Ala Ser Asp Val Trp Ser Phe Gly
        1055                1060                1065

Val Thr Leu His Glu Leu Leu Thr Tyr Cys Asp Ser Asp Ser Ser
        1070                1075                1080

Pro Met Ala Leu Phe Leu Lys Met Ile Gly Pro Thr His Gly Gln
        1085                1090                1095

Met Thr Val Thr Arg Leu Val Asn Thr Leu Lys Glu Gly Lys Arg
        1100                1105                1110

Leu Pro Cys Pro Pro Asn Cys Pro Asp Glu Val Tyr Gln Leu Met
        1115                1120                1125

Arg Lys Cys Trp Glu Phe Gln Pro Ser Asn Arg Thr Ser Phe Gln
        1130                1135                1140

Asn Leu Ile Glu Gly Phe Glu Ala Leu Leu Lys
        1145                1150

<210> SEQ ID NO 24
<211> LENGTH: 1132
<212> TYPE: PRT
<213> ORGANISM: HUMAN
<300> PUBLICATION INFORMATION:
<301> AUTHORS: Gupta,M., Han,J.J., Stenson,M., Maurer,M., Wellik,L.,
      Hu,G.,
<302> TITLE: Elevated serum IL-10 levels in diffuse large B-cell
      lymphoma: a
<303> JOURNAL: Blood
<304> VOLUME: 119
<305> ISSUE: 12
<306> PAGES: 2844-2853
<307> DATE: 2012-02-08
<308> DATABASE ACCESSION NUMBER: NP_004963
<309> DATABASE ENTRY DATE: 2012-05-13
<313> RELEVANT RESIDUES IN SEQ ID NO: (1)..(1132)

<400> SEQUENCE: 24

Met Gly Met Ala Cys Leu Thr Met Thr Glu Met Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160
```

-continued

Phe Val His Gly Trp Ile Lys Val Pro Val Thr His Glu Thr Gln Glu
            165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
            195                 200                 205

Phe Leu Pro Lys Cys Ile Arg Ala Lys Ile Gln Asp Tyr His Ile Leu
            210                 215                 220

Thr Arg Lys Arg Ile Arg Tyr Arg Phe Arg Phe Ile Gln Gln Phe
225                 230                 235                 240

Ser Gln Cys Lys Ala Thr Ala Arg Asn Leu Lys Leu Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
            325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
            405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
            450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
            485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
            530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
            565                 570                 575

-continued

Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
        595                 600                 605
Leu Val Leu Asn Tyr Gly Val Cys Val Cys Gly Asp Glu Asn Ile Leu
    610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
                645                 650                 655
Leu Ala Trp Ala Met His Phe Leu Glu Glu Asn Thr Leu Ile His Gly
            660                 665                 670
Asn Val Cys Ala Lys Asn Ile Leu Leu Ile Arg Glu Glu Asp Arg Lys
        675                 680                 685
Thr Gly Asn Pro Pro Phe Ile Lys Leu Ser Asp Pro Gly Ile Ser Ile
    690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                725                 730                 735
Trp Ser Phe Gly Thr Thr Leu Trp Glu Ile Cys Ser Gly Gly Asp Lys
            740                 745                 750
Pro Leu Ser Ala Leu Asp Ser Gln Arg Lys Leu Gln Phe Tyr Glu Asp
        755                 760                 765
Arg His Gln Leu Pro Ala Pro Lys Trp Ala Glu Leu Ala Asn Leu Ile
    770                 775                 780
Asn Asn Cys Met Asp Tyr Glu Pro Asp Phe Arg Pro Ser Phe Arg Ala
785                 790                 795                 800
Ile Ile Arg Asp Leu Asn Ser Leu Phe Thr Pro Asp Tyr Glu Leu Leu
                805                 810                 815
Thr Glu Asn Asp Met Leu Pro Asn Met Arg Ile Gly Ala Leu Gly Phe
            820                 825                 830
Ser Gly Ala Phe Glu Asp Arg Asp Pro Thr Gln Phe Glu Glu Arg His
        835                 840                 845
Leu Lys Phe Leu Gln Gln Leu Gly Lys Gly Asn Phe Gly Ser Val Glu
    850                 855                 860
Met Cys Arg Tyr Asp Pro Leu Gln Asp Asn Thr Gly Glu Val Val Ala
865                 870                 875                 880
Val Lys Lys Leu Gln His Ser Thr Glu Glu His Leu Arg Asp Phe Glu
                885                 890                 895
Arg Glu Ile Glu Ile Leu Lys Ser Leu Gln His Asp Asn Ile Val Lys
            900                 905                 910
Tyr Lys Gly Val Cys Tyr Ser Ala Gly Arg Arg Asn Leu Lys Leu Ile
        915                 920                 925
Met Glu Tyr Leu Pro Tyr Gly Ser Leu Arg Asp Tyr Leu Gln Lys His
    930                 935                 940
Lys Glu Arg Ile Asp His Ile Lys Leu Leu Gln Tyr Thr Ser Gln Ile
945                 950                 955                 960
Cys Lys Gly Met Glu Tyr Leu Gly Thr Lys Arg Tyr Ile His Arg Asp
                965                 970                 975
Leu Ala Thr Arg Asn Ile Leu Val Glu Asn Glu Asn Arg Val Lys Ile
            980                 985                 990
Gly Asp Phe Gly Leu Thr Lys Val  Leu Pro Gln Asp Lys  Glu Tyr Tyr

```
                 995                 1000                1005
Lys Val Lys Glu Pro Gly Glu Ser Pro Ile Phe Trp Tyr Ala Pro
        1010                1015                1020

Glu Ser Leu Thr Glu Ser Lys Phe Ser Val Ala Ser Asp Val Trp
        1025                1030                1035

Ser Phe Gly Val Val Leu Tyr Glu Leu Phe Thr Tyr Ile Glu Lys
        1040                1045                1050

Ser Lys Ser Pro Pro Ala Glu Phe Met Arg Met Ile Gly Asn Asp
        1055                1060                1065

Lys Gln Gly Gln Met Ile Val Phe His Leu Ile Glu Leu Leu Lys
        1070                1075                1080

Asn Asn Gly Arg Leu Pro Arg Pro Asp Gly Cys Pro Asp Glu Ile
        1085                1090                1095

Tyr Met Ile Met Thr Glu Cys Trp Asn Asn Asn Val Asn Gln Arg
        1100                1105                1110

Pro Ser Phe Arg Asp Leu Ala Leu Arg Val Asp Gln Ile Arg Asp
        1115                1120                1125

Asn Met Ala Gly
        1130

<210> SEQ ID NO 25
<211> LENGTH: 1124
<212> TYPE: PRT
<213> ORGANISM: HUMAN
<300> PUBLICATION INFORMATION:
<301> AUTHORS: Bhavsar,S.K., Gu,S., Bobbala,D. and Lang,F.
<302> TITLE: Janus kinase 3 is expressed in erythrocytes, phosphorylated
      upon
<303> JOURNAL: Cell. Physiol. Biochem.
<304> VOLUME: 27
<305> ISSUE: 5
<306> PAGES: 547-556
<307> DATE: 2011-06-15
<308> DATABASE ACCESSION NUMBER: NP_000206
<309> DATABASE ENTRY DATE: 2012-05-20
<313> RELEVANT RESIDUES IN SEQ ID NO: (1)..(1124)

<400> SEQUENCE: 25

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160
```

```
Glu Cys Leu Ser Leu Ala Val Leu Asp Leu Ala Arg Met Ala Arg Glu
            165                 170                 175
Gln Ala Gln Arg Pro Gly Glu Leu Leu Lys Thr Val Ser Tyr Lys Ala
        180                 185                 190
Cys Leu Pro Pro Ser Leu Arg Asp Leu Ile Gln Gly Leu Ser Phe Val
    195                 200                 205
Thr Arg Arg Arg Ile Arg Arg Thr Val Arg Arg Ala Leu Arg Arg Val
210                 215                 220
Ala Ala Cys Gln Ala Asp Arg His Ser Leu Met Ala Lys Tyr Ile Met
225                 230                 235                 240
Asp Leu Glu Arg Leu Asp Pro Ala Gly Ala Glu Thr Phe His Val
            245                 250                 255
Gly Leu Pro Gly Ala Leu Gly Gly His Asp Gly Leu Gly Leu Leu Arg
        260                 265                 270
Val Ala Gly Asp Gly Gly Ile Ala Trp Thr Gln Gly Glu Gln Glu Val
    275                 280                 285
Leu Gln Pro Phe Cys Asp Phe Pro Glu Ile Val Asp Ile Ser Ile Lys
    290                 295                 300
Gln Ala Pro Arg Val Gly Pro Ala Gly Glu His Arg Leu Val Thr Val
305                 310                 315                 320
Thr Arg Thr Asp Asn Gln Ile Leu Glu Ala Glu Phe Pro Gly Leu Pro
            325                 330                 335
Glu Ala Leu Ser Phe Val Ala Leu Val Asp Gly Tyr Phe Arg Leu Thr
        340                 345                 350
Thr Asp Ser Gln His Phe Phe Cys Lys Glu Val Ala Pro Pro Arg Leu
    355                 360                 365
Leu Glu Glu Val Ala Glu Gln Cys His Gly Pro Ile Thr Leu Asp Phe
    370                 375                 380
Ala Ile Asn Lys Leu Lys Thr Gly Gly Ser Arg Pro Gly Ser Tyr Val
385                 390                 395                 400
Leu Arg Arg Ser Pro Gln Asp Phe Asp Ser Phe Leu Leu Thr Val Cys
            405                 410                 415
Val Gln Asn Pro Leu Gly Pro Asp Tyr Lys Gly Cys Leu Ile Arg Arg
        420                 425                 430
Ser Pro Thr Gly Thr Phe Leu Leu Val Gly Leu Ser Arg Pro His Ser
    435                 440                 445
Ser Leu Arg Glu Leu Leu Ala Thr Cys Trp Asp Gly Gly Leu His Val
    450                 455                 460
Asp Gly Val Ala Val Thr Leu Thr Ser Cys Cys Ile Pro Arg Pro Lys
465                 470                 475                 480
Glu Lys Ser Asn Leu Ile Val Val Gln Arg Gly His Ser Pro Pro Thr
            485                 490                 495
Ser Ser Leu Val Gln Pro Gln Ser Gln Tyr Gln Leu Ser Gln Met Thr
        500                 505                 510
Phe His Lys Ile Pro Ala Asp Ser Leu Glu Trp His Glu Asn Leu Gly
    515                 520                 525
His Gly Ser Phe Thr Lys Ile Tyr Arg Gly Cys Arg His Glu Val Val
    530                 535                 540
Asp Gly Glu Ala Arg Lys Thr Glu Val Leu Leu Lys Val Met Asp Ala
545                 550                 555                 560
Lys His Lys Asn Cys Met Glu Ser Phe Leu Glu Ala Ala Ser Leu Met
            565                 570                 575
Ser Gln Val Ser Tyr Arg His Leu Val Leu Leu His Gly Val Cys Met
```

```
                580               585                590
Ala Gly Asp Ser Thr Met Val Gln Glu Phe Val His Leu Gly Ala Ile
            595               600              605

Asp Met Tyr Leu Arg Lys Arg Gly His Leu Val Pro Ala Ser Trp Lys
            610               615              620

Leu Gln Val Val Lys Gln Leu Ala Tyr Ala Leu Asn Tyr Leu Glu Asp
625               630              635               640

Lys Gly Leu Pro His Gly Asn Val Ser Ala Arg Lys Val Leu Leu Ala
            645               650              655

Arg Glu Gly Ala Asp Gly Ser Pro Pro Phe Ile Lys Leu Ser Asp Pro
            660               665              670

Gly Val Ser Pro Ala Val Leu Ser Leu Glu Met Leu Thr Asp Arg Ile
            675               680              685

Pro Trp Val Ala Pro Glu Cys Leu Arg Glu Ala Gln Thr Leu Ser Leu
            690               695              700

Glu Ala Asp Lys Trp Gly Phe Gly Ala Thr Val Trp Glu Val Phe Ser
705               710              715               720

Gly Val Thr Met Pro Ile Ser Ala Leu Asp Pro Ala Lys Lys Leu Gln
            725               730              735

Phe Tyr Glu Asp Arg Gln Gln Leu Pro Ala Pro Lys Trp Thr Glu Leu
            740               745              750

Ala Leu Leu Ile Gln Gln Cys Met Ala Tyr Glu Pro Val Gln Arg Pro
            755               760              765

Ser Phe Arg Ala Val Ile Arg Asp Leu Asn Ser Leu Ile Ser Ser Asp
            770               775              780

Tyr Glu Leu Leu Ser Asp Pro Thr Pro Gly Ala Leu Ala Pro Arg Asp
785               790              795               800

Gly Leu Trp Asn Gly Ala Gln Leu Tyr Ala Cys Gln Asp Pro Thr Ile
            805               810              815

Phe Glu Glu Arg His Leu Lys Tyr Ile Ser Gln Leu Gly Lys Gly Asn
            820               825              830

Phe Gly Ser Val Glu Leu Cys Arg Tyr Asp Pro Leu Gly Asp Asn Thr
            835               840              845

Gly Ala Leu Val Ala Val Lys Gln Leu Gln His Ser Gly Pro Asp Gln
850               855              860

Gln Arg Asp Phe Gln Arg Glu Ile Gln Ile Leu Lys Ala Leu His Ser
865               870              875               880

Asp Phe Ile Val Lys Tyr Arg Gly Val Ser Tyr Gly Pro Gly Arg Gln
            885               890              895

Ser Leu Arg Leu Val Met Glu Tyr Leu Pro Ser Gly Cys Leu Arg Asp
            900               905              910

Phe Leu Gln Arg His Arg Ala Arg Leu Asp Ala Ser Arg Leu Leu Leu
            915               920              925

Tyr Ser Ser Gln Ile Cys Lys Gly Met Glu Tyr Leu Gly Ser Arg Arg
            930               935              940

Cys Val His Arg Asp Leu Ala Ala Arg Asn Ile Leu Val Glu Ser Glu
945               950              955               960

Ala His Val Lys Ile Ala Asp Phe Gly Leu Ala Lys Leu Leu Pro Leu
            965               970              975

Asp Lys Asp Tyr Tyr Val Val Arg Glu Pro Gly Gln Ser Pro Ile Phe
            980               985              990

Trp Tyr Ala Pro Glu Ser Leu Ser Asp Asn Ile Phe Ser Arg Gln Ser
            995              1000             1005
```

```
Asp Val Trp Ser Phe Gly Val Val Leu Tyr Glu Leu Phe Thr Tyr
    1010            1015                1020

Cys Asp Lys Ser Cys Ser Pro Ser Ala Glu Phe Leu Arg Met Met
    1025            1030                1035

Gly Cys Glu Arg Asp Val Pro Ala Leu Cys Arg Leu Leu Glu Leu
    1040            1045                1050

Leu Glu Glu Gly Gln Arg Leu Pro Ala Pro Pro Ala Cys Pro Ala
    1055            1060                1065

Glu Val His Glu Leu Met Lys Leu Cys Trp Ala Pro Ser Pro Gln
    1070            1075                1080

Asp Arg Pro Ser Phe Ser Ala Leu Gly Pro Gln Leu Asp Met Leu
    1085            1090                1095

Trp Ser Gly Ser Arg Gly Cys Glu Thr His Ala Phe Thr Ala His
    1100            1105                1110

Pro Glu Gly Lys His His Ser Leu Ser Phe Ser
    1115            1120
```

<210> SEQ ID NO 26
<211> LENGTH: 1356
<212> TYPE: PRT
<213> ORGANISM: HUMAN
<300> PUBLICATION INFORMATION:
<301> AUTHORS: Meyer,R.D., Dayanir,V., Majnoun,F. and Rahimi,N.
<302> TITLE: The presence of a single tyrosine residue at the carboxyl
       domain of
<303> JOURNAL: J. Biol. Chem.
<304> VOLUME: 277
<305> ISSUE: 30
<306> PAGES: 27081-27087
<307> DATE: 2002-05-22
<308> DATABASE ACCESSION NUMBER: NP_002244
<309> DATABASE ENTRY DATE: 2012-05-13
<313> RELEVANT RESIDUES IN SEQ ID NO: (1)..(1356)

<400> SEQUENCE: 26

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
```

-continued

```
                180                 185                 190
Ser Tyr Ala Gly Met Val Phe Cys Glu Ala Lys Ile Asn Asp Glu Ser
            195                 200                 205
Tyr Gln Ser Ile Met Tyr Ile Val Val Val Gly Tyr Arg Ile Tyr
    210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
            260                 265                 270
Val Asn Arg Asp Leu Lys Thr Gln Ser Gly Ser Glu Met Lys Lys Phe
    275                 280                 285
Leu Ser Thr Leu Thr Ile Asp Gly Val Thr Arg Ser Asp Gln Gly Leu
        290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
        355                 360                 365
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
```

```
Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
            755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
    850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
    915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020
```

```
Cys Ile His Arg Asp Leu Ala Ala Arg Asn Ile Leu Leu Ser Glu
    1025                1030                1035
Lys Asn Val Val Lys Ile Cys Asp Phe Gly Leu Ala Arg Asp Ile
    1040                1045                1050
Tyr Lys Asp Pro Asp Tyr Val Arg Lys Gly Asp Ala Arg Leu Pro
    1055                1060                1065
Leu Lys Trp Met Ala Pro Glu Thr Ile Phe Asp Arg Val Tyr Thr
    1070                1075                1080
Ile Gln Ser Asp Val Trp Ser Phe Gly Val Leu Leu Trp Glu Ile
    1085                1090                1095
Phe Ser Leu Gly Ala Ser Pro Tyr Pro Gly Val Lys Ile Asp Glu
    1100                1105                1110
Glu Phe Cys Arg Arg Leu Lys Glu Gly Thr Arg Met Arg Ala Pro
    1115                1120                1125
Asp Tyr Thr Thr Pro Glu Met Tyr Gln Thr Met Leu Asp Cys Trp
    1130                1135                1140
His Gly Glu Pro Ser Gln Arg Pro Thr Phe Ser Glu Leu Val Glu
    1145                1150                1155
His Leu Gly Asn Leu Leu Gln Ala Asn Ala Gln Gln Asp Gly Lys
    1160                1165                1170
Asp Tyr Ile Val Leu Pro Ile Ser Glu Thr Leu Ser Met Glu Glu
    1175                1180                1185
Asp Ser Gly Leu Ser Leu Pro Thr Ser Pro Val Ser Cys Met Glu
    1190                1195                1200
Glu Glu Glu Val Cys Asp Pro Lys Phe His Tyr Asp Asn Thr Ala
    1205                1210                1215
Gly Ile Ser Gln Tyr Leu Gln Asn Ser Lys Arg Lys Ser Arg Pro
    1220                1225                1230
Val Ser Val Lys Thr Phe Glu Asp Ile Pro Leu Glu Glu Pro Glu
    1235                1240                1245
Val Lys Val Ile Pro Asp Asp Asn Gln Thr Asp Ser Gly Met Val
    1250                1255                1260
Leu Ala Ser Glu Glu Leu Lys Thr Leu Glu Asp Arg Thr Lys Leu
    1265                1270                1275
Ser Pro Ser Phe Gly Gly Met Val Pro Ser Lys Ser Arg Glu Ser
    1280                1285                1290
Val Ala Ser Glu Gly Ser Asn Gln Thr Ser Gly Tyr Gln Ser Gly
    1295                1300                1305
Tyr His Ser Asp Asp Thr Asp Thr Thr Val Tyr Ser Ser Glu Glu
    1310                1315                1320
Ala Glu Leu Leu Lys Leu Ile Glu Ile Gly Val Gln Thr Gly Ser
    1325                1330                1335
Thr Ala Gln Ile Leu Gln Pro Asp Ser Gly Thr Thr Leu Ser Ser
    1340                1345                1350
Pro Pro Val
    1355

<210> SEQ ID NO 27
<211> LENGTH: 509
<212> TYPE: PRT
<213> ORGANISM: HUMAN
<300> PUBLICATION INFORMATION:
<301> AUTHORS: Weber,J.R., Bell,G.M., Han,M.Y., Pawson,T. and
      Imboden,J.B.
<302> TITLE: Association of the tyrosine kinase LCK with phospholipase
      C-gamma 1
```

```
<303> JOURNAL: J. Exp. Med.
<304> VOLUME: 176
<305> ISSUE: 2
<306> PAGES: 373-379
<307> DATE: 1992-08-01
<308> DATABASE ACCESSION NUMBER: NP_001036236
<309> DATABASE ENTRY DATE: 2012-04-22
<313> RELEVANT RESIDUES IN SEQ ID NO: (1)..(509)

<400> SEQUENCE: 27

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
    130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365
```

```
Asn Ile Leu Val Ser Asp Thr Leu Ser Cys Lys Ile Ala Asp Phe Gly
        370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
                420                 425                 430

Ile Val Thr His Gly Arg Ile Pro Tyr Pro Gly Met Thr Asn Pro Glu
                435                 440                 445

Val Ile Gln Asn Leu Glu Arg Gly Tyr Arg Met Val Arg Pro Asp Asn
        450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
                500                 505

<210> SEQ ID NO 28
<211> LENGTH: 2527
<212> TYPE: PRT
<213> ORGANISM: HUMAN
<300> PUBLICATION INFORMATION:
<301> AUTHORS: Inzelberg,R., Cohen,O.S., Aharon-Peretz,J.,
       Schlesinger,I.,
<302> TITLE: The LRRK2 G2019S mutation is associated with Parkinson
       disease and
<303> JOURNAL: Neurology
<304> VOLUME: 78
<305> ISSUE: 11
<306> PAGES: 781-786
<307> DATE: 2012-02-08
<308> DATABASE ACCESSION NUMBER: NP_940980
<309> DATABASE ENTRY DATE: 2012-05-20
<313> RELEVANT RESIDUES IN SEQ ID NO: (1)..(2527)

<400> SEQUENCE: 28

Met Ala Ser Gly Ser Cys Gln Gly Cys Glu Asp Glu Glu Thr Leu
1               5                   10                  15

Lys Lys Leu Ile Val Arg Leu Asn Asn Val Gln Glu Gly Lys Gln Ile
                20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
                100                 105                 110

Gly Val His Gln Leu Ile Leu Lys Met Leu Thr Val His Asn Ala Ser
            115                 120                 125

Val Asn Leu Ser Val Ile Gly Leu Lys Thr Leu Asp Leu Leu Leu Thr
        130                 135                 140

Ser Gly Lys Ile Thr Leu Leu Ile Leu Asp Glu Glu Ser Asp Ile Phe
145                 150                 155                 160
```

```
Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
            245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
            275                 280                 285

Asn Glu Val His Glu Phe Val Val Lys Ala Val Gln Gln Tyr Pro Glu
            290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Asp Lys Leu Phe Trp Leu Glu Ala
            340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
            370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
435                 440                 445

Met Gln Lys His Ile His Ser Pro Glu Val Ala Glu Ser Gly Cys Lys
        450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
            485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
            530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
```

-continued

```
            580                 585                 590
Leu Gln Met Tyr Pro Asp Asp Gln Glu Ile Gln Cys Leu Gly Leu Ser
            595                 600                 605
Leu Ile Gly Tyr Leu Ile Thr Lys Lys Asn Val Phe Ile Gly Thr Gly
            610                 615                 620
His Leu Leu Ala Lys Ile Leu Val Ser Ser Leu Tyr Arg Phe Lys Asp
625                 630                 635                 640
Val Ala Glu Ile Gln Thr Lys Gly Phe Gln Thr Ile Leu Ala Ile Leu
                    645                 650                 655
Lys Leu Ser Ala Ser Phe Ser Lys Leu Leu Val His His Ser Phe Asp
                660                 665                 670
Leu Val Ile Phe His Gln Met Ser Ser Asn Ile Met Glu Gln Lys Asp
            675                 680                 685
Gln Gln Phe Leu Asn Leu Cys Cys Lys Cys Phe Ala Lys Val Ala Met
        690                 695                 700
Asp Asp Tyr Leu Lys Asn Val Met Leu Glu Arg Ala Cys Asp Gln Asn
705                 710                 715                 720
Asn Ser Ile Met Val Glu Cys Leu Leu Leu Gly Ala Asp Ala Asn
                    725                 730                 735
Gln Ala Lys Glu Gly Ser Ser Leu Ile Cys Gln Val Cys Glu Lys Glu
                740                 745                 750
Ser Ser Pro Lys Leu Val Glu Leu Leu Asn Ser Gly Ser Arg Glu
            755                 760                 765
Gln Asp Val Arg Lys Ala Leu Thr Ile Ser Ile Gly Lys Gly Asp Ser
        770                 775                 780
Gln Ile Ile Ser Leu Leu Leu Arg Arg Leu Ala Leu Asp Val Ala Asn
785                 790                 795                 800
Asn Ser Ile Cys Leu Gly Gly Phe Cys Ile Gly Lys Val Glu Pro Ser
                    805                 810                 815
Trp Leu Gly Pro Leu Phe Pro Asp Lys Thr Ser Asn Leu Arg Lys Gln
                820                 825                 830
Thr Asn Ile Ala Ser Thr Leu Ala Arg Met Val Ile Arg Tyr Gln Met
            835                 840                 845
Lys Ser Ala Val Glu Glu Gly Thr Ala Ser Gly Ser Asp Gly Asn Phe
        850                 855                 860
Ser Glu Asp Val Leu Ser Lys Phe Asp Glu Trp Thr Phe Ile Pro Asp
865                 870                 875                 880
Ser Ser Met Asp Ser Val Phe Ala Gln Ser Asp Asp Leu Asp Ser Glu
                    885                 890                 895
Gly Ser Glu Gly Ser Phe Leu Val Lys Lys Ser Asn Ser Ile Ser
                900                 905                 910
Val Gly Glu Phe Tyr Arg Asp Ala Val Leu Gln Arg Cys Ser Pro Asn
            915                 920                 925
Leu Gln Arg His Ser Asn Ser Leu Gly Pro Ile Phe Asp His Glu Asp
        930                 935                 940
Leu Leu Lys Arg Lys Arg Lys Ile Leu Ser Ser Asp Asp Ser Leu Arg
945                 950                 955                 960
Ser Ser Lys Leu Gln Ser His Met Arg His Ser Asp Ser Ile Ser Ser
                    965                 970                 975
Leu Ala Ser Glu Arg Glu Tyr Ile Thr Ser Leu Asp Leu Ser Ala Asn
                980                 985                 990
Glu Leu Arg Asp Ile Asp Ala Leu  Ser Gln Lys Cys Cys  Ile Ser Val
            995                 1000                1005
```

-continued

```
His Leu Glu His Leu Glu Lys Leu Glu Leu His Gln Asn Ala Leu
    1010            1015            1020

Thr Ser Phe Pro Gln Gln Leu Cys Glu Thr Leu Lys Ser Leu Thr
    1025            1030            1035

His Leu Asp Leu His Ser Asn Lys Phe Thr Ser Phe Pro Ser Tyr
    1040            1045            1050

Leu Leu Lys Met Ser Cys Ile Ala Asn Leu Asp Val Ser Arg Asn
    1055            1060            1065

Asp Ile Gly Pro Ser Val Val Leu Asp Pro Thr Val Lys Cys Pro
    1070            1075            1080

Thr Leu Lys Gln Phe Asn Leu Ser Tyr Asn Gln Leu Ser Phe Val
    1085            1090            1095

Pro Glu Asn Leu Thr Asp Val Val Glu Lys Leu Glu Gln Leu Ile
    1100            1105            1110

Leu Glu Gly Asn Lys Ile Ser Gly Ile Cys Ser Pro Leu Arg Leu
    1115            1120            1125

Lys Glu Leu Lys Ile Leu Asn Leu Ser Lys Asn His Ile Ser Ser
    1130            1135            1140

Leu Ser Glu Asn Phe Leu Glu Ala Cys Pro Lys Val Glu Ser Phe
    1145            1150            1155

Ser Ala Arg Met Asn Phe Leu Ala Ala Met Pro Phe Leu Pro Pro
    1160            1165            1170

Ser Met Thr Ile Leu Lys Leu Ser Gln Asn Lys Phe Ser Cys Ile
    1175            1180            1185

Pro Glu Ala Ile Leu Asn Leu Pro His Leu Arg Ser Leu Asp Met
    1190            1195            1200

Ser Ser Asn Asp Ile Gln Tyr Leu Pro Gly Pro Ala His Trp Lys
    1205            1210            1215

Ser Leu Asn Leu Arg Glu Leu Leu Phe Ser His Asn Gln Ile Ser
    1220            1225            1230

Ile Leu Asp Leu Ser Glu Lys Ala Tyr Leu Trp Ser Arg Val Glu
    1235            1240            1245

Lys Leu His Leu Ser His Asn Lys Leu Lys Glu Ile Pro Pro Glu
    1250            1255            1260

Ile Gly Cys Leu Glu Asn Leu Thr Ser Leu Asp Val Ser Tyr Asn
    1265            1270            1275

Leu Glu Leu Arg Ser Phe Pro Asn Glu Met Gly Lys Leu Ser Lys
    1280            1285            1290

Ile Trp Asp Leu Pro Leu Asp Glu Leu His Leu Asn Phe Asp Phe
    1295            1300            1305

Lys His Ile Gly Cys Lys Ala Lys Asp Ile Ile Arg Phe Leu Gln
    1310            1315            1320

Gln Arg Leu Lys Lys Ala Val Pro Tyr Asn Arg Met Lys Leu Met
    1325            1330            1335

Ile Val Gly Asn Thr Gly Ser Gly Lys Thr Thr Leu Leu Gln Gln
    1340            1345            1350

Leu Met Lys Thr Lys Lys Ser Asp Leu Gly Met Gln Ser Ala Thr
    1355            1360            1365

Val Gly Ile Asp Val Lys Asp Trp Pro Ile Gln Ile Arg Asp Lys
    1370            1375            1380

Arg Lys Arg Asp Leu Val Leu Asn Val Trp Asp Phe Ala Gly Arg
    1385            1390            1395
```

```
Glu Glu Phe Tyr Ser Thr His Pro His Phe Met Thr Gln Arg Ala
    1400            1405            1410

Leu Tyr Leu Ala Val Tyr Asp Leu Ser Lys Gly Gln Ala Glu Val
    1415            1420            1425

Asp Ala Met Lys Pro Trp Leu Phe Asn Ile Lys Ala Arg Ala Ser
    1430            1435            1440

Ser Ser Pro Val Ile Leu Val Gly Thr His Leu Asp Val Ser Asp
    1445            1450            1455

Glu Lys Gln Arg Lys Ala Cys Met Ser Lys Ile Thr Lys Glu Leu
    1460            1465            1470

Leu Asn Lys Arg Gly Phe Pro Ala Ile Arg Asp Tyr His Phe Val
    1475            1480            1485

Asn Ala Thr Glu Glu Ser Asp Ala Leu Ala Lys Leu Arg Lys Thr
    1490            1495            1500

Ile Ile Asn Glu Ser Leu Asn Phe Lys Ile Arg Asp Gln Leu Val
    1505            1510            1515

Val Gly Gln Leu Ile Pro Asp Cys Tyr Val Glu Leu Glu Lys Ile
    1520            1525            1530

Ile Leu Ser Glu Arg Lys Asn Val Pro Ile Glu Phe Pro Val Ile
    1535            1540            1545

Asp Arg Lys Arg Leu Leu Gln Leu Val Arg Glu Asn Gln Leu Gln
    1550            1555            1560

Leu Asp Glu Asn Glu Leu Pro His Ala Val His Phe Leu Asn Glu
    1565            1570            1575

Ser Gly Val Leu Leu His Phe Gln Asp Pro Ala Leu Gln Leu Ser
    1580            1585            1590

Asp Leu Tyr Phe Val Glu Pro Lys Trp Leu Cys Lys Ile Met Ala
    1595            1600            1605

Gln Ile Leu Thr Val Lys Val Glu Gly Cys Pro Lys His Pro Lys
    1610            1615            1620

Gly Ile Ile Ser Arg Arg Asp Val Glu Lys Phe Leu Ser Lys Lys
    1625            1630            1635

Arg Lys Phe Pro Lys Asn Tyr Met Ser Gln Tyr Phe Lys Leu Leu
    1640            1645            1650

Glu Lys Phe Gln Ile Ala Leu Pro Ile Gly Glu Glu Tyr Leu Leu
    1655            1660            1665

Val Pro Ser Ser Leu Ser Asp His Arg Pro Val Ile Glu Leu Pro
    1670            1675            1680

His Cys Glu Asn Ser Glu Ile Ile Ile Arg Leu Tyr Glu Met Pro
    1685            1690            1695

Tyr Phe Pro Met Gly Phe Trp Ser Arg Leu Ile Asn Arg Leu Leu
    1700            1705            1710

Glu Ile Ser Pro Tyr Met Leu Ser Gly Arg Glu Arg Ala Leu Arg
    1715            1720            1725

Pro Asn Arg Met Tyr Trp Arg Gln Gly Ile Tyr Leu Asn Trp Ser
    1730            1735            1740

Pro Glu Ala Tyr Cys Leu Val Gly Ser Glu Val Leu Asp Asn His
    1745            1750            1755

Pro Glu Ser Phe Leu Lys Ile Thr Val Pro Ser Cys Arg Lys Gly
    1760            1765            1770

Cys Ile Leu Leu Gly Gln Val Val Asp His Ile Asp Ser Leu Met
    1775            1780            1785

Glu Glu Trp Phe Pro Gly Leu Leu Glu Ile Asp Ile Cys Gly Glu
```

-continued

```
            1790                1795                1800
Gly Glu Thr Leu Leu Lys Lys Trp Ala Leu Tyr Ser Phe Asn Asp
    1805                1810                1815
Gly Glu Glu His Gln Lys Ile Leu Leu Asp Asp Leu Met Lys Lys
    1820                1825                1830
Ala Glu Glu Gly Asp Leu Leu Val Asn Pro Asp Gln Pro Arg Leu
    1835                1840                1845
Thr Ile Pro Ile Ser Gln Ile Ala Pro Asp Leu Ile Leu Ala Asp
    1850                1855                1860
Leu Pro Arg Asn Ile Met Leu Asn Asn Asp Glu Leu Glu Phe Glu
    1865                1870                1875
Gln Ala Pro Glu Phe Leu Leu Gly Asp Gly Ser Phe Gly Ser Val
    1880                1885                1890
Tyr Arg Ala Ala Tyr Glu Gly Glu Glu Val Ala Val Lys Ile Phe
    1895                1900                1905
Asn Lys His Thr Ser Leu Arg Leu Leu Arg Gln Glu Leu Val Val
    1910                1915                1920
Leu Cys His Leu His His Pro Ser Leu Ile Ser Leu Leu Ala Ala
    1925                1930                1935
Gly Ile Arg Pro Arg Met Leu Val Met Glu Leu Ala Ser Lys Gly
    1940                1945                1950
Ser Leu Asp Arg Leu Leu Gln Gln Asp Lys Ala Ser Leu Thr Arg
    1955                1960                1965
Thr Leu Gln His Arg Ile Ala Leu His Val Ala Asp Gly Leu Arg
    1970                1975                1980
Tyr Leu His Ser Ala Met Ile Ile Tyr Arg Asp Leu Lys Pro His
    1985                1990                1995
Asn Val Leu Leu Phe Thr Leu Tyr Pro Asn Ala Ala Ile Ile Ala
    2000                2005                2010
Lys Ile Ala Asp Tyr Ser Ile Ala Gln Tyr Cys Cys Arg Met Gly
    2015                2020                2025
Ile Lys Thr Ser Glu Gly Thr Pro Gly Phe Arg Ala Pro Glu Val
    2030                2035                2040
Ala Arg Gly Asn Val Ile Tyr Asn Gln Gln Ala Asp Val Tyr Ser
    2045                2050                2055
Phe Gly Leu Leu Leu Tyr Asp Ile Leu Thr Thr Gly Gly Arg Ile
    2060                2065                2070
Val Glu Gly Leu Lys Phe Pro Asn Glu Phe Asp Glu Leu Glu Ile
    2075                2080                2085
Gln Gly Lys Leu Pro Asp Pro Val Lys Glu Tyr Gly Cys Ala Pro
    2090                2095                2100
Trp Pro Met Val Glu Lys Leu Ile Lys Gln Cys Leu Lys Glu Asn
    2105                2110                2115
Pro Gln Glu Arg Pro Thr Ser Ala Gln Val Phe Asp Ile Leu Asn
    2120                2125                2130
Ser Ala Glu Leu Val Cys Leu Thr Arg Arg Ile Leu Leu Pro Lys
    2135                2140                2145
Asn Val Ile Val Glu Cys Met Val Ala Thr His His Asn Ser Arg
    2150                2155                2160
Asn Ala Ser Ile Trp Leu Gly Cys Gly His Thr Asp Arg Gly Gln
    2165                2170                2175
Leu Ser Phe Leu Asp Leu Asn Thr Glu Gly Tyr Thr Ser Glu Glu
    2180                2185                2190
```

Val Ala Asp Ser Arg Ile Leu Cys Leu Ala Leu Val His Leu Pro
2195                2200                2205

Val Glu Lys Glu Ser Trp Ile Val Ser Gly Thr Gln Ser Gly Thr
2210                2215                2220

Leu Leu Val Ile Asn Thr Glu Asp Gly Lys Lys Arg His Thr Leu
2225                2230                2235

Glu Lys Met Thr Asp Ser Val Thr Cys Leu Tyr Cys Asn Ser Phe
2240                2245                2250

Ser Lys Gln Ser Lys Gln Lys Asn Phe Leu Leu Val Gly Thr Ala
2255                2260                2265

Asp Gly Lys Leu Ala Ile Phe Glu Asp Lys Thr Val Lys Leu Lys
2270                2275                2280

Gly Ala Ala Pro Leu Lys Ile Leu Asn Ile Gly Asn Val Ser Thr
2285                2290                2295

Pro Leu Met Cys Leu Ser Glu Ser Thr Asn Ser Thr Glu Arg Asn
2300                2305                2310

Val Met Trp Gly Gly Cys Gly Thr Lys Ile Phe Ser Phe Ser Asn
2315                2320                2325

Asp Phe Thr Ile Gln Lys Leu Ile Glu Thr Arg Thr Ser Gln Leu
2330                2335                2340

Phe Ser Tyr Ala Ala Phe Ser Asp Ser Asn Ile Ile Thr Val Val
2345                2350                2355

Val Asp Thr Ala Leu Tyr Ile Ala Lys Gln Asn Ser Pro Val Val
2360                2365                2370

Glu Val Trp Asp Lys Lys Thr Glu Lys Leu Cys Gly Leu Ile Asp
2375                2380                2385

Cys Val His Phe Leu Arg Glu Val Met Val Lys Glu Asn Lys Glu
2390                2395                2400

Ser Lys His Lys Met Ser Tyr Ser Gly Arg Val Lys Thr Leu Cys
2405                2410                2415

Leu Gln Lys Asn Thr Ala Leu Trp Ile Gly Thr Gly Gly Gly His
2420                2425                2430

Ile Leu Leu Leu Asp Leu Ser Thr Arg Arg Leu Ile Arg Val Ile
2435                2440                2445

Tyr Asn Phe Cys Asn Ser Val Arg Val Met Met Thr Ala Gln Leu
2450                2455                2460

Gly Ser Leu Lys Asn Val Met Leu Val Leu Gly Tyr Asn Arg Lys
2465                2470                2475

Asn Thr Glu Gly Thr Gln Lys Gln Lys Glu Ile Gln Ser Cys Leu
2480                2485                2490

Thr Val Trp Asp Ile Asn Leu Pro His Glu Val Gln Asn Leu Glu
2495                2500                2505

Lys His Ile Glu Val Arg Lys Glu Leu Ala Glu Lys Met Arg Arg
2510                2515                2520

Thr Ser Val Glu
2525

<210> SEQ ID NO 29
<211> LENGTH: 2527
<212> TYPE: PRT
<213> ORGANISM: HUMAN
<300> PUBLICATION INFORMATION:
<301> AUTHORS: Inzelberg,R., Cohen,O.S., Aharon-Peretz,J.,
      Schlesinger,I.,
<302> TITLE: The LRRK2 G2019S mutation is associated with Parkinson

```
                            disease and
<303> JOURNAL: Neurology
<304> VOLUME: 78
<305> ISSUE: 11
<306> PAGES: 781-786
<307> DATE: 2012-02-08
<308> DATABASE ACCESSION NUMBER: NP_940980
<309> DATABASE ENTRY DATE: 2012-05-20
<313> RELEVANT RESIDUES IN SEQ ID NO: (1)..(2527)

<400> SEQUENCE: 29

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
```

-continued

```
            355                 360                 365
Ala Ala Cys Trp Ala Leu Asn Asn Leu Leu Met Tyr Gln Asn Ser Leu
370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780
```

```
Gln Ile Ile Ser Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
            805                 810                 815

Trp Leu Gly Pro Leu Phe Pro Asp Lys Thr Ser Asn Leu Arg Lys Gln
        820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
            885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
            995                 1000                1005

His Leu Glu His Leu Glu Lys Leu Glu Leu His Gln Asn Ala Leu
    1010            1015               1020

Thr Ser Phe Pro Gln Gln Leu Cys Glu Thr Leu Lys Ser Leu Thr
    1025            1030               1035

His Leu Asp Leu His Ser Asn Lys Phe Thr Ser Phe Pro Ser Tyr
    1040            1045               1050

Leu Leu Lys Met Ser Cys Ile Ala Asn Leu Asp Val Ser Arg Asn
    1055            1060               1065

Asp Ile Gly Pro Ser Val Val Leu Asp Pro Thr Val Lys Cys Pro
    1070            1075               1080

Thr Leu Lys Gln Phe Asn Leu Ser Tyr Asn Gln Leu Ser Phe Val
    1085            1090               1095

Pro Glu Asn Leu Thr Asp Val Val Glu Lys Leu Glu Gln Leu Ile
    1100            1105               1110

Leu Glu Gly Asn Lys Ile Ser Gly Ile Cys Ser Pro Leu Arg Leu
    1115            1120               1125

Lys Glu Leu Lys Ile Leu Asn Leu Ser Lys Asn His Ile Ser Ser
    1130            1135               1140

Leu Ser Glu Asn Phe Leu Glu Ala Cys Pro Lys Val Glu Ser Phe
    1145            1150               1155

Ser Ala Arg Met Asn Phe Leu Ala Ala Met Pro Phe Leu Pro Pro
    1160            1165               1170

Ser Met Thr Ile Leu Lys Leu Ser Gln Asn Lys Phe Ser Cys Ile
    1175            1180               1185
```

-continued

```
Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
    1280                1285                1290

Ile Trp Asp Leu Pro Leu Asp Glu Leu His Leu Asn Phe Asp Phe
    1295                1300                1305

Lys His Ile Gly Cys Lys Ala Lys Asp Ile Ile Arg Phe Leu Gln
    1310                1315                1320

Gln Arg Leu Lys Lys Ala Val Pro Tyr Asn Arg Met Lys Leu Met
    1325                1330                1335

Ile Val Gly Asn Thr Gly Ser Gly Lys Thr Thr Leu Leu Gln Gln
    1340                1345                1350

Leu Met Lys Thr Lys Lys Ser Asp Leu Gly Met Gln Ser Ala Thr
    1355                1360                1365

Val Gly Ile Asp Val Lys Asp Trp Pro Ile Gln Ile Arg Asp Lys
    1370                1375                1380

Arg Lys Arg Asp Leu Val Leu Asn Val Trp Asp Phe Ala Gly Arg
    1385                1390                1395

Glu Glu Phe Tyr Ser Thr His Pro His Phe Met Thr Gln Arg Ala
    1400                1405                1410

Leu Tyr Leu Ala Val Tyr Asp Leu Ser Lys Gly Gln Ala Glu Val
    1415                1420                1425

Asp Ala Met Lys Pro Trp Leu Phe Asn Ile Lys Ala Arg Ala Ser
    1430                1435                1440

Ser Ser Pro Val Ile Leu Val Gly Thr His Leu Asp Val Ser Asp
    1445                1450                1455

Glu Lys Gln Arg Lys Ala Cys Met Ser Lys Ile Thr Lys Glu Leu
    1460                1465                1470

Leu Asn Lys Arg Gly Phe Pro Ala Ile Arg Asp Tyr His Phe Val
    1475                1480                1485

Asn Ala Thr Glu Glu Ser Asp Ala Leu Ala Lys Leu Arg Lys Thr
    1490                1495                1500

Ile Ile Asn Glu Ser Leu Asn Phe Lys Ile Arg Asp Gln Leu Val
    1505                1510                1515

Val Gly Gln Leu Ile Pro Asp Cys Tyr Val Glu Leu Glu Lys Ile
    1520                1525                1530

Ile Leu Ser Glu Arg Lys Asn Val Pro Ile Glu Phe Pro Val Ile
    1535                1540                1545

Asp Arg Lys Arg Leu Leu Gln Leu Val Arg Glu Asn Gln Leu Gln
    1550                1555                1560

Leu Asp Glu Asn Glu Leu Pro His Ala Val His Phe Leu Asn Glu
    1565                1570                1575

Ser Gly Val Leu Leu His Phe Gln Asp Pro Ala Leu Gln Leu Ser
```

```
            1580                1585                1590

Asp Leu Tyr Phe Val Glu Pro Lys Trp Leu Cys Lys Ile Met Ala
    1595                1600                1605

Gln Ile Leu Thr Val Lys Val Glu Gly Cys Pro Lys His Pro Lys
    1610                1615                1620

Gly Ile Ile Ser Arg Arg Asp Val Glu Lys Phe Leu Ser Lys Lys
    1625                1630                1635

Arg Lys Phe Pro Lys Asn Tyr Met Ser Gln Tyr Phe Lys Leu Leu
    1640                1645                1650

Glu Lys Phe Gln Ile Ala Leu Pro Ile Gly Glu Glu Tyr Leu Leu
    1655                1660                1665

Val Pro Ser Ser Leu Ser Asp His Arg Pro Val Ile Glu Leu Pro
    1670                1675                1680

His Cys Glu Asn Ser Glu Ile Ile Ile Arg Leu Tyr Glu Met Pro
    1685                1690                1695

Tyr Phe Pro Met Gly Phe Trp Ser Arg Leu Ile Asn Arg Leu Leu
    1700                1705                1710

Glu Ile Ser Pro Tyr Met Leu Ser Gly Arg Glu Arg Ala Leu Arg
    1715                1720                1725

Pro Asn Arg Met Tyr Trp Arg Gln Gly Ile Tyr Leu Asn Trp Ser
    1730                1735                1740

Pro Glu Ala Tyr Cys Leu Val Gly Ser Glu Val Leu Asp Asn His
    1745                1750                1755

Pro Glu Ser Phe Leu Lys Ile Thr Val Pro Ser Cys Arg Lys Gly
    1760                1765                1770

Cys Ile Leu Leu Gly Gln Val Val Asp His Ile Asp Ser Leu Met
    1775                1780                1785

Glu Glu Trp Phe Pro Gly Leu Leu Glu Ile Asp Ile Cys Gly Glu
    1790                1795                1800

Gly Glu Thr Leu Leu Lys Lys Trp Ala Leu Tyr Ser Phe Asn Asp
    1805                1810                1815

Gly Glu Glu His Gln Lys Ile Leu Leu Asp Asp Leu Met Lys Lys
    1820                1825                1830

Ala Glu Glu Gly Asp Leu Leu Val Asn Pro Asp Gln Pro Arg Leu
    1835                1840                1845

Thr Ile Pro Ile Ser Gln Ile Ala Pro Asp Leu Ile Leu Ala Asp
    1850                1855                1860

Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980
```

```
Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu Tyr Asp Ile Leu Thr Thr Gly Gly Arg Ile
    2060            2065            2070

Val Glu Gly Leu Lys Phe Pro Asn Glu Phe Asp Glu Leu Glu Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Lys Gln Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Val Cys Leu Thr Arg Arg Ile Leu Leu Pro Lys
    2135            2140            2145

Asn Val Ile Val Glu Cys Met Val Ala Thr His His Asn Ser Arg
    2150            2155            2160

Asn Ala Ser Ile Trp Leu Gly Cys Gly His Thr Asp Arg Gly Gln
    2165            2170            2175

Leu Ser Phe Leu Asp Leu Asn Thr Glu Gly Tyr Thr Ser Glu Glu
    2180            2185            2190

Val Ala Asp Ser Arg Ile Leu Cys Leu Ala Leu Val His Leu Pro
    2195            2200            2205

Val Glu Lys Glu Ser Trp Ile Val Ser Gly Thr Gln Ser Gly Thr
    2210            2215            2220

Leu Leu Val Ile Asn Thr Glu Asp Gly Lys Lys Arg His Thr Leu
    2225            2230            2235

Glu Lys Met Thr Asp Ser Val Thr Cys Leu Tyr Cys Asn Ser Phe
    2240            2245            2250

Ser Lys Gln Ser Lys Gln Lys Asn Phe Leu Leu Val Gly Thr Ala
    2255            2260            2265

Asp Gly Lys Leu Ala Ile Phe Glu Asp Lys Thr Val Lys Leu Lys
    2270            2275            2280

Gly Ala Ala Pro Leu Lys Ile Leu Asn Ile Gly Asn Val Ser Thr
    2285            2290            2295

Pro Leu Met Cys Leu Ser Glu Ser Thr Asn Ser Thr Glu Arg Asn
    2300            2305            2310

Val Met Trp Gly Gly Cys Gly Thr Lys Ile Phe Ser Phe Ser Asn
    2315            2320            2325

Asp Phe Thr Ile Gln Lys Leu Ile Glu Thr Arg Thr Ser Gln Leu
    2330            2335            2340

Phe Ser Tyr Ala Ala Phe Ser Asp Ser Asn Ile Ile Thr Val Val
    2345            2350            2355

Val Asp Thr Ala Leu Tyr Ile Ala Lys Gln Asn Ser Pro Val Val
    2360            2365            2370
```

```
Glu Val Trp Asp Lys Lys Thr Glu Lys Leu Cys Gly Leu Ile Asp
    2375                2380                2385

Cys Val His Phe Leu Arg Glu Val Met Val Lys Glu Asn Lys Glu
    2390                2395                2400

Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly Gly His
    2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
    2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
    2480                2485                2490

Thr Val Trp Asp Ile Asn Leu Pro His Gly Val Gln Asn Leu Glu
    2495                2500                2505

Lys His Ile Glu Val Arg Lys Glu Leu Ala Glu Lys Met Arg Arg
    2510                2515                2520

Thr Ser Val Glu
    2525

<210> SEQ ID NO 30
<211> LENGTH: 1165
<212> TYPE: PRT
<213> ORGANISM: HUMAN
<300> PUBLICATION INFORMATION:
<301> AUTHORS: Liang,J.J., Wang,H., Rashid,A., Tan,T.H., Hwang,R.F.,
<302> TITLE: Expression of MAP4K4 is associated with worse prognosis in
      patients
<303> JOURNAL: Clin. Cancer Res.
<304> VOLUME: 14
<305> ISSUE: 21
<306> PAGES: 7043-7049
<307> DATE: 2008-11-01
<308> DATABASE ACCESSION NUMBER: NP_004825
<309> DATABASE ENTRY DATE: 2012-04-30
<313> RELEVANT RESIDUES IN SEQ ID NO: (1)..(1165)

<400> SEQUENCE: 30

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
        130                 135                 140
```

```
His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Leu Arg Glu Gln
370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Gln Gln Arg Arg Glu
                405                 410                 415

Arg Glu Ala Arg Arg Gln Gln Glu Arg Glu Gln Arg Arg Glu Gln
            420                 425                 430

Glu Glu Lys Arg Arg Leu Glu Glu Leu Glu Arg Arg Lys Glu Glu
        435                 440                 445

Glu Glu Arg Arg Arg Ala Glu Glu Lys Arg Arg Val Glu Arg Glu
450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Pro Val Arg Thr Thr Ser
    530                 535                 540

Arg Ser Pro Val Leu Ser Arg Arg Asp Ser Pro Leu Gln Gly Ser Gly
545                 550                 555                 560
```

```
Gln Gln Asn Ser Gln Ala Gly Gln Arg Asn Ser Thr Ser Ile Glu Pro
                565                 570                 575
Arg Leu Leu Trp Glu Arg Val Glu Lys Leu Val Pro Arg Pro Gly Ser
            580                 585                 590
Gly Ser Ser Ser Gly Ser Ser Asn Ser Gly Ser Gln Pro Gly Ser His
        595                 600                 605
Pro Gly Ser Gln Ser Gly Ser Gly Glu Arg Phe Arg Val Arg Ser Ser
    610                 615                 620
Ser Lys Ser Glu Gly Ser Pro Ser Gln Arg Leu Glu Asn Ala Val Lys
625                 630                 635                 640
Lys Pro Glu Asp Lys Lys Glu Val Phe Arg Pro Leu Lys Pro Ala Gly
                645                 650                 655
Glu Val Asp Leu Thr Ala Leu Ala Lys Glu Leu Arg Ala Val Glu Asp
            660                 665                 670
Val Arg Pro Pro His Lys Val Thr Asp Tyr Ser Ser Ser Ser Glu Glu
        675                 680                 685
Ser Gly Thr Thr Asp Glu Glu Asp Asp Val Glu Gln Glu Gly Ala
    690                 695                 700
Asp Glu Ser Thr Ser Gly Pro Glu Asp Thr Arg Ala Ala Ser Ser Leu
705                 710                 715                 720
Asn Leu Ser Asn Gly Glu Thr Glu Ser Val Lys Thr Met Ile Val His
                725                 730                 735
Asp Asp Val Glu Ser Glu Pro Ala Met Thr Pro Ser Lys Glu Gly Thr
            740                 745                 750
Leu Ile Val Arg Gln Thr Gln Ser Ala Ser Ser Thr Leu Gln Lys His
        755                 760                 765
Lys Ser Ser Ser Ser Phe Thr Pro Phe Ile Asp Pro Arg Leu Leu Gln
770                 775                 780
Ile Ser Pro Ser Ser Gly Thr Thr Val Thr Ser Val Val Gly Phe Ser
785                 790                 795                 800
Cys Asp Gly Met Arg Pro Glu Ala Ile Arg Gln Asp Pro Thr Arg Lys
                805                 810                 815
Gly Ser Val Val Asn Val Asn Pro Thr Asn Thr Arg Pro Gln Ser Asp
            820                 825                 830
Thr Pro Glu Ile Arg Lys Tyr Lys Lys Arg Phe Asn Ser Glu Ile Leu
        835                 840                 845
Cys Ala Ala Leu Trp Gly Val Asn Leu Leu Val Gly Thr Glu Ser Gly
    850                 855                 860
Leu Met Leu Leu Asp Arg Ser Gly Gln Gly Lys Val Tyr Pro Leu Ile
865                 870                 875                 880
Asn Arg Arg Arg Phe Gln Gln Met Asp Val Leu Glu Gly Leu Asn Val
                885                 890                 895
Leu Val Thr Ile Ser Gly Lys Lys Asp Lys Leu Arg Val Tyr Tyr Leu
            900                 905                 910
Ser Trp Leu Arg Asn Lys Ile Leu His Asn Asp Pro Glu Val Glu Lys
        915                 920                 925
Lys Gln Gly Trp Thr Thr Val Gly Asp Leu Glu Gly Cys Val His Tyr
    930                 935                 940
Lys Val Val Lys Tyr Glu Arg Ile Lys Phe Leu Val Ile Ala Leu Lys
945                 950                 955                 960
Ser Ser Val Glu Val Tyr Ala Trp Ala Pro Lys Pro Tyr His Lys Phe
                965                 970                 975
Met Ala Phe Lys Ser Phe Gly Glu Leu Val His Lys Pro Leu Leu Val
```

```
                      980             985             990
        Asp Leu Thr Val Glu Glu Gly Gln Arg Leu Lys Val Ile Tyr Gly Ser
                995             1000            1005

Cys Ala Gly Phe His Ala Val Asp Val Asp Ser Gly Ser Val Tyr
            1010            1015            1020

Asp Ile Tyr Leu Pro Thr His Val Arg Lys Asn Pro His Ser Met
            1025            1030            1035

Ile Gln Cys Ser Ile Lys Pro His Ala Ile Ile Ile Leu Pro Asn
            1040            1045            1050

Thr Asp Gly Met Glu Leu Leu Val Cys Tyr Glu Asp Glu Gly Val
            1055            1060            1065

Tyr Val Asn Thr Tyr Gly Arg Ile Thr Lys Asp Val Val Leu Gln
            1070            1075            1080

Trp Gly Glu Met Pro Thr Ser Val Ala Tyr Ile Arg Ser Asn Gln
            1085            1090            1095

Thr Met Gly Trp Gly Glu Lys Ala Ile Glu Ile Arg Ser Val Glu
            1100            1105            1110

Thr Gly His Leu Asp Gly Val Phe Met His Lys Arg Ala Gln Arg
            1115            1120            1125

Leu Lys Phe Leu Cys Glu Arg Asn Asp Lys Val Phe Phe Ala Ser
            1130            1135            1140

Val Arg Ser Gly Gly Ser Ser Gln Val Tyr Phe Met Thr Leu Gly
            1145            1150            1155

Arg Thr Ser Leu Leu Ser Trp
            1160            1165

<210> SEQ ID NO 31
<211> LENGTH: 651
<212> TYPE: PRT
<213> ORGANISM: HUMAN
<300> PUBLICATION INFORMATION:
<301> AUTHORS: Choi,S. and Ku,J.L.
<302> TITLE: Resistance of colorectal cancer cells to radiation and
      5-FU is
<303> JOURNAL: Biochem. Biophys. Res. Commun.
<304> VOLUME: 412
<305> ISSUE: 2
<306> PAGES: 207-213
<307> DATE: 2011-07-22
<308> DATABASE ACCESSION NUMBER: NP_055606
<309> DATABASE ENTRY DATE: 2012-04-30
<313> RELEVANT RESIDUES IN SEQ ID NO: (1)..(651)

<400> SEQUENCE: 31

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
                20                  25                  30

Thr Gly Glu Met Val Ala Ile Lys Ile Met Asp Lys Asn Thr Leu Gly
            35                  40                  45

Ser Asp Leu Pro Arg Ile Lys Thr Glu Ile Glu Ala Leu Lys Asn Leu
        50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Glu Thr Arg Val Val
                100                 105                 110
```

-continued

```
Phe Arg Gln Ile Val Ser Ala Val Ala Tyr Val His Ser Gln Gly Tyr
            115                 120                 125

Ala His Arg Asp Leu Lys Pro Glu Asn Leu Leu Phe Asp Glu Tyr His
130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
            195                 200                 205

Phe Asp Asp Asp Asn Val Met Ala Leu Tyr Lys Lys Ile Met Arg Gly
            210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
            275                 280                 285

Glu Leu Ser Val His His Arg Asn Asn Arg Gln Thr Met Glu Asp Leu
            290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
                325                 330                 335

Phe Ser Cys Gly Gln Ala Ser Ala Thr Pro Phe Thr Asp Ile Lys Ser
            340                 345                 350

Asn Asn Trp Ser Leu Glu Asp Val Thr Ala Ser Asp Lys Asn Tyr Val
            355                 360                 365

Ala Gly Leu Ile Asp Tyr Asp Trp Cys Glu Asp Asp Leu Ser Thr Gly
            370                 375                 380

Ala Ala Thr Pro Arg Thr Ser Gln Phe Thr Lys Tyr Trp Thr Glu Ser
385                 390                 395                 400

Asn Gly Val Glu Ser Lys Ser Leu Thr Pro Ala Leu Cys Arg Thr Pro
                405                 410                 415

Ala Asn Lys Leu Lys Asn Lys Glu Asn Val Tyr Thr Pro Lys Ser Ala
            420                 425                 430

Val Lys Asn Glu Glu Tyr Phe Met Phe Pro Glu Pro Lys Thr Pro Val
            435                 440                 445

Asn Lys Asn Gln His Lys Arg Glu Ile Leu Thr Thr Pro Asn Arg Tyr
            450                 455                 460

Thr Thr Pro Ser Lys Ala Arg Asn Gln Cys Leu Lys Glu Thr Pro Ile
465                 470                 475                 480

Lys Ile Pro Val Asn Ser Thr Gly Thr Asp Lys Leu Met Thr Gly Val
                485                 490                 495

Ile Ser Pro Glu Arg Arg Cys Arg Ser Val Glu Leu Asp Leu Asn Gln
            500                 505                 510

Ala His Met Glu Glu Thr Pro Lys Arg Lys Gly Ala Lys Val Phe Gly
            515                 520                 525

Ser Leu Glu Arg Gly Leu Asp Lys Val Ile Thr Val Leu Thr Arg Ser
```

```
                530             535             540
Lys Arg Lys Gly Ser Ala Arg Asp Gly Pro Arg Arg Leu Lys Leu His
545                 550                 555                 560

Tyr Asn Val Thr Thr Thr Arg Leu Val Asn Pro Asp Gln Leu Leu Asn
                565                 570                 575

Glu Ile Met Ser Ile Leu Pro Lys Lys His Val Asp Phe Val Gln Lys
            580                 585                 590

Gly Tyr Thr Leu Lys Cys Gln Thr Gln Ser Asp Phe Gly Lys Val Thr
                595                 600                 605

Met Gln Phe Glu Leu Glu Val Cys Gln Leu Gln Lys Pro Asp Val Val
            610                 615                 620

Gly Ile Arg Arg Gln Arg Leu Lys Gly Asp Ala Trp Val Tyr Lys Arg
625                 630                 635                 640

Leu Val Glu Asp Ile Leu Ser Ser Cys Lys Val
                645                 650

<210> SEQ ID NO 32
<211> LENGTH: 471
<212> TYPE: PRT
<213> ORGANISM: HUMAN
<300> PUBLICATION INFORMATION:
<301> AUTHORS: Sun,L., Wang,H., Wang,Z., He,S., Chen,S., Liao,D.,
      Wang,L., Yan,J.,
<302> TITLE: Mixed lineage kinase domain-like protein mediates necrosis
<303> JOURNAL: Cell
<304> VOLUME: 148
<305> ISSUE: 1
<306> PAGES: 213-227
<307> DATE: 2012-01-20
<308> DATABASE ACCESSION NUMBER: NP_689862
<309> DATABASE ENTRY DATE: 2012-03-31
<313> RELEVANT RESIDUES IN SEQ ID NO: (1)..(471)

<400> SEQUENCE: 32

Met Glu Asn Leu Lys His Ile Ile Thr Leu Gly Gln Val Ile His Lys
1               5                   10                  15

Arg Cys Glu Glu Met Lys Tyr Cys Lys Lys Gln Cys Arg Arg Leu Gly
            20                  25                  30

His Arg Val Leu Gly Leu Ile Lys Pro Leu Glu Met Leu Gln Asp Gln
        35                  40                  45

Gly Lys Arg Ser Val Pro Ser Glu Lys Leu Thr Thr Ala Met Asn Arg
    50                  55                  60

Phe Lys Ala Ala Leu Glu Glu Ala Asn Gly Glu Ile Glu Lys Phe Ser
65                  70                  75                  80

Asn Arg Ser Asn Ile Cys Arg Phe Leu Thr Ala Ser Gln Asp Lys Ile
                85                  90                  95

Leu Phe Lys Asp Val Asn Arg Lys Leu Ser Asp Val Trp Lys Glu Leu
            100                 105                 110

Ser Leu Leu Leu Gln Val Glu Gln Arg Met Pro Val Ser Pro Ile Ser
        115                 120                 125

Gln Gly Ala Ser Trp Ala Gln Glu Asp Gln Gln Asp Ala Asp Glu Asp
    130                 135                 140

Arg Arg Ala Phe Gln Met Leu Arg Arg Asp Asn Glu Lys Ile Glu Ala
145                 150                 155                 160

Ser Leu Arg Arg Leu Glu Ile Asn Met Lys Glu Ile Lys Glu Thr Leu
                165                 170                 175

Arg Gln Tyr Leu Pro Pro Lys Cys Met Gln Glu Ile Pro Gln Glu Gln
            180                 185                 190
```

```
Ile Lys Glu Ile Lys Lys Glu Gln Leu Ser Gly Ser Pro Trp Ile Leu
        195                 200                 205

Leu Arg Glu Asn Glu Val Ser Thr Leu Tyr Lys Gly Glu Tyr His Arg
    210                 215                 220

Ala Pro Val Ala Ile Lys Val Phe Lys Lys Leu Gln Ala Gly Ser Ile
225                 230                 235                 240

Ala Ile Val Arg Gln Thr Phe Asn Lys Glu Ile Lys Thr Met Lys Lys
                245                 250                 255

Phe Glu Ser Pro Asn Ile Leu Arg Ile Phe Gly Ile Cys Ile Asp Glu
                260                 265                 270

Thr Val Thr Pro Pro Gln Phe Ser Ile Val Met Glu Tyr Cys Glu Leu
                275                 280                 285

Gly Thr Leu Arg Glu Leu Leu Asp Arg Glu Lys Asp Leu Thr Leu Gly
        290                 295                 300

Lys Arg Met Val Leu Val Leu Gly Ala Ala Arg Gly Leu Tyr Arg Leu
305                 310                 315                 320

His His Ser Glu Ala Pro Glu Leu His Gly Lys Ile Arg Ser Ser Asn
                325                 330                 335

Phe Leu Val Thr Gln Gly Tyr Gln Val Lys Leu Ala Gly Phe Glu Leu
                340                 345                 350

Arg Lys Thr Gln Thr Ser Met Ser Leu Gly Thr Thr Arg Glu Lys Thr
        355                 360                 365

Asp Arg Val Lys Ser Thr Ala Tyr Leu Ser Pro Gln Glu Leu Glu Asp
        370                 375                 380

Val Phe Tyr Gln Tyr Asp Val Lys Ser Glu Ile Tyr Ser Phe Gly Ile
385                 390                 395                 400

Val Leu Trp Glu Ile Ala Thr Gly Asp Ile Pro Phe Gln Gly Cys Asn
                405                 410                 415

Ser Glu Lys Ile Arg Lys Leu Val Ala Val Lys Arg Gln Gln Glu Pro
                420                 425                 430

Leu Gly Glu Asp Cys Pro Ser Glu Leu Arg Glu Ile Ile Asp Glu Cys
        435                 440                 445

Arg Ala His Asp Pro Ser Val Arg Pro Ser Val Asp Glu Ile Leu Lys
        450                 455                 460

Lys Leu Ser Thr Phe Ser Lys
465                 470

<210> SEQ ID NO 33
<211> LENGTH: 271
<212> TYPE: PRT
<213> ORGANISM: HUMAN
<300> PUBLICATION INFORMATION:
<301> AUTHORS: Hudkins,R.L., Diebold,J.L., Tao,M., Josef,K.A.,
      Park,C.H.,
<302> TITLE: Mixed-lineage kinase 1 and mixed-lineage kinase 3
      subtype-selective
<303> JOURNAL: J. Med. Chem.
<304> VOLUME: 51
<305> ISSUE: 18
<306> PAGES: 5680-5689
<307> DATE: 2008-08-21
<308> DATABASE ACCESSION NUMBER: 3DTC_A
<309> DATABASE ENTRY DATE: 2009-04-01
<313> RELEVANT RESIDUES IN SEQ ID NO: (1)..(271)

<400> SEQUENCE: 33

Leu Leu Glu Ile Asp Phe Ala Glu Leu Thr Leu Glu Glu Ile Ile Gly
1               5                   10                  15

Ile Gly Gly Phe Gly Lys Val Tyr Arg Ala Phe Trp Ile Gly Asp Glu
```

```
                    20                  25                  30

Val Ala Val Lys Ala Ala Arg His Asp Pro Asp Glu Asp Ile Ser Gln
                35                  40                  45

Thr Ile Glu Asn Val Arg Gln Glu Ala Lys Leu Phe Ala Met Leu Lys
        50                  55                  60

His Pro Asn Ile Ile Ala Leu Arg Gly Val Cys Leu Lys Glu Pro Asn
65                  70                  75                  80

Leu Cys Leu Val Met Glu Phe Ala Arg Gly Gly Pro Leu Asn Arg Val
                85                  90                  95

Leu Ser Gly Lys Arg Ile Pro Pro Asp Ile Leu Val Asn Trp Ala Val
            100                 105                 110

Gln Ile Ala Arg Gly Met Asn Tyr Leu His Asp Glu Ala Ile Val Pro
        115                 120                 125

Ile Ile His Arg Asp Leu Lys Ser Ser Asn Ile Leu Ile Leu Gln Lys
    130                 135                 140

Val Glu Asn Gly Asp Leu Ser Asn Lys Ile Leu Lys Ile Thr Asp Phe
145                 150                 155                 160

Gly Leu Ala Arg Glu Trp His Arg Thr Thr Lys Met Ser Ala Ala Gly
                165                 170                 175

Ala Tyr Ala Trp Met Ala Pro Glu Val Ile Arg Ala Ser Met Phe Ser
            180                 185                 190

Lys Gly Ser Asp Val Trp Ser Tyr Gly Val Leu Leu Trp Glu Leu Leu
        195                 200                 205

Thr Gly Glu Val Pro Phe Arg Gly Ile Asp Gly Leu Ala Val Ala Tyr
    210                 215                 220

Gly Val Ala Met Asn Lys Leu Ala Leu Pro Ile Pro Ser Thr Cys Pro
225                 230                 235                 240

Glu Pro Phe Ala Lys Leu Met Glu Asp Cys Trp Asn Pro Asp Pro His
                245                 250                 255

Ser Arg Pro Ser Phe Thr Asn Ile Leu Asp Gln Leu Thr Thr Ile
            260                 265                 270

<210> SEQ ID NO 34
<211> LENGTH: 1118
<212> TYPE: PRT
<213> ORGANISM: HUMAN
<300> PUBLICATION INFORMATION:
<301> AUTHORS: Durkin,J.T., Holskin,B.P., Kopec,K.K., Reed,M.S.,
      Spais,C.M.,
<302> TITLE: Phosphoregulation of mixed-lineage kinase 1 activity by
      multiple
<303> JOURNAL: Biochemistry Intern'l
<304> VOLUME: 43
<305> ISSUE: 51
<306> PAGES: 16348-16355
<307> DATE: 2004-12-28
<308> DATABASE ACCESSION NUMBER: NP_149132
<309> DATABASE ENTRY DATE: 2012-04-01
<313> RELEVANT RESIDUES IN SEQ ID NO: (1)..(1118)

<400> SEQUENCE: 34

Met Glu Pro Ser Arg Ala Leu Leu Gly Cys Leu Ala Ser Ala Ala Ala
1               5                   10                  15

Ala Ala Pro Pro Gly Glu Asp Gly Ala Gly Ala Gly Ala Glu Glu Glu
                20                  25                  30

Glu Glu Glu Glu Glu Glu Ala Ala Ala Ala Val Gly Pro Gly Glu Leu
            35                  40                  45

Gly Cys Asp Ala Pro Leu Pro Tyr Trp Thr Ala Val Phe Glu Tyr Glu
        50                  55                  60
```

```
            Ala Ala Gly Glu Asp Glu Leu Thr Leu Arg Leu Gly Asp Val Val Glu
            65              70                  75                  80

Val Leu Ser Lys Asp Ser Gln Val Ser Gly Asp Glu Gly Trp Trp Thr
                            85                  90                  95

Gly Gln Leu Asn Gln Arg Val Gly Ile Phe Pro Ser Asn Tyr Val Thr
                        100                 105                 110

Pro Arg Ser Ala Phe Ser Ser Arg Cys Gln Pro Gly Gly Glu Asp Pro
                        115                 120                 125

Ser Cys Tyr Pro Pro Ile Gln Leu Leu Glu Ile Asp Phe Ala Glu Leu
                        130                 135                 140

Thr Leu Glu Glu Ile Ile Gly Ile Gly Gly Phe Gly Lys Val Tyr Arg
            145                 150                 155                 160

Ala Phe Trp Ile Gly Asp Glu Val Ala Val Lys Ala Ala Arg His Asp
                            165                 170                 175

Pro Asp Glu Asp Ile Ser Gln Thr Ile Glu Asn Val Arg Gln Glu Ala
                        180                 185                 190

Lys Leu Phe Ala Met Leu Lys His Pro Asn Ile Ile Ala Leu Arg Gly
                        195                 200                 205

Val Cys Leu Lys Glu Pro Asn Leu Cys Leu Val Met Glu Phe Ala Arg
                        210                 215                 220

Gly Gly Pro Leu Asn Arg Val Leu Ser Gly Lys Arg Ile Pro Pro Asp
            225                 230                 235                 240

Ile Leu Val Asn Trp Ala Val Gln Ile Ala Arg Gly Met Asn Tyr Leu
                            245                 250                 255

His Asp Glu Ala Ile Val Pro Ile Ile His Arg Asp Leu Lys Ser Ser
                        260                 265                 270

Asn Ile Leu Ile Leu Gln Lys Val Glu Asn Gly Asp Leu Ser Asn Lys
                        275                 280                 285

Ile Leu Lys Ile Thr Asp Phe Gly Leu Ala Arg Glu Trp His Arg Thr
                        290                 295                 300

Thr Lys Met Ser Ala Ala Gly Thr Tyr Ala Trp Met Ala Pro Glu Val
            305                 310                 315                 320

Ile Arg Ala Ser Met Phe Ser Lys Gly Ser Asp Val Trp Ser Tyr Gly
                            325                 330                 335

Val Leu Leu Trp Glu Leu Leu Thr Gly Glu Val Pro Phe Arg Gly Ile
                        340                 345                 350

Asp Gly Leu Ala Val Ala Tyr Gly Val Ala Met Asn Lys Leu Ala Leu
                        355                 360                 365

Pro Ile Pro Ser Thr Cys Pro Glu Pro Phe Ala Lys Leu Met Glu Asp
                        370                 375                 380

Cys Trp Asn Pro Asp Pro His Ser Arg Pro Ser Phe Thr Asn Ile Leu
            385                 390                 395                 400

Asp Gln Leu Thr Thr Ile Glu Glu Ser Gly Phe Phe Glu Met Pro Lys
                            405                 410                 415

Asp Ser Phe His Cys Leu Gln Asp Asn Trp Lys His Glu Ile Gln Glu
                        420                 425                 430

Met Phe Asp Gln Leu Arg Ala Lys Glu Lys Glu Leu Arg Thr Trp Glu
                        435                 440                 445

Glu Glu Leu Thr Arg Ala Ala Leu Gln Gln Lys Asn Gln Glu Glu Leu
                        450                 455                 460

Leu Arg Arg Arg Glu Gln Glu Leu Ala Glu Arg Glu Ile Asp Ile Leu
            465                 470                 475                 480
```

```
Glu Arg Glu Leu Asn Ile Ile Ile His Gln Leu Cys Gln Glu Lys Pro
            485                 490                 495

Arg Val Lys Lys Arg Lys Gly Lys Phe Arg Lys Ser Arg Leu Lys Leu
        500                 505                 510

Lys Asp Gly Asn Arg Ile Ser Leu Pro Ser Asp Phe Gln His Lys Phe
            515                 520                 525

Thr Val Gln Ala Ser Pro Thr Met Asp Lys Arg Lys Ser Leu Ile Asn
        530                 535                 540

Ser Arg Ser Ser Pro Pro Ala Ser Pro Thr Ile Ile Pro Arg Leu Arg
545                 550                 555                 560

Ala Ile Gln Leu Thr Pro Gly Glu Ser Ser Lys Thr Trp Gly Arg Ser
            565                 570                 575

Ser Val Val Pro Lys Glu Glu Gly Glu Glu Glu Lys Arg Ala Pro
        580                 585                 590

Lys Lys Lys Gly Arg Thr Trp Gly Pro Gly Thr Leu Gly Gln Lys Glu
            595                 600                 605

Leu Ala Ser Gly Asp Glu Gly Ser Pro Gln Arg Arg Glu Lys Ala Asn
        610                 615                 620

Gly Leu Ser Thr Pro Ser Glu Ser Pro His Phe His Leu Gly Leu Lys
625                 630                 635                 640

Ser Leu Val Asp Gly Tyr Lys Gln Trp Ser Ser Ser Ala Pro Asn Leu
            645                 650                 655

Val Lys Gly Pro Arg Ser Ser Pro Ala Leu Pro Gly Phe Thr Ser Leu
        660                 665                 670

Met Glu Met Ala Leu Leu Ala Ala Ser Trp Val Val Pro Ile Asp Ile
            675                 680                 685

Glu Glu Asp Glu Asp Ser Glu Gly Pro Gly Ser Gly Glu Ser Arg Leu
        690                 695                 700

Gln His Ser Pro Ser Gln Ser Tyr Leu Cys Ile Pro Phe Pro Arg Gly
705                 710                 715                 720

Glu Asp Gly Asp Gly Pro Ser Ser Asp Gly Ile His Glu Glu Pro Thr
            725                 730                 735

Pro Val Asn Ser Ala Thr Ser Thr Pro Gln Leu Thr Pro Thr Asn Ser
        740                 745                 750

Leu Lys Arg Gly Gly Ala His His Arg Arg Cys Glu Val Ala Leu Leu
            755                 760                 765

Gly Cys Gly Ala Val Leu Ala Ala Thr Gly Leu Gly Phe Asp Leu Leu
        770                 775                 780

Glu Ala Gly Lys Cys Gln Leu Leu Pro Leu Glu Glu Pro Glu Pro Pro
785                 790                 795                 800

Ala Arg Glu Glu Lys Lys Arg Arg Glu Gly Leu Phe Gln Arg Ser Ser
            805                 810                 815

Arg Pro Arg Arg Ser Thr Ser Pro Pro Ser Arg Lys Leu Phe Lys Lys
        820                 825                 830

Glu Glu Pro Met Leu Leu Leu Gly Asp Pro Ser Ala Ser Leu Thr Leu
            835                 840                 845

Leu Ser Leu Ser Ser Ile Ser Glu Cys Asn Ser Thr Arg Ser Leu Leu
850                 855                 860

Arg Ser Asp Ser Asp Glu Ile Val Val Tyr Glu Met Pro Val Ser Pro
865                 870                 875                 880

Val Glu Ala Pro Pro Leu Ser Pro Cys Thr His Asn Pro Leu Val Asn
            885                 890                 895

Val Arg Val Glu Arg Phe Lys Arg Asp Pro Asn Gln Ser Leu Thr Pro
```

```
                        900                 905                 910
Thr His Val Thr Leu Thr Thr Pro Ser Gln Pro Ser His Arg Arg
            915                 920                 925
Thr Pro Ser Asp Gly Ala Leu Lys Pro Glu Thr Leu Leu Ala Ser Arg
            930                 935                 940
Ser Pro Ser Ser Asn Gly Leu Ser Pro Ser Pro Gly Ala Gly Met Leu
945                 950                 955                 960
Lys Thr Pro Ser Pro Ser Arg Asp Pro Gly Glu Phe Pro Arg Leu Pro
                965                 970                 975
Asp Pro Asn Val Val Phe Pro Pro Thr Pro Arg Arg Trp Asn Thr Gln
            980                 985                 990
Gln Asp Ser Thr Leu Glu Arg Pro Lys Thr Leu Glu Phe Leu Pro Arg
            995                 1000                1005
Pro Arg Pro Ser Ala Asn Arg Gln Arg Leu Asp Pro Trp Trp Phe
            1010                1015                1020
Val Ser Pro Ser His Ala Arg Ser Thr Ser Pro Ala Asn Ser Ser
            1025                1030                1035
Ser Thr Glu Thr Pro Ser Asn Leu Asp Ser Cys Phe Ala Ser Ser
            1040                1045                1050
Ser Ser Thr Val Glu Glu Arg Pro Gly Leu Pro Ala Leu Leu Pro
            1055                1060                1065
Phe Gln Ala Gly Pro Leu Pro Pro Thr Glu Arg Thr Leu Leu Asp
            1070                1075                1080
Leu Asp Ala Glu Gly Gln Ser Gln Asp Ser Thr Val Pro Leu Cys
            1085                1090                1095
Arg Ala Glu Leu Asn Thr His Arg Pro Ala Pro Tyr Glu Ile Gln
            1100                1105                1110
Gln Glu Phe Trp Ser
            1115

<210> SEQ ID NO 35
<211> LENGTH: 846
<212> TYPE: PRT
<213> ORGANISM: HUMAN
<300> PUBLICATION INFORMATION:
<301> AUTHORS: Rikova,K., Guo,A., Zeng,Q., Possemato,A., Yu,J.,
      Haack,H.,
<302> TITLE: Global survey of phosphotyrosine signaling identifies
      oncogenic
<303> JOURNAL: Cell
<304> VOLUME: 131
<305> ISSUE: 6
<306> PAGES: 1190-1203
<307> DATE: 2007-12-14
<308> DATABASE ACCESSION NUMBER: NP_006566
<309> DATABASE ENTRY DATE: 2012-05-05
<313> RELEVANT RESIDUES IN SEQ ID NO: (1)..(846)

<400> SEQUENCE: 35

Met Glu Ala Pro Leu Arg Pro Ala Ala Asp Ile Leu Arg Arg Asn Pro
1               5                   10                  15
Gln Gln Asp Tyr Glu Leu Val Gln Arg Val Gly Ser Gly Thr Tyr Gly
            20                  25                  30
Asp Val Tyr Lys Ala Arg Asn Val His Thr Gly Glu Leu Ala Ala Val
        35                  40                  45
Lys Ile Ile Lys Leu Glu Pro Gly Asp Asp Phe Ser Leu Ile Gln Gln
    50                  55                  60
Glu Ile Phe Met Val Lys Glu Cys Lys His Cys Asn Ile Val Ala Tyr
65                  70                  75                  80
```

-continued

```
Phe Gly Ser Tyr Leu Ser Arg Glu Lys Leu Trp Ile Cys Met Glu Tyr
                85                  90                  95
Cys Gly Gly Gly Ser Leu Gln Asp Ile Tyr His Val Thr Gly Pro Leu
            100                 105                 110
Ser Glu Leu Gln Ile Ala Tyr Val Cys Arg Glu Thr Leu Gln Gly Leu
        115                 120                 125
Ala Tyr Leu His Thr Lys Gly Lys Met His Arg Asp Ile Lys Gly Ala
    130                 135                 140
Asn Ile Leu Leu Thr Asp His Gly Asp Val Lys Leu Ala Asp Phe Gly
145                 150                 155                 160
Val Ala Ala Lys Ile Thr Ala Thr Ile Ala Lys Arg Lys Ser Phe Ile
                165                 170                 175
Gly Thr Pro Tyr Trp Met Ala Pro Glu Val Ala Ala Val Glu Lys Asn
            180                 185                 190
Gly Gly Tyr Asn Gln Leu Cys Asp Ile Trp Ala Val Gly Ile Thr Ala
        195                 200                 205
Ile Glu Leu Gly Glu Leu Gln Pro Pro Met Phe Asp Leu His Pro Met
    210                 215                 220
Arg Ala Leu Phe Leu Met Ser Lys Ser Asn Phe Gln Pro Pro Lys Leu
225                 230                 235                 240
Lys Asp Lys Thr Lys Trp Ser Ser Thr Phe His Asn Phe Val Lys Ile
                245                 250                 255
Ala Leu Thr Lys Asn Pro Lys Lys Arg Pro Thr Ala Glu Arg Leu Leu
            260                 265                 270
Thr His Thr Phe Val Ala Gln Pro Gly Leu Ser Arg Ala Leu Ala Val
        275                 280                 285
Glu Leu Leu Asp Lys Val Asn Asn Pro Asp Asn His Ala His Tyr Thr
    290                 295                 300
Glu Ala Asp Asp Asp Phe Glu Pro His Ala Ile Ile Arg His Thr
305                 310                 315                 320
Ile Arg Ser Thr Asn Arg Asn Ala Arg Ala Glu Arg Thr Ala Ser Glu
                325                 330                 335
Ile Asn Phe Asp Lys Leu Gln Phe Glu Pro Pro Leu Arg Lys Glu Thr
            340                 345                 350
Glu Ala Arg Asp Glu Met Gly Leu Ser Ser Asp Pro Asn Phe Met Leu
        355                 360                 365
Gln Trp Asn Pro Phe Val Asp Gly Ala Asn Thr Gly Lys Ser Thr Ser
    370                 375                 380
Lys Arg Ala Ile Pro Pro Leu Pro Pro Lys Pro Arg Ile Ser Ser
385                 390                 395                 400
Tyr Pro Glu Asp Asn Phe Pro Asp Glu Glu Lys Ala Ser Thr Ile Lys
                405                 410                 415
His Cys Pro Asp Ser Glu Ser Arg Ala Pro Gln Ile Leu Arg Arg Gln
            420                 425                 430
Ser Ser Pro Ser Cys Gly Pro Val Ala Glu Thr Ser Ser Ile Gly Asn
        435                 440                 445
Gly Asp Gly Ile Ser Lys Leu Met Ser Glu Asn Thr Glu Gly Ser Ala
    450                 455                 460
Gln Ala Pro Gln Leu Pro Arg Lys Lys Asp Lys Arg Asp Phe Pro Lys
465                 470                 475                 480
Pro Ala Ile Asn Gly Leu Pro Pro Thr Pro Lys Val Leu Met Gly Ala
                485                 490                 495
```

```
Cys Phe Ser Lys Val Phe Asp Gly Cys Pro Leu Lys Ile Asn Cys Ala
            500                 505                 510

Thr Ser Trp Ile His Pro Asp Thr Lys Asp Gln Tyr Ile Ile Phe Gly
            515                 520                 525

Thr Glu Asp Gly Ile Tyr Thr Leu Asn Leu Asn Glu Leu His Glu Ala
            530                 535                 540

Thr Met Glu Gln Leu Phe Pro Arg Lys Cys Thr Trp Leu Tyr Val Ile
545                 550                 555                 560

Asn Asn Thr Leu Met Ser Leu Ser Glu Gly Lys Thr Phe Gln Leu Tyr
            565                 570                 575

Ser His Asn Leu Ile Ala Leu Phe Glu His Ala Lys Lys Pro Gly Leu
            580                 585                 590

Ala Ala His Ile Gln Thr His Arg Phe Pro Asp Arg Ile Leu Pro Arg
            595                 600                 605

Lys Phe Ala Leu Thr Thr Lys Ile Pro Asp Thr Lys Gly Cys His Lys
            610                 615                 620

Cys Cys Ile Val Arg Asn Pro Tyr Thr Gly His Lys Tyr Leu Cys Gly
625                 630                 635                 640

Ala Leu Gln Ser Gly Ile Val Leu Leu Gln Trp Tyr Glu Pro Met Gln
            645                 650                 655

Lys Phe Met Leu Ile Lys His Phe Asp Phe Pro Leu Pro Ser Pro Leu
            660                 665                 670

Asn Val Phe Glu Met Leu Val Ile Pro Glu Gln Glu Tyr Pro Met Val
            675                 680                 685

Cys Val Ala Ile Ser Lys Gly Thr Glu Ser Asn Gln Val Val Gln Phe
690                 695                 700

Glu Thr Ile Asn Leu Asn Ser Ala Ser Ser Trp Phe Thr Glu Ile Gly
705                 710                 715                 720

Ala Gly Ser Gln Gln Leu Asp Ser Ile His Val Thr Gln Leu Glu Arg
            725                 730                 735

Asp Thr Val Leu Val Cys Leu Asp Lys Phe Val Lys Ile Val Asn Leu
            740                 745                 750

Gln Gly Lys Leu Lys Ser Ser Lys Lys Leu Ala Ser Glu Leu Ser Phe
            755                 760                 765

Asp Phe Arg Ile Glu Ser Val Val Cys Leu Gln Asp Ser Val Leu Ala
            770                 775                 780

Phe Trp Lys His Gly Met Gln Gly Lys Ser Phe Lys Ser Asp Glu Val
785                 790                 795                 800

Thr Gln Glu Ile Ser Asp Glu Thr Arg Val Phe Arg Leu Leu Gly Ser
            805                 810                 815

Asp Arg Val Val Val Leu Glu Ser Arg Pro Thr Glu Asn Pro Thr Ala
            820                 825                 830

His Ser Asn Leu Tyr Ile Leu Ala Gly His Glu Asn Ser Tyr
            835                 840                 845

<210> SEQ ID NO 36
<211> LENGTH: 1312
<212> TYPE: PRT
<213> ORGANISM: HUMAN
<300> PUBLICATION INFORMATION:
<301> AUTHORS: Hussain,N.K., Hsin,H., Huganir,R.L. and Sheng,M.
<302> TITLE: MINK and TNIK differentially act on Rap2-mediated signal
<303> JOURNAL: J. Neurosci.
<304> VOLUME: 30
<305> ISSUE: 44
<306> PAGES: 14786-14794
<307> DATE: 2010-11-03
```

<308> DATABASE ACCESSION NUMBER: NP_001020108
<309> DATABASE ENTRY DATE: 2012-04-29
<313> RELEVANT RESIDUES IN SEQ ID NO: (1)..(1312)

<400> SEQUENCE: 36

```
Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
            100                 105                 110

Val Thr Asp Leu Val Lys Asn Thr Lys Gly Asn Ala Leu Lys Glu Asp
        115                 120                 125

Cys Ile Ala Tyr Ile Cys Arg Glu Ile Leu Arg Gly Leu Ala His Leu
    130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Ile Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Ile Asp Phe Ile Asp Thr Cys Leu Ile Lys
            260                 265                 270

Thr Tyr Leu Ser Arg Pro Pro Thr Glu Gln Leu Leu Lys Phe Pro Phe
        275                 280                 285

Ile Arg Asp Gln Pro Thr Glu Arg Gln Val Arg Ile Gln Leu Lys Asp
    290                 295                 300

His Ile Asp Arg Ser Arg Lys Lys Arg Gly Glu Lys Glu Thr Glu
305                 310                 315                 320

Tyr Glu Tyr Ser Gly Ser Glu Glu Asp Asp Ser His Gly Glu Glu
                325                 330                 335

Gly Glu Pro Ser Ser Ile Met Asn Val Pro Gly Glu Ser Thr Leu Arg
            340                 345                 350

Arg Glu Phe Leu Arg Leu Gln Gln Glu Asn Lys Ser Asn Ser Glu Ala
        355                 360                 365

Leu Lys Gln Gln Gln Gln Leu Gln Gln Gln Gln Arg Asp Pro Glu
    370                 375                 380

Ala His Ile Lys His Leu Leu His Gln Arg Gln Arg Arg Ile Glu Glu
```

```
              385                 390                 395                 400
         Gln Lys Glu Glu Arg Arg Val Glu Glu Gln Gln Arg Arg Glu Arg
                         405                 410                 415
         Glu Gln Arg Lys Leu Gln Glu Lys Glu Gln Gln Arg Arg Leu Glu Asp
                         420                 425                 430
         Met Gln Ala Leu Arg Arg Glu Glu Arg Arg Gln Ala Glu Arg Glu
                         435                 440                 445
         Gln Glu Tyr Lys Arg Lys Gln Leu Glu Glu Gln Arg Gln Ser Glu Arg
                         450                 455                 460
         Leu Gln Arg Gln Leu Gln Gln Glu His Ala Tyr Leu Lys Ser Leu Gln
         465                 470                 475                 480
         Gln Gln Gln Gln Gln Gln Leu Gln Lys Gln Gln Gln Gln Leu
                         485                 490                 495
         Leu Pro Gly Asp Arg Lys Pro Leu Tyr His Tyr Gly Arg Gly Met Asn
                         500                 505                 510
         Pro Ala Asp Lys Pro Ala Trp Ala Arg Glu Val Glu Glu Arg Thr Arg
                         515                 520                 525
         Met Asn Lys Gln Gln Asn Ser Pro Leu Ala Lys Ser Lys Pro Gly Ser
                         530                 535                 540
         Thr Gly Pro Glu Pro Pro Ile Pro Gln Ala Ser Pro Gly Pro Pro Gly
         545                 550                 555                 560
         Pro Leu Ser Gln Thr Pro Pro Met Gln Arg Pro Val Glu Pro Gln Glu
                         565                 570                 575
         Gly Pro His Lys Ser Leu Gln Asp Gln Pro Thr Arg Asn Leu Ala Ala
                         580                 585                 590
         Phe Pro Ala Ser His Asp Pro Asp Pro Ala Ile Pro Ala Pro Thr Ala
                         595                 600                 605
         Thr Pro Ser Ala Arg Gly Ala Val Ile Arg Gln Asn Ser Asp Pro Thr
                         610                 615                 620
         Ser Glu Gly Pro Gly Pro Ser Pro Asn Pro Pro Ala Trp Val Arg Pro
         625                 630                 635                 640
         Asp Asn Glu Ala Pro Pro Lys Val Pro Gln Arg Thr Ser Ser Ile Ala
                         645                 650                 655
         Thr Ala Leu Asn Thr Ser Gly Ala Gly Gly Ser Arg Pro Ala Gln Ala
                         660                 665                 670
         Val Arg Ala Arg Pro Arg Ser Asn Ser Ala Trp Gln Ile Tyr Leu Gln
                         675                 680                 685
         Arg Arg Ala Glu Arg Gly Thr Pro Lys Pro Pro Gly Pro Pro Ala Gln
                         690                 695                 700
         Pro Pro Gly Pro Pro Asn Ala Ser Ser Asn Pro Asp Leu Arg Arg Ser
         705                 710                 715                 720
         Asp Pro Gly Trp Glu Arg Ser Asp Ser Val Leu Pro Ala Ser His Gly
                         725                 730                 735
         His Leu Pro Gln Ala Gly Ser Leu Glu Arg Asn Arg Val Gly Val Ser
                         740                 745                 750
         Ser Lys Pro Asp Ser Ser Pro Val Leu Ser Pro Gly Asn Lys Ala Lys
                         755                 760                 765
         Pro Asp Asp His Arg Ser Arg Pro Gly Arg Pro Ala Asp Phe Val Leu
                         770                 775                 780
         Leu Lys Glu Arg Thr Leu Asp Glu Ala Pro Arg Pro Pro Lys Lys Ala
         785                 790                 795                 800
         Met Asp Tyr Ser Ser Ser Ser Glu Glu Val Glu Ser Ser Glu Asp Asp
                         805                 810                 815
```

-continued

Glu Glu Glu Gly Glu Gly Gly Pro Ala Glu Gly Ser Arg Asp Thr Pro
                820                 825                 830

Gly Gly Arg Ser Asp Gly Asp Thr Asp Ser Val Ser Thr Met Val Val
835                 840                 845

His Asp Val Glu Glu Ile Thr Gly Thr Gln Pro Pro Tyr Gly Gly Gly
850                 855                 860

Thr Met Val Val Gln Arg Thr Pro Glu Glu Arg Asn Leu Leu His
865                 870                 875                 880

Ala Asp Ser Asn Gly Tyr Thr Asn Leu Pro Asp Val Val Gln Pro Ser
                885                 890                 895

His Ser Pro Thr Glu Asn Ser Lys Gly Gln Ser Pro Ser Lys Asp
                900                 905                 910

Gly Ser Gly Asp Tyr Gln Ser Arg Gly Leu Val Lys Ala Pro Gly Lys
                915                 920                 925

Ser Ser Phe Thr Met Phe Val Asp Leu Gly Ile Tyr Gln Pro Gly Gly
    930                 935                 940

Ser Gly Asp Ser Ile Pro Ile Thr Ala Leu Val Gly Gly Glu Gly Thr
945                 950                 955                 960

Arg Leu Asp Gln Leu Gln Tyr Asp Val Arg Lys Gly Ser Val Val Asn
                965                 970                 975

Val Asn Pro Thr Asn Thr Arg Ala His Ser Glu Thr Pro Glu Ile Arg
                980                 985                 990

Lys Tyr Lys Lys Arg Phe Asn Ser Glu Ile Leu Cys Ala Ala Leu Trp
                995                 1000                1005

Gly Val Asn Leu Leu Val Gly Thr Glu Asn Gly Leu Met Leu Leu
    1010                1015                1020

Asp Arg Ser Gly Gln Gly Lys Val Tyr Gly Leu Ile Gly Arg Arg
    1025                1030                1035

Arg Phe Gln Gln Met Asp Val Leu Glu Gly Leu Asn Leu Leu Ile
    1040                1045                1050

Thr Ile Ser Gly Lys Arg Asn Lys Leu Arg Val Tyr Tyr Leu Ser
    1055                1060                1065

Trp Leu Arg Asn Lys Ile Leu His Asn Asp Pro Glu Val Glu Lys
    1070                1075                1080

Lys Gln Gly Trp Thr Thr Val Gly Asp Met Glu Gly Cys Gly His
    1085                1090                1095

Tyr Arg Val Val Lys Tyr Glu Arg Ile Lys Phe Leu Val Ile Ala
    1100                1105                1110

Leu Lys Ser Ser Val Glu Val Tyr Ala Trp Ala Pro Lys Pro Tyr
    1115                1120                1125

His Lys Phe Met Ala Phe Lys Ser Phe Ala Asp Leu Pro His Arg
    1130                1135                1140

Pro Leu Leu Val Asp Leu Thr Val Glu Glu Gly Gln Arg Leu Lys
    1145                1150                1155

Val Ile Tyr Gly Ser Ser Ala Gly Phe His Ala Val Asp Val Asp
    1160                1165                1170

Ser Gly Asn Ser Tyr Asp Ile Tyr Ile Pro Val His Ile Gln Ser
    1175                1180                1185

Gln Ile Thr Pro His Ala Ile Ile Phe Leu Pro Asn Thr Asp Gly
    1190                1195                1200

Met Glu Met Leu Leu Cys Tyr Glu Asp Glu Gly Val Tyr Val Asn
    1205                1210                1215

-continued

```
Thr Tyr Gly Arg Ile Ile Lys Asp Val Val Leu Gln Trp Gly Glu
    1220            1225                1230

Met Pro Thr Ser Val Ala Tyr Ile Cys Ser Asn Gln Ile Met Gly
1235            1240                1245

Trp Gly Glu Lys Ala Ile Glu Ile Arg Ser Val Glu Thr Gly His
    1250            1255                1260

Leu Asp Gly Val Phe Met His Lys Arg Ala Gln Arg Leu Lys Phe
1265            1270                1275

Leu Cys Glu Arg Asn Asp Lys Val Phe Phe Ala Ser Val Arg Ser
    1280            1285                1290

Gly Gly Ser Ser Gln Val Tyr Phe Met Thr Leu Asn Arg Asn Cys
1295            1300                1305

Ile Met Asn Trp
    1310

<210> SEQ ID NO 37
<211> LENGTH: 795
<212> TYPE: PRT
<213> ORGANISM: HUMAN
<300> PUBLICATION INFORMATION:
<301> AUTHORS: Timm,T., Marx,A., Panneerselvam,S., Mandelkow,E. and
      Mandelkow,E.M.
<302> TITLE: Structure and regulation of MARK, a kinase involved in
      abnormal
<303> JOURNAL: BMC Neurosci
<304> VOLUME: 9
<305> ISSUE: 2
<306> PAGES: S9
<307> DATE: 2008-12-08
<308> DATABASE ACCESSION NUMBER: NP_061120
<309> DATABASE ENTRY DATE: 2012-03-25
<313> RELEVANT RESIDUES IN SEQ ID NO: (1)..(795)

<400> SEQUENCE: 37

Met Ser Ala Arg Thr Pro Leu Pro Thr Val Asn Glu Arg Asp Thr Glu
1               5                   10                  15

Asn His Thr Ser Val Asp Gly Tyr Thr Glu Pro His Ile Gln Pro Thr
            20                  25                  30

Lys Ser Ser Ser Arg Gln Asn Ile Pro Arg Cys Arg Asn Ser Ile Thr
        35                  40                  45

Ser Ala Thr Asp Glu Gln Pro His Ile Gly Asn Tyr Arg Leu Gln Lys
    50                  55                  60

Thr Ile Gly Lys Gly Asn Phe Ala Lys Val Lys Leu Ala Arg His Val
65                  70                  75                  80

Leu Thr Gly Arg Glu Val Ala Val Lys Ile Ile Asp Lys Thr Gln Leu
                85                  90                  95

Asn Pro Thr Ser Leu Gln Lys Leu Phe Arg Glu Val Arg Ile Met Lys
            100                 105                 110

Ile Leu Asn His Pro Asn Ile Val Lys Leu Phe Glu Val Ile Glu Thr
        115                 120                 125

Glu Lys Thr Leu Tyr Leu Val Met Glu Tyr Ala Ser Gly Gly Glu Val
    130                 135                 140

Phe Asp Tyr Leu Val Ala His Gly Arg Met Lys Glu Lys Glu Ala Arg
145                 150                 155                 160

Ala Lys Phe Arg Gln Ile Val Ser Ala Val Gln Tyr Cys His Gln Lys
                165                 170                 175

Tyr Ile Val His Arg Asp Leu Lys Ala Glu Asn Leu Leu Leu Asp Gly
            180                 185                 190

Asp Met Asn Ile Lys Ile Ala Asp Phe Gly Phe Ser Asn Glu Phe Thr
```

```
            195                 200                 205
Val Gly Asn Lys Leu Asp Thr Phe Cys Gly Ser Pro Pro Tyr Ala Ala
210                 215                 220

Pro Glu Leu Phe Gln Gly Lys Lys Tyr Asp Gly Pro Glu Val Asp Val
225                 230                 235                 240

Trp Ser Leu Gly Val Ile Leu Tyr Thr Leu Val Ser Gly Ser Leu Pro
                    245                 250                 255

Phe Asp Gly Gln Asn Leu Lys Glu Leu Arg Glu Arg Val Leu Arg Gly
                260                 265                 270

Lys Tyr Arg Ile Pro Phe Tyr Met Ser Thr Asp Cys Glu Asn Leu Leu
            275                 280                 285

Lys Lys Leu Leu Val Leu Asn Pro Ile Lys Arg Gly Ser Leu Glu Gln
290                 295                 300

Ile Met Lys Asp Arg Trp Met Asn Val Gly His Glu Glu Glu Glu Leu
305                 310                 315                 320

Lys Pro Tyr Thr Glu Pro Asp Pro Asp Phe Asn Asp Thr Lys Arg Ile
                    325                 330                 335

Asp Ile Met Val Thr Met Gly Phe Ala Arg Asp Glu Ile Asn Asp Ala
                340                 345                 350

Leu Ile Asn Gln Lys Tyr Asp Glu Val Met Ala Thr Tyr Ile Leu Leu
            355                 360                 365

Gly Arg Lys Pro Pro Glu Phe Glu Gly Gly Glu Ser Leu Ser Ser Gly
370                 375                 380

Asn Leu Cys Gln Arg Ser Arg Pro Ser Ser Asp Leu Asn Asn Ser Thr
385                 390                 395                 400

Leu Gln Ser Pro Ala His Leu Lys Val Gln Arg Ser Ile Ser Ala Asn
                    405                 410                 415

Gln Lys Gln Arg Arg Phe Ser Asp His Ala Gly Pro Ser Ile Pro Pro
                420                 425                 430

Ala Val Ser Tyr Thr Lys Arg Pro Gln Ala Asn Ser Val Glu Ser Glu
            435                 440                 445

Gln Lys Glu Glu Trp Asp Lys Asp Val Ala Arg Lys Leu Gly Ser Thr
450                 455                 460

Thr Val Gly Ser Lys Ser Glu Met Thr Ala Ser Pro Leu Val Gly Pro
465                 470                 475                 480

Glu Arg Lys Lys Ser Ser Thr Ile Pro Ser Asn Asn Val Tyr Ser Gly
                    485                 490                 495

Gly Ser Met Ala Arg Arg Asn Thr Tyr Val Cys Glu Arg Thr Thr Asp
                500                 505                 510

Arg Tyr Val Ala Leu Gln Asn Gly Lys Asp Ser Ser Leu Thr Glu Met
            515                 520                 525

Ser Val Ser Ser Ile Ser Ser Ala Gly Ser Ser Val Ala Ser Ala Val
530                 535                 540

Pro Ser Ala Arg Pro Arg His Gln Lys Ser Met Ser Thr Ser Gly His
545                 550                 555                 560

Pro Ile Lys Val Thr Leu Pro Thr Ile Lys Asp Gly Ser Glu Ala Tyr
                    565                 570                 575

Arg Pro Gly Thr Thr Gln Arg Val Pro Ala Ala Ser Pro Ser Ala His
                580                 585                 590

Ser Ile Ser Thr Ala Thr Pro Asp Arg Thr Arg Phe Pro Arg Gly Ser
            595                 600                 605

Ser Ser Arg Ser Thr Phe His Gly Glu Gln Leu Arg Glu Arg Arg Ser
610                 615                 620
```

```
Val Ala Tyr Asn Gly Pro Pro Ala Ser Pro Ser His Glu Thr Gly Ala
625                 630                 635                 640

Phe Ala His Ala Arg Arg Gly Thr Ser Thr Gly Ile Ile Ser Lys Ile
            645                 650                 655

Thr Ser Lys Phe Val Arg Arg Asp Pro Ser Glu Gly Glu Ala Ser Gly
        660                 665                 670

Arg Thr Asp Thr Ser Arg Ser Thr Ser Gly Glu Pro Lys Glu Arg Asp
        675                 680                 685

Lys Glu Glu Gly Lys Asp Ser Lys Pro Arg Ser Leu Arg Phe Thr Trp
690                 695                 700

Ser Met Lys Thr Thr Ser Ser Met Asp Pro Asn Asp Met Met Arg Glu
705                 710                 715                 720

Ile Arg Lys Val Leu Asp Ala Asn Asn Cys Asp Tyr Glu Gln Lys Glu
            725                 730                 735

Arg Phe Leu Leu Phe Cys Val His Gly Asp Ala Arg Gln Asp Ser Leu
            740                 745                 750

Val Gln Trp Glu Met Glu Val Cys Lys Leu Pro Arg Leu Ser Leu Asn
            755                 760                 765

Gly Val Arg Phe Lys Arg Ile Ser Gly Thr Ser Ile Ala Phe Lys Asn
        770                 775                 780

Ile Ala Ser Lys Ile Ala Asn Glu Leu Lys Leu
785                 790                 795

<210> SEQ ID NO 38
<211> LENGTH: 788
<212> TYPE: PRT
<213> ORGANISM: HUMAN
<300> PUBLICATION INFORMATION:
<301> AUTHORS: Drewes,G., Ebneth,A., Preuss,U., Mandelkow,E.M. and
      Mandelkow,E.
<302> TITLE: MARK, a novel family of protein kinases that phosphorylate
<303> JOURNAL: Cell
<304> VOLUME: 89
<305> ISSUE: 2
<306> PAGES: 297-308
<307> DATE: 1997-04-18
<308> DATABASE ACCESSION NUMBER: NP_001034558
<309> DATABASE ENTRY DATE: 2012-05-06
<313> RELEVANT RESIDUES IN SEQ ID NO: (1)..(788)

<400> SEQUENCE: 38

Met Ser Ser Ala Arg Thr Pro Leu Pro Thr Leu Asn Glu Arg Asp Thr
1               5                   10                  15

Glu Gln Pro Thr Leu Gly His Leu Asp Ser Lys Pro Ser Ser Lys Ser
                20                  25                  30

Asn Met Ile Arg Gly Arg Asn Ser Ala Thr Ser Ala Asp Glu Gln Pro
            35                  40                  45

His Ile Gly Asn Tyr Arg Leu Leu Lys Thr Ile Gly Lys Gly Asn Phe
        50                  55                  60

Ala Lys Val Lys Leu Ala Arg His Ile Leu Thr Gly Lys Glu Val Ala
65                  70                  75                  80

Val Lys Ile Ile Asp Lys Thr Gln Leu Asn Ser Ser Ser Leu Gln Lys
                85                  90                  95

Leu Phe Arg Glu Val Arg Ile Met Lys Val Leu Asn His Pro Asn Ile
            100                 105                 110

Val Lys Leu Phe Glu Val Ile Glu Thr Glu Lys Thr Leu Tyr Leu Val
        115                 120                 125

Met Glu Tyr Ala Ser Gly Gly Glu Val Phe Asp Tyr Leu Val Ala His
```

-continued

```
                130                 135                 140
Gly Arg Met Lys Glu Lys Glu Ala Arg Ala Lys Phe Arg Gln Ile Val
145                 150                 155                 160

Ser Ala Val Gln Tyr Cys His Gln Lys Phe Ile Val His Arg Asp Leu
                165                 170                 175

Lys Ala Glu Asn Leu Leu Leu Asp Ala Asp Met Asn Ile Lys Ile Ala
                180                 185                 190

Asp Phe Gly Phe Ser Asn Glu Phe Thr Phe Gly Asn Lys Leu Asp Thr
                195                 200                 205

Phe Cys Gly Ser Pro Pro Tyr Ala Ala Pro Glu Leu Phe Gln Gly Lys
                210                 215                 220

Lys Tyr Asp Gly Pro Glu Val Asp Val Trp Ser Leu Gly Val Ile Leu
225                 230                 235                 240

Tyr Thr Leu Val Ser Gly Ser Leu Pro Phe Asp Gly Gln Asn Leu Lys
                245                 250                 255

Glu Leu Arg Glu Arg Val Leu Arg Gly Lys Tyr Arg Ile Pro Phe Tyr
                260                 265                 270

Met Ser Thr Asp Cys Glu Asn Leu Leu Lys Lys Phe Leu Ile Leu Asn
                275                 280                 285

Pro Ser Lys Arg Gly Thr Leu Glu Gln Ile Met Lys Asp Arg Trp Met
290                 295                 300

Asn Val Gly His Glu Asp Asp Glu Leu Lys Pro Tyr Val Glu Pro Leu
305                 310                 315                 320

Pro Asp Tyr Lys Asp Pro Arg Arg Thr Glu Leu Met Val Ser Met Gly
                325                 330                 335

Tyr Thr Arg Glu Glu Ile Gln Asp Ser Leu Val Gly Gln Arg Tyr Asn
                340                 345                 350

Glu Val Met Ala Thr Tyr Leu Leu Leu Gly Tyr Lys Ser Ser Glu Leu
                355                 360                 365

Glu Gly Asp Thr Ile Thr Leu Lys Pro Arg Pro Ser Ala Asp Leu Thr
                370                 375                 380

Asn Ser Ser Ala Pro Ser Pro Ser His Lys Val Gln Arg Ser Val Ser
385                 390                 395                 400

Ala Asn Pro Lys Gln Arg Arg Phe Ser Asp Gln Ala Ala Gly Pro Ala
                405                 410                 415

Ile Pro Thr Ser Asn Ser Tyr Ser Lys Lys Thr Gln Ser Asn Asn Ala
                420                 425                 430

Glu Asn Lys Arg Pro Glu Glu Asp Arg Glu Ser Gly Arg Lys Ala Ser
                435                 440                 445

Ser Thr Ala Lys Val Pro Ala Ser Pro Leu Pro Gly Leu Glu Arg Lys
450                 455                 460

Lys Thr Thr Pro Thr Pro Ser Thr Asn Ser Val Leu Ser Thr Ser Thr
465                 470                 475                 480

Asn Arg Ser Arg Asn Ser Pro Leu Leu Glu Arg Ala Ser Leu Gly Gln
                485                 490                 495

Ala Ser Ile Gln Asn Gly Lys Asp Ser Leu Thr Met Pro Gly Ser Arg
                500                 505                 510

Ala Ser Thr Ala Ser Ala Ser Ala Ala Val Ser Ala Ala Arg Pro Arg
                515                 520                 525

Gln His Gln Lys Ser Met Ser Ala Ser Val His Pro Asn Lys Ala Ser
                530                 535                 540

Gly Leu Pro Pro Thr Glu Ser Asn Cys Glu Val Pro Arg Pro Ser Thr
545                 550                 555                 560
```

```
Ala Pro Gln Arg Val Pro Val Ala Ser Pro Ser Ala His Asn Ile Ser
            565                 570                 575

Ser Ser Gly Gly Ala Pro Asp Arg Thr Asn Phe Pro Arg Gly Val Ser
        580                 585                 590

Ser Arg Ser Thr Phe His Ala Gly Gln Leu Arg Gln Val Arg Asp Gln
        595                 600                 605

Gln Asn Leu Pro Tyr Gly Val Thr Pro Ala Ser Pro Ser Gly His Ser
610                 615                 620

Gln Gly Arg Arg Gly Ala Ser Gly Ser Ile Phe Ser Lys Phe Thr Ser
625                 630                 635                 640

Lys Phe Val Arg Arg Asn Leu Ser Phe Arg Phe Ala Arg Arg Asn Leu
            645                 650                 655

Asn Glu Pro Glu Ser Lys Asp Arg Val Glu Thr Leu Arg Pro His Val
            660                 665                 670

Val Gly Ser Gly Gly Asn Asp Lys Glu Lys Glu Glu Phe Arg Glu Ala
            675                 680                 685

Lys Pro Arg Ser Leu Arg Phe Thr Trp Ser Met Lys Thr Thr Ser Ser
            690                 695                 700

Met Glu Pro Asn Glu Met Met Arg Glu Ile Arg Lys Val Leu Asp Ala
705                 710                 715                 720

Asn Ser Cys Gln Ser Glu Leu His Glu Lys Tyr Met Leu Leu Cys Met
            725                 730                 735

His Gly Thr Pro Gly His Glu Asp Phe Val Gln Trp Glu Met Glu Val
            740                 745                 750

Cys Lys Leu Pro Arg Leu Ser Leu Asn Gly Val Arg Phe Lys Arg Ile
            755                 760                 765

Ser Gly Thr Ser Met Ala Phe Lys Asn Ile Ala Ser Lys Ile Ala Asn
            770                 775                 780

Glu Leu Lys Leu
785

<210> SEQ ID NO 39
<211> LENGTH: 753
<212> TYPE: PRT
<213> ORGANISM: HUMAN
<300> PUBLICATION INFORMATION:
<301> AUTHORS: Chia CY, Lim CW, Leong WT, Ling MH.
<302> TITLE: High expression stability of microtubule affinity
       regulating kinase 3 (MARK3) makes it a reliable reference gene.
<303> JOURNAL: IUBMB Life.
<304> VOLUME: 62
<305> ISSUE: 3
<306> PAGES: 200-203
<307> DATE: 2010-03-01
<308> DATABASE ACCESSION NUMBER: NP_001122390
<309> DATABASE ENTRY DATE: 2012-04-29
<313> RELEVANT RESIDUES IN SEQ ID NO: (1)..(753)

<400> SEQUENCE: 39

Met Ser Thr Arg Thr Pro Leu Pro Thr Val Asn Glu Arg Asp Thr Glu
1               5                   10                  15

Asn His Thr Ser His Gly Asp Gly Arg Gln Glu Val Thr Ser Arg Thr
            20                  25                  30

Ser Arg Ser Gly Ala Arg Cys Arg Asn Ser Ile Ala Ser Cys Ala Asp
        35                  40                  45

Glu Gln Pro His Ile Gly Asn Tyr Arg Leu Leu Lys Thr Ile Gly Lys
    50                  55                  60

Gly Asn Phe Ala Lys Val Lys Leu Ala Arg His Ile Leu Thr Gly Arg
```

```
            65                  70                  75                  80
        Glu Val Ala Ile Lys Ile Ile Asp Lys Thr Gln Leu Asn Pro Thr Ser
                            85                  90                  95

Leu Gln Lys Leu Phe Arg Glu Val Arg Ile Met Lys Ile Leu Asn His
                        100                 105                 110

Pro Asn Ile Val Lys Leu Phe Glu Val Ile Glu Thr Glu Lys Thr Leu
                        115                 120                 125

Tyr Leu Ile Met Glu Tyr Ala Ser Gly Gly Glu Val Phe Asp Tyr Leu
                    130                 135                 140

Val Ala His Gly Arg Met Lys Glu Lys Glu Ala Arg Ser Lys Phe Arg
        145                 150                 155                 160

Gln Ile Val Ser Ala Val Gln Tyr Cys His Gln Lys Arg Ile Val His
                            165                 170                 175

Arg Asp Leu Lys Ala Glu Asn Leu Leu Leu Asp Ala Asp Met Asn Ile
                        180                 185                 190

Lys Ile Ala Asp Phe Gly Phe Ser Asn Glu Phe Thr Val Gly Gly Lys
                    195                 200                 205

Leu Asp Thr Phe Cys Gly Ser Pro Pro Tyr Ala Ala Pro Glu Leu Phe
                210                 215                 220

Gln Gly Lys Lys Tyr Asp Gly Pro Glu Val Asp Val Trp Ser Leu Gly
        225                 230                 235                 240

Val Ile Leu Tyr Thr Leu Val Ser Gly Ser Leu Pro Phe Asp Gly Gln
                            245                 250                 255

Asn Leu Lys Glu Leu Arg Glu Arg Val Leu Arg Gly Lys Tyr Arg Ile
                        260                 265                 270

Pro Phe Tyr Met Ser Thr Asp Cys Glu Asn Leu Leu Lys Arg Phe Leu
                    275                 280                 285

Val Leu Asn Pro Ile Lys Arg Gly Thr Leu Glu Gln Ile Met Lys Asp
                290                 295                 300

Arg Trp Ile Asn Ala Gly His Glu Glu Asp Glu Leu Lys Pro Phe Val
        305                 310                 315                 320

Glu Pro Glu Leu Asp Ile Ser Asp Gln Lys Arg Ile Asp Ile Met Val
                            325                 330                 335

Gly Met Gly Tyr Ser Gln Glu Glu Ile Gln Glu Ser Leu Ser Lys Met
                        340                 345                 350

Lys Tyr Asp Glu Ile Thr Ala Thr Tyr Leu Leu Leu Gly Arg Lys Ser
                    355                 360                 365

Ser Glu Leu Asp Ala Ser Asp Ser Ser Ser Ser Asn Leu Ser Leu
                370                 375                 380

Ala Lys Val Arg Pro Ser Ser Asp Leu Asn Asn Ser Thr Gly Gln Ser
        385                 390                 395                 400

Pro His His Lys Val Gln Arg Ser Val Phe Ser Gln Lys Gln Arg
                            405                 410                 415

Arg Tyr Ser Asp His Ala Gly Pro Ala Ile Pro Ser Val Val Ala Tyr
                        420                 425                 430

Pro Lys Arg Ser Gln Thr Ser Thr Ala Asp Ser Asp Leu Lys Glu Asp
                    435                 440                 445

Gly Ile Ser Ser Arg Lys Ser Gly Ser Ala Val Gly Gly Lys Gly
                450                 455                 460

Ile Ala Pro Ala Ser Pro Met Leu Gly Asn Ala Ser Asn Pro Asn Lys
        465                 470                 475                 480

Ala Asp Ile Pro Glu Arg Lys Lys Ser Ser Thr Val Pro Ser Ser Asn
                            485                 490                 495
```

```
Thr Ala Ser Gly Gly Met Thr Arg Arg Asn Thr Tyr Val Cys Ser Glu
            500                 505                 510
Arg Thr Thr Ala Asp Arg His Ser Val Ile Gln Asn Gly Lys Glu Asn
        515                 520                 525
Ser Thr Ile Pro Asp Gln Arg Thr Pro Val Ala Ser Thr His Ser Ile
    530                 535                 540
Ser Ser Ala Ala Thr Pro Asp Arg Ile Arg Phe Pro Arg Gly Thr Ala
545                 550                 555                 560
Ser Arg Ser Thr Phe His Gly Gln Pro Arg Glu Arg Arg Thr Ala Thr
                565                 570                 575
Tyr Asn Gly Pro Pro Ala Ser Pro Ser Leu Ser His Glu Ala Thr Pro
            580                 585                 590
Leu Ser Gln Thr Arg Ser Arg Gly Ser Thr Asn Leu Phe Ser Lys Leu
        595                 600                 605
Thr Ser Lys Leu Thr Arg Arg Asn Met Ser Phe Arg Phe Ile Lys Arg
    610                 615                 620
Leu Pro Thr Glu Tyr Glu Arg Asn Gly Arg Tyr Glu Gly Ser Ser Arg
625                 630                 635                 640
Asn Val Ser Ala Glu Gln Lys Asp Glu Asn Lys Glu Ala Lys Pro Arg
                645                 650                 655
Ser Leu Arg Phe Thr Trp Ser Met Lys Thr Thr Ser Ser Met Asp Pro
            660                 665                 670
Gly Asp Met Met Arg Glu Ile Arg Lys Val Leu Asp Ala Asn Asn Cys
        675                 680                 685
Asp Tyr Glu Gln Arg Glu Arg Phe Leu Leu Phe Cys Val His Gly Asp
    690                 695                 700
Gly His Ala Glu Asn Leu Val Gln Trp Glu Met Glu Val Cys Lys Leu
705                 710                 715                 720
Pro Arg Leu Ser Leu Asn Gly Val Arg Phe Lys Arg Ile Ser Gly Thr
                725                 730                 735
Ser Ile Ala Phe Lys Asn Ile Ala Ser Lys Ile Ala Asn Glu Leu Lys
            740                 745                 750
Leu
```

<210> SEQ ID NO 40
<211> LENGTH: 752
<212> TYPE: PRT
<213> ORGANISM: human
<300> PUBLICATION INFORMATION:
<301> AUTHORS: Trinczek,B., Brajenovic,M., Ebneth,A. and Drewes,G.
<302> TITLE: MARK4 is a novel microtubule-associated
       proteins/microtubule
<303> JOURNAL: J. Biol. Chem.
<304> VOLUME: 279
<305> ISSUE: 7
<306> PAGES: 5915-5923
<307> DATE: 2004-11-01
<308> DATABASE ACCESSION NUMBER: NP_001186796
<309> DATABASE ENTRY DATE: 2012-05-13
<313> RELEVANT RESIDUES IN SEQ ID NO: (1)..(752)

<400> SEQUENCE: 40

```
Met Ser Ser Arg Thr Val Leu Ala Pro Gly Asn Asp Arg Asn Ser Asp
1               5                   10                  15
Thr His Gly Thr Leu Gly Ser Gly Arg Ser Ser Asp Lys Gly Pro Ser
            20                  25                  30
Trp Ser Ser Arg Ser Leu Gly Ala Arg Cys Arg Asn Ser Ile Ala Ser
        35                  40                  45
```

```
Cys Pro Glu Glu Gln Pro His Val Gly Asn Tyr Arg Leu Leu Arg Thr
 50                  55                  60

Ile Gly Lys Gly Asn Phe Ala Lys Val Lys Leu Ala Arg His Ile Leu
 65                  70                  75                  80

Thr Gly Arg Glu Val Ala Ile Lys Ile Ile Asp Lys Thr Gln Leu Asn
                     85                  90                  95

Pro Ser Ser Leu Gln Lys Leu Phe Arg Glu Val Arg Ile Met Lys Gly
                    100                 105                 110

Leu Asn His Pro Asn Ile Val Lys Leu Phe Glu Val Ile Glu Thr Glu
                115                 120                 125

Lys Thr Leu Tyr Leu Val Met Glu Tyr Ala Ser Ala Gly Glu Val Phe
            130                 135                 140

Asp Tyr Leu Val Ser His Gly Arg Met Lys Glu Lys Glu Ala Arg Ala
145                 150                 155                 160

Lys Phe Arg Gln Ile Val Ser Ala Val His Tyr Cys His Gln Lys Asn
                    165                 170                 175

Ile Val His Arg Asp Leu Lys Ala Glu Asn Leu Leu Leu Asp Ala Glu
                180                 185                 190

Ala Asn Ile Lys Ile Ala Asp Phe Gly Phe Ser Asn Glu Phe Thr Leu
            195                 200                 205

Gly Ser Lys Leu Asp Thr Phe Cys Gly Ser Pro Pro Tyr Ala Ala Pro
210                 215                 220

Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                    245                 250                 255

Asp Gly His Asn Leu Lys Glu Leu Arg Glu Arg Val Leu Arg Gly Lys
                260                 265                 270

Tyr Arg Val Pro Phe Tyr Met Ser Thr Asp Cys Glu Ser Ile Leu Arg
            275                 280                 285

Arg Phe Leu Val Leu Asn Pro Ala Lys Arg Cys Thr Leu Glu Gln Ile
290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                    325                 330                 335

Val Met Val Gly Met Gly Tyr Thr Arg Glu Glu Ile Lys Glu Ser Leu
                340                 345                 350

Thr Ser Gln Lys Tyr Asn Glu Val Thr Ala Thr Tyr Leu Leu Leu Gly
            355                 360                 365

Arg Lys Thr Glu Glu Gly Gly Asp Arg Gly Ala Pro Gly Leu Ala Leu
370                 375                 380

Ala Arg Val Arg Ala Pro Ser Asp Thr Thr Asn Gly Thr Ser Ser Ser
385                 390                 395                 400

Lys Gly Thr Ser His Ser Lys Gly Gln Arg Ser Ser Ser Thr Tyr
                    405                 410                 415

His Arg Gln Arg Arg His Ser Asp Phe Cys Gly Pro Ser Pro Ala Pro
                420                 425                 430

Leu His Pro Lys Arg Ser Pro Thr Ser Thr Gly Glu Ala Glu Leu Lys
            435                 440                 445

Glu Glu Arg Leu Pro Gly Arg Lys Ala Ser Cys Ser Thr Ala Gly Ser
450                 455                 460
```

```
Gly Ser Arg Gly Leu Pro Pro Ser Pro Met Val Ser Ala His
465                 470                 475                 480

Asn Pro Asn Lys Ala Glu Ile Pro Glu Arg Arg Lys Asp Ser Thr Ser
                485                 490                 495

Thr Pro Asn Asn Leu Pro Pro Ser Met Met Thr Arg Arg Asn Thr Tyr
                500                 505                 510

Val Cys Thr Glu Arg Pro Gly Ala Glu Arg Pro Ser Leu Leu Pro Asn
            515                 520                 525

Gly Lys Glu Asn Ser Ser Gly Thr Pro Arg Val Pro Pro Ala Ser Pro
        530                 535                 540

Ser Ser His Ser Leu Ala Pro Pro Ser Gly Glu Arg Ser Arg Leu Ala
545                 550                 555                 560

Arg Gly Ser Thr Ile Arg Ser Thr Phe His Gly Gly Gln Val Arg Asp
                565                 570                 575

Arg Arg Ala Gly Gly Gly Gly Gly Val Gln Asn Gly Pro Pro
                580                 585                 590

Ala Ser Pro Thr Leu Ala His Glu Ala Ala Pro Leu Pro Ala Gly Arg
            595                 600                 605

Pro Arg Pro Thr Thr Asn Leu Phe Thr Lys Leu Thr Ser Lys Leu Thr
        610                 615                 620

Arg Arg Val Ala Asp Glu Pro Glu Arg Ile Gly Gly Pro Glu Val Thr
625                 630                 635                 640

Ser Cys His Leu Pro Trp Asp Gln Thr Glu Thr Ala Pro Arg Leu Leu
                645                 650                 655

Arg Phe Pro Trp Ser Val Lys Leu Thr Ser Ser Arg Pro Pro Glu Ala
                660                 665                 670

Leu Met Ala Ala Leu Arg Gln Ala Thr Ala Ala Arg Cys Arg Cys
            675                 680                 685

Arg Gln Pro Gln Pro Phe Leu Leu Ala Cys Leu His Gly Gly Ala Gly
        690                 695                 700

Gly Pro Glu Pro Leu Ser His Phe Glu Val Val Cys Gln Leu Pro
705                 710                 715                 720

Arg Pro Gly Leu Arg Gly Val Leu Phe Arg Arg Val Ala Gly Thr Ala
                725                 730                 735

Leu Ala Phe Arg Thr Leu Val Thr Arg Ile Ser Asn Asp Leu Glu Leu
            740                 745                 750

<210> SEQ ID NO 41
<211> LENGTH: 1106
<212> TYPE: PRT
<213> ORGANISM: HUMAN
<300> PUBLICATION INFORMATION:
<301> AUTHORS: Cornfield,D., Shah,U., Cross,N., Bennett,C. and Sun,G.
<302> TITLE: Philadelphia chromosome-negative myeloproliferative
       neoplasm with a
<303> JOURNAL: J. Clin. Oncol.
<304> VOLUME: 30
<305> ISSUE: 9
<306> PAGES: E109-E111
<307> DATE: 2012-03-20
<308> DATABASE ACCESSION NUMBER: NP_002600
<309> DATABASE ENTRY DATE: 2012-05-13
<313> RELEVANT RESIDUES IN SEQ ID NO: (1)..(1106)

<400> SEQUENCE: 41

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
                20                  25                  30
```

```
Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
 50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                 85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
            370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
            435                 440                 445
```

-continued

```
Ser Ala Cys Arg Asp Leu Lys Arg Cys Pro Arg Glu Leu Pro Pro Thr
    450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                    485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Pro His Ser Leu
            515                 520                 525
Pro Phe Lys Val Val Ile Ser Ala Ile Leu Ala Leu Val Val Leu
    530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                    565                 570                 575
His Glu Tyr Ile Tyr Val Asp Pro Met Gln Leu Pro Tyr Asp Ser Thr
            580                 585                 590
Trp Glu Leu Pro Arg Asp Gln Leu Val Leu Gly Arg Thr Leu Gly Ser
    595                 600                 605
Gly Ala Phe Gly Gln Val Val Glu Ala Thr Ala His Gly Leu Ser His
    610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                    645                 650                 655
His Leu Gly Pro His Leu Asn Val Val Asn Leu Leu Gly Ala Cys Thr
            660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
    690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                    725                 730                 735
Asp Gly Gly Tyr Met Asp Met Ser Lys Asp Glu Ser Val Asp Tyr Val
            740                 745                 750
Pro Met Leu Asp Met Lys Gly Asp Val Lys Tyr Ala Asp Ile Glu Ser
            755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                    805                 810                 815
Leu Ala Ser Lys Asn Cys Val His Arg Asp Leu Ala Ala Arg Asn Val
            820                 825                 830
Leu Ile Cys Glu Gly Lys Leu Val Lys Ile Cys Asp Phe Gly Leu Ala
            835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
```

```
                        865                 870                 875                 880
            Thr Thr Leu Ser Asp Val Trp Ser Phe Gly Ile Leu Leu Trp Glu Ile
                            885                 890                 895

Phe Thr Leu Gly Gly Thr Pro Tyr Pro Glu Leu Pro Met Asn Glu Gln
                        900                 905                 910

Phe Tyr Asn Ala Ile Lys Arg Gly Tyr Arg Met Ala Gln Pro Ala His
                        915                 920                 925

Ala Ser Asp Glu Ile Tyr Glu Ile Met Gln Lys Cys Trp Glu Glu Lys
                        930                 935                 940

Phe Glu Ile Arg Pro Pro Phe Ser Gln Leu Val Leu Leu Leu Glu Arg
            945                 950                 955                 960

Leu Leu Gly Glu Gly Tyr Lys Lys Tyr Gln Gln Val Asp Glu Glu
                                965                 970                 975

Phe Leu Arg Ser Asp His Pro Ala Ile Leu Arg Ser Gln Ala Arg Leu
                            980                 985                 990

Pro Gly Phe His Gly Leu Arg Ser Pro Leu Asp Thr Ser Ser Val Leu
                        995                 1000                1005

Tyr Thr Ala Val Gln Pro Asn Glu Gly Asp Asn Asp Tyr Ile Ile
                1010                1015                1020

Pro Leu Pro Asp Pro Lys Pro Glu Val Ala Asp Glu Gly Pro Leu
                1025                1030                1035

Glu Gly Ser Pro Ser Leu Ala Ser Ser Thr Leu Asn Glu Val Asn
                1040                1045                1050

Thr Ser Ser Thr Ile Ser Cys Asp Ser Pro Leu Glu Pro Gln Asp
                1055                1060                1065

Glu Pro Glu Pro Glu Pro Gln Leu Glu Leu Gln Val Glu Pro Glu
                1070                1075                1080

Pro Glu Leu Glu Gln Leu Pro Asp Ser Gly Cys Pro Ala Pro Arg
                1085                1090                1095

Ala Glu Ala Glu Asp Ser Phe Leu
                1100                1105

<210> SEQ ID NO 42
<211> LENGTH: 672
<212> TYPE: PRT
<213> ORGANISM: HUMAN
<300> PUBLICATION INFORMATION:
<301> AUTHORS: Lin,Y.M., Su,C.C., Su,W.W., Hwang,J.M., Hsu,H.H.,
      Tsai,C.H.,
<302> TITLE: Expression of protein kinase C isoforms in cancerous breast
      tissue
<303> JOURNAL: Chin J Physiol
<304> VOLUME: 55
<305> ISSUE: 1
<306> PAGES: 55-61
<307> DATE: 2012-02-29
<308> DATABASE ACCESSION NUMBER: NP_002728
<309> DATABASE ENTRY DATE: 2012-04-22
<313> RELEVANT RESIDUES IN SEQ ID NO: (1)..(672)

<400> SEQUENCE: 42

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
                20                  25                  30

Glu Val Lys Asp His Lys Phe Ile Ala Arg Phe Phe Lys Gln Pro Thr
            35                  40                  45

Phe Cys Ser His Cys Thr Asp Phe Ile Trp Gly Phe Gly Lys Gln Gly
        50                  55                  60
```

-continued

```
Phe Gln Cys Gln Val Cys Cys Phe Val Val His Lys Arg Cys His Glu
 65                  70                  75                  80

Phe Val Thr Phe Ser Cys Pro Gly Ala Asp Lys Gly Pro Asp Thr Asp
                 85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Asp Met Asn Val His Lys Gln Cys Val
130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
            195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
            275                 280                 285

Pro Ile Pro Glu Gly Asp Glu Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
            355                 360                 365

Ile Leu Lys Lys Asp Val Val Ile Gln Asp Asp Asp Val Glu Cys Thr
    370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
            435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480
```

-continued

```
Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
        595                 600                 605

Glu Ile Gln Pro Pro Phe Lys Pro Lys Val Cys Gly Lys Gly Ala Glu
    610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
            660                 665                 670

<210> SEQ ID NO 43
<211> LENGTH: 643
<212> TYPE: PRT
<213> ORGANISM: HUMAN
<300> PUBLICATION INFORMATION:
<301> AUTHORS: Baier,G., Telford,D., Giampa,L., Coggeshall,K.M.,
<302> TITLE: Molecular cloning and characterization of PKC theta, a
      novel member
<303> JOURNAL: J. Biol. Chem.
<304> VOLUME: 268
<305> ISSUE: 7
<306> PAGES: 4997-5004
<307> DATE: 1993-03-05
<308> DATABASE ACCESSION NUMBER: NP_001229342
<309> DATABASE ENTRY DATE: 2012-05-13
<313> RELEVANT RESIDUES IN SEQ ID NO: (1)..(643)

<400> SEQUENCE: 43

Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125
```

```
Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
        355                 360                 365

Pro Ser Leu Gln Ile Lys Leu Lys Ile Glu Asp Phe Ile Leu His Lys
    370                 375                 380

Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
    450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Lys Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
    530                 535                 540
```

-continued

```
Tyr Ile Ala Pro Glu Leu Phe Val Arg Glu Pro Glu Lys Arg Leu Gly
545                 550                 555                 560

Val Arg Gly Asp Ile Arg Gln His Pro Leu Phe Arg Glu Ile Asn Trp
            565                 570                 575

Glu Glu Leu Glu Arg Lys Glu Ile Asp Pro Pro Phe Arg Pro Lys Val
                580                 585                 590

Lys Ser Pro Phe Asp Cys Ser Asn Phe Asp Lys Glu Phe Leu Asn Glu
            595                 600                 605

Lys Pro Arg Leu Ser Phe Ala Asp Arg Ala Leu Ile Asn Ser Met Asp
        610                 615                 620

Gln Asn Met Phe Arg Asn Phe Ser Phe Met Asn Pro Gly Met Glu Arg
625                 630                 635                 640

Leu Ile Ser
```

<210> SEQ ID NO 44
<211> LENGTH: 404
<212> TYPE: PRT
<213> ORGANISM: HUMAN
<300> PUBLICATION INFORMATION:
<301> AUTHORS: Telerman,A., Amson,R., Zakut-Houri,R. and Givol,D.
<302> TITLE: Identification of the human pim-1 gene product as a
       33-kilodalton
<303> JOURNAL: Mol. Cell. Biol.
<304> VOLUME: 8
<305> ISSUE: 4
<306> PAGES: 1498-1503
<307> DATE: 1988-04-08
<308> DATABASE ACCESSION NUMBER: NP_001230115
<309> DATABASE ENTRY DATE: 2012-05-06
<313> RELEVANT RESIDUES IN SEQ ID NO: (1)..(404)

<400> SEQUENCE: 44

```
Met Pro His Glu Pro His Glu Pro Leu Thr Pro Pro Phe Ser Ala Leu
1               5                   10                  15

Pro Asp Pro Ala Gly Ala Pro Ser Arg Arg Gln Ser Arg Gln Arg Pro
            20                  25                  30

Gln Leu Ser Ser Asp Ser Pro Ser Ala Phe Arg Ala Ser Arg Ser His
        35                  40                  45

Ser Arg Asn Ala Thr Arg Ser His Ser His Ser His Ser Pro Arg His
    50                  55                  60

Ser Leu Arg His Ser Pro Gly Ser Gly Ser Cys Gly Ser Ser Ser Gly
65                  70                  75                  80

His Arg Pro Cys Ala Asp Ile Leu Glu Val Gly Met Leu Leu Ser Lys
                85                  90                  95

Ile Asn Ser Leu Ala His Leu Arg Ala Ala Pro Cys Asn Asp Leu His
            100                 105                 110

Ala Thr Lys Leu Ala Pro Gly Lys Glu Lys Glu Pro Leu Glu Ser Gln
        115                 120                 125

Tyr Gln Val Gly Pro Leu Leu Gly Ser Gly Gly Phe Gly Ser Val Tyr
    130                 135                 140

Ser Gly Ile Arg Val Ser Asp Asn Leu Pro Val Ala Ile Lys His Val
145                 150                 155                 160

Glu Lys Asp Arg Ile Ser Asp Trp Gly Glu Leu Pro Asn Gly Thr Arg
                165                 170                 175

Val Pro Met Glu Val Val Leu Leu Lys Lys Val Ser Ser Gly Phe Ser
            180                 185                 190

Gly Val Ile Arg Leu Leu Asp Trp Phe Glu Arg Pro Asp Ser Phe Val
        195                 200                 205
```

-continued

```
Leu Ile Leu Glu Arg Pro Glu Pro Val Gln Asp Leu Phe Asp Phe Ile
    210                 215                 220

Thr Glu Arg Gly Ala Leu Gln Glu Glu Leu Ala Arg Ser Phe Phe Trp
225                 230                 235                 240

Gln Val Leu Glu Ala Val Arg His Cys His Asn Cys Gly Val Leu His
                245                 250                 255

Arg Asp Ile Lys Asp Glu Asn Ile Leu Ile Asp Leu Asn Arg Gly Glu
                260                 265                 270

Leu Lys Leu Ile Asp Phe Gly Ser Gly Ala Leu Leu Lys Asp Thr Val
                275                 280                 285

Tyr Thr Asp Phe Asp Gly Thr Arg Val Tyr Ser Pro Pro Glu Trp Ile
            290                 295                 300

Arg Tyr His Arg Tyr His Gly Arg Ser Ala Ala Val Trp Ser Leu Gly
305                 310                 315                 320

Ile Leu Leu Tyr Asp Met Val Cys Gly Asp Ile Pro Phe Glu His Asp
                325                 330                 335

Glu Glu Ile Ile Arg Gly Gln Val Phe Phe Arg Gln Arg Val Ser Ser
                340                 345                 350

Glu Cys Gln His Leu Ile Arg Trp Cys Leu Ala Leu Arg Pro Ser Asp
                355                 360                 365

Arg Pro Thr Phe Glu Glu Ile Gln Asn His Pro Trp Met Gln Asp Val
            370                 375                 380

Leu Leu Pro Gln Glu Thr Ala Glu Ile His Leu His Ser Leu Ser Pro
385                 390                 395                 400

Gly Pro Ser Lys

<210> SEQ ID NO 45
<211> LENGTH: 1072
<212> TYPE: PRT
<213> ORGANISM: HUMAN
<300> PUBLICATION INFORMATION:
<301> AUTHORS: Schulten,H.J., Al-Maghrabi,J., Al-Ghamdi,K., Salama,S.,
<302> TITLE: Mutational screening of RET, HRAS, KRAS, NRAS, BRAF, AKT1,
       and
<303> JOURNAL: Anticancer Res.
<304> VOLUME: 31
<305> ISSUE: 12
<306> PAGES: 4179-4183
<307> DATE: 2011-12-31
<308> DATABASE ACCESSION NUMBER: NP_06568
<309> DATABASE ENTRY DATE: 2012-05-20
<313> RELEVANT RESIDUES IN SEQ ID NO: (1)..(1072)

<400> SEQUENCE: 45

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Trp Glu Lys Leu Ser Val Arg
                100                 105                 110
```

```
Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
        130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
```

```
               530                 535                 540
Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590

Gly His Glu Pro Gly Glu Pro Arg Gly Ile Lys Ala Gly Tyr Gly Thr
                595                 600                 605

Cys Asn Cys Phe Pro Glu Glu Lys Cys Phe Cys Glu Pro Glu Asp
610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
                660                 665                 670

Glu Met Thr Phe Arg Arg Pro Ala Gln Ala Phe Pro Val Ser Tyr Ser
                675                 680                 685

Ser Ser Gly Ala Arg Arg Pro Ser Leu Asp Ser Met Glu Asn Gln Val
                690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
                740                 745                 750

Thr Thr Val Ala Val Lys Met Leu Lys Glu Asn Ala Ser Pro Ser Glu
                755                 760                 765

Leu Arg Asp Leu Leu Ser Glu Phe Asn Val Leu Lys Gln Val Asn His
                770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
                820                 825                 830

Arg Asn Ser Ser Ser Leu Asp His Pro Asp Glu Arg Ala Leu Thr Met
                835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
                900                 905                 910

Ile Pro Val Lys Trp Met Ala Ile Glu Ser Leu Phe Asp His Ile Tyr
                915                 920                 925

Thr Thr Gln Ser Asp Val Trp Ser Phe Gly Val Leu Leu Trp Glu Ile
                930                 935                 940

Val Thr Leu Gly Gly Asn Pro Tyr Pro Gly Ile Pro Pro Glu Arg Leu
945                 950                 955                 960
```

```
Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Arg Ile Ser His Ala
    1055                1060                1065

Phe Thr Arg Phe
    1070

<210> SEQ ID NO 46
<211> LENGTH: 1354
<212> TYPE: PRT
<213> ORGANISM: HUMAN
<300> PUBLICATION INFORMATION:
<301> AUTHORS: Fujisawa,K., Fujita,A., Ishizaki,T., Saito,Y. and
      Narumiya,S.
<302> TITLE: Identification of the Rho-binding domain of p160ROCK, a
<303> JOURNAL: J. Biol. Chem.
<304> VOLUME: 271
<305> ISSUE: 38
<306> PAGES: 23022-23028
<307> DATE: 1996-09-20
<308> DATABASE ACCESSION NUMBER: NP_005397
<309> DATABASE ENTRY DATE: 2012-04-29
<313> RELEVANT RESIDUES IN SEQ ID NO: (1)..(1354)

<400> SEQUENCE: 46

Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
```

```
            180                 185                 190
Gly Phe Ile His Arg Asp Val Lys Pro Asp Asn Met Leu Leu Asp Lys
        195                 200                 205
Ser Gly His Leu Lys Leu Ala Asp Phe Gly Thr Cys Met Lys Met Asn
210                 215                 220
Lys Glu Gly Met Val Arg Cys Asp Thr Ala Val Gly Thr Pro Asp Tyr
225                 230                 235                 240
Ile Ser Pro Glu Val Leu Lys Ser Gln Gly Gly Asp Gly Tyr Tyr Gly
                245                 250                 255
Arg Glu Cys Asp Trp Trp Ser Val Gly Val Phe Leu Tyr Glu Met Leu
            260                 265                 270
Val Gly Asp Thr Pro Phe Tyr Ala Asp Ser Leu Val Gly Thr Tyr Ser
        275                 280                 285
Lys Ile Met Asn His Lys Asn Ser Leu Thr Phe Pro Asp Asp Asn Asp
290                 295                 300
Ile Ser Lys Glu Ala Lys Asn Leu Ile Cys Ala Phe Leu Thr Asp Arg
305                 310                 315                 320
Glu Val Arg Leu Gly Arg Asn Gly Val Glu Glu Ile Lys Arg His Leu
                325                 330                 335
Phe Phe Lys Asn Asp Gln Trp Ala Trp Glu Thr Leu Arg Asp Thr Val
            340                 345                 350
Ala Pro Val Val Pro Asp Leu Ser Ser Asp Ile Asp Thr Ser Asn Phe
        355                 360                 365
Asp Asp Leu Glu Glu Asp Lys Gly Glu Glu Thr Phe Pro Ile Pro
370                 375                 380
Lys Ala Phe Val Gly Asn Gln Leu Pro Phe Val Gly Phe Thr Tyr Tyr
385                 390                 395                 400
Ser Asn Arg Arg Tyr Leu Ser Ser Ala Asn Pro Asn Asp Asn Arg Thr
                405                 410                 415
Ser Ser Asn Ala Asp Lys Ser Leu Gln Glu Ser Leu Gln Lys Thr Ile
            420                 425                 430
Tyr Lys Leu Glu Glu Gln Leu His Asn Glu Met Gln Leu Lys Asp Glu
        435                 440                 445
Met Glu Gln Lys Cys Arg Thr Ser Asn Ile Lys Leu Asp Lys Ile Met
450                 455                 460
Lys Glu Leu Asp Glu Glu Gly Asn Gln Arg Arg Asn Leu Glu Ser Thr
465                 470                 475                 480
Val Ser Gln Ile Glu Lys Glu Lys Met Leu Leu Gln His Arg Ile Asn
                485                 490                 495
Glu Tyr Gln Arg Lys Ala Glu Gln Glu Asn Glu Lys Arg Arg Asn Val
            500                 505                 510
Glu Asn Glu Val Ser Thr Leu Lys Asp Gln Leu Glu Asp Leu Lys Lys
        515                 520                 525
Val Ser Gln Asn Ser Gln Leu Ala Asn Glu Lys Leu Ser Gln Leu Gln
530                 535                 540
Lys Gln Leu Glu Glu Ala Asn Asp Leu Leu Arg Thr Glu Ser Asp Thr
545                 550                 555                 560
Ala Val Arg Leu Arg Lys Ser His Thr Glu Met Ser Lys Ser Ile Ser
                565                 570                 575
Gln Leu Glu Ser Leu Asn Arg Glu Leu Gln Glu Arg Asn Arg Ile Leu
            580                 585                 590
Glu Asn Ser Lys Ser Gln Thr Asp Lys Asp Tyr Tyr Gln Leu Gln Ala
        595                 600                 605
```

```
Ile Leu Glu Ala Glu Arg Arg Asp Arg Gly His Asp Ser Glu Met Ile
            610                 615                 620
Gly Asp Leu Gln Ala Arg Ile Thr Ser Leu Gln Glu Glu Val Lys His
625                 630                 635                 640
Leu Lys His Asn Leu Glu Lys Val Glu Gly Glu Arg Lys Glu Ala Gln
                645                 650                 655
Asp Met Leu Asn His Ser Glu Lys Glu Lys Asn Asn Leu Glu Ile Asp
                660                 665                 670
Leu Asn Tyr Lys Leu Lys Ser Leu Gln Gln Arg Leu Glu Gln Glu Val
                675                 680                 685
Asn Glu His Lys Val Thr Lys Ala Arg Leu Thr Asp Lys His Gln Ser
690                 695                 700
Ile Glu Ala Lys Ser Val Ala Met Cys Glu Met Glu Lys Lys Leu
705                 710                 715                 720
Lys Glu Glu Arg Glu Ala Arg Glu Lys Ala Glu Asn Arg Val Val Gln
                725                 730                 735
Ile Glu Lys Gln Cys Ser Met Leu Asp Val Asp Leu Lys Gln Ser Gln
                740                 745                 750
Gln Lys Leu Glu His Leu Thr Gly Asn Lys Glu Arg Met Glu Asp Glu
                755                 760                 765
Val Lys Asn Leu Thr Leu Gln Leu Glu Gln Glu Ser Asn Lys Arg Leu
770                 775                 780
Leu Leu Gln Asn Glu Leu Lys Thr Gln Ala Phe Glu Ala Asp Asn Leu
785                 790                 795                 800
Lys Gly Leu Glu Lys Gln Met Lys Gln Glu Ile Asn Thr Leu Leu Glu
                805                 810                 815
Ala Lys Arg Leu Leu Glu Phe Glu Leu Ala Gln Leu Thr Lys Gln Tyr
                820                 825                 830
Arg Gly Asn Glu Gly Gln Met Arg Glu Leu Gln Asp Gln Leu Glu Ala
                835                 840                 845
Glu Gln Tyr Phe Ser Thr Leu Tyr Lys Thr Gln Val Lys Glu Leu Lys
                850                 855                 860
Glu Glu Ile Glu Glu Lys Asn Arg Glu Asn Leu Lys Lys Ile Gln Glu
865                 870                 875                 880
Leu Gln Asn Glu Lys Glu Thr Leu Ala Thr Gln Leu Asp Leu Ala Glu
                885                 890                 895
Thr Lys Ala Glu Ser Glu Gln Leu Ala Arg Gly Leu Leu Glu Glu Gln
                900                 905                 910
Tyr Phe Glu Leu Thr Gln Glu Ser Lys Lys Ala Ala Ser Arg Asn Arg
                915                 920                 925
Gln Glu Ile Thr Asp Lys Asp His Thr Val Ser Arg Leu Glu Glu Ala
                930                 935                 940
Asn Ser Met Leu Thr Lys Asp Ile Glu Ile Leu Arg Arg Glu Asn Glu
945                 950                 955                 960
Glu Leu Thr Glu Lys Met Lys Lys Ala Glu Glu Tyr Lys Leu Glu
                965                 970                 975
Lys Glu Glu Glu Ile Ser Asn Leu Lys Ala Ala Phe Glu Lys Asn Ile
                980                 985                 990
Asn Thr Glu Arg Thr Leu Lys Thr Gln Ala Val Asn Lys Leu Ala Glu
                995                 1000                1005
Ile Met Asn Arg Lys Asp Phe Lys Ile Asp Arg Lys Lys Ala Asn
        1010                1015                1020
```

```
Thr Gln Asp Leu Arg Lys Lys Glu Lys Glu Asn Arg Lys Leu Gln
    1025                1030                1035

Leu Glu Leu Asn Gln Glu Arg Glu Lys Phe Asn Gln Met Val Val
    1040                1045                1050

Lys His Gln Lys Glu Leu Asn Asp Met Gln Ala Gln Leu Val Glu
    1055                1060                1065

Glu Cys Ala His Arg Asn Glu Leu Gln Met Gln Leu Ala Ser Lys
    1070                1075                1080

Glu Ser Asp Ile Glu Gln Leu Arg Ala Lys Leu Leu Asp Leu Ser
    1085                1090                1095

Asp Ser Thr Ser Val Ala Ser Phe Pro Ser Ala Asp Glu Thr Asp
    1100                1105                1110

Gly Asn Leu Pro Glu Ser Arg Ile Glu Gly Trp Leu Ser Val Pro
    1115                1120                1125

Asn Arg Gly Asn Ile Lys Arg Tyr Gly Trp Lys Lys Gln Tyr Val
    1130                1135                1140

Val Val Ser Ser Lys Lys Ile Leu Phe Tyr Asn Asp Glu Gln Asp
    1145                1150                1155

Lys Glu Gln Ser Asn Pro Ser Met Val Leu Asp Ile Asp Lys Leu
    1160                1165                1170

Phe His Val Arg Pro Val Thr Gln Gly Asp Val Tyr Arg Ala Glu
    1175                1180                1185

Thr Glu Glu Ile Pro Lys Ile Phe Gln Ile Leu Tyr Ala Asn Glu
    1190                1195                1200

Gly Glu Cys Arg Lys Asp Val Glu Met Glu Pro Val Gln Gln Ala
    1205                1210                1215

Glu Lys Thr Asn Phe Gln Asn His Lys Gly His Glu Phe Ile Pro
    1220                1225                1230

Thr Leu Tyr His Phe Pro Ala Asn Cys Asp Ala Cys Ala Lys Pro
    1235                1240                1245

Leu Trp His Val Phe Lys Pro Pro Pro Ala Leu Glu Cys Arg Arg
    1250                1255                1260

Cys His Val Lys Cys His Arg Asp His Leu Asp Lys Lys Glu Asp
    1265                1270                1275

Leu Ile Cys Pro Cys Lys Val Ser Tyr Asp Val Thr Ser Ala Arg
    1280                1285                1290

Asp Met Leu Leu Leu Ala Cys Ser Gln Asp Glu Gln Lys Lys Trp
    1295                1300                1305

Val Thr His Leu Val Lys Lys Ile Pro Lys Asn Pro Pro Ser Gly
    1310                1315                1320

Phe Val Arg Ala Ser Pro Arg Thr Leu Ser Thr Arg Ser Thr Ala
    1325                1330                1335

Asn Gln Ser Phe Arg Lys Val Val Lys Asn Thr Ser Gly Lys Thr
    1340                1345                1350

Ser
```

Ser

<210> SEQ ID NO 47
<211> LENGTH: 1388
<212> TYPE: PRT
<213> ORGANISM: HUMAN
<300> PUBLICATION INFORMATION:
<301> AUTHORS: Fukata,Y., Oshiro,N., Kinoshita,N., Kawano,Y.,
       Matsuoka,Y.,
<302> TITLE: Phosphorylation of adducin by Rho-kinase plays a crucial
       role in
<303> JOURNAL: J. Cell Biol.

<304> VOLUME: 145
<305> ISSUE: 2
<306> PAGES: 347-361
<307> DATE: 1999-04-19
<308> DATABASE ACCESSION NUMBER: NP_004841
<309> DATABASE ENTRY DATE: 2012-04-29
<313> RELEVANT RESIDUES IN SEQ ID NO: (1)..(1388)

<400> SEQUENCE: 47

```
Met Ser Arg Pro Pro Thr Gly Lys Met Pro Gly Ala Pro Glu Thr
1               5                   10                  15

Ala Pro Gly Asp Gly Ala Gly Ala Ser Arg Gln Arg Lys Leu Glu Ala
                20                  25                  30

Leu Ile Arg Asp Pro Arg Ser Pro Ile Asn Val Glu Ser Leu Leu Asp
            35                  40                  45

Gly Leu Asn Ser Leu Val Leu Asp Leu Asp Phe Pro Ala Leu Arg Lys
50                  55                  60

Asn Lys Asn Ile Asp Asn Phe Leu Asn Arg Tyr Glu Lys Ile Val Lys
65                  70                  75                  80

Lys Ile Arg Gly Leu Gln Met Lys Ala Glu Asp Tyr Asp Val Val Lys
                85                  90                  95

Val Ile Gly Arg Gly Ala Phe Gly Glu Val Gln Leu Val Arg His Lys
            100                 105                 110

Ala Ser Gln Lys Val Tyr Ala Met Lys Leu Leu Ser Lys Phe Glu Met
        115                 120                 125

Ile Lys Arg Ser Asp Ser Ala Phe Phe Trp Glu Glu Arg Asp Ile Met
130                 135                 140

Ala Phe Ala Asn Ser Pro Trp Val Val Gln Leu Phe Tyr Ala Phe Gln
145                 150                 155                 160

Asp Asp Arg Tyr Leu Tyr Met Val Met Glu Tyr Met Pro Gly Gly Asp
                165                 170                 175

Leu Val Asn Leu Met Ser Asn Tyr Asp Val Pro Glu Lys Trp Ala Lys
            180                 185                 190

Phe Tyr Thr Ala Glu Val Val Leu Ala Leu Asp Ala Ile His Ser Met
        195                 200                 205

Gly Leu Ile His Arg Asp Val Lys Pro Asp Asn Met Leu Leu Asp Lys
210                 215                 220

His Gly His Leu Lys Leu Ala Asp Phe Gly Thr Cys Met Lys Met Asp
225                 230                 235                 240

Glu Thr Gly Met Val His Cys Asp Thr Ala Val Gly Thr Pro Asp Tyr
                245                 250                 255

Ile Ser Pro Glu Val Leu Lys Ser Gln Gly Gly Asp Gly Phe Tyr Gly
            260                 265                 270

Arg Glu Cys Asp Trp Trp Ser Val Gly Val Phe Leu Tyr Glu Met Leu
        275                 280                 285

Val Gly Asp Thr Pro Phe Tyr Ala Asp Ser Leu Val Gly Thr Tyr Ser
290                 295                 300

Lys Ile Met Asp His Lys Asn Ser Leu Cys Phe Pro Glu Asp Ala Glu
305                 310                 315                 320

Ile Ser Lys His Ala Lys Asn Leu Ile Cys Ala Phe Leu Thr Asp Arg
                325                 330                 335

Glu Val Arg Leu Gly Arg Asn Gly Val Glu Glu Ile Arg Gln His Pro
            340                 345                 350

Phe Phe Lys Asn Asp Gln Trp His Trp Asp Asn Ile Arg Glu Thr Ala
        355                 360                 365
```

-continued

```
Ala Pro Val Val Pro Glu Leu Ser Ser Asp Ile Asp Ser Ser Asn Phe
    370             375             380

Asp Asp Ile Glu Asp Lys Gly Asp Val Glu Thr Phe Pro Ile Pro
385             390             395                 400

Lys Ala Phe Val Gly Asn Gln Leu Pro Phe Ile Gly Phe Thr Tyr Tyr
                405             410             415

Arg Glu Asn Leu Leu Leu Ser Asp Ser Pro Ser Cys Arg Glu Thr Asp
            420             425             430

Ser Ile Gln Ser Arg Lys Asn Glu Ser Gln Glu Ile Gln Lys Lys
            435             440             445

Leu Tyr Thr Leu Glu Glu His Leu Ser Asn Glu Met Gln Ala Lys Glu
    450             455             460

Glu Leu Glu Gln Lys Cys Lys Ser Val Asn Thr Arg Leu Glu Lys Thr
465             470             475             480

Ala Lys Glu Leu Glu Glu Ile Thr Leu Arg Lys Ser Val Glu Ser
                485             490             495

Ala Leu Arg Gln Leu Glu Arg Glu Lys Ala Leu Leu Gln His Lys Asn
            500             505             510

Ala Glu Tyr Gln Arg Lys Ala Asp His Glu Ala Asp Lys Lys Arg Asn
            515             520             525

Leu Glu Asn Asp Val Asn Ser Leu Lys Asp Gln Leu Glu Asp Leu Lys
            530             535             540

Lys Arg Asn Gln Asn Ser Gln Ile Ser Thr Glu Lys Val Asn Gln Leu
545             550             555             560

Gln Arg Gln Leu Asp Glu Thr Asn Ala Leu Leu Arg Thr Glu Ser Asp
                565             570             575

Thr Ala Ala Arg Leu Arg Lys Thr Gln Ala Glu Ser Ser Lys Gln Ile
            580             585             590

Gln Gln Leu Glu Ser Asn Asn Arg Asp Leu Gln Asp Lys Asn Cys Leu
        595             600             605

Leu Glu Thr Ala Lys Leu Lys Leu Glu Lys Glu Phe Ile Asn Leu Gln
    610             615             620

Ser Ala Leu Glu Ser Glu Arg Arg Asp Arg Thr His Gly Ser Glu Ile
625             630             635             640

Ile Asn Asp Leu Gln Gly Arg Ile Cys Gly Leu Glu Glu Asp Leu Lys
                645             650             655

Asn Gly Lys Ile Leu Leu Ala Lys Val Glu Leu Glu Lys Arg Gln Leu
            660             665             670

Gln Glu Arg Phe Thr Asp Leu Glu Lys Glu Lys Ser Asn Met Glu Ile
        675             680             685

Asp Met Thr Tyr Gln Leu Lys Val Ile Gln Gln Ser Leu Glu Gln Glu
    690             695             700

Glu Ala Glu His Lys Ala Thr Lys Ala Arg Leu Ala Asp Lys Asn Lys
705             710             715             720

Ile Tyr Glu Ser Ile Glu Glu Ala Lys Ser Ala Met Lys Glu Met
                725             730             735

Glu Lys Lys Leu Leu Glu Glu Arg Thr Leu Lys Gln Lys Val Glu Asn
            740             745             750

Leu Leu Leu Glu Ala Glu Lys Arg Cys Ser Leu Leu Asp Cys Asp Leu
            755             760             765

Lys Gln Ser Gln Gln Lys Ile Asn Glu Leu Leu Lys Gln Lys Asp Val
        770             775             780

Leu Asn Glu Asp Val Arg Asn Leu Thr Leu Lys Ile Glu Gln Glu Thr
```

```
                785                 790                 795                 800
Gln Lys Arg Cys Leu Thr Gln Asn Asp Leu Lys Met Gln Thr Gln Gln
                    805                 810                 815
Val Asn Thr Leu Lys Met Ser Glu Lys Gln Leu Lys Gln Glu Asn Asn
                    820                 825                 830
His Leu Met Glu Met Lys Met Asn Leu Glu Lys Gln Asn Ala Glu Leu
                    835                 840                 845
Arg Lys Glu Arg Gln Asp Ala Asp Gly Gln Met Lys Glu Leu Gln Asp
        850                 855                 860
Gln Leu Glu Ala Glu Gln Tyr Phe Ser Thr Leu Tyr Lys Thr Gln Val
865                 870                 875                 880
Arg Glu Leu Lys Glu Glu Cys Glu Glu Lys Thr Lys Leu Gly Lys Glu
                    885                 890                 895
Leu Gln Gln Lys Lys Gln Glu Leu Gln Asp Glu Arg Asp Ser Leu Ala
                900                 905                 910
Ala Gln Leu Glu Ile Thr Leu Thr Lys Ala Asp Ser Glu Gln Leu Ala
                    915                 920                 925
Arg Ser Ile Ala Glu Glu Gln Tyr Ser Asp Leu Glu Lys Glu Lys Ile
        930                 935                 940
Met Lys Glu Leu Glu Ile Lys Glu Met Met Ala Arg His Lys Gln Glu
945                 950                 955                 960
Leu Thr Glu Lys Asp Ala Thr Ile Ala Ser Leu Glu Glu Thr Asn Arg
                    965                 970                 975
Thr Leu Thr Ser Asp Val Ala Asn Leu Ala Asn Glu Lys Glu Glu Leu
                    980                 985                 990
Asn Asn Lys Leu Lys Asp Val Gln Glu Gln Leu Ser Arg Leu Lys Asp
                995                 1000                1005
Glu Glu Ile Ser Ala Ala Ala Ile Lys Ala Gln Phe Glu Lys Gln
        1010                1015                1020
Leu Leu Thr Glu Arg Thr Leu Lys Thr Gln Ala Val Asn Lys Leu
        1025                1030                1035
Ala Glu Ile Met Asn Arg Lys Glu Pro Val Lys Arg Gly Asn Asp
        1040                1045                1050
Thr Asp Val Arg Arg Lys Glu Lys Glu Asn Arg Lys Leu His Met
        1055                1060                1065
Glu Leu Lys Ser Glu Arg Glu Lys Leu Thr Gln Gln Met Ile Lys
        1070                1075                1080
Tyr Gln Lys Glu Leu Asn Glu Met Gln Ala Gln Ile Ala Glu Glu
        1085                1090                1095
Ser Gln Ile Arg Ile Glu Leu Gln Met Thr Leu Asp Ser Lys Asp
        1100                1105                1110
Ser Asp Ile Glu Gln Leu Arg Ser Gln Leu Gln Ala Leu His Ile
        1115                1120                1125
Gly Leu Asp Ser Ser Ser Ile Gly Ser Gly Pro Gly Asp Ala Glu
        1130                1135                1140
Ala Asp Asp Gly Phe Pro Glu Ser Arg Leu Glu Gly Trp Leu Ser
        1145                1150                1155
Leu Pro Val Arg Asn Asn Thr Lys Lys Phe Gly Trp Val Lys Lys
        1160                1165                1170
Tyr Val Ile Val Ser Ser Lys Lys Ile Leu Phe Tyr Asp Ser Glu
        1175                1180                1185
Gln Asp Lys Glu Gln Ser Asn Pro Tyr Met Val Leu Asp Ile Asp
        1190                1195                1200
```

-continued

```
Lys Leu Phe His Val Arg Pro Val Thr Gln Thr Asp Val Tyr Arg
    1205                1210                1215

Ala Asp Ala Lys Glu Ile Pro Arg Ile Phe Gln Ile Leu Tyr Ala
    1220                1225                1230

Asn Glu Gly Glu Ser Lys Lys Glu Gln Glu Phe Pro Val Glu Pro
    1235                1240                1245

Val Gly Glu Lys Ser Asn Tyr Ile Cys His Lys Gly His Glu Phe
    1250                1255                1260

Ile Pro Thr Leu Tyr His Phe Pro Thr Asn Cys Glu Ala Cys Met
    1265                1270                1275

Lys Pro Leu Trp His Met Phe Lys Pro Pro Pro Ala Leu Glu Cys
    1280                1285                1290

Arg Arg Cys His Ile Lys Cys His Lys Asp His Met Asp Lys Lys
    1295                1300                1305

Glu Glu Ile Ile Ala Pro Cys Lys Val Tyr Tyr Asp Ile Ser Thr
    1310                1315                1320

Ala Lys Asn Leu Leu Leu Ala Asn Ser Thr Glu Glu Gln Gln
    1325                1330                1335

Lys Trp Val Ser Arg Leu Val Lys Lys Ile Pro Lys Lys Pro Pro
    1340                1345                1350

Ala Pro Asp Pro Phe Ala Arg Ser Ser Pro Arg Thr Ser Met Lys
    1355                1360                1365

Ile Gln Gln Asn Gln Ser Ile Arg Arg Pro Ser Arg Gln Leu Ala
    1370                1375                1380

Pro Asn Lys Pro Ser
    1385

<210> SEQ ID NO 48
<211> LENGTH: 744
<212> TYPE: PRT
<213> ORGANISM: HUMAN
<300> PUBLICATION INFORMATION:
<301> AUTHORS: Jensen,C.J., Buch,M.B., Krag,T.O., Hemmings,B.A.,
      Gammeltoft,S. and
<302> TITLE: 90-kDa ribosomal S6 kinase is phosphorylated and activated
      by
<303> JOURNAL: J. Biol. Chem.
<304> VOLUME: 274
<305> ISSUE: 38
<306> PAGES: 27168-27176
<307> DATE: 1999-09-17
<308> DATABASE ACCESSION NUMBER: NP_001006666
<309> DATABASE ENTRY DATE: 2012-05-06
<313> RELEVANT RESIDUES IN SEQ ID NO: (1)..(744)

<400> SEQUENCE: 48

Met Glu Gln Asp Pro Lys Pro Pro Arg Leu Arg Leu Trp Ala Leu Ile
1               5                   10                  15

Pro Trp Leu Pro Arg Lys Gln Arg Pro Arg Ile Ser Gln Thr Ser Leu
                20                  25                  30

Pro Val Pro Gly Pro Gly Ser Gly Pro Gln Arg Asp Ser Asp Glu Gly
            35                  40                  45

Val Leu Lys Glu Ile Ser Ile Thr His His Val Lys Ala Gly Ser Glu
        50                  55                  60

Lys Ala Asp Pro Ser His Phe Glu Leu Leu Lys Val Leu Gly Gln Gly
65                  70                  75                  80

Ser Phe Gly Lys Val Phe Leu Val Arg Lys Val Thr Arg Pro Asp Ser
                85                  90                  95
```

```
Gly His Leu Tyr Ala Met Lys Val Leu Lys Lys Ala Thr Leu Lys Val
            100                 105                 110

Arg Asp Arg Val Arg Thr Lys Met Glu Arg Asp Ile Leu Ala Asp Val
        115                 120                 125

Asn His Pro Phe Val Val Lys Leu His Tyr Ala Phe Gln Thr Glu Gly
    130                 135                 140

Lys Leu Tyr Leu Ile Leu Asp Phe Leu Arg Gly Gly Asp Leu Phe Thr
145                 150                 155                 160

Arg Leu Ser Lys Glu Val Met Phe Thr Glu Glu Asp Val Lys Phe Tyr
                165                 170                 175

Leu Ala Glu Leu Ala Leu Gly Leu Asp His Leu His Ser Leu Gly Ile
            180                 185                 190

Ile Tyr Arg Asp Leu Lys Pro Glu Asn Ile Leu Leu Asp Glu Glu Gly
        195                 200                 205

His Ile Lys Leu Thr Asp Phe Gly Leu Ser Lys Glu Ala Ile Asp His
    210                 215                 220

Glu Lys Lys Ala Tyr Ser Phe Cys Gly Thr Val Glu Tyr Met Ala Pro
225                 230                 235                 240

Glu Val Val Asn Arg Gln Gly His Ser His Ser Ala Asp Trp Trp Ser
                245                 250                 255

Tyr Gly Val Leu Met Phe Glu Met Leu Thr Gly Ser Leu Pro Phe Gln
            260                 265                 270

Gly Lys Asp Arg Lys Glu Thr Met Thr Leu Ile Leu Lys Ala Lys Leu
        275                 280                 285

Gly Met Pro Gln Phe Leu Ser Thr Glu Ala Gln Ser Leu Leu Arg Ala
    290                 295                 300

Leu Phe Lys Arg Asn Pro Ala Asn Arg Leu Gly Ser Gly Pro Asp Gly
305                 310                 315                 320

Ala Glu Glu Ile Lys Arg His Val Phe Tyr Ser Thr Ile Asp Trp Asn
                325                 330                 335

Lys Leu Tyr Arg Arg Glu Ile Lys Pro Pro Phe Lys Pro Ala Val Ala
            340                 345                 350

Gln Pro Asp Asp Thr Phe Tyr Phe Asp Thr Glu Phe Thr Ser Arg Thr
        355                 360                 365

Pro Lys Asp Ser Pro Gly Ile Pro Pro Ser Ala Gly Ala His Gln Leu
370                 375                 380

Phe Arg Gly Phe Ser Phe Val Ala Thr Gly Leu Met Glu Asp Asp Gly
385                 390                 395                 400

Lys Pro Arg Ala Pro Gln Ala Pro Leu His Ser Val Val Gln Gln Leu
                405                 410                 415

His Gly Lys Asn Leu Val Phe Ser Asp Gly Tyr Val Val Lys Glu Thr
            420                 425                 430

Ile Gly Val Gly Ser Tyr Ser Glu Cys Lys Arg Cys Val His Lys Ala
        435                 440                 445

Thr Asn Met Glu Tyr Ala Val Lys Val Ile Asp Lys Ser Lys Arg Asp
    450                 455                 460

Pro Ser Glu Glu Ile Glu Ile Leu Leu Arg Tyr Gly Gln His Pro Asn
465                 470                 475                 480

Ile Ile Thr Leu Lys Asp Val Tyr Asp Asp Gly Lys His Val Tyr Leu
                485                 490                 495

Val Thr Glu Leu Met Arg Gly Gly Glu Leu Leu Asp Lys Ile Leu Arg
            500                 505                 510

Gln Lys Phe Phe Ser Glu Arg Glu Ala Ser Phe Val Leu His Thr Ile
```

```
                515                 520                 525
Gly Lys Thr Val Glu Tyr Leu His Ser Gln Gly Val Val His Arg Asp
            530                 535                 540

Leu Lys Pro Ser Asn Ile Leu Tyr Val Asp Glu Ser Gly Asn Pro Glu
545                 550                 555                 560

Cys Leu Arg Ile Cys Asp Phe Gly Phe Ala Lys Gln Leu Arg Ala Glu
                565                 570                 575

Asn Gly Leu Leu Met Thr Pro Cys Tyr Thr Ala Asn Phe Val Ala Pro
            580                 585                 590

Glu Val Leu Lys Arg Gln Gly Tyr Asp Glu Gly Cys Asp Ile Trp Ser
                595                 600                 605

Leu Gly Ile Leu Leu Tyr Thr Met Leu Ala Gly Tyr Thr Pro Phe Ala
            610                 615                 620

Asn Gly Pro Ser Asp Thr Pro Glu Glu Ile Leu Thr Arg Ile Gly Ser
625                 630                 635                 640

Gly Lys Phe Thr Leu Ser Gly Gly Asn Trp Asn Thr Val Ser Glu Thr
                645                 650                 655

Ala Lys Asp Leu Val Ser Lys Met Leu His Val Asp Pro His Gln Arg
            660                 665                 670

Leu Thr Ala Lys Gln Val Leu Gln His Pro Trp Val Thr Gln Lys Asp
                675                 680                 685

Lys Leu Pro Gln Ser Gln Leu Ser His Gln Asp Leu Gln Leu Val Lys
            690                 695                 700

Gly Ala Met Ala Ala Thr Tyr Ser Ala Leu Asn Ser Ser Lys Pro Thr
705                 710                 715                 720

Pro Gln Leu Lys Pro Ile Glu Ser Ser Ile Leu Ala Gln Arg Arg Val
                725                 730                 735

Arg Lys Leu Pro Ser Thr Thr Leu
            740

<210> SEQ ID NO 49
<211> LENGTH: 733
<212> TYPE: PRT
<213> ORGANISM: HUMAN
<300> PUBLICATION INFORMATION:
<301> AUTHORS: Elf,S., Blevins,D., Jin,L., Chung,T.W., Williams,I.R.,
      Lee,B.H.,
<302> TITLE: p90RSK2 is essential for FLT3-ITD- but dispensable for
<303> JOURNAL: Blood
<304> VOLUME: 117
<305> ISSUE: 25
<306> PAGES: 6885-6894
<307> DATE: 2011-04-28
<308> DATABASE ACCESSION NUMBER: NP_066958
<309> DATABASE ENTRY DATE: 2012-05-19
<313> RELEVANT RESIDUES IN SEQ ID NO: (1)..(733)

<400> SEQUENCE: 49

Met Asp Leu Ser Met Lys Lys Phe Ala Val Arg Arg Phe Phe Ser Val
1               5                   10                  15

Tyr Leu Arg Arg Lys Ser Arg Ser Lys Ser Ser Ser Leu Ser Arg Leu
                20                  25                  30

Glu Glu Glu Gly Val Val Lys Glu Ile Asp Ile Ser His His Val Lys
            35                  40                  45

Glu Gly Phe Glu Lys Ala Asp Pro Ser Gln Phe Glu Leu Leu Lys Val
        50                  55                  60

Leu Gly Gln Gly Ser Tyr Gly Lys Val Phe Leu Val Arg Lys Val Lys
65                  70                  75                  80
```

```
Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
    130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Ser Leu Gly Ile Ile Tyr Arg Asp Leu Lys Pro Glu Asn Ile Leu Leu
            180                 185                 190

Asp Glu Glu Gly His Ile Lys Ile Thr Asp Phe Gly Leu Ser Lys Glu
        195                 200                 205

Ala Ile Asp His Asp Lys Arg Ala Tyr Ser Phe Cys Gly Thr Ile Glu
    210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Gly Glu Ala Gln Ser
        275                 280                 285

Leu Leu Arg Ala Leu Phe Lys Arg Asn Pro Cys Asn Arg Leu Gly Ala
    290                 295                 300

Gly Ile Asp Gly Val Glu Glu Ile Lys Arg His Pro Phe Phe Val Thr
305                 310                 315                 320

Ile Asp Trp Asn Thr Leu Tyr Arg Lys Glu Ile Lys Pro Pro Phe Lys
                325                 330                 335

Pro Ala Val Gly Arg Pro Glu Asp Thr Phe His Phe Asp Pro Glu Phe
            340                 345                 350

Thr Ala Arg Thr Pro Thr Asp Ser Pro Gly Val Pro Pro Ser Ala Asn
        355                 360                 365

Ala His His Leu Phe Arg Gly Phe Ser Phe Val Ala Ser Ser Leu Ile
    370                 375                 380

Gln Glu Pro Ser Gln Gln Asp Leu His Lys Val Pro Val His Pro Ile
385                 390                 395                 400

Val Gln Gln Leu His Gly Asn Asn Ile His Phe Thr Asp Gly Tyr Glu
                405                 410                 415

Ile Lys Glu Asp Ile Gly Val Gly Ser Tyr Ser Val Cys Lys Arg Cys
            420                 425                 430

Val His Lys Ala Thr Asp Thr Glu Tyr Ala Val Lys Ile Ile Asp Lys
        435                 440                 445

Ser Lys Arg Asp Pro Ser Glu Glu Ile Glu Ile Leu Leu Arg Tyr Gly
    450                 455                 460

Gln His Pro Asn Ile Ile Thr Leu Lys Asp Val Tyr Asp Asp Gly Lys
465                 470                 475                 480

Phe Val Tyr Leu Val Met Glu Leu Met Arg Gly Gly Glu Leu Leu Asp
                485                 490                 495

Arg Ile Leu Arg Gln Arg Tyr Phe Ser Glu Arg Glu Ala Ser Asp Val
```

```
                500              505              510
Leu Cys Thr Ile Thr Lys Thr Met Asp Tyr Leu His Ser Gln Gly Val
            515              520              525

Val His Arg Asp Leu Lys Pro Ser Asn Ile Leu Tyr Arg Asp Glu Ser
            530              535              540

Gly Ser Pro Glu Ser Ile Arg Val Cys Asp Phe Gly Phe Ala Lys Gln
545              550              555              560

Leu Arg Ala Gly Asn Gly Leu Leu Met Thr Pro Cys Tyr Thr Ala Asn
            565              570              575

Phe Val Ala Pro Glu Val Leu Lys Arg Gln Gly Tyr Asp Ala Ala Cys
            580              585              590

Asp Ile Trp Ser Leu Gly Ile Leu Leu Tyr Thr Met Leu Ala Gly Phe
            595              600              605

Thr Pro Phe Ala Asn Gly Pro Asp Asp Thr Pro Glu Glu Ile Leu Ala
            610              615              620

Arg Ile Gly Ser Gly Lys Tyr Ala Leu Ser Gly Gly Asn Trp Asp Ser
625              630              635              640

Ile Ser Asp Ala Ala Lys Asp Val Val Ser Lys Met Leu His Val Asp
            645              650              655

Pro His Gln Arg Leu Thr Ala Met Gln Val Leu Lys His Pro Trp Val
            660              665              670

Val Asn Arg Glu Tyr Leu Ser Pro Asn Gln Leu Ser Arg Gln Asp Val
            675              680              685

His Leu Val Lys Gly Ala Met Ala Ala Thr Tyr Phe Ala Leu Asn Arg
            690              695              700

Thr Pro Gln Ala Pro Arg Leu Glu Pro Val Leu Ser Ser Asn Leu Ala
705              710              715              720

Gln Arg Arg Gly Met Lys Arg Leu Thr Ser Thr Arg Leu
            725              730

<210> SEQ ID NO 50
<211> LENGTH: 525
<212> TYPE: PRT
<213> ORGANISM: HUMAN
<300> PUBLICATION INFORMATION:
<301> AUTHORS: Proud,C.G.
<302> TITLE: p70 S6 kinase: an enigma with variations
<303> JOURNAL: Trends Biochem. Sci.
<304> VOLUME: 21
<305> ISSUE: 5
<306> PAGES: 181-185
<307> DATE: 2007-09-19
<308> DATABASE ACCESSION NUMBER: NP_003152
<309> DATABASE ENTRY DATE: 2012-04-30
<313> RELEVANT RESIDUES IN SEQ ID NO: (1)..(525)

<400> SEQUENCE: 50

Met Arg Arg Arg Arg Arg Asp Gly Phe Tyr Pro Ala Pro Asp Phe
1               5               10              15

Arg Asp Arg Glu Ala Glu Asp Met Ala Gly Val Phe Asp Ile Asp Leu
            20              25              30

Asp Gln Pro Glu Asp Ala Gly Ser Glu Asp Glu Leu Glu Glu Gly Gly
            35              40              45

Gln Leu Asn Glu Ser Met Asp His Gly Gly Val Gly Pro Tyr Glu Leu
            50              55              60

Gly Met Glu His Cys Glu Lys Phe Glu Ile Ser Glu Thr Ser Val Asn
65              70              75              80

Arg Gly Pro Glu Lys Ile Arg Pro Glu Cys Phe Glu Leu Leu Arg Val
```

```
                     85                  90                  95
Leu Gly Lys Gly Gly Tyr Gly Lys Val Phe Gln Val Arg Lys Val Thr
                100                 105                 110
Gly Ala Asn Thr Gly Lys Ile Phe Ala Met Lys Val Leu Lys Lys Ala
                115                 120                 125
Met Ile Val Arg Asn Ala Lys Asp Thr Ala His Thr Lys Ala Glu Arg
130                 135                 140
Asn Ile Leu Glu Glu Val Lys His Pro Phe Ile Val Asp Leu Ile Tyr
145                 150                 155                 160
Ala Phe Gln Thr Gly Gly Lys Leu Tyr Leu Ile Leu Glu Tyr Leu Ser
                165                 170                 175
Gly Gly Glu Leu Phe Met Gln Leu Glu Arg Glu Gly Ile Phe Met Glu
                180                 185                 190
Asp Thr Ala Cys Phe Tyr Leu Ala Glu Ile Ser Met Ala Leu Gly His
                195                 200                 205
Leu His Gln Lys Gly Ile Ile Tyr Arg Asp Leu Lys Pro Glu Asn Ile
                210                 215                 220
Met Leu Asn His Gln Gly His Val Lys Leu Thr Asp Phe Gly Leu Cys
225                 230                 235                 240
Lys Glu Ser Ile His Asp Gly Thr Val Thr His Thr Phe Cys Gly Thr
                245                 250                 255
Ile Glu Tyr Met Ala Pro Glu Ile Leu Met Arg Ser Gly His Asn Arg
                260                 265                 270
Ala Val Asp Trp Trp Ser Leu Gly Ala Leu Met Tyr Asp Met Leu Thr
                275                 280                 285
Gly Ala Pro Pro Phe Thr Gly Glu Asn Arg Lys Lys Thr Ile Asp Lys
                290                 295                 300
Ile Leu Lys Cys Lys Leu Asn Leu Pro Pro Tyr Leu Thr Gln Glu Ala
305                 310                 315                 320
Arg Asp Leu Leu Lys Lys Leu Leu Lys Arg Asn Ala Ala Ser Arg Leu
                325                 330                 335
Gly Ala Gly Pro Gly Asp Ala Gly Glu Val Gln Ala His Pro Phe Phe
                340                 345                 350
Arg His Ile Asn Trp Glu Glu Leu Leu Ala Arg Lys Val Glu Pro Pro
                355                 360                 365
Phe Lys Pro Leu Leu Gln Ser Glu Glu Asp Val Ser Gln Phe Asp Ser
                370                 375                 380
Lys Phe Thr Arg Gln Thr Pro Val Asp Ser Pro Asp Asp Ser Thr Leu
385                 390                 395                 400
Ser Glu Ser Ala Asn Gln Val Phe Leu Gly Phe Thr Tyr Val Ala Pro
                405                 410                 415
Ser Val Leu Glu Ser Val Lys Glu Lys Phe Ser Phe Glu Pro Lys Ile
                420                 425                 430
Arg Ser Pro Arg Arg Phe Ile Gly Ser Pro Arg Thr Pro Val Ser Pro
                435                 440                 445
Val Lys Phe Ser Pro Gly Asp Phe Trp Gly Arg Gly Ala Ser Ala Ser
                450                 455                 460
Thr Ala Asn Pro Gln Thr Pro Val Glu Tyr Pro Met Glu Thr Ser Gly
465                 470                 475                 480
Ile Glu Gln Met Asp Val Thr Met Ser Gly Glu Ala Ser Ala Pro Leu
                485                 490                 495
Pro Ile Arg Gln Pro Asn Ser Gly Pro Tyr Lys Lys Gln Ala Phe Pro
                500                 505                 510
```

```
Met Ile Ser Lys Arg Pro Glu His Leu Arg Met Asn Leu
            515                 520                 525

<210> SEQ ID NO 51
<211> LENGTH: 526
<212> TYPE: PRT
<213> ORGANISM: HUMAN
<300> PUBLICATION INFORMATION:
<301> AUTHORS: Kobayashi,T., Deak,M., Morrice,N. and Cohen,P.
<302> TITLE: Characterization of the structure and regulation of two
       novel
<303> JOURNAL: Biochem. J.
<304> VOLUME: 344
<305> ISSUE: 1
<306> PAGES: 189-197
<307> DATE: 1999-11-15
<308> DATABASE ACCESSION NUMBER: NP_001137148
<309> DATABASE ENTRY DATE: 2012-05-26
<313> RELEVANT RESIDUES IN SEQ ID NO: (1)..(526)

<400> SEQUENCE: 51

Met Val Asn Lys Asp Met Asn Gly Phe Pro Val Lys Cys Ser Ala
1               5                   10                  15

Phe Gln Phe Phe Lys Lys Arg Val Arg Arg Trp Ile Lys Ser Pro Met
                20                  25                  30

Val Ser Val Asp Lys His Gln Ser Pro Ser Leu Lys Tyr Thr Gly Ser
            35                  40                  45

Ser Met Val His Ile Pro Pro Gly Glu Pro Asp Phe Glu Ser Ser Leu
    50                  55                  60

Cys Gln Thr Cys Leu Gly Glu His Ala Phe Gln Arg Gly Val Leu Pro
65                  70                  75                  80

Gln Glu Asn Glu Ser Cys Ser Trp Glu Thr Gln Ser Gly Cys Glu Val
                85                  90                  95

Arg Glu Pro Cys Asn His Ala Asn Ile Leu Thr Lys Pro Asp Pro Arg
            100                 105                 110

Thr Phe Trp Thr Asn Asp Asp Pro Ala Phe Met Lys Gln Arg Arg Met
        115                 120                 125

Gly Leu Asn Asp Phe Ile Gln Lys Ile Ala Asn Asn Ser Tyr Ala Cys
    130                 135                 140

Lys His Pro Glu Val Gln Ser Ile Leu Lys Ile Ser Gln Pro Gln Glu
145                 150                 155                 160

Pro Glu Leu Met Asn Ala Asn Pro Ser Pro Pro Ser Pro Ser Ser Gln
                165                 170                 175

Gln Ile Asn Leu Gly Pro Ser Ser Asn Pro His Ala Lys Pro Ser Asp
            180                 185                 190

Phe His Phe Leu Lys Val Ile Gly Lys Gly Ser Phe Gly Lys Val Leu
        195                 200                 205

Leu Ala Arg His Lys Ala Glu Glu Val Phe Tyr Ala Val Lys Val Leu
    210                 215                 220

Gln Lys Lys Ala Ile Leu Lys Lys Glu Lys His Ile Met Ser
225                 230                 235                 240

Glu Arg Asn Val Leu Leu Lys Asn Val Lys His Pro Phe Leu Val Gly
                245                 250                 255

Leu His Phe Ser Phe Gln Thr Ala Asp Lys Leu Tyr Phe Val Leu Asp
            260                 265                 270

Tyr Ile Asn Gly Gly Glu Leu Phe Tyr His Leu Gln Arg Glu Arg Cys
        275                 280                 285

Phe Leu Glu Pro Arg Ala Arg Phe Tyr Ala Ala Glu Ile Ala Ser Ala
```

```
        290                 295                 300
Leu Gly Tyr Leu His Ser Leu Asn Ile Val Tyr Arg Asp Leu Lys Pro
305                 310                 315                 320

Glu Asn Ile Leu Leu Asp Ser Gln Gly His Ile Val Leu Thr Asp Phe
                325                 330                 335

Gly Leu Cys Lys Glu Asn Ile Glu His Asn Ser Thr Thr Ser Thr Phe
            340                 345                 350

Cys Gly Thr Pro Glu Tyr Leu Ala Pro Glu Val Leu His Lys Gln Pro
        355                 360                 365

Tyr Asp Arg Thr Val Asp Trp Trp Cys Leu Gly Ala Val Leu Tyr Glu
    370                 375                 380

Met Leu Tyr Gly Leu Pro Pro Phe Tyr Ser Arg Asn Thr Ala Glu Met
385                 390                 395                 400

Tyr Asp Asn Ile Leu Asn Lys Pro Leu Gln Leu Lys Pro Asn Ile Thr
                405                 410                 415

Asn Ser Ala Arg His Leu Leu Glu Gly Leu Leu Gln Lys Asp Arg Thr
            420                 425                 430

Lys Arg Leu Gly Ala Lys Asp Asp Phe Met Glu Ile Lys Ser His Val
        435                 440                 445

Phe Phe Ser Leu Ile Asn Trp Asp Asp Leu Ile Asn Lys Lys Ile Thr
    450                 455                 460

Pro Pro Phe Asn Pro Asn Val Ser Gly Pro Asn Asp Leu Arg His Phe
465                 470                 475                 480

Asp Pro Glu Phe Thr Glu Glu Pro Val Pro Asn Ser Ile Gly Lys Ser
                485                 490                 495

Pro Asp Ser Val Leu Val Thr Ala Ser Val Lys Glu Ala Ala Glu Ala
            500                 505                 510

Phe Leu Gly Phe Ser Tyr Ala Pro Pro Thr Asp Ser Phe Leu
        515                 520                 525

<210> SEQ ID NO 52
<211> LENGTH: 783
<212> TYPE: PRT
<213> ORGANISM: HUMAN
<300> PUBLICATION INFORMATION:
<301> AUTHORS: Hashimoto,Y.K., Satoh,T., Okamoto,M. and Takemori,H.
<302> TITLE: Importance of autophosphorylation at Ser186 in the A-loop
       of salt
<303> JOURNAL: J. Cell. Biochem.
<304> VOLUME: 104
<305> ISSUE: 5
<306> PAGES: 1724-1739
<307> DATE: 2008-08-01
<308> DATABASE ACCESSION NUMBER: NP_775490
<309> DATABASE ENTRY DATE: 2012-04-21
<313> RELEVANT RESIDUES IN SEQ ID NO: (1)..(783)

<400> SEQUENCE: 52

Met Val Ile Met Ser Glu Phe Ser Ala Asp Pro Ala Gly Gln Gly Gln
1               5                   10                  15

Gly Gln Gln Lys Pro Leu Arg Val Gly Phe Tyr Asp Ile Glu Arg Thr
            20                  25                  30

Leu Gly Lys Gly Asn Phe Ala Val Val Lys Leu Ala Arg His Arg Val
        35                  40                  45

Thr Lys Thr Gln Val Ala Ile Lys Ile Ile Asp Lys Thr Arg Leu Asp
    50                  55                  60

Ser Ser Asn Leu Glu Lys Ile Tyr Arg Glu Val Gln Leu Met Lys Leu
65                  70                  75                  80
```

```
Leu Asn His Pro His Ile Ile Lys Leu Tyr Gln Val Met Glu Thr Lys
                85                  90                  95
Asp Met Leu Tyr Ile Val Thr Glu Phe Ala Lys Asn Gly Glu Met Phe
            100                 105                 110
Asp Tyr Leu Thr Ser Asn Gly His Leu Ser Glu Asn Glu Ala Arg Lys
            115                 120                 125
Lys Phe Trp Gln Ile Leu Ser Ala Val Glu Tyr Cys His Asp His His
        130                 135                 140
Ile Val His Arg Asp Leu Lys Thr Glu Asn Leu Leu Leu Asp Gly Asn
145                 150                 155                 160
Met Asp Ile Lys Leu Ala Asp Phe Gly Phe Gly Asn Phe Tyr Lys Ser
                165                 170                 175
Gly Glu Pro Leu Ser Thr Trp Cys Gly Ser Pro Pro Tyr Ala Ala Pro
            180                 185                 190
Glu Val Phe Glu Gly Lys Glu Tyr Glu Gly Pro Gln Leu Asp Ile Trp
            195                 200                 205
Ser Leu Gly Val Val Leu Tyr Val Leu Val Cys Gly Ser Leu Pro Phe
        210                 215                 220
Asp Gly Pro Asn Leu Pro Thr Leu Arg Gln Arg Val Leu Glu Gly Arg
225                 230                 235                 240
Phe Arg Ile Pro Phe Phe Met Ser Gln Asp Cys Glu Ser Leu Ile Arg
                245                 250                 255
Arg Met Leu Val Val Asp Pro Ala Arg Arg Ile Thr Ile Ala Gln Ile
            260                 265                 270
Arg Gln His Arg Trp Met Arg Ala Glu Pro Cys Leu Pro Gly Pro Ala
        275                 280                 285
Cys Pro Ala Phe Ser Ala His Ser Tyr Thr Ser Asn Leu Gly Asp Tyr
        290                 295                 300
Asp Glu Gln Ala Leu Gly Ile Met Gln Thr Leu Gly Val Asp Arg Gln
305                 310                 315                 320
Arg Thr Val Glu Ser Leu Gln Asn Ser Ser Tyr Asn His Phe Ala Ala
                325                 330                 335
Ile Tyr Tyr Leu Leu Leu Glu Arg Leu Lys Glu Tyr Arg Asn Ala Gln
            340                 345                 350
Cys Ala Arg Pro Gly Pro Ala Arg Gln Pro Arg Pro Arg Ser Ser Asp
        355                 360                 365
Leu Ser Gly Leu Glu Val Pro Gln Glu Gly Leu Ser Thr Asp Pro Phe
        370                 375                 380
Arg Pro Ala Leu Leu Cys Pro Gln Pro Gln Thr Leu Val Gln Ser Val
385                 390                 395                 400
Leu Gln Ala Glu Met Asp Cys Glu Leu Gln Ser Ser Leu Gln Trp Pro
                405                 410                 415
Leu Phe Phe Pro Val Asp Ala Ser Cys Ser Gly Val Phe Arg Pro Arg
            420                 425                 430
Pro Val Ser Pro Ser Ser Leu Leu Asp Thr Ala Ile Ser Glu Glu Ala
        435                 440                 445
Arg Gln Gly Pro Gly Leu Glu Glu Gln Asp Thr Gln Glu Ser Leu
        450                 455                 460
Pro Ser Ser Thr Gly Arg Arg His Thr Leu Ala Glu Val Ser Thr Arg
465                 470                 475                 480
Leu Ser Pro Leu Thr Ala Pro Cys Ile Val Val Ser Pro Ser Thr Thr
                485                 490                 495
Ala Ser Pro Ala Glu Gly Thr Ser Ser Asp Ser Cys Leu Thr Phe Ser
```

```
                    500                 505                 510
Ala Ser Lys Ser Pro Ala Gly Leu Ser Gly Thr Pro Ala Thr Gln Gly
            515                 520                 525

Leu Leu Gly Ala Cys Ser Pro Val Arg Leu Ala Ser Pro Phe Leu Gly
        530                 535                 540

Ser Gln Ser Ala Thr Pro Val Leu Gln Ala Gln Gly Gly Leu Gly Gly
545                 550                 555                 560

Ala Val Leu Leu Pro Val Ser Phe Gln Glu Gly Arg Arg Ala Ser Asp
                565                 570                 575

Thr Ser Leu Thr Gln Gly Leu Lys Ala Phe Arg Gln Gln Leu Arg Lys
            580                 585                 590

Thr Thr Arg Thr Lys Gly Phe Leu Gly Leu Asn Lys Ile Lys Gly Leu
        595                 600                 605

Ala Arg Gln Val Cys Gln Ala Pro Ala Ser Arg Ala Ser Arg Gly Gly
    610                 615                 620

Leu Ser Pro Phe His Ala Pro Ala Gln Ser Pro Gly Leu His Gly Gly
625                 630                 635                 640

Ala Ala Gly Ser Arg Glu Gly Trp Ser Leu Leu Glu Glu Val Leu Glu
                645                 650                 655

Gln Gln Arg Leu Leu Gln Leu Gln His His Pro Ala Ala Pro Gly
            660                 665                 670

Cys Ser Gln Ala Pro Gln Pro Ala Pro Ala Pro Phe Val Ile Ala Pro
        675                 680                 685

Cys Asp Gly Pro Gly Ala Ala Pro Leu Pro Ser Thr Leu Leu Thr Ser
    690                 695                 700

Gly Leu Pro Leu Leu Pro Pro Pro Leu Leu Gln Thr Gly Ala Ser Pro
705                 710                 715                 720

Val Ala Ser Ala Ala Gln Leu Leu Asp Thr His Leu His Ile Gly Thr
                725                 730                 735

Gly Pro Thr Ala Leu Pro Ala Val Pro Pro Arg Leu Ala Arg Leu
            740                 745                 750

Ala Pro Gly Cys Glu Pro Leu Gly Leu Leu Gln Gly Asp Cys Glu Met
        755                 760                 765

Glu Asp Leu Met Pro Cys Ser Leu Gly Thr Phe Val Leu Val Gln
    770                 775                 780
```

<210> SEQ ID NO 53
<211> LENGTH: 926
<212> TYPE: PRT
<213> ORGANISM: HUMAN
<300> PUBLICATION INFORMATION:
<301> AUTHORS: Ahmed,A.A., Lu,Z., Jennings,N.B., Etemadmoghadam,D., Capalbo,L.,
<302> TITLE: SIK2 is a centrosome kinase required for bipolar mitotic spindle
<303> JOURNAL: Cancer Cell
<304> VOLUME: 18
<305> ISSUE: 2
<306> PAGES: 109-121
<307> DATE: 2010-08-17
<308> DATABASE ACCESSION NUMBER: NP_056006
<309> DATABASE ENTRY DATE: 2012-03-25
<313> RELEVANT RESIDUES IN SEQ ID NO: (1)..(926)

<400> SEQUENCE: 53

```
Met Val Met Ala Asp Gly Pro Arg His Leu Gln Arg Gly Pro Val Arg
1               5                   10                  15

Val Gly Phe Tyr Asp Ile Glu Gly Thr Leu Gly Lys Gly Asn Phe Ala
            20                  25                  30
```

```
Val Val Lys Leu Gly Arg His Arg Ile Thr Lys Thr Glu Val Ala Ile
         35                  40                  45

Lys Ile Ile Asp Lys Ser Gln Leu Asp Ala Val Asn Leu Glu Lys Ile
 50                  55                  60

Tyr Arg Glu Val Gln Ile Met Lys Met Leu Asp His Pro His Ile Ile
 65                  70                  75                  80

Lys Leu Tyr Gln Val Met Glu Thr Lys Ser Met Leu Tyr Leu Val Thr
                 85                  90                  95

Glu Tyr Ala Lys Asn Gly Glu Ile Phe Asp Tyr Leu Ala Asn His Gly
             100                 105                 110

Arg Leu Asn Glu Ser Glu Ala Arg Arg Lys Phe Trp Gln Ile Leu Ser
         115                 120                 125

Ala Val Asp Tyr Cys His Gly Arg Lys Ile Val His Arg Asp Leu Lys
 130                 135                 140

Ala Glu Asn Leu Leu Leu Asp Asn Asn Met Asn Ile Lys Ile Ala Asp
145                 150                 155                 160

Phe Gly Phe Gly Asn Phe Phe Lys Ser Gly Glu Leu Leu Ala Thr Trp
                 165                 170                 175

Cys Gly Ser Pro Pro Tyr Ala Ala Pro Glu Val Phe Glu Gly Gln Gln
             180                 185                 190

Tyr Glu Gly Pro Gln Leu Asp Ile Trp Ser Met Gly Val Val Leu Tyr
         195                 200                 205

Val Leu Val Cys Gly Ala Leu Pro Phe Asp Gly Pro Thr Leu Pro Ile
 210                 215                 220

Leu Arg Gln Arg Val Leu Glu Gly Arg Phe Arg Ile Pro Tyr Phe Met
225                 230                 235                 240

Ser Glu Asp Cys Glu His Leu Ile Arg Arg Met Leu Val Leu Asp Pro
                 245                 250                 255

Ser Lys Arg Leu Thr Ile Ala Gln Ile Lys Glu His Lys Trp Met Leu
             260                 265                 270

Ile Glu Val Pro Val Gln Arg Pro Val Leu Tyr Pro Gln Glu Gln Glu
         275                 280                 285

Asn Glu Pro Ser Ile Gly Glu Phe Asn Glu Gln Val Leu Arg Leu Met
 290                 295                 300

His Ser Leu Gly Ile Asp Gln Gln Lys Thr Ile Glu Ser Leu Gln Asn
305                 310                 315                 320

Lys Ser Tyr Asn His Phe Ala Ala Ile Tyr Phe Leu Leu Val Glu Arg
                 325                 330                 335

Leu Lys Ser His Arg Ser Ser Phe Pro Val Glu Gln Arg Leu Asp Gly
             340                 345                 350

Arg Gln Arg Arg Pro Ser Thr Ile Ala Glu Gln Thr Val Ala Lys Ala
         355                 360                 365

Gln Thr Val Gly Leu Pro Val Thr Met His Ser Pro Asn Met Arg Leu
 370                 375                 380

Leu Arg Ser Ala Leu Leu Pro Gln Ala Ser Asn Val Glu Ala Phe Ser
385                 390                 395                 400

Phe Pro Ala Ser Gly Cys Gln Ala Glu Ala Ala Phe Met Glu Glu Glu
                 405                 410                 415

Cys Val Asp Thr Pro Lys Val Asn Gly Cys Leu Leu Asp Pro Val Pro
             420                 425                 430

Pro Val Leu Val Arg Lys Gly Cys Gln Ser Leu Pro Ser Asn Met Met
         435                 440                 445
```

```
Glu Thr Ser Ile Asp Glu Gly Leu Glu Thr Glu Gly Glu Ala Glu Glu
    450                 455                 460
Asp Pro Ala His Ala Phe Glu Ala Phe Gln Ser Thr Arg Ser Gly Gln
465                 470                 475                 480
Arg Arg His Thr Leu Ser Glu Val Thr Asn Gln Leu Val Val Met Pro
                485                 490                 495
Gly Ala Gly Lys Ile Phe Ser Met Asn Asp Ser Pro Ser Leu Asp Ser
                500                 505                 510
Val Asp Ser Glu Tyr Asp Met Gly Ser Val Gln Arg Asp Leu Asn Phe
            515                 520                 525
Leu Glu Asp Asn Pro Ser Leu Lys Asp Ile Met Leu Ala Asn Gln Pro
530                 535                 540
Ser Pro Arg Met Thr Ser Pro Phe Ile Ser Leu Arg Pro Thr Asn Pro
545                 550                 555                 560
Ala Met Gln Ala Leu Ser Ser Gln Lys Arg Glu Val His Asn Arg Ser
                565                 570                 575
Pro Val Ser Phe Arg Glu Gly Arg Arg Ala Ser Asp Thr Ser Leu Thr
                580                 585                 590
Gln Gly Ile Val Ala Phe Arg Gln His Leu Gln Asn Leu Ala Arg Thr
                595                 600                 605
Lys Gly Ile Leu Glu Leu Asn Lys Val Gln Leu Leu Tyr Glu Gln Ile
610                 615                 620
Gly Pro Glu Ala Asp Pro Asn Leu Ala Pro Ala Pro Gln Leu Gln
625                 630                 635                 640
Asp Leu Ala Ser Ser Cys Pro Gln Glu Val Ser Gln Gln Glu
                645                 650                 655
Ser Val Ser Thr Leu Pro Ala Ser Val His Pro Gln Leu Ser Pro Arg
                660                 665                 670
Gln Ser Leu Glu Thr Gln Tyr Leu Gln His Arg Leu Gln Lys Pro Ser
                675                 680                 685
Leu Leu Ser Lys Ala Gln Asn Thr Cys Gln Leu Tyr Cys Lys Glu Pro
                690                 695                 700
Pro Arg Ser Leu Glu Gln Gln Leu Gln Glu His Arg Leu Gln Gln Lys
705                 710                 715                 720
Arg Leu Phe Leu Gln Lys Gln Ser Gln Leu Gln Ala Tyr Phe Asn Gln
                725                 730                 735
Met Gln Ile Ala Glu Ser Ser Tyr Pro Gln Pro Ser Gln Gln Leu Pro
                740                 745                 750
Leu Pro Arg Gln Glu Thr Pro Pro Ser Gln Ala Pro Pro Phe
                755                 760                 765
Ser Leu Thr Gln Pro Leu Ser Pro Val Leu Glu Pro Ser Ser Glu Gln
                770                 775                 780
Met Gln Tyr Ser Pro Phe Leu Ser Gln Tyr Gln Glu Met Gln Leu Gln
785                 790                 795                 800
Pro Leu Pro Ser Thr Ser Gly Pro Arg Ala Ala Pro Leu Pro Thr
                805                 810                 815
Gln Leu Gln Gln Gln Pro Pro Pro Pro Pro Pro Pro Pro
                820                 825                 830
Arg Gln Pro Gly Ala Ala Pro Ala Pro Leu Gln Phe Ser Tyr Gln Thr
                835                 840                 845
Cys Glu Leu Pro Ser Ala Ala Ser Pro Ala Pro Asp Tyr Pro Thr Pro
850                 855                 860
Cys Gln Tyr Pro Val Asp Gly Ala Gln Gln Ser Asp Leu Thr Gly Pro
```

-continued

```
               865                 870                 875                 880

Asp Cys Pro Arg Ser Pro Gly Leu Gln Glu Ala Pro Ser Ser Tyr Asp
                    885                 890                 895

Pro Leu Ala Leu Ser Glu Leu Pro Gly Leu Phe Asp Cys Glu Met Leu
                    900                 905                 910

Asp Ala Val Asp Pro Gln His Asn Gly Tyr Val Leu Val Asn
                    915                 920                 925

<210> SEQ ID NO 54
<211> LENGTH: 612
<212> TYPE: PRT
<213> ORGANISM: HUMAN
<300> PUBLICATION INFORMATION:
<301> AUTHORS: Cheng,S., Coffey,G., Zhang,X.H., Shaknovich,R., Song,Z.,
      Lu,P.
<302> TITLE: SYK inhibition and response prediction in diffuse large
      B-cell
<303> JOURNAL: Blood
<304> VOLUME: 118
<305> ISSUE: 24
<306> PAGES: 6342-6352
<307> DATE: 2011-10-24
<308> DATABASE ACCESSION NUMBER: NP_001128524
<309> DATABASE ENTRY DATE: 2012-05-13
<313> RELEVANT RESIDUES IN SEQ ID NO: (1)..(612)

<400> SEQUENCE: 54

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
                20                  25                  30

Gly Met Ser Asp Gly Leu Tyr Leu Leu Arg Gln Ser Arg Asn Tyr Leu
            35                  40                  45

Gly Gly Phe Ala Leu Ser Val Ala His Gly Arg Lys Ala His His Tyr
        50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
                100                 105                 110

Val Gln Pro Lys Thr Gly Pro Phe Glu Asp Leu Lys Glu Asn Leu Ile
            115                 120                 125

Arg Glu Tyr Val Lys Gln Thr Trp Asn Leu Gln Gly Gln Ala Leu Glu
        130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
        210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255
```

Val Pro Cys Gln Lys Ile Gly Thr Gln Gly Asn Val Asn Phe Gly Gly
            260                 265                 270

Arg Pro Gln Leu Pro Gly Ser His Pro Ala Ser Ser Pro Ala Gln Gly
            275                 280                 285

Asn Arg Gln Glu Ser Thr Val Ser Phe Asn Pro Tyr Glu Pro Glu Leu
            290                 295                 300

Ala Pro Trp Ala Ala Asp Lys Gly Pro Gln Arg Glu Ala Leu Pro Met
305                 310                 315                 320

Asp Thr Glu Val Tyr Glu Ser Pro Tyr Ala Asp Pro Glu Glu Ile Arg
            325                 330                 335

Pro Lys Glu Val Tyr Leu Asp Arg Lys Leu Leu Thr Leu Glu Asp Lys
            340                 345                 350

Glu Leu Gly Ser Gly Asn Phe Gly Thr Val Lys Lys Gly Tyr Tyr Gln
            355                 360                 365

Met Lys Lys Val Val Lys Thr Val Ala Val Lys Ile Leu Lys Asn Glu
            370                 375                 380

Ala Asn Asp Pro Ala Leu Lys Asp Glu Leu Leu Ala Glu Ala Asn Val
385                 390                 395                 400

Met Gln Gln Leu Asp Asn Pro Tyr Ile Val Arg Met Ile Gly Ile Cys
            405                 410                 415

Glu Ala Glu Ser Trp Met Leu Val Met Glu Met Ala Glu Leu Gly Pro
            420                 425                 430

Leu Asn Lys Tyr Leu Gln Gln Asn Arg His Val Lys Asp Lys Asn Ile
            435                 440                 445

Ile Glu Leu Val His Gln Val Ser Met Gly Met Lys Tyr Leu Glu Glu
            450                 455                 460

Ser Asn Phe Val His Arg Asp Leu Ala Ala Arg Asn Val Leu Leu Val
465                 470                 475                 480

Thr Gln His Tyr Ala Lys Ile Ser Asp Phe Gly Leu Ser Lys Ala Leu
            485                 490                 495

Arg Ala Asp Glu Asn Tyr Tyr Lys Ala Gln Thr His Gly Lys Trp Pro
            500                 505                 510

Val Lys Trp Tyr Ala Pro Glu Cys Ile Asn Tyr Tyr Lys Phe Ser Ser
            515                 520                 525

Lys Ser Asp Val Trp Ser Phe Gly Val Leu Met Trp Glu Ala Phe Ser
530                 535                 540

Tyr Gly Gln Lys Pro Tyr Arg Gly Met Lys Gly Ser Glu Val Thr Ala
545                 550                 555                 560

Met Leu Glu Lys Gly Glu Arg Met Gly Cys Pro Ala Gly Cys Pro Arg
            565                 570                 575

Glu Met Tyr Asp Leu Met Asn Leu Cys Trp Thr Tyr Asp Val Glu Asn
            580                 585                 590

Arg Pro Gly Phe Ala Ala Val Glu Leu Arg Leu Arg Asn Tyr Tyr Tyr
            595                 600                 605

Asp Val Val Asn
            610

<210> SEQ ID NO 55
<211> LENGTH: 1352
<212> TYPE: PRT
<213> ORGANISM: HUMAN
<300> PUBLICATION INFORMATION:
<301> AUTHORS: Fu,C.A., Shen,M., Huang,B.C., Lasaga,J., Payan,D.G. and
      Luo,Y.
<302> TITLE: TNIK, a novel member of the germinal center kinase family

```
          that
<303> JOURNAL: J. Biol. Chem.
<304> VOLUME: 274
<305> ISSUE: 43
<306> PAGES: 30729-30737
<307> DATE: 1999-10-22
<308> DATABASE ACCESSION NUMBER: NP_001155032
<309> DATABASE ENTRY DATE: 2012-03-26
<313> RELEVANT RESIDUES IN SEQ ID NO: (1)..(1352)

<400> SEQUENCE: 55

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Arg Gly Glu Lys Asp Glu Thr Glu
305                 310                 315                 320

Tyr Glu Tyr Ser Gly Ser Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
```

-continued

```
            355                 360                 365
Arg Arg Gln Gln Leu Glu Gln Gln Arg Glu Asn Glu Glu His Lys
    370                 375                 380
Arg Gln Leu Leu Ala Glu Arg Gln Lys Arg Ile Glu Glu Gln Lys Glu
385                 390                 395                 400
Gln Arg Arg Arg Leu Glu Glu Gln Arg Glu Lys Glu Leu Arg
                405                 410                 415
Lys Gln Gln Glu Arg Glu Gln Arg Arg His Tyr Glu Glu Gln Met Arg
            420                 425                 430
Arg Glu Glu Glu Arg Arg Ala Glu His Glu Gln Glu Tyr Ile Arg
        435                 440                 445
Arg Gln Leu Glu Glu Glu Gln Arg Gln Leu Glu Ile Leu Gln Gln Gln
    450                 455                 460
Leu Leu His Glu Gln Ala Leu Leu Leu Glu Tyr Lys Arg Lys Gln Leu
465                 470                 475                 480
Glu Glu Gln Arg Gln Ala Glu Arg Leu Gln Arg Gln Leu Lys Gln Glu
                485                 490                 495
Arg Asp Tyr Leu Val Ser Leu Gln His Gln Arg Gln Glu Gln Arg Pro
            500                 505                 510
Val Glu Lys Lys Pro Leu Tyr His Tyr Lys Glu Gly Met Ser Pro Ser
        515                 520                 525
Glu Lys Pro Ala Trp Ala Lys Glu Val Glu Glu Arg Ser Arg Leu Asn
    530                 535                 540
Arg Gln Ser Ser Pro Ala Met Pro His Lys Val Ala Asn Arg Ile Ser
545                 550                 555                 560
Asp Pro Asn Leu Pro Pro Arg Ser Glu Ser Phe Ser Ile Ser Gly Val
                565                 570                 575
Gln Pro Ala Arg Thr Pro Met Leu Arg Pro Val Asp Pro Gln Ile
            580                 585                 590
Pro His Leu Val Ala Val Lys Ser Gln Gly Pro Ala Leu Thr Ala Ser
        595                 600                 605
Gln Ser Val His Glu Gln Pro Thr Lys Gly Leu Ser Gly Phe Gln Glu
    610                 615                 620
Ala Leu Asn Val Thr Ser His Arg Val Glu Met Pro Arg Gln Asn Ser
625                 630                 635                 640
Asp Pro Thr Ser Glu Asn Pro Pro Leu Pro Thr Arg Ile Glu Lys Phe
                645                 650                 655
Asp Arg Ser Ser Trp Leu Arg Gln Glu Glu Asp Ile Pro Pro Lys Val
            660                 665                 670
Pro Gln Arg Thr Thr Ser Ile Ser Pro Ala Leu Ala Arg Lys Asn Ser
        675                 680                 685
Pro Gly Asn Gly Ser Ala Leu Gly Pro Arg Leu Gly Ser Gln Pro Ile
    690                 695                 700
Arg Ala Ser Asn Pro Asp Leu Arg Arg Thr Glu Pro Ile Leu Glu Ser
705                 710                 715                 720
Pro Leu Gln Arg Thr Ser Ser Gly Ser Ser Ser Ser Ser Thr Pro
                725                 730                 735
Ser Ser Gln Pro Ser Ser Gln Gly Gly Ser Gln Pro Gly Ser Gln Ala
            740                 745                 750
Gly Ser Ser Glu Arg Thr Arg Val Arg Ala Asn Ser Lys Ser Glu Gly
        755                 760                 765
Ser Pro Val Leu Pro His Glu Pro Ala Lys Val Lys Pro Glu Glu Ser
    770                 775                 780
```

-continued

Arg Asp Ile Thr Arg Pro Ser Arg Pro Ala Asp Leu Thr Ala Leu Ala
785                 790                 795                 800

Lys Glu Leu Arg Glu Leu Arg Ile Glu Glu Thr Asn Arg Pro Met Lys
            805                 810                 815

Lys Val Thr Asp Tyr Ser Ser Ser Glu Glu Ser Glu Ser Ser Glu
            820                 825                 830

Glu Glu Glu Glu Asp Gly Glu Ser Glu Thr His Asp Gly Thr Val Ala
            835                 840                 845

Val Ser Asp Ile Pro Arg Leu Ile Pro Thr Gly Ala Pro Gly Ser Asn
850                 855                 860

Glu Gln Tyr Asn Val Gly Met Val Gly Thr His Gly Leu Glu Thr Ser
865                 870                 875                 880

His Ala Asp Ser Phe Ser Gly Ser Ile Ser Arg Glu Gly Thr Leu Met
                885                 890                 895

Ile Arg Glu Thr Ser Gly Glu Lys Lys Arg Ser Gly His Ser Asp Ser
            900                 905                 910

Asn Gly Phe Ala Gly His Ile Asn Leu Pro Asp Leu Val Gln Gln Ser
            915                 920                 925

His Ser Pro Ala Gly Thr Pro Thr Glu Gly Leu Gly Arg Val Ser Thr
930                 935                 940

His Ser Gln Glu Met Asp Ser Gly Thr Glu Tyr Gly Met Gly Ser Ser
945                 950                 955                 960

Thr Lys Ala Ser Phe Thr Pro Phe Val Asp Pro Arg Val Tyr Gln Thr
                965                 970                 975

Ser Pro Thr Asp Glu Asp Glu Asp Glu Ser Ser Ala Ala Ala
            980                 985                 990

Leu Phe Thr Ser Glu Leu Leu Arg Gln Glu Gln Ala Lys Leu Asn Glu
            995                 1000                1005

Ala Arg Lys Ile Ser Val Val Asn Val Asn Pro Thr Asn Ile Arg
    1010                1015                1020

Pro His Ser Asp Thr Pro Glu Ile Arg Lys Tyr Lys Lys Arg Phe
    1025                1030                1035

Asn Ser Glu Ile Leu Cys Ala Ala Leu Trp Gly Val Asn Leu Leu
    1040                1045                1050

Val Gly Thr Glu Asn Gly Leu Met Leu Leu Asp Arg Ser Gly Gln
    1055                1060                1065

Gly Lys Val Tyr Asn Leu Ile Asn Arg Arg Arg Phe Gln Gln Met
    1070                1075                1080

Asp Val Leu Glu Gly Leu Asn Val Leu Val Thr Ile Ser Gly Lys
    1085                1090                1095

Lys Asn Lys Leu Arg Val Tyr Tyr Leu Ser Trp Leu Arg Asn Arg
    1100                1105                1110

Ile Leu His Asn Asp Pro Glu Val Glu Lys Lys Gln Gly Trp Ile
    1115                1120                1125

Thr Val Gly Asp Leu Glu Gly Cys Ile His Tyr Lys Val Val Lys
    1130                1135                1140

Tyr Glu Arg Ile Lys Phe Leu Val Ile Ala Leu Lys Asn Ala Val
    1145                1150                1155

Glu Ile Tyr Ala Trp Ala Pro Lys Pro Tyr His Lys Phe Met Ala
    1160                1165                1170

Phe Lys Ser Phe Ala Asp Leu Gln His Lys Pro Leu Leu Val Asp
    1175                1180                1185

-continued

```
Leu Thr Val Glu Glu Gly Gln Arg Leu Lys Val Ile Phe Gly Ser
    1190                1195                1200

His Thr Gly Phe His Val Ile Asp Val Asp Ser Gly Asn Ser Tyr
    1205                1210                1215

Asp Ile Tyr Ile Pro Ser His Ile Gln Gly Asn Ile Thr Pro His
    1220                1225                1230

Ala Ile Val Ile Leu Pro Lys Thr Asp Gly Met Glu Met Leu Val
    1235                1240                1245

Cys Tyr Glu Asp Glu Gly Val Tyr Val Asn Thr Tyr Gly Arg Ile
    1250                1255                1260

Thr Lys Asp Val Val Leu Gln Trp Gly Glu Met Pro Thr Ser Val
    1265                1270                1275

Ala Tyr Ile His Ser Asn Gln Ile Met Gly Trp Gly Glu Lys Ala
    1280                1285                1290

Ile Glu Ile Arg Ser Val Glu Thr Gly His Leu Asp Gly Val Phe
    1295                1300                1305

Met His Lys Arg Ala Gln Arg Leu Lys Phe Leu Cys Glu Arg Asn
    1310                1315                1320

Asp Lys Val Phe Phe Ala Ser Val Arg Ser Gly Gly Ser Ser Gln
    1325                1330                1335

Val Phe Phe Met Thr Leu Asn Arg Asn Ser Met Met Asn Trp
    1340                1345                1350

<210> SEQ ID NO 56
<211> LENGTH: 760
<212> TYPE: PRT
<213> ORGANISM: HUMAN
<300> PUBLICATION INFORMATION:
<301> AUTHORS: Demont,Y., Corbet,C., Page,A., Ataman-Onal,Y.,
<302> TITLE: Pro-nerve growth factor induces autocrine stimulation of
      breast
<303> JOURNAL: J. Biol. Chem.
<304> VOLUME: 287
<305> ISSUE: 3
<306> PAGES: 1923-1931
<307> DATE: 2012-01-13
<308> DATABASE ACCESSION NUMBER: NP_001007793
<309> DATABASE ENTRY DATE: 2012-05-05
<313> RELEVANT RESIDUES IN SEQ ID NO: (1)..(760)

<400> SEQUENCE: 56

Met Lys Glu Ala Ala Leu Ile Cys Leu Ala Pro Ser Val Pro Ile
1               5                   10                  15

Leu Thr Val Lys Ser Trp Asp Thr Met Gln Leu Arg Ala Ala Arg Ser
                20                  25                  30

Arg Cys Thr Asn Leu Leu Ala Ala Ser Tyr Ile Glu Asn Gln Gln His
        35                  40                  45

Leu Gln His Leu Glu Leu Arg Asp Leu Arg Gly Leu Gly Glu Leu Arg
    50                  55                  60

Asn Leu Thr Ile Val Lys Ser Gly Leu Arg Phe Val Ala Pro Asp Ala
65                  70                  75                  80

Phe His Phe Thr Pro Arg Leu Ser Arg Leu Asn Leu Ser Phe Asn Ala
                85                  90                  95

Leu Glu Ser Leu Ser Trp Lys Thr Val Gln Gly Leu Ser Leu Gln Glu
                100                 105                 110

Leu Val Leu Ser Gly Asn Pro Leu His Cys Ser Cys Ala Leu Arg Trp
            115                 120                 125

Leu Gln Arg Trp Glu Glu Glu Gly Leu Gly Gly Val Pro Glu Gln Lys
    130                 135                 140
```

```
Leu Gln Cys His Gly Gln Gly Pro Leu Ala His Met Pro Asn Ala Ser
145                 150                 155                 160

Cys Gly Val Pro Thr Leu Lys Val Gln Val Pro Asn Ala Ser Val Asp
            165                 170                 175

Val Gly Asp Asp Val Leu Leu Arg Cys Gln Val Glu Gly Arg Gly Leu
        180                 185                 190

Glu Gln Ala Gly Trp Ile Leu Thr Glu Leu Gln Ser Ala Thr Val
    195                 200                 205

Met Lys Ser Gly Gly Leu Pro Ser Leu Gly Leu Thr Leu Ala Asn Val
210                 215                 220

Thr Ser Asp Leu Asn Arg Lys Asn Val Thr Cys Trp Ala Glu Asn Asp
225                 230                 235                 240

Val Gly Arg Ala Glu Val Ser Val Gln Val Asn Val Ser Phe Pro Ala
                245                 250                 255

Ser Val Gln Leu His Thr Ala Val Glu Met His His Trp Cys Ile Pro
            260                 265                 270

Phe Ser Val Asp Gly Gln Pro Ala Pro Ser Leu Arg Trp Leu Phe Asn
        275                 280                 285

Gly Ser Val Leu Asn Glu Thr Ser Phe Ile Phe Thr Glu Phe Leu Glu
    290                 295                 300

Pro Ala Ala Asn Glu Thr Val Arg His Gly Cys Leu Arg Leu Asn Gln
305                 310                 315                 320

Pro Thr His Val Asn Asn Gly Asn Tyr Thr Leu Leu Ala Ala Asn Pro
                325                 330                 335

Phe Gly Gln Ala Ser Ala Ser Ile Met Ala Ala Phe Met Asp Asn Pro
            340                 345                 350

Phe Glu Phe Asn Pro Glu Asp Pro Ile Pro Asp Thr Asn Ser Thr Ser
        355                 360                 365

Gly Asp Pro Val Glu Lys Lys Asp Glu Thr Pro Phe Gly Val Ser Val
    370                 375                 380

Ala Val Gly Leu Ala Val Phe Ala Cys Leu Phe Leu Ser Thr Leu Leu
385                 390                 395                 400

Leu Val Leu Asn Lys Cys Gly Arg Arg Asn Lys Phe Gly Ile Asn Arg
                405                 410                 415

Pro Ala Val Leu Ala Pro Glu Asp Gly Leu Ala Met Ser Leu His Phe
            420                 425                 430

Met Thr Leu Gly Gly Ser Ser Leu Ser Pro Thr Glu Gly Lys Gly Ser
        435                 440                 445

Gly Leu Gln Gly His Ile Ile Glu Asn Pro Gln Tyr Phe Ser Asp Ala
    450                 455                 460

Cys Val His His Ile Lys Arg Arg Asp Ile Val Leu Lys Trp Glu Leu
465                 470                 475                 480

Gly Glu Gly Ala Phe Gly Lys Val Phe Leu Ala Glu Cys His Asn Leu
                485                 490                 495

Leu Pro Glu Gln Asp Lys Met Leu Val Ala Val Lys Ala Leu Lys Glu
            500                 505                 510

Ala Ser Glu Ser Ala Arg Gln Asp Phe Gln Arg Glu Ala Glu Leu Leu
        515                 520                 525

Thr Met Leu Gln His Gln His Ile Val Arg Phe Phe Gly Val Cys Thr
    530                 535                 540

Glu Gly Arg Pro Leu Leu Met Val Phe Glu Tyr Met Arg His Gly Asp
545                 550                 555                 560
```

Leu Asn Arg Phe Leu Arg Ser His Gly Pro Asp Ala Lys Leu Leu Ala
            565                 570                 575

Gly Gly Glu Asp Val Ala Pro Gly Pro Leu Gly Leu Gly Gln Leu Leu
        580                 585                 590

Ala Val Ala Ser Gln Val Ala Ala Gly Met Val Tyr Leu Ala Gly Leu
        595                 600                 605

His Phe Val His Arg Asp Leu Ala Thr Arg Asn Cys Leu Val Gly Gln
610                 615                 620

Gly Leu Val Val Lys Ile Gly Asp Phe Gly Met Ser Arg Asp Ile Tyr
625                 630                 635                 640

Ser Thr Asp Tyr Tyr Arg Val Gly Gly Arg Thr Met Leu Pro Ile Arg
                645                 650                 655

Trp Met Pro Pro Glu Ser Ile Leu Tyr Arg Lys Phe Thr Thr Glu Ser
            660                 665                 670

Asp Val Trp Ser Phe Gly Val Val Leu Trp Glu Ile Phe Thr Tyr Gly
        675                 680                 685

Lys Gln Pro Trp Tyr Gln Leu Ser Asn Thr Glu Ala Ile Asp Cys Ile
        690                 695                 700

Thr Gln Gly Arg Glu Leu Glu Arg Pro Arg Ala Cys Pro Pro Glu Val
705                 710                 715                 720

Tyr Ala Ile Met Arg Gly Cys Trp Gln Arg Glu Pro Gln Gln Arg His
                725                 730                 735

Ser Ile Lys Asp Val His Ala Arg Leu Gln Ala Leu Ala Gln Ala Pro
            740                 745                 750

Pro Val Tyr Leu Asp Val Leu Gly
            755                 760

<210> SEQ ID NO 57
<211> LENGTH: 477
<212> TYPE: PRT
<213> ORGANISM: HUMAN
<300> PUBLICATION INFORMATION:
<301> AUTHORS: Guo,D., Hou,X., Zhang,H., Sun,W., Zhu,L., Liang,J. and
      Jiang,X.
<302> TITLE: More expressions of BDNF and TrkB in multiple
      hepatocellular
<303> JOURNAL: J. Exp. Clin. Cancer Res.
<304> VOLUME: 30
<305> ISSUE: 97
<306> PAGES: 97-100
<307> DATE: 2011-10-14
<308> DATABASE ACCESSION NUMBER: NP_001007098
<309> DATABASE ENTRY DATE: 2012-05-13
<313> RELEVANT RESIDUES IN SEQ ID NO: (1)..(477)

<400> SEQUENCE: 57

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu

```
                100                 105                 110
Lys Asn Ser Asn Leu Gln His Ile Asn Phe Thr Arg Asn Lys Leu Thr
            115                 120                 125

Ser Leu Ser Arg Lys His Phe Arg His Leu Asp Leu Ser Glu Leu Ile
        130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Gly Phe Val Leu Phe His Lys Ile Pro Leu Asp Gly
465                 470                 475

<210> SEQ ID NO 58
<211> LENGTH: 817
<212> TYPE: PRT
<213> ORGANISM: HUMAN
<300> PUBLICATION INFORMATION:
<301> AUTHORS: Shelton,D.L., Sutherland,J., Gripp,J., Camerato,T.,
      Armanini,M.P.,
```

```
<302> TITLE: Human trks: molecular cloning, tissue distribution, and
      expression
<303> JOURNAL: J. Neurosci.
<304> VOLUME: 13
<305> ISSUE: 1
<306> PAGES: 477-491
<307> DATE: 1995-01-01
<308> DATABASE ACCESSION NUMBER: NP_001230030
<309> DATABASE ENTRY DATE: 2012-05-13
<313> RELEVANT RESIDUES IN SEQ ID NO: (1)..(817)

<400> SEQUENCE: 58
```

| | | | | | | | | | | | | | | |
|---|---|---|---|---|---|---|---|---|---|---|---|---|---|---|
| Met | Asp | Val | Ser | Leu | Cys | Pro | Ala | Lys | Cys | Ser | Phe | Trp | Arg | Ile | Phe |
| 1 | | | | 5 | | | | | 10 | | | | | 15 | |
| Leu | Leu | Gly | Ser | Val | Trp | Leu | Asp | Tyr | Val | Gly | Ser | Val | Leu | Ala | Cys |
| | | | 20 | | | | | 25 | | | | | 30 | | |
| Pro | Ala | Asn | Cys | Val | Cys | Ser | Lys | Thr | Glu | Ile | Asn | Cys | Arg | Arg | Pro |
| | | 35 | | | | | 40 | | | | | 45 | | | |
| Asp | Asp | Gly | Asn | Leu | Phe | Pro | Leu | Leu | Glu | Gly | Gln | Asp | Ser | Gly | Asn |
| | 50 | | | | | 55 | | | | | 60 | | | | |
| Ser | Asn | Gly | Asn | Ala | Ser | Ile | Asn | Ile | Thr | Asp | Ile | Ser | Arg | Asn | Ile |
| 65 | | | | | 70 | | | | | 75 | | | | | 80 |
| Thr | Ser | Ile | His | Ile | Glu | Asn | Trp | Arg | Ser | Leu | His | Thr | Leu | Asn | Ala |
| | | | | 85 | | | | | 90 | | | | | 95 | |
| Val | Asp | Met | Glu | Leu | Tyr | Thr | Gly | Leu | Gln | Lys | Leu | Thr | Ile | Lys | Asn |
| | | | 100 | | | | | 105 | | | | | 110 | | |
| Ser | Gly | Leu | Arg | Ser | Ile | Gln | Pro | Arg | Ala | Phe | Ala | Lys | Asn | Pro | His |
| | | 115 | | | | | 120 | | | | | 125 | | | |
| Leu | Arg | Tyr | Ile | Asn | Leu | Ser | Ser | Asn | Arg | Leu | Thr | Thr | Leu | Ser | Trp |
| | 130 | | | | | 135 | | | | | 140 | | | | |
| Gln | Leu | Phe | Gln | Thr | Leu | Ser | Leu | Arg | Glu | Leu | Gln | Leu | Glu | Gln | Asn |
| 145 | | | | | 150 | | | | | 155 | | | | | 160 |
| Phe | Phe | Asn | Cys | Ser | Cys | Asp | Ile | Arg | Trp | Met | Gln | Leu | Trp | Gln | Glu |
| | | | | 165 | | | | | 170 | | | | | 175 | |
| Gln | Gly | Glu | Ala | Lys | Leu | Asn | Ser | Gln | Asn | Leu | Tyr | Cys | Ile | Asn | Ala |
| | | | 180 | | | | | 185 | | | | | 190 | | |
| Asp | Gly | Ser | Gln | Leu | Pro | Leu | Phe | Arg | Met | Asn | Ile | Ser | Gln | Cys | Asp |
| | | 195 | | | | | 200 | | | | | 205 | | | |
| Leu | Pro | Glu | Ile | Ser | Val | Ser | His | Val | Asn | Leu | Thr | Val | Arg | Glu | Gly |
| | 210 | | | | | 215 | | | | | 220 | | | | |
| Asp | Asn | Ala | Val | Ile | Thr | Cys | Asn | Gly | Ser | Gly | Ser | Pro | Leu | Pro | Asp |
| 225 | | | | | 230 | | | | | 235 | | | | | 240 |
| Val | Asp | Trp | Ile | Val | Thr | Gly | Leu | Gln | Ser | Ile | Asn | Thr | His | Gln | Thr |
| | | | | 245 | | | | | 250 | | | | | 255 | |
| Asn | Leu | Asn | Trp | Thr | Asn | Val | His | Ala | Ile | Asn | Leu | Thr | Leu | Val | Asn |
| | | | 260 | | | | | 265 | | | | | 270 | | |
| Val | Thr | Ser | Glu | Asp | Asn | Gly | Phe | Thr | Leu | Thr | Cys | Ile | Ala | Glu | Asn |
| | | 275 | | | | | 280 | | | | | 285 | | | |
| Val | Val | Gly | Met | Ser | Asn | Ala | Ser | Val | Ala | Leu | Thr | Val | Tyr | Tyr | Pro |
| | 290 | | | | | 295 | | | | | 300 | | | | |
| Pro | Arg | Val | Val | Ser | Leu | Glu | Glu | Pro | Glu | Leu | Arg | Leu | Glu | His | Cys |
| 305 | | | | | 310 | | | | | 315 | | | | | 320 |
| Ile | Glu | Phe | Val | Val | Arg | Gly | Asn | Pro | Pro | Pro | Thr | Leu | His | Trp | Leu |
| | | | | 325 | | | | | 330 | | | | | 335 | |
| His | Asn | Gly | Gln | Pro | Leu | Arg | Glu | Ser | Lys | Ile | Ile | His | Val | Glu | Tyr |
| | | | 340 | | | | | 345 | | | | | 350 | | |

-continued

```
Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Val Asp Glu Val Ser Pro Thr Pro Ile Thr Val Thr His Lys
                405                 410                 415

Pro Glu Glu Asp Thr Phe Gly Val Ser Ile Ala Val Gly Leu Ala Ala
            420                 425                 430

Phe Ala Cys Val Leu Leu Val Val Leu Phe Val Met Ile Asn Lys Tyr
        435                 440                 445

Gly Arg Arg Ser Lys Phe Gly Met Lys Gly Pro Val Ala Val Ile Ser
    450                 455                 460

Gly Glu Glu Asp Ser Ala Ser Pro Leu His His Ile Asn His Gly Ile
465                 470                 475                 480

Thr Thr Pro Ser Ser Leu Asp Ala Gly Pro Asp Thr Val Val Ile Gly
                485                 490                 495

Met Thr Arg Ile Pro Val Ile Glu Asn Pro Gln Tyr Phe Arg Gln Gly
            500                 505                 510

His Asn Cys His Lys Pro Asp Thr Tyr Val Gln His Ile Lys Arg Arg
        515                 520                 525

Asp Ile Val Leu Lys Arg Glu Leu Gly Glu Gly Ala Phe Gly Lys Val
    530                 535                 540

Phe Leu Ala Glu Cys Tyr Asn Leu Ser Pro Thr Lys Asp Lys Met Leu
545                 550                 555                 560

Val Ala Val Lys Ala Leu Lys Asp Pro Thr Leu Ala Ala Arg Lys Asp
                565                 570                 575

Phe Gln Arg Glu Ala Glu Leu Leu Thr Asn Leu Gln His Glu His Ile
            580                 585                 590

Val Lys Phe Tyr Gly Val Cys Gly Asp Gly Asp Pro Leu Ile Met Val
        595                 600                 605

Phe Glu Tyr Met Lys His Gly Asp Leu Asn Lys Phe Leu Arg Ala His
    610                 615                 620

Gly Pro Asp Ala Met Ile Leu Val Asp Gly Gln Pro Arg Gln Ala Lys
625                 630                 635                 640

Gly Glu Leu Gly Leu Ser Gln Met Leu His Ile Ala Ser Gln Ile Ala
                645                 650                 655

Ser Gly Met Val Tyr Leu Ala Ser Gln His Phe Val His Arg Asp Leu
            660                 665                 670

Ala Thr Arg Asn Cys Leu Val Gly Ala Asn Leu Leu Val Lys Ile Gly
        675                 680                 685

Asp Phe Gly Met Ser Arg Asp Val Tyr Ser Thr Asp Tyr Tyr Arg Val
    690                 695                 700

Gly Gly His Thr Met Leu Pro Ile Arg Trp Met Pro Pro Glu Ser Ile
705                 710                 715                 720

Met Tyr Arg Lys Phe Thr Thr Glu Ser Asp Val Trp Ser Phe Gly Val
                725                 730                 735

Ile Leu Trp Glu Ile Phe Thr Tyr Gly Lys Gln Pro Trp Phe Gln Leu
            740                 745                 750

Ser Asn Thr Glu Val Ile Glu Cys Ile Thr Gln Gly Arg Val Leu Glu
        755                 760                 765

Arg Pro Arg Val Cys Pro Lys Glu Val Tyr Asp Val Met Leu Gly Cys
```

```
                    770               775               780
Trp Gln Arg Glu Pro Gln Gln Arg Leu Asn Ile Lys Glu Ile Tyr Lys
785                 790               795               800

Ile Leu His Ala Leu Gly Lys Ala Thr Pro Ile Tyr Leu Asp Ile Leu
                    805               810               815

Gly

<210> SEQ ID NO 59
<211> LENGTH: 579
<212> TYPE: PRT
<213> ORGANISM: HUMAN
<300> PUBLICATION INFORMATION:
<301> AUTHORS: Yamaguchi,K., Shirakabe,K., Shibuya,H., Irie,K.,
      Oishi,I., Ueno,N.,
<302> TITLE: Identification of a member of the MAPKKK family as a
      potential
<303> JOURNAL: Science
<304> VOLUME: 270
<305> ISSUE: 5244
<306> PAGES: 2008-2011
<307> DATE: 1995-12-22
<308> DATABASE ACCESSION NUMBER: NP_003179
<309> DATABASE ENTRY DATE: 2012-05-13
<313> RELEVANT RESIDUES IN SEQ ID NO: (1)..(579)

<400> SEQUENCE: 59

Met Ser Thr Ala Ser Ala Ala Ser Ser Ser Ser Ser Ser Ser Ala Gly
1               5                   10                  15

Glu Met Ile Glu Ala Pro Ser Gln Val Leu Asn Phe Glu Glu Ile Asp
                20                  25                  30

Tyr Lys Glu Ile Glu Val Glu Val Val Gly Arg Gly Ala Phe Gly
            35                  40                  45

Val Val Cys Lys Ala Lys Trp Arg Ala Lys Asp Val Ala Ile Lys Gln
50                  55                  60

Ile Glu Ser Glu Ser Glu Arg Lys Ala Phe Ile Val Glu Leu Arg Gln
65                  70                  75                  80

Leu Ser Arg Val Asn His Pro Asn Ile Val Lys Leu Tyr Gly Ala Cys
                85                  90                  95

Leu Asn Pro Val Cys Leu Val Met Glu Tyr Ala Glu Gly Gly Ser Leu
                100                 105                 110

Tyr Asn Val Leu His Gly Ala Glu Pro Leu Pro Tyr Tyr Thr Ala Ala
            115                 120                 125

His Ala Met Ser Trp Cys Leu Gln Cys Ser Gln Gly Val Ala Tyr Leu
130                 135                 140

His Ser Met Gln Pro Lys Ala Leu Ile His Arg Asp Leu Lys Pro Pro
145                 150                 155                 160

Asn Leu Leu Leu Val Ala Gly Gly Thr Val Leu Lys Ile Cys Asp Phe
                165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
        195                 200                 205

Lys Cys Asp Val Phe Ser Trp Gly Ile Ile Leu Trp Glu Val Ile Thr
    210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255
```

```
Lys Pro Ile Glu Ser Leu Met Thr Arg Cys Trp Ser Lys Asp Pro Ser
            260                 265                 270

Gln Arg Pro Ser Met Glu Glu Ile Val Lys Ile Met Thr His Leu Met
        275                 280                 285

Arg Tyr Phe Pro Gly Ala Asp Glu Pro Leu Gln Tyr Pro Cys Gln Tyr
    290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu
        355                 360                 365

Gly Ala Ser Arg Gly Ser Ser Val Glu Ser Leu Pro Pro Thr Ser Glu
    370                 375                 380

Gly Lys Arg Met Ser Ala Asp Met Ser Glu Ile Glu Ala Arg Ile Ala
385                 390                 395                 400

Ala Thr Thr Gly Asn Gly Gln Pro Arg Arg Arg Ser Ile Gln Asp Leu
                405                 410                 415

Thr Val Thr Gly Thr Glu Pro Gly Gln Val Ser Ser Arg Ser Ser Ser
            420                 425                 430

Pro Ser Val Arg Met Ile Thr Thr Ser Gly Pro Thr Ser Glu Lys Pro
        435                 440                 445

Thr Arg Ser His Pro Trp Thr Pro Asp Asp Ser Thr Asp Thr Asn Gly
    450                 455                 460

Ser Asp Asn Ser Ile Pro Met Ala Tyr Leu Thr Leu Asp His Gln Leu
465                 470                 475                 480

Gln Pro Leu Ala Pro Cys Pro Asn Ser Lys Glu Ser Met Ala Val Phe
                485                 490                 495

Glu Gln His Cys Lys Met Ala Gln Glu Tyr Met Lys Val Gln Thr Glu
            500                 505                 510

Ile Ala Leu Leu Leu Gln Arg Lys Gln Glu Leu Val Ala Glu Leu Asp
        515                 520                 525

Gln Asp Glu Lys Asp Gln Gln Asn Thr Ser Arg Leu Val Gln Glu His
    530                 535                 540

Lys Lys Leu Leu Asp Glu Asn Lys Ser Leu Ser Thr Tyr Tyr Gln Gln
545                 550                 555                 560

Cys Lys Lys Gln Leu Glu Val Ile Arg Ser Gln Gln Gln Lys Arg Gln
                565                 570                 575

Gly Thr Ser
```

<210> SEQ ID NO 60
<211> LENGTH: 1124
<212> TYPE: PRT
<213> ORGANISM: HUMAN
<300> PUBLICATION INFORMATION:
<301> AUTHORS: Singh,H., Hansen,T.M., Patel,N. and Brindle,N.P.
<302> TITLE: The molecular balance between receptor tyrosine kinases
       Tie1 and
<303> JOURNAL: PLoS ONE
<304> VOLUME: 7
<305> ISSUE: 1
<306> PAGES: E29319
<307> DATE: 2012-01-03
<308> DATABASE ACCESSION NUMBER: NP_000450
<309> DATABASE ENTRY DATE: 2012-05-20
<313> RELEVANT RESIDUES IN SEQ ID NO: (1)..(1124)

<400> SEQUENCE: 60

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
```

```
            405                 410                 415
Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
            435                 440                 445

Asn Ala Pro Asn Val Ile Asp Thr Gly His Asn Phe Ala Val Ile Asn
            450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
            530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
            610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
            675                 680                 685

Ile Lys Asn Ala Thr Ile Thr Gln Tyr Gln Leu Lys Gly Leu Glu Pro
            690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
            770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830
```

```
Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
        915                 920                 925

Ala Asn Ser Thr Ala Ser Thr Leu Ser Ser Gln Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu Pro Val Arg Trp Met Ala Ile Glu
        995                 1000                1005

Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Thr Leu Tyr Glu Lys Phe Thr Tyr
    1100                1105                1110

Ala Gly Ile Asp Cys Ser Ala Glu Glu Ala Ala
    1115                1120

<210> SEQ ID NO 61
<211> LENGTH: 503
<212> TYPE: PRT
<213> ORGANISM: HUMAN
<300> PUBLICATION INFORMATION:
<301> AUTHORS: Arnault,J.P., Mateus,C., Escudier,B., Tomasic,G.,
      Wechsler,J.,
<302> TITLE: Skin tumors induced by sorafenib; paradoxic RAS-RAF pathway
<303> JOURNAL: Clin. Cancer Res.
<304> VOLUME: 18
<305> ISSUE: 1
<306> PAGES: 263-272
<307> DATE: 2012-01-01
<308> DATABASE ACCESSION NUMBER: NP_004603
<309> DATABASE ENTRY DATE: 2012-05-06
<313> RELEVANT RESIDUES IN SEQ ID NO: (1)..(502)

<400> SEQUENCE: 61

Met Glu Ala Ala Val Ala Ala Pro Arg Pro Arg Leu Leu Leu Leu Val
```

-continued

```
1               5                   10                  15
Leu Ala Ala Ala Ala Ala Ala Ala Leu Leu Pro Gly Ala Thr
                20                  25              30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
50                      55                  60

Val Ile His Asn Ser Met Cys Ile Ala Glu Ile Asp Leu Ile Pro Arg
65                  70                  75                  80

Asp Arg Pro Phe Val Cys Ala Pro Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
            115                 120                 125

Val Ile Ala Gly Pro Val Cys Phe Val Cys Ile Ser Leu Met Leu Met
        130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
            275                 280                 285

Phe Asp Tyr Leu Asn Arg Tyr Thr Val Thr Val Glu Gly Met Ile Lys
        290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430
```

```
Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500
```

<210> SEQ ID NO 62
<211> LENGTH: 2527
<212> TYPE: PRT
<213> ORGANISM: HUMAN
<300> PUBLICATION INFORMATION:
<301> AUTHORS: Zimprich,A., Biskup,S., Leitner,P., Lichtner,P.,
      Farrer,M.,
<302> TITLE: Mutations in LRRK2 cause autosomal-dominant parkinsonism
      with
<303> JOURNAL: Neuron
<304> VOLUME: 44
<305> ISSUE: 4
<306> PAGES: 601-607
<307> DATE: 2004-11-18
<308> DATABASE ACCESSION NUMBER: NP_940980
<309> DATABASE ENTRY DATE: 2012-05-27
<313> RELEVANT RESIDUES IN SEQ ID NO: (1)..(2527)

<400> SEQUENCE: 62

```
Met Ala Ser Gly Ser Cys Gln Gly Cys Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
    210                 215                 220
```

-continued

```
Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
            245                 250                 255

Met Lys Ala Phe Pro Met Ser Glu Arg Ile Gln Glu Val Ser Cys Cys
        260                 265                 270

Leu Leu His Arg Leu Thr Leu Gly Asn Phe Phe Asn Ile Leu Val Leu
    275                 280                 285

Asn Glu Val His Glu Phe Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
```

```
                645                 650                 655
Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
            690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
            755                 760                 765

Gln Asp Val Arg Lys Ala Leu Thr Ile Ser Ile Gly Lys Gly Asp Ser
            770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
            930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
            995                 1000                1005

His Leu Glu His Leu Glu Lys Leu Glu Leu His Gln Asn Ala Leu
            1010                1015                1020

Thr Ser Phe Pro Gln Gln Leu Cys Glu Thr Leu Lys Ser Leu Thr
            1025                1030                1035

His Leu Asp Leu His Ser Asn Lys Phe Thr Ser Phe Pro Ser Tyr
            1040                1045                1050

Leu Leu Lys Met Ser Cys Ile Ala Asn Leu Asp Val Ser Arg Asn
            1055                1060                1065
```

-continued

```
Asp Ile Gly Pro Ser Val Val Leu Asp Pro Thr Val Lys Cys Pro
    1070            1075               1080

Thr Leu Lys Gln Phe Asn Leu Ser Tyr Asn Gln Leu Ser Phe Val
    1085            1090               1095

Pro Glu Asn Leu Thr Asp Val Val Glu Lys Leu Glu Gln Leu Ile
    1100            1105               1110

Leu Glu Gly Asn Lys Ile Ser Gly Ile Cys Ser Pro Leu Arg Leu
    1115            1120               1125

Lys Glu Leu Lys Ile Leu Asn Leu Ser Lys Asn His Ile Ser Ser
    1130            1135               1140

Leu Ser Glu Asn Phe Leu Glu Ala Cys Pro Lys Val Glu Ser Phe
    1145            1150               1155

Ser Ala Arg Met Asn Phe Leu Ala Ala Met Pro Phe Leu Pro Pro
    1160            1165               1170

Ser Met Thr Ile Leu Lys Leu Ser Gln Asn Lys Phe Ser Cys Ile
    1175            1180               1185

Pro Glu Ala Ile Leu Asn Leu Pro His Leu Arg Ser Leu Asp Met
    1190            1195               1200

Ser Ser Asn Asp Ile Gln Tyr Leu Pro Gly Pro Ala His Trp Lys
    1205            1210               1215

Ser Leu Asn Leu Arg Glu Leu Leu Phe Ser His Asn Gln Ile Ser
    1220            1225               1230

Ile Leu Asp Leu Ser Glu Lys Ala Tyr Leu Trp Ser Arg Val Glu
    1235            1240               1245

Lys Leu His Leu Ser His Asn Lys Leu Lys Glu Ile Pro Pro Glu
    1250            1255               1260

Ile Gly Cys Leu Glu Asn Leu Thr Ser Leu Asp Val Ser Tyr Asn
    1265            1270               1275

Leu Glu Leu Arg Ser Phe Pro Asn Glu Met Gly Lys Leu Ser Lys
    1280            1285               1290

Ile Trp Asp Leu Pro Leu Asp Glu Leu His Leu Asn Phe Asp Phe
    1295            1300               1305

Lys His Ile Gly Cys Lys Ala Lys Asp Ile Ile Arg Phe Leu Gln
    1310            1315               1320

Gln Arg Leu Lys Lys Ala Val Pro Tyr Asn Arg Met Lys Leu Met
    1325            1330               1335

Ile Val Gly Asn Thr Gly Ser Gly Lys Thr Thr Leu Leu Gln Gln
    1340            1345               1350

Leu Met Lys Thr Lys Lys Ser Asp Leu Gly Met Gln Ser Ala Thr
    1355            1360               1365

Val Gly Ile Asp Val Lys Asp Trp Pro Ile Gln Ile Arg Asp Lys
    1370            1375               1380

Arg Lys Arg Asp Leu Val Leu Asn Val Trp Asp Phe Ala Gly Arg
    1385            1390               1395

Glu Glu Phe Tyr Ser Thr His Pro His Phe Met Thr Gln Arg Ala
    1400            1405               1410

Leu Tyr Leu Ala Val Tyr Asp Leu Ser Lys Gly Gln Ala Glu Val
    1415            1420               1425

Asp Ala Met Lys Pro Trp Leu Phe Asn Ile Lys Ala Arg Ala Ser
    1430            1435               1440

Ser Ser Pro Val Ile Leu Val Gly Thr His Leu Asp Val Ser Asp
    1445            1450               1455
```

```
Glu Lys Gln Arg Lys Ala Cys Met Ser Lys Ile Thr Lys Glu Leu
1460                     1465                 1470

Leu Asn Lys Arg Gly Phe Pro Ala Ile Arg Asp Tyr His Phe Val
1475                     1480                 1485

Asn Ala Thr Glu Glu Ser Asp Ala Leu Ala Lys Leu Arg Lys Thr
1490                     1495                 1500

Ile Ile Asn Glu Ser Leu Asn Phe Lys Ile Arg Asp Gln Leu Val
1505                     1510                 1515

Val Gly Gln Leu Ile Pro Asp Cys Tyr Val Glu Leu Glu Lys Ile
1520                     1525                 1530

Ile Leu Ser Glu Arg Lys Asn Val Pro Ile Glu Phe Pro Val Ile
1535                     1540                 1545

Asp Arg Lys Arg Leu Leu Gln Leu Val Arg Glu Asn Gln Leu Gln
1550                     1555                 1560

Leu Asp Glu Asn Glu Leu Pro His Ala Val His Phe Leu Asn Glu
1565                     1570                 1575

Ser Gly Val Leu Leu His Phe Gln Asp Pro Ala Leu Gln Leu Ser
1580                     1585                 1590

Asp Leu Tyr Phe Val Glu Pro Lys Trp Leu Cys Lys Ile Met Ala
1595                     1600                 1605

Gln Ile Leu Thr Val Lys Val Glu Gly Cys Pro Lys His Pro Lys
1610                     1615                 1620

Gly Ile Ile Ser Arg Arg Asp Val Glu Lys Phe Leu Ser Lys Lys
1625                     1630                 1635

Arg Lys Phe Pro Lys Asn Tyr Met Ser Gln Tyr Phe Lys Leu Leu
1640                     1645                 1650

Glu Lys Phe Gln Ile Ala Leu Pro Ile Gly Glu Glu Tyr Leu Leu
1655                     1660                 1665

Val Pro Ser Ser Leu Ser Asp His Arg Pro Val Ile Glu Leu Pro
1670                     1675                 1680

His Cys Glu Asn Ser Glu Ile Ile Ile Arg Leu Tyr Glu Met Pro
1685                     1690                 1695

Tyr Phe Pro Met Gly Phe Trp Ser Arg Leu Ile Asn Arg Leu Leu
1700                     1705                 1710

Glu Ile Ser Pro Tyr Met Leu Ser Gly Arg Glu Arg Ala Leu Arg
1715                     1720                 1725

Pro Asn Arg Met Tyr Trp Arg Gln Gly Ile Tyr Leu Asn Trp Ser
1730                     1735                 1740

Pro Glu Ala Tyr Cys Leu Val Gly Ser Glu Val Leu Asp Asn His
1745                     1750                 1755

Pro Glu Ser Phe Leu Lys Ile Thr Val Pro Ser Cys Arg Lys Gly
1760                     1765                 1770

Cys Ile Leu Leu Gly Gln Val Val Asp His Ile Asp Ser Leu Met
1775                     1780                 1785

Glu Glu Trp Phe Pro Gly Leu Leu Glu Ile Asp Ile Cys Gly Glu
1790                     1795                 1800

Gly Glu Thr Leu Leu Lys Lys Trp Ala Leu Tyr Ser Phe Asn Asp
1805                     1810                 1815

Gly Glu Glu His Gln Lys Ile Leu Leu Asp Asp Leu Met Lys Lys
1820                     1825                 1830

Ala Glu Glu Gly Asp Leu Leu Val Asn Pro Asp Gln Pro Arg Leu
1835                     1840                 1845

Thr Ile Pro Ile Ser Gln Ile Ala Pro Asp Leu Ile Leu Ala Asp
```

-continued

|   |   |   |   |   |   |   |   |   |   |
|---|---|---|---|---|---|---|---|---|---|
| | 1850 | | | 1855 | | | 1860 | | |
| Leu | Pro | Arg | Asn | Ile | Met | Leu | Asn | Asn | Asp | Glu | Leu | Glu | Phe | Glu |
| | 1865 | | | | 1870 | | | 1875 | | |
| Gln | Ala | Pro | Glu | Phe | Leu | Leu | Gly | Asp | Gly | Ser | Phe | Gly | Ser | Val |
| | 1880 | | | | 1885 | | | 1890 | | |
| Tyr | Arg | Ala | Ala | Tyr | Glu | Gly | Glu | Val | Ala | Val | Lys | Ile | Phe |
| | 1895 | | | | 1900 | | | 1905 | | |
| Asn | Lys | His | Thr | Ser | Leu | Arg | Leu | Leu | Arg | Gln | Glu | Leu | Val | Val |
| | 1910 | | | | 1915 | | | 1920 | | |
| Leu | Cys | His | Leu | His | His | Pro | Ser | Leu | Ile | Ser | Leu | Leu | Ala | Ala |
| | 1925 | | | | 1930 | | | 1935 | | |
| Gly | Ile | Arg | Pro | Arg | Met | Leu | Val | Met | Glu | Leu | Ala | Ser | Lys | Gly |
| | 1940 | | | | 1945 | | | 1950 | | |
| Ser | Leu | Asp | Arg | Leu | Leu | Gln | Gln | Asp | Lys | Ala | Ser | Leu | Thr | Arg |
| | 1955 | | | | 1960 | | | 1965 | | |
| Thr | Leu | Gln | His | Arg | Ile | Ala | Leu | His | Val | Ala | Asp | Gly | Leu | Arg |
| | 1970 | | | | 1975 | | | 1980 | | |
| Tyr | Leu | His | Ser | Ala | Met | Ile | Ile | Tyr | Arg | Asp | Leu | Lys | Pro | His |
| | 1985 | | | | 1990 | | | 1995 | | |
| Asn | Val | Leu | Leu | Phe | Thr | Leu | Tyr | Pro | Asn | Ala | Ala | Ile | Ile | Ala |
| | 2000 | | | | 2005 | | | 2010 | | |
| Lys | Ile | Ala | Asp | Tyr | Gly | Ile | Ala | Gln | Tyr | Cys | Cys | Arg | Met | Gly |
| | 2015 | | | | 2020 | | | 2025 | | |
| Ile | Lys | Thr | Ser | Glu | Gly | Thr | Pro | Gly | Phe | Arg | Ala | Pro | Glu | Val |
| | 2030 | | | | 2035 | | | 2040 | | |
| Ala | Arg | Gly | Asn | Val | Ile | Tyr | Asn | Gln | Gln | Ala | Asp | Val | Tyr | Ser |
| | 2045 | | | | 2050 | | | 2055 | | |
| Phe | Gly | Leu | Leu | Leu | Tyr | Asp | Ile | Leu | Thr | Thr | Gly | Gly | Arg | Ile |
| | 2060 | | | | 2065 | | | 2070 | | |
| Val | Glu | Gly | Leu | Lys | Phe | Pro | Asn | Glu | Phe | Asp | Glu | Leu | Glu | Ile |
| | 2075 | | | | 2080 | | | 2085 | | |
| Gln | Gly | Lys | Leu | Pro | Asp | Pro | Val | Lys | Glu | Tyr | Gly | Cys | Ala | Pro |
| | 2090 | | | | 2095 | | | 2100 | | |
| Trp | Pro | Met | Val | Glu | Lys | Leu | Ile | Lys | Gln | Cys | Leu | Lys | Glu | Asn |
| | 2105 | | | | 2110 | | | 2115 | | |
| Pro | Gln | Glu | Arg | Pro | Thr | Ser | Ala | Gln | Val | Phe | Asp | Ile | Leu | Asn |
| | 2120 | | | | 2125 | | | 2130 | | |
| Ser | Ala | Glu | Leu | Val | Cys | Leu | Thr | Arg | Arg | Ile | Leu | Leu | Pro | Lys |
| | 2135 | | | | 2140 | | | 2145 | | |
| Asn | Val | Ile | Val | Glu | Cys | Met | Val | Ala | Thr | His | His | Asn | Ser | Arg |
| | 2150 | | | | 2155 | | | 2160 | | |
| Asn | Ala | Ser | Ile | Trp | Leu | Gly | Cys | Gly | His | Thr | Asp | Arg | Gly | Gln |
| | 2165 | | | | 2170 | | | 2175 | | |
| Leu | Ser | Phe | Leu | Asp | Leu | Asn | Thr | Glu | Gly | Tyr | Thr | Ser | Glu | Glu |
| | 2180 | | | | 2185 | | | 2190 | | |
| Val | Ala | Asp | Ser | Arg | Ile | Leu | Cys | Leu | Ala | Leu | Val | His | Leu | Pro |
| | 2195 | | | | 2200 | | | 2205 | | |
| Val | Glu | Lys | Glu | Ser | Trp | Ile | Val | Ser | Gly | Thr | Gln | Ser | Gly | Thr |
| | 2210 | | | | 2215 | | | 2220 | | |
| Leu | Leu | Val | Ile | Asn | Thr | Glu | Asp | Gly | Lys | Lys | Arg | His | Thr | Leu |
| | 2225 | | | | 2230 | | | 2235 | | |
| Glu | Lys | Met | Thr | Asp | Ser | Val | Thr | Cys | Leu | Tyr | Cys | Asn | Ser | Phe |
| | 2240 | | | | 2245 | | | 2250 | | |

Ser Lys Gln Ser Lys Gln Lys Asn Phe Leu Leu Val Gly Thr Ala
2255              2260                    2265

Asp Gly Lys Leu Ala Ile Phe Glu Asp Lys Thr Val Lys Leu Lys
2270              2275                    2280

Gly Ala Ala Pro Leu Lys Ile Leu Asn Ile Gly Asn Val Ser Thr
2285              2290                    2295

Pro Leu Met Cys Leu Ser Glu Ser Thr Asn Ser Thr Glu Arg Asn
2300              2305                    2310

Val Met Trp Gly Gly Cys Gly Thr Lys Ile Phe Ser Phe Ser Asn
2315              2320                    2325

Asp Phe Thr Ile Gln Lys Leu Ile Glu Thr Arg Thr Ser Gln Leu
2330              2335                    2340

Phe Ser Tyr Ala Ala Phe Ser Asp Ser Asn Ile Ile Thr Val Val
2345              2350                    2355

Val Asp Thr Ala Leu Tyr Ile Ala Lys Gln Asn Ser Pro Val Val
2360              2365                    2370

Glu Val Trp Asp Lys Lys Thr Glu Lys Leu Cys Gly Leu Ile Asp
2375              2380                    2385

Cys Val His Phe Leu Arg Glu Val Met Val Lys Glu Asn Lys Glu
2390              2395                    2400

Ser Lys His Lys Met Ser Tyr Ser Gly Arg Val Lys Thr Leu Cys
2405              2410                    2415

Leu Gln Lys Asn Thr Ala Leu Trp Ile Gly Thr Gly Gly Gly His
2420              2425                    2430

Ile Leu Leu Leu Asp Leu Ser Thr Arg Arg Leu Ile Arg Val Ile
2435              2440                    2445

Tyr Asn Phe Cys Asn Ser Val Arg Val Met Met Thr Ala Gln Leu
2450              2455                    2460

Gly Ser Leu Lys Asn Val Met Leu Val Leu Gly Tyr Asn Arg Lys
2465              2470                    2475

Asn Thr Glu Gly Thr Gln Lys Gln Lys Glu Ile Gln Ser Cys Leu
2480              2485                    2490

Thr Val Trp Asp Ile Asn Leu Pro His Glu Val Gln Asn Leu Glu
2495              2500                    2505

Lys His Ile Glu Val Arg Lys Glu Leu Ala Glu Lys Met Arg Arg
2510              2515                    2520

Thr Ser Val Glu
2525

```
<210> SEQ ID NO 63
<211> LENGTH: 351
<212> TYPE: PRT
<213> ORGANISM: Human
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<300> PUBLICATION INFORMATION:
<301> AUTHORS: Lin,X., Murray,J.M., Rico,A.C., Wang,M.X., Chu,D.T.,
      Zhou,Y., Del
<302> TITLE: Discovery of 2-pyrimidyl-5-amidothiophenes as potent
      inhibitors for
<303> JOURNAL: Bioorg. Med. Chem. Lett.
<304> VOLUME: 16
<305> ISSUE: 16
```

<306> PAGES: 4163-4168
<307> DATE: 2006-06-09
<308> DATABASE ACCESSION NUMBER: P1761
<309> DATABASE ENTRY DATE: 2012-05-16
<313> RELEVANT RESIDUES IN SEQ ID NO: (1)..(351)

<400> SEQUENCE: 63

```
Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
            35                  40                  45

Thr Leu Gly Thr Gly Ser Phe Gly Arg Val Met Leu Val Lys His Lys
50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
            115                 120                 125

Met Phe Ser His Leu Arg Arg Ile Gly Arg Phe Ser Glu Pro His Ala
            130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Xaa Leu Cys Gly Thr Pro Glu Tyr Leu Ala Pro
            195                 200                 205

Glu Ile Ile Leu Ser Lys Gly Tyr Asn Lys Ala Val Asp Trp Trp Ala
            210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
            275                 280                 285

Val Asn Asp Ile Lys Asn His Lys Trp Phe Ala Thr Thr Asp Trp Ile
            290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Xaa Ile Asn Glu Lys Cys Gly Lys Glu Phe Ser Glu Phe
            340                 345                 350
```

<210> SEQ ID NO 64
<211> LENGTH: 926
<212> TYPE: PRT
<213> ORGANISM: HUMAN

```
<300> PUBLICATION INFORMATION:
<301> AUTHORS: Hashimoto,Y.K., Satoh,T., Okamoto,M. and Takemori,H.
<302> TITLE: Importance of autophosphorylation at Ser186 in the A-1
<303> JOURNAL: J. Cell. Biochem.
<304> VOLUME: 104
<305> ISSUE: 5
<306> PAGES: 1724-1739
<307> DATE: 2008-08-01
<308> DATABASE ACCESSION NUMBER: NP_775490
<309> DATABASE ENTRY DATE: 2012-04-21
<313> RELEVANT RESIDUES IN SEQ ID NO: (1)..(783)

<400> SEQUENCE: 64
```

| | | | | | | | | | | | | | | |
|---|---|---|---|---|---|---|---|---|---|---|---|---|---|---|
| Met | Val | Met | Ala | Asp | Gly | Pro | Arg | His | Leu | Gln | Arg | Gly | Pro | Val | Arg |
| 1 | | | | 5 | | | | | 10 | | | | | 15 | |

| | | | | | | | | | | | | | | |
|---|---|---|---|---|---|---|---|---|---|---|---|---|---|---|
| Val | Gly | Phe | Tyr | Asp | Ile | Glu | Gly | Thr | Leu | Gly | Lys | Gly | Asn | Phe | Ala |
| | | | 20 | | | | | 25 | | | | | 30 | | |

| Val | Val | Lys | Leu | Gly | Arg | His | Arg | Ile | Thr | Lys | Thr | Glu | Val | Ala | Ile |
|---|---|---|---|---|---|---|---|---|---|---|---|---|---|---|---|
| | | 35 | | | | | 40 | | | | | 45 | | | |

| Lys | Ile | Ile | Asp | Lys | Ser | Gln | Leu | Asp | Ala | Val | Asn | Leu | Glu | Lys | Ile |
|---|---|---|---|---|---|---|---|---|---|---|---|---|---|---|---|
| 50 | | | | | 55 | | | | | 60 | | | | | |

| Tyr | Arg | Glu | Val | Gln | Ile | Met | Lys | Met | Leu | Asp | His | Pro | His | Ile | Ile |
|---|---|---|---|---|---|---|---|---|---|---|---|---|---|---|---|
| 65 | | | | | 70 | | | | | 75 | | | | | 80 |

| Lys | Leu | Tyr | Gln | Val | Met | Glu | Thr | Lys | Ser | Met | Leu | Tyr | Leu | Val | Thr |
|---|---|---|---|---|---|---|---|---|---|---|---|---|---|---|---|
| | | | | 85 | | | | | 90 | | | | | 95 | |

| Glu | Tyr | Ala | Lys | Asn | Gly | Glu | Ile | Phe | Asp | Tyr | Leu | Ala | Asn | His | Gly |
|---|---|---|---|---|---|---|---|---|---|---|---|---|---|---|---|
| | | | | 100 | | | | | 105 | | | | | 110 | |

| Arg | Leu | Asn | Glu | Ser | Glu | Ala | Arg | Arg | Lys | Phe | Trp | Gln | Ile | Leu | Ser |
|---|---|---|---|---|---|---|---|---|---|---|---|---|---|---|---|
| | | | 115 | | | | | 120 | | | | | 125 | | |

| Ala | Val | Asp | Tyr | Cys | His | Gly | Arg | Lys | Ile | Val | His | Arg | Asp | Leu | Lys |
|---|---|---|---|---|---|---|---|---|---|---|---|---|---|---|---|
| | 130 | | | | | 135 | | | | | 140 | | | | |

| Ala | Glu | Asn | Leu | Leu | Leu | Asp | Asn | Asn | Met | Asn | Ile | Lys | Ile | Ala | Asp |
|---|---|---|---|---|---|---|---|---|---|---|---|---|---|---|---|
| 145 | | | | | 150 | | | | | 155 | | | | | 160 |

| Phe | Gly | Phe | Gly | Asn | Phe | Phe | Lys | Ser | Gly | Glu | Leu | Leu | Ala | Thr | Trp |
|---|---|---|---|---|---|---|---|---|---|---|---|---|---|---|---|
| | | | | 165 | | | | | 170 | | | | | 175 | |

| Cys | Gly | Ser | Pro | Pro | Tyr | Ala | Ala | Pro | Glu | Val | Phe | Glu | Gly | Gln | Gln |
|---|---|---|---|---|---|---|---|---|---|---|---|---|---|---|---|
| | | | 180 | | | | | 185 | | | | | 190 | | |

| Tyr | Glu | Gly | Pro | Gln | Leu | Asp | Ile | Trp | Ser | Met | Gly | Val | Val | Leu | Tyr |
|---|---|---|---|---|---|---|---|---|---|---|---|---|---|---|---|
| | | 195 | | | | | 200 | | | | | 205 | | | |

| Val | Leu | Val | Cys | Gly | Ala | Leu | Pro | Phe | Asp | Gly | Pro | Thr | Leu | Pro | Ile |
|---|---|---|---|---|---|---|---|---|---|---|---|---|---|---|---|
| | 210 | | | | | 215 | | | | | 220 | | | | |

| Leu | Arg | Gln | Arg | Val | Leu | Glu | Gly | Arg | Phe | Arg | Ile | Pro | Tyr | Phe | Met |
|---|---|---|---|---|---|---|---|---|---|---|---|---|---|---|---|
| 225 | | | | | 230 | | | | | 235 | | | | | 240 |

| Ser | Glu | Asp | Cys | Glu | His | Leu | Ile | Arg | Arg | Met | Leu | Val | Leu | Asp | Pro |
|---|---|---|---|---|---|---|---|---|---|---|---|---|---|---|---|
| | | | | 245 | | | | | 250 | | | | | 255 | |

| Ser | Lys | Arg | Leu | Thr | Ile | Ala | Gln | Ile | Lys | Glu | His | Lys | Trp | Met | Leu |
|---|---|---|---|---|---|---|---|---|---|---|---|---|---|---|---|
| | | | 260 | | | | | 265 | | | | | 270 | | |

| Ile | Glu | Val | Pro | Val | Gln | Arg | Pro | Val | Leu | Tyr | Pro | Gln | Glu | Gln | Glu |
|---|---|---|---|---|---|---|---|---|---|---|---|---|---|---|---|
| | | 275 | | | | | 280 | | | | | 285 | | | |

| Asn | Glu | Pro | Ser | Ile | Gly | Glu | Phe | Asn | Glu | Gln | Val | Leu | Arg | Leu | Met |
|---|---|---|---|---|---|---|---|---|---|---|---|---|---|---|---|
| | 290 | | | | | 295 | | | | | 300 | | | | |

| His | Ser | Leu | Gly | Ile | Asp | Gln | Gln | Lys | Thr | Ile | Glu | Ser | Leu | Gln | Asn |
|---|---|---|---|---|---|---|---|---|---|---|---|---|---|---|---|
| 305 | | | | | 310 | | | | | 315 | | | | | 320 |

| Lys | Ser | Tyr | Asn | His | Phe | Ala | Ala | Ile | Tyr | Phe | Leu | Leu | Val | Glu | Arg |
|---|---|---|---|---|---|---|---|---|---|---|---|---|---|---|---|
| | | | | 325 | | | | | 330 | | | | | 335 | |

| Leu | Lys | Ser | His | Arg | Ser | Ser | Phe | Pro | Val | Glu | Gln | Arg | Leu | Asp | Gly |
|---|---|---|---|---|---|---|---|---|---|---|---|---|---|---|---|
| | | | 340 | | | | | 345 | | | | | 350 | | |

```
Arg Gln Arg Arg Pro Ser Thr Ile Ala Glu Gln Thr Val Ala Lys Ala
            355                 360                 365

Gln Thr Val Gly Leu Pro Val Thr Met His Ser Pro Asn Met Arg Leu
    370                 375                 380

Leu Arg Ser Ala Leu Leu Pro Gln Ala Ser Asn Val Glu Ala Phe Ser
385                 390                 395                 400

Phe Pro Ala Ser Gly Cys Gln Ala Glu Ala Ala Phe Met Glu Glu Glu
                405                 410                 415

Cys Val Asp Thr Pro Lys Val Asn Gly Cys Leu Leu Asp Pro Val Pro
            420                 425                 430

Pro Val Leu Val Arg Lys Gly Cys Gln Ser Leu Pro Ser Asn Met Met
            435                 440                 445

Glu Thr Ser Ile Asp Glu Gly Leu Glu Thr Glu Gly Glu Ala Glu Glu
            450                 455                 460

Asp Pro Ala His Ala Phe Glu Ala Phe Gln Ser Thr Arg Ser Gly Gln
465                 470                 475                 480

Arg Arg His Thr Leu Ser Glu Val Thr Asn Gln Leu Val Val Met Pro
            485                 490                 495

Gly Ala Gly Lys Ile Phe Ser Met Asn Asp Ser Pro Ser Leu Asp Ser
            500                 505                 510

Val Asp Ser Glu Tyr Asp Met Gly Ser Val Gln Arg Asp Leu Asn Phe
            515                 520                 525

Leu Glu Asp Asn Pro Ser Leu Lys Asp Ile Met Leu Ala Asn Gln Pro
            530                 535                 540

Ser Pro Arg Met Thr Ser Pro Phe Ile Ser Leu Arg Pro Thr Asn Pro
545                 550                 555                 560

Ala Met Gln Ala Leu Ser Ser Gln Lys Arg Glu Val His Asn Arg Ser
            565                 570                 575

Pro Val Ser Phe Arg Glu Gly Arg Arg Ala Ser Asp Thr Ser Leu Thr
            580                 585                 590

Gln Gly Ile Val Ala Phe Arg His Leu Gln Asn Leu Ala Arg Thr
            595                 600                 605

Lys Gly Ile Leu Glu Leu Asn Lys Val Gln Leu Leu Tyr Glu Gln Ile
            610                 615                 620

Gly Pro Glu Ala Asp Pro Asn Leu Ala Pro Ala Pro Gln Leu Gln
625                 630                 635                 640

Asp Leu Ala Ser Ser Cys Pro Gln Glu Glu Val Ser Gln Gln Gln Glu
            645                 650                 655

Ser Val Ser Thr Leu Pro Ala Ser Val His Pro Gln Leu Ser Pro Arg
            660                 665                 670

Gln Ser Leu Glu Thr Gln Tyr Leu Gln His Arg Leu Gln Lys Pro Ser
            675                 680                 685

Leu Leu Ser Lys Ala Gln Asn Thr Cys Gln Leu Tyr Cys Lys Glu Pro
            690                 695                 700

Pro Arg Ser Leu Glu Gln Gln Leu Gln Glu His Arg Leu Gln Gln Lys
705                 710                 715                 720

Arg Leu Phe Leu Gln Lys Gln Ser Gln Leu Gln Ala Tyr Phe Asn Gln
            725                 730                 735

Met Gln Ile Ala Glu Ser Ser Tyr Pro Gln Pro Ser Gln Gln Leu Pro
            740                 745                 750

Leu Pro Arg Gln Glu Thr Pro Pro Ser Gln Ala Pro Pro Phe
            755                 760                 765
```

```
Ser Leu Thr Gln Pro Leu Ser Pro Val Leu Glu Pro Ser Glu Gln
    770             775             780

Met Gln Tyr Ser Pro Phe Leu Ser Gln Tyr Gln Glu Met Gln Leu Gln
785             790             795             800

Pro Leu Pro Ser Thr Ser Gly Pro Arg Ala Ala Pro Pro Leu Pro Thr
            805             810             815

Gln Leu Gln Gln Gln Gln Pro Pro Pro Pro Pro Pro Pro Pro Pro Pro
        820             825             830

Arg Gln Pro Gly Ala Ala Pro Ala Pro Leu Gln Phe Ser Tyr Gln Thr
        835             840             845

Cys Glu Leu Pro Ser Ala Ala Ser Pro Ala Pro Asp Tyr Pro Thr Pro
850             855             860

Cys Gln Tyr Pro Val Asp Gly Ala Gln Gln Ser Asp Leu Thr Gly Pro
865             870             875             880

Asp Cys Pro Arg Ser Pro Gly Leu Gln Glu Ala Pro Ser Ser Tyr Asp
            885             890             895

Pro Leu Ala Leu Ser Glu Leu Pro Gly Leu Phe Asp Cys Glu Met Leu
            900             905             910

Asp Ala Val Asp Pro Gln His Asn Gly Tyr Val Leu Val Asn
        915             920             925
```